US010873034B2

(12) United States Patent
Lee et al.

(10) Patent No.: US 10,873,034 B2
(45) Date of Patent: Dec. 22, 2020

(54) CONDENSED CYCLIC COMPOUND AND ORGANIC LIGHT-EMITTING DEVICE INCLUDING THE SAME

(71) Applicants: SAMSUNG ELECTRONICS CO., LTD., Suwon-si (KR); Samsung SDI Co., Ltd., Yongin-si (KR)

(72) Inventors: Saeyoun Lee, Suwon-si (KR); Masaki Numata, Suwon-si (KR); Hiroshi Miyazaki, Suwon-si (KR); Soonok Jeon, Seoul (KR); Hosuk Kang, Suwon-si (KR); Sooghang Ihn, Hwaseong-si (KR); Miyoung Chae, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 38 days.

(21) Appl. No.: 15/413,831

(22) Filed: Jan. 24, 2017

(65) Prior Publication Data

US 2017/0237015 A1 Aug. 17, 2017

(30) Foreign Application Priority Data

Feb. 11, 2016 (KR) ........................ 10-2016-0015674

(51) Int. Cl.

| | |
|---|---|
| ***H01L 51/50*** | (2006.01) |
| ***H01L 51/00*** | (2006.01) |
| ***C07D 519/00*** | (2006.01) |
| ***C09K 11/02*** | (2006.01) |
| ***C09K 11/06*** | (2006.01) |

(52) U.S. Cl.

CPC ........ *H01L 51/0071* (2013.01); *C07D 519/00* (2013.01); *C09K 11/025* (2013.01); *C09K 11/06* (2013.01); *H01L 51/0072* (2013.01); *C09K 2211/1007* (2013.01); *C09K 2211/1048* (2013.01); *C09K 2211/1051* (2013.01); *H01L 51/5004* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(58) Field of Classification Search

None

See application file for complete search history.

(56) References Cited

U.S. PATENT DOCUMENTS

| | | | | |
|---|---|---|---|---|
| 2010/0187984 | A1 | 7/2010 | Lin et al. | |
| 2015/0243893 | A1* | 8/2015 | Joseph | C07D 491/04 257/40 |
| 2016/0308143 | A1* | 10/2016 | Kim | H01L 51/006 |
| 2017/0062718 | A1 | 3/2017 | Numata et al. | |
| 2018/0141957 | A1* | 5/2018 | Park | C07D 495/04 |

FOREIGN PATENT DOCUMENTS

KR 10-2014-0000611 A 1/2014

* cited by examiner

*Primary Examiner* — Gregory D Clark

(74) *Attorney, Agent, or Firm* — Cantor Colburn LLP

(57) ABSTRACT

A condensed cyclic compound represented by Formula 1:

$Ar_1\text{-}(L_1)_{a1}\text{-}Ar_2$ Formula 1 wherein, in Formula 1, $Ar_1$, $Ar_2$, $L_1$, and a1 are the same as described in the specification.

19 Claims, 1 Drawing Sheet

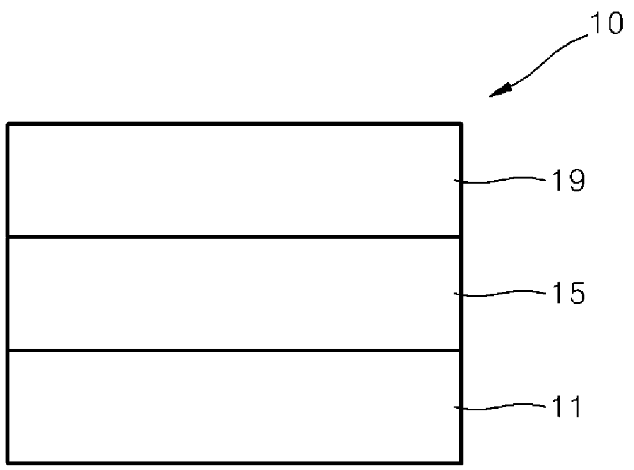
10
19
15
11

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0015674, filed on Feb. 11, 2016, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the condensed cyclic compound.

2. Description of the Related Art

Organic light-emitting devices (OLEDs) are self-emission devices that have wide viewing angles, high contrast ratios, and short response times. OLEDs also exhibit excellent brightness, driving voltage, and response speed characteristics, compared to devices in the art, and produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state, thereby generating light.

SUMMARY

Provided are a condensed cyclic compound and an organic light-emitting device including the condensed cyclic compound.

Additional aspects will be set forth in part in the description which follows and, in part, will be apparent from the description, or may be learned by practice of the presented embodiments.

According to an aspect of an embodiment, a condensed cyclic compound is represented by Formula 1:

Formula 1

$$Ar_1-(L_1)_{a1}-Ar_2$$

Formula 2-1

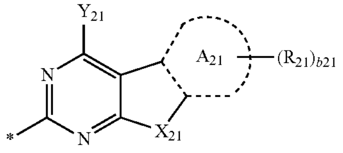

-continued

Formula 2-2

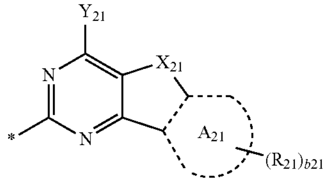

Formula 2-3

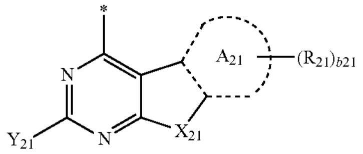

Formula 2-4

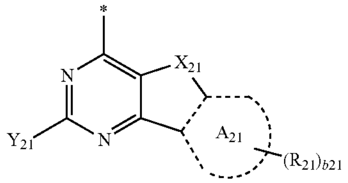

Formula 3-1

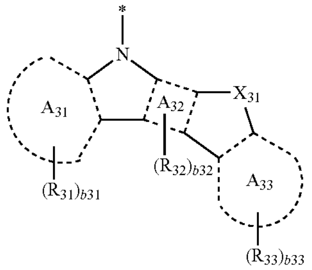

Formula 3-2

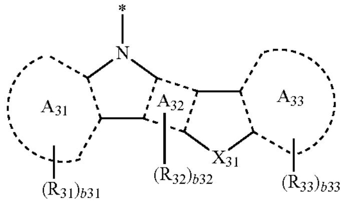

wherein, in Formulae 1, 2-1 to 2-4, 3-1, and 3-2, $Ar_1$ is selected from groups represented by Formulae 2-1 to 2-4;

$Ar_2$ is selected from groups represented by Formulae 3-1 and 3-2;

$L_1$ is selected from a single bond, a substituted or unsubstituted $C_6$-$C_{60}$ arylene group, and a substituted or unsubstituted $C_1$-$C_{60}$ heteroarylene group;

a1 is selected from 0, 1, 2, and 3;

$X_{21}$ is selected from O, S, $C(R_{22})(R_{23})$, $Si(R_{22})(R_{23})$, $Ge(R_{22})(R_{23})$, and $P(=O)(R_{22})$;

$X_{31}$ is selected from O, S, $N(R_{34})$, $C(R_{34})(R_{35})$, $Si(R_{34})(R_{35})$, and $Ge(R_{34})(R_{35})$;

$A_{21}$, $A_{31}$, and $A_{33}$ are each independently selected from a $C_5$-$C_{20}$ carbocyclic group and a $C_1$-$C_{20}$ heterocyclic group;

$A_{32}$ is selected from a $C_5$-$C_{20}$ carbocyclic group;

$Y_{21}$ is selected from a substituted or unsubstituted $C_6$-$C_{60}$ aryl group and a substituted or unsubstituted $C_1$-$C_{60}$ heteroaryl group;

$R_{21}$ to $R_{23}$ and $R_{31}$ to $R_{35}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 is selected from 1, 2, 3, 4, 5, 6, 7, and 8;

b31 to b33 are each independently selected from 1, 2, 3, 4, 5, and 6; and

* denotes a binding site to a neighboring atom.

According to an aspect of another embodiment, an organic light-emitting device includes:

a first electrode;

a second electrode; and an organic layer disposed between the first electrode and the second electrode, wherein the organic layer comprises an emission layer and at least one of the condensed cyclic compound.

BRIEF DESCRIPTION OF THE DRAWINGS

These and/or other aspects will become apparent and more readily appreciated from the following description of the embodiments, taken in conjunction with FIG. 1, which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound according to an embodiment is represented by Formula 1:

$$Ar_1\text{-}(L_1)_{a1}\text{-}Ar_2 \qquad \text{Formula 1}$$

In Formula 1, $Ar_1$ may be selected from groups represented by Formulae 2-1 to 2-4:

Formula 2-1

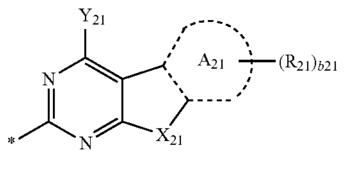

-continued

Formula 2-2

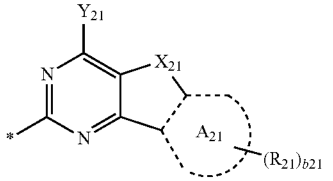

Formula 2-3

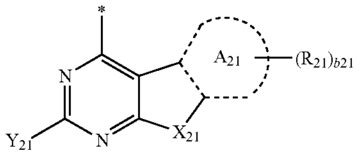

Formula 2-4

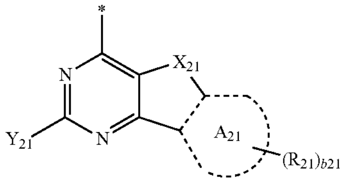

In Formulae 2-1 to 2-4, $X_{21}$, $A_{21}$, $Y_{21}$, $R_{21}$, and b21 may be understood by referring to the description provided herein; and

* denotes a binding site to a neighboring atom.

In Formula 1, $Ar_2$ may be selected from groups represented by Formulae 3-1 and 3-2:

Formula 3-1

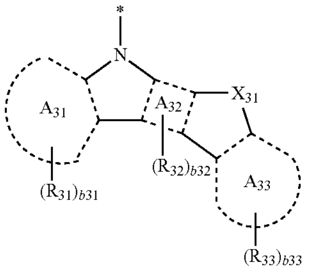

Formula 3-2

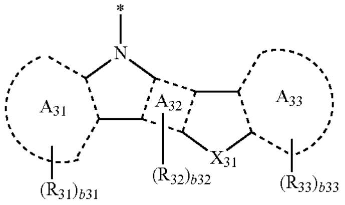

wherein, in Formulae 3-1 and 3-2, $A_{31}$ to $A_{33}$, $X_{31}$, $R_{31}$ to $R_{33}$, and b31 to b33 may be understood by referring to the description provided herein; and

* denotes a binding site to a neighboring atom.

In Formula 1, $L_1$ may be selected from a single bond, a substituted or unsubstituted $C_6$-$C_{60}$ arylene group, and a substituted or unsubstituted $C_1$-$C_{60}$ heteroarylene group.

For example, in Formula 1, $L_1$ may be selected from a single bond, a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group, but embodiments are not limited thereto.

In some embodiments, in Formula 1, $L_1$ may be selected from a single bond and groups represented by Formulae 4-1 to 4-15, but embodiments are not limited thereto:

4-1

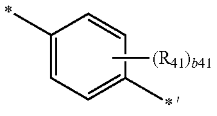

4-2

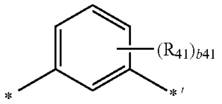

4-3

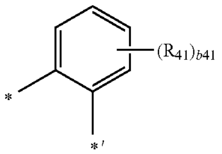

4-4

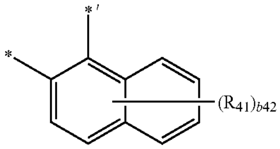

4-5

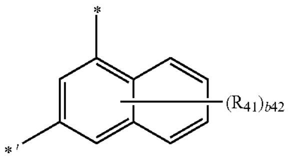

4-6

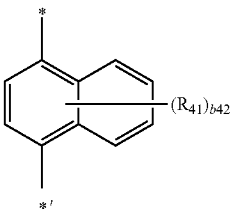

4-7

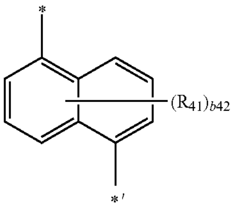

-continued 4-8

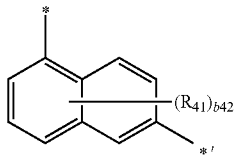

4-9

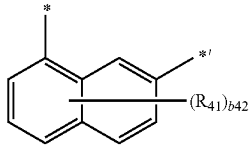

4-10

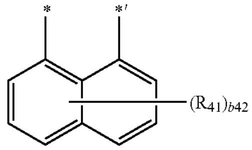

4-11

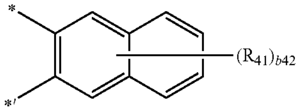

4-12

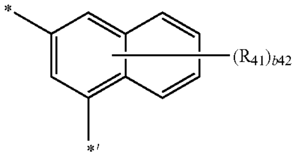

4-13

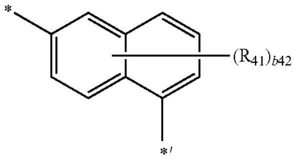

4-14

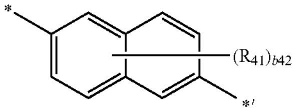

4-15

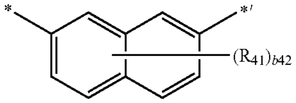

wherein, in Formulae 4-1 to 4-15, $R_{41}$ may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group;

b41 may be selected from 1, 2, 3, and 4;

b42 may be selected from 1, 2, 3, 4, 5, and 6; and

* and *' each independently denote a binding site to a neighboring atom.

In Formula 1, a1 denotes the number of groups $L_1$, and a1 may be selected from 0, 1, 2, and 3.

For example, in Formula 1, a1 may be selected from 0 and 1, but embodiments are not limited thereto.

In some embodiments, in Formula 1, $(L_1)_{a1}$ may be selected from a single bond and groups represented by Formulae 5-1 to 5-3, but embodiments are not limited thereto:

5-1

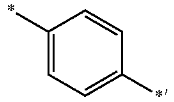

5-2

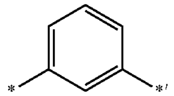

5-3

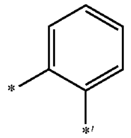

In Formulae 5-1 to 5-3,

* and *' each independently denote a binding site to a neighboring atom.

In Formulae 2-1 to 2-4, $X_{21}$ may be selected from O, S, $C(R_{22})(R_{23})$, $Si(R_{22})(R_{23})$, $Ge(R_{22})(R_{23})$, and $P(=O)(R_{22})$, and $R_{22}$ and $R_{23}$ may be understood by referring to the description provided herein.

For example, in Formulae 2-1 to 2-4, $X_{21}$ may be selected from O, S, $Si(R_{22})(R_{23})$, and $Ge(R_{22})(R_{23})$, but embodiments are not limited thereto.

In Formulae 3-1 and 3-2, $X_{31}$ may be selected from O, S, $N(R_{34})$, $C(R_{34})(R_{35})$, $Si(R_{34})(R_{35})$, and $Ge(R_{34})(R_{35})$, and $R_{34}$ and $R_{35}$ may be understood by referring to the description provided herein.

For example, in Formula 3-1 and 3-2, $X_{31}$ may be selected from O, S, $N(R_{34})$, and $C(R_{34})(R_{35})$, but embodiments are not limited thereto.

In Formulae 2-1 to 2-4, 3-1, and 3-2, $A_{21}$, $A_{31}$, and $A_{33}$ may be each independently selected from a $C_5$-$C_{20}$ carbocyclic group and a $C_1$-$C_{20}$ heterocyclic group, but embodiments are not limited thereto.

For example, in Formulae 2-1 to 2-4, 3-1, and 3-2, $A_{21}$, $A_{31}$, and $A_{33}$ may be each independently selected from a benzene group, a naphthalene group, an anthracene group, a phenanthrene group, a triphenylene group, a pyridine group, a pyrimidine group, a pyrazine group, a quinoline group, an isoquinoline group, a 2,6-naphthyridine group, a 1,8-naphthyridine group, a 1,5-naphthyridine group, a 1,6-naphthyridine group, a 1,7-naphthyridine group, a 2,7-naphthyridine group, a quinoxaline group, a phthalazine group, a quinazoline group, and a cinnoline group, but embodiments are not limited thereto.

In some embodiments, in Formulae 2-1 to 2-4, 3-1, and 3-2, $A_{21}$, $A_{31}$, and $A_{33}$ may be each independently selected from a benzene group, a naphthalene group, a pyridine group, a pyrimidine group, a pyrazine group, a quinoline group, and an isoquinoline group, but embodiments are not limited thereto.

In some embodiments, in Formulae 2-1 to 2-4, 3-1, and 3-2, $A_{21}$, $A_{31}$, and $A_{33}$ may be each independently selected from a benzene group and a naphthalene group, but embodiments are not limited thereto.

In some embodiments, in Formulae 2-1 to 2-4, 3-1, and 3-2, $A_{21}$, $A_{31}$, and $A_{33}$ may be each independently a benzene group, but embodiments are not limited thereto.

In Formulae 3-1 and 3-2, $A_{32}$ may be a $C_5$-$C_{20}$ carbocyclic group.

For example, in Formulae 3-1 and 3-2, $A_{32}$ may be selected from a benzene group, a naphthalene group, an anthracene group, a phenanthrene group, and a triphenylene group, but embodiments are not limited thereto.

In some embodiments, in Formulae 3-1 and 3-2, $A_{32}$ may be selected from a benzene group and a naphthalene group, but embodiments are not limited thereto.

In some embodiments, in Formulae 3-1 and 3-2, $A_{32}$ may be selected from a benzene group, but embodiments are not limited thereto.

In Formulae 2-1 to 2-4, $Y_{21}$ may be selected from a substituted or unsubstituted $C_6$-$C_{60}$ aryl group and a substituted or unsubstituted $C_1$-$C_{60}$ heteroaryl group, but embodiments are not limited thereto.

For example, in Formulae 2-1 to 2-4, $Y_{21}$ may be selected from a phenyl group, a biphenyl group, a terphenyl group, a pentalenyl group, a naphthyl group, an azulenyl group, a heptalenyl group, an indacenyl group, an acenaphthyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a furanyl group, a benzofuranyl group, a thiophenyl group, a benzothiophenyl group, and a triazinyl group; and a phenyl group, a biphenyl group, a terphenyl group, a pentalenyl group, a naphthyl group, an azulenyl group, a heptalenyl group, an indacenyl group, an acenaphthyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a furanyl group, a benzofuranyl group, a thiophenyl group, a benzothiophenyl group, and a triazinyl group, each substituted with at least one selected from deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, and a naphthyl group, but embodiments are not limited thereto.

In some embodiments, in Formulae 2-1 to 2-4, $Y_{21}$ may be selected from a phenyl group, a biphenyl group, a terphenyl group, a naphthyl group, a phenanthrenyl group, an anthracenyl group, a triphenylenyl group, a pyrenyl group, and a chrysenyl group; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{20}$ alkyl group, a $C_1$-$C_{20}$ alkoxy group, a phenyl group, a biphenyl group, a terphenyl group, and a naphthyl group, but embodiments are not limited thereto.

In some embodiments, in Formulae 2-1 to 2-4, $Y_{21}$ may be selected from groups represented by Formulae 6-1 to 6-4, but embodiments are not limited thereto:

6-1

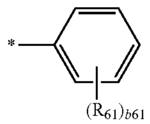

6-2

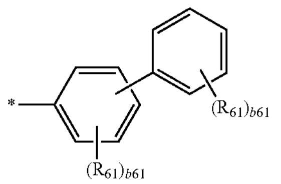

6-3

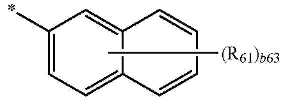

6-4

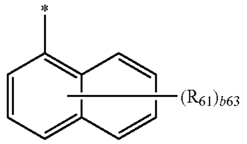

In Formulae 6-1 to 6-4, $R_{61}$ may be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b61 may be selected from 1, 2, 3, 4, and 5;

b62 may be selected from 1, 2, 3, and 4;

b63 is selected from 1, 2, 3, 4, 5, 6, and 7; and

* denotes a binding site to a neighboring atom.

In some embodiments, in Formulae 2-1 to 2-4, $Y_{21}$ may be selected from groups represented by Formulae 7-1 to 7-4, but embodiments are not limited thereto:

7-1

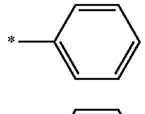

7-2

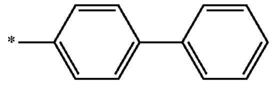

-continued 7-3

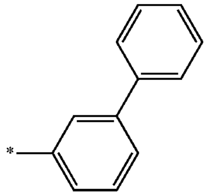

7-4

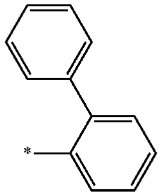

In Formulae 7-1 to 7-4,

* denotes a binding site to a neighboring atom.

In Formulae 2-1 to 2-4, 3-1, and 3-2, $R_{21}$ to $R_{23}$ and $R_{31}$ to $R_{35}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; but embodiments are not limited thereto.

For example, in Formulae 2-1 to 2-4, 3-1, and 3-2, $R_{21}$ to $R_{26}$ and $R_{31}$ to $R_{35}$ may be each independently selected from hydrogen, deuterium, —F, —Cl, —Br, —I, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group, but embodiments are not limited thereto.

In some embodiments, in Formulae 2-1 to 2-4, 3-1, and 3-2, $R_{21}$ to $R_{26}$ and $R_{31}$ to $R_{35}$ may be each independently selected from hydrogen, deuterium, —F, —Cl, —Br, —I, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;

a phenyl group, a biphenyl group, a terphenyl group, a naphthyl group, a fluorenyl group, a thiophenyl group, a furanyl group, a carbazolyl group, a benzofuranyl group, a benzothiophenyl group, a dibenzofuranyl group, and a dibenzothiophenyl group; and a phenyl group, a biphenyl group, a terphenyl group, a fluorenyl group, a thiophenyl group, a furanyl group, a carbazolyl group, a benzofuranyl group, a benzothiophenyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group, but embodiments are not limited thereto.

In some embodiments, in Formulae 2-1 to 2-4, 3-1, and 3-2, $R_{22}$, $R_{23}$, $R_{34}$, and $R_{35}$ may be each independently selected from a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, and a fluorenyl group; and a phenyl group, a biphenyl group, a terphenyl group, a naphthyl group, and a fluorenyl group, each substituted with at least one selected from a methyl group, an ethyl group, an n-propyl group, an iso-propyl group, an n-butyl group, an iso-butyl group, a sec-butyl group, and a tert-butyl group, but embodiments are not limited thereto.

In Formulae 2-1 to 2-4, b21 denotes the number of groups $R_{21}$, and b21 may be selected from 1, 2, 3, 4, 5, 6, 7, and 8.

In Formulae 3-1 and 3-2, b31 denotes the number of groups $R_{31}$, and b31 may be selected from 1, 2, 3, 4, 5, and 6, but embodiments are not limited thereto.

In Formulae 3-1 and 3-2, b32 denotes the number of groups $R_{32}$, and b32 may be selected from 1, 2, 3, 4, 5, and 6, but embodiments are not limited thereto.

In Formulae 3-1 and 3-2, b33 denotes the number of groups $R_{33}$, and b33 may be selected from 1, 2, 3, 4, 5, and 6, but embodiments are not limited thereto.

For example, in Formula 1, $Ar_1$ may be selected from groups represented by Formulae 2-11 to 2-14, but embodiments are not limited thereto:

2-11

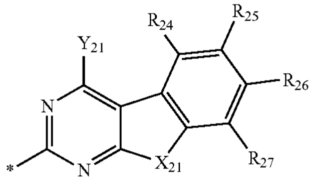

2-12

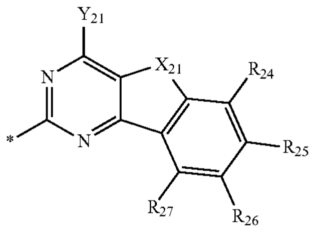

2-13

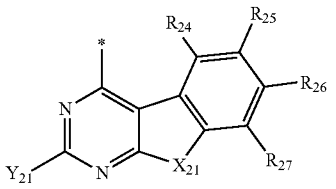

2-14

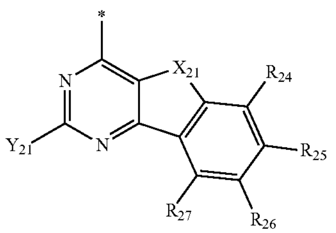

In Formulae 2-11 to 2-14, $Y_{21}$ and $X_{21}$ are the same as described in connection with Formulae 2-1 to 2-4;

$R_{24}$ to $R_{27}$ are the same as described in connection with $R_{21}$ in Formulae 2-1 to 2-4;

* denotes a binding site to a neighboring atom.

For example, in Formula 1, $Ar_2$ may be selected from groups represented by Formulae 3-11 to 3-16, but embodiments are not limited thereto:

3-11

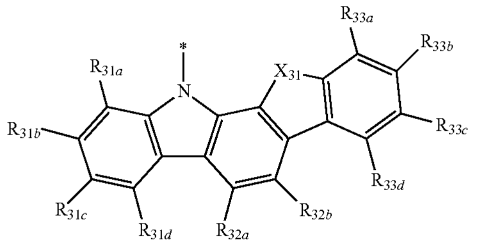

3-12

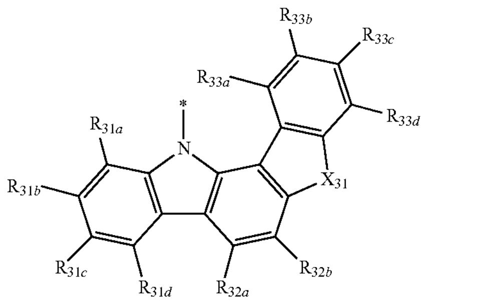

3-13

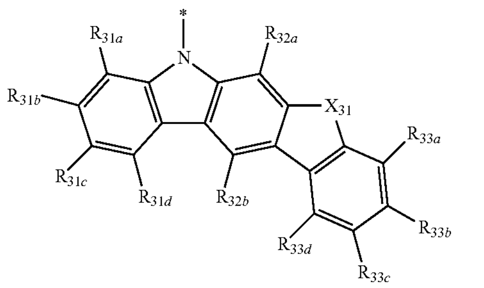

3-14

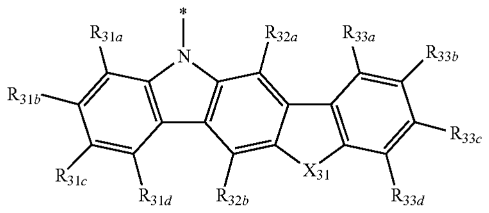

3-15

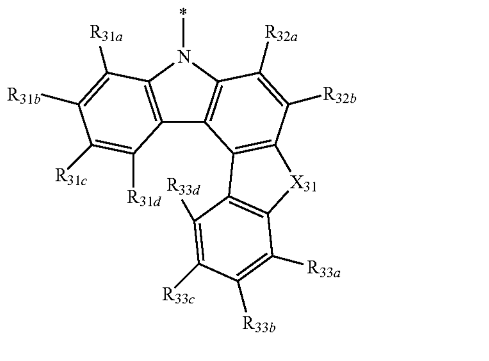

-continued 3-16

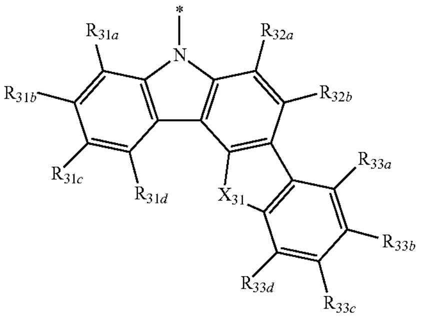

In Formulae 3-11 to 3-16, $X_{31}$ is the same as described in connection with Formulae 3-1 and 3-2;

$R_{31a}$, $R_{31b}$, $R_{31c}$, and $R_{31d}$ are each independently the same as described in connection with $R_{31}$ in Formulae 3-1 and 3-2;

$R_{32a}$ and $R_{32b}$ are each independently the same as described in connection with $R_{32}$ in Formulae 3-1 and 3-2;

$R_{33a}$, $R_{33b}$, $R_{33c}$, and $R_{33d}$ are each independently the same as described in connection with $R_{33}$ in Formulae 3-1 and 3-2; and

* denotes a binding site to a neighboring atom.

For example, the condensed cyclic compound represented by Formula 1 may be selected from compounds represented by Formulae 1-1 to 1-24, but embodiments are not limited thereto:

1-1

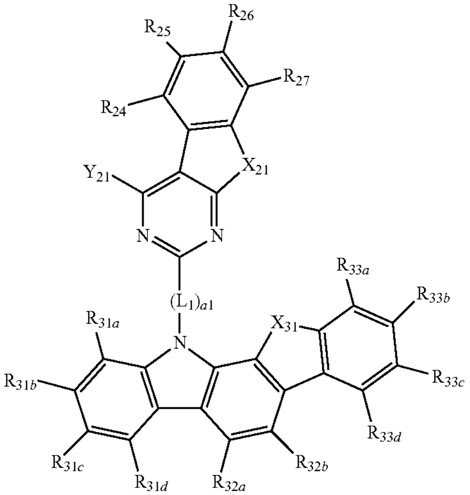

-continued 1-2

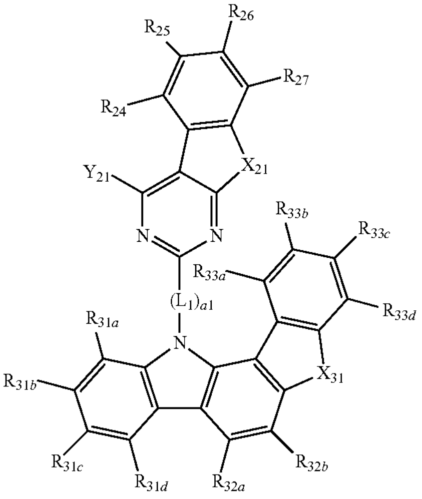

1-3

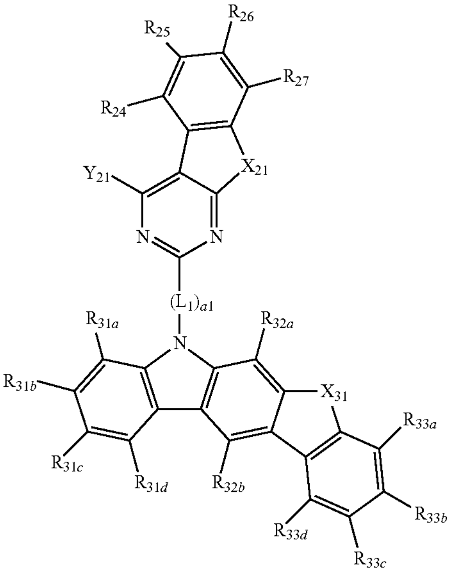

1-4

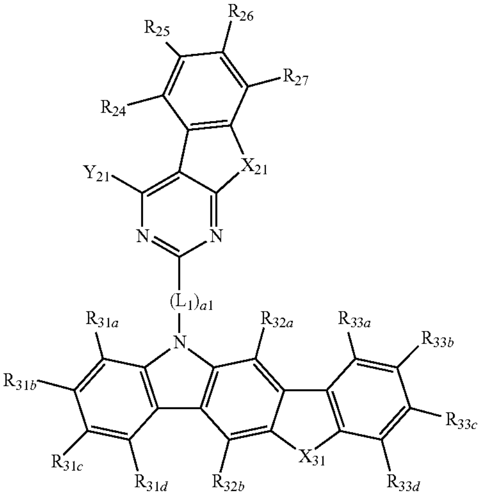

-continued
1-5
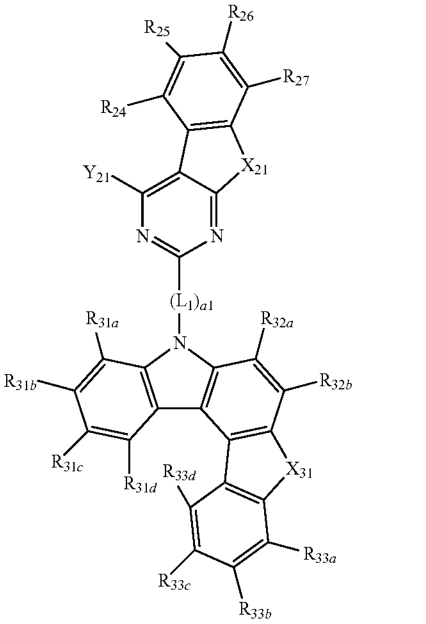
1-6
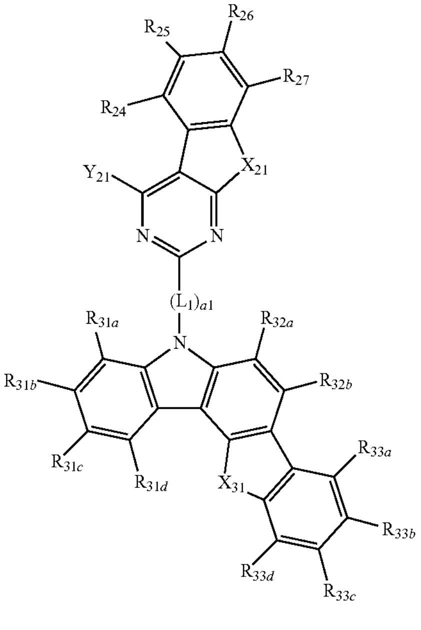
-continued
1-7
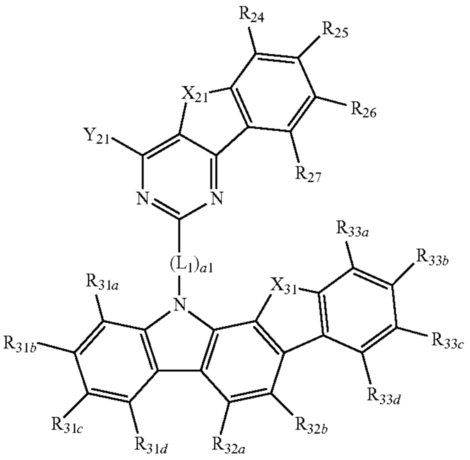
1-8
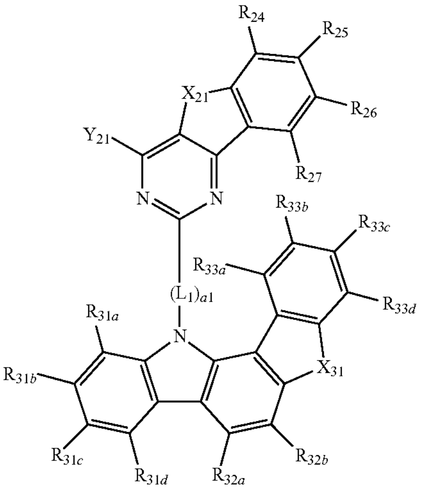
1-9
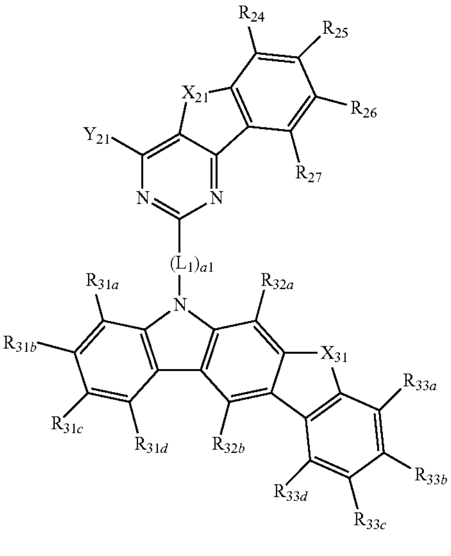

-continued
1-10
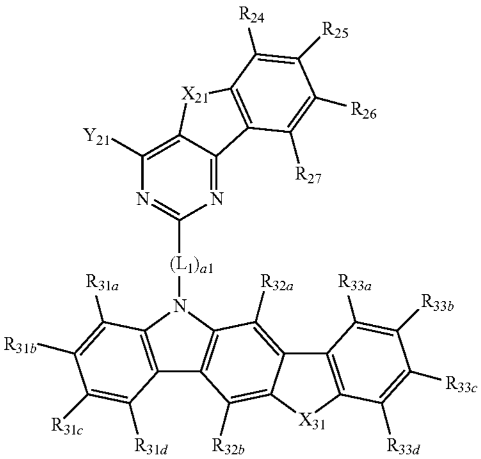
1-11
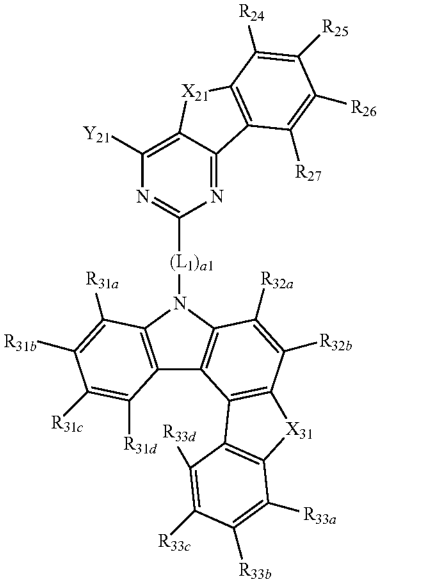
1-12
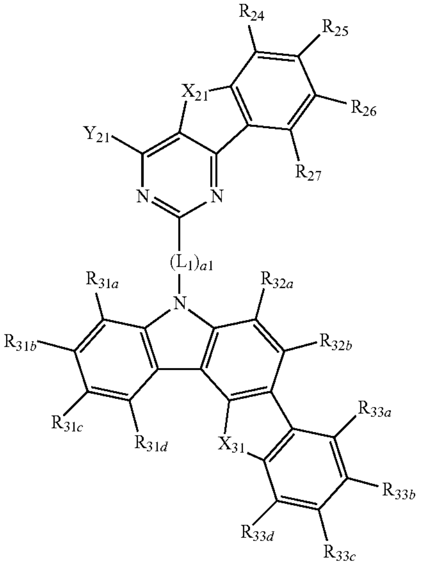
-continued
1-13
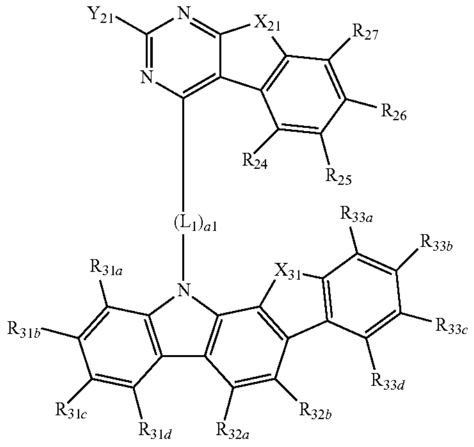
1-14
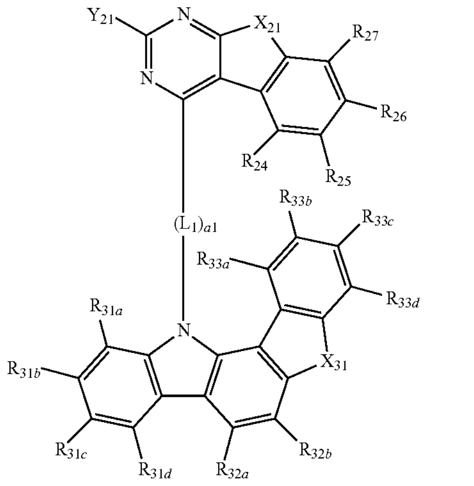
1-15
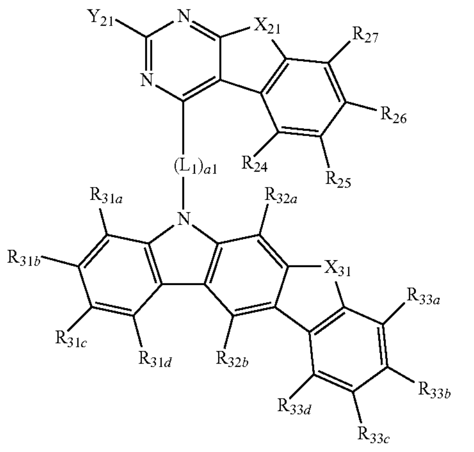

-continued
1-16
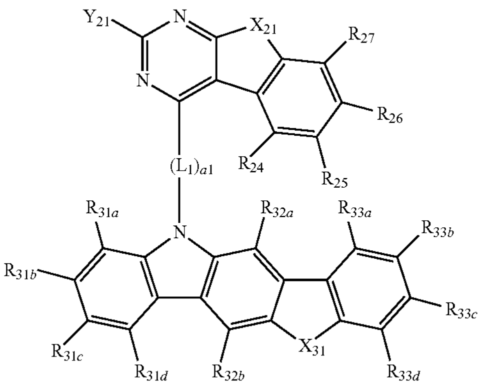
1-17
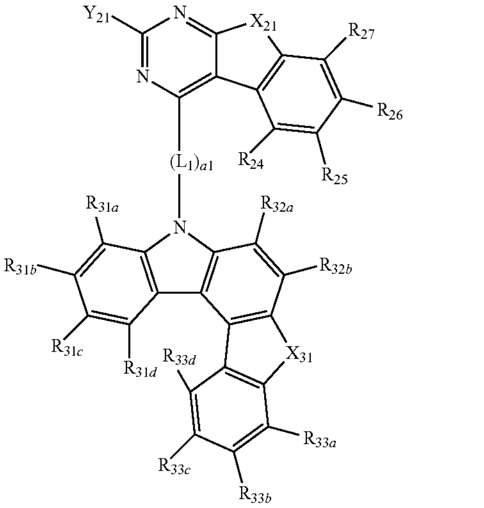
1-18
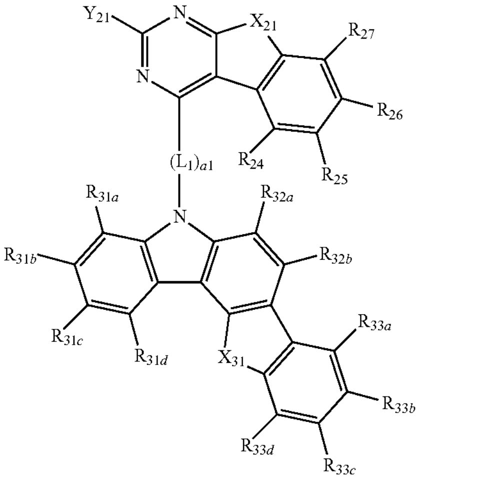
-continued
1-19
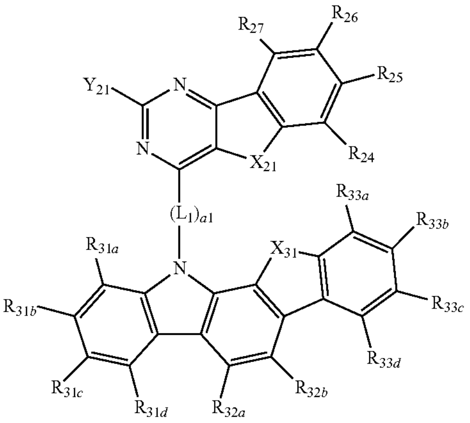
1-20
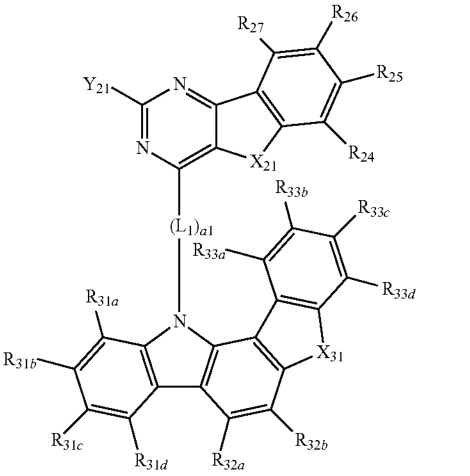
1-21
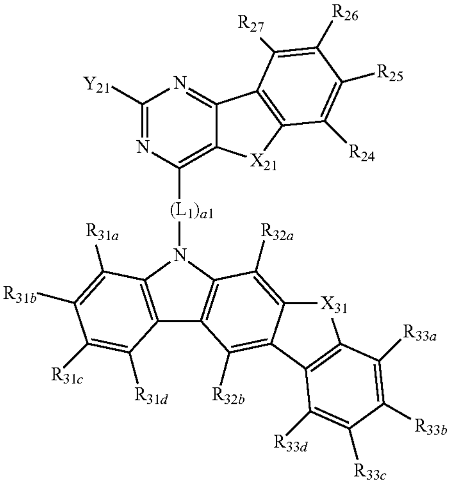

-continued 1-22

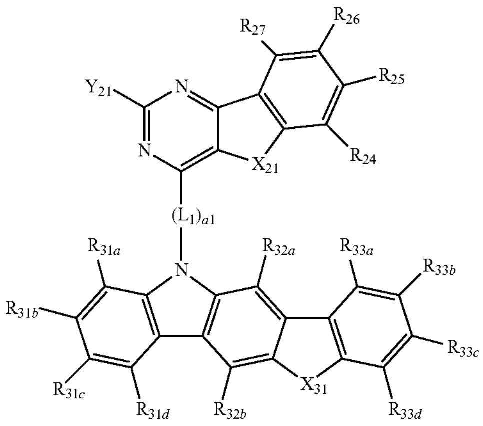

1-23

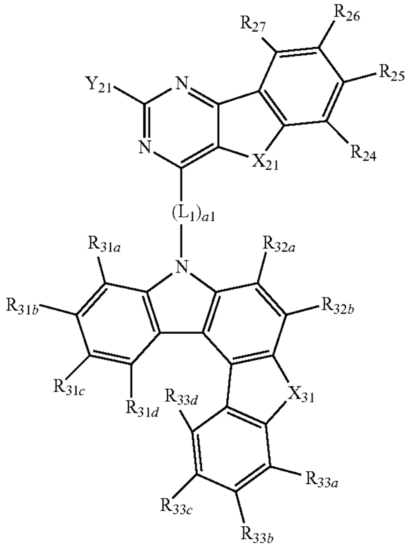

1-24

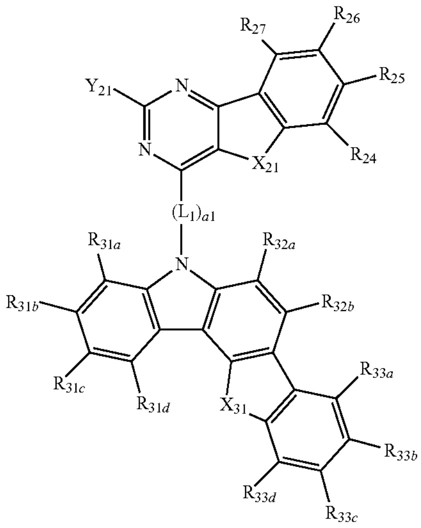

In Formulae 1-1 to 1-24, $L_1$ may be selected from a single bond, a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group;

a1 may be selected from 0 and 1;

$Y_{21}$ and $X_{21}$ are the same as described in connection with Formulae 2-1 to 2-4;

$R_{24}$ to $R_{27}$ are each independently the same as described in connection with $R_{21}$ in Formulae 2-1 to 2-4;

$X_{31}$ is the same as described in connection with Formulae 3-1 and 3-2;

$R_{31a}$, $R_{31b}$, $R_{31c}$, and $R_{31d}$ are each independently the same as described in connection with $R_{31}$ in Formulae 3-1 and 3-2;

$R_{32a}$ and $R_{32b}$ are each independently the same as described in connection with $R_{32}$ in Formulae 3-1 and 3-2;

$R_{33a}$, $R_{33b}$, $R_{33c}$, and $R_{33d}$ are each independently the same as described in connection with $R_{33}$ in Formulae 3-1 and 3-2.

For example, in Formulae 1-1 to 1-24, $(L_1)_{a1}$ may be selected from a single bond and groups represented by Formulae 5-1 to 5-3, but embodiments are not limited thereto:

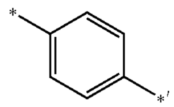

5-1

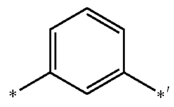

5-2

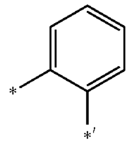

5-3

In Formulae 5-1 to 5-3,

* and *' each independently denote a binding site to a neighboring atom.

In some embodiments, the condensed cyclic compound represented by Formula 1 may be selected from Compounds 1 to 2390, but embodiments are not limited thereto:

-continued
1
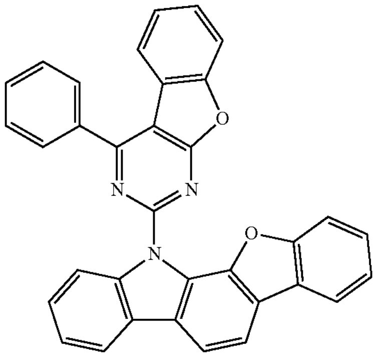
2
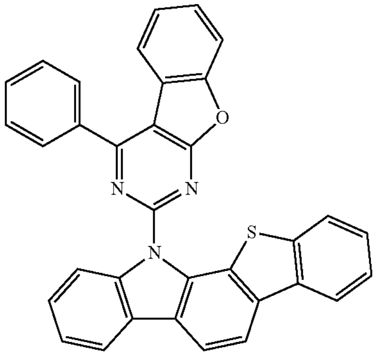
3
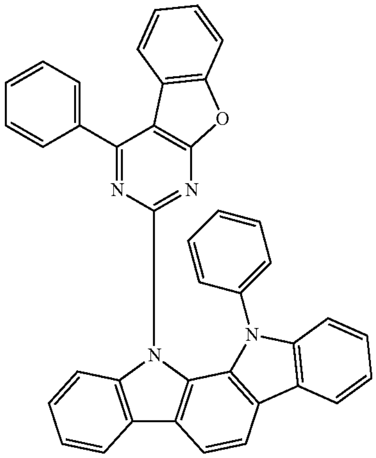
4
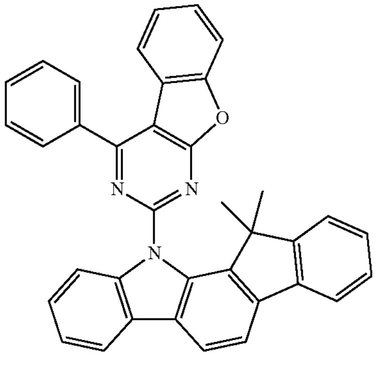
5
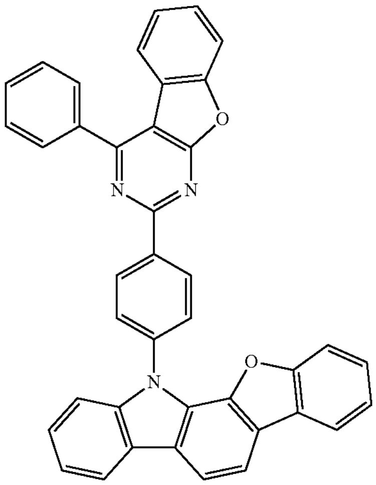
6
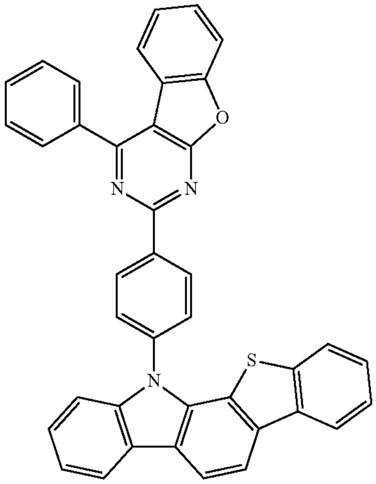
7
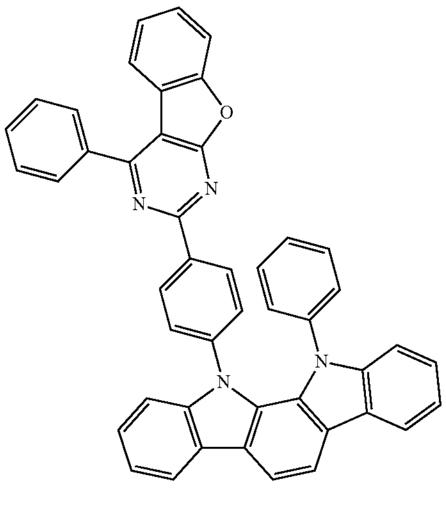

-continued
8
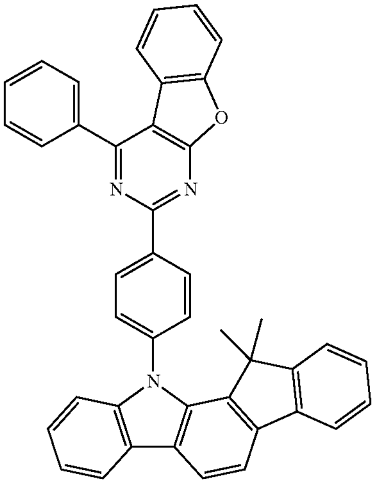
9
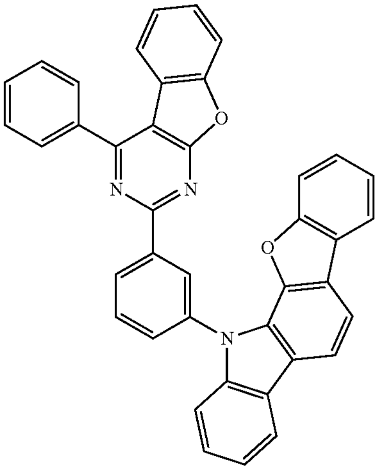
10
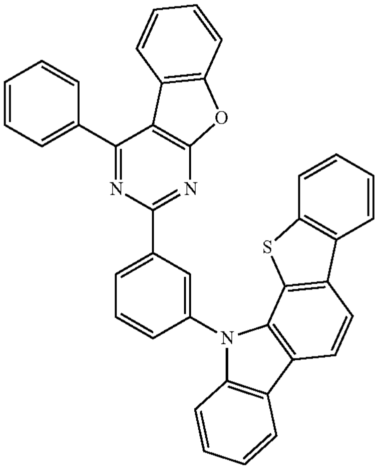
-continued
11
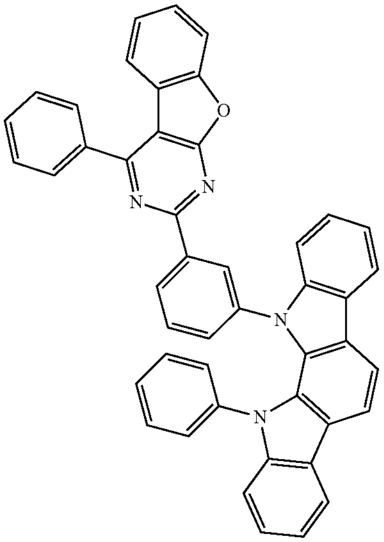
12
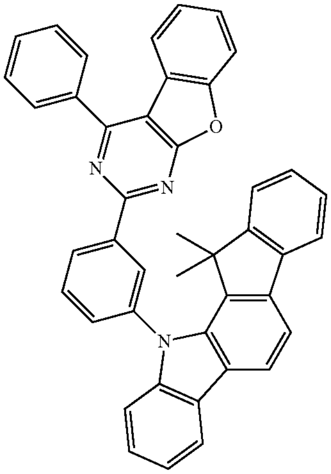
13
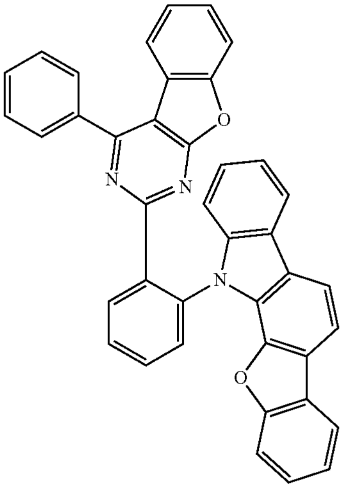

-continued
14
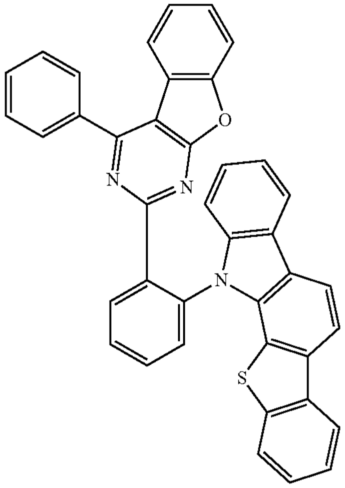
15
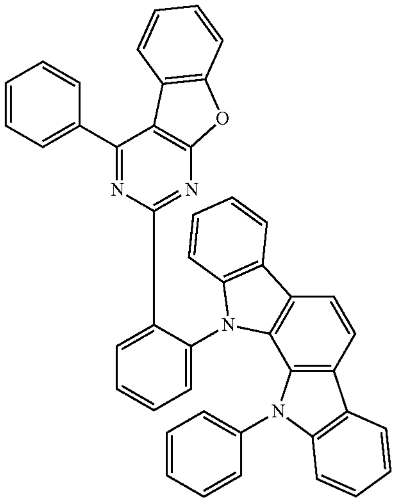
16
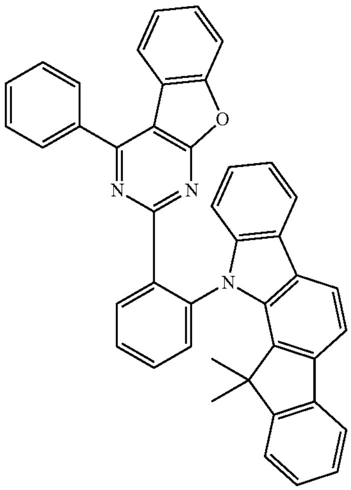
-continued
17
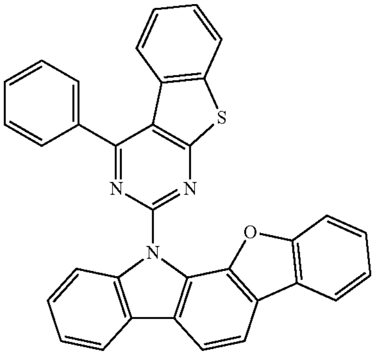
18
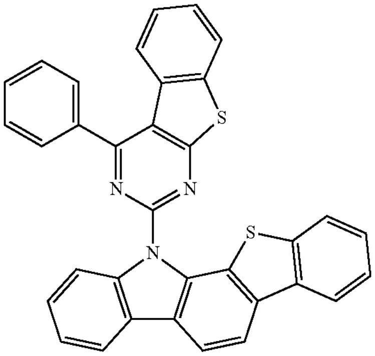
19
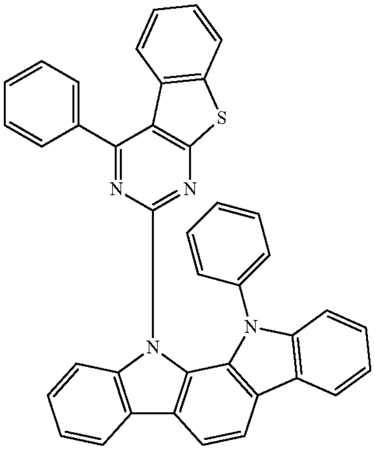
20
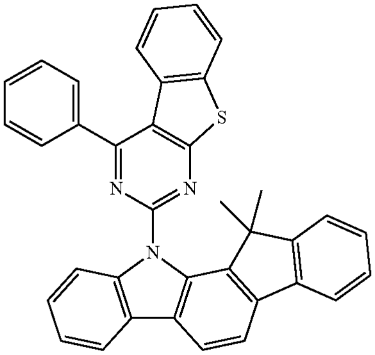

-continued
21
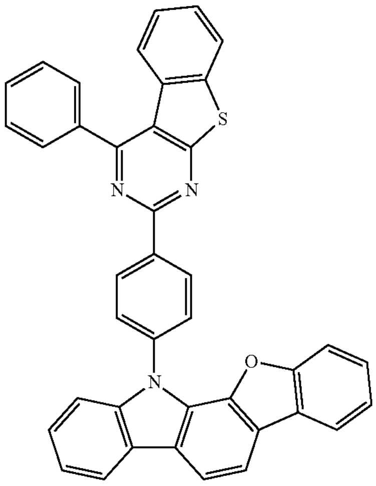
22
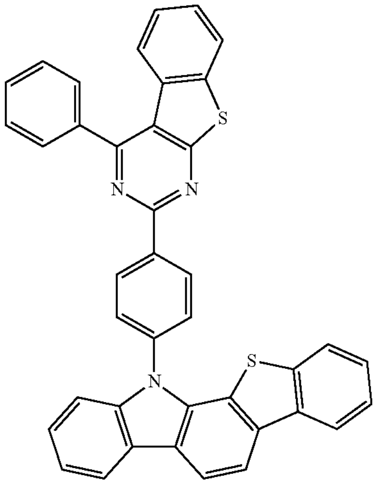
23
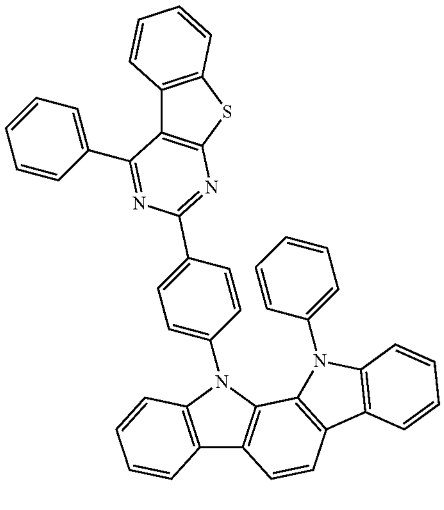
-continued
24
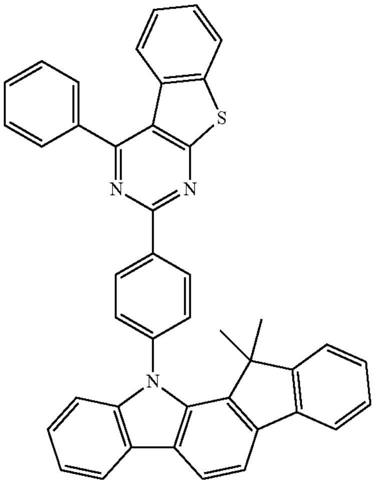
25
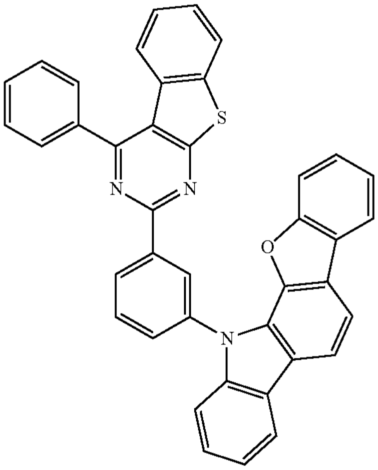
26
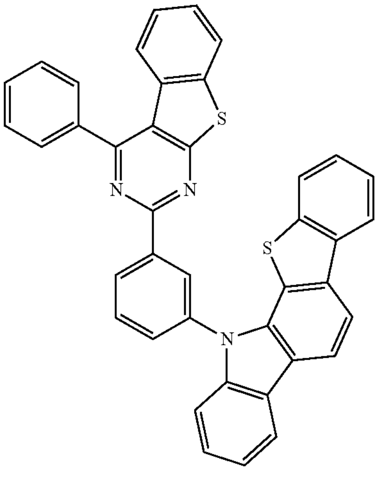

-continued
27
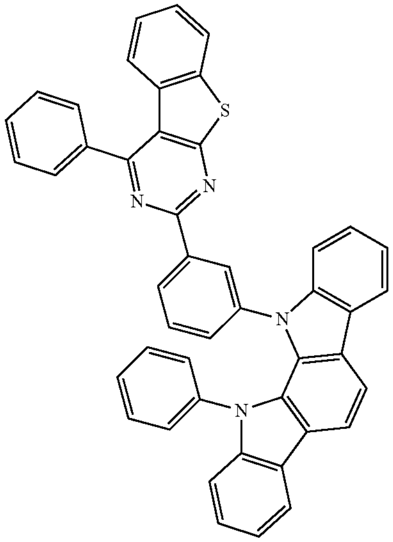
28
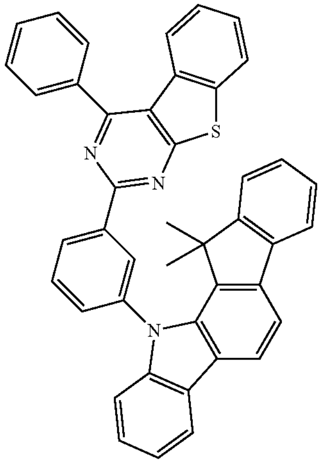
29
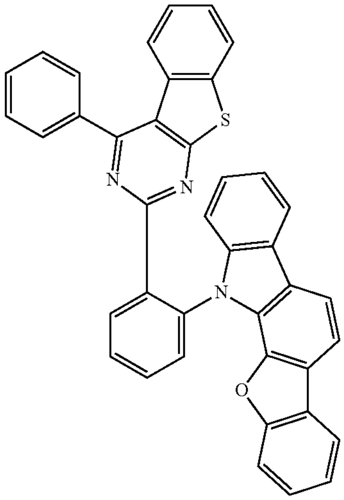
-continued
30
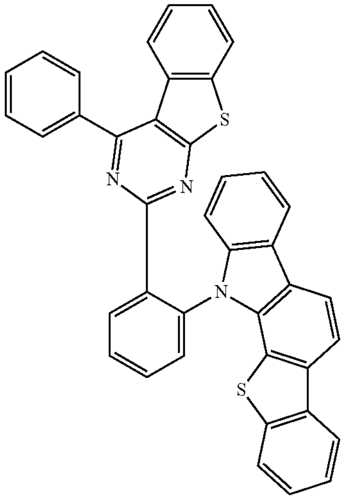
31
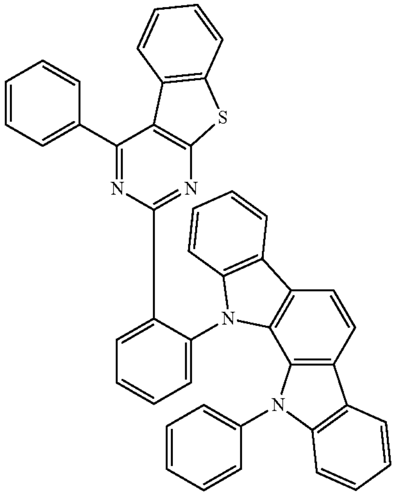
32
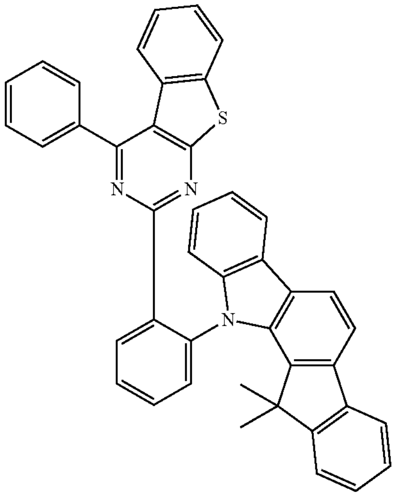

-continued
33
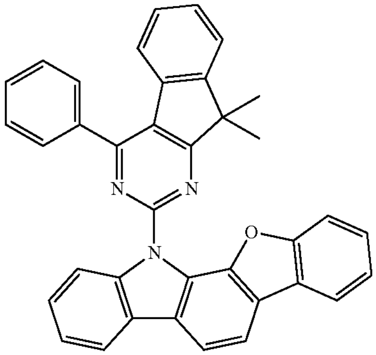
34
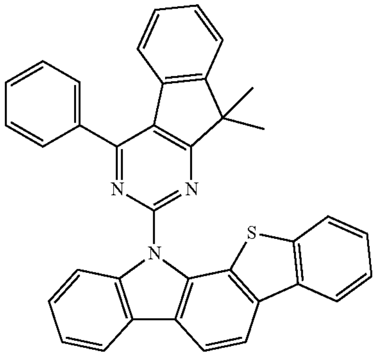
35
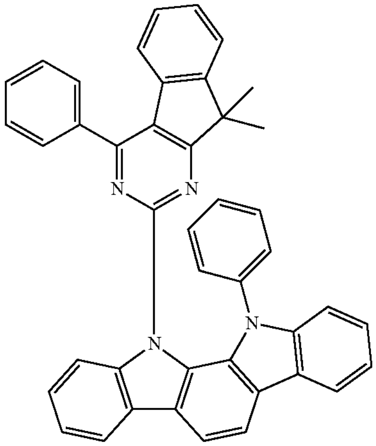
36
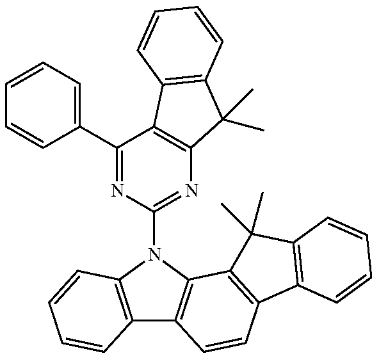
-continued
37
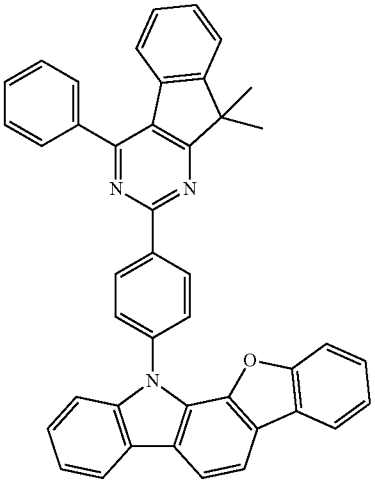
38
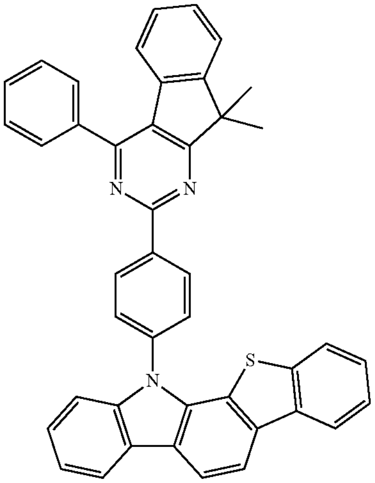
39
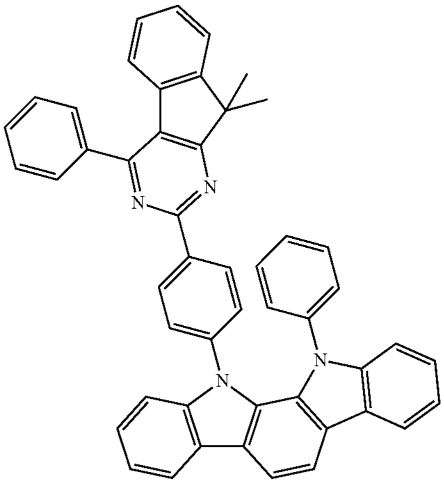

-continued
40
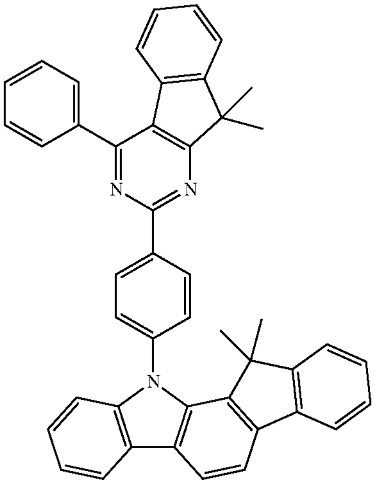
41
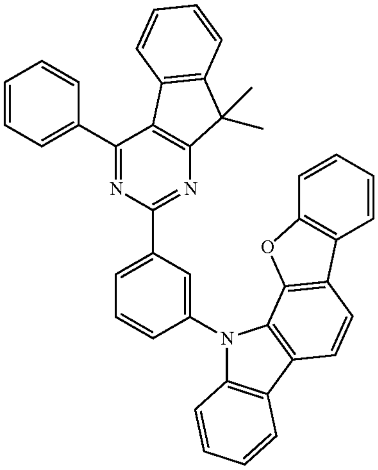
42
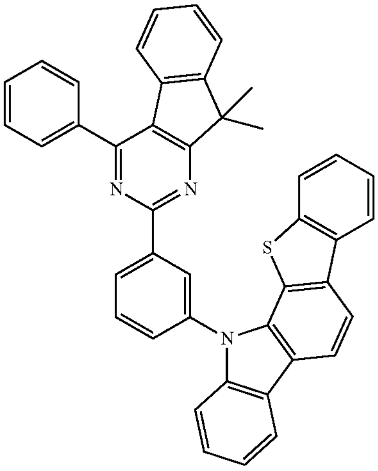
-continued
43
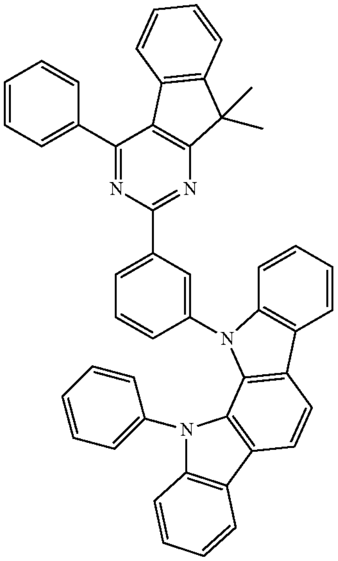
44
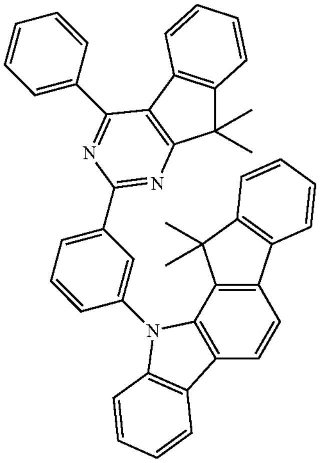
45
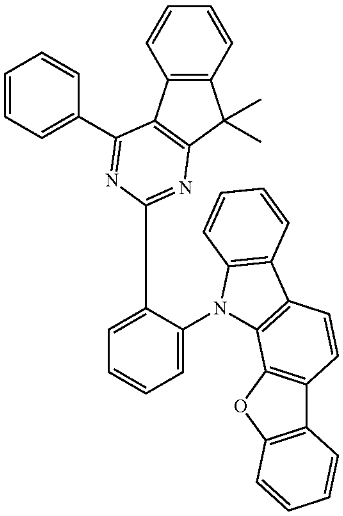

46
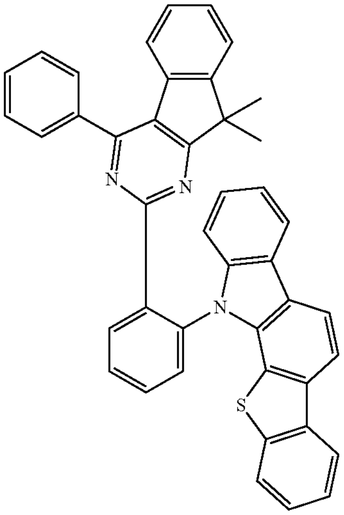
47
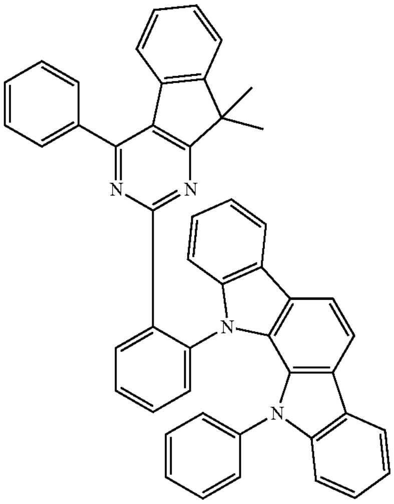
48
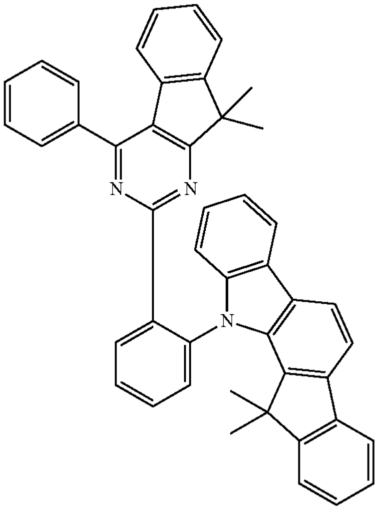
49
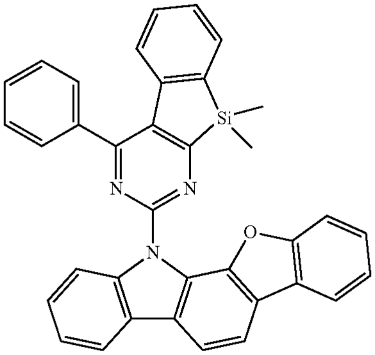
50
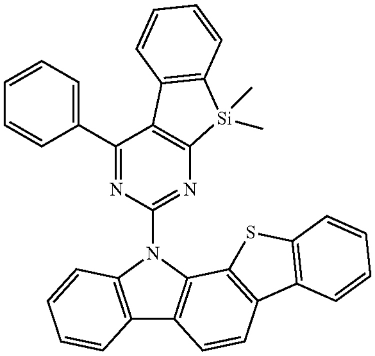
51
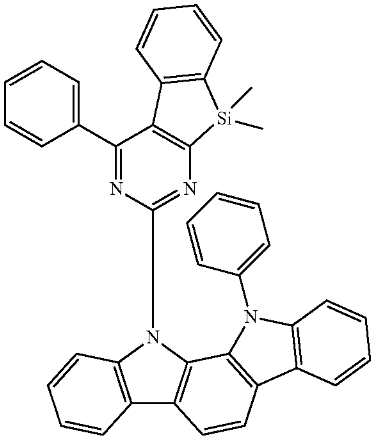
52
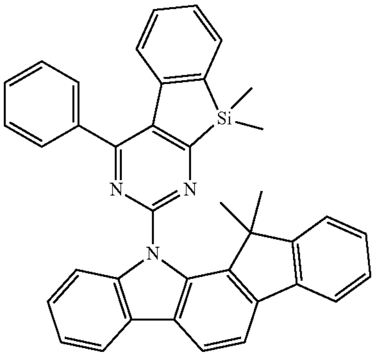

-continued
53
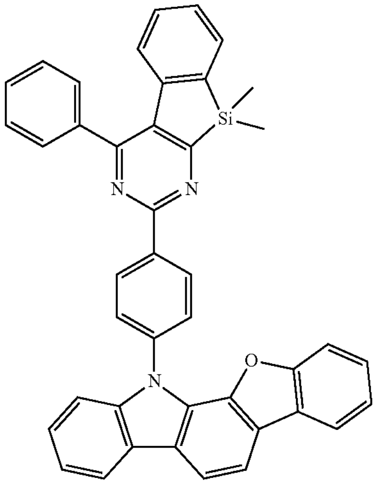
54
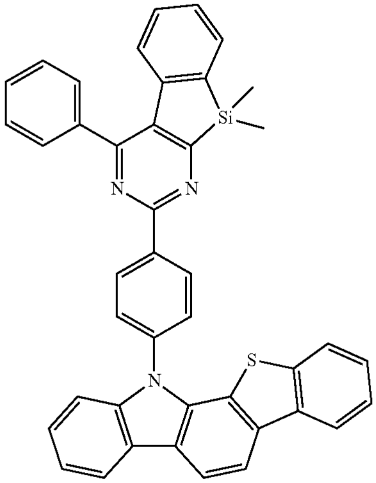
55
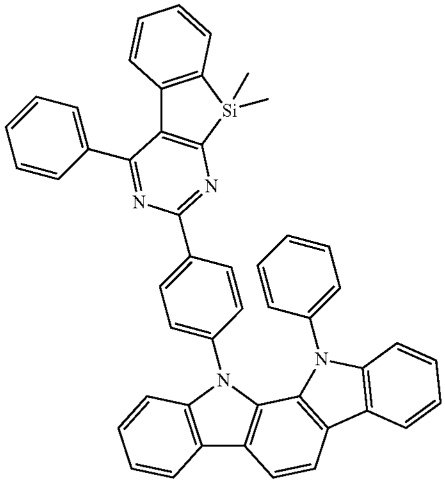
-continued
56
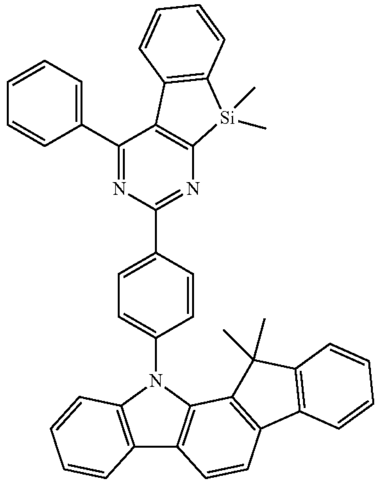
57
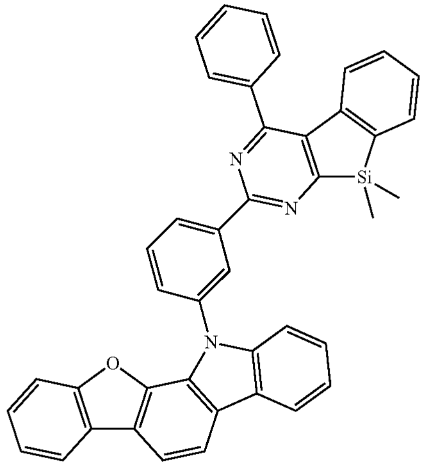
58
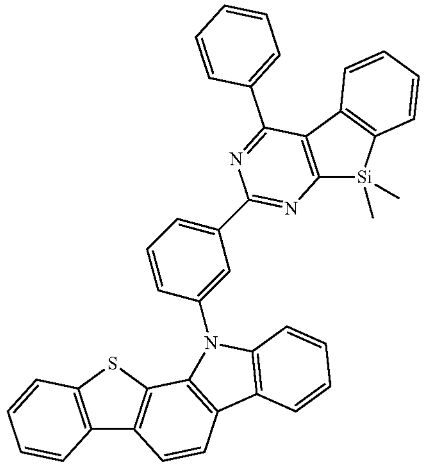

59
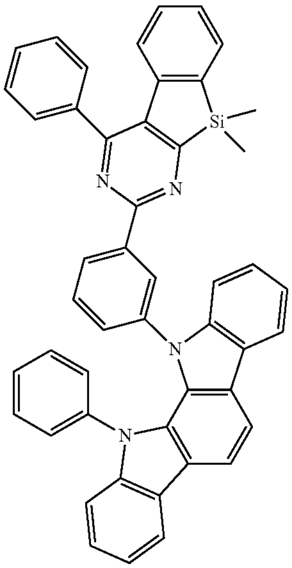
60
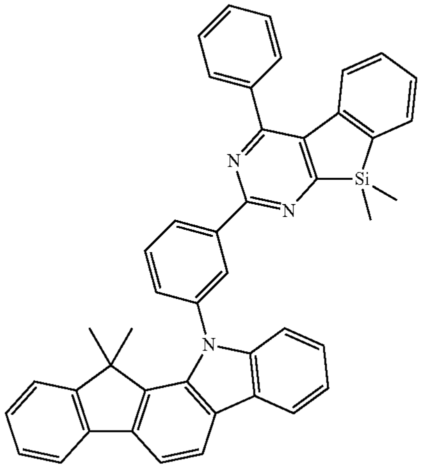
61
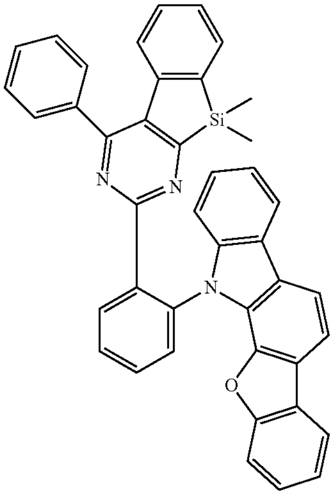
62
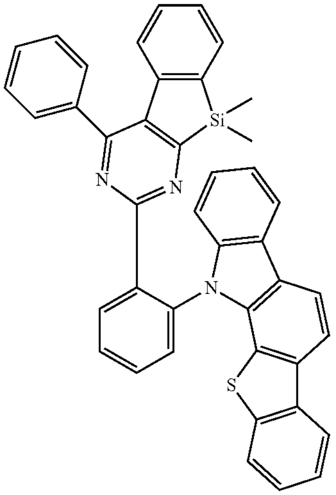
63
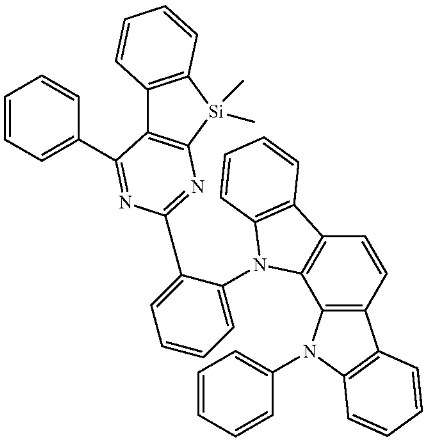
64
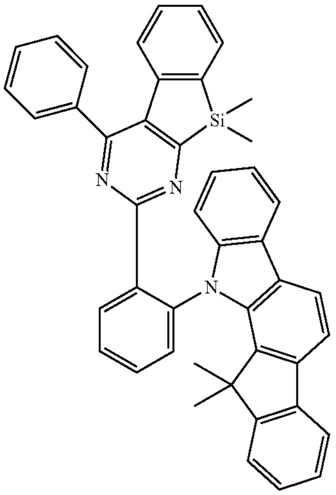

65
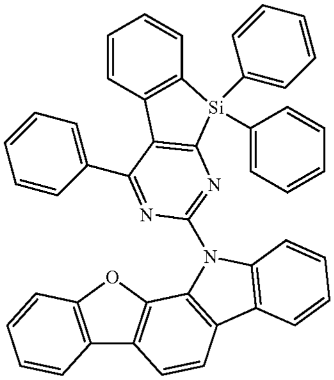
66
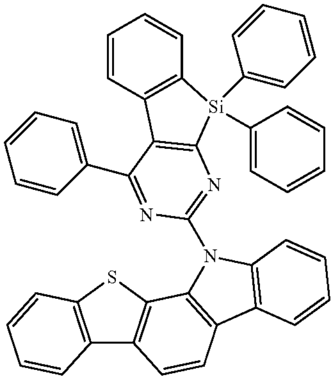
67
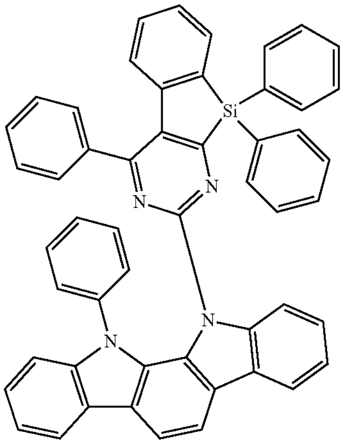
68
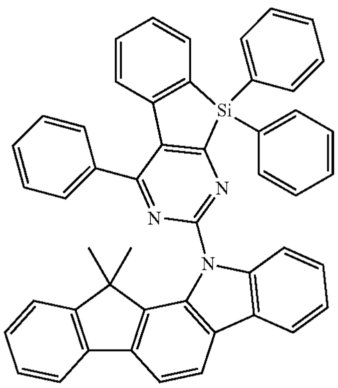
69
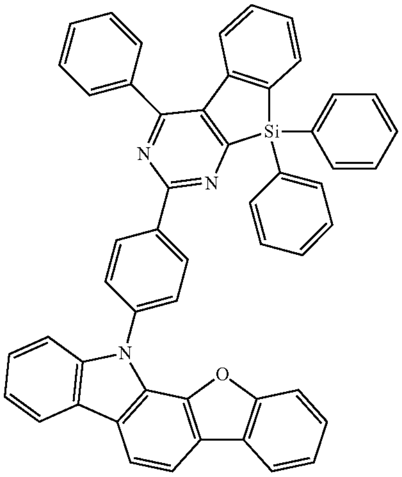
70
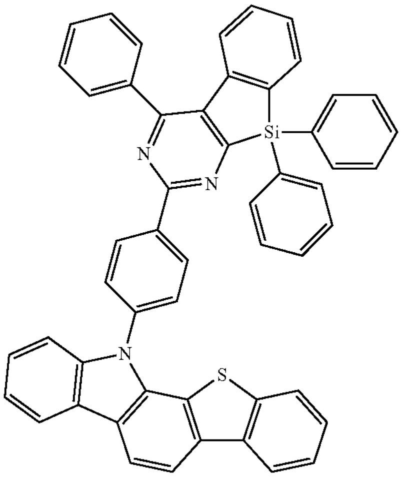
71
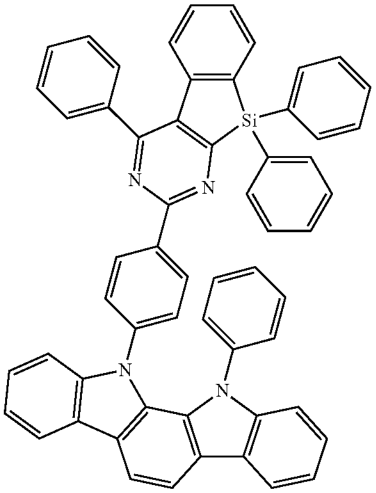

-continued
72
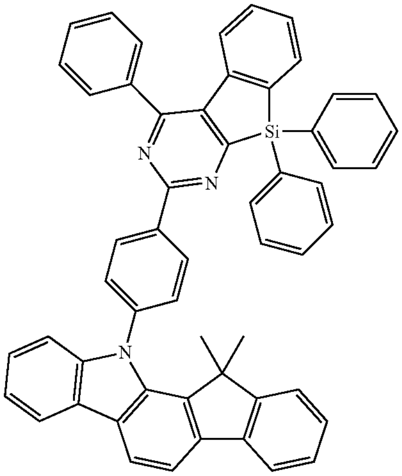
73
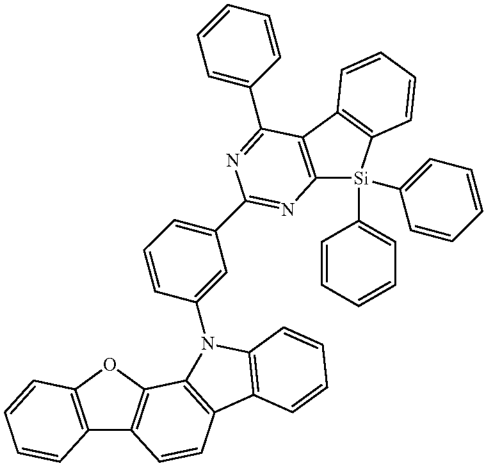
74
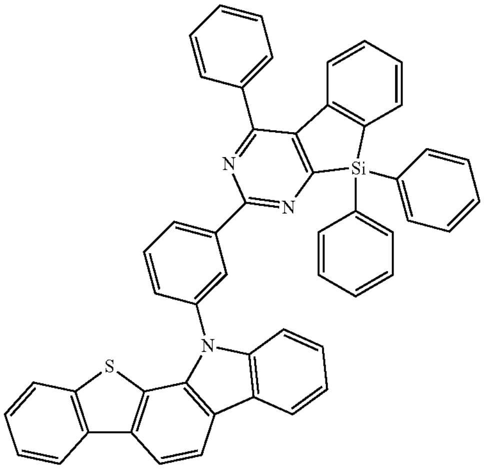
-continued
75
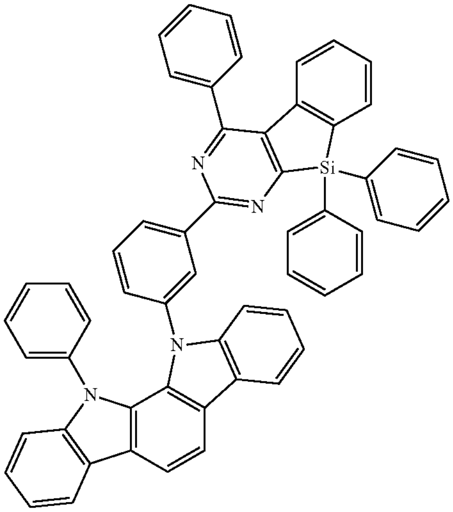
76
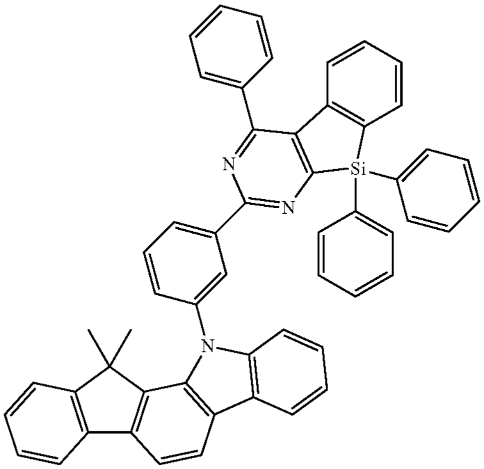
77
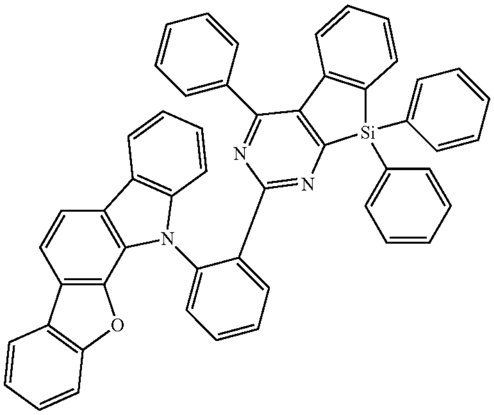

-continued
78
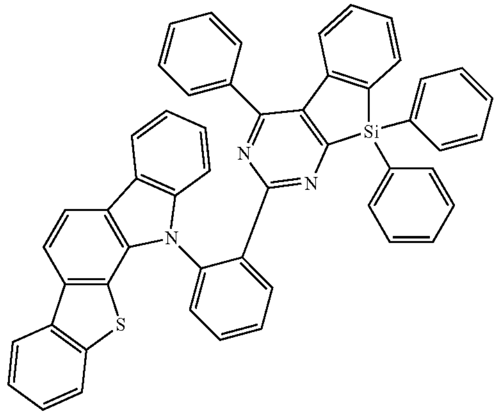
79
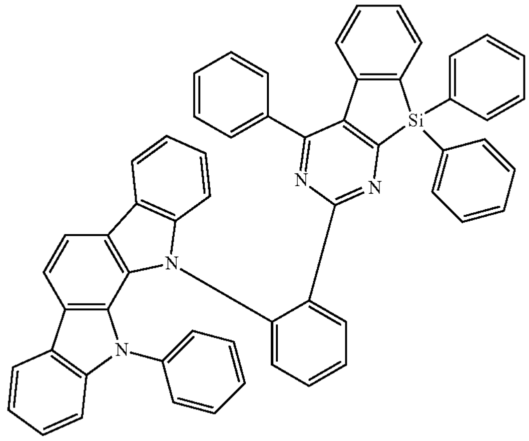
80
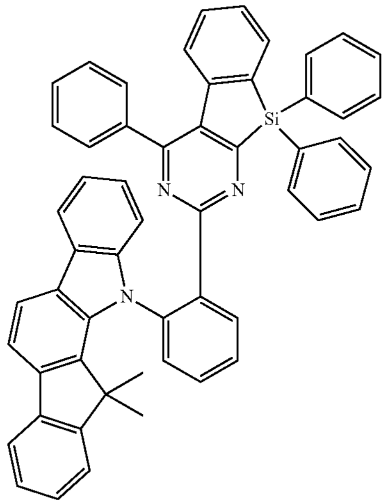
-continued
81
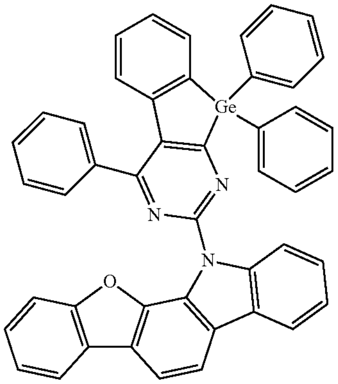
82
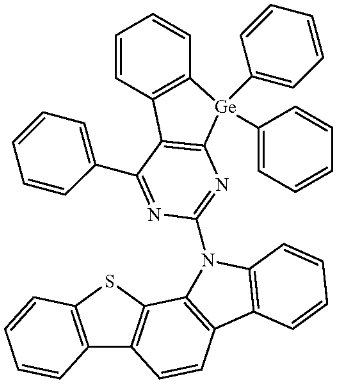
83
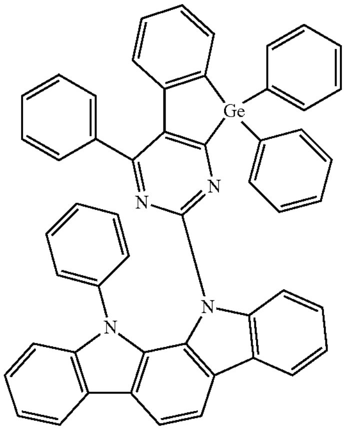
84
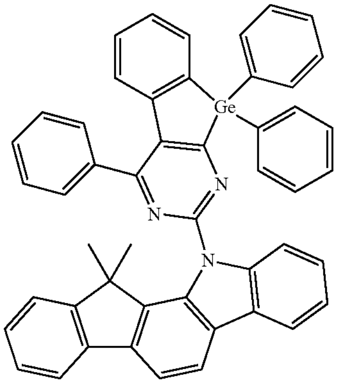

85
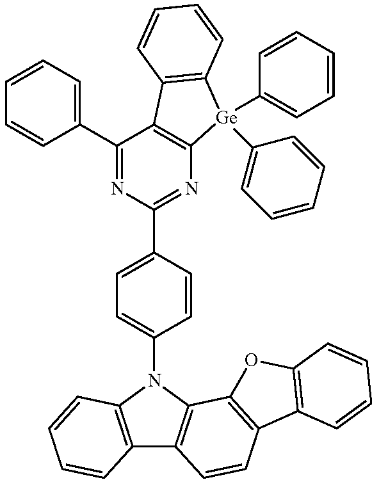
86
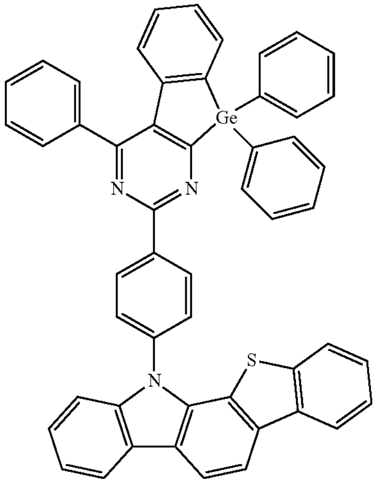
87
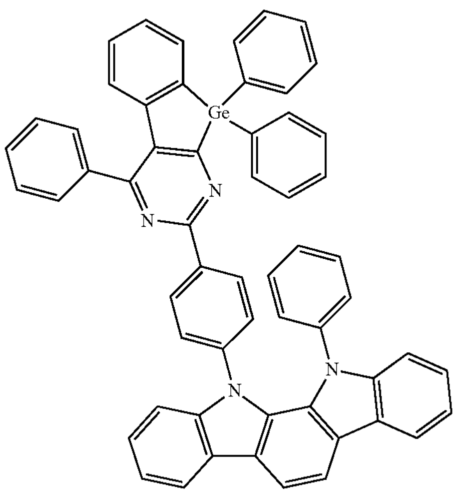
88
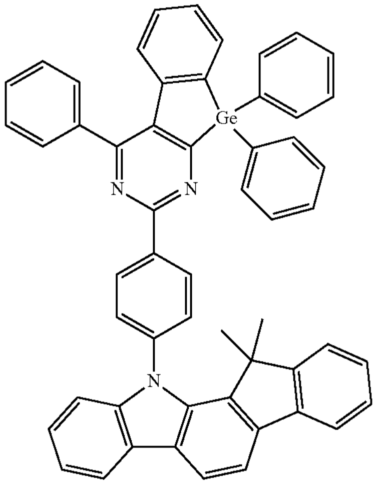
89
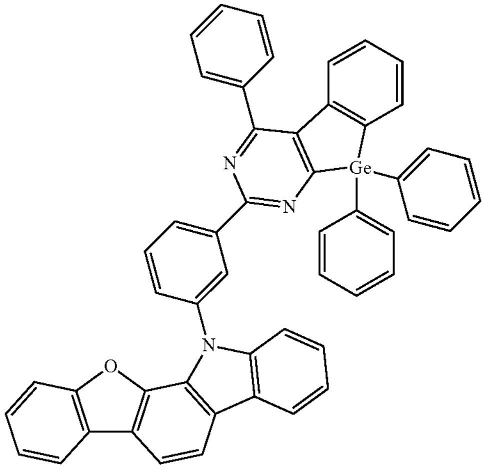
90
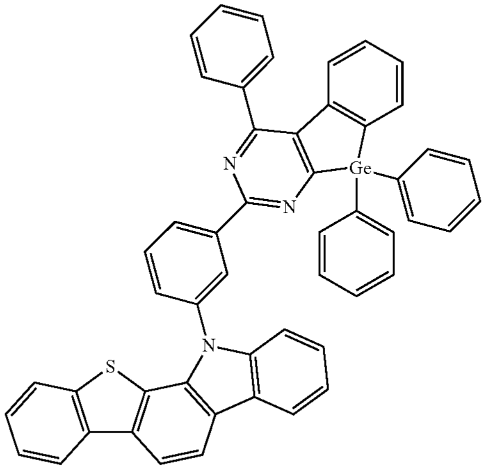

-continued
91
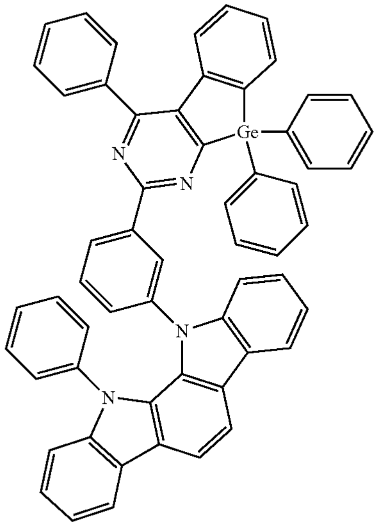
92
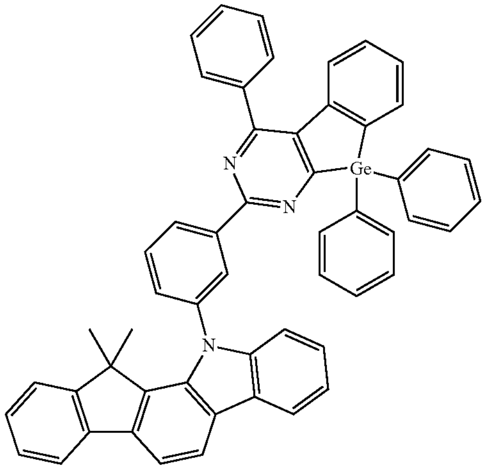
93
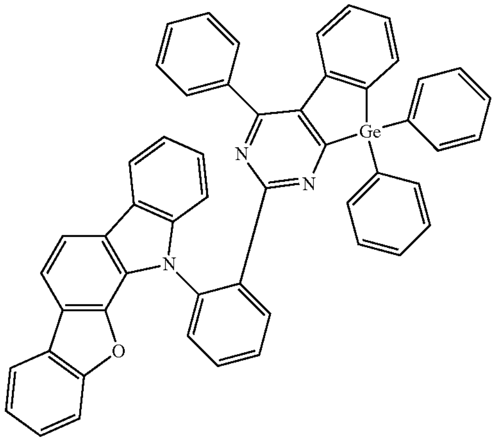
-continued
94
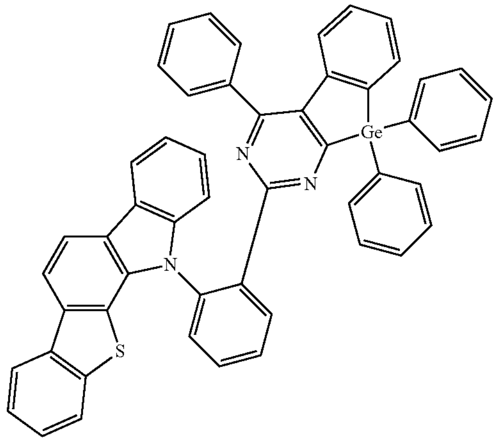
95
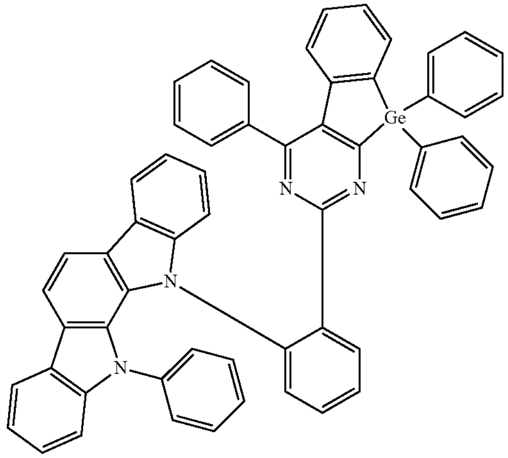
96
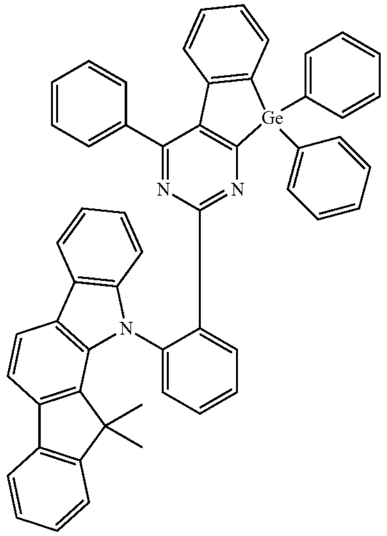

-continued
97
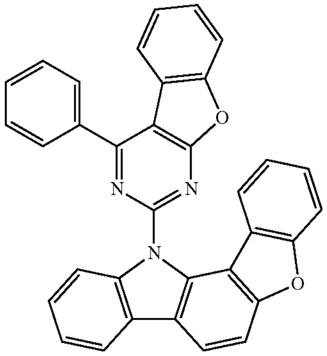
98
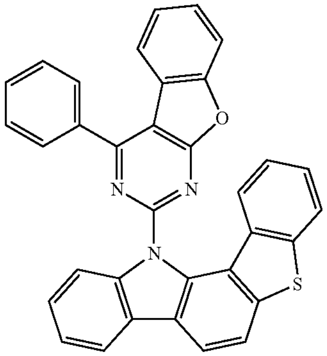
99
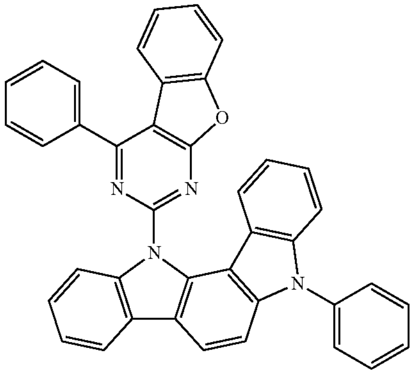
100
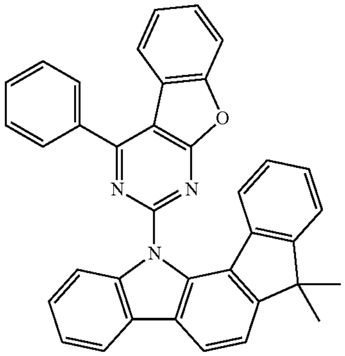
-continued
101
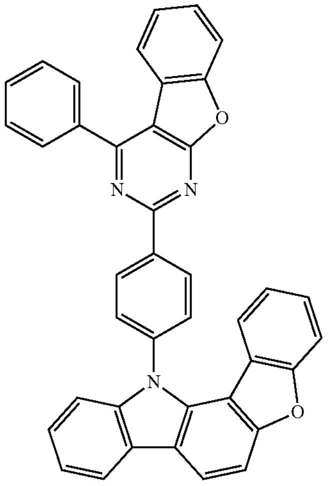
102
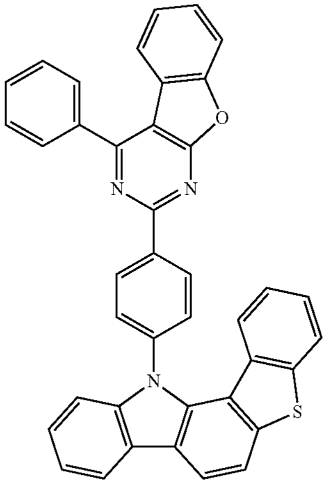
103
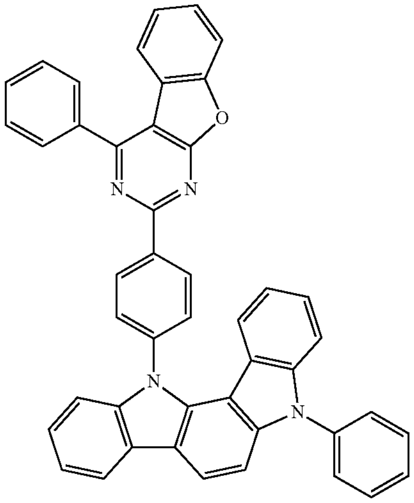

-continued
104
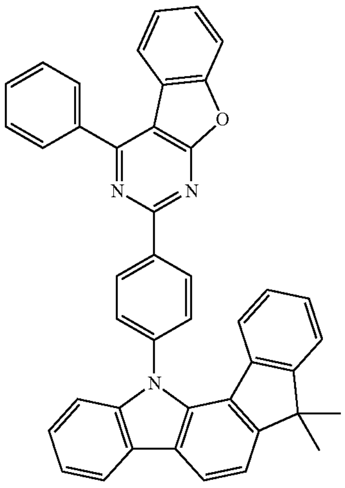
105
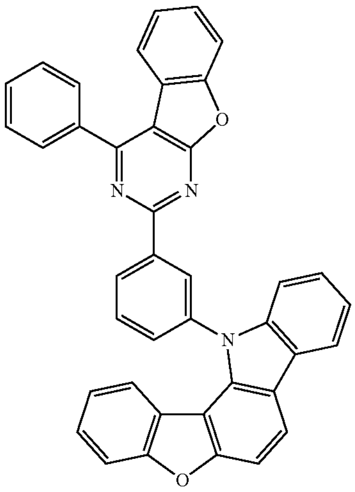
106
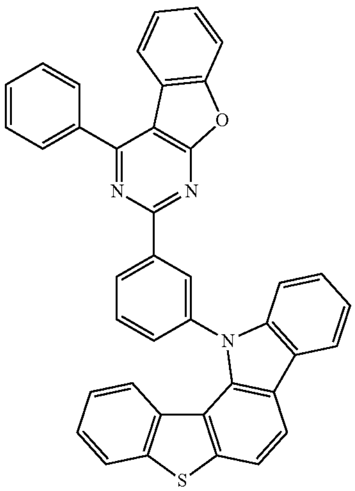
-continued
107
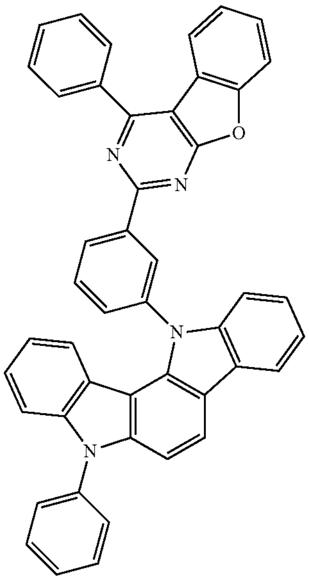
108
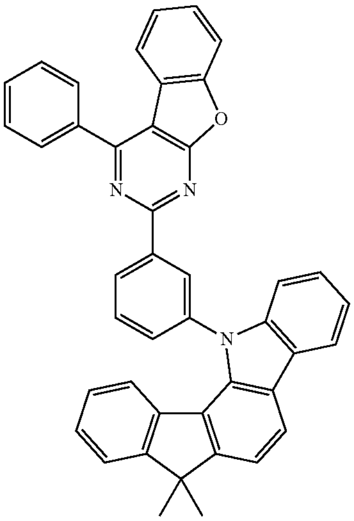
109
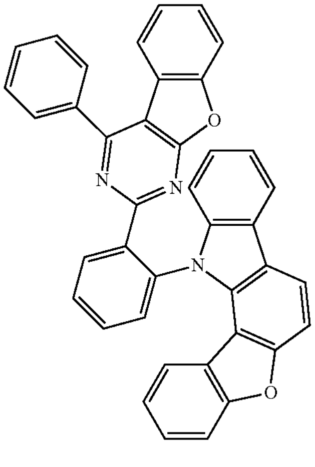

-continued
110
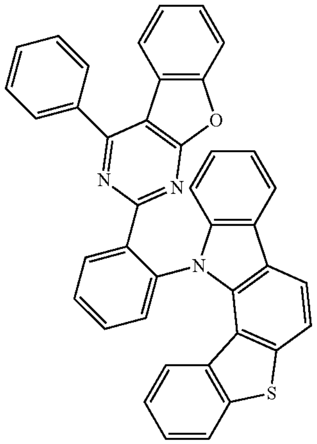
111
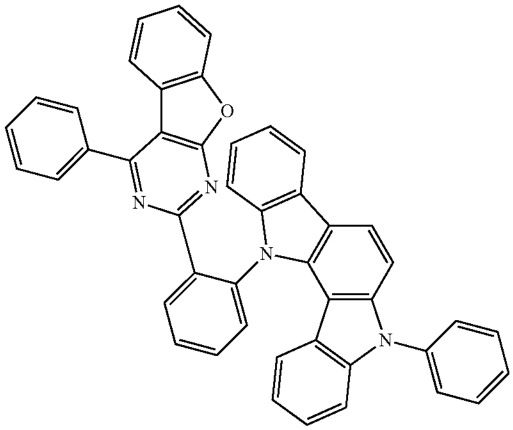
112
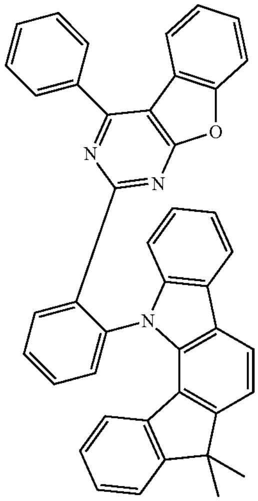
-continued
113
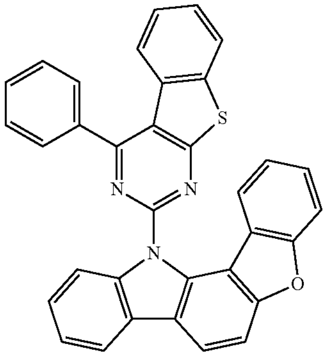
114
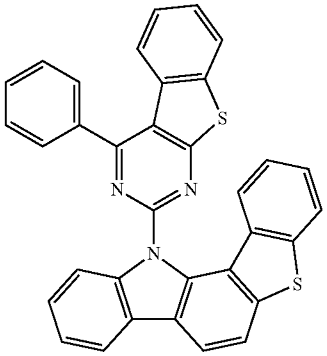
115
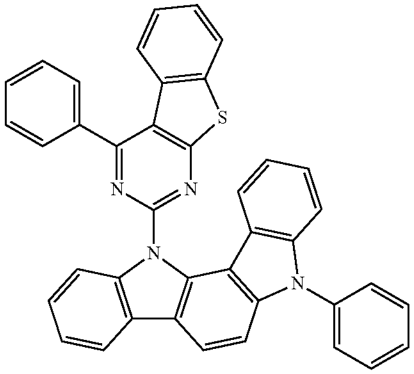
116
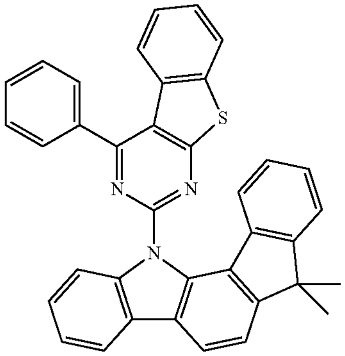

-continued
117
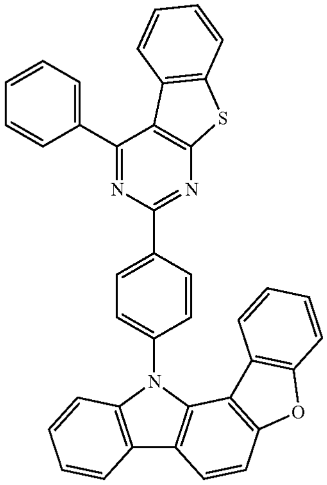
118
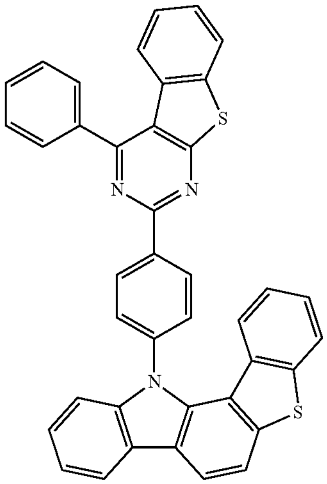
119
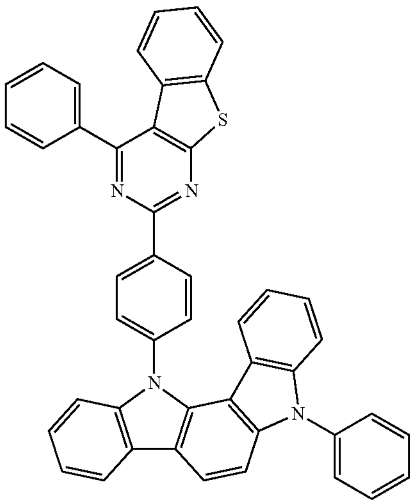
-continued
120
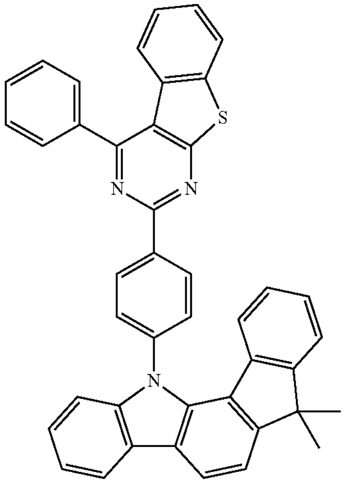
121
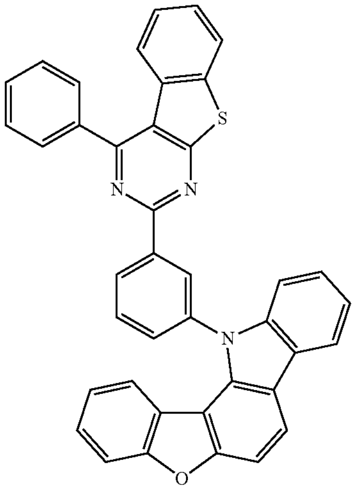
122
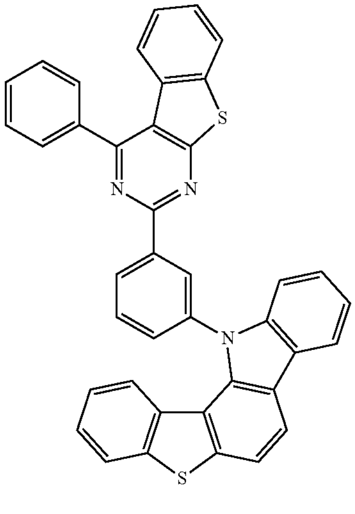

-continued
123
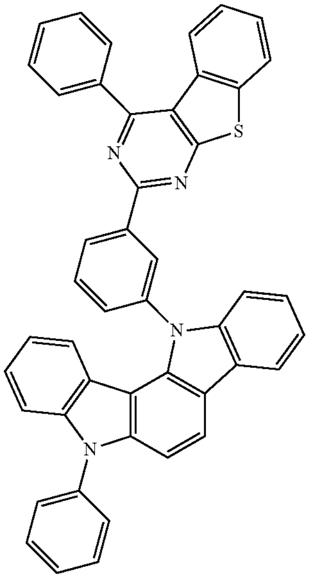
124
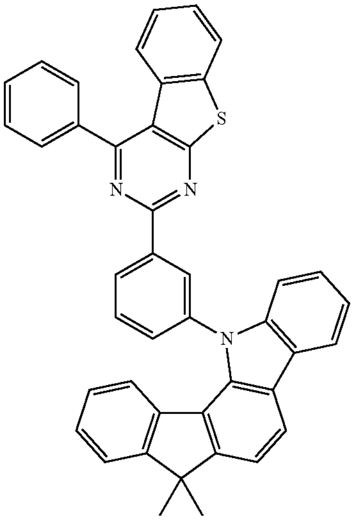
125
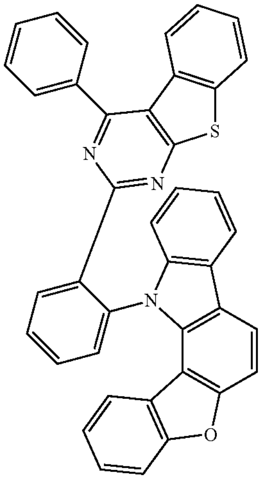
-continued
126
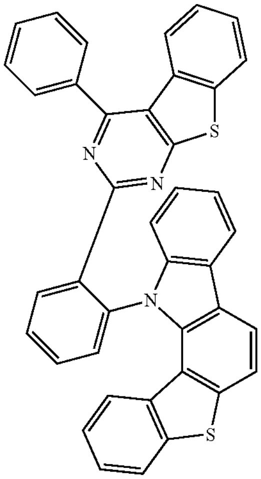
127
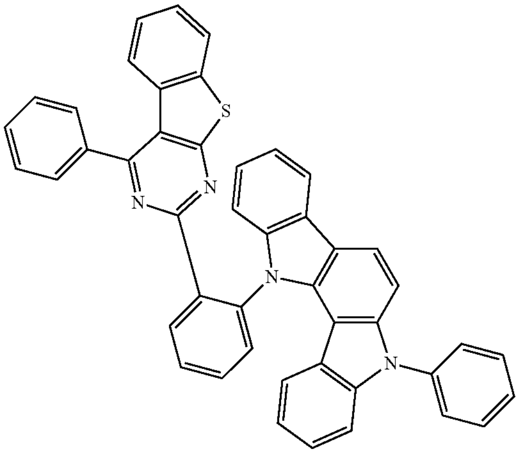
128
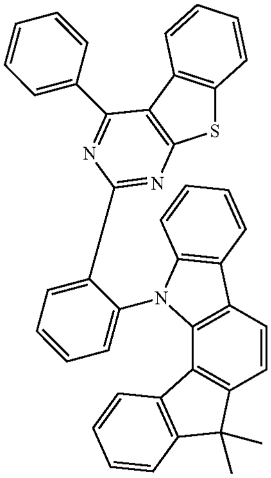

129
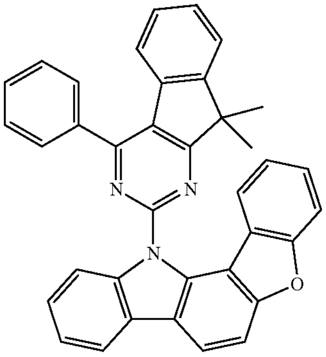
130
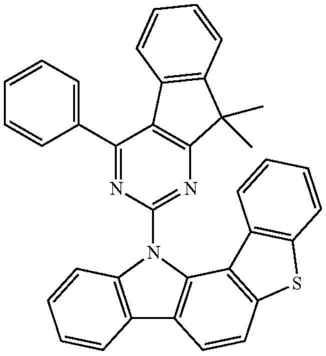
131
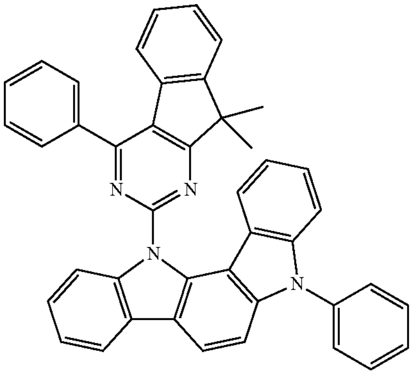
132
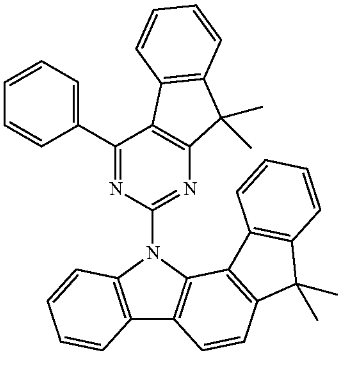
133
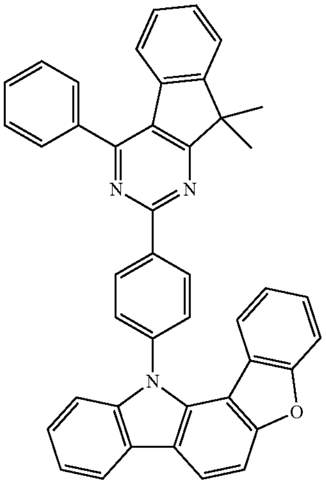
134
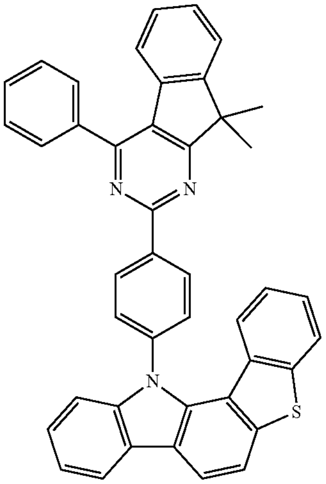
135
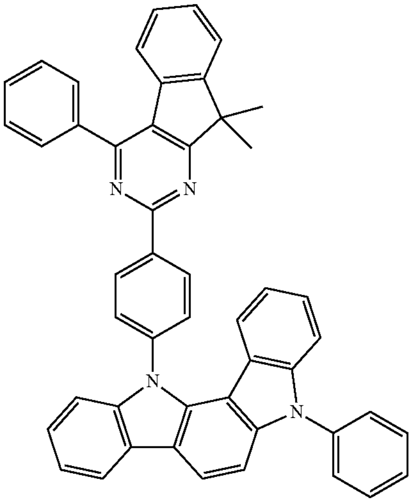

-continued
136
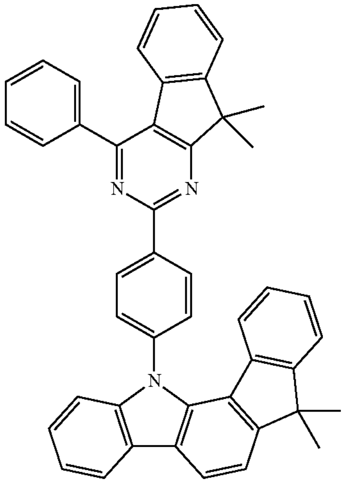
137
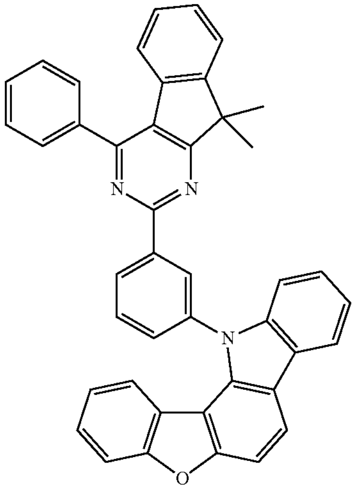
138
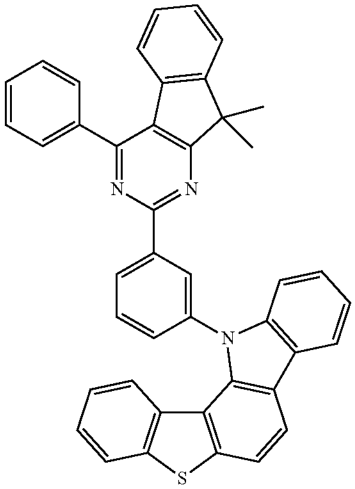
-continued
139
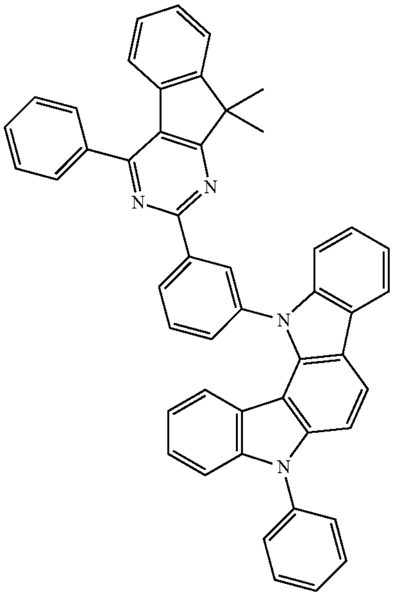
140
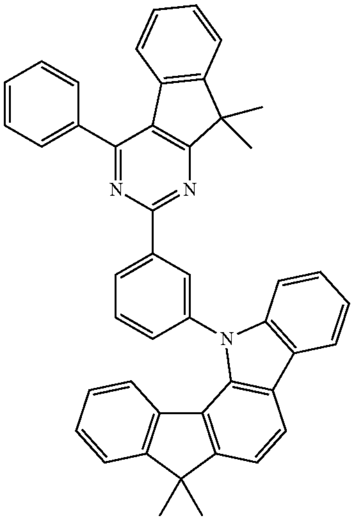
141
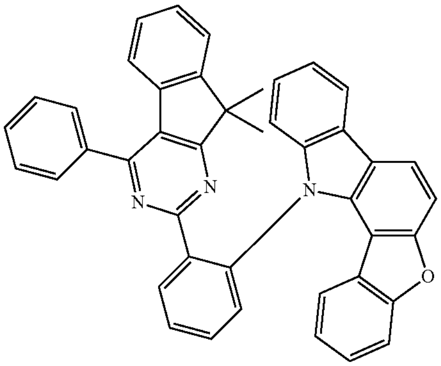

-continued
142
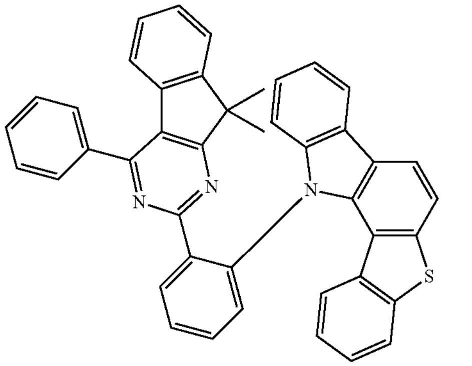
143
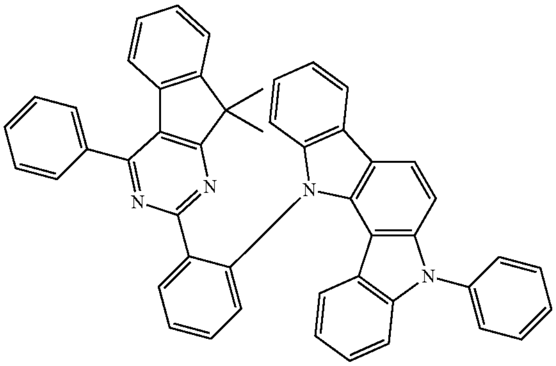
144
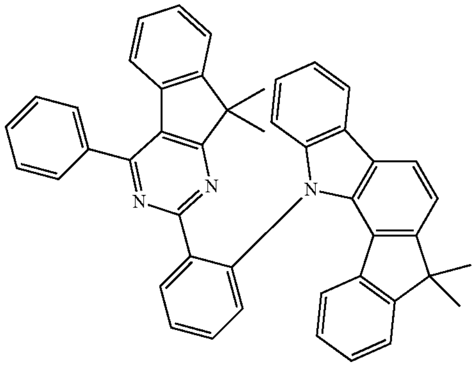
145
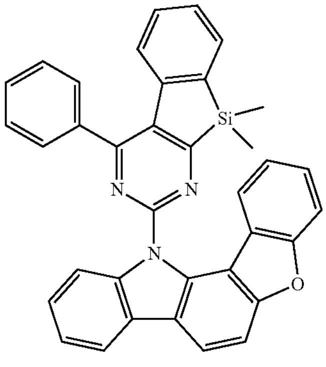
-continued
146
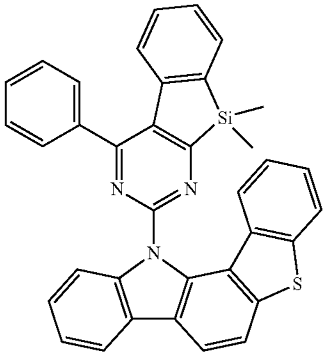
147
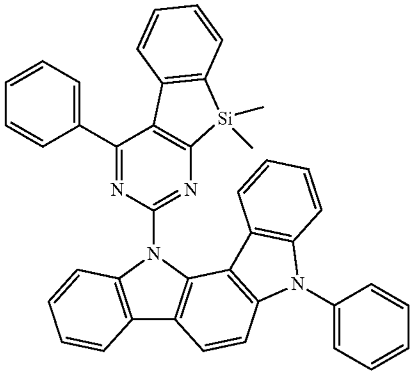
148
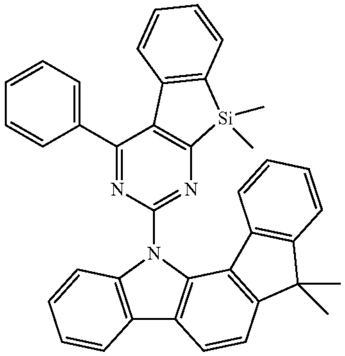
149
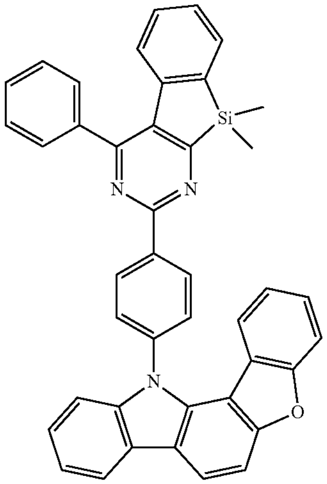

-continued
150
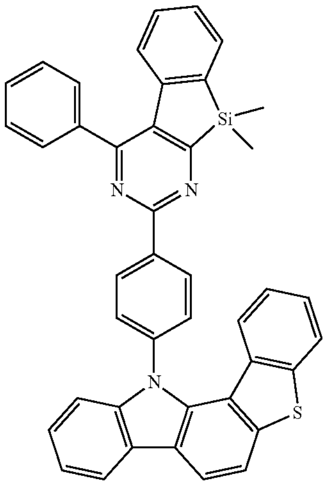
151
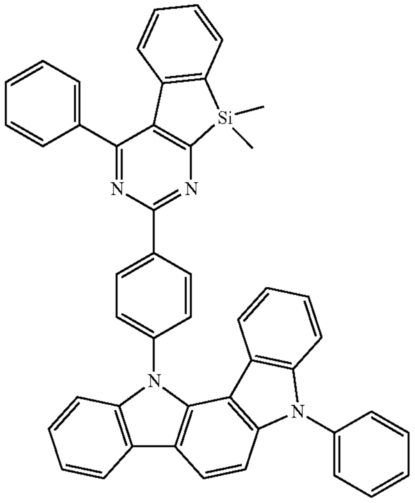
152
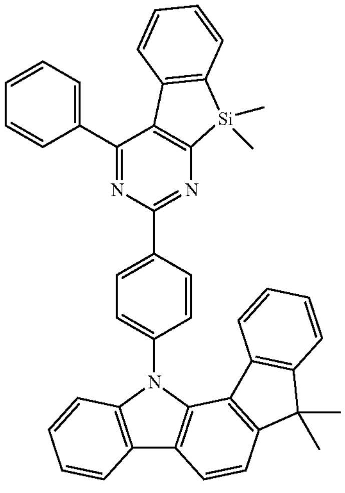
-continued
153
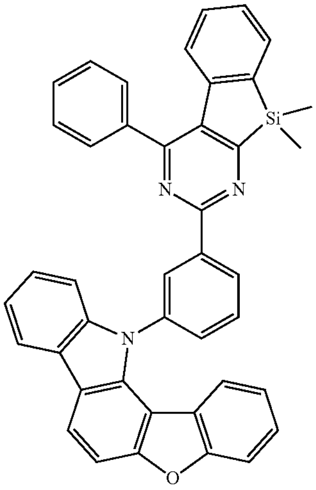
154
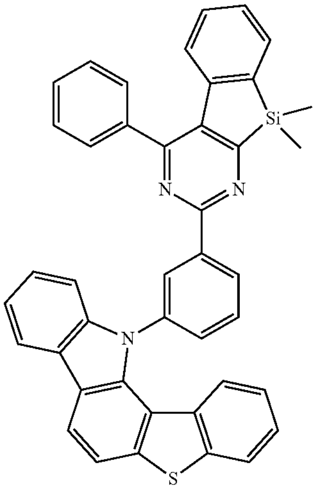
155
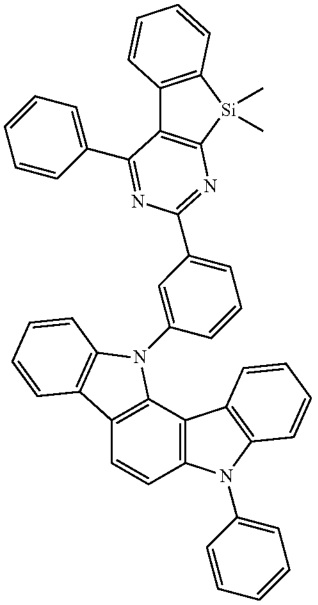

-continued
156
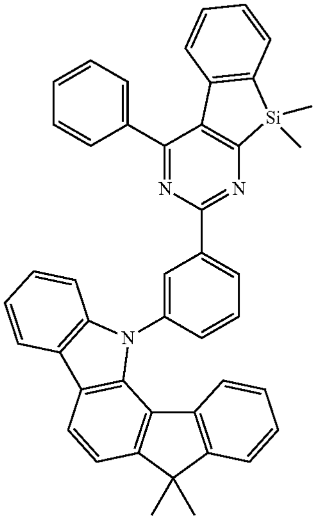
157
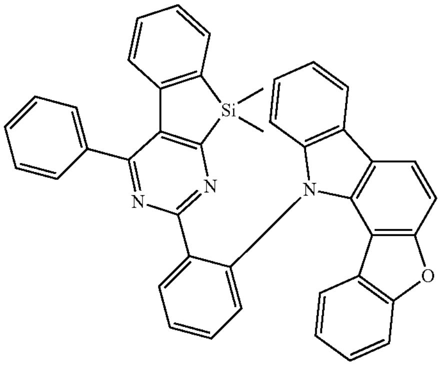
158
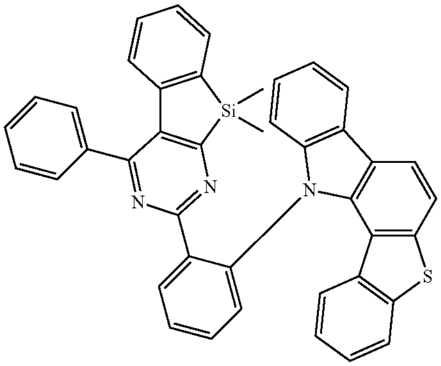
159
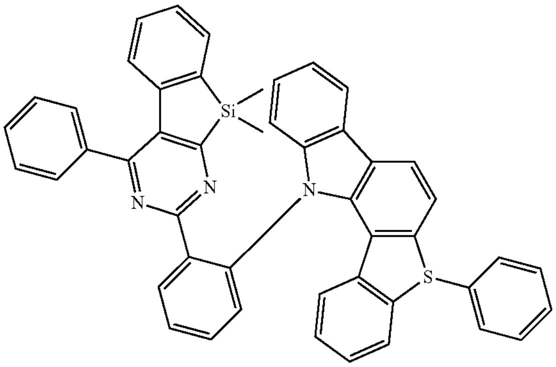
-continued
160
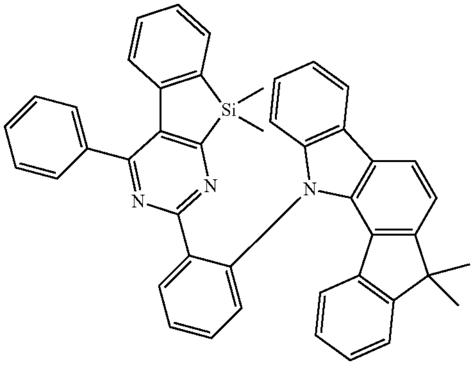
161
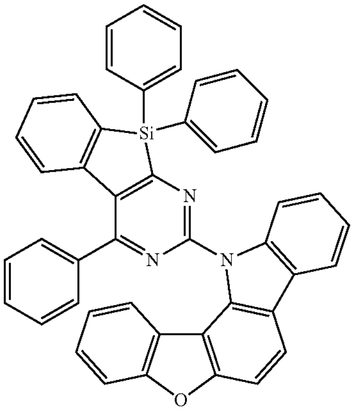
162
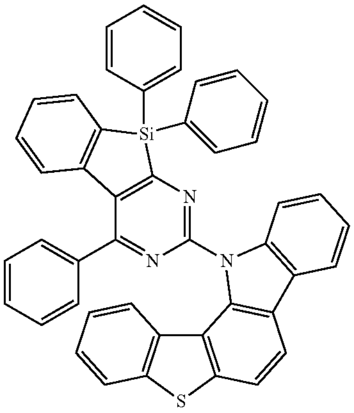

-continued
163
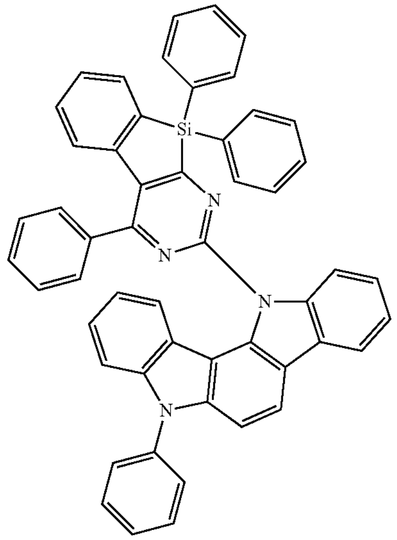
164
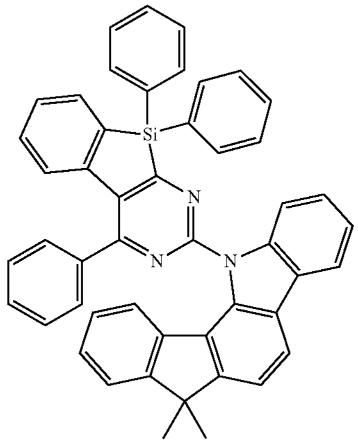
165
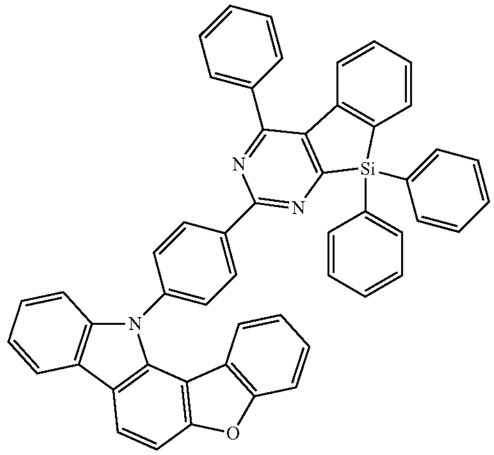
-continued
166
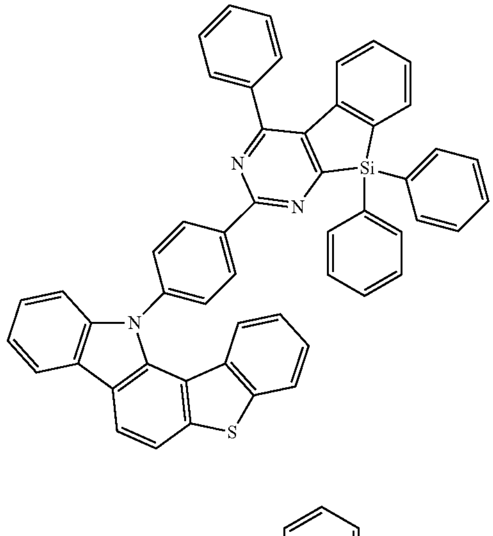
167
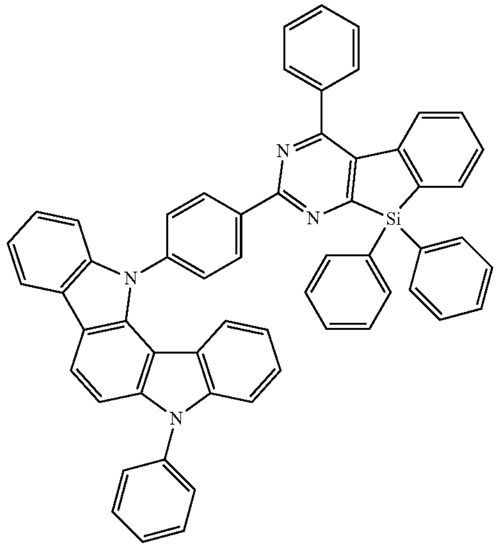
168
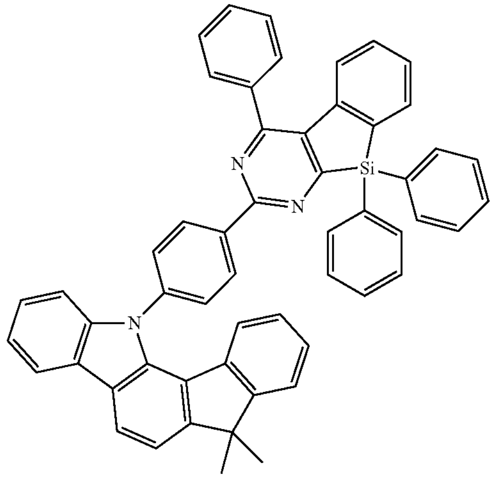

-continued
169
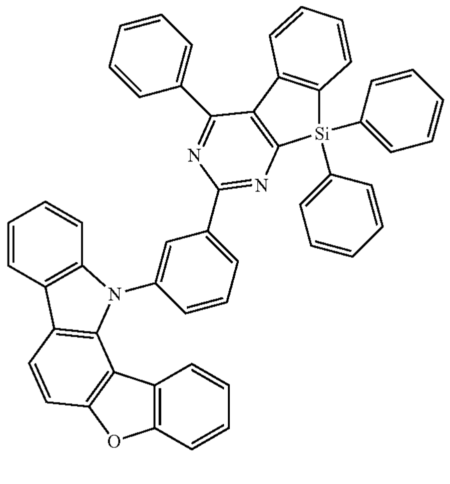
170
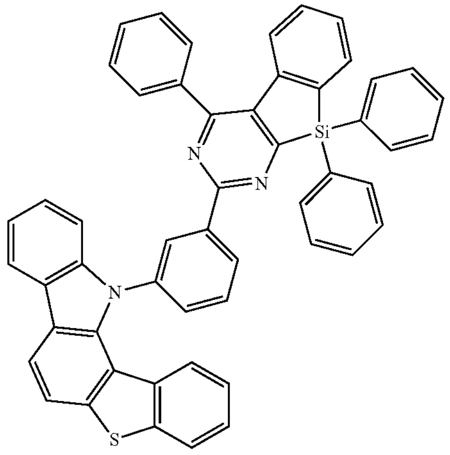
171
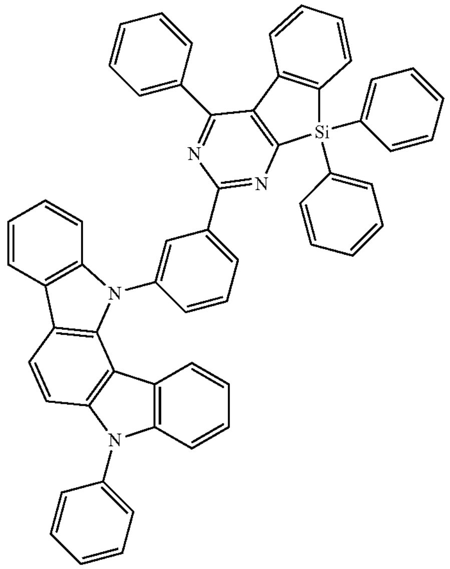
-continued
172
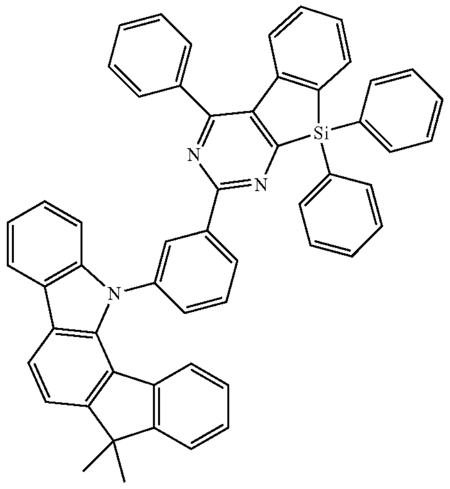
173
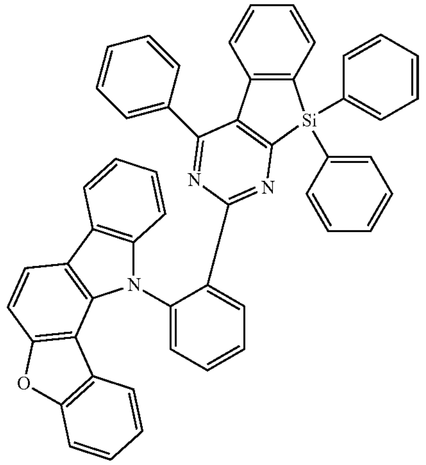
174
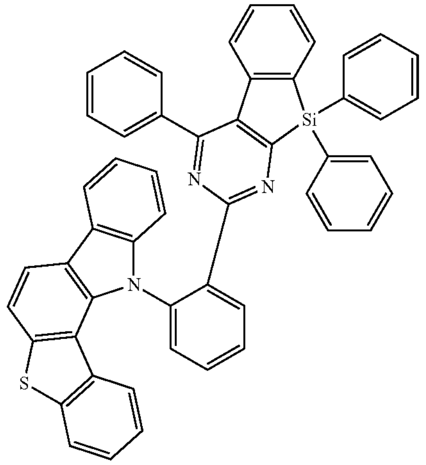

175
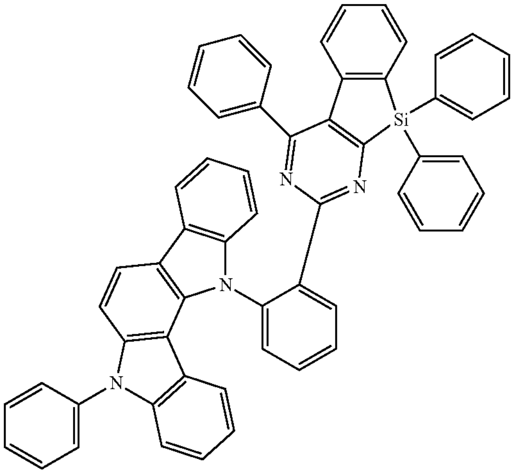
176
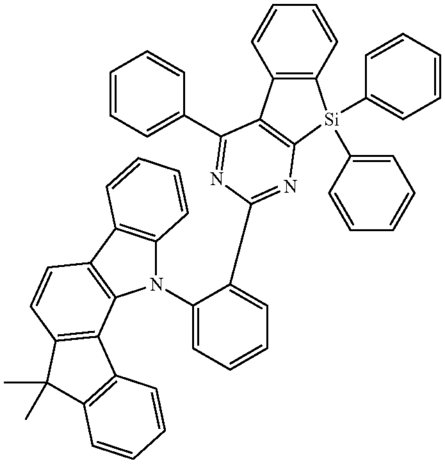
177
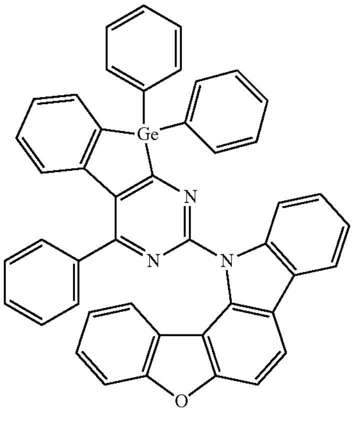
178
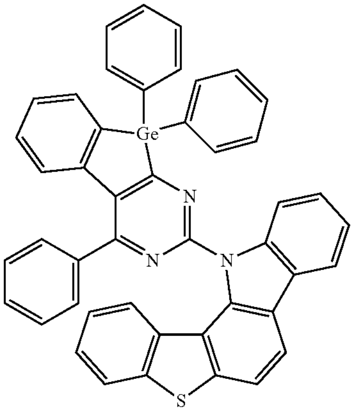
179
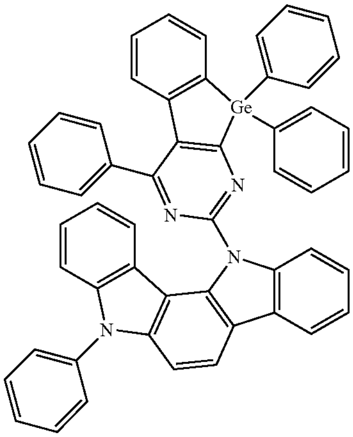
180
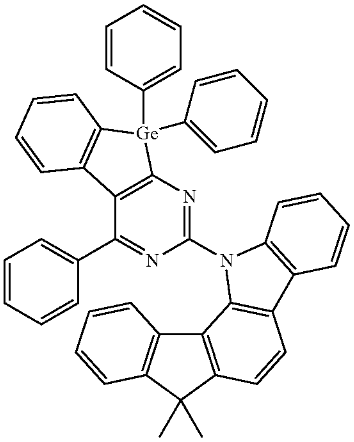

-continued
181
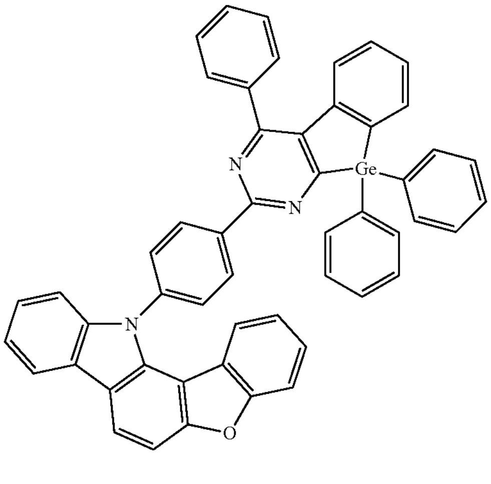
182
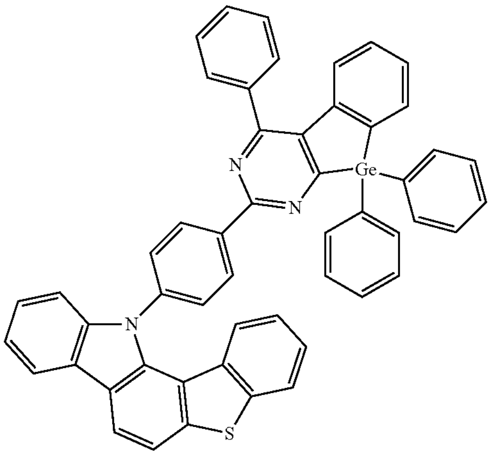
183
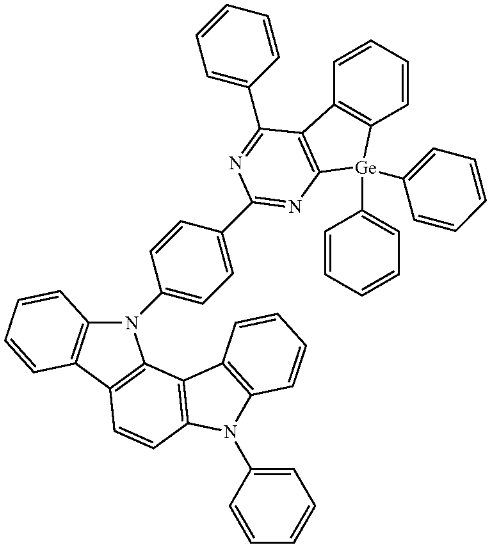
-continued
184
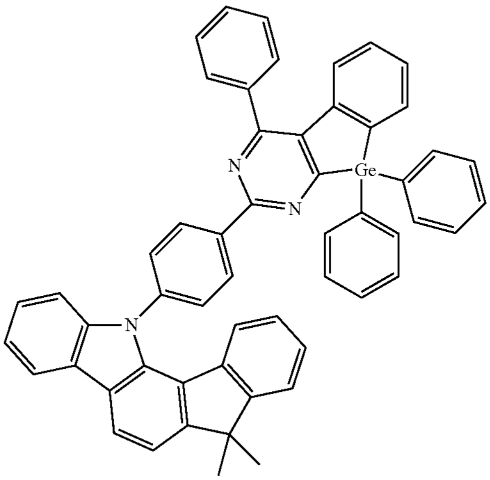
185
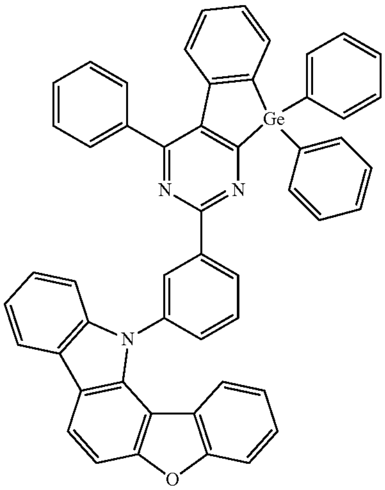
186
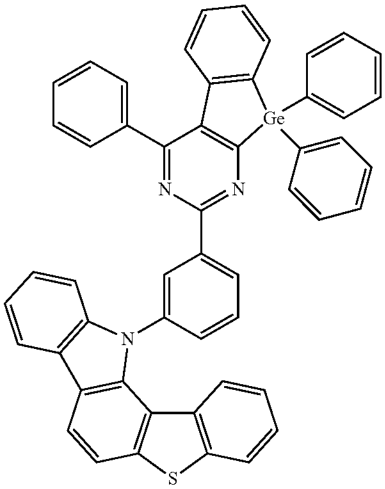

-continued
187
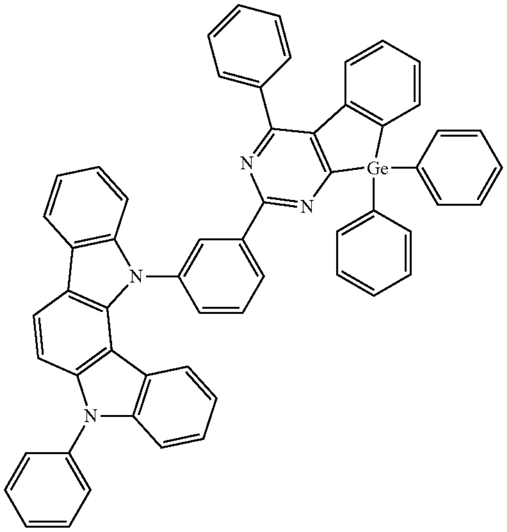
188
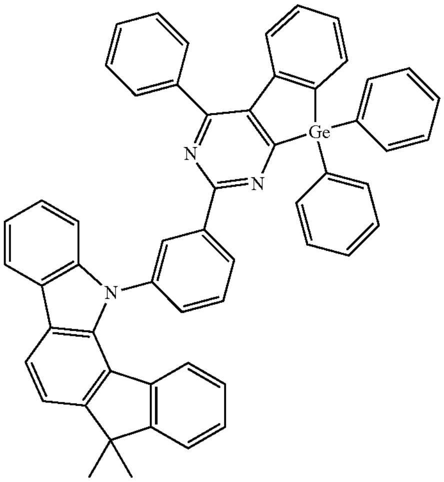
189
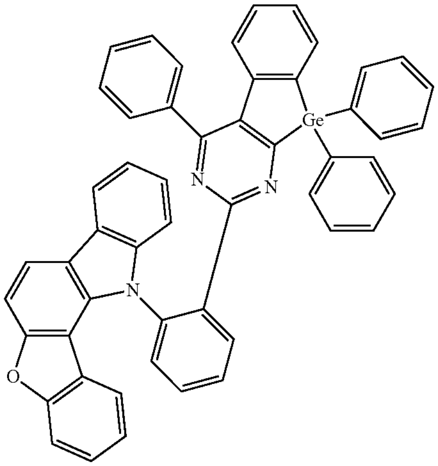
-continued
190
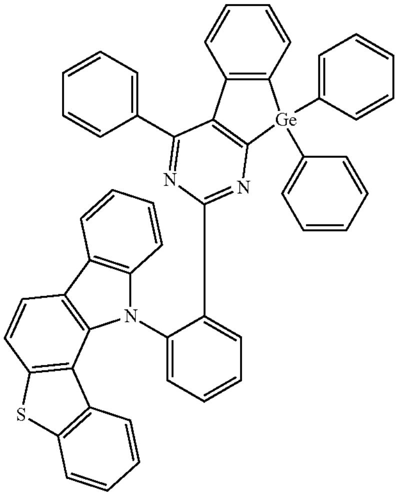
191
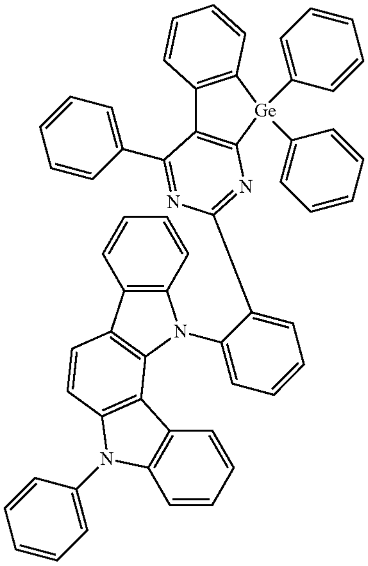
192
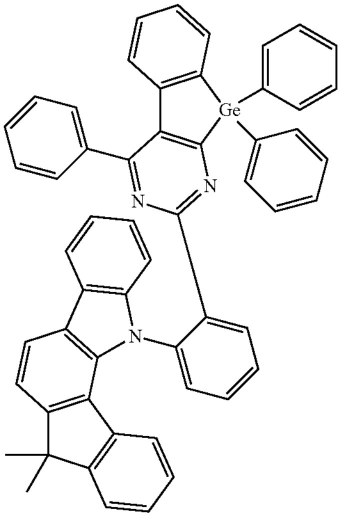

-continued
193
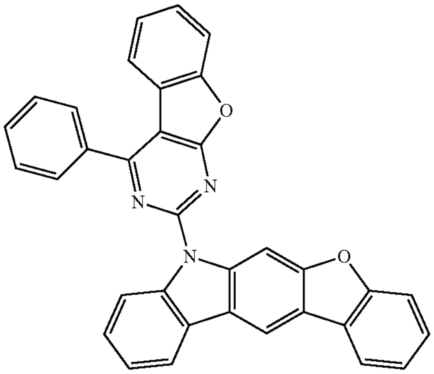
194
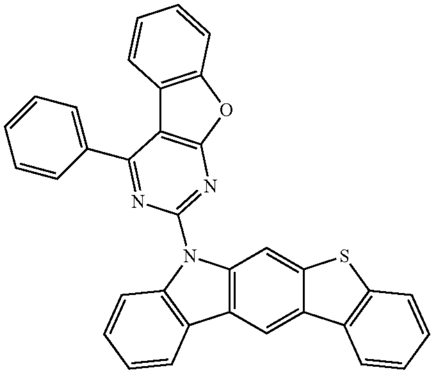
195
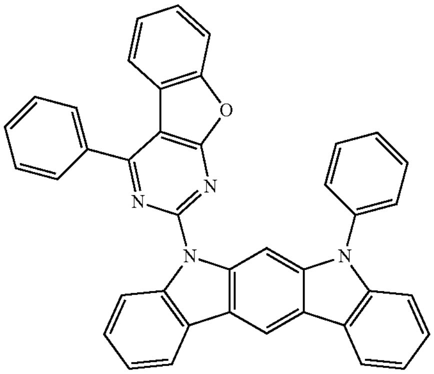
196
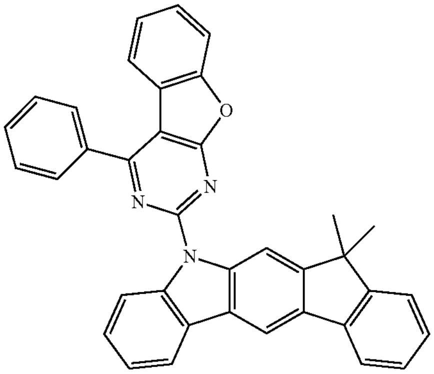
-continued
197
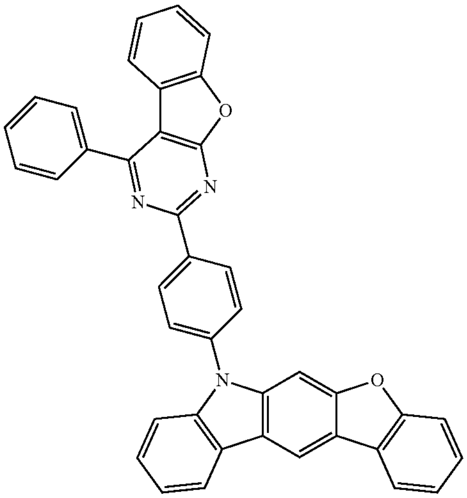
198
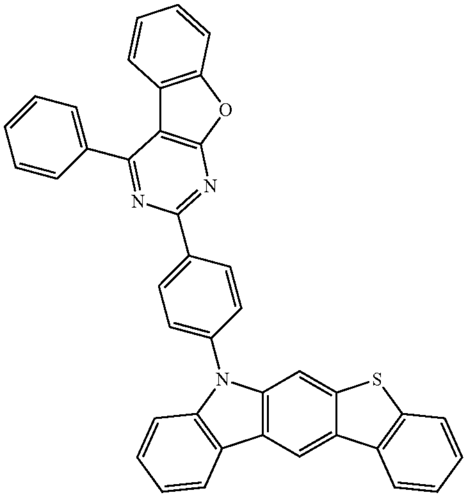
199
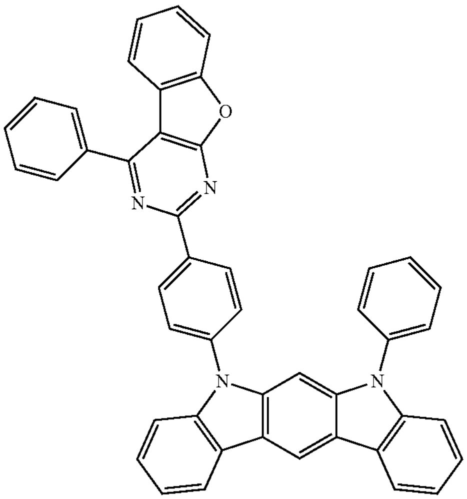

-continued
200
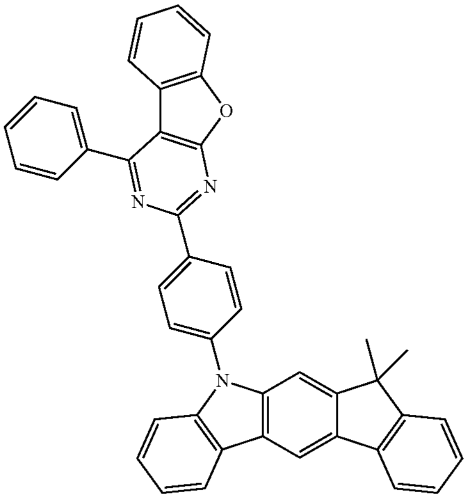
201
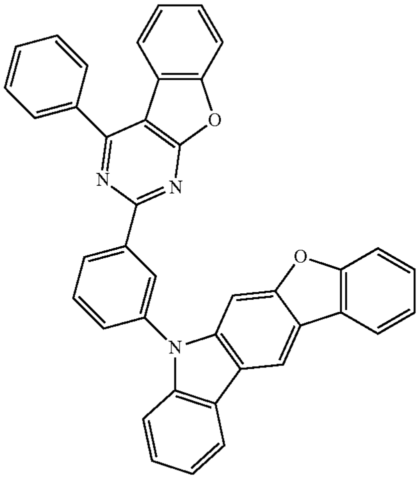
202
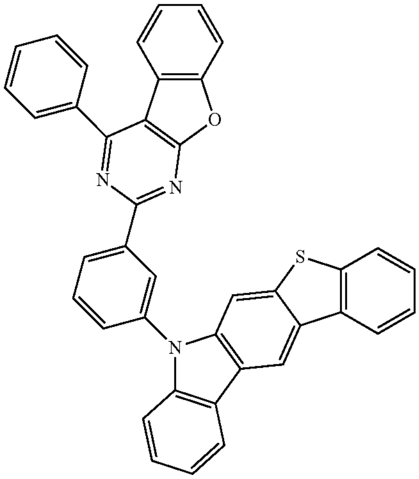
-continued
203
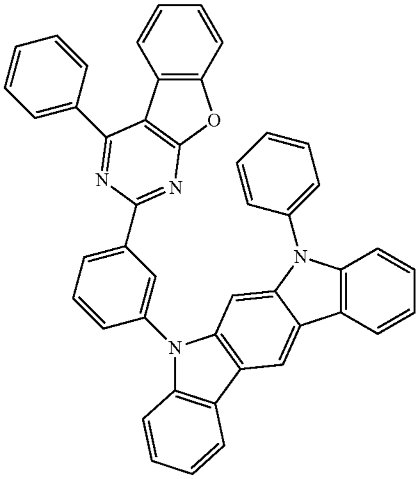
204
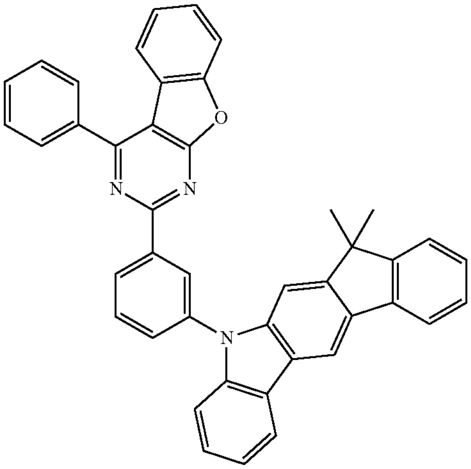
205
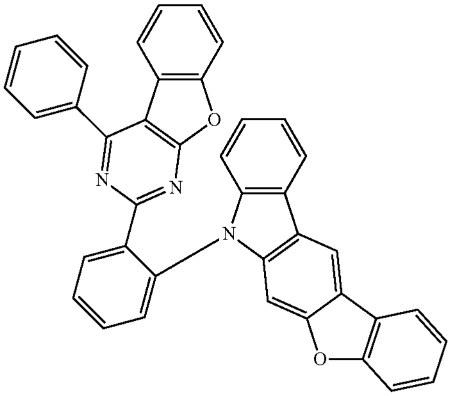

-continued
206
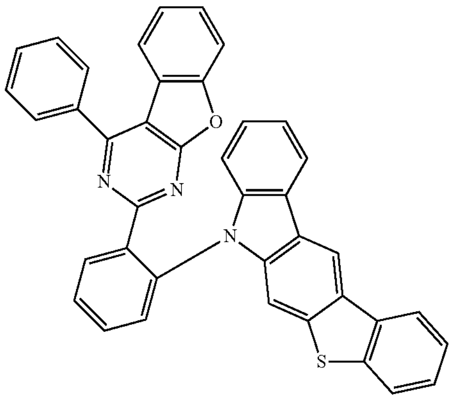
207
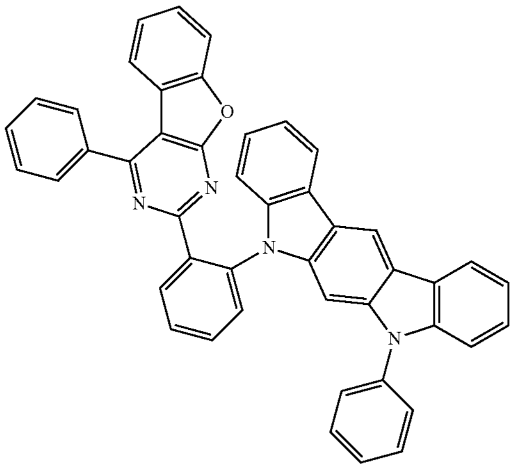
208
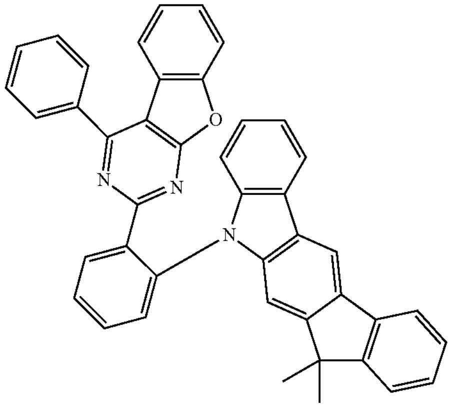
209
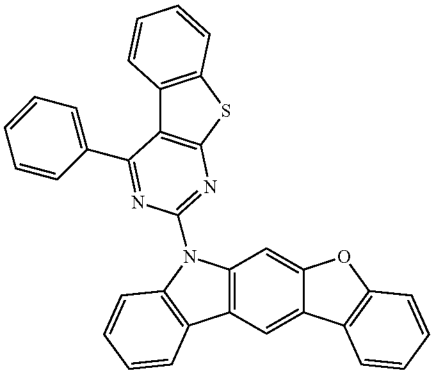
210
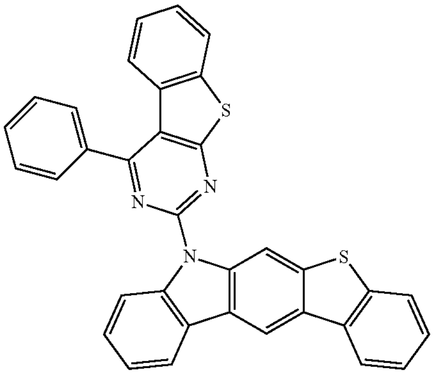
211
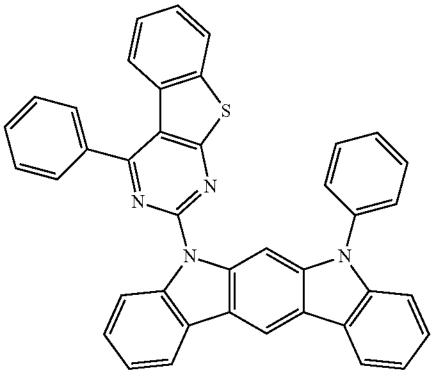
212
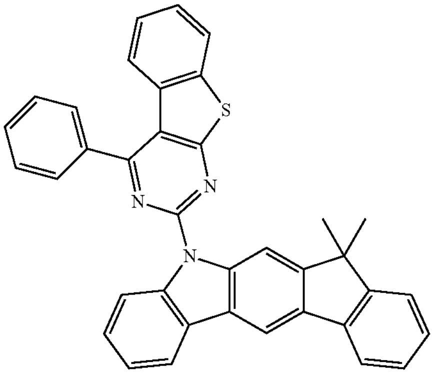

-continued
213
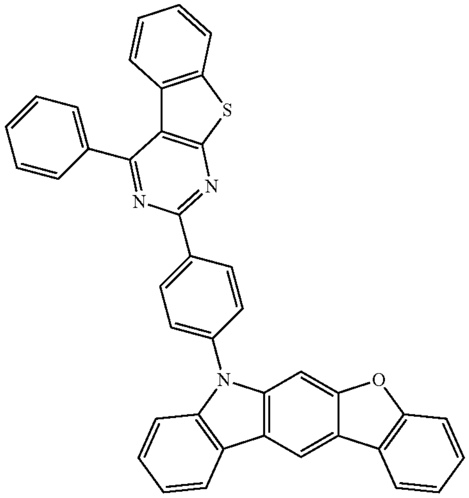
214
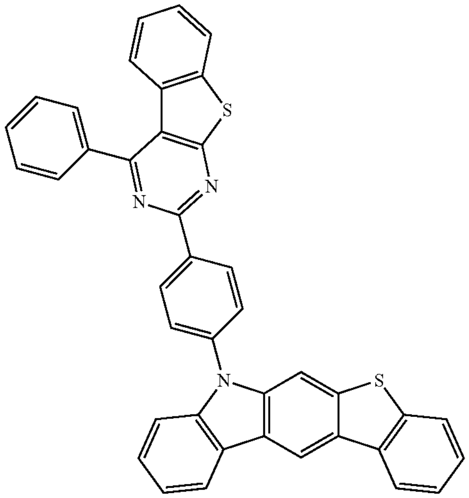
215
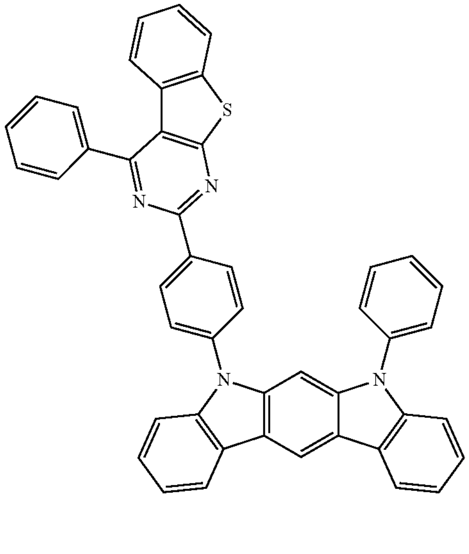
-continued
216
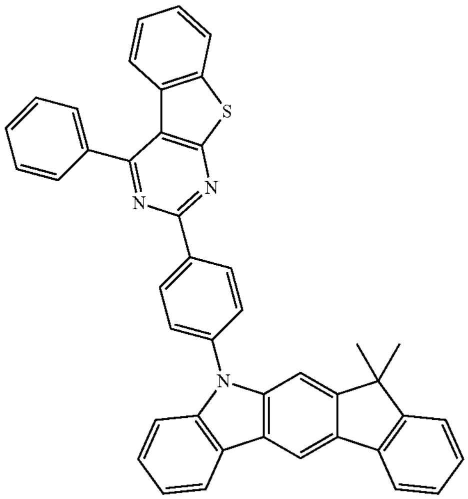
217
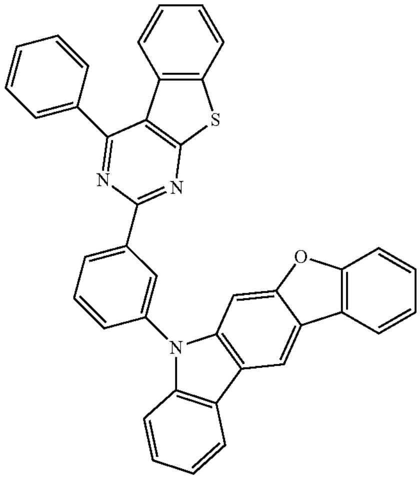
218
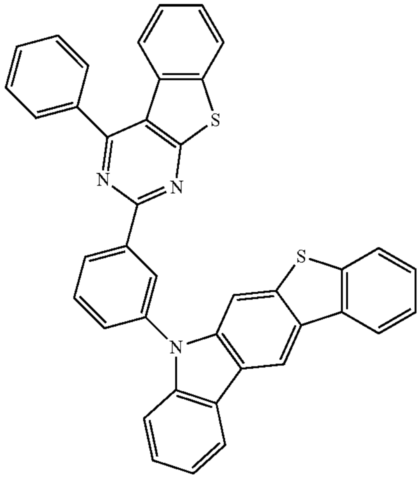

-continued
219
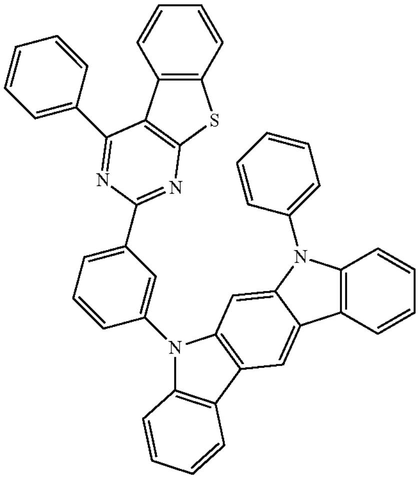
220
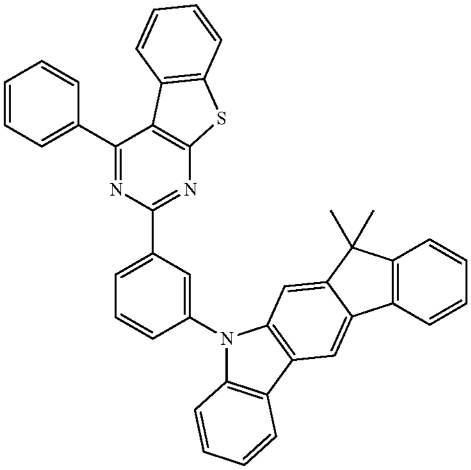
221
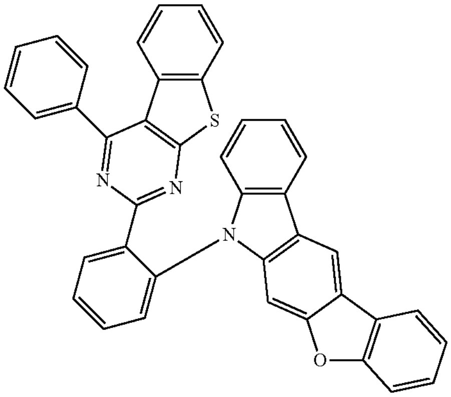
-continued
222
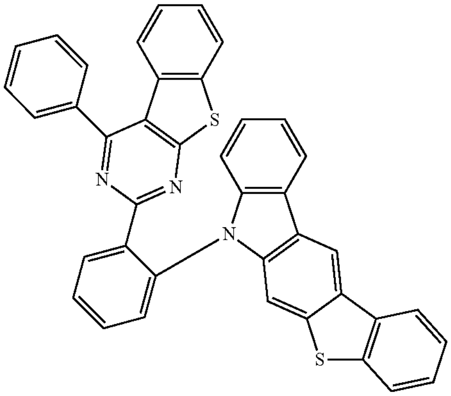
223
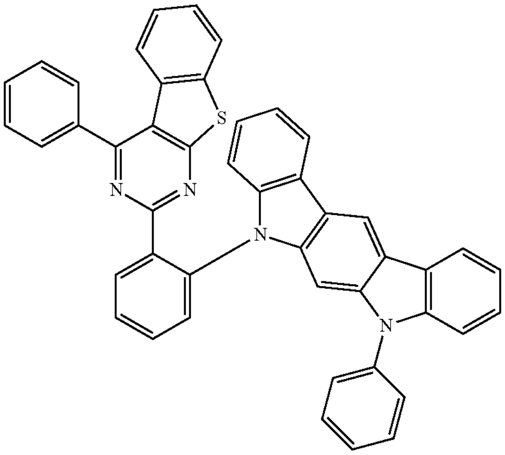
224
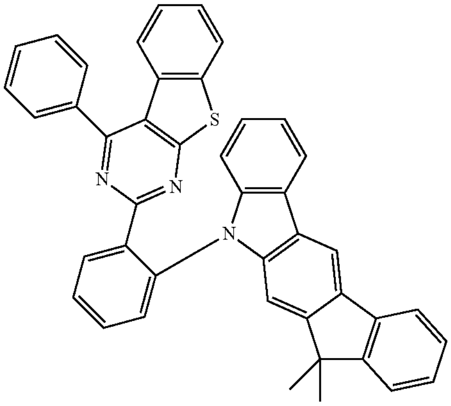

-continued
225
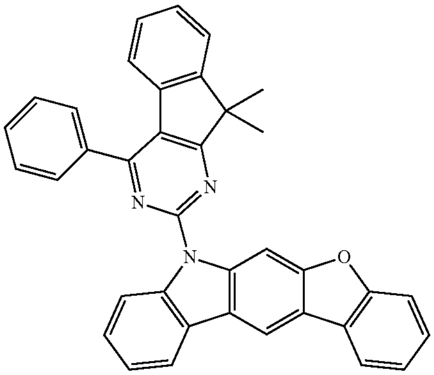
226
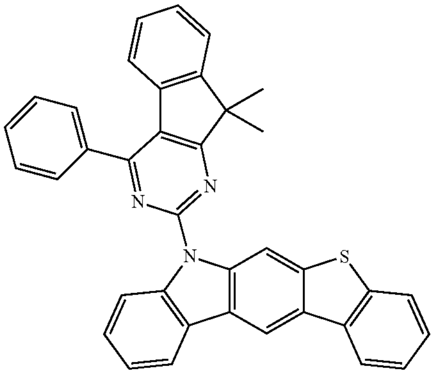
227
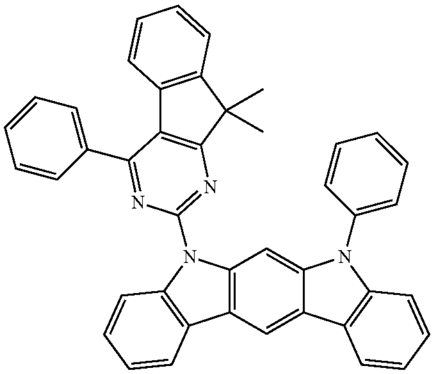
228
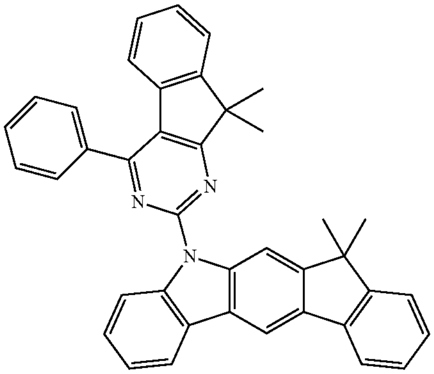
-continued
229
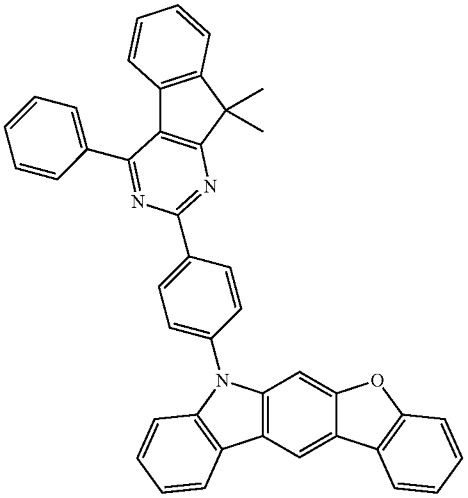
230
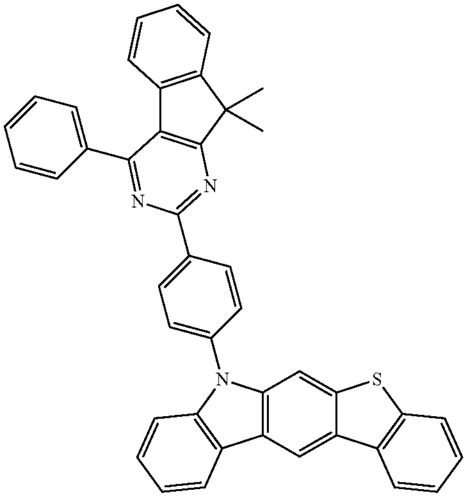
231
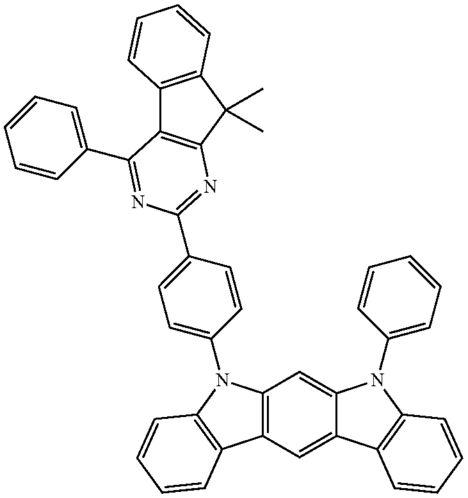

-continued
232
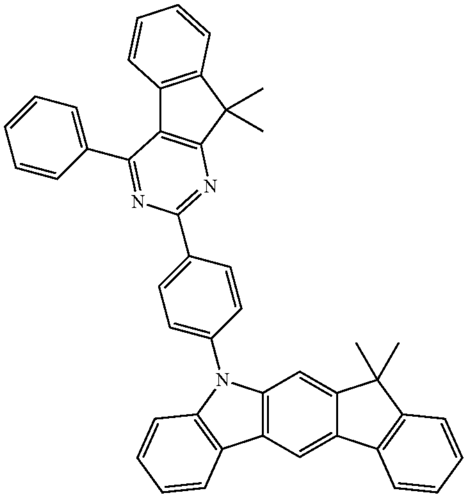
233
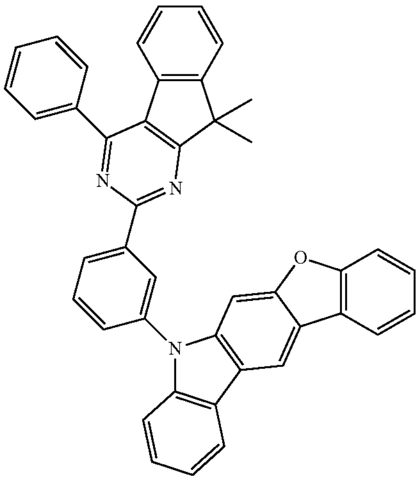
234
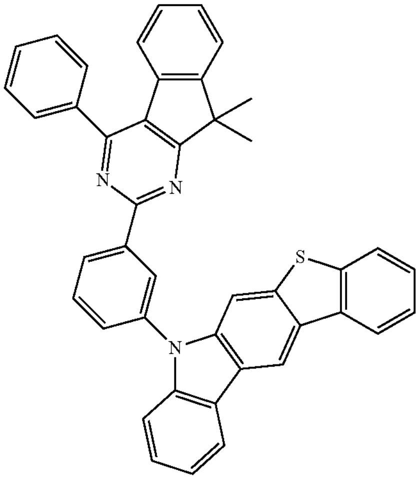
-continued
235
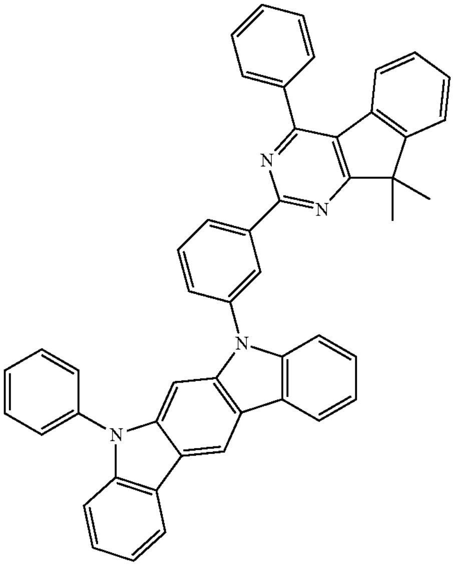
236
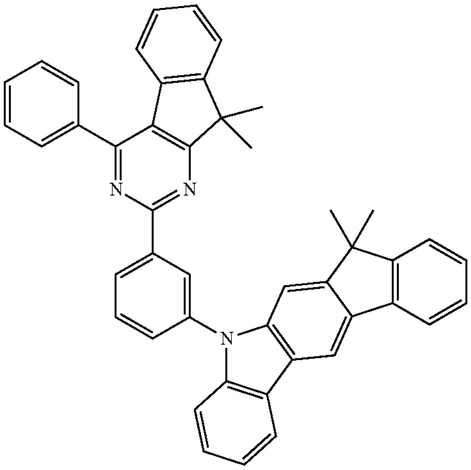
237
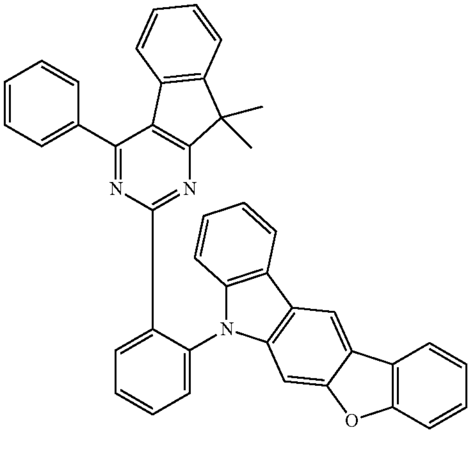

-continued
238
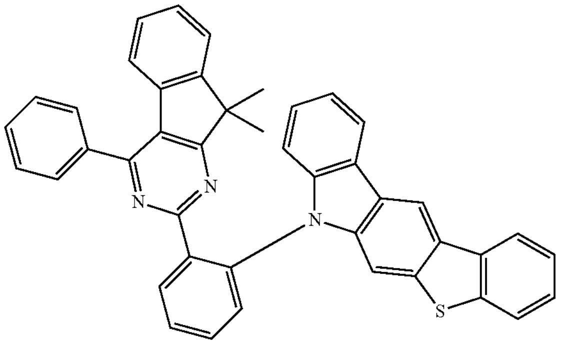
239
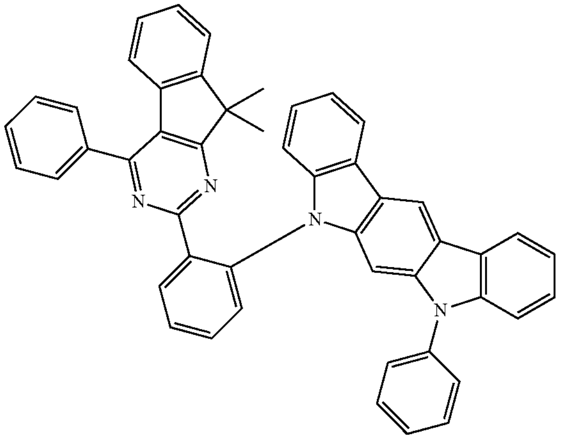
240
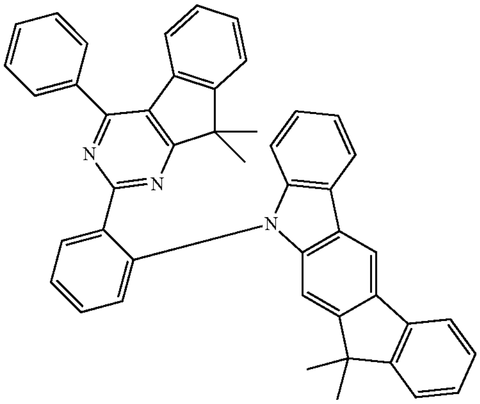
241
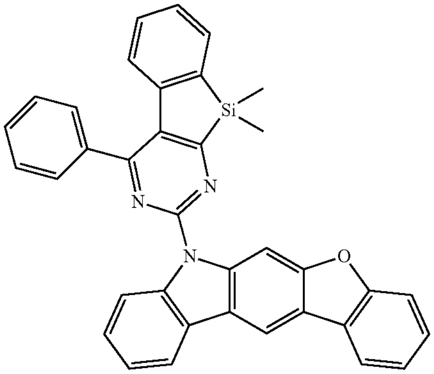
-continued
242
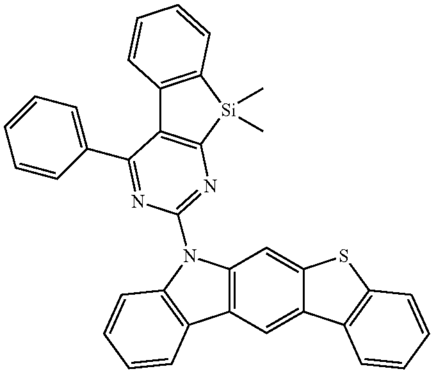
243
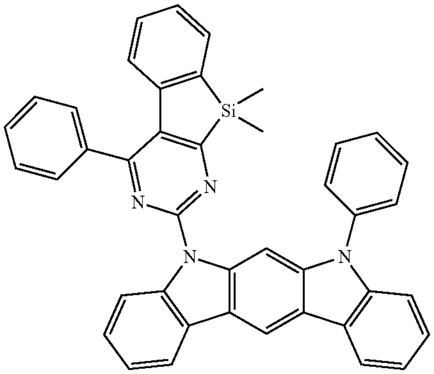
244
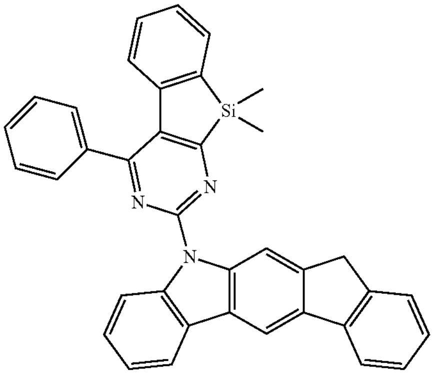
245
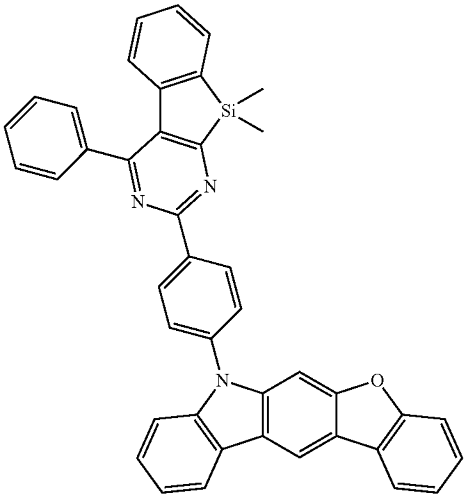

-continued
246
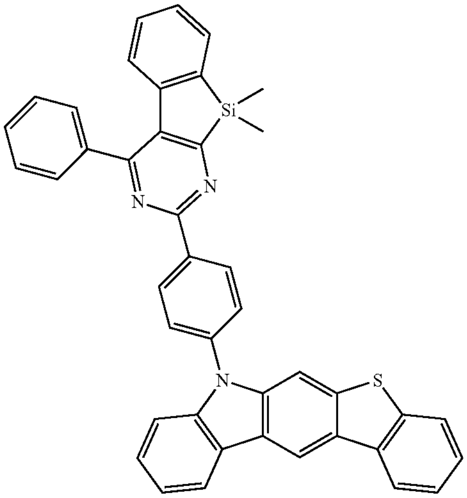
247
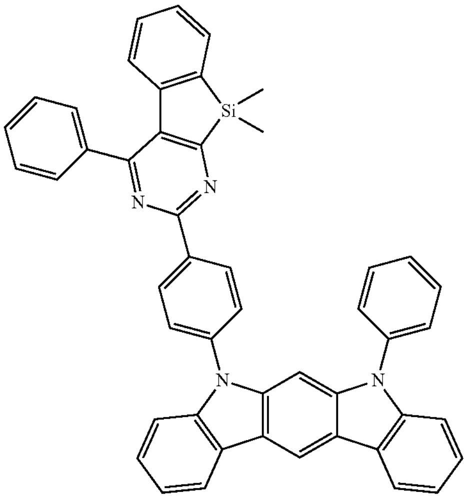
248
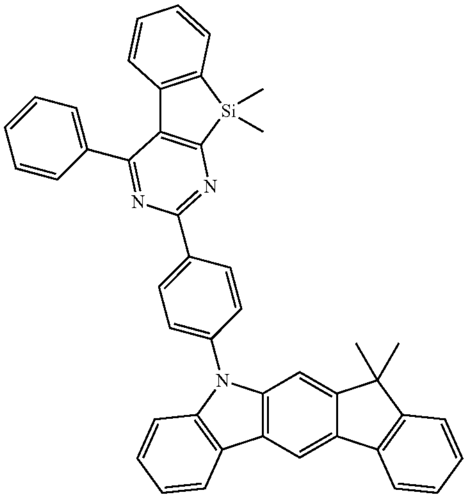
-continued
249
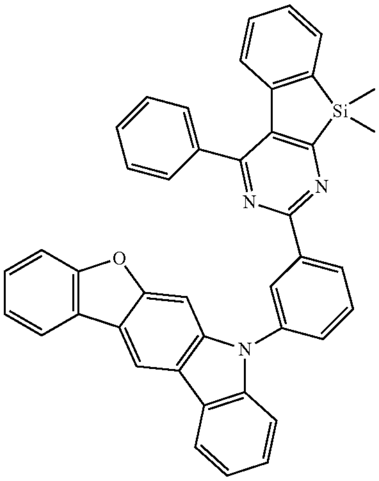
250
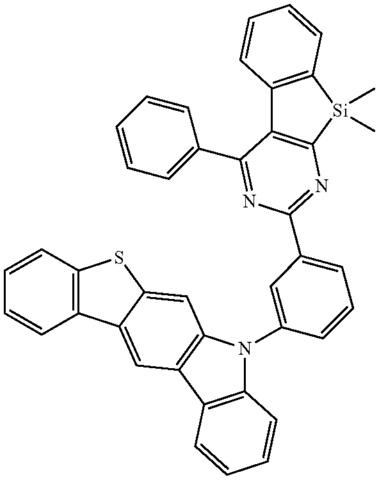
251
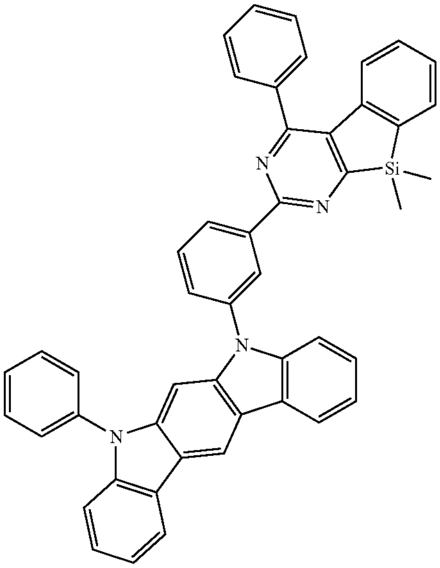

-continued
252
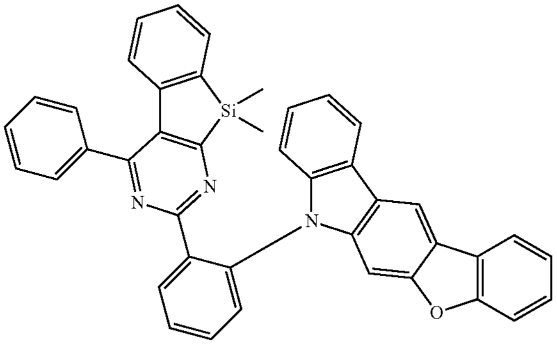
253
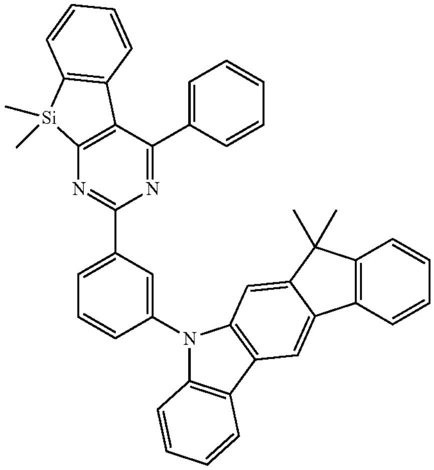
254
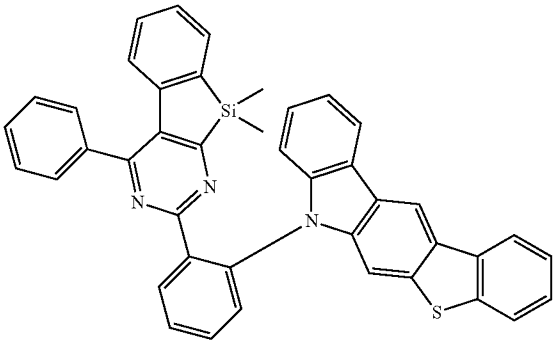
-continued
255
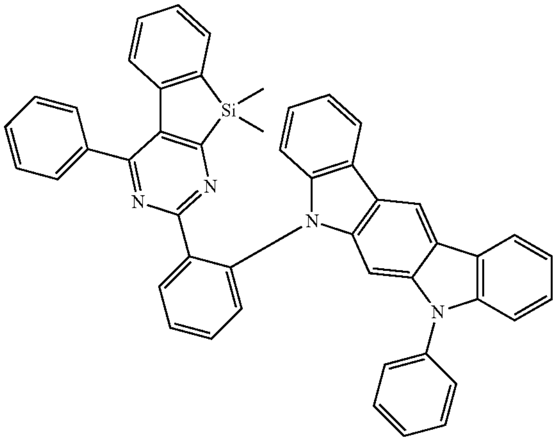
256
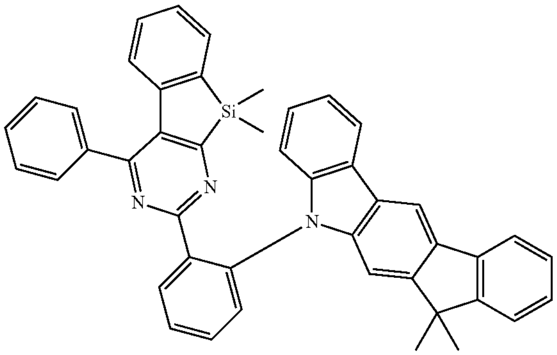
257
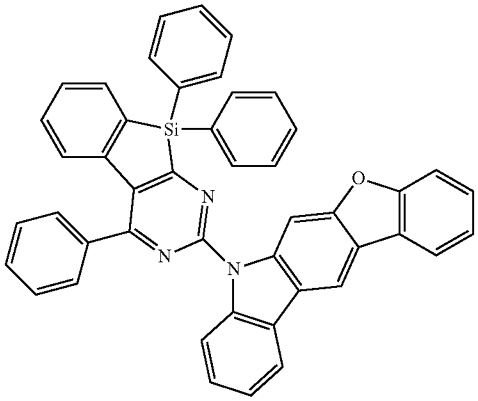

-continued
258
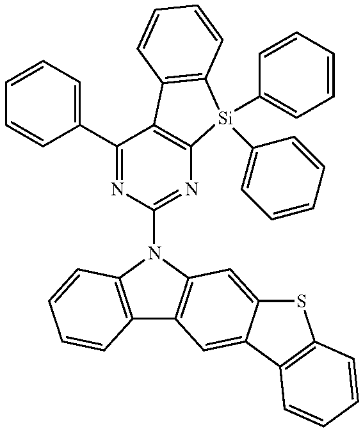
259
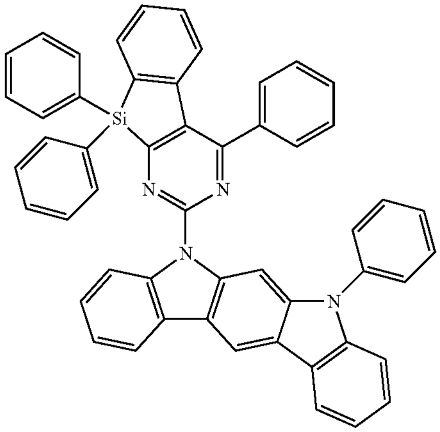
260
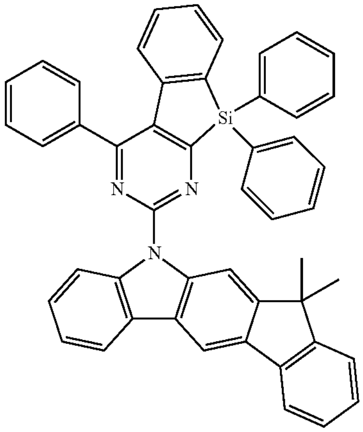
-continued
261
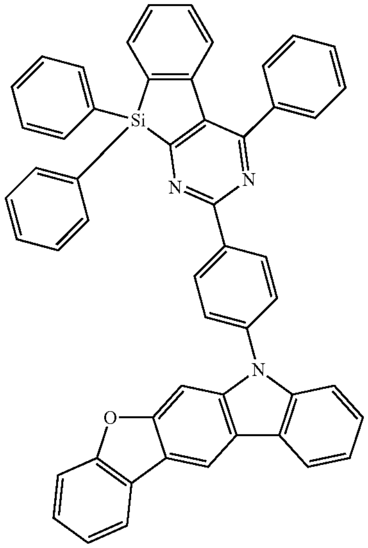
262
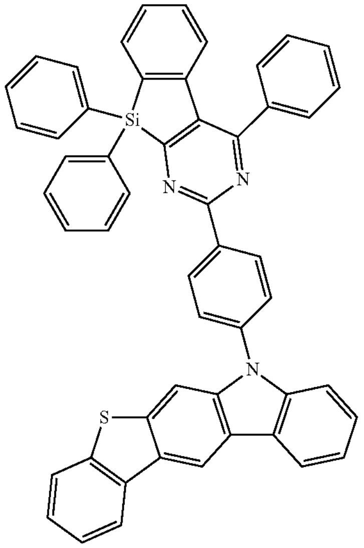
263
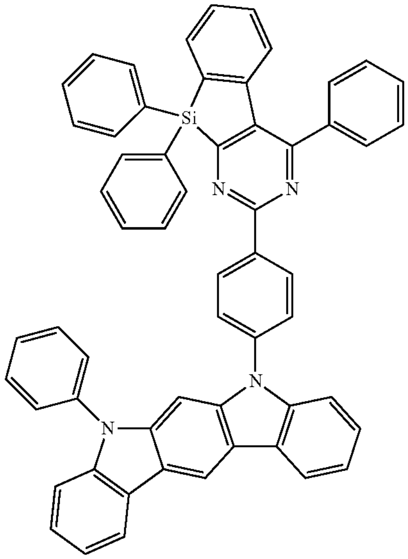

264
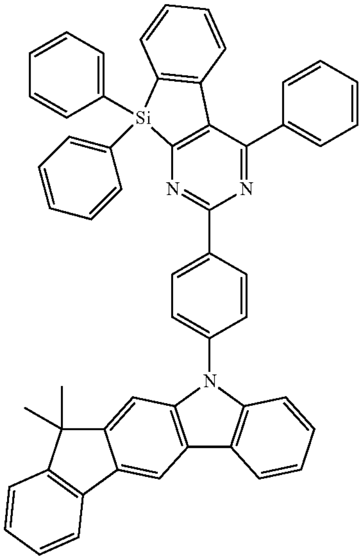
265
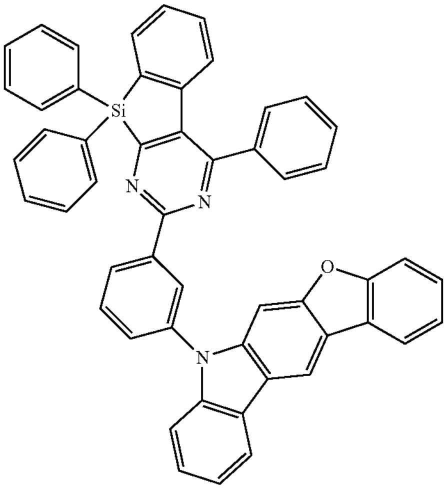
266
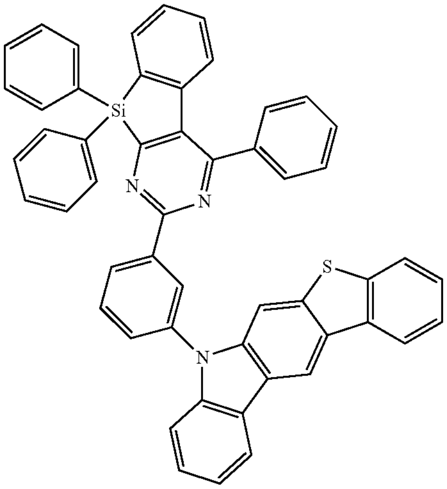
267
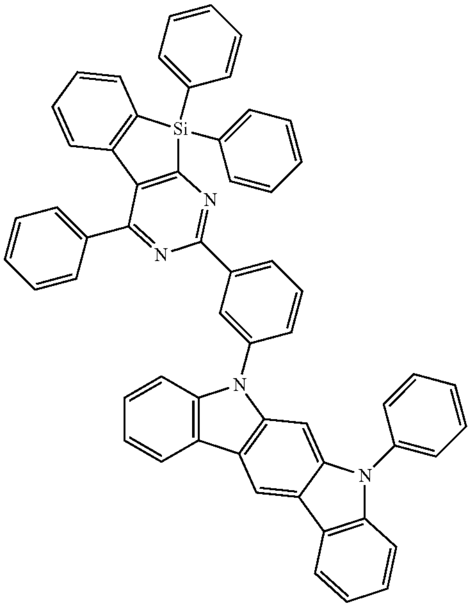
268
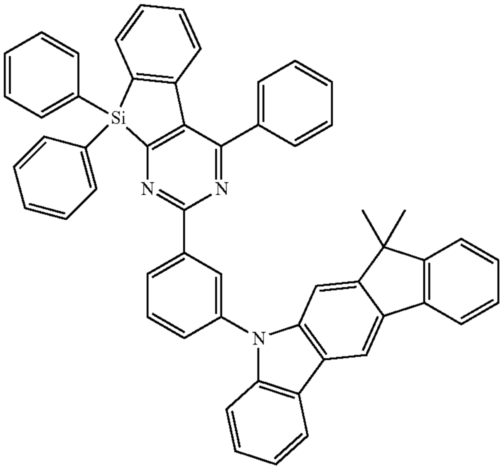

-continued
269
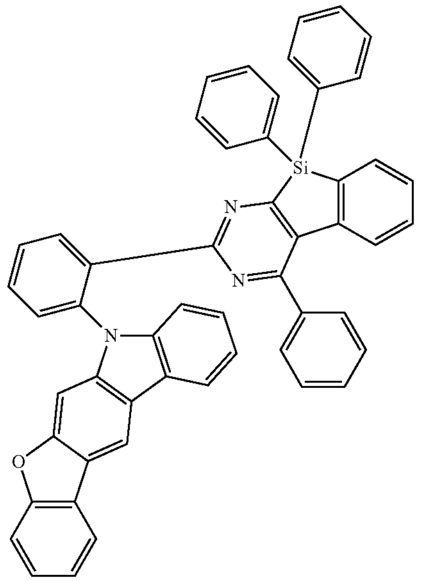
270
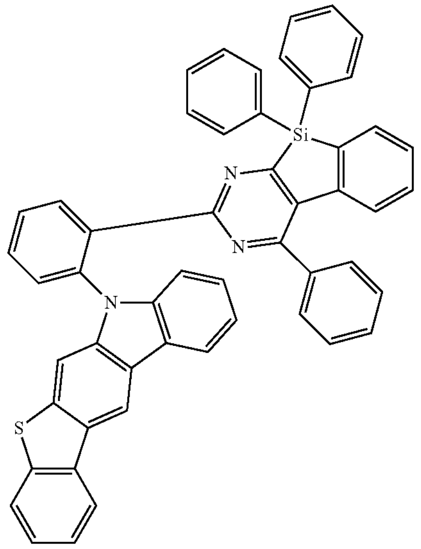
-continued
271
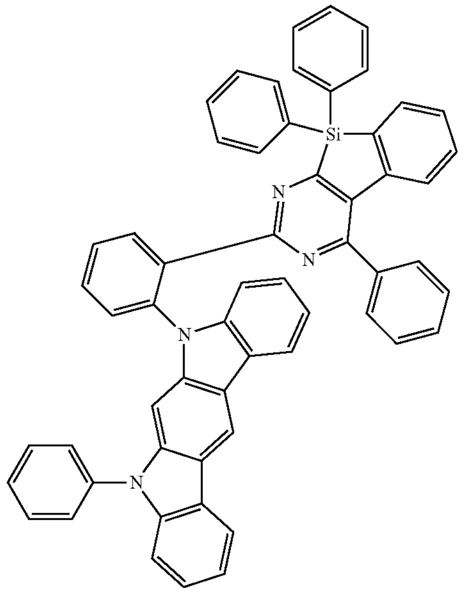
272
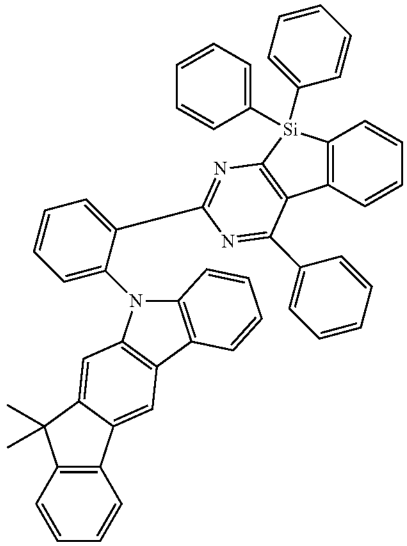
273
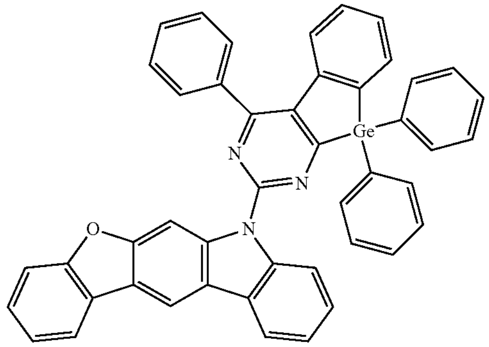

-continued
274
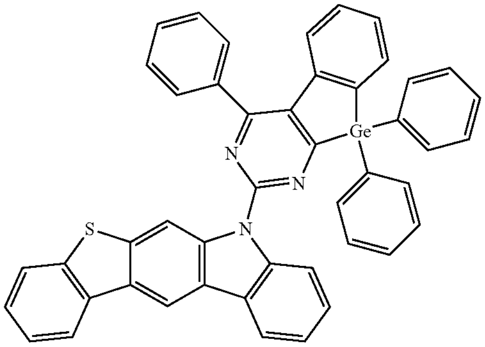
275
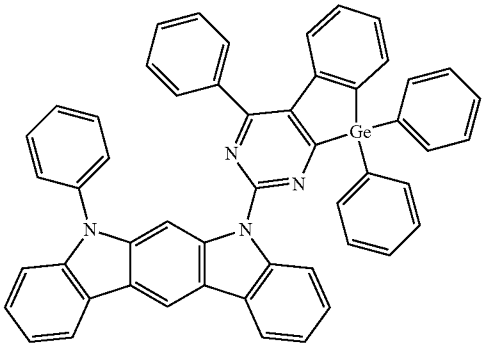
276
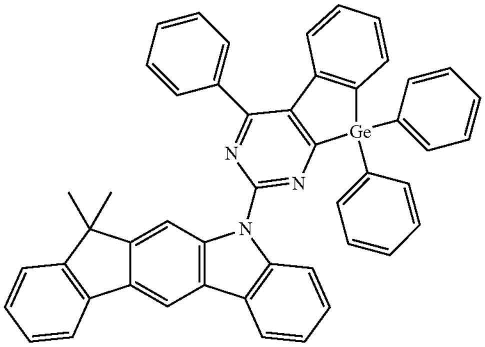
277
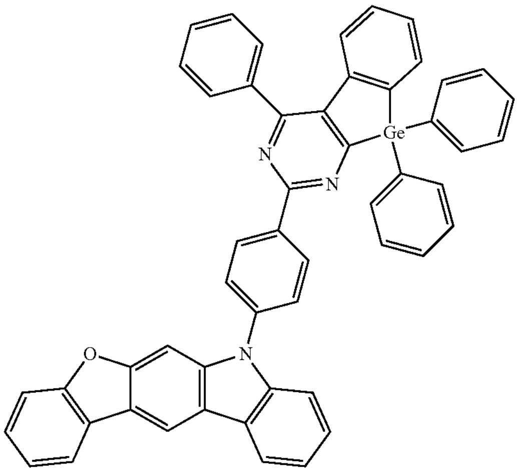
-continued
278
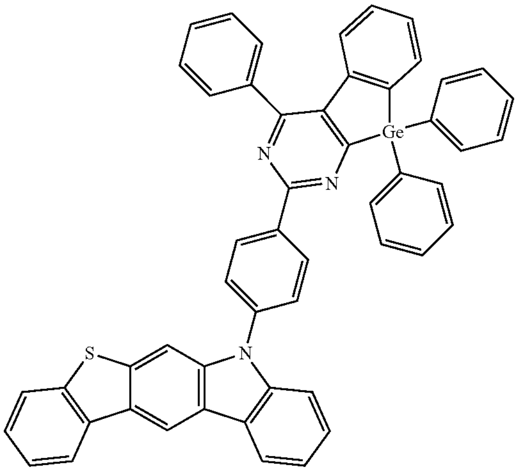
279
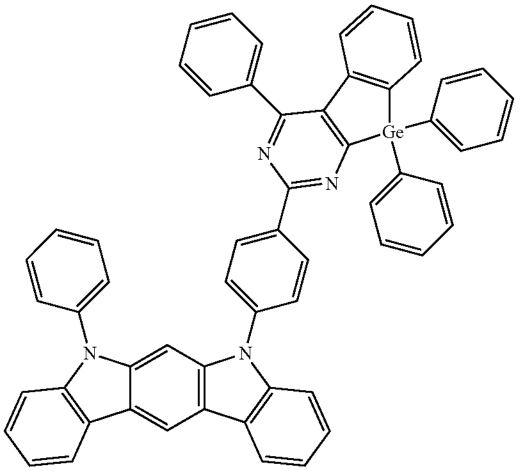
280
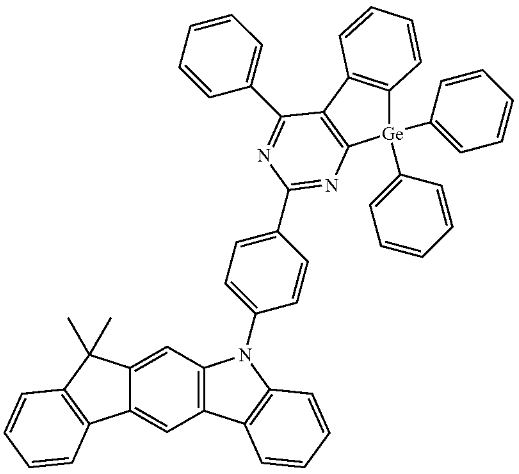

-continued
281
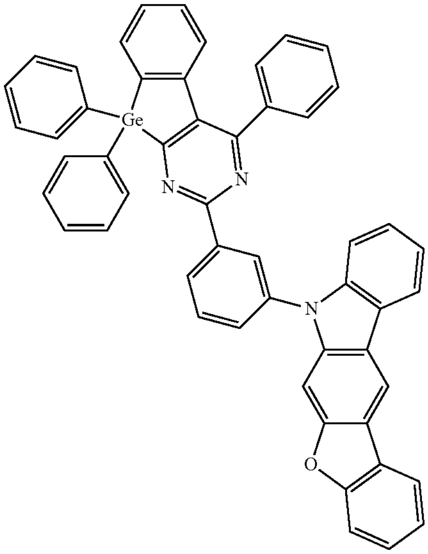
282
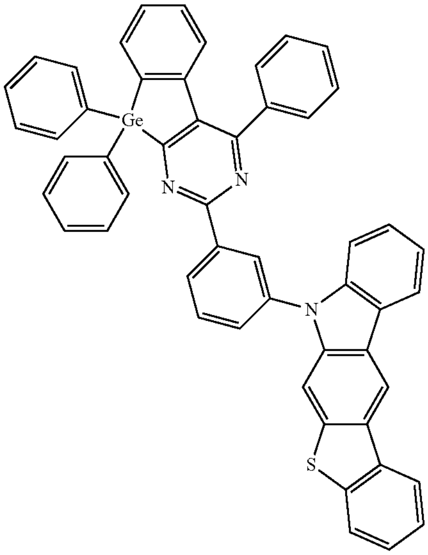
283
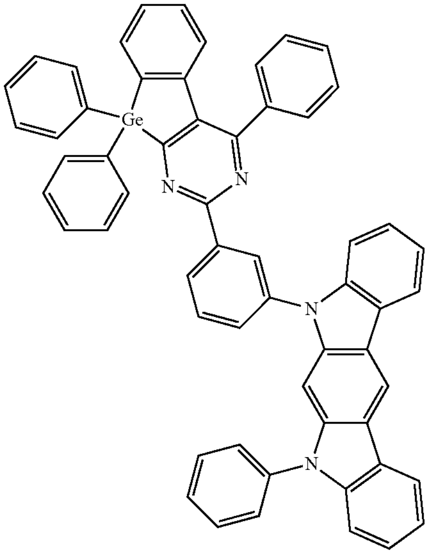
-continued
284
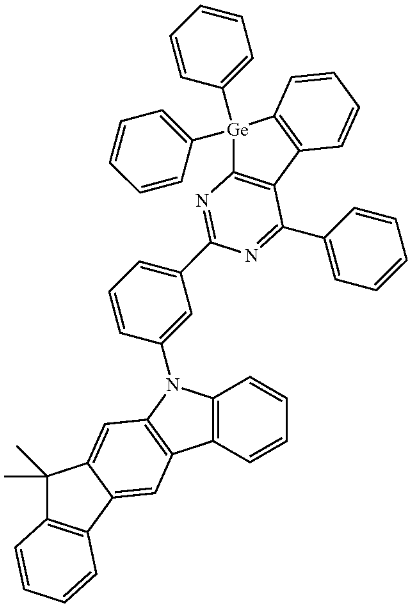
285
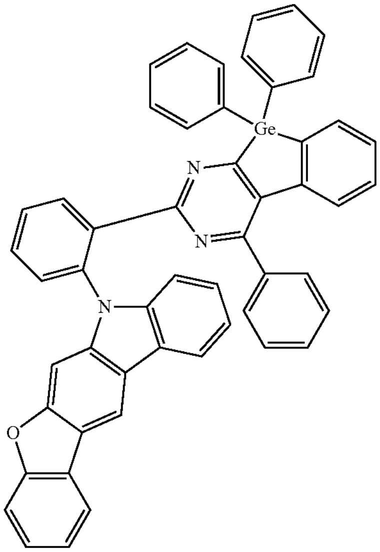

-continued
286
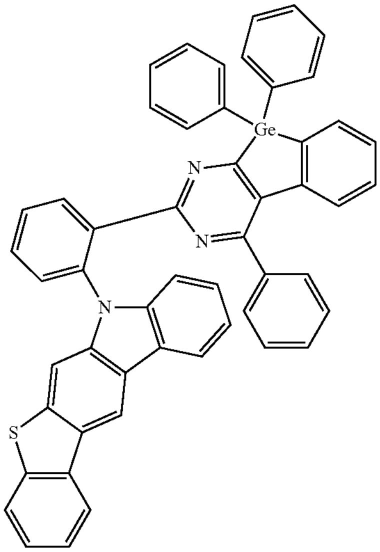
287
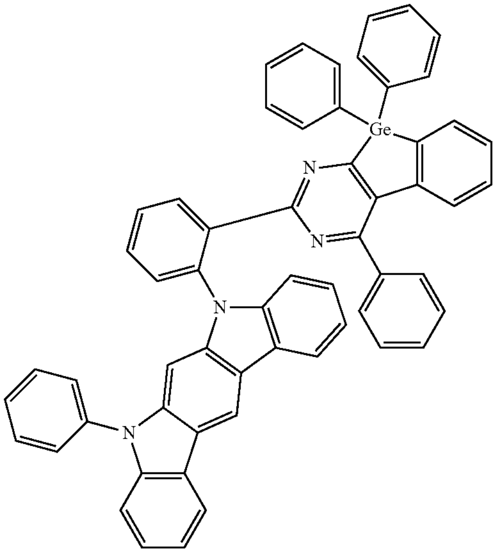
-continued
288
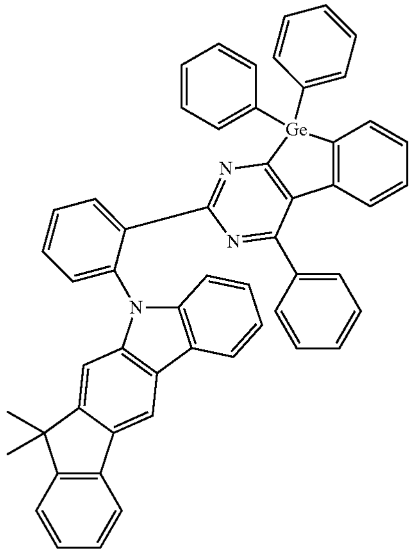
289
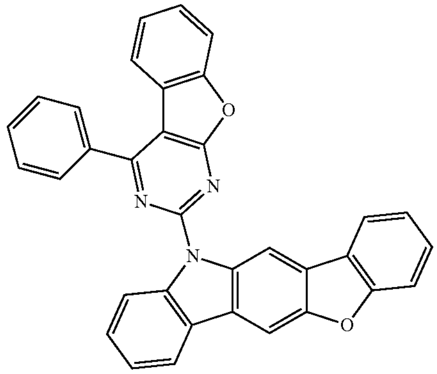
290
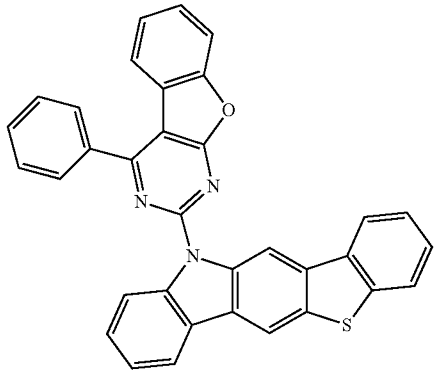

-continued
291
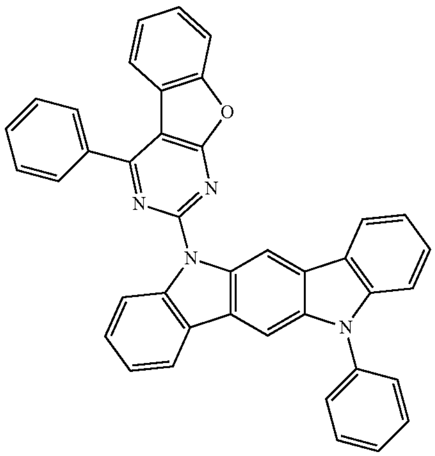
292
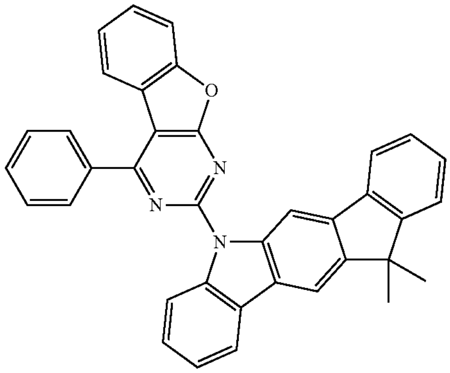
293
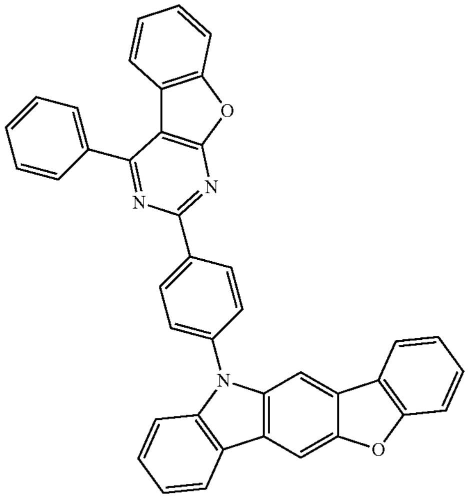
-continued
294
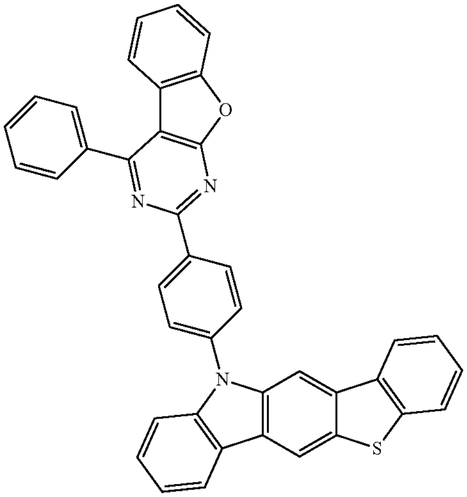
295
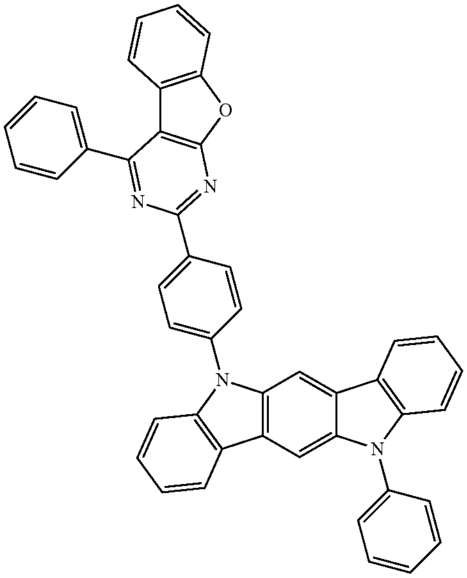
296
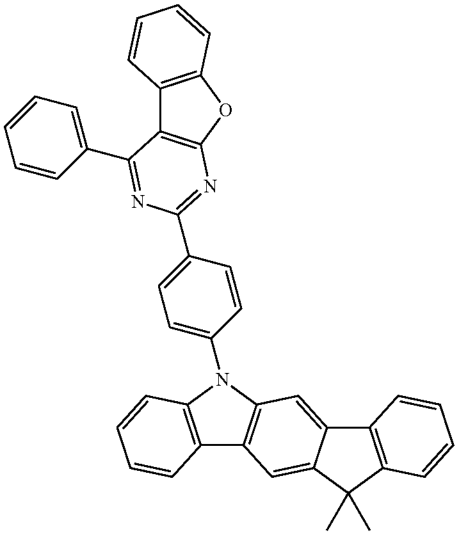

-continued
297
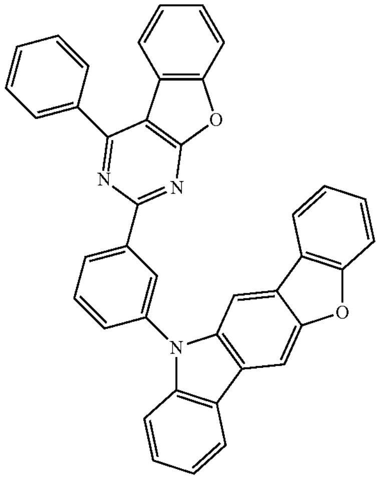
298
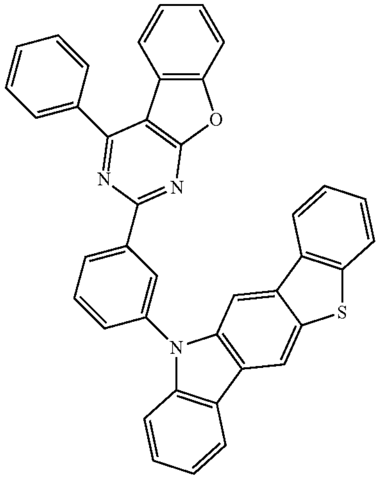
299
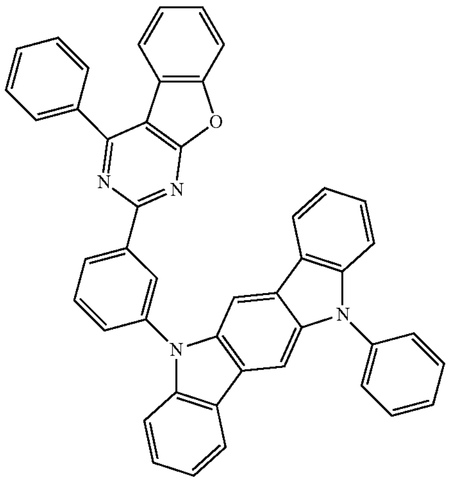
-continued
300
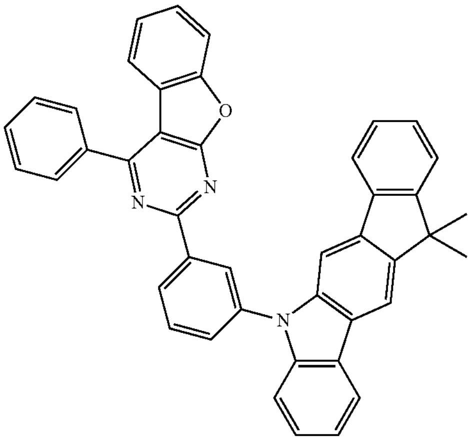
301
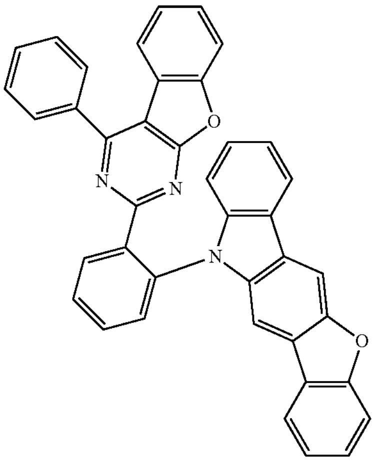
302
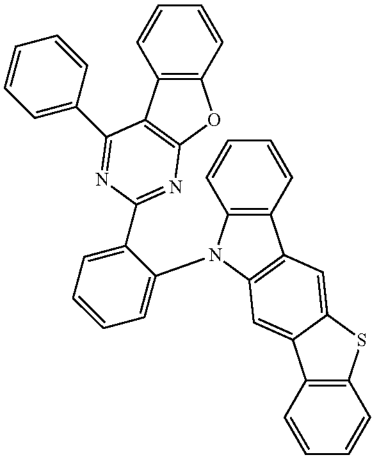

-continued
303
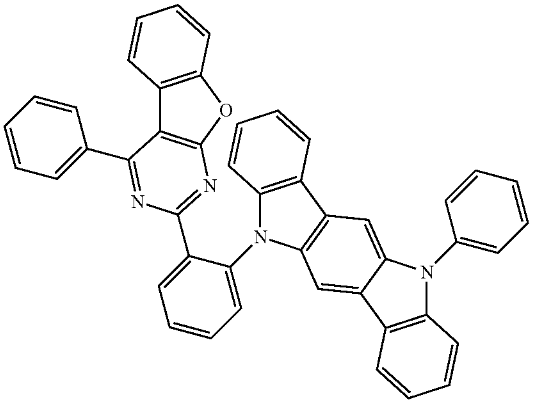
304
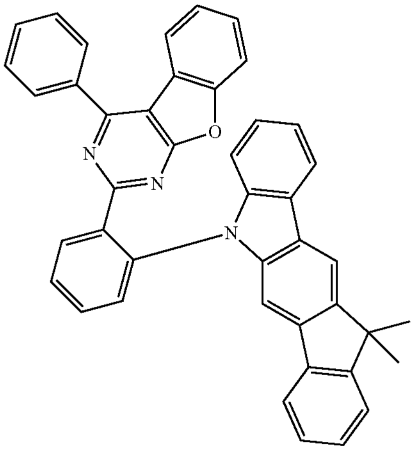
305
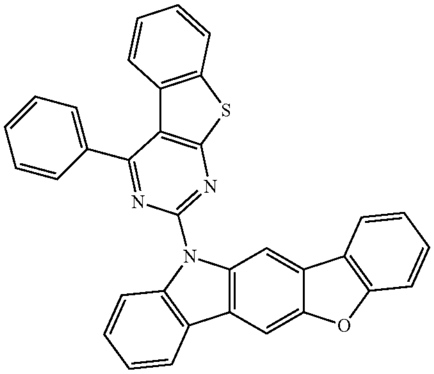
306
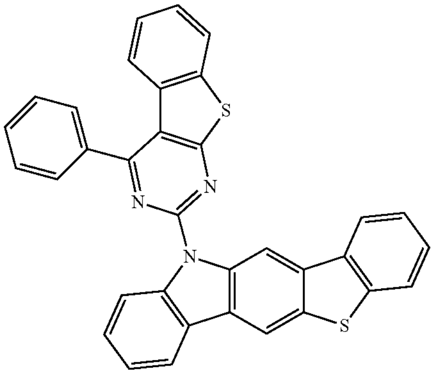
-continued
307
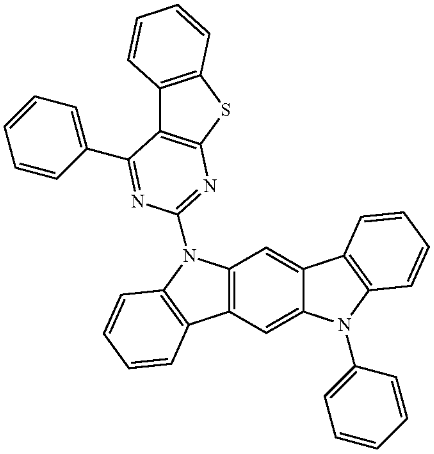
308
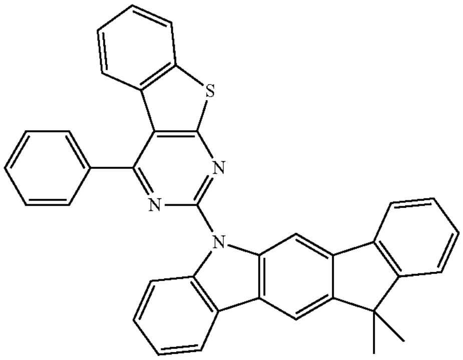
309
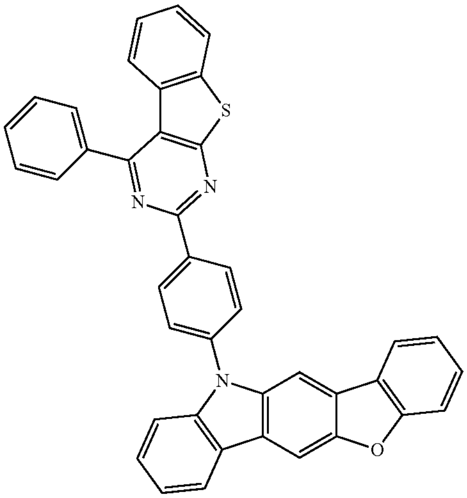

-continued
310
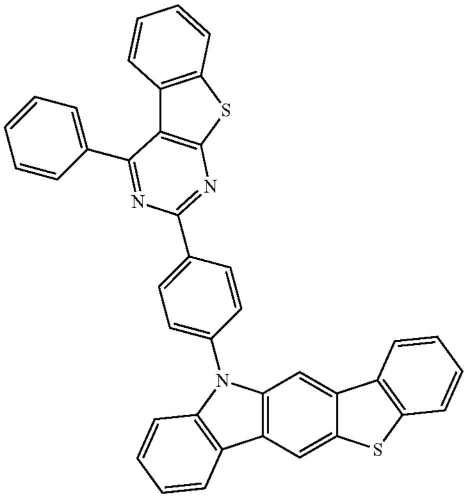
311
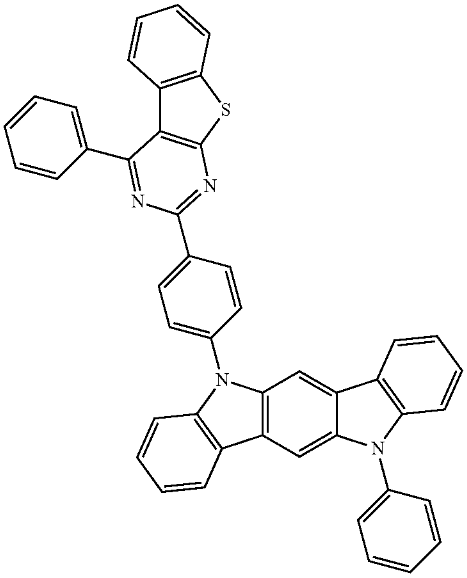
312
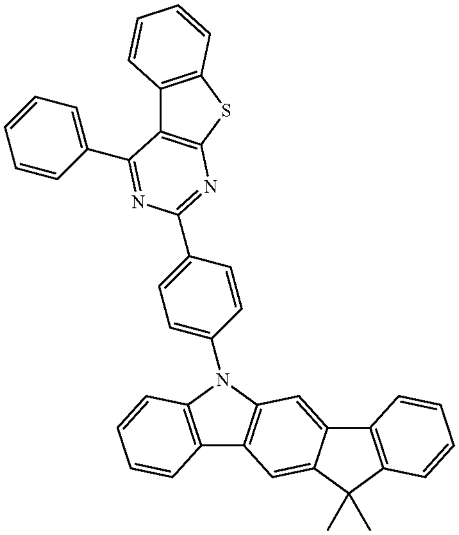
-continued
313
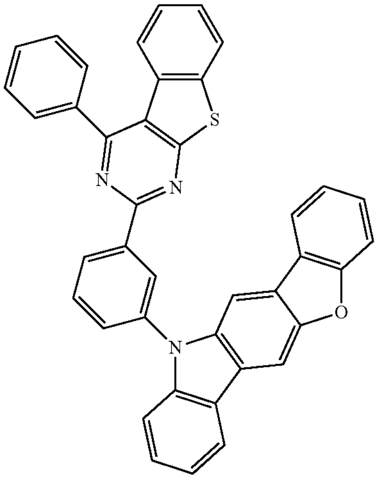
314
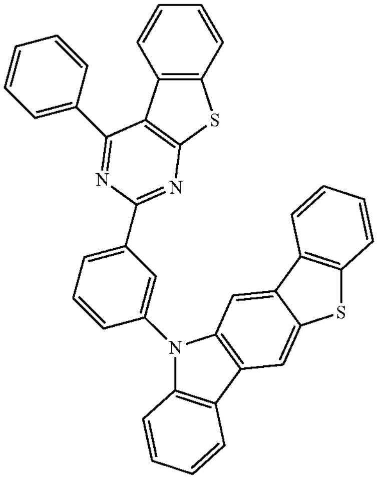
315
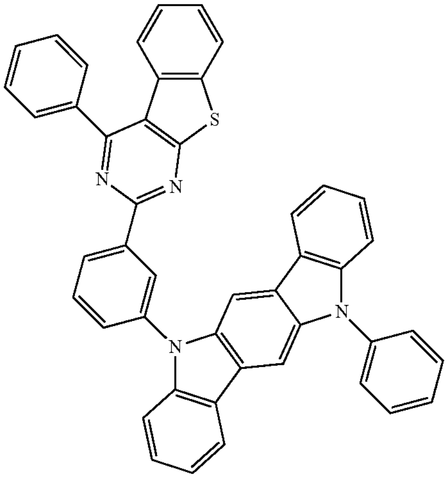

-continued
316
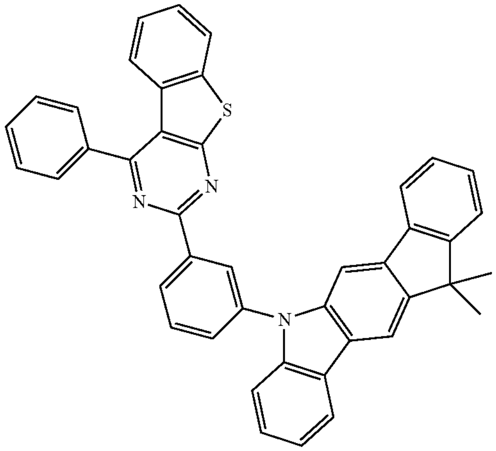
317
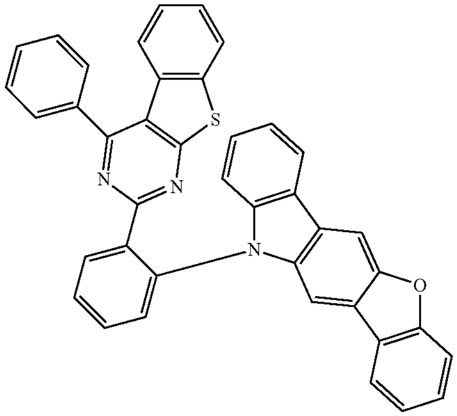
318
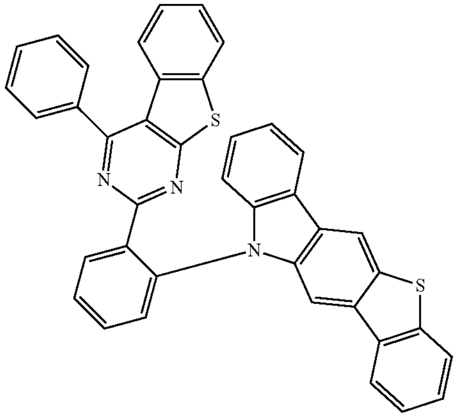
-continued
319
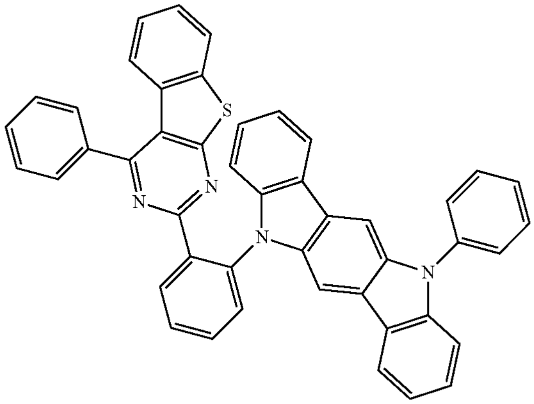
320
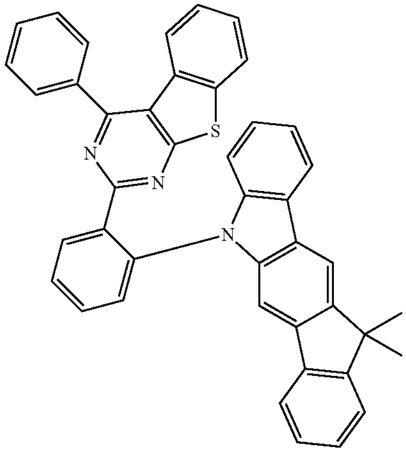
321
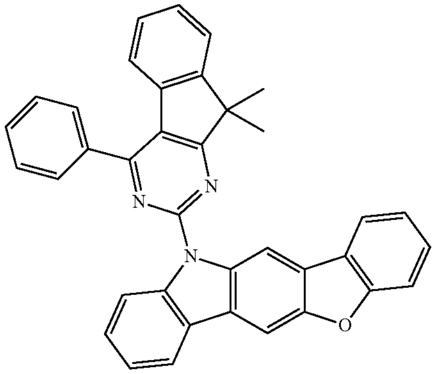
322
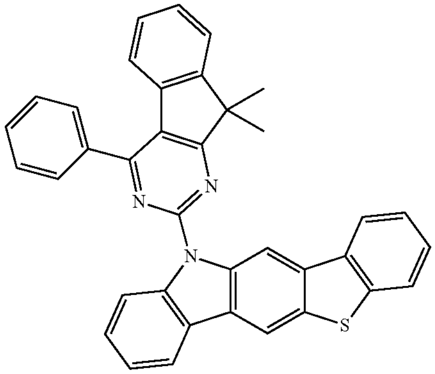

-continued
323
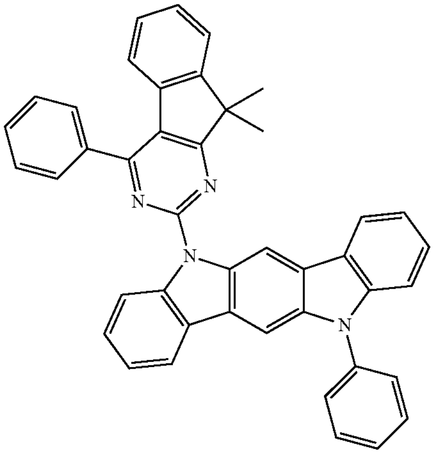
324
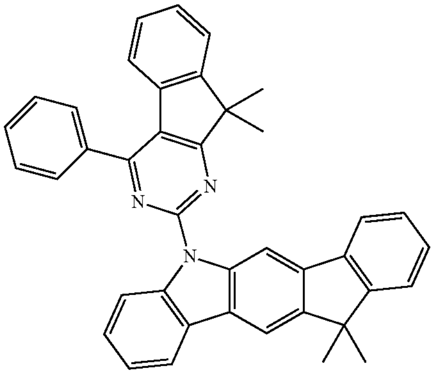
325
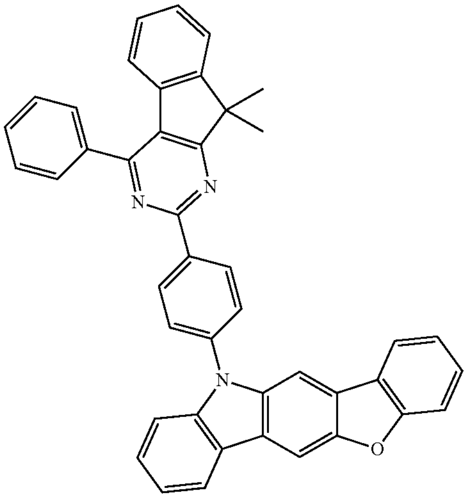
-continued
326
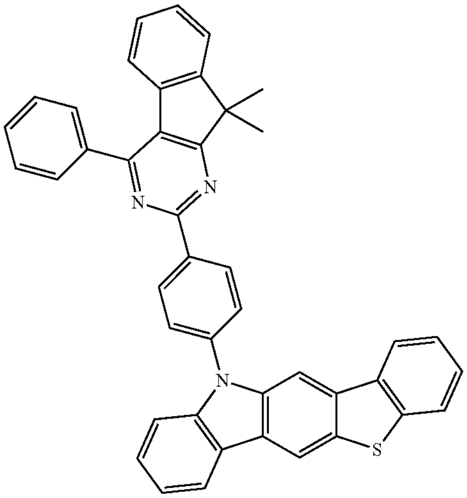
327
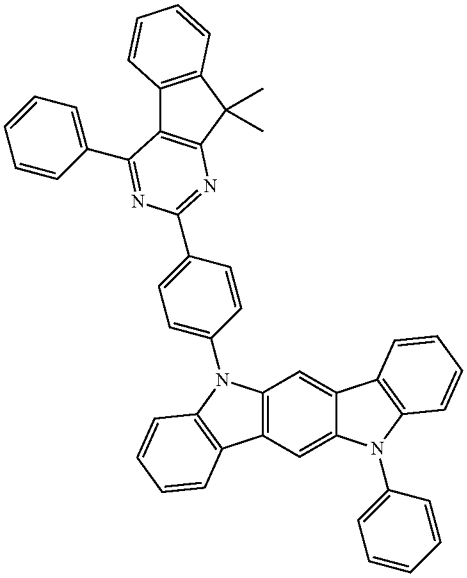
328
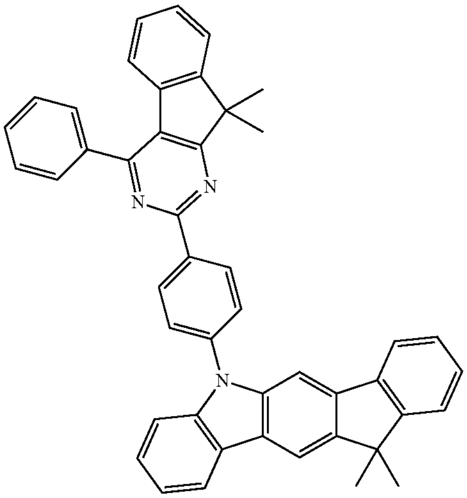

-continued
329
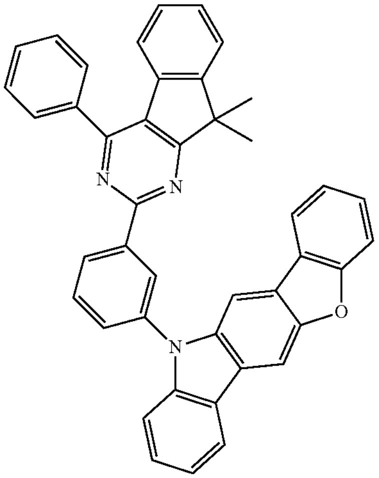
330
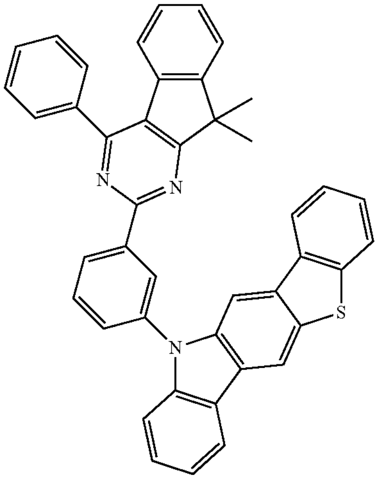
331
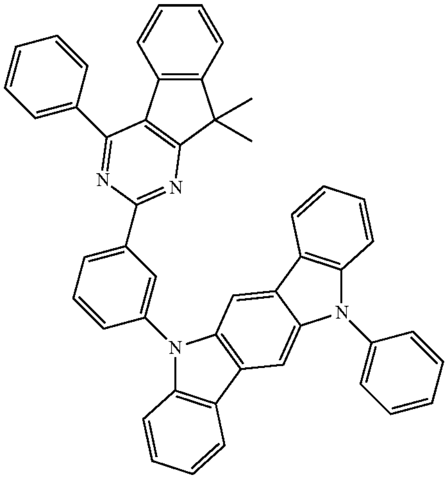
-continued
332
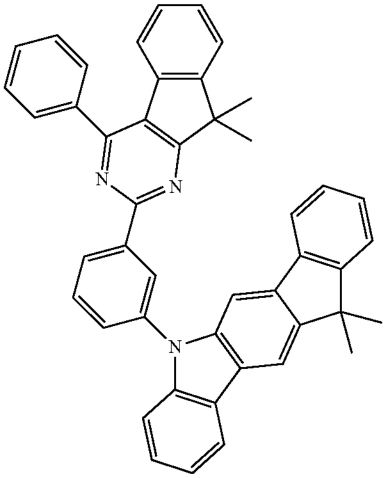
333
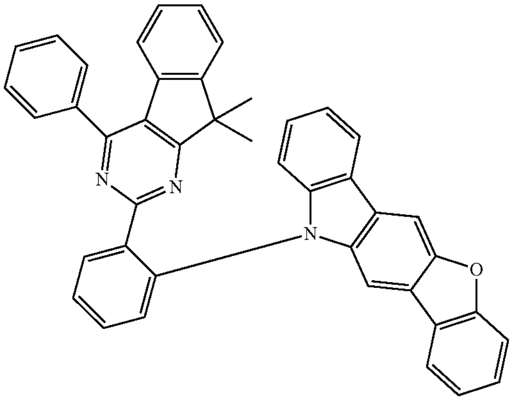
334
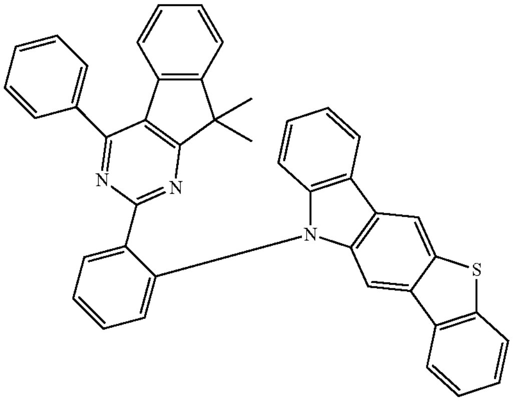

-continued
335
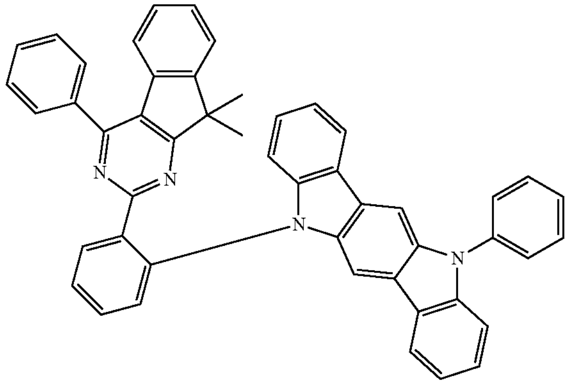
336
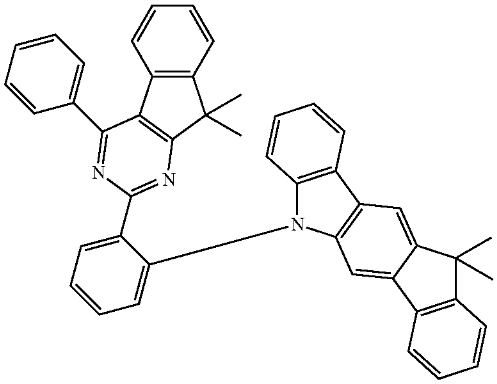
337
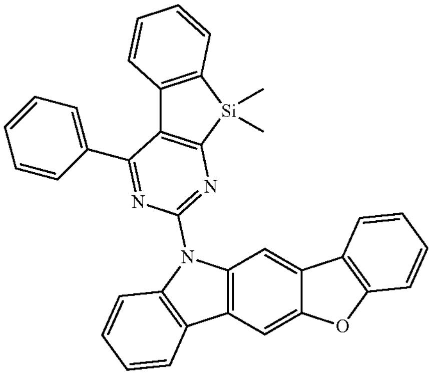
338
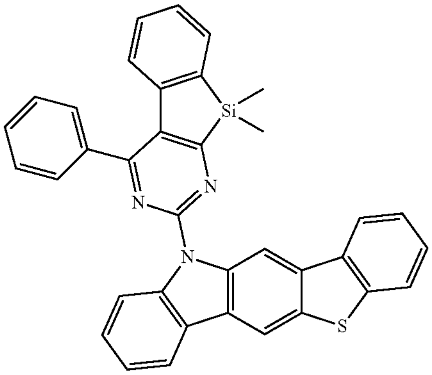
-continued
339
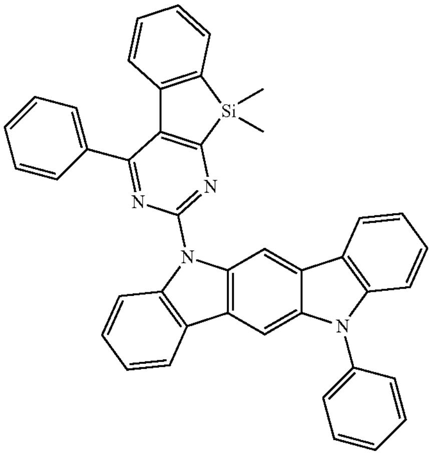
340
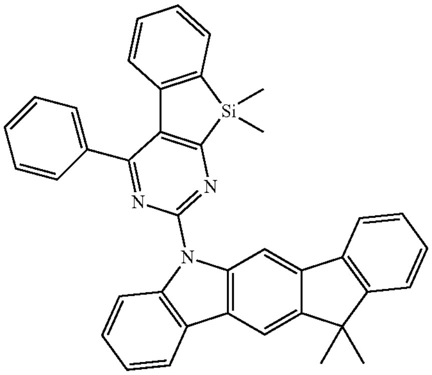
341
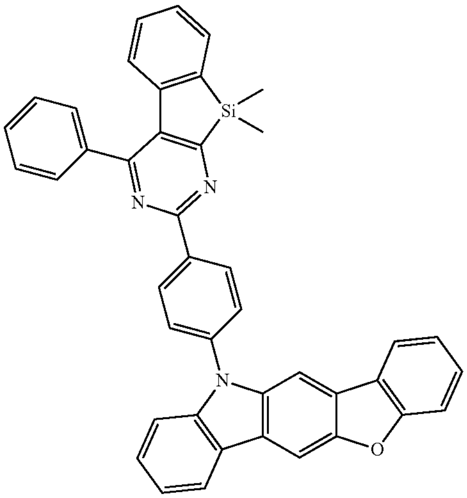

-continued
342
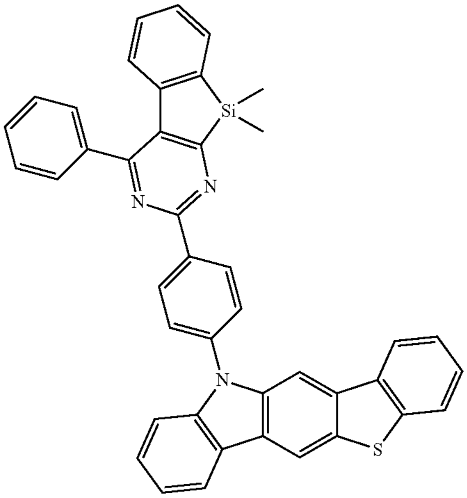
343
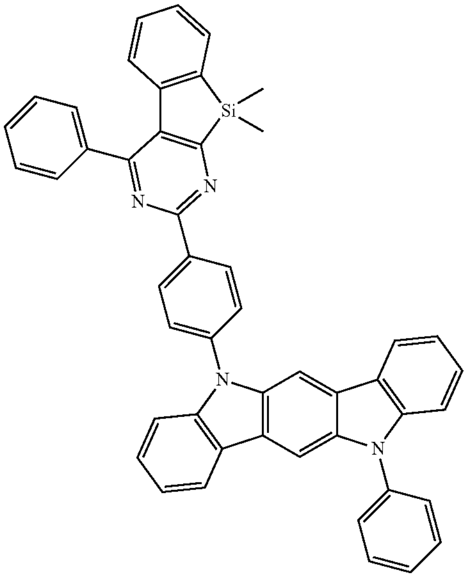
344
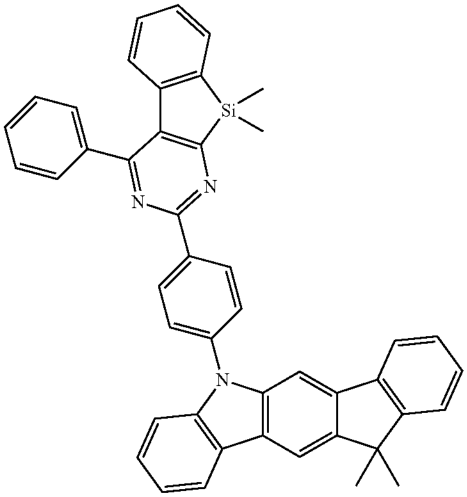
-continued
345
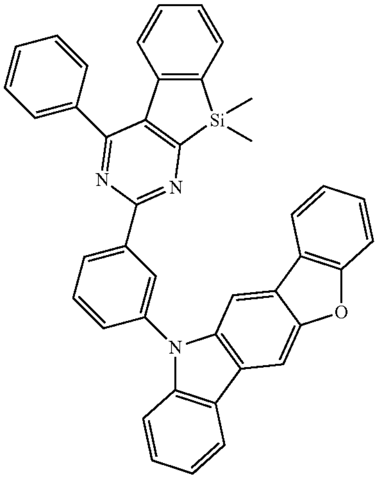
346
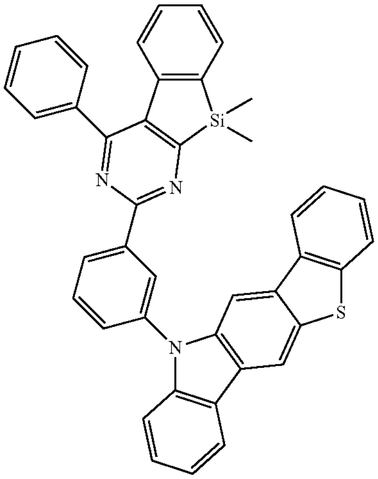
347
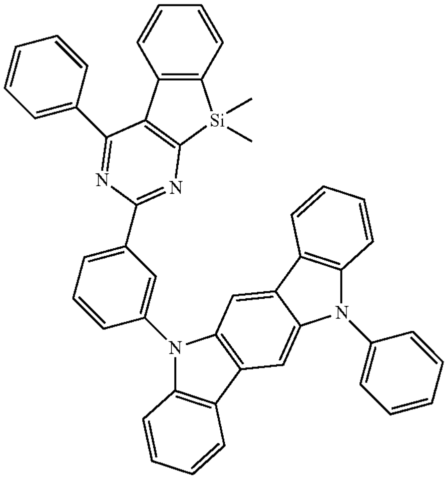

-continued
348
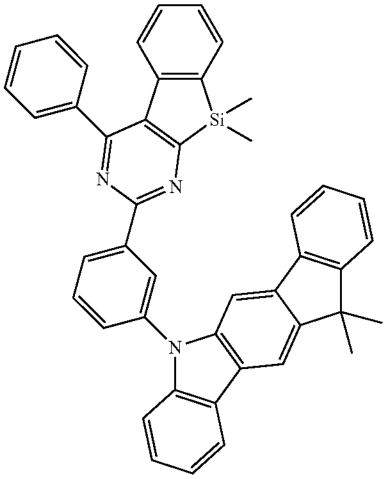
349
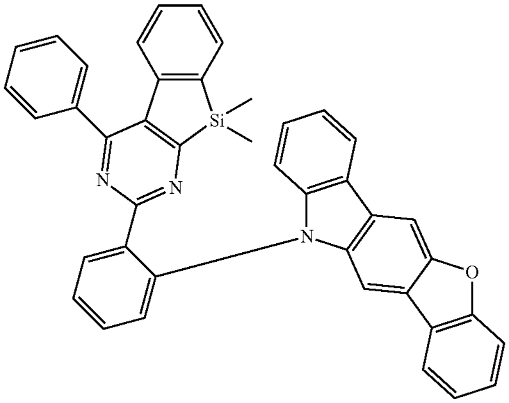
350
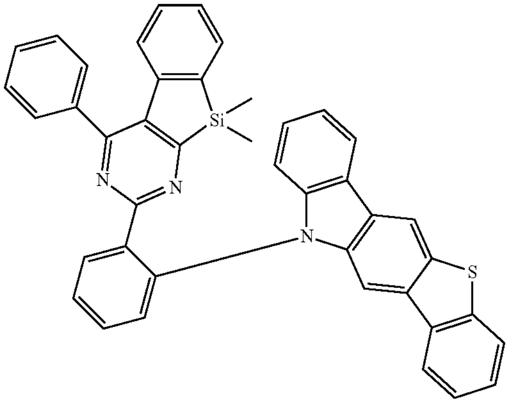
-continued
351
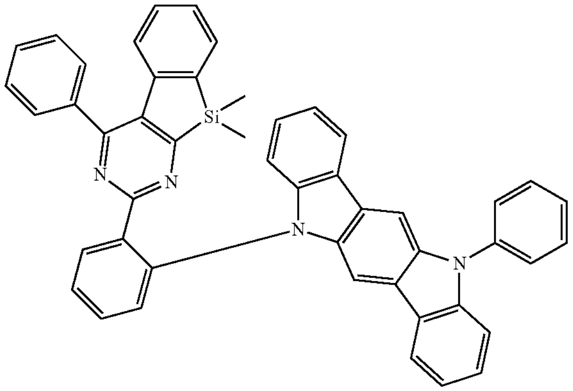
352
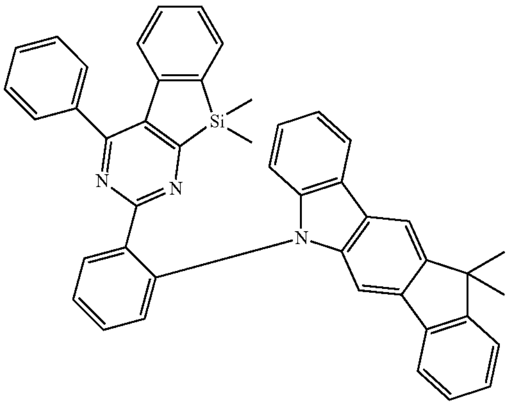
353
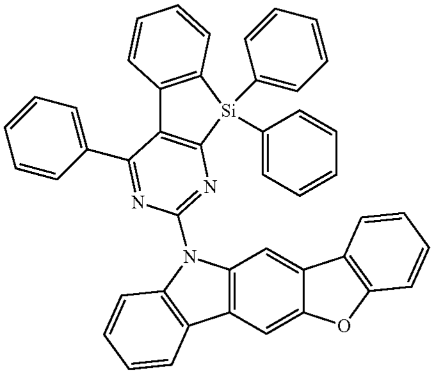
354
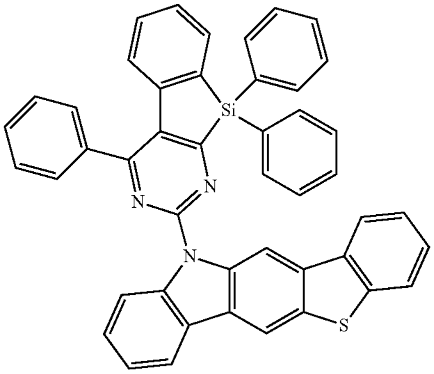

-continued
355
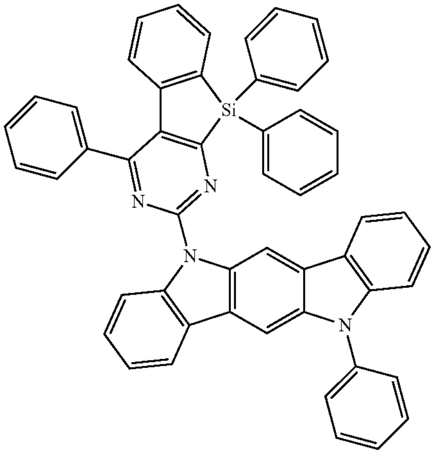
356
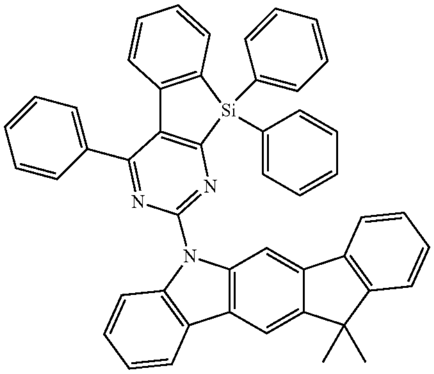
357
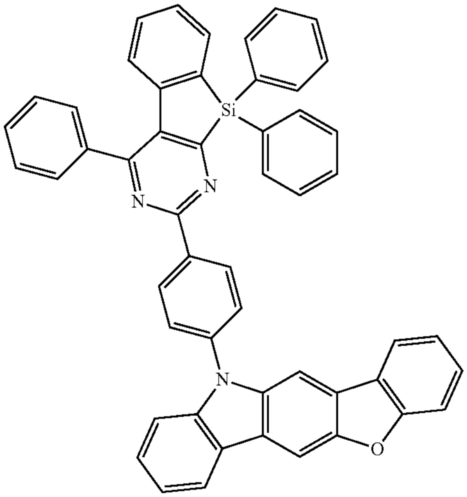
-continued
358
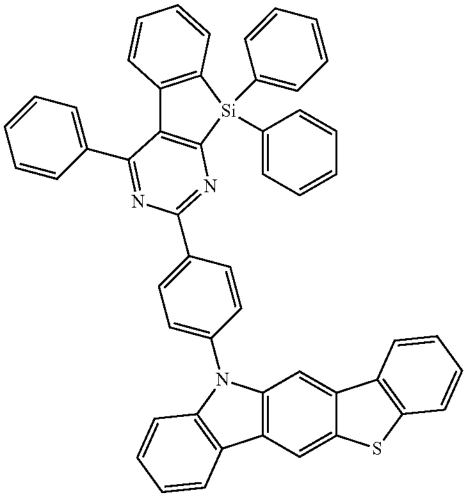
359
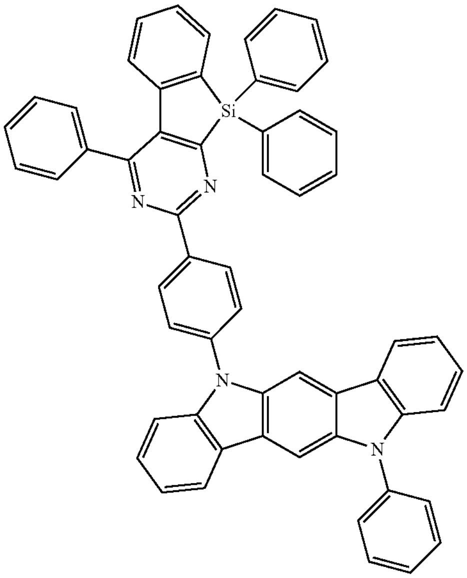
360
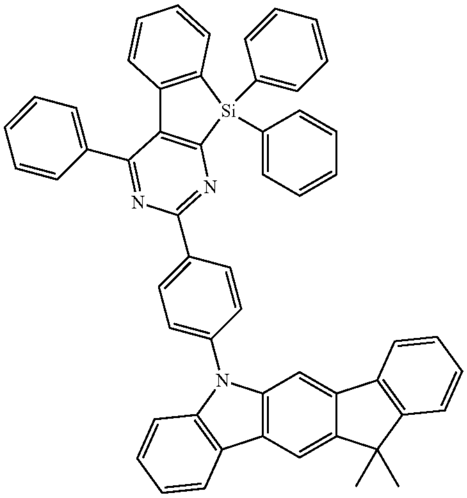

-continued
361
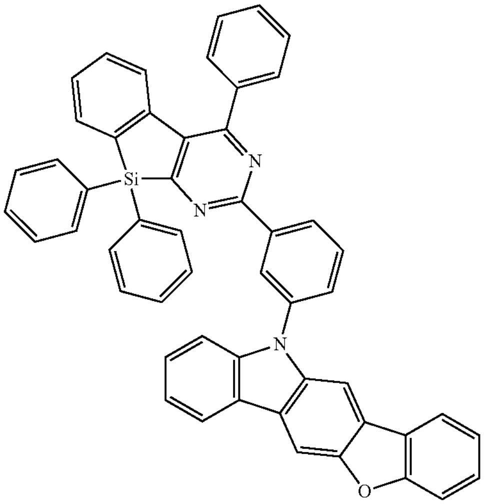
362
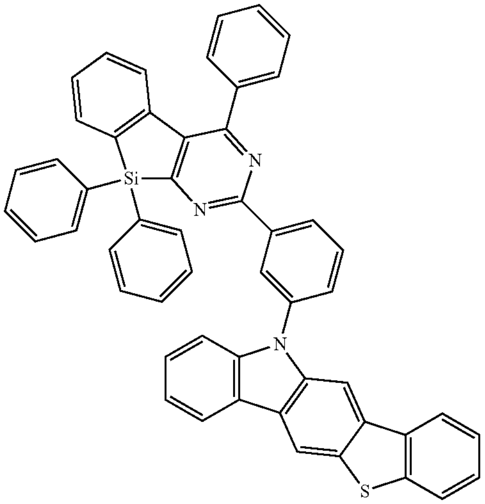
363
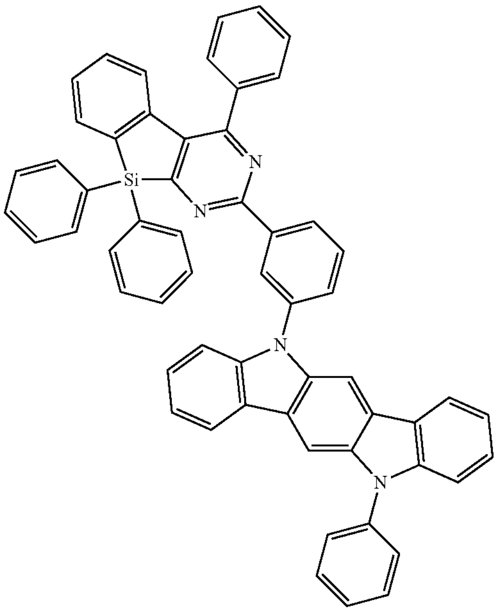
-continued
364
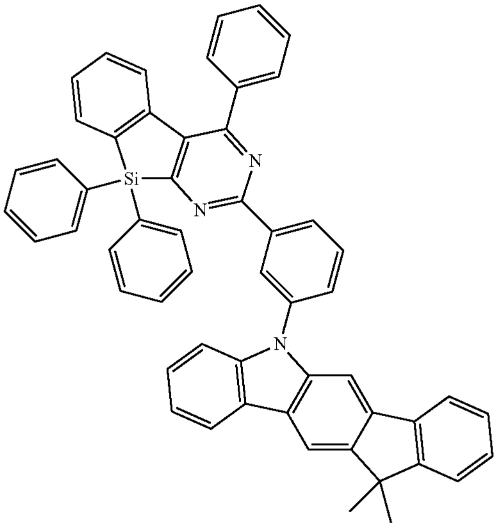
365
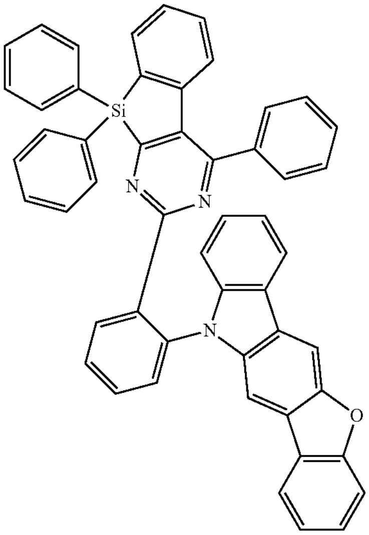
366
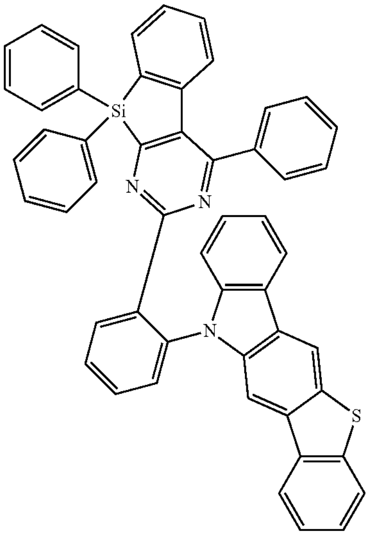

-continued
367
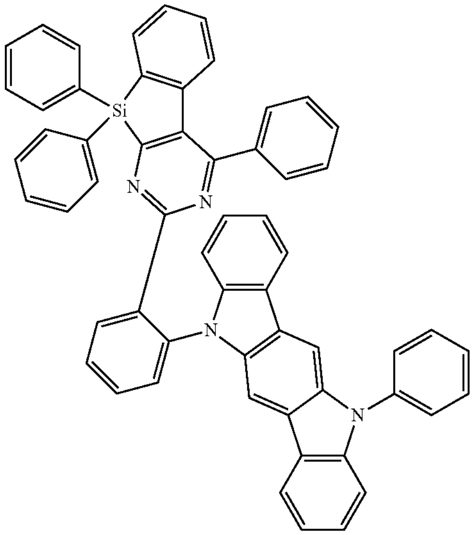
368
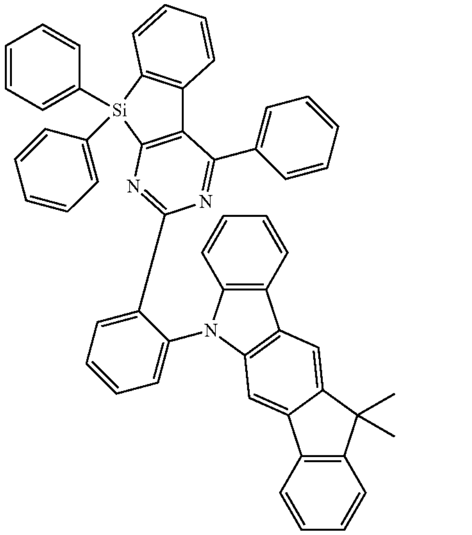
369
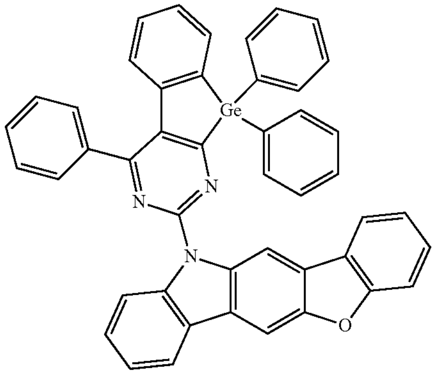
-continued
370
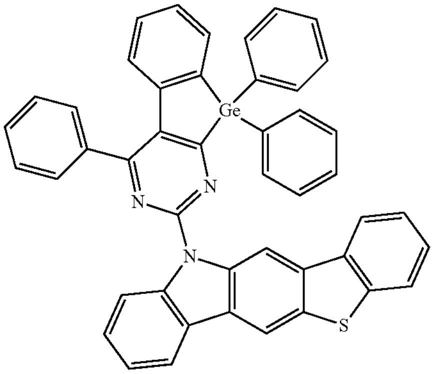
371
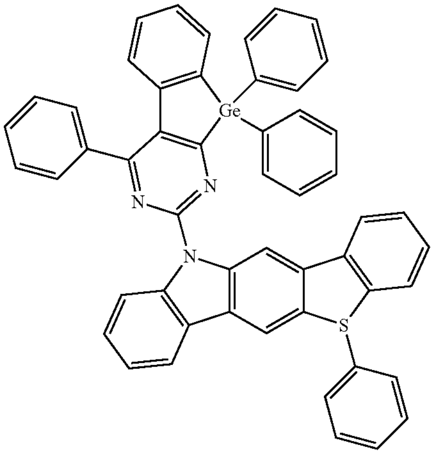
372
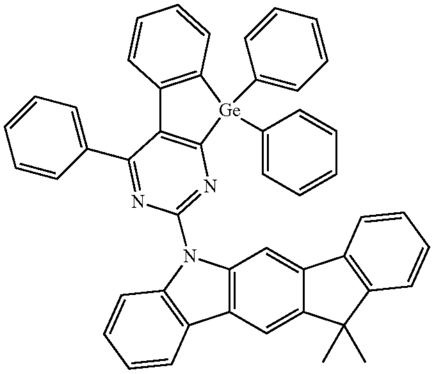

-continued
373
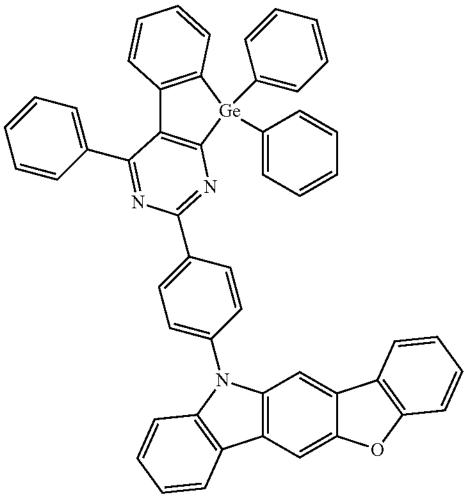
374
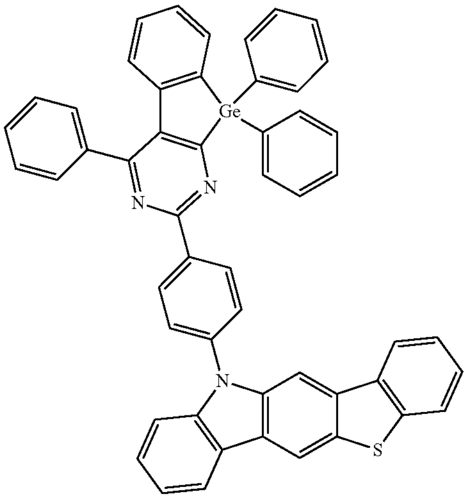
375
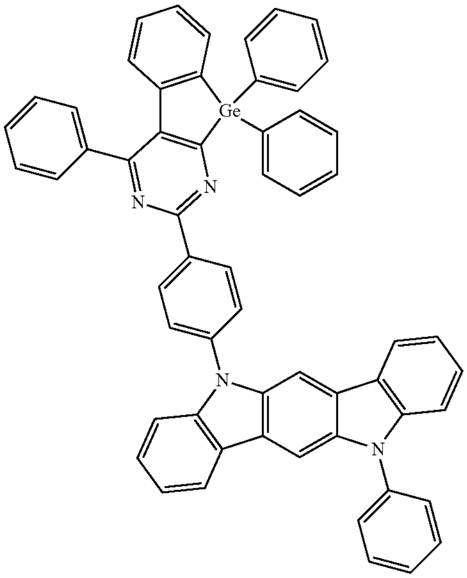
-continued
376
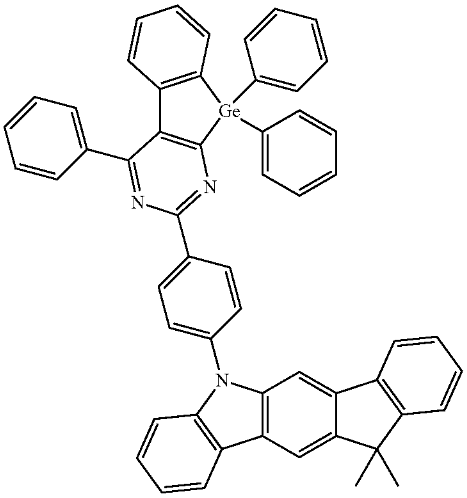
377
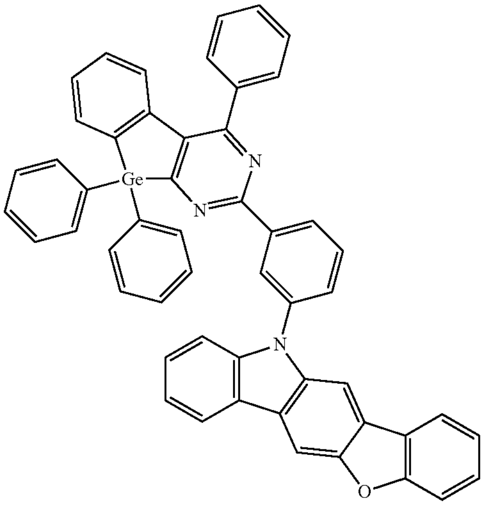
378
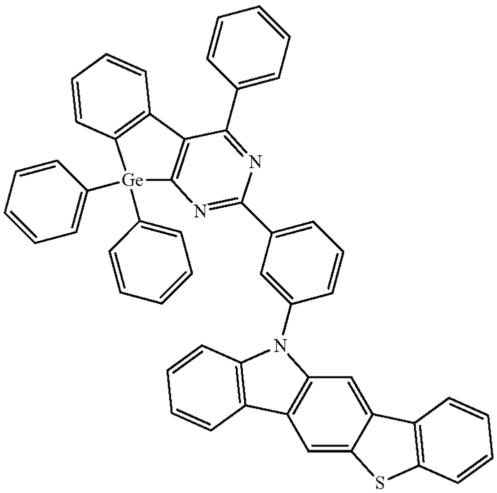

-continued
379
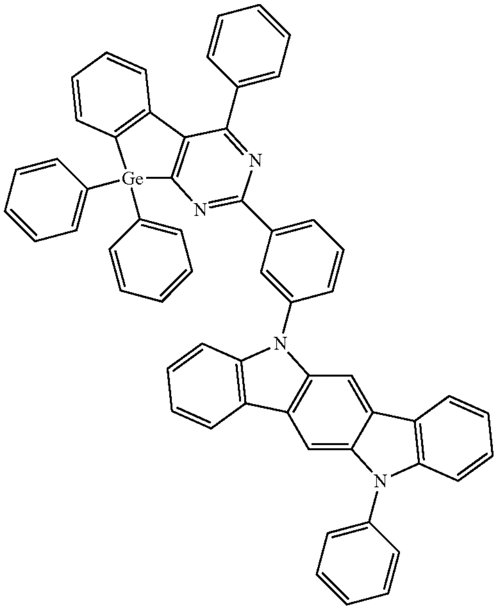
380
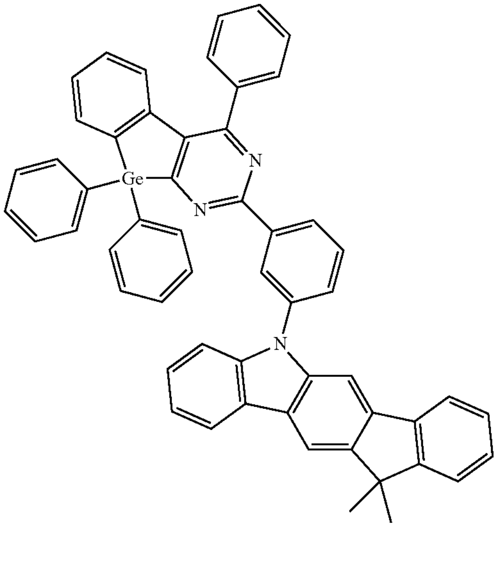
-continued
381
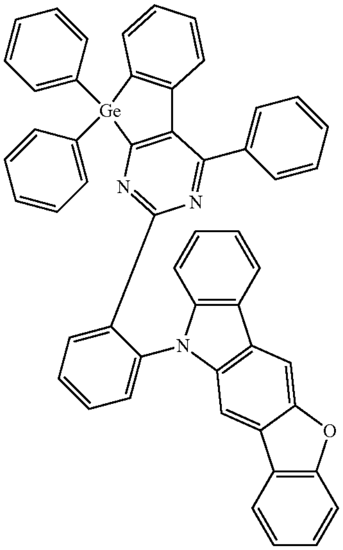
382
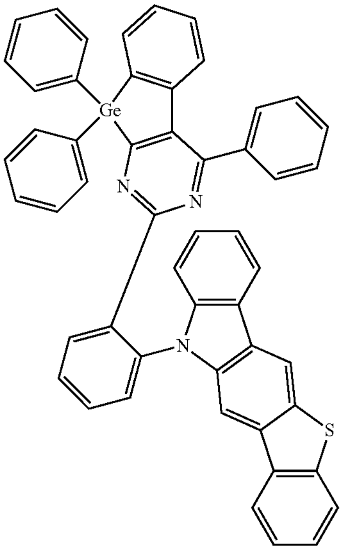
383
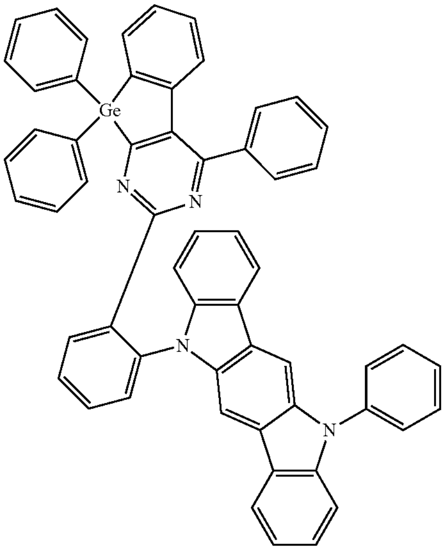

-continued
384
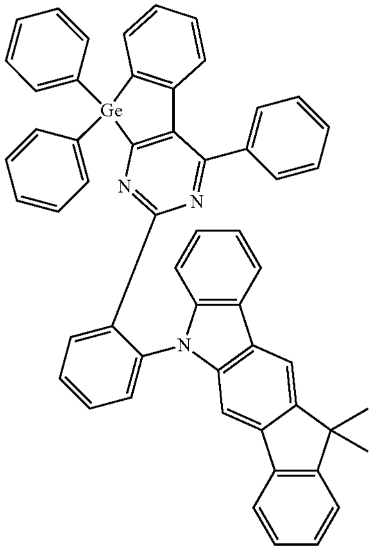
385
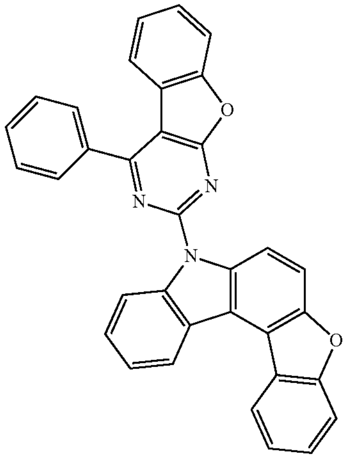
386
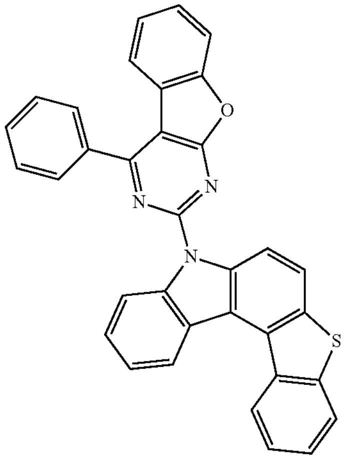
-continued
387
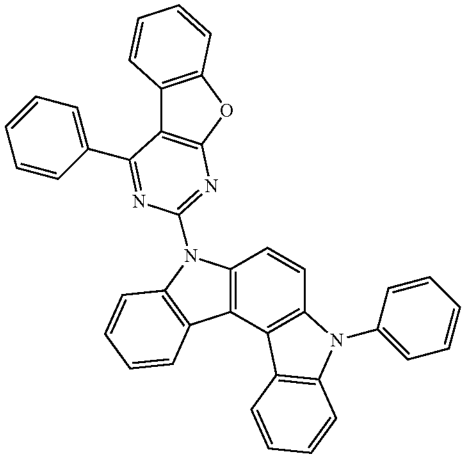
388
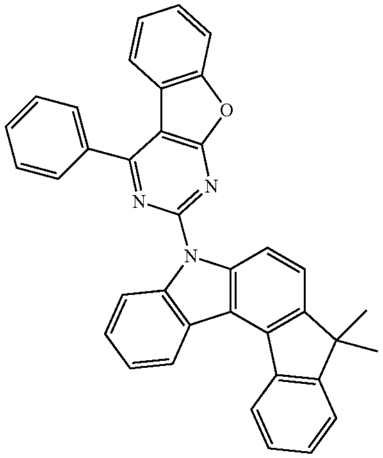
389
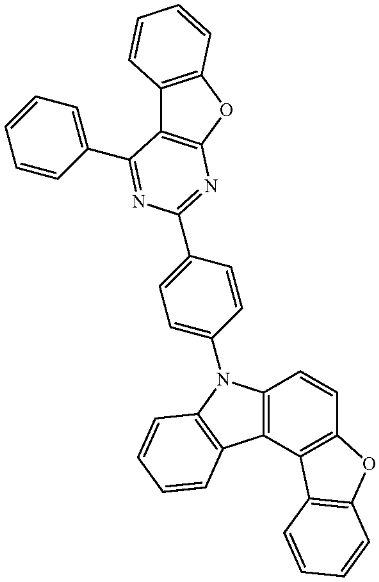

-continued
390
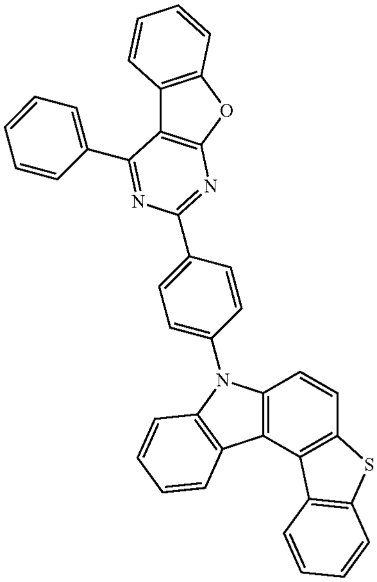
391
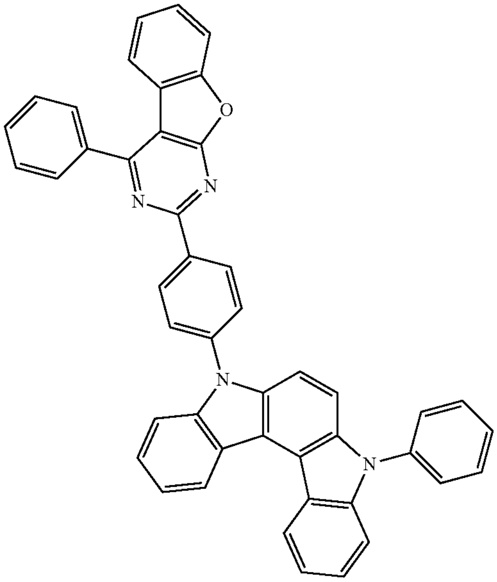
-continued
392
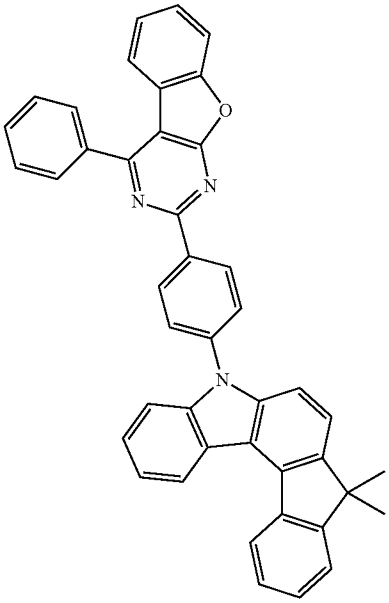
393
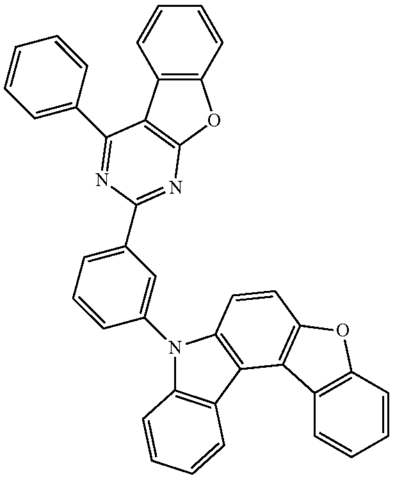
394
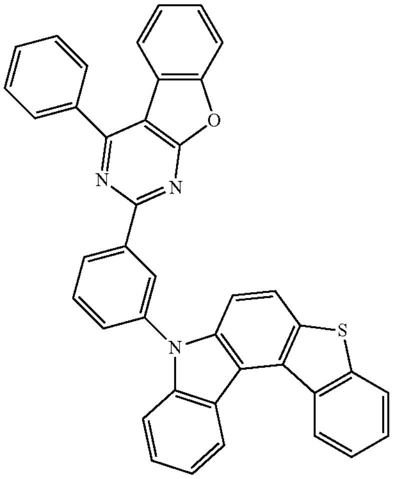

-continued
395
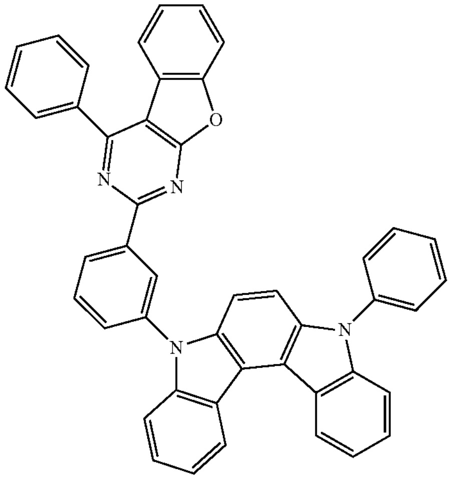
396
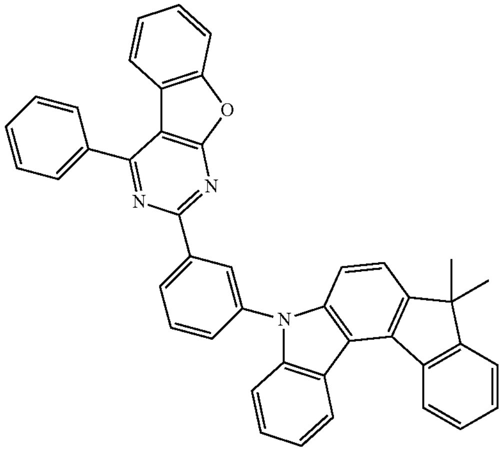
397
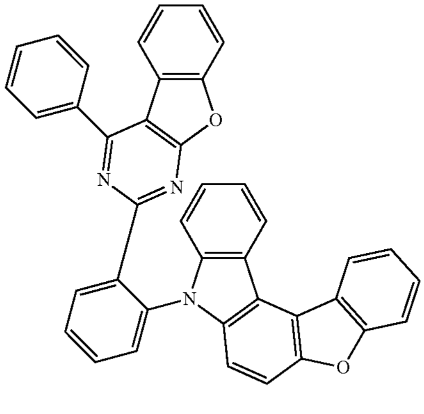
-continued
398
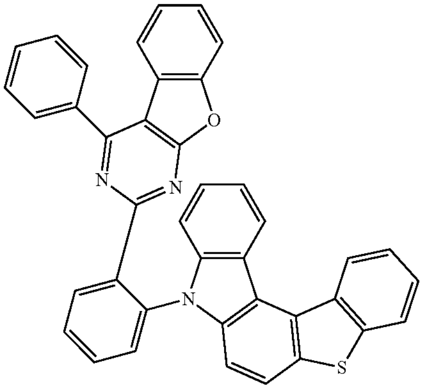
399
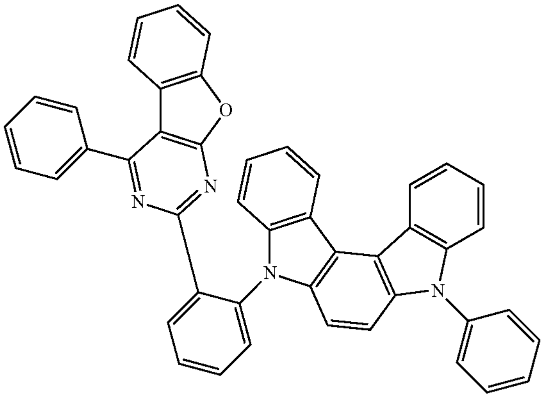
400
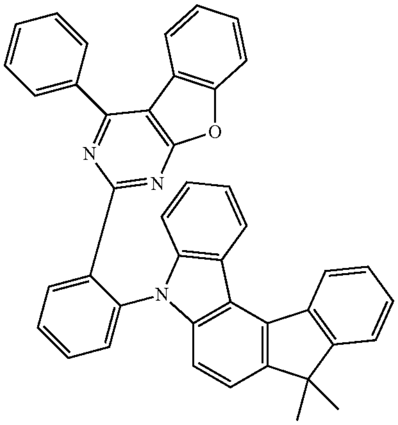

-continued
401
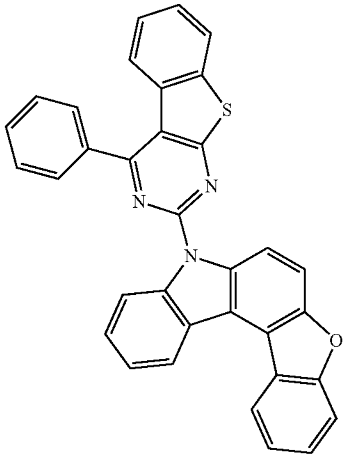
402
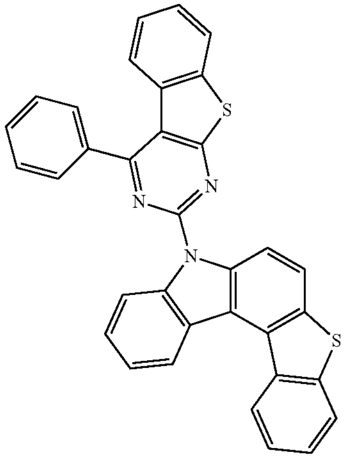
403
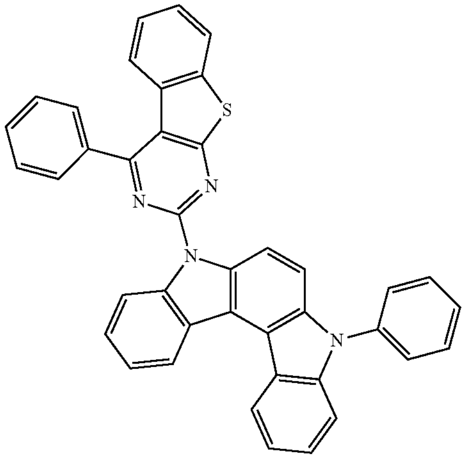
-continued
404
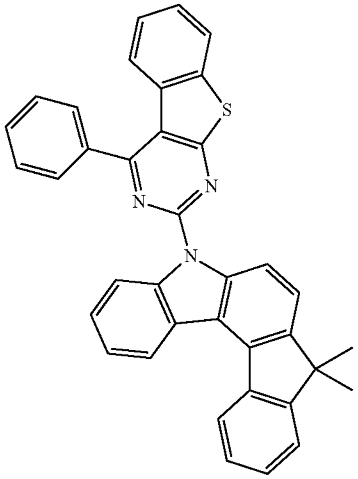
405
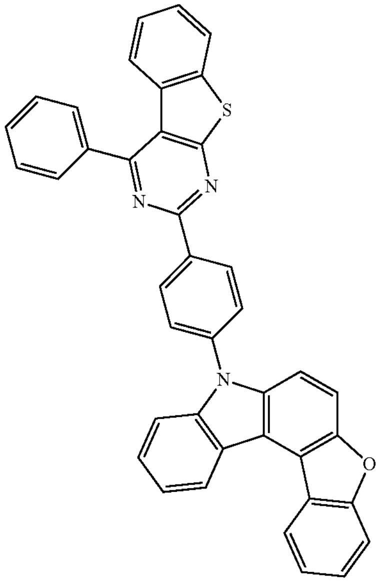
406
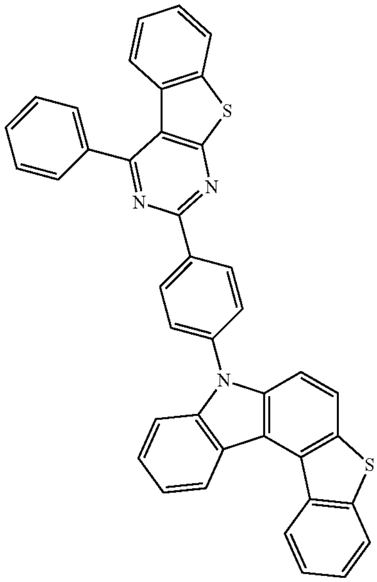

-continued
407
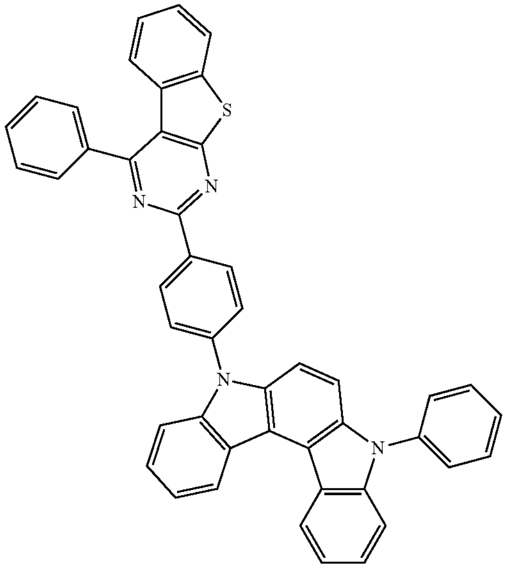
408
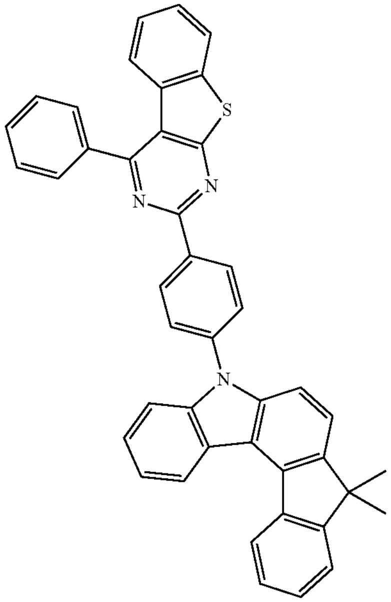
-continued
409
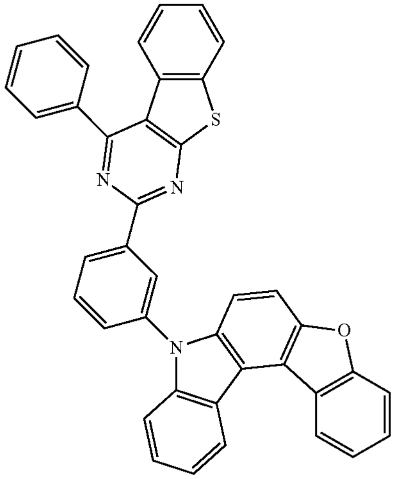
410
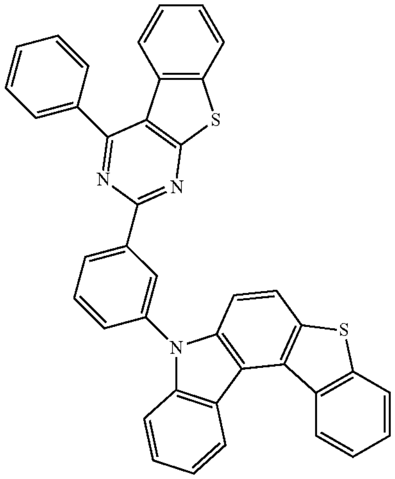
411
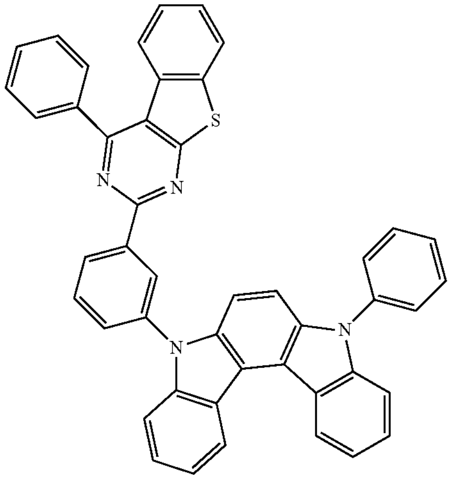

-continued
412
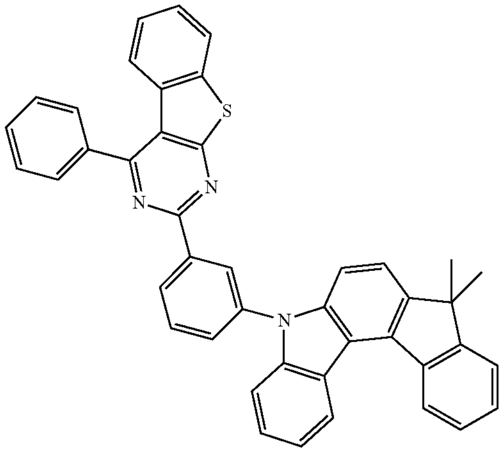
413
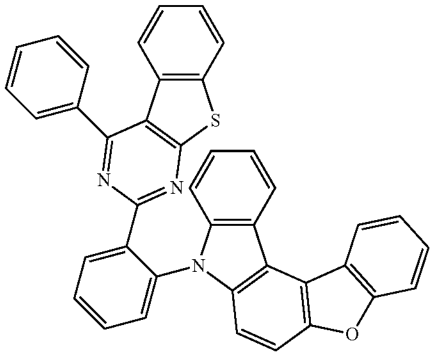
414
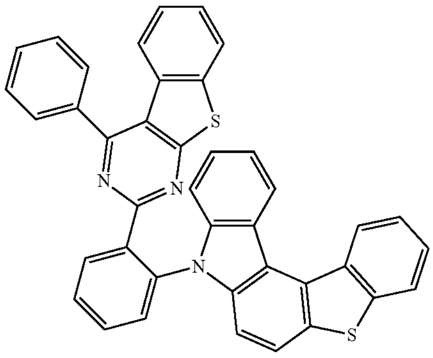
-continued
415
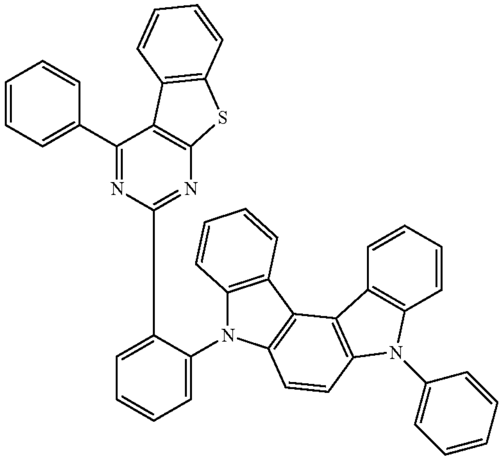
416
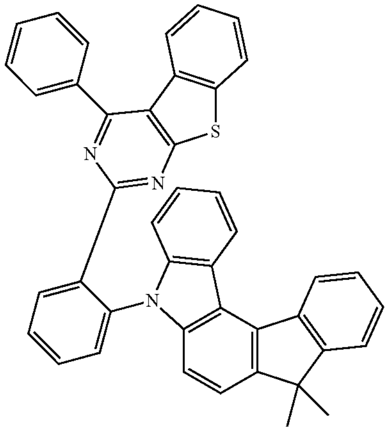
417
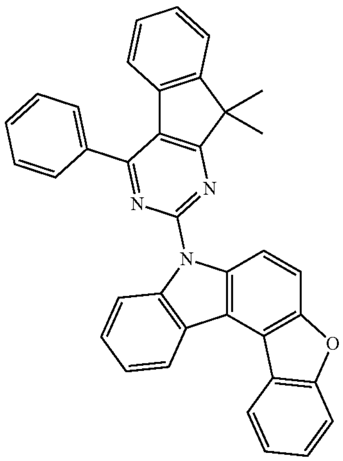

418
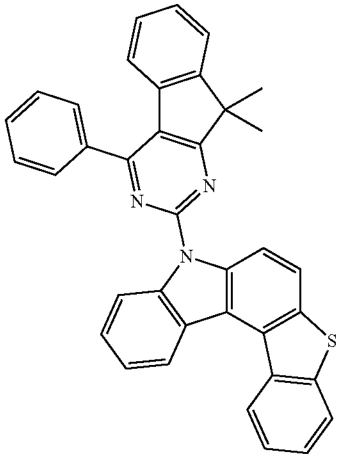
419
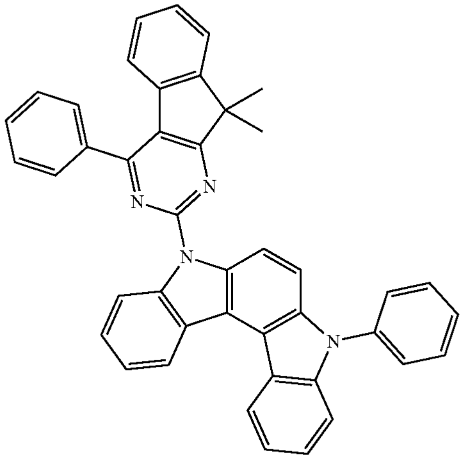
420
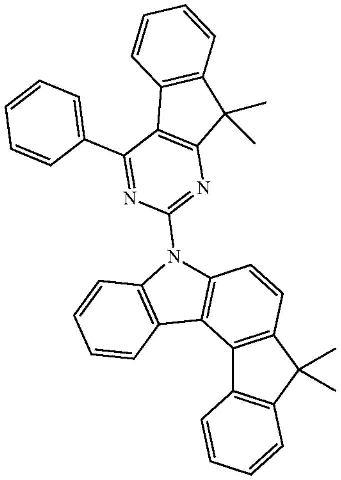
421
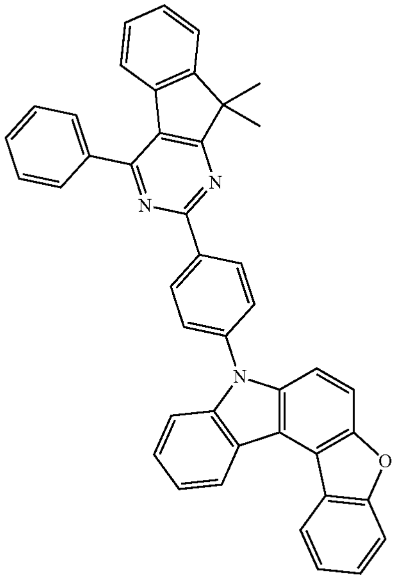
422
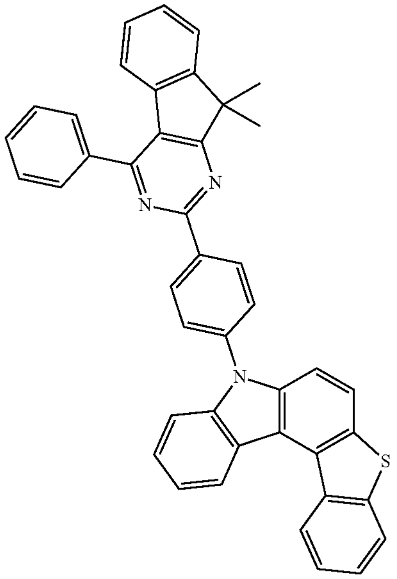

-continued
423
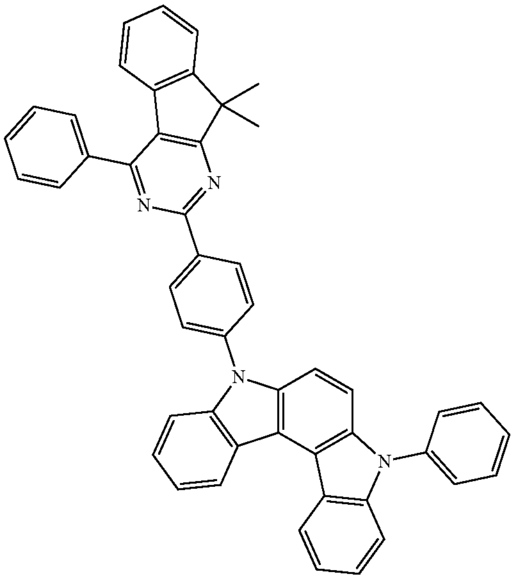
424
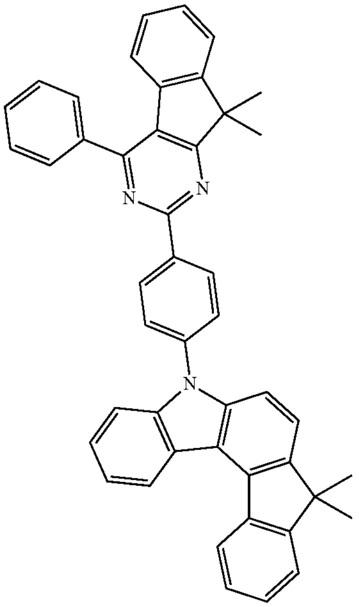
-continued
425
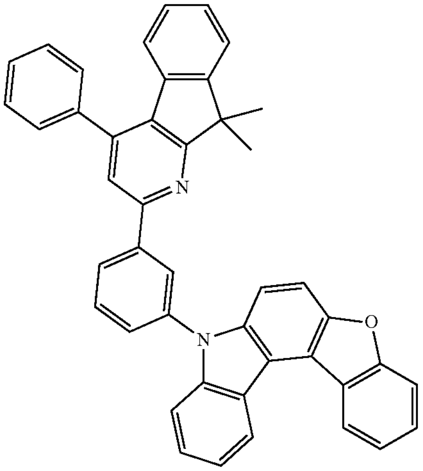
426
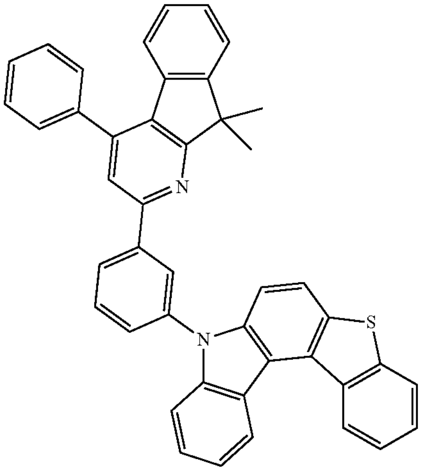
427
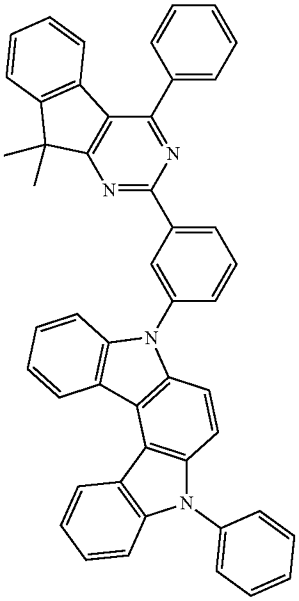

-continued
428
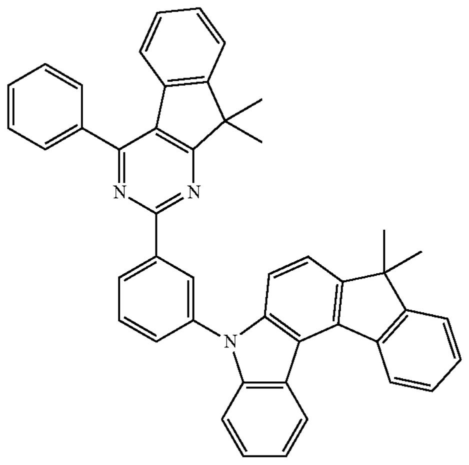
429
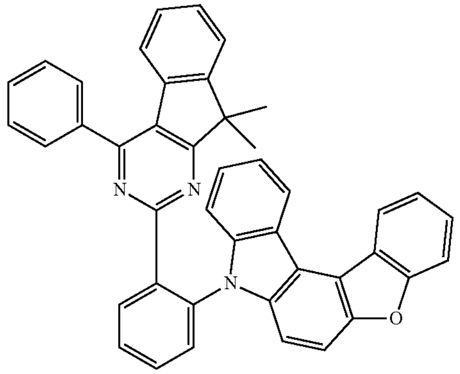
430
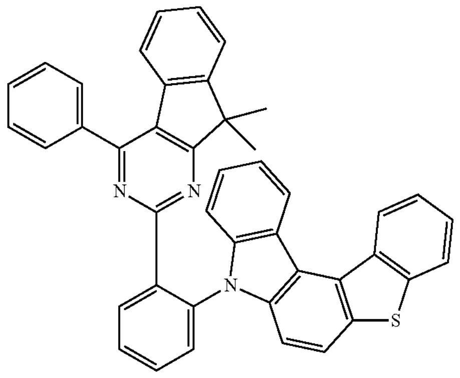
-continued
431
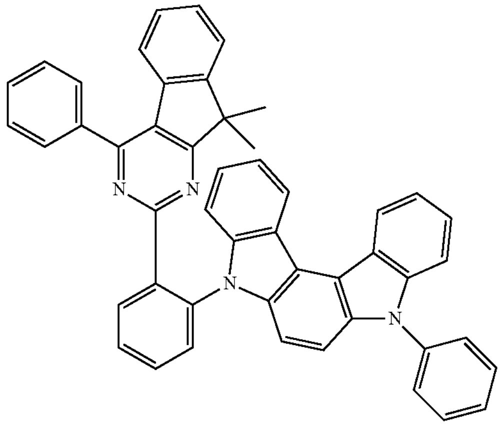
432
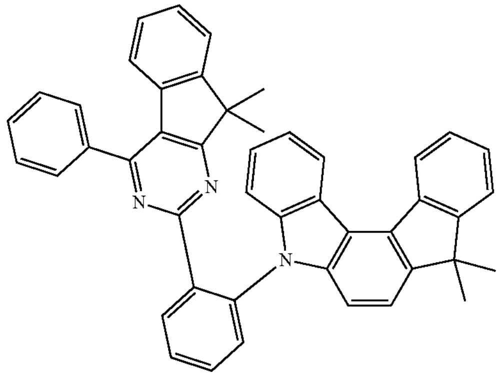
433
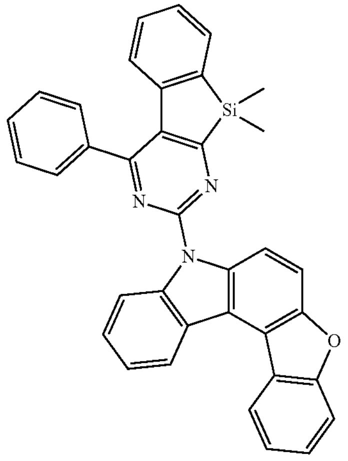

-continued
434
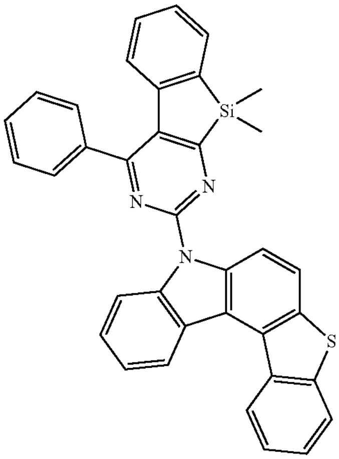
435
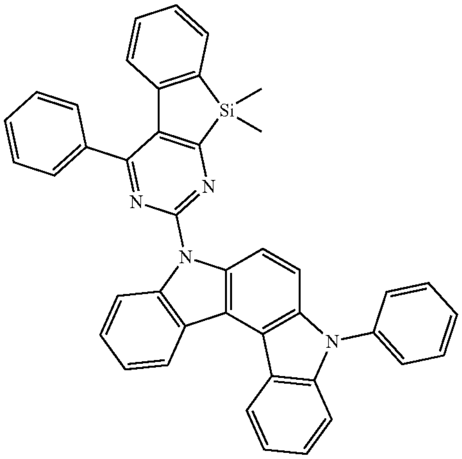
436
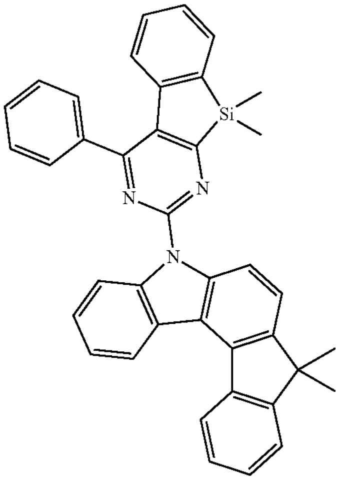
-continued
437
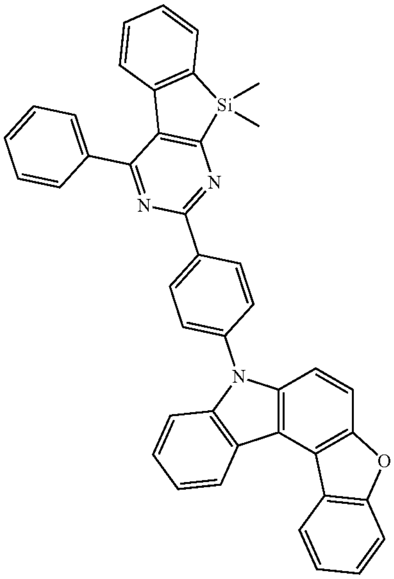
438
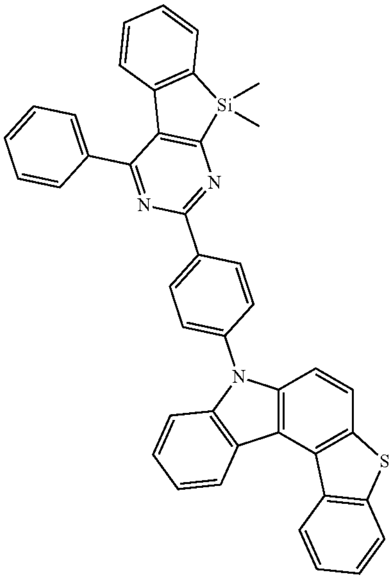

-continued
439
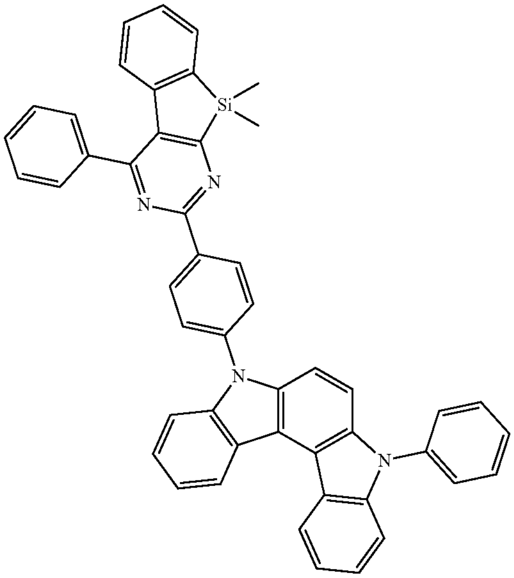
440
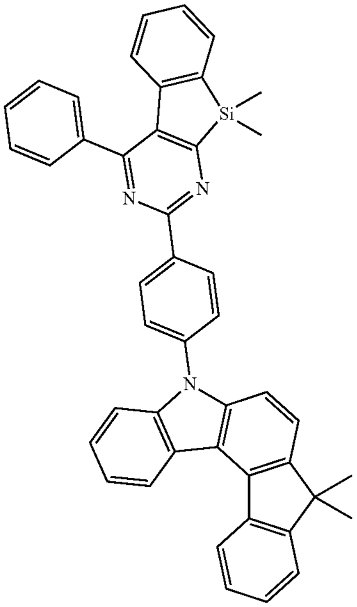
-continued
441
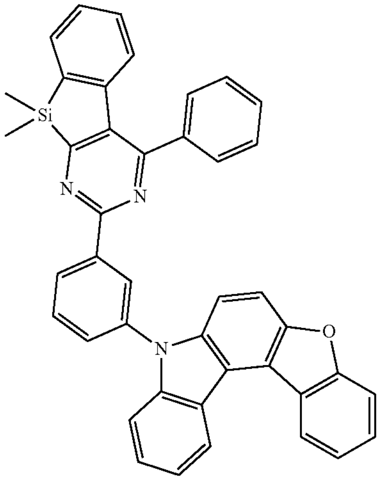
442
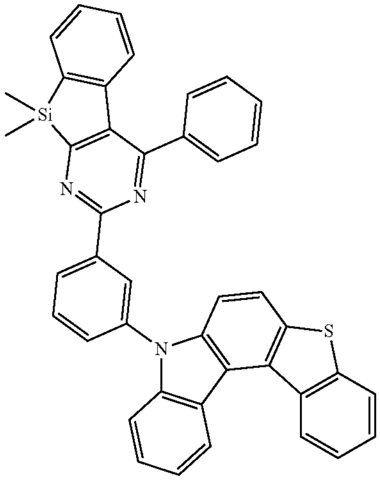
443
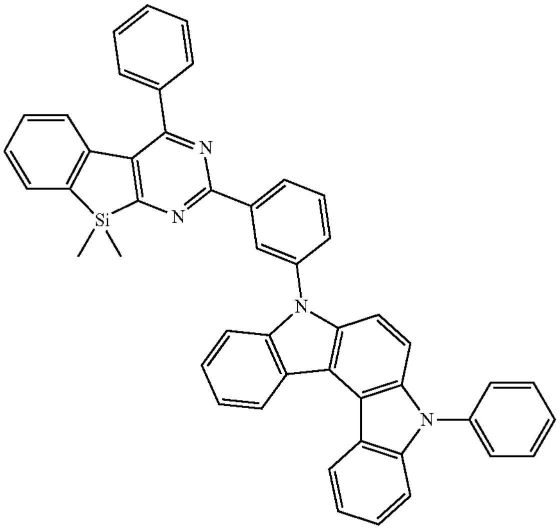

-continued
444
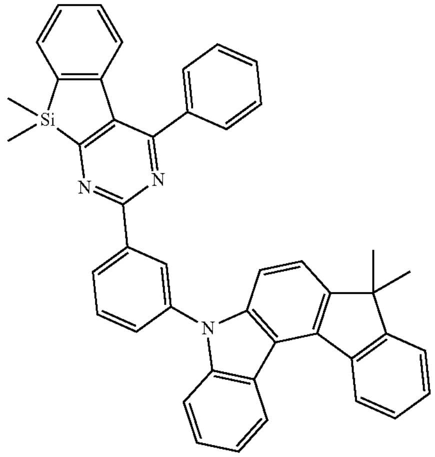
445
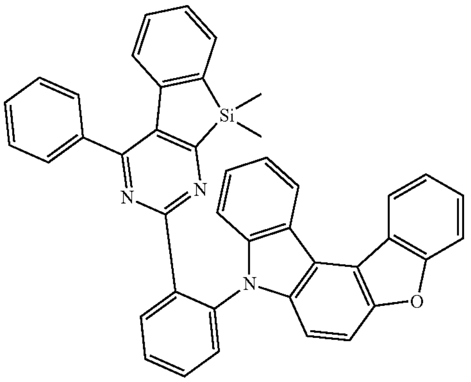
446
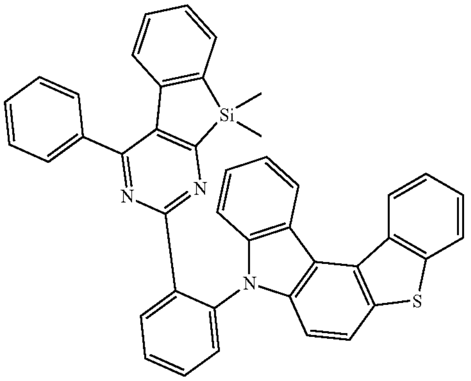
-continued
447
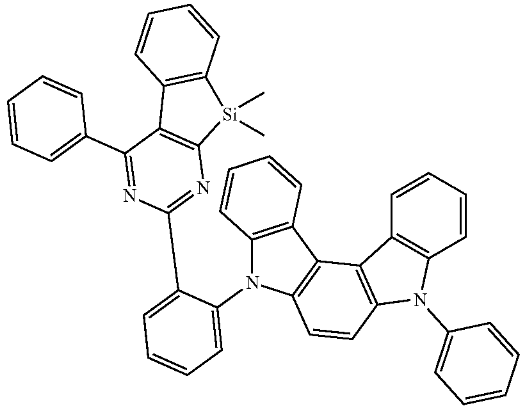
448
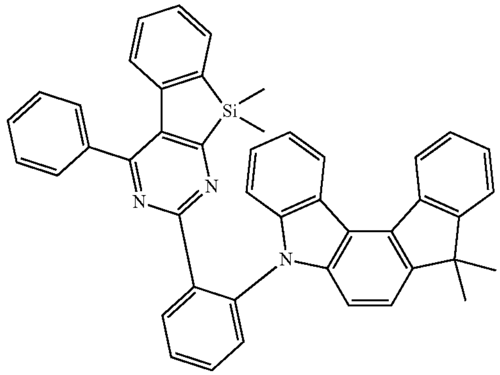
449
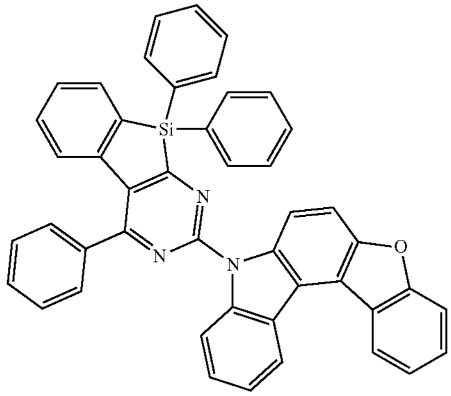
450
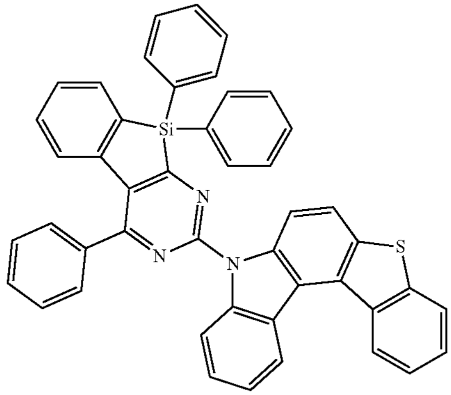

-continued
451
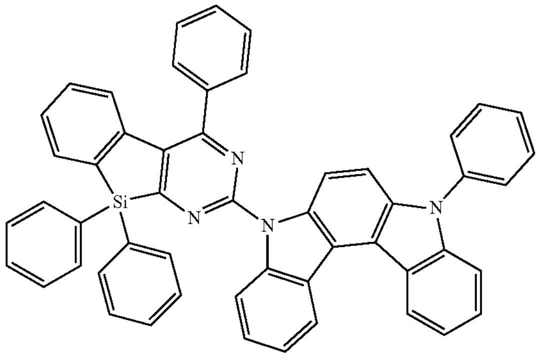
452
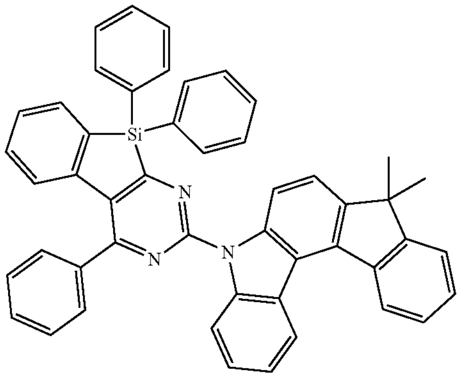
453
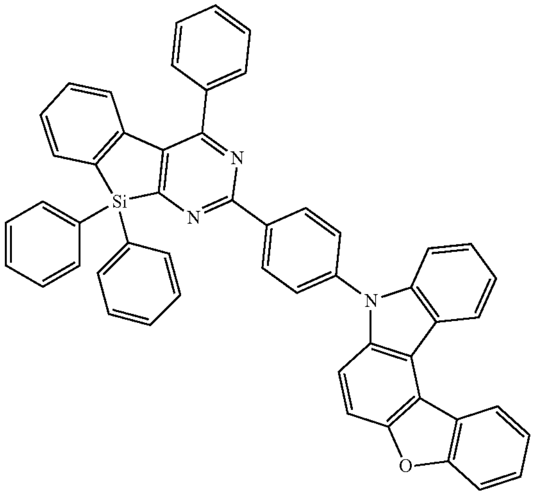
-continued
454
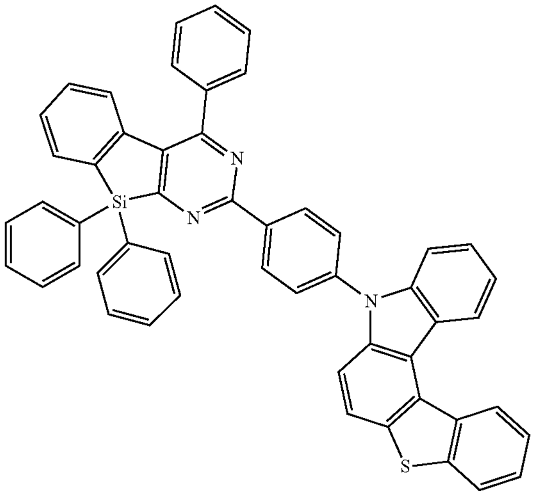
455
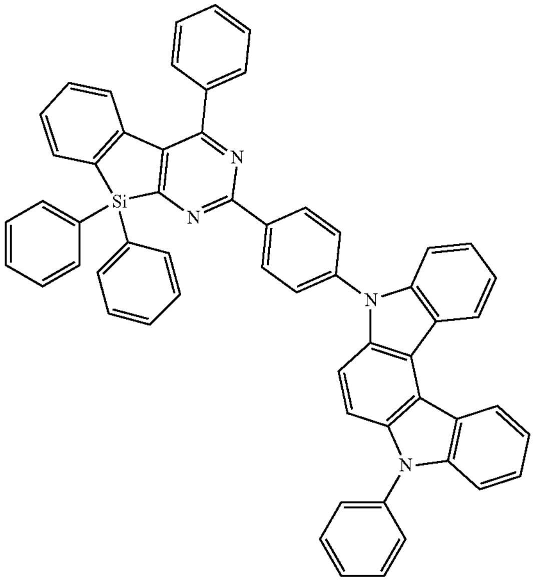
456
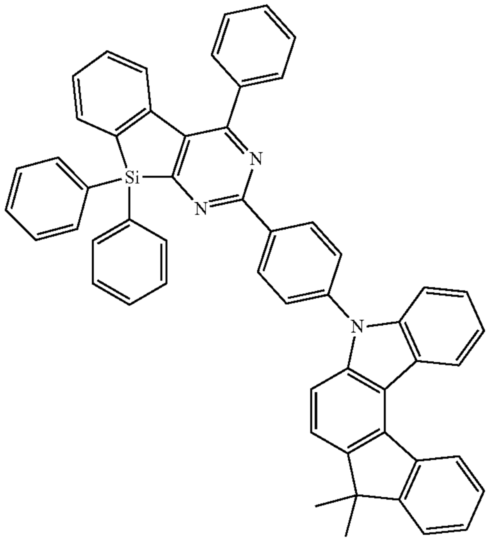

457
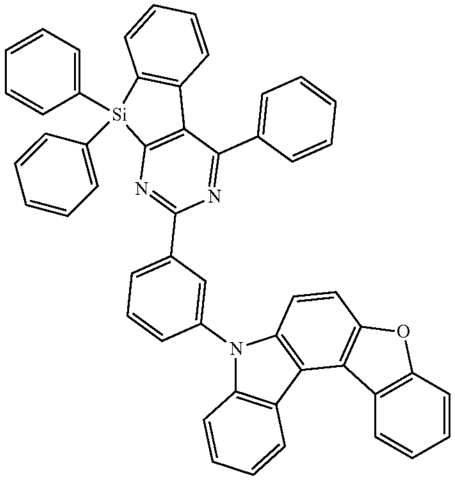
458
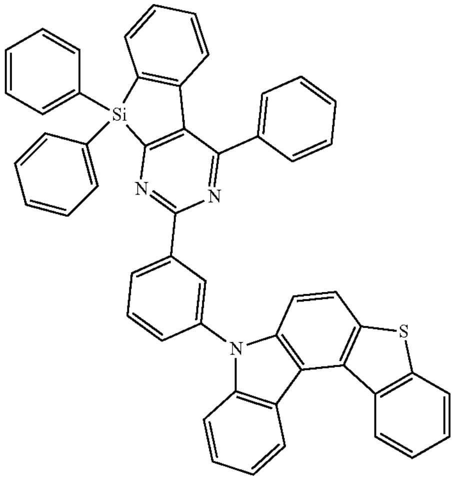
459
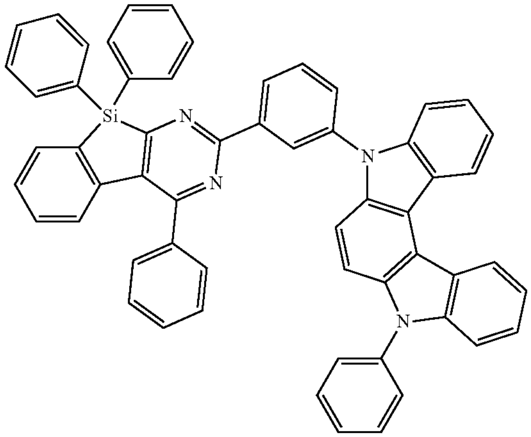
460
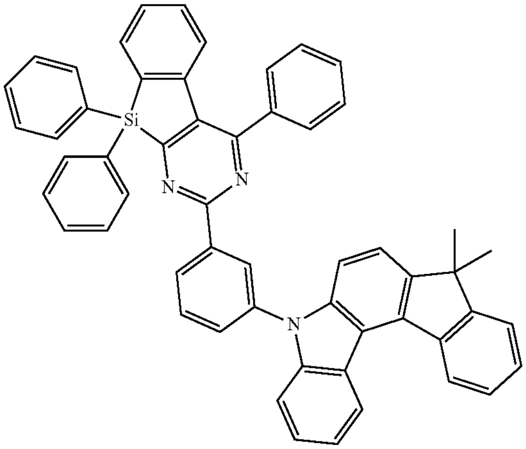
461
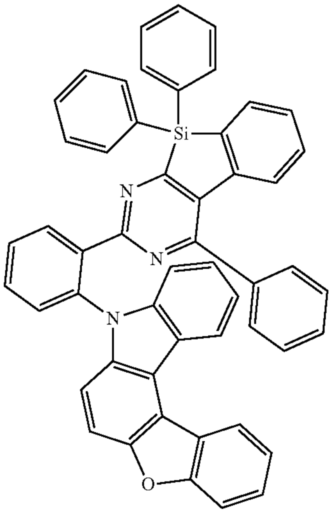
462
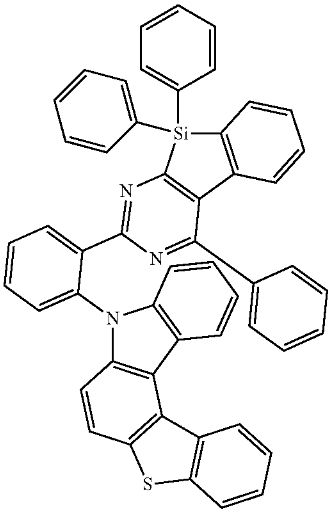

-continued
463
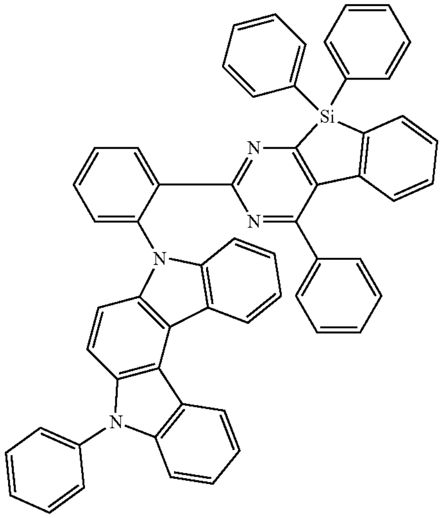
464
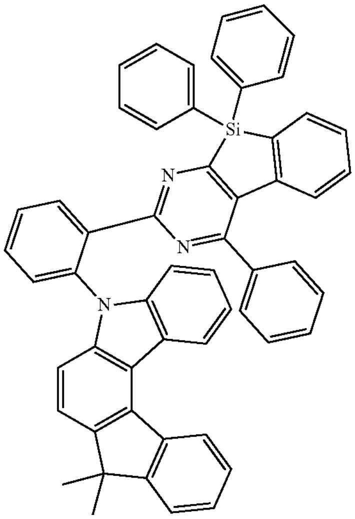
465
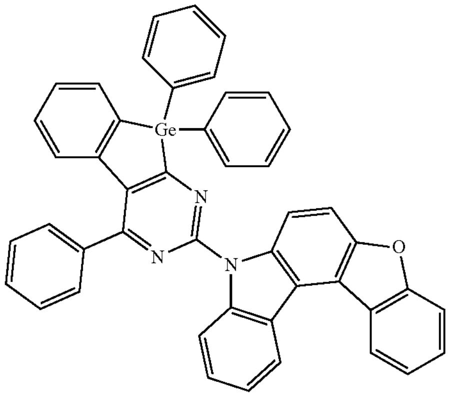
-continued
466
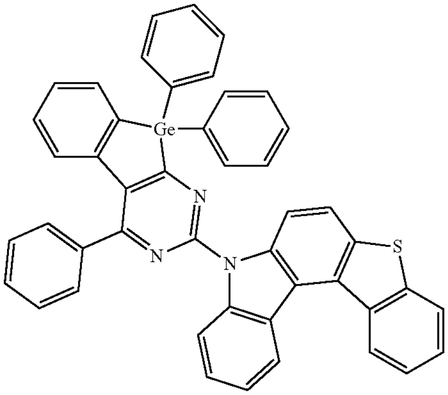
467
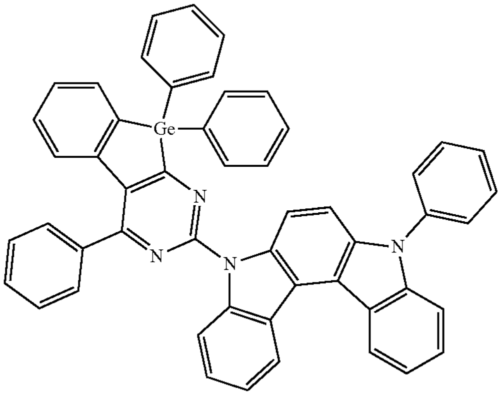
468
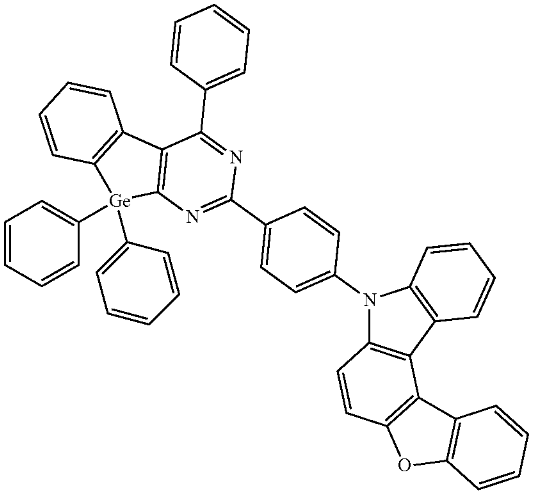

-continued
469
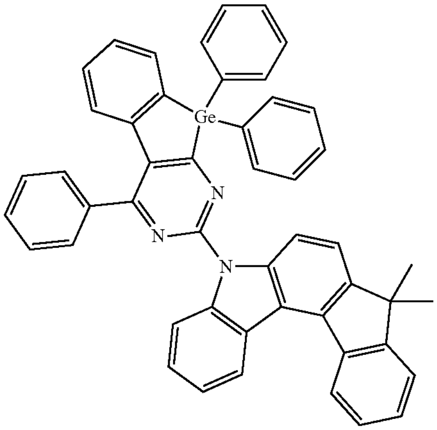
470
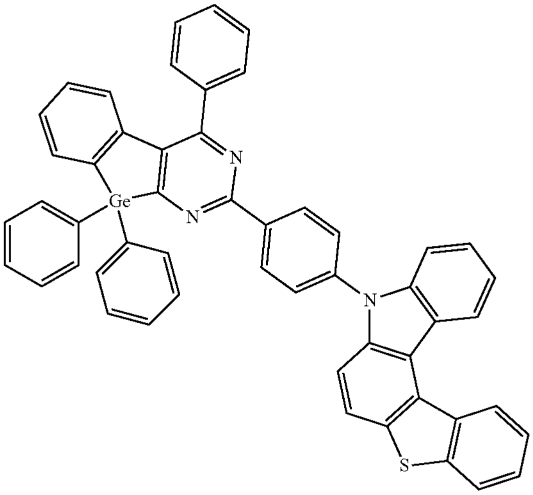
471
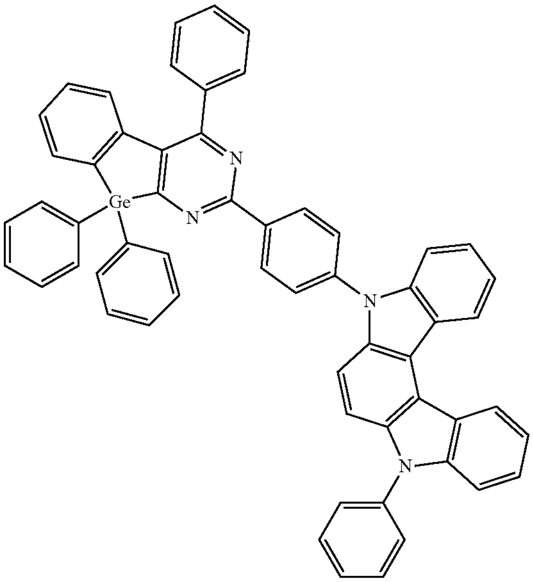
-continued
472
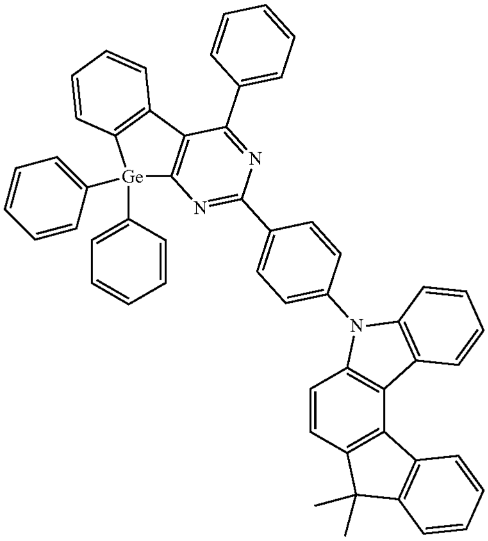
473
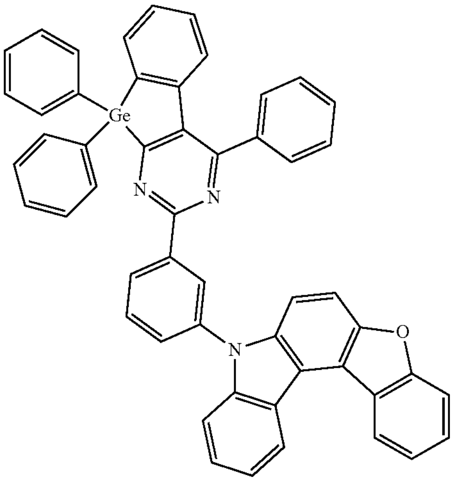
474
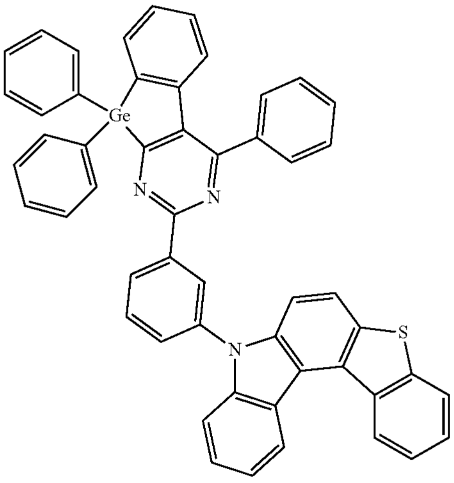

475
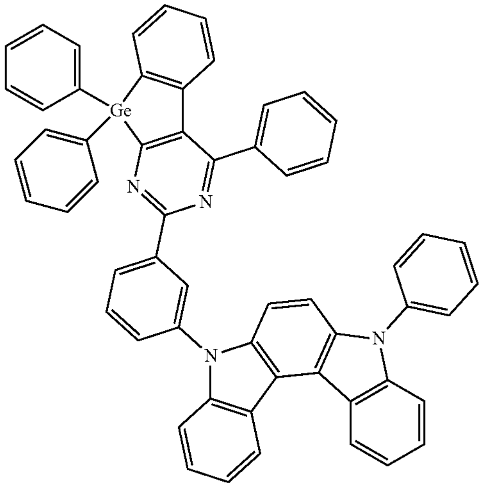
476
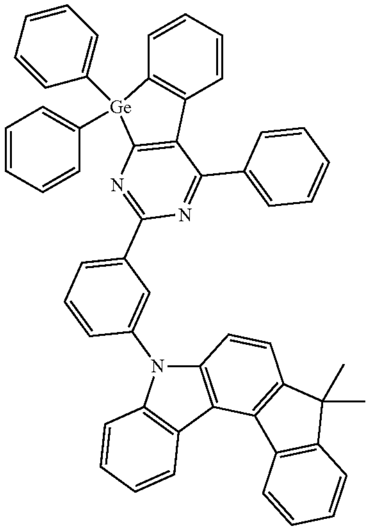
477
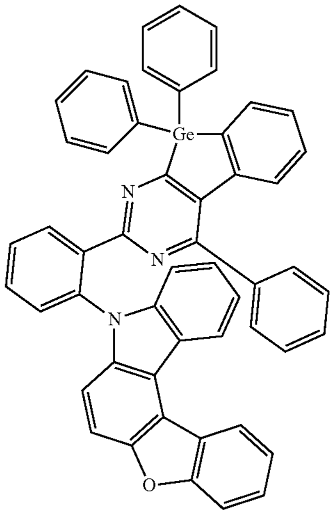
478
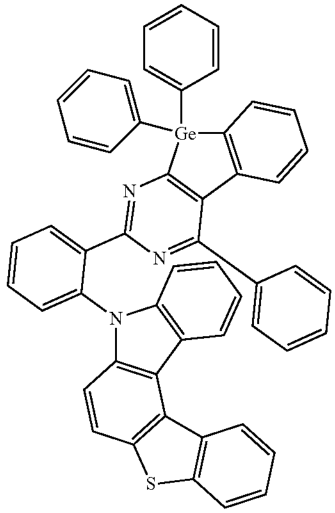
479
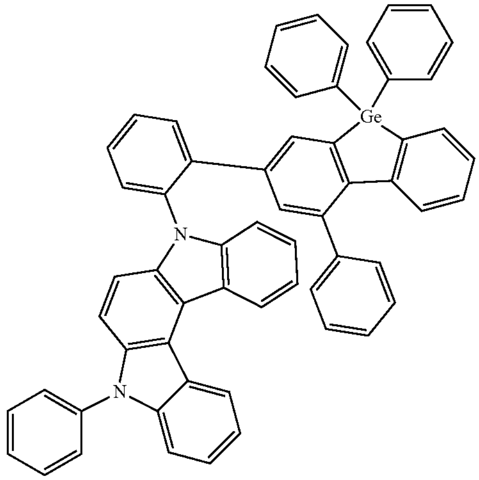
480
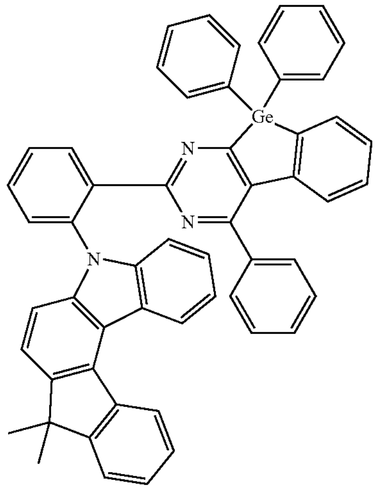

-continued
481
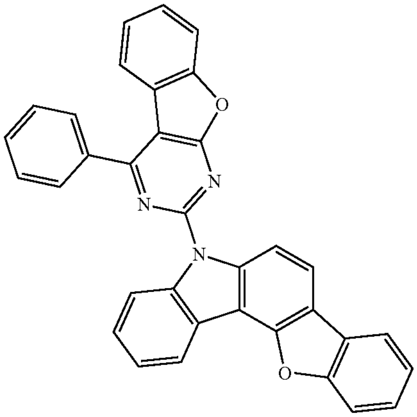
482
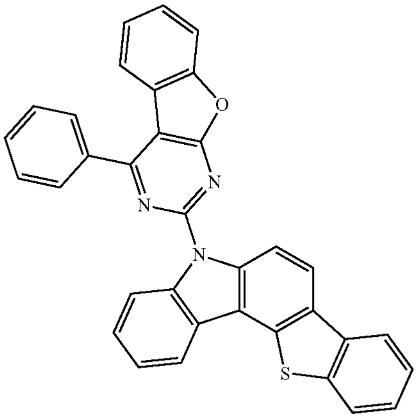
483
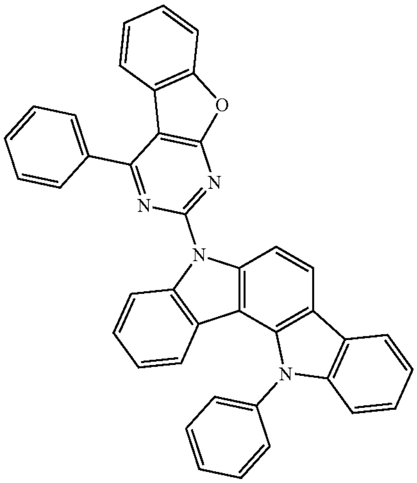
-continued
484
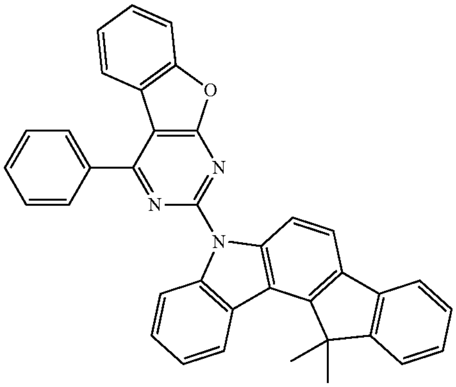
485
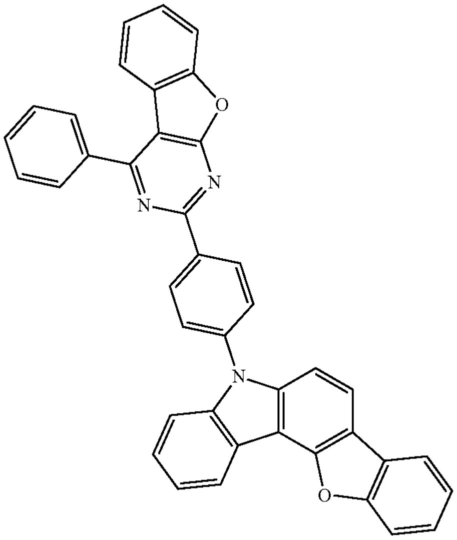
486
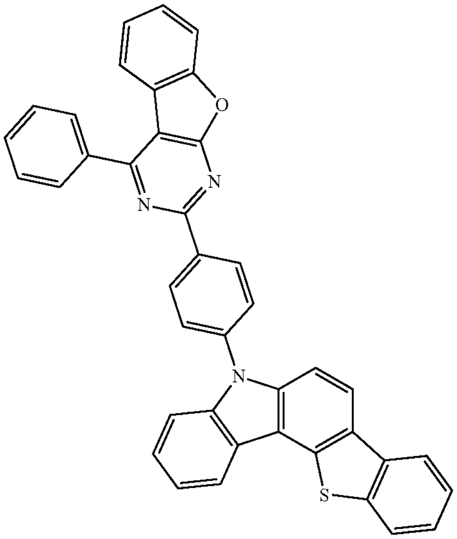

-continued
487
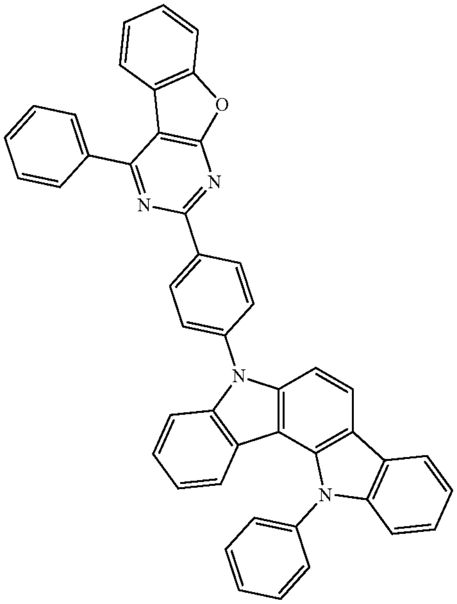
488
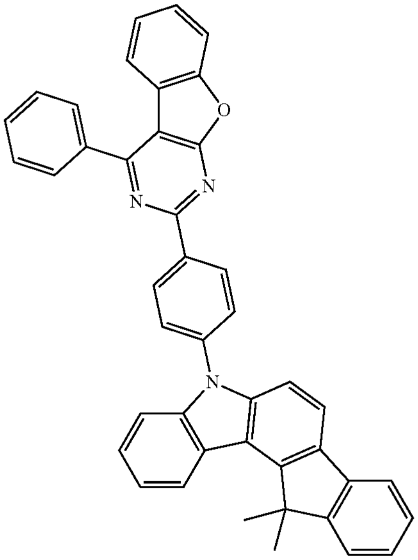
489
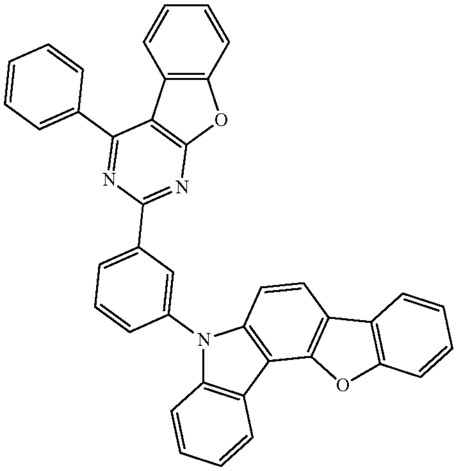
-continued
490
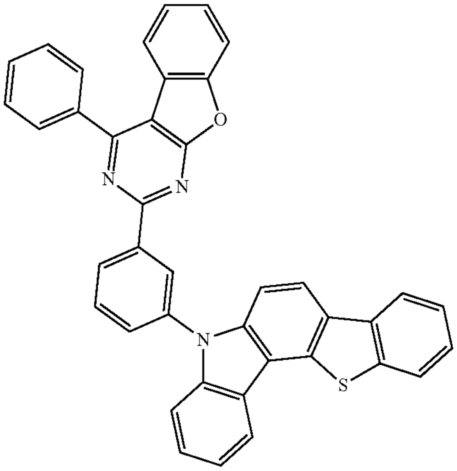
491
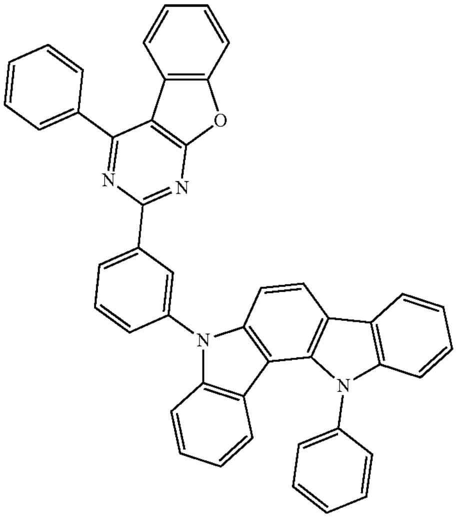
492
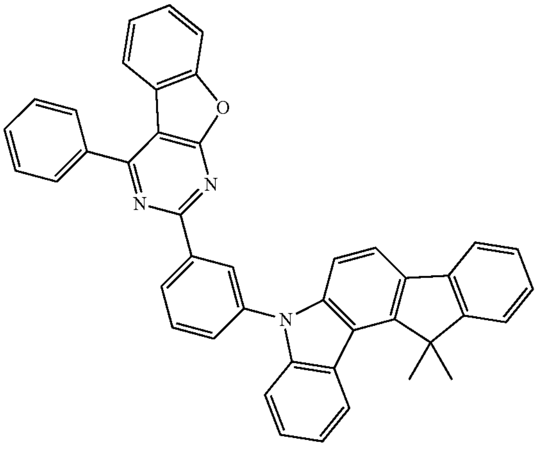

-continued
493
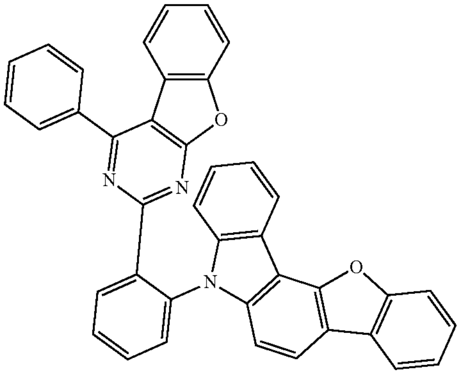
494
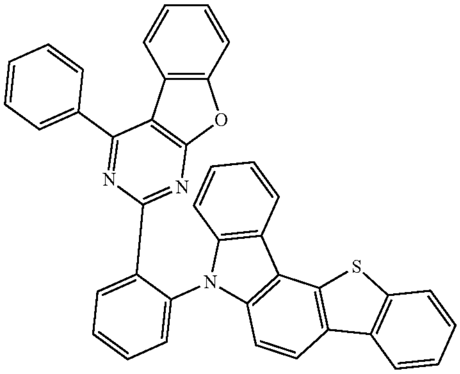
495
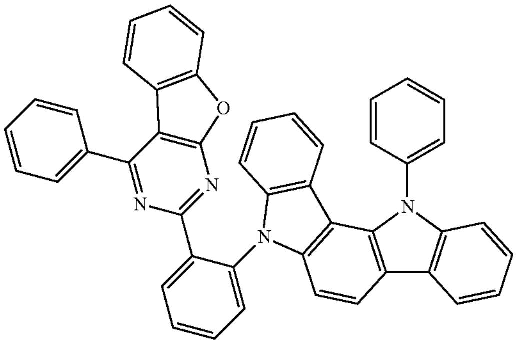
496
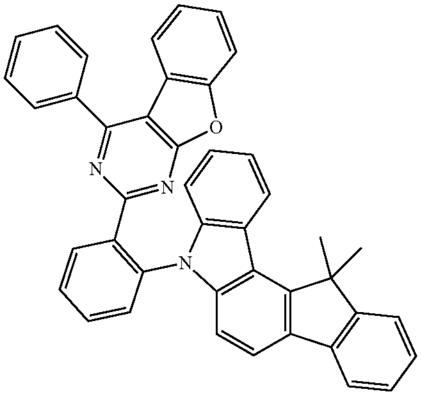
-continued
497
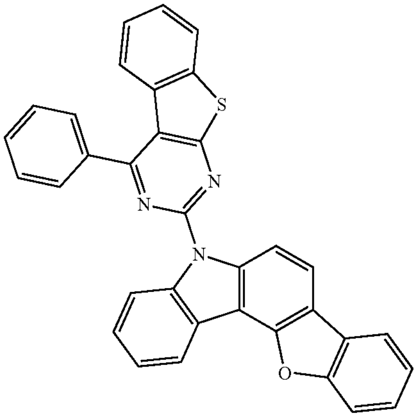
498
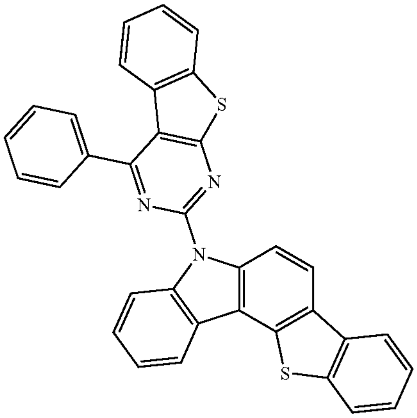
499
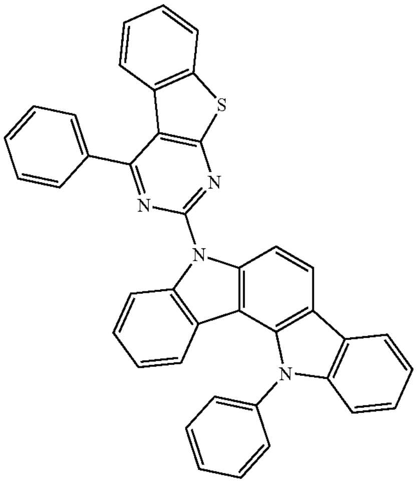

-continued
500
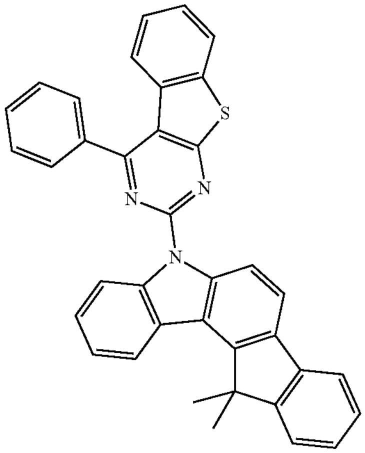
501
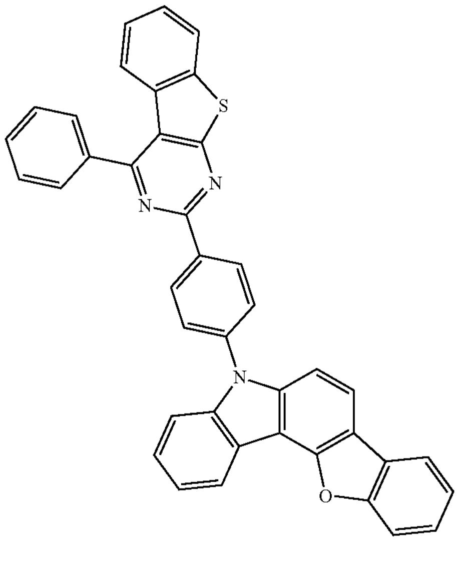
502
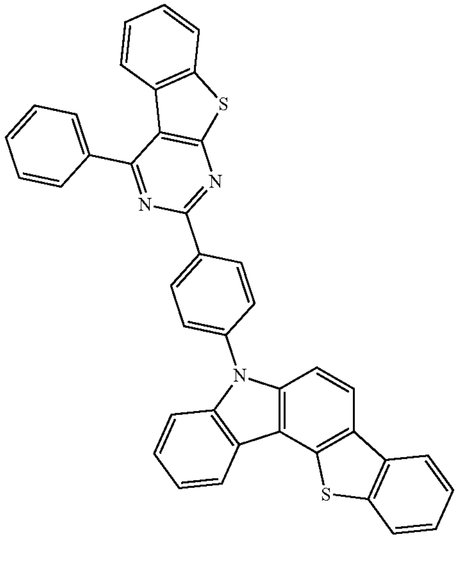
-continued
503
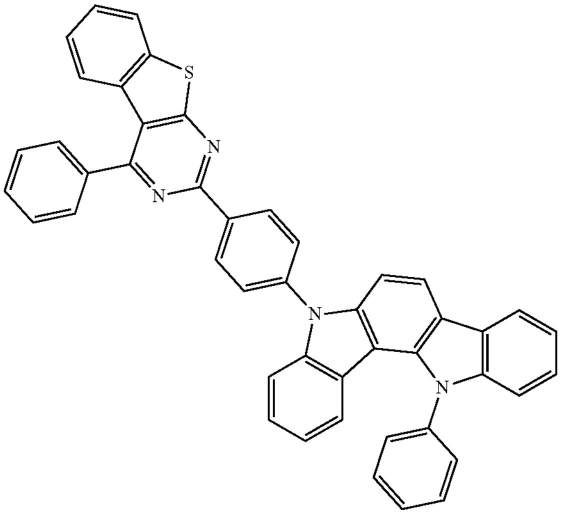
504
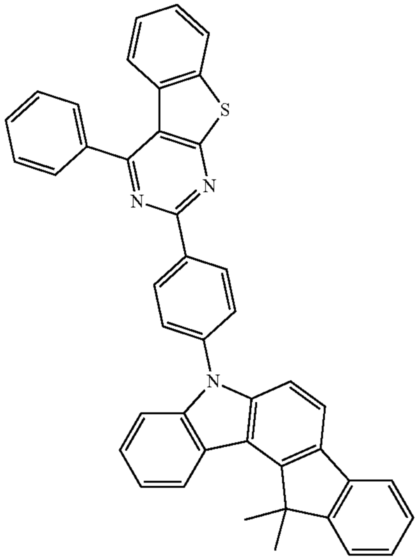
505
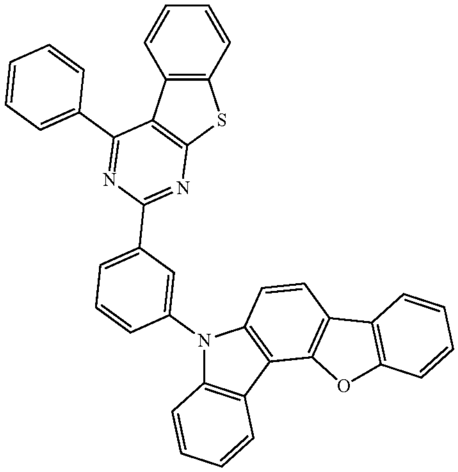

-continued
506
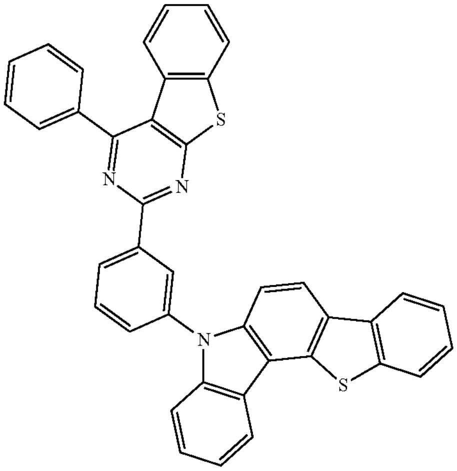
507
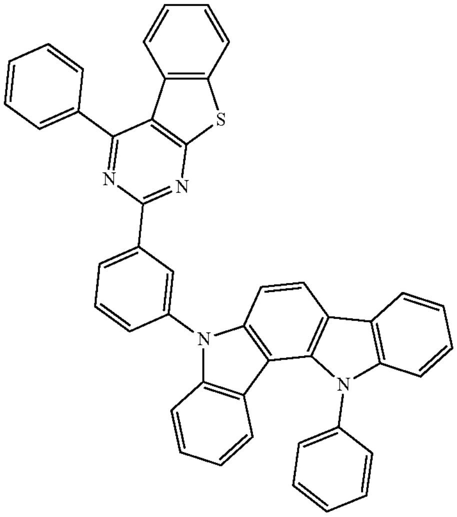
508
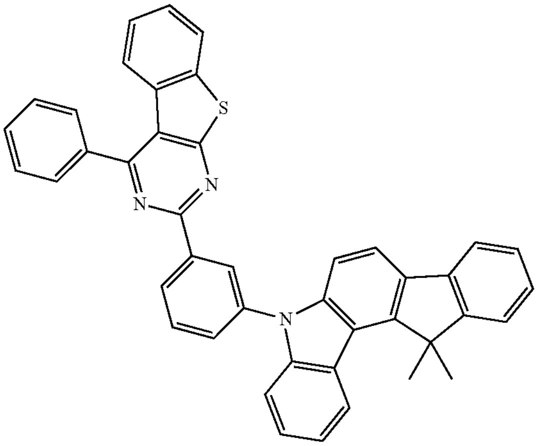
-continued
509
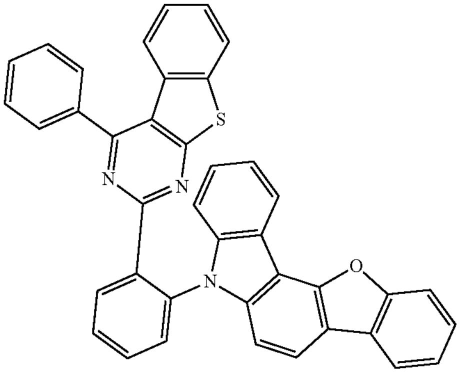
510
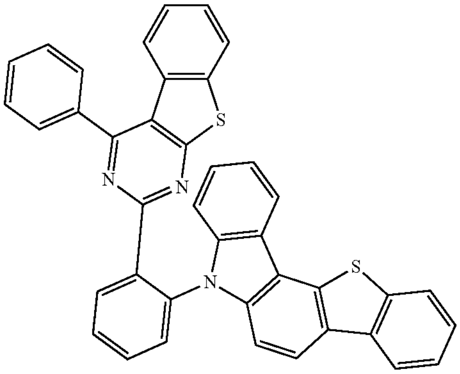
511
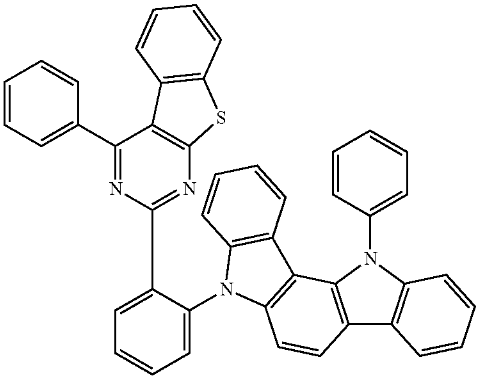
512
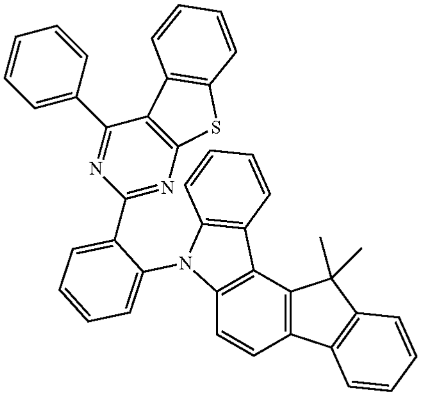

-continued
513
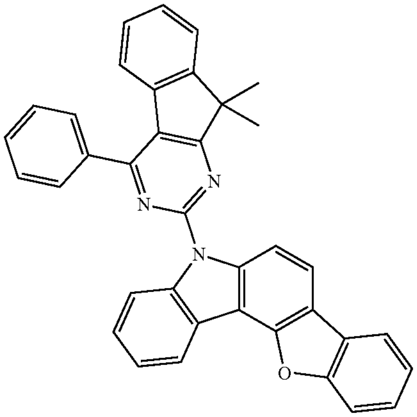
514
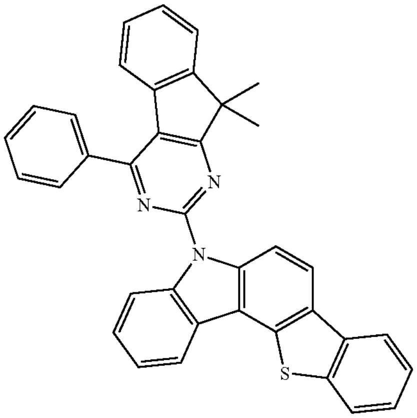
515
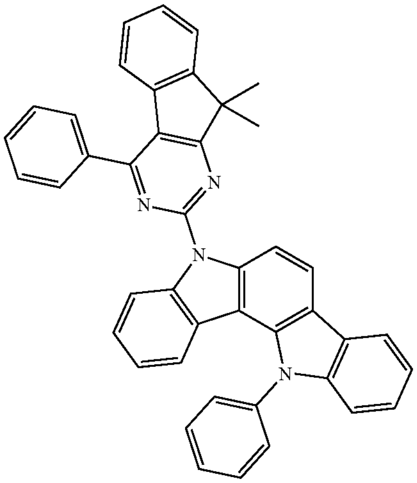
-continued
516
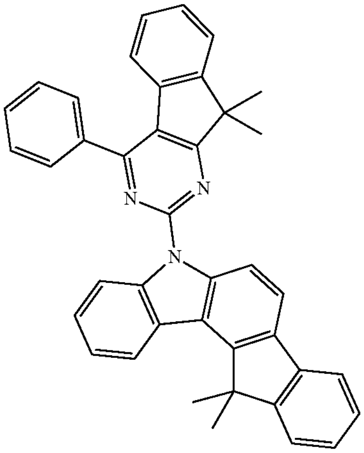
517
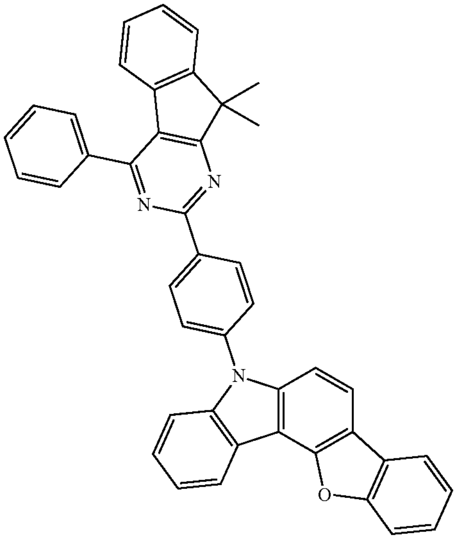
518
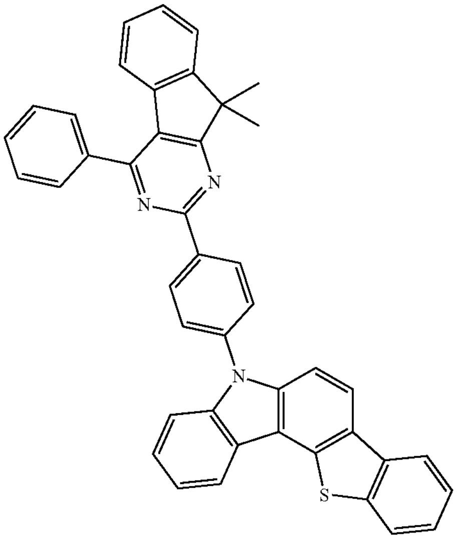

-continued
519
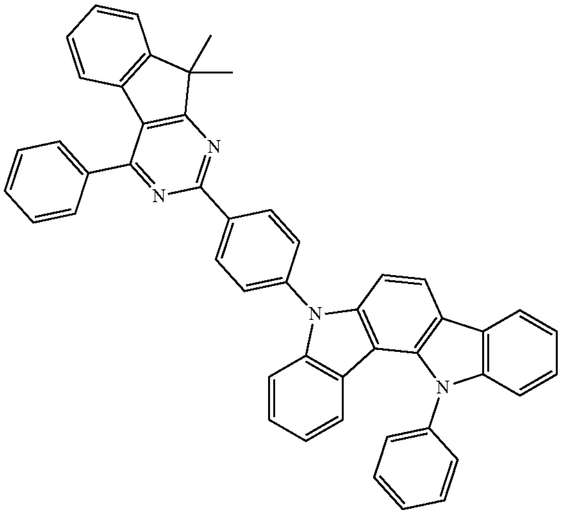
520
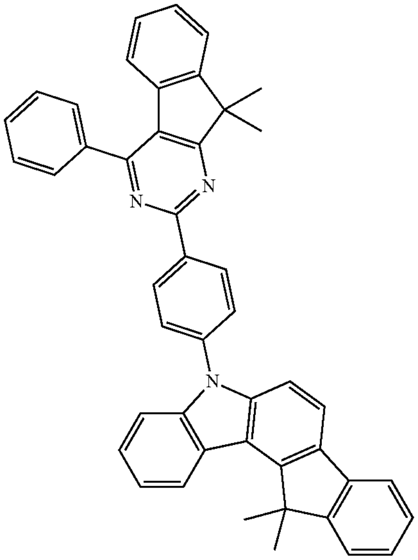
521
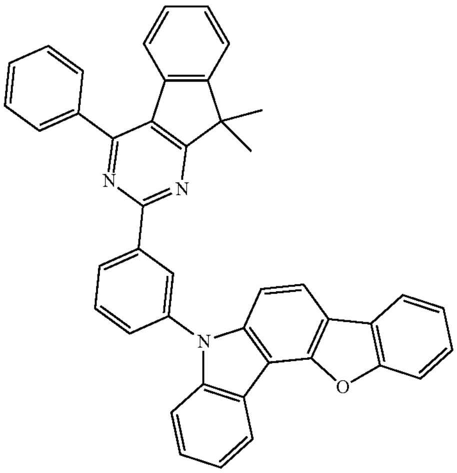
-continued
522
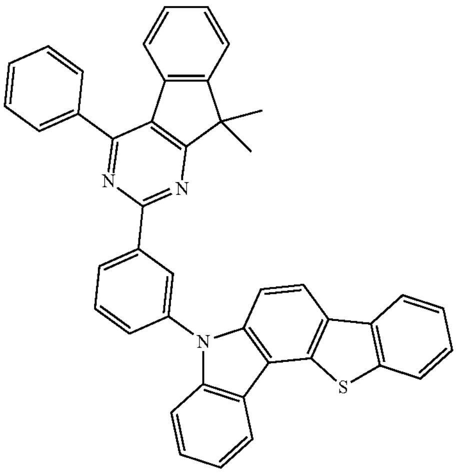
523
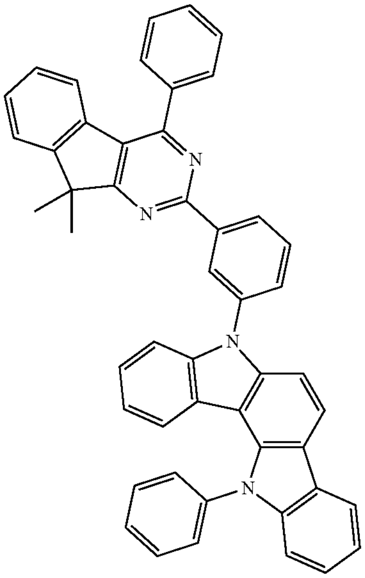
524
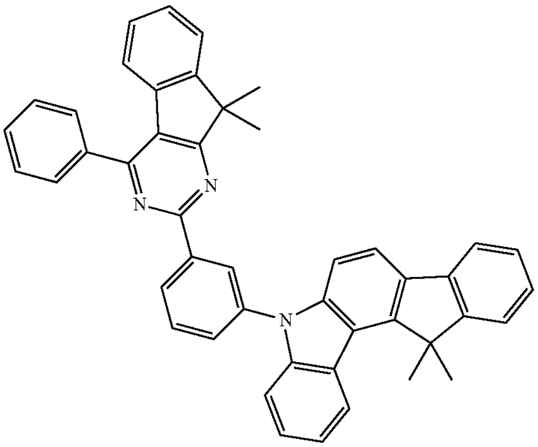

-continued
525
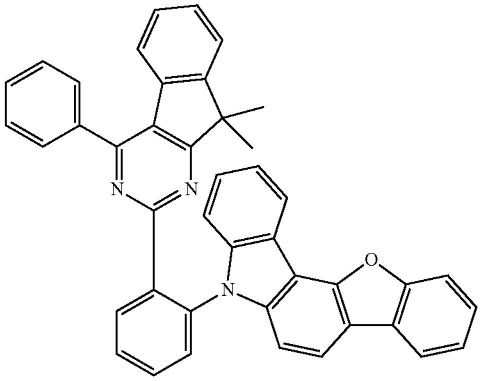
526
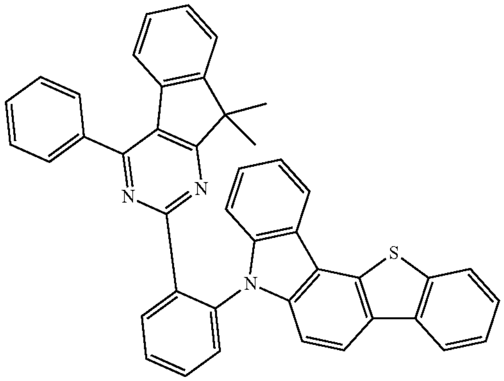
527
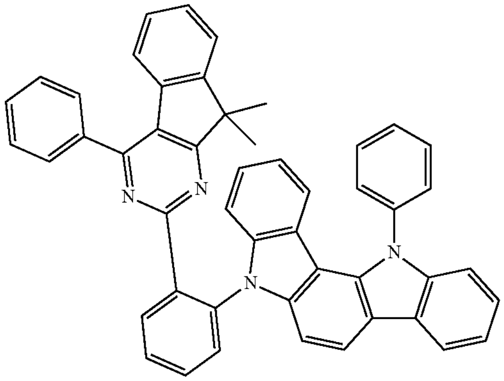
528
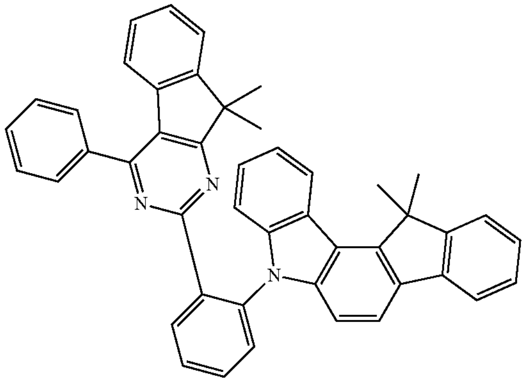
-continued
529
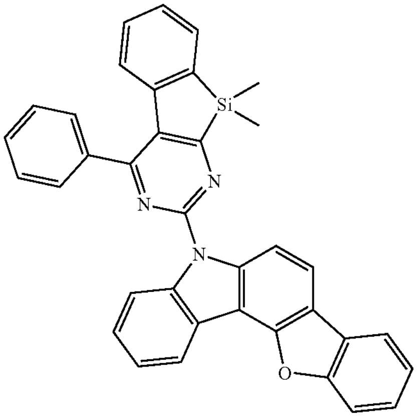
530
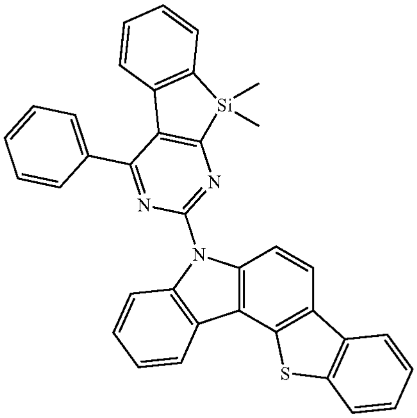
531
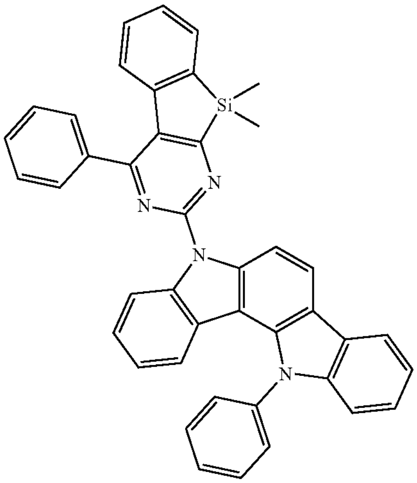

-continued
532
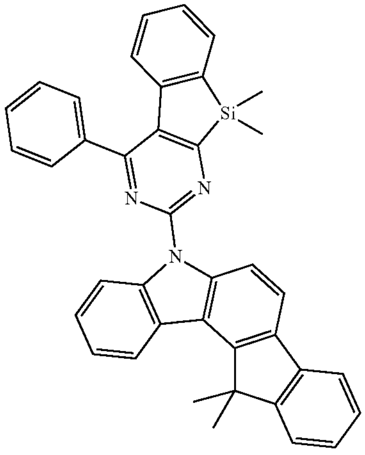
533
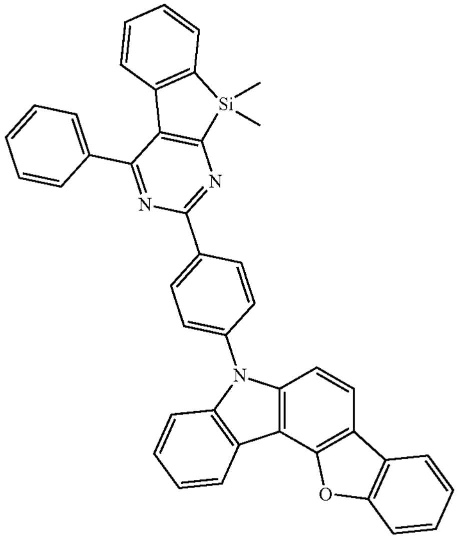
534
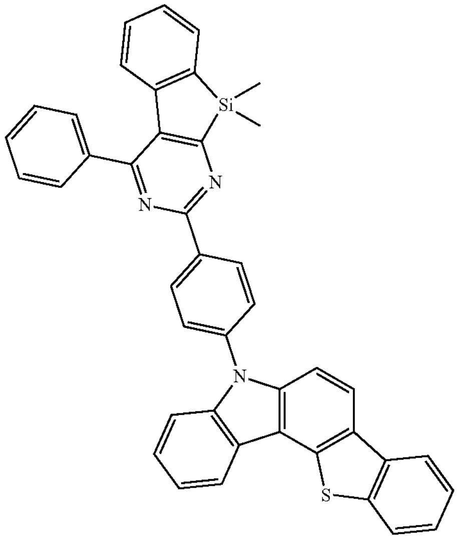
-continued
535
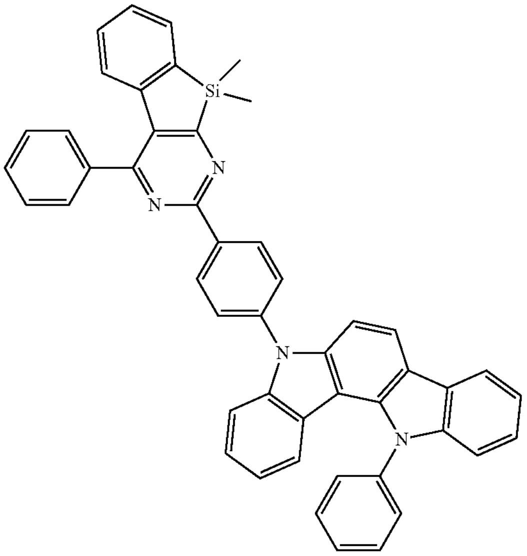
536
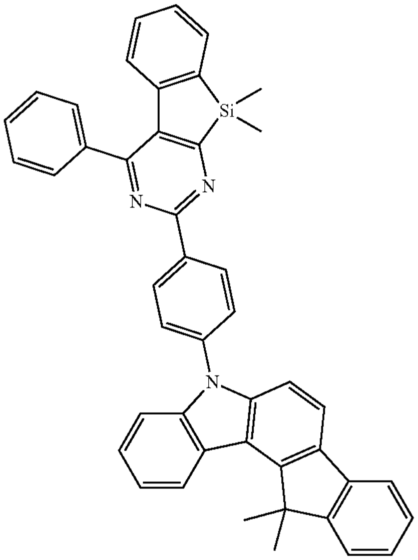
537
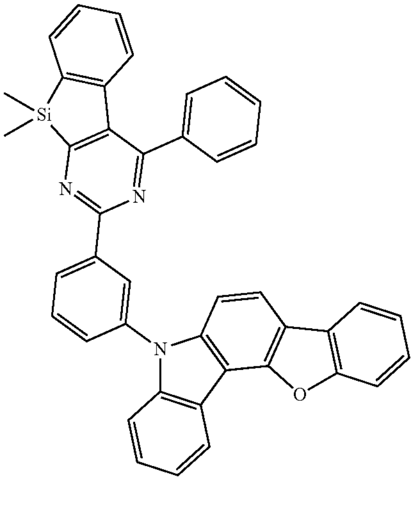

-continued
538
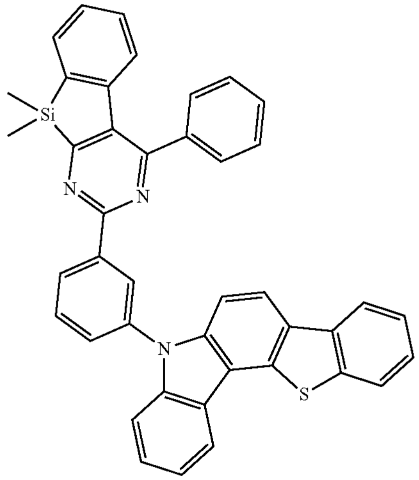
539
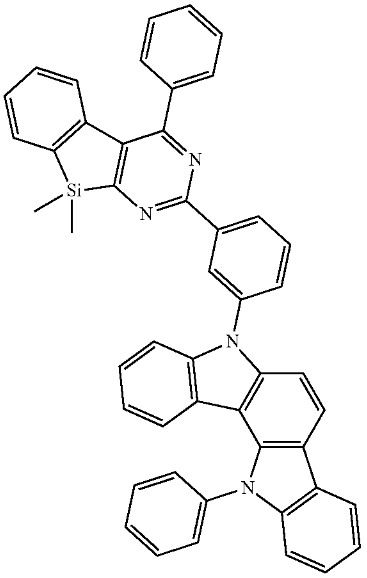
540
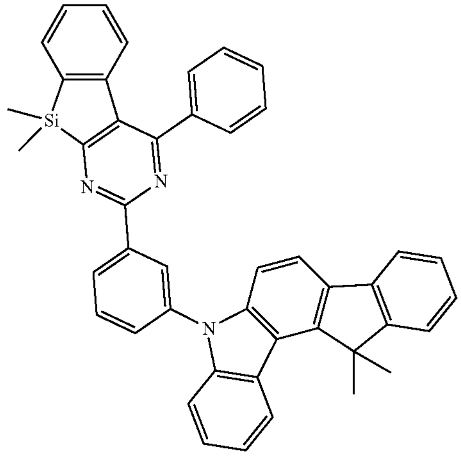
-continued
541
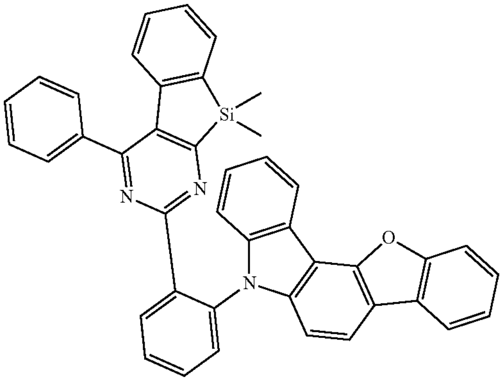
542
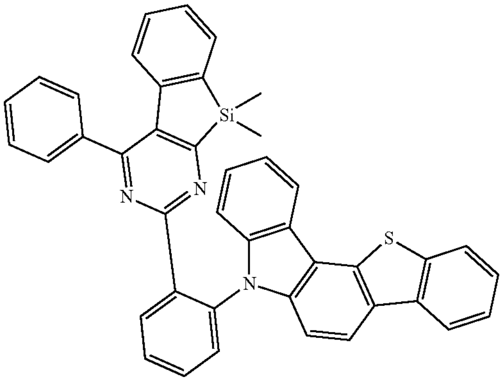
543
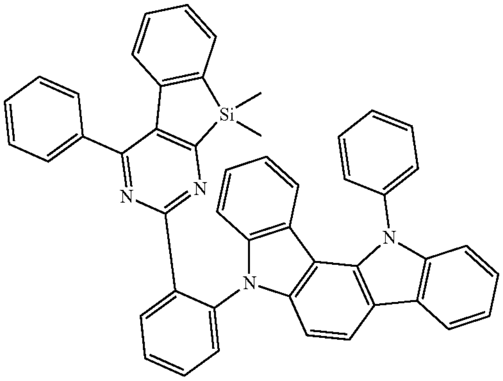
544
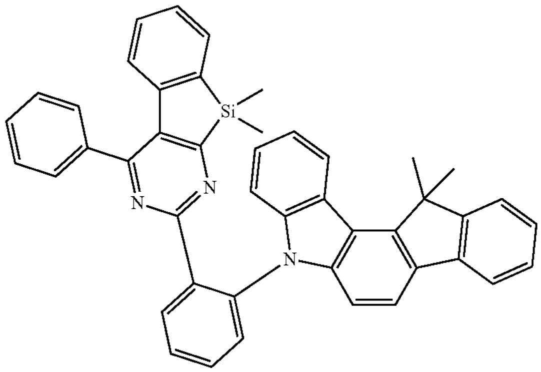

-continued
545
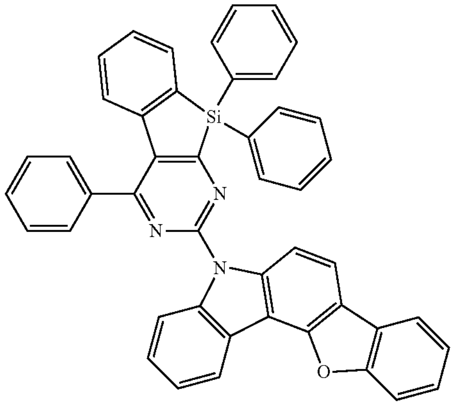
546
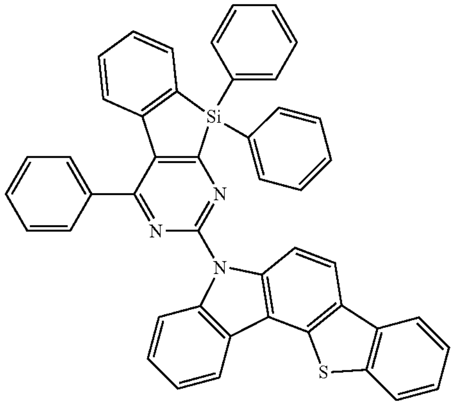
547
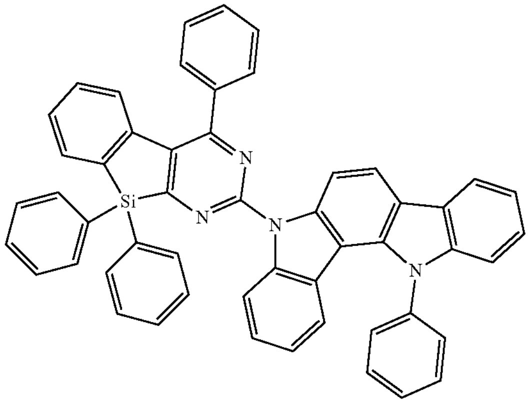
548
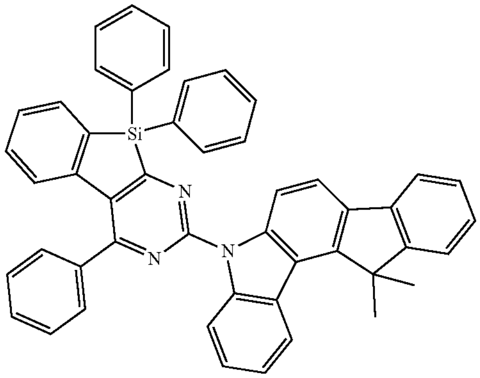
-continued
549
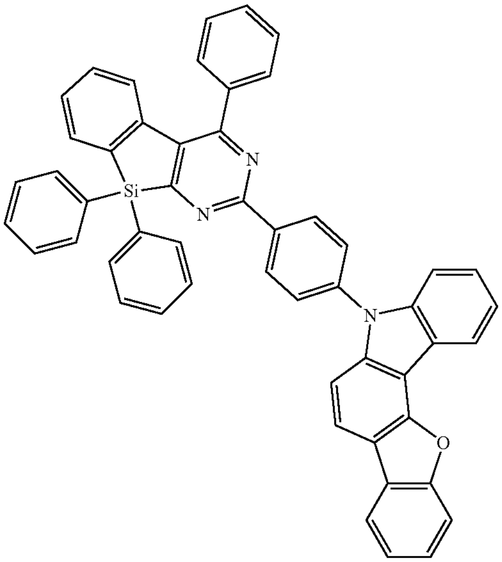
550
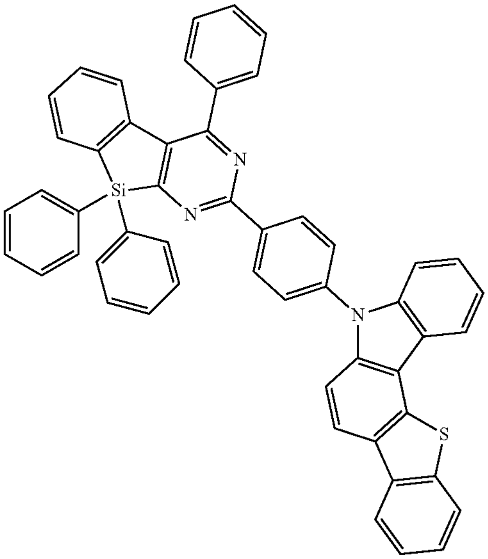

-continued
551
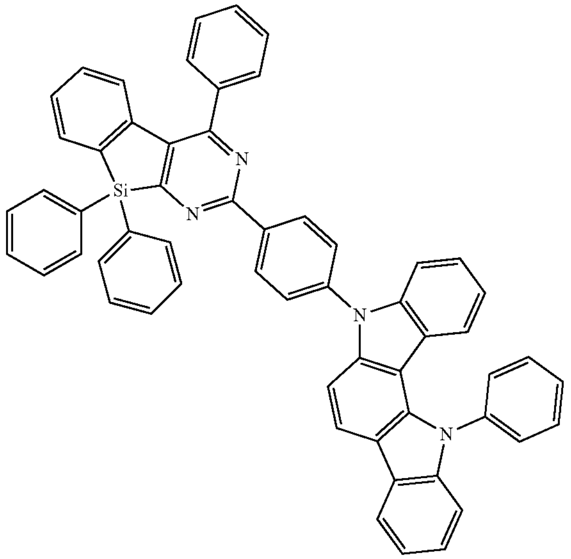
552
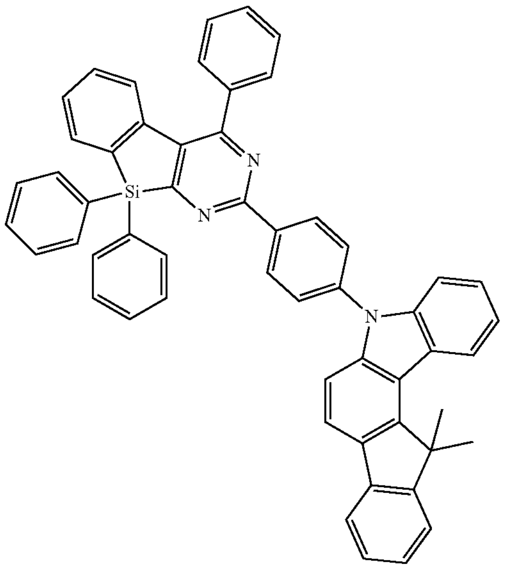
553
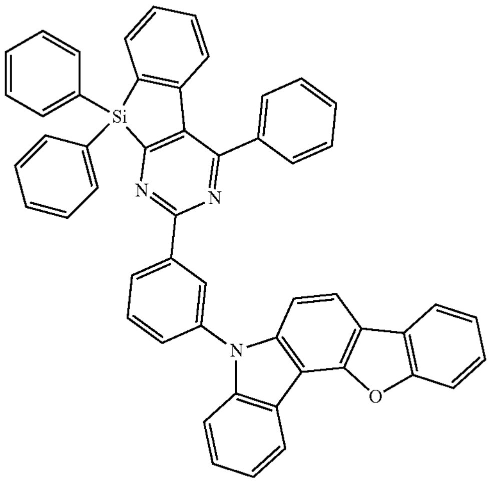
-continued
554
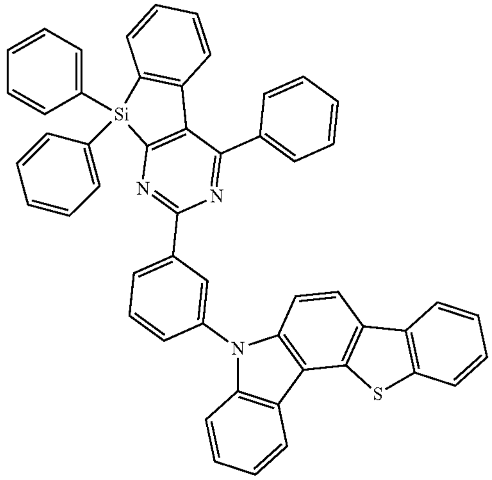
555
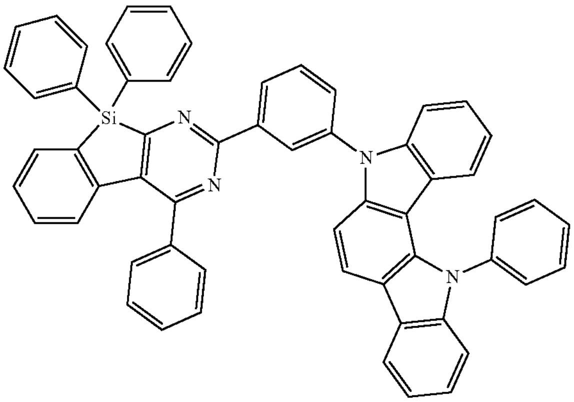
556
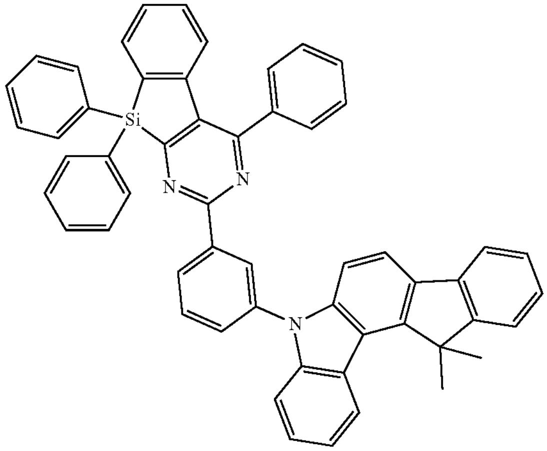

-continued
557
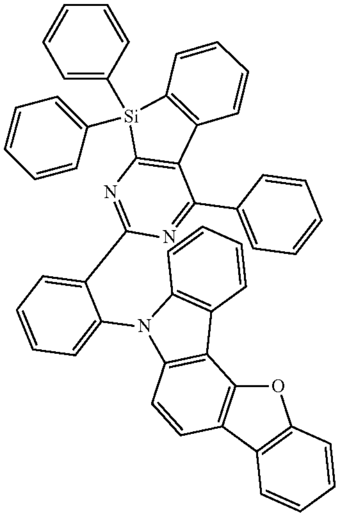
558
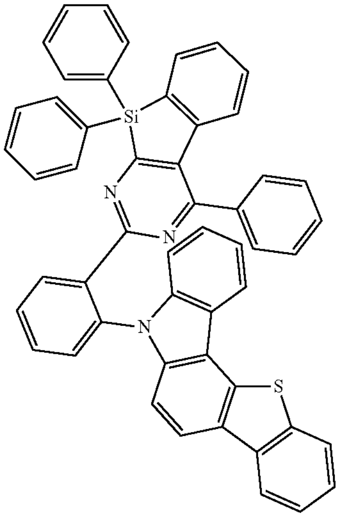
559
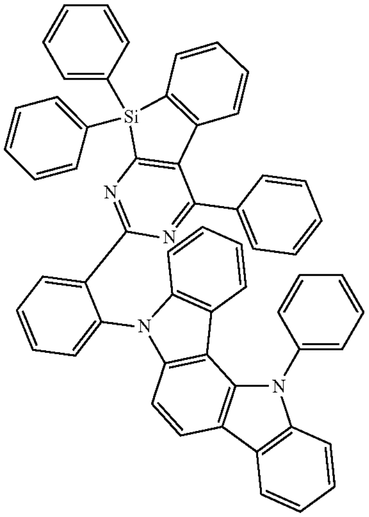
-continued
560
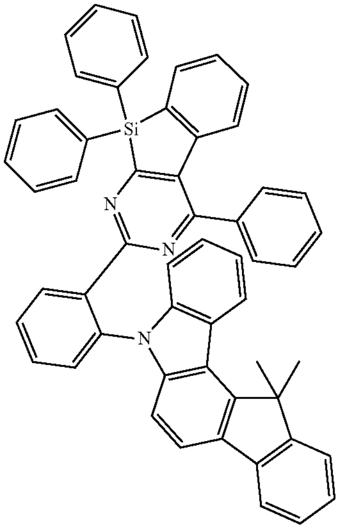
561
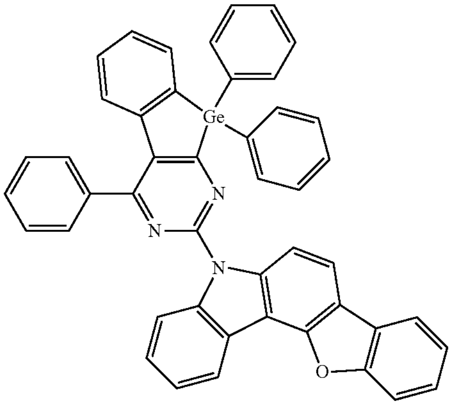
562
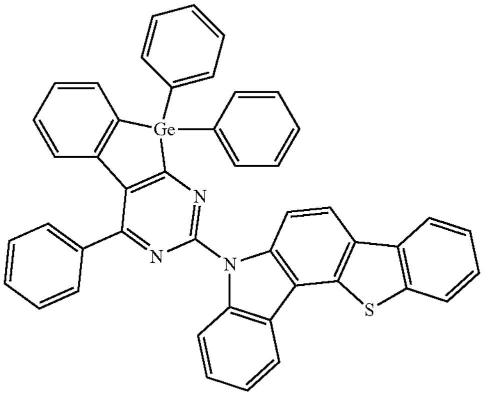

-continued
563
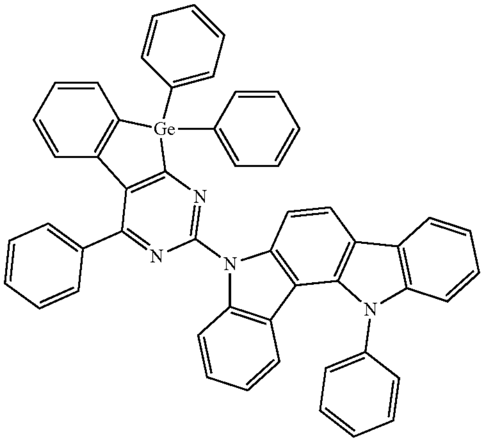
564
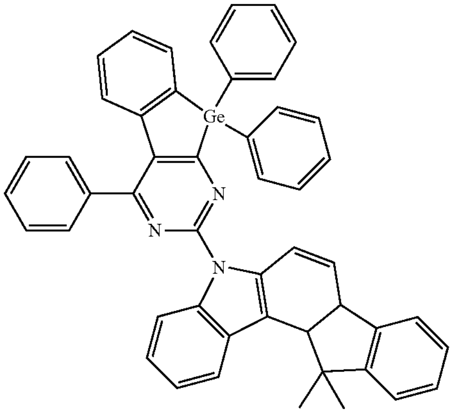
565
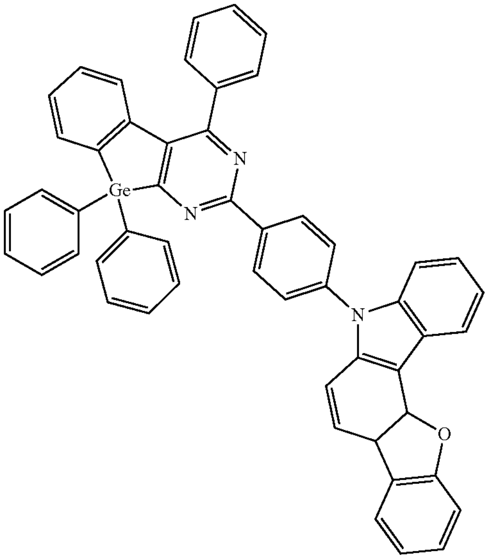
-continued
566
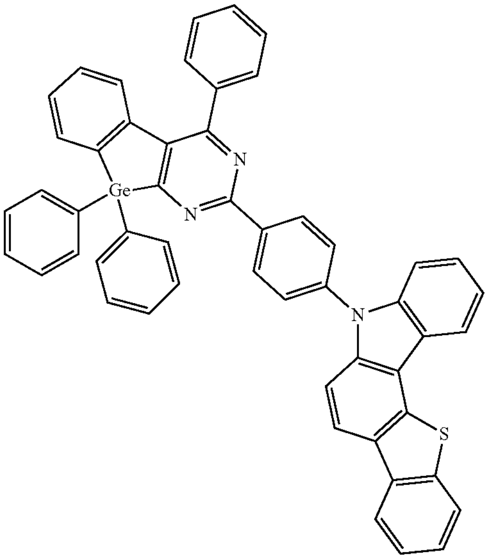
567
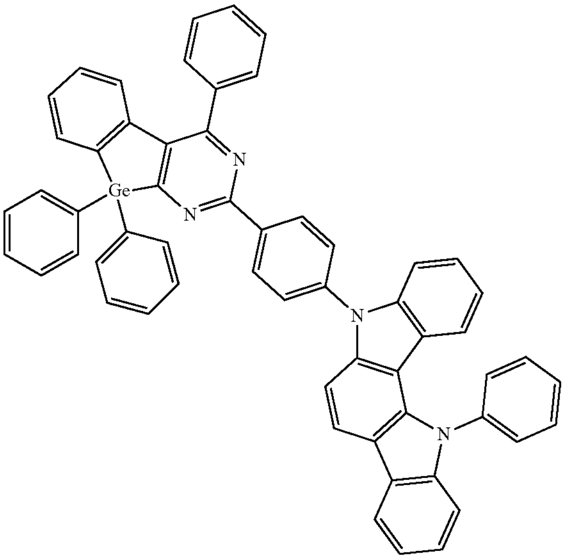

-continued
568
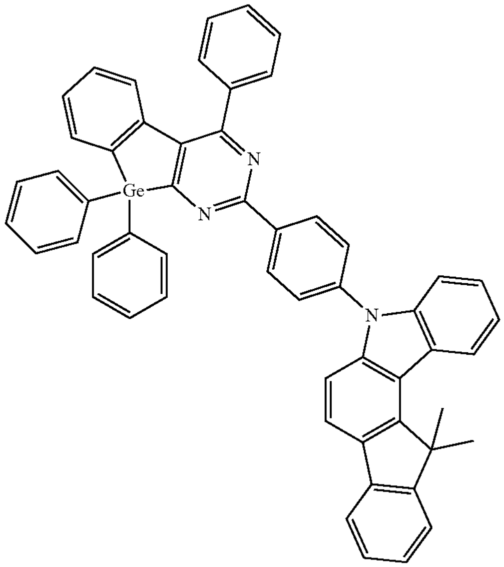
569
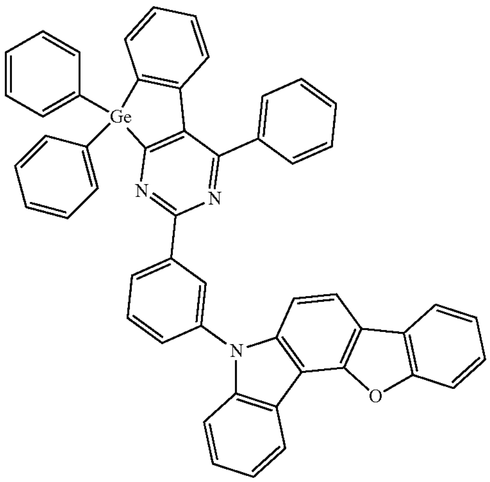
570
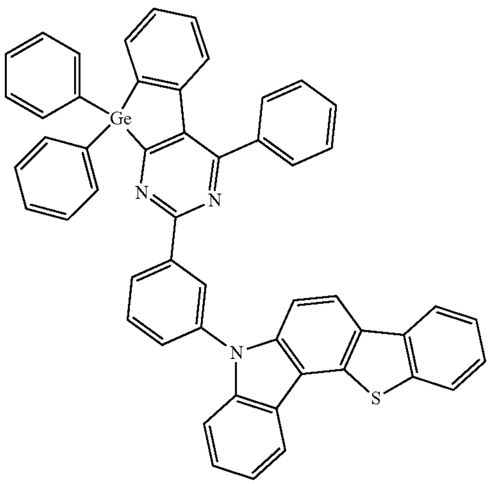
-continued
571
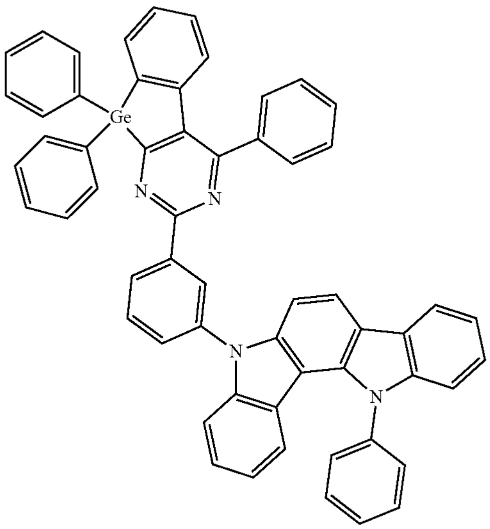
572
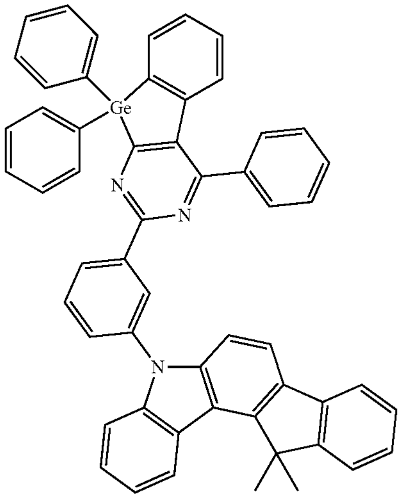
573
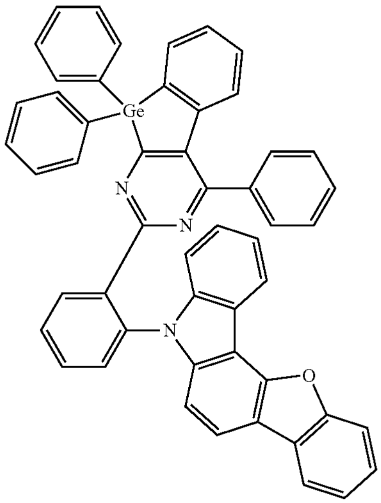

-continued
574
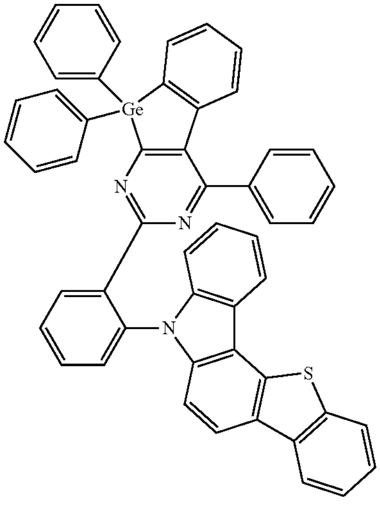
575
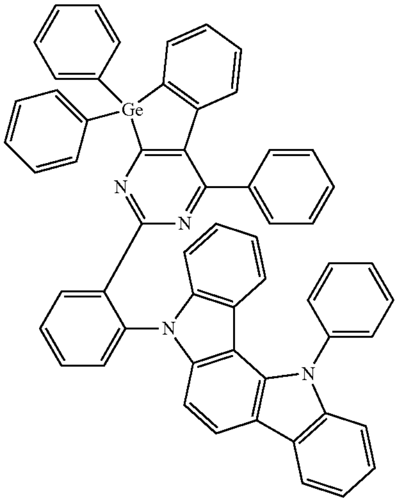
576
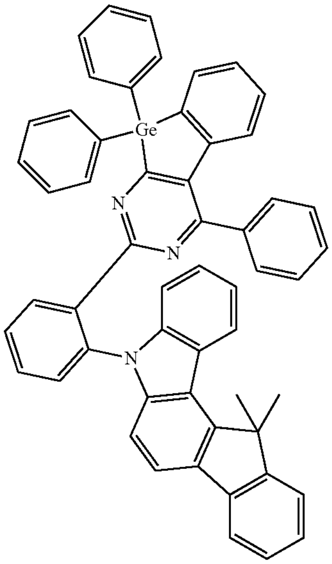
-continued
577
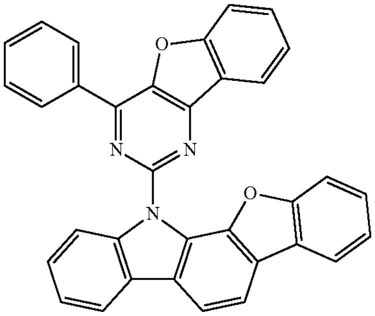
578
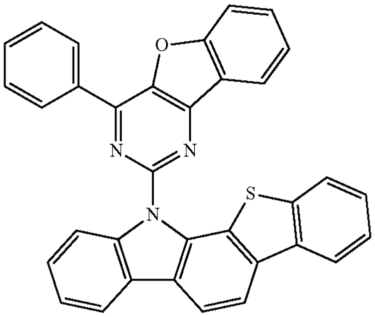
579
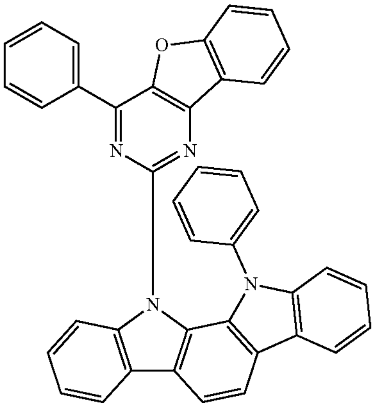
580
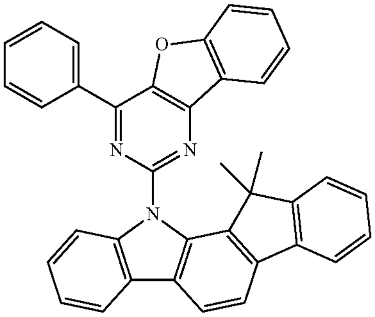

-continued
581
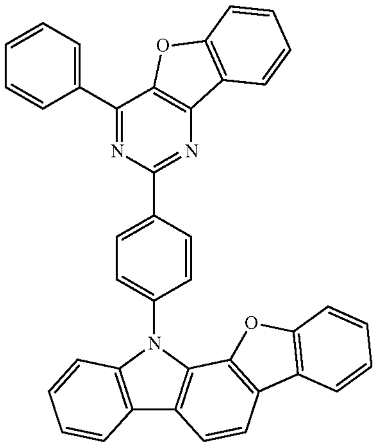
582
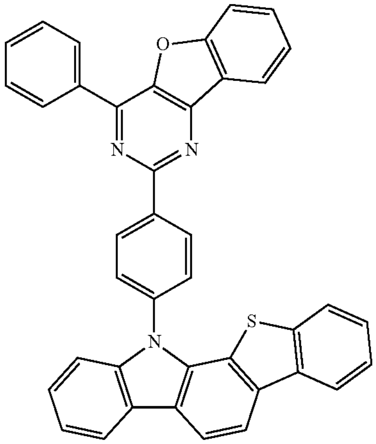
583
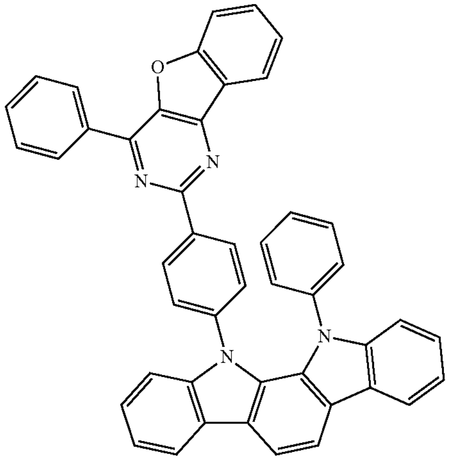
-continued
584
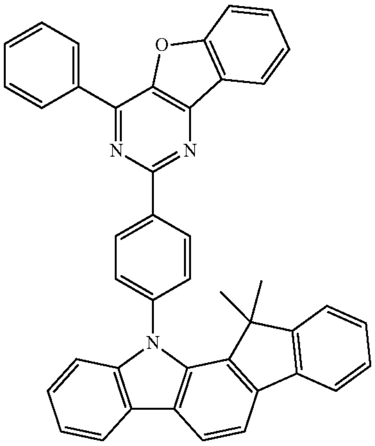
585
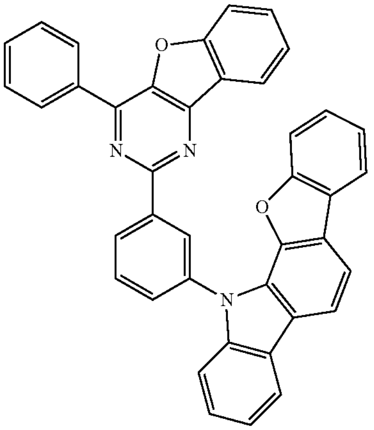
586
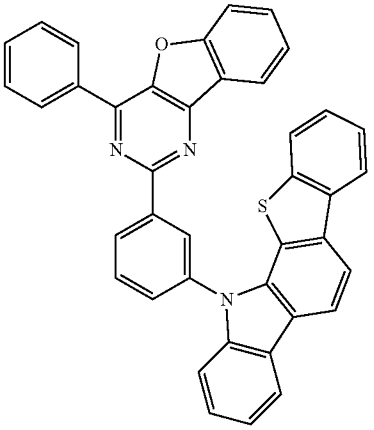

-continued
587
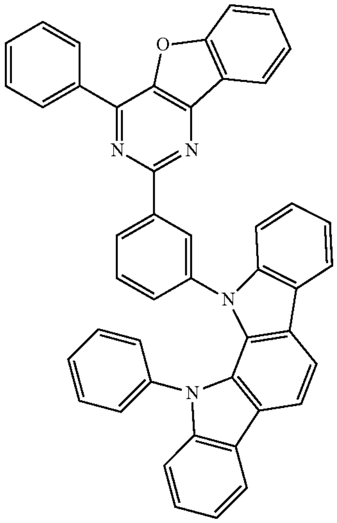
588
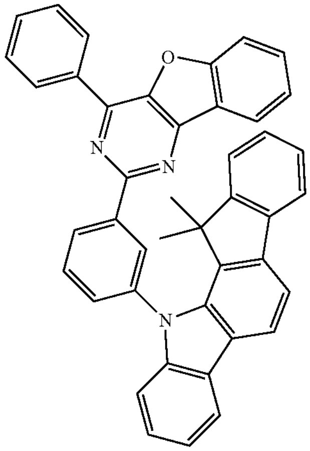
589
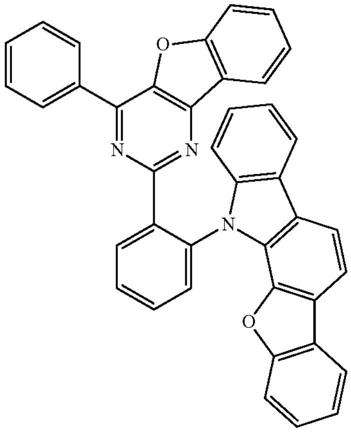
-continued
590
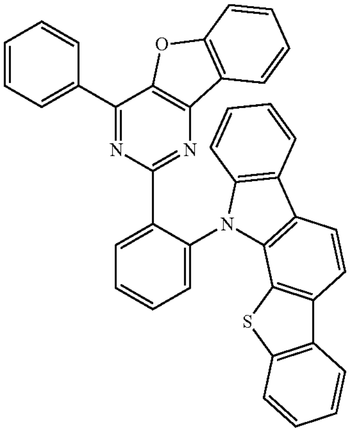
591
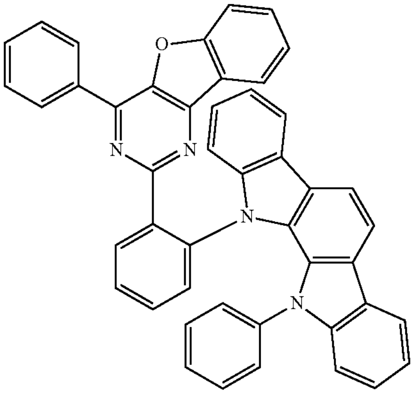
592
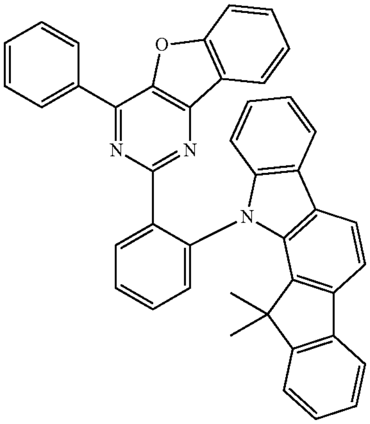
593
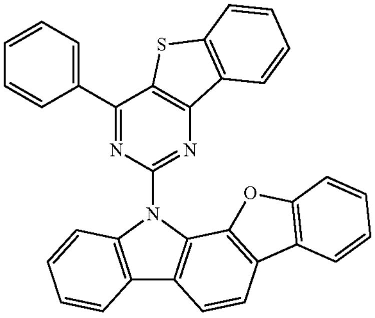

-continued
594
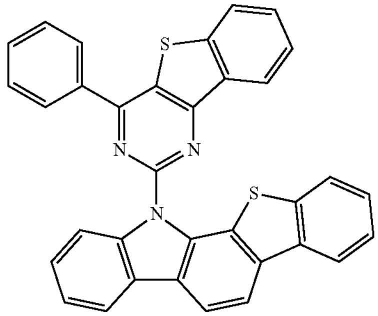
595
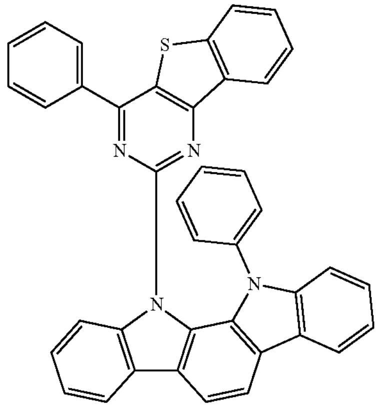
596
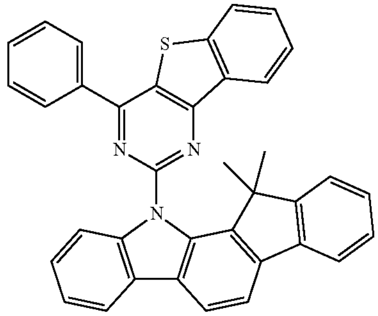
597
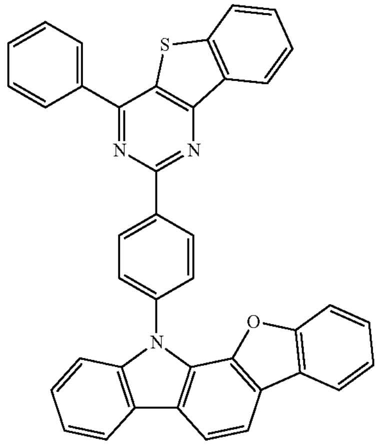
-continued
598
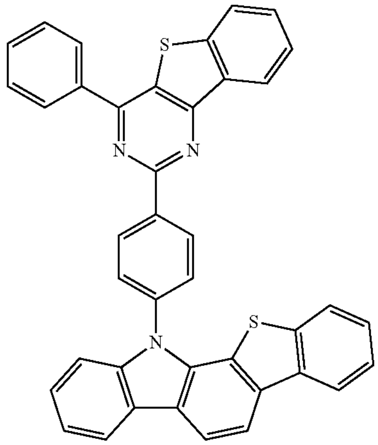
599
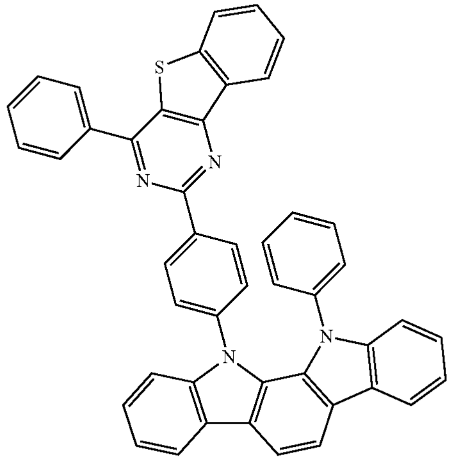
600
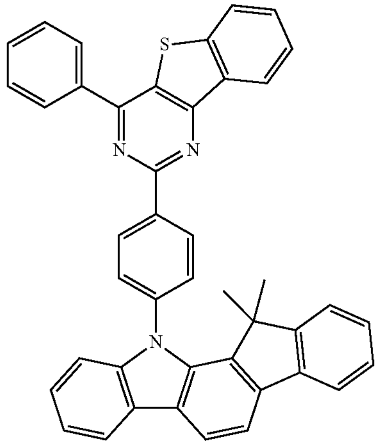

-continued
601
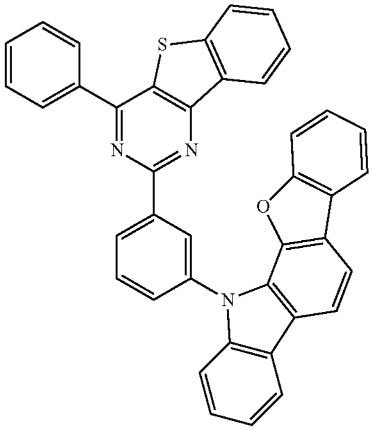
602
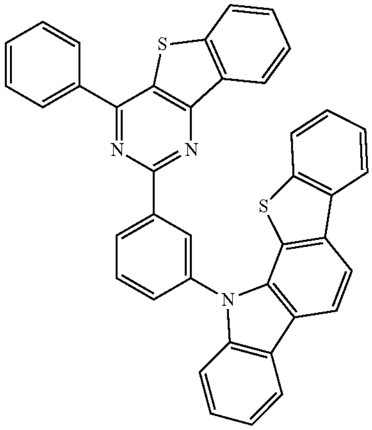
603
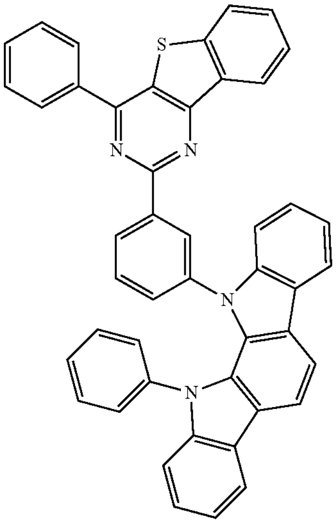
-continued
604
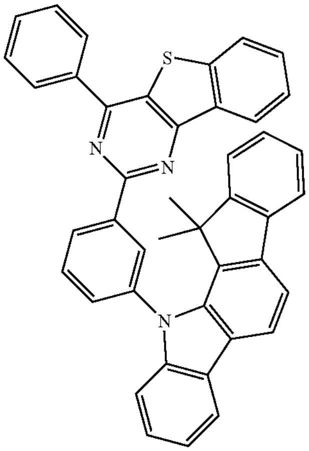
605
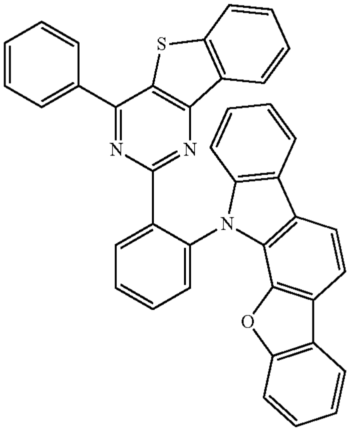
606
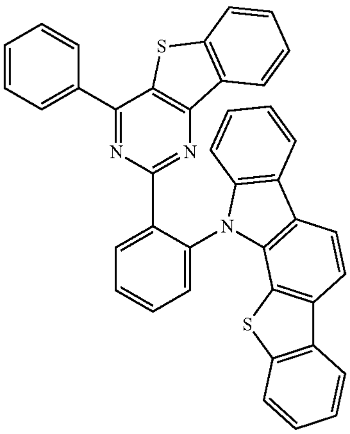

-continued
607
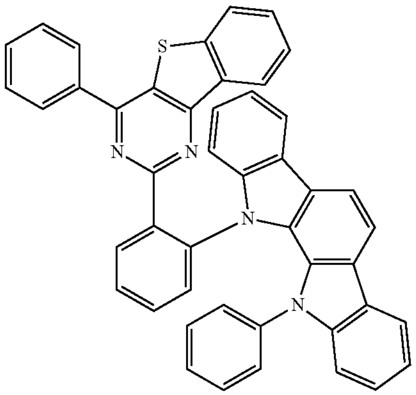
608
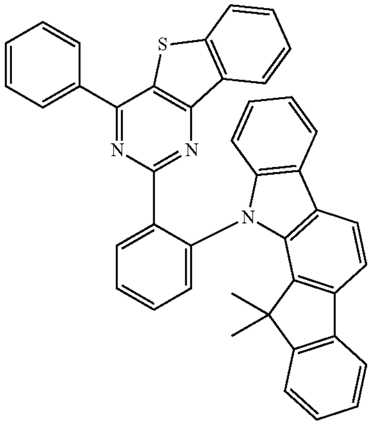
609
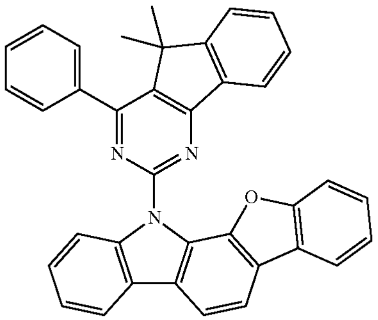
610
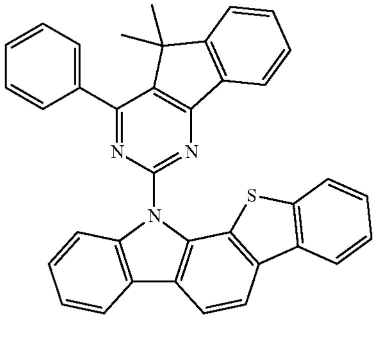
-continued
611
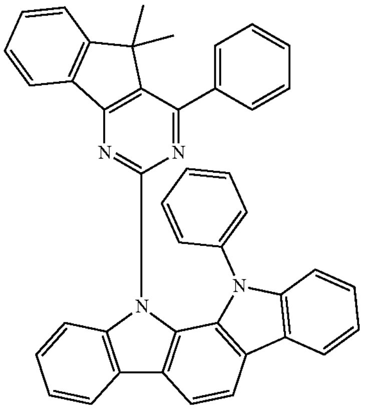
612
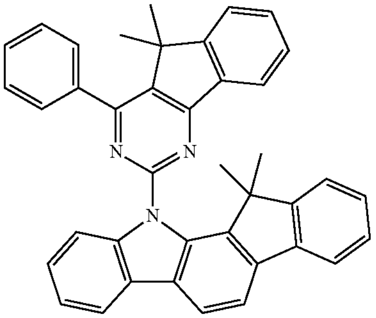
613
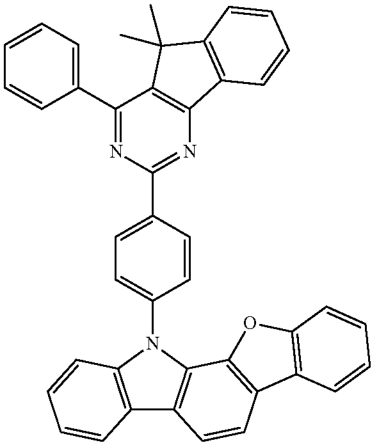
614
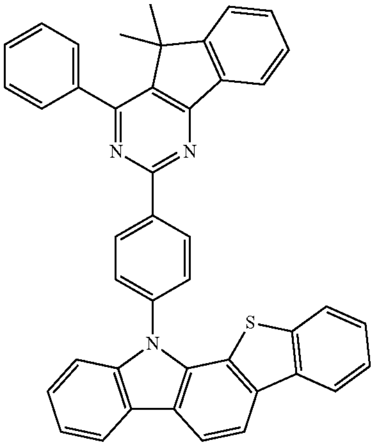

-continued
615
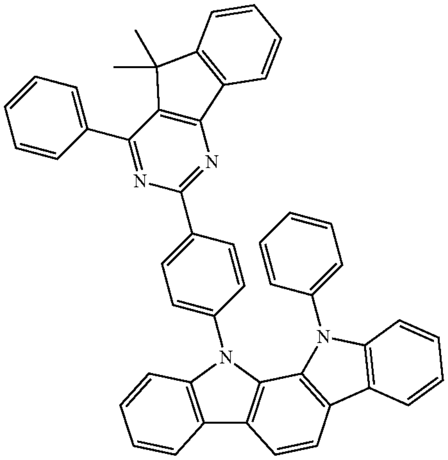
616
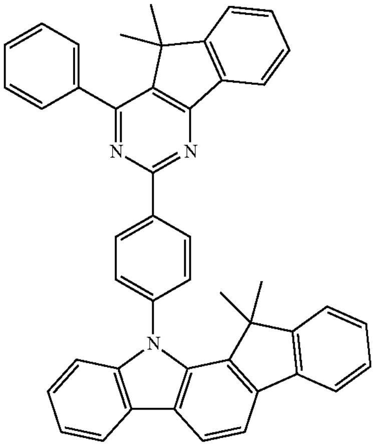
617
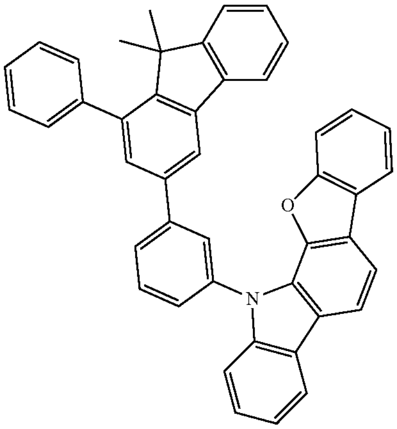
-continued
618
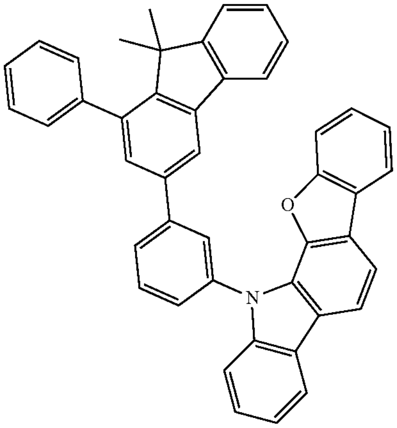
619
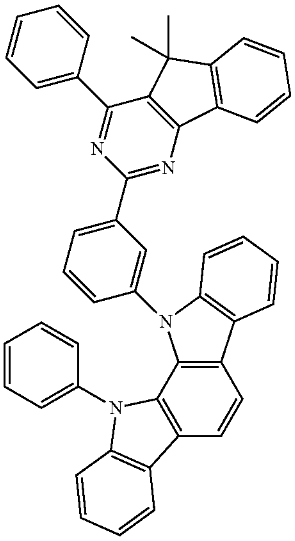
620
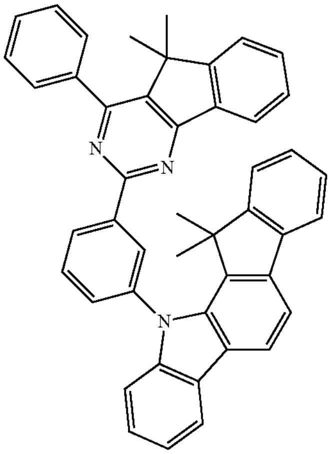

-continued
621
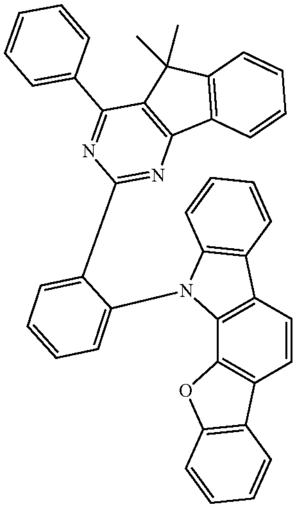
622
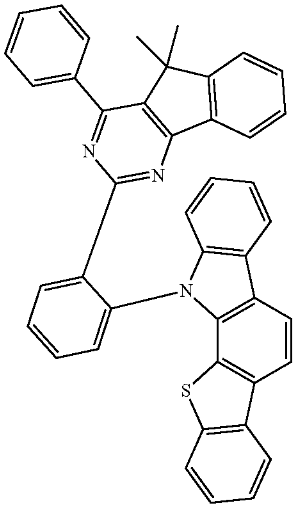
623
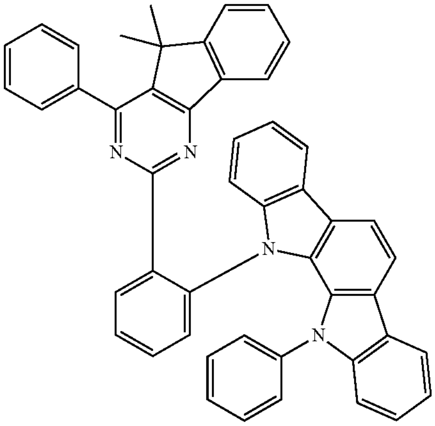
-continued
624
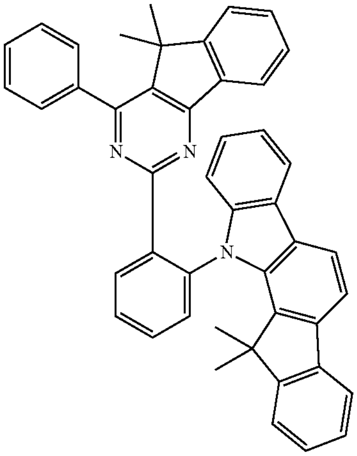
625
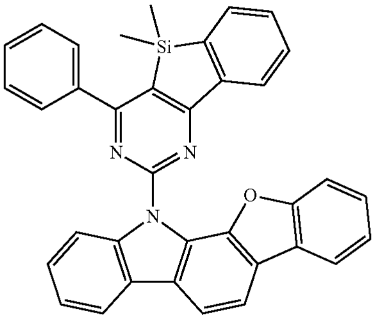
626
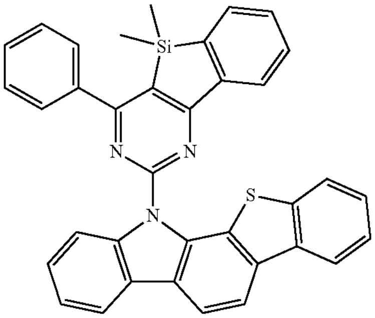
627
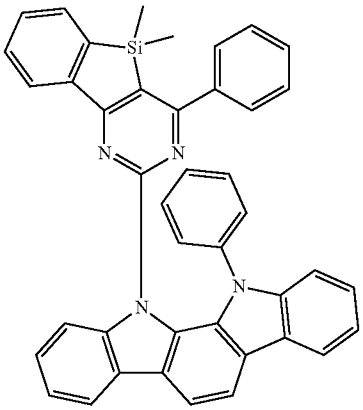

-continued
628
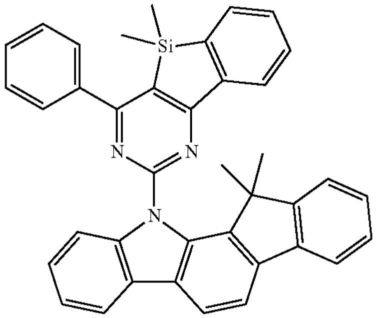
629
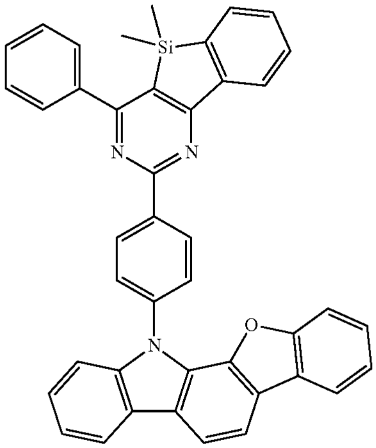
630
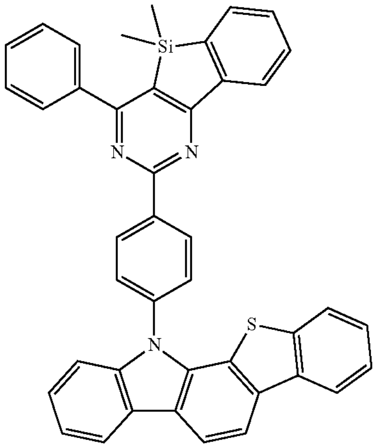
-continued
631
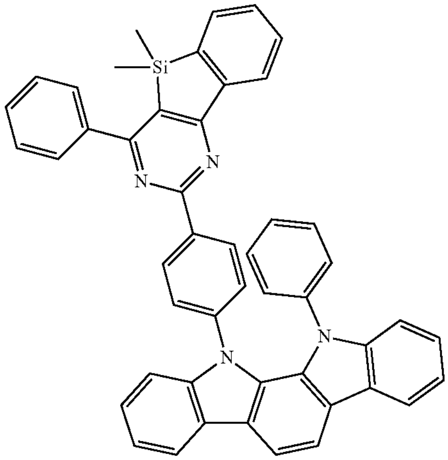
632
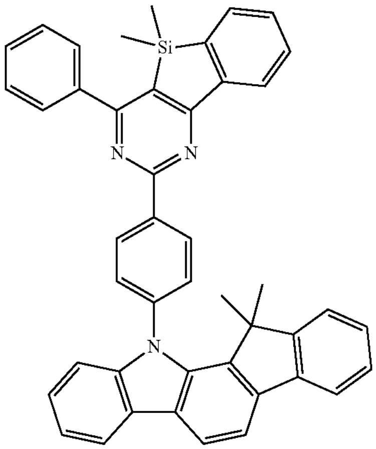
633
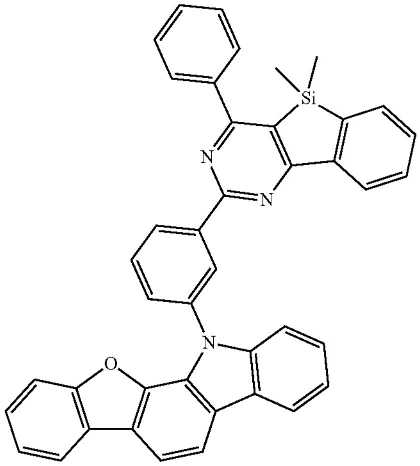

-continued
634
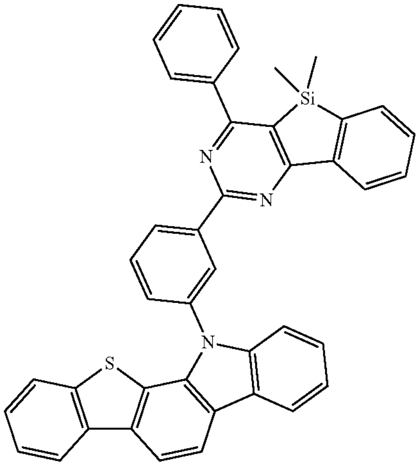
635
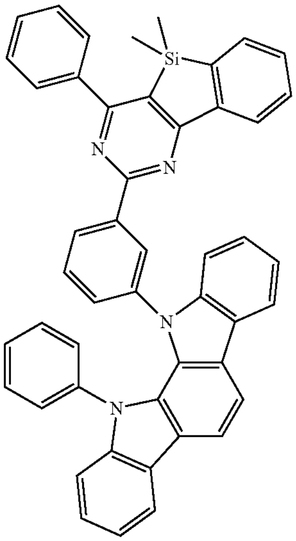
636
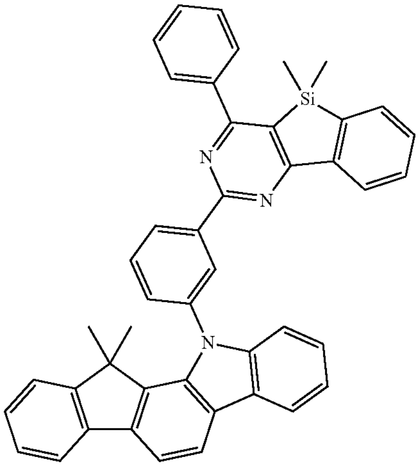
-continued
637
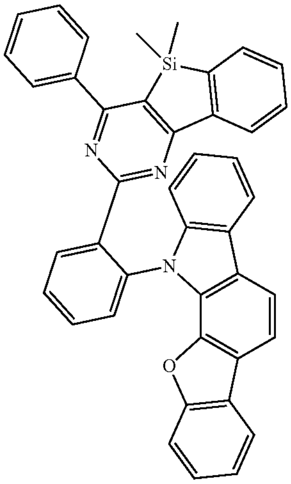
638
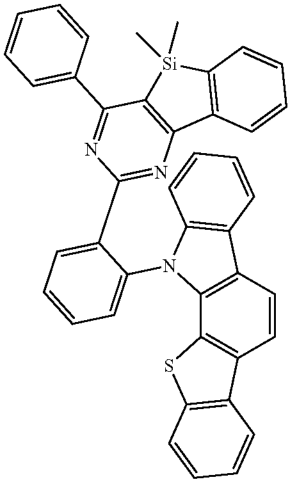
639
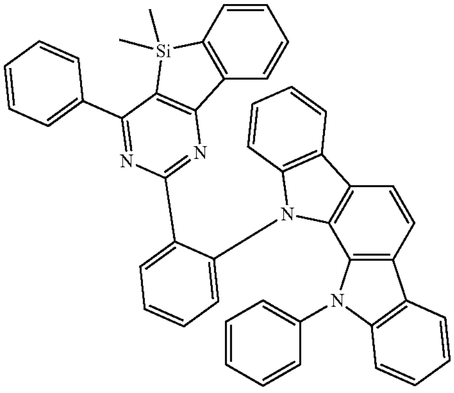

-continued
640
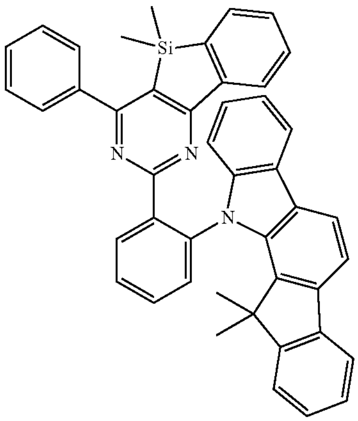
641
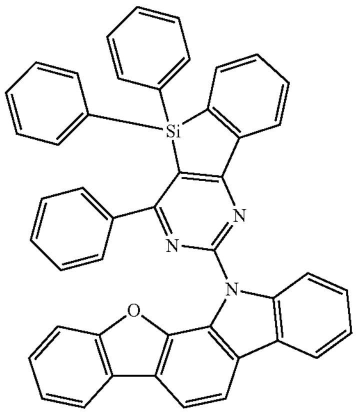
642
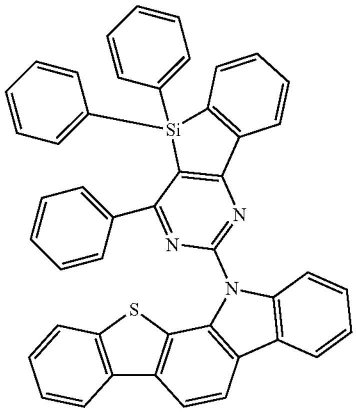
-continued
643
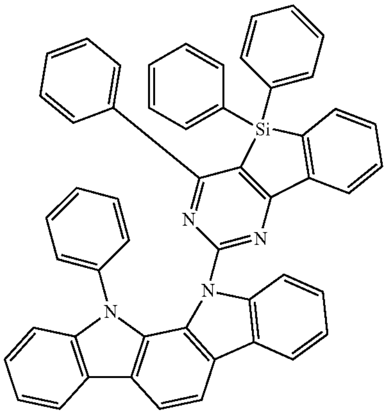
644
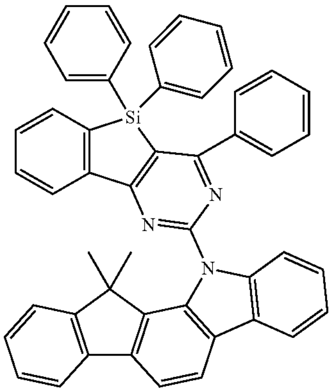
645
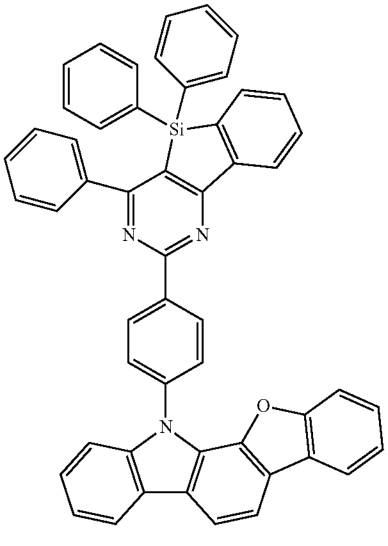

-continued
646
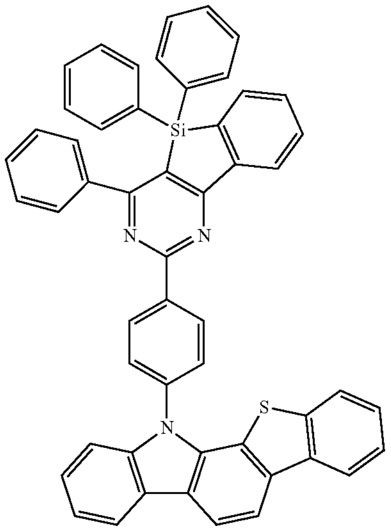
647
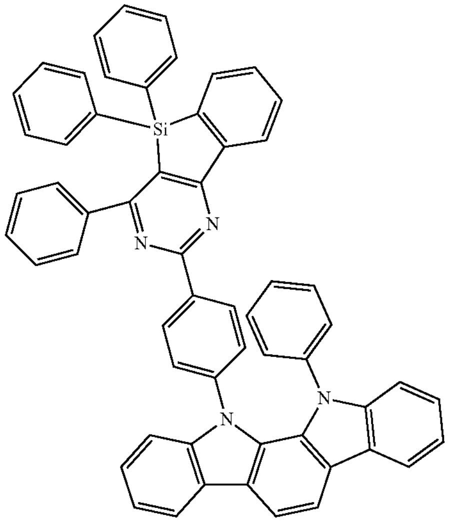
648
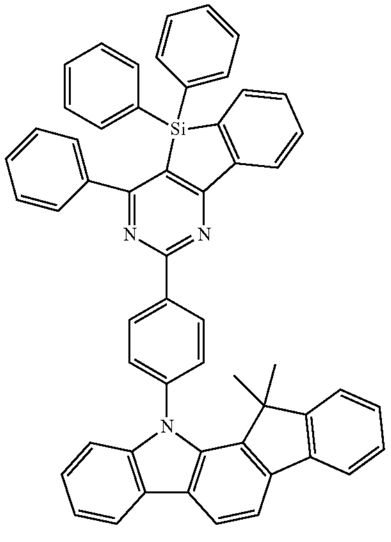
-continued
649
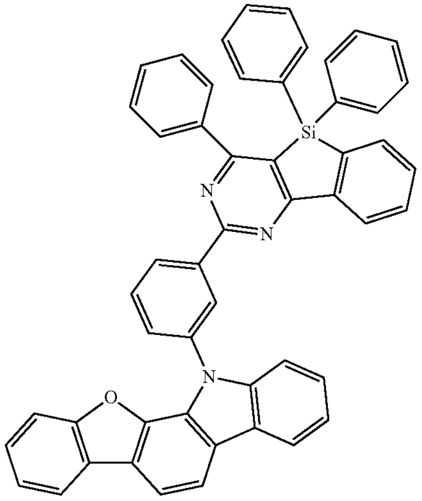
650
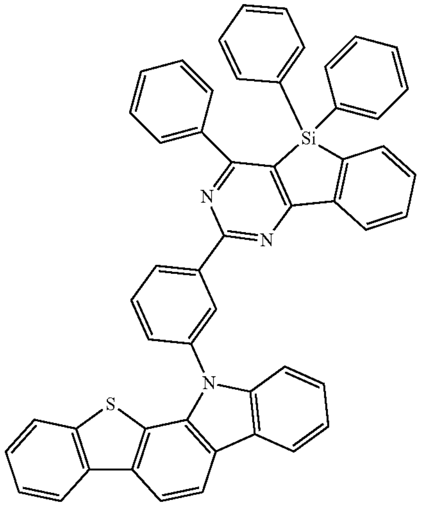
651
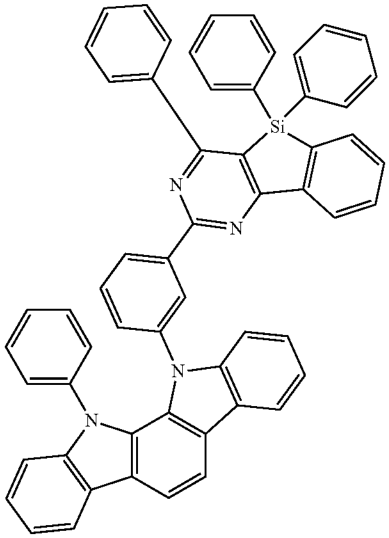

-continued
652
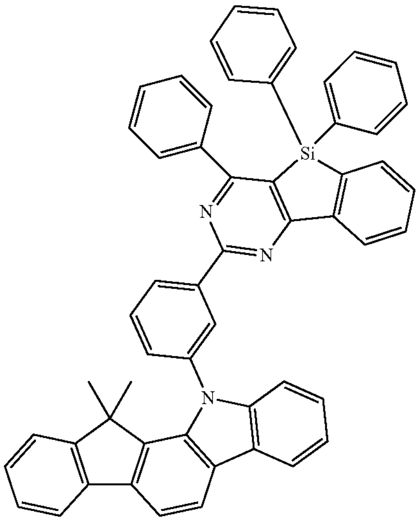
653
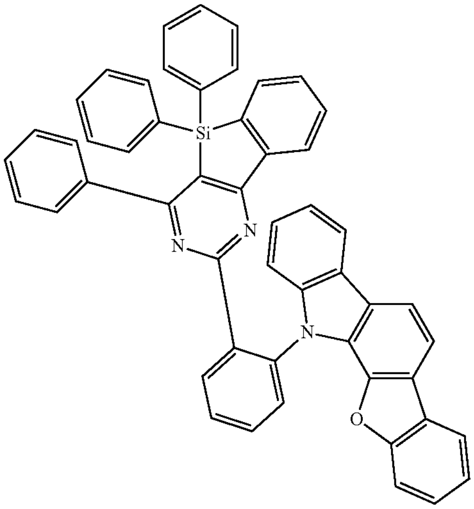
654
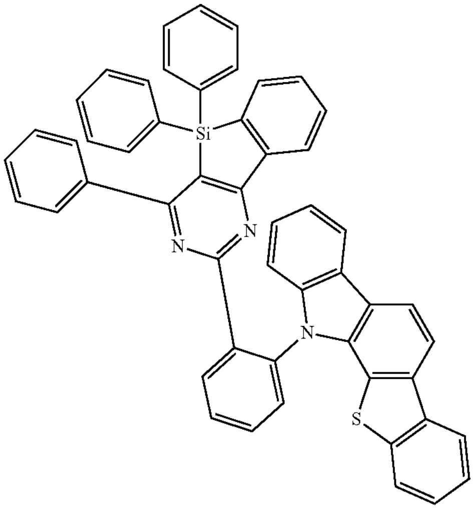
-continued
655
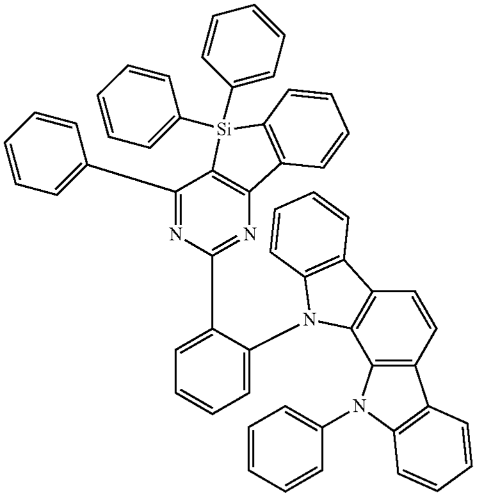
656
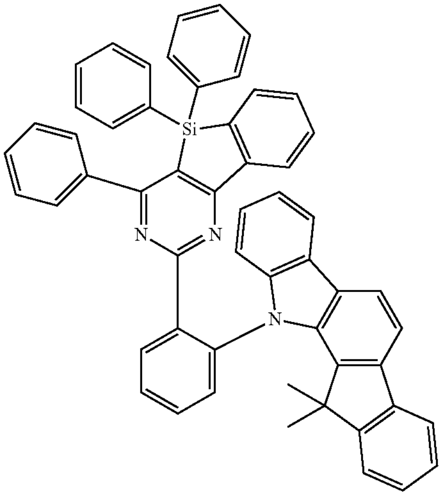
657
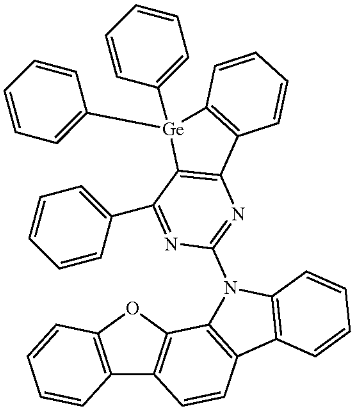

-continued
658
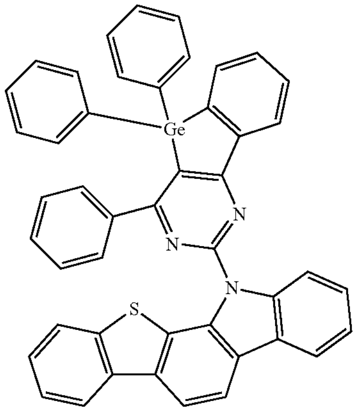
659
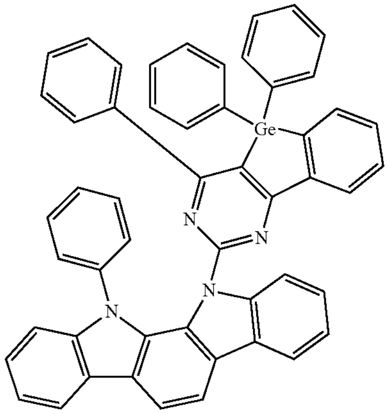
660
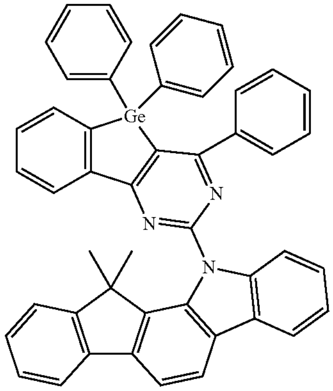
-continued
661
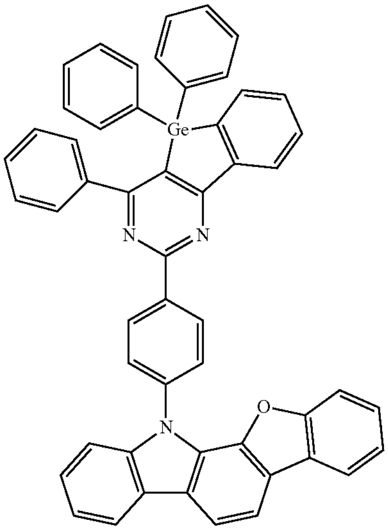
662
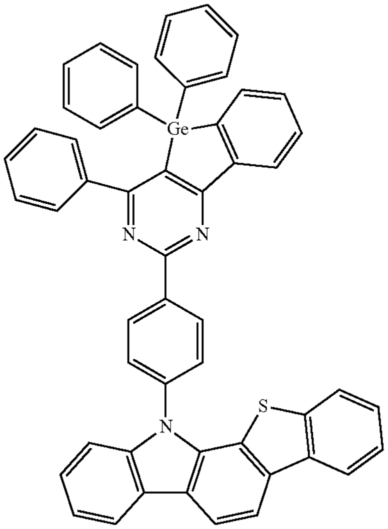
663
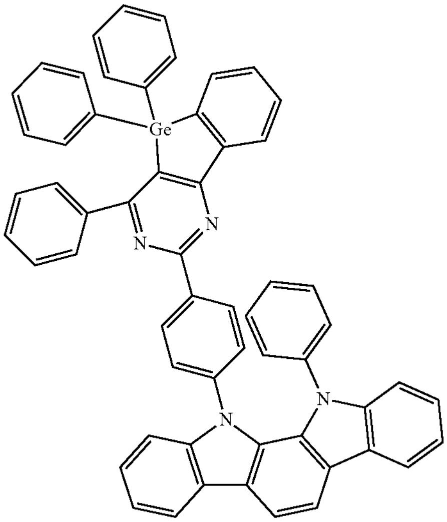

-continued
664
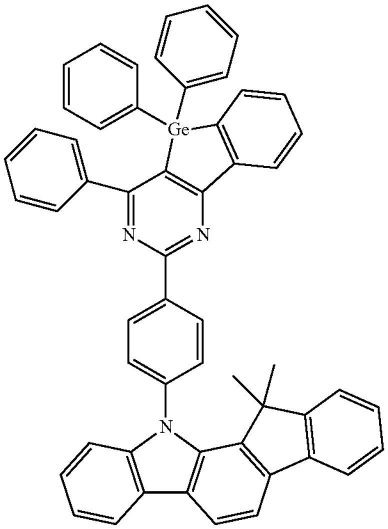
665
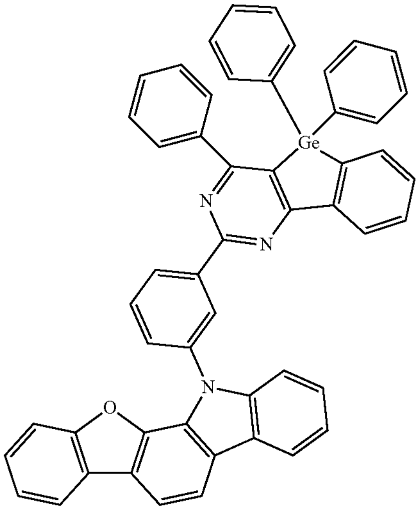
666
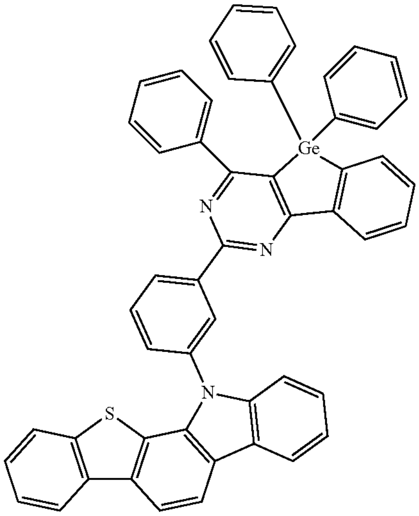
-continued
667
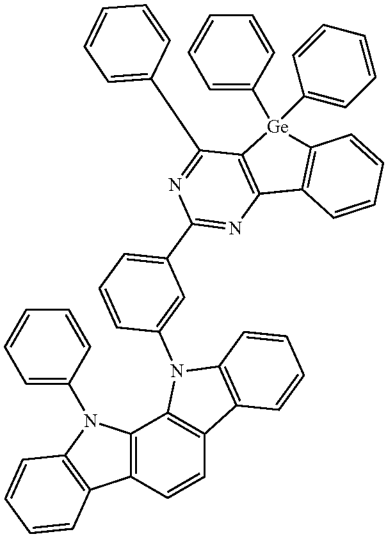
668
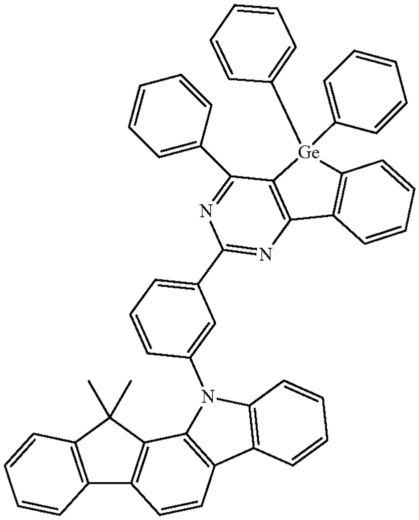
669
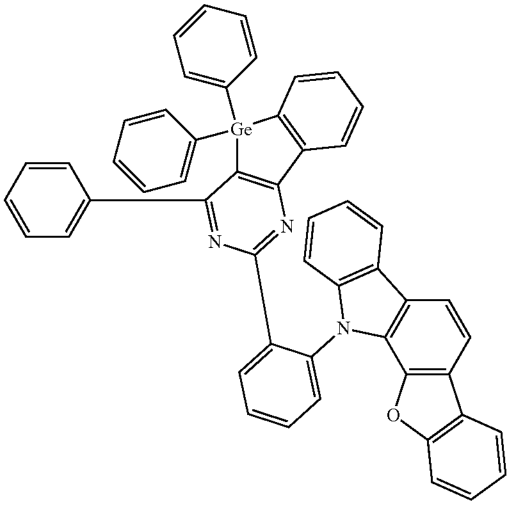

-continued
670
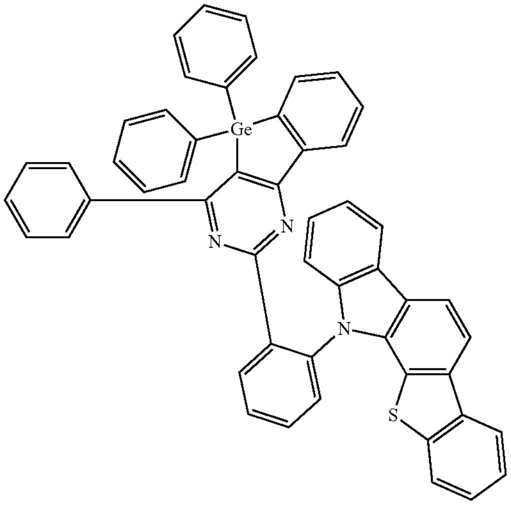
671
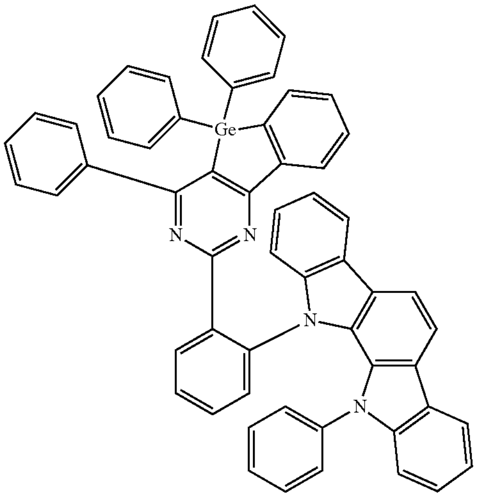
672
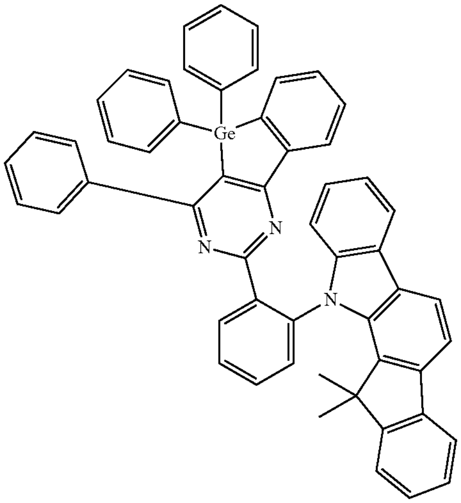
-continued
673
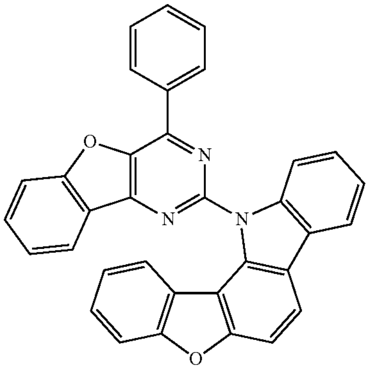
674
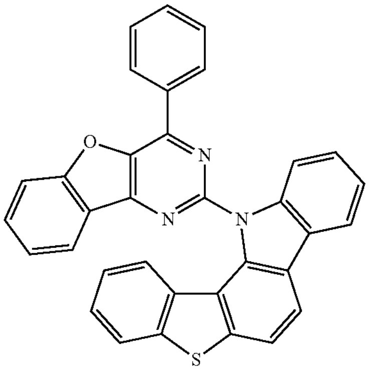
675
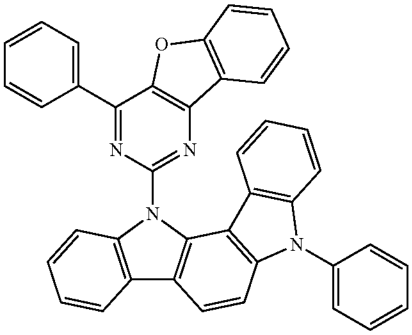
676
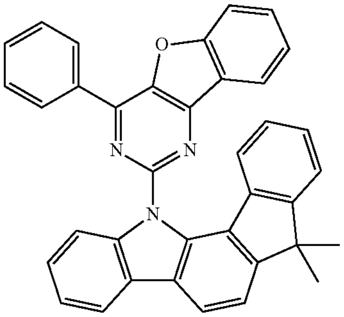

-continued
677
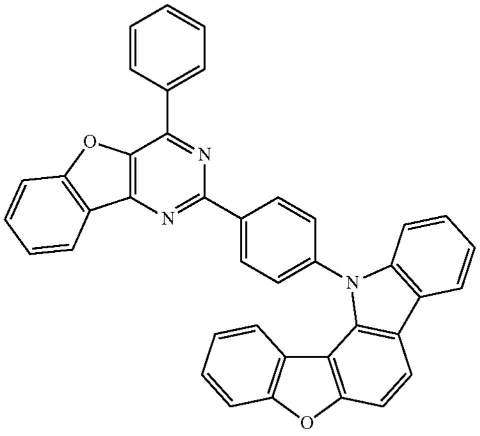
678
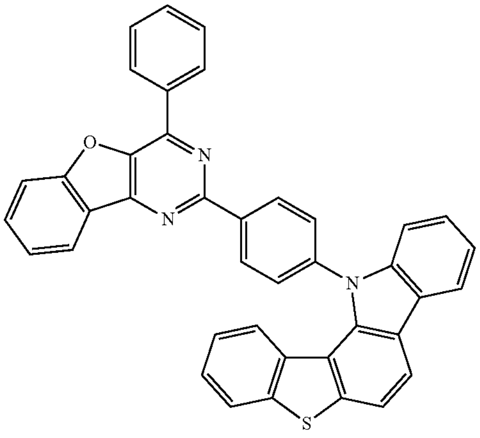
679
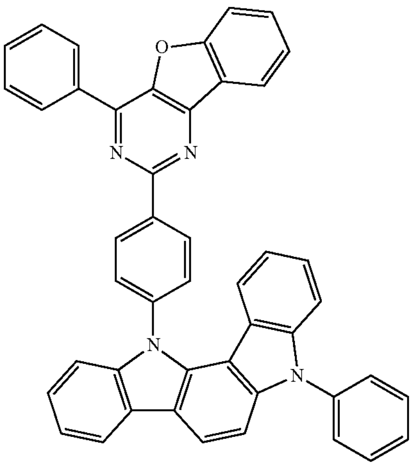
-continued
680
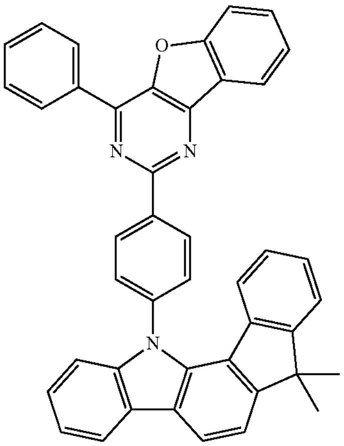
681
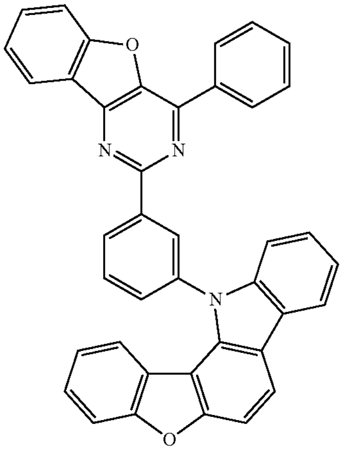
682
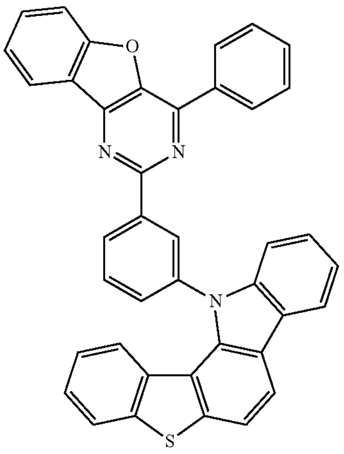

683
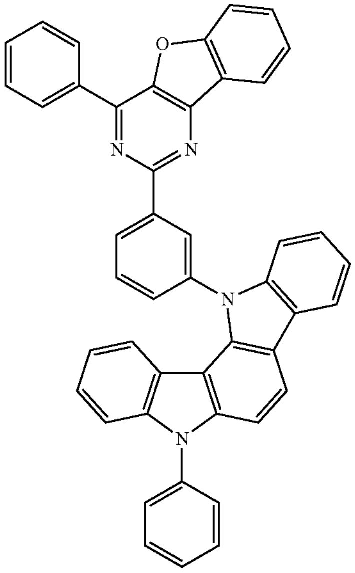
684
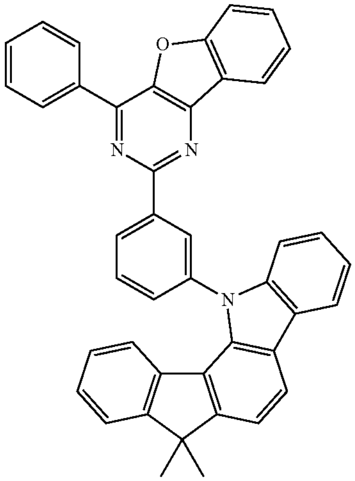
685
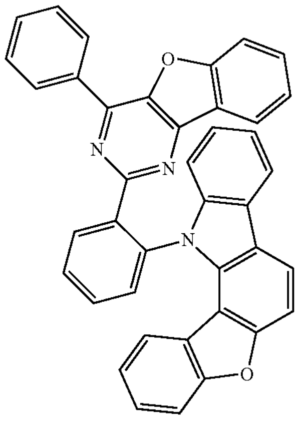
686
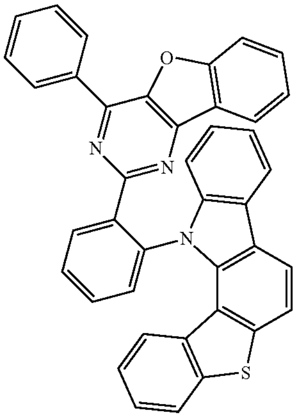
687
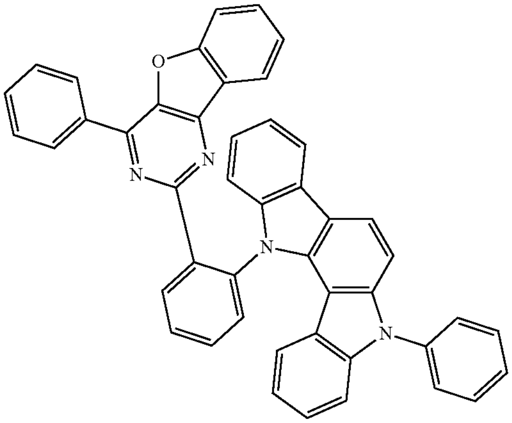
688
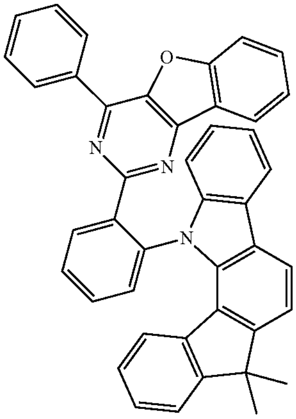

-continued
689
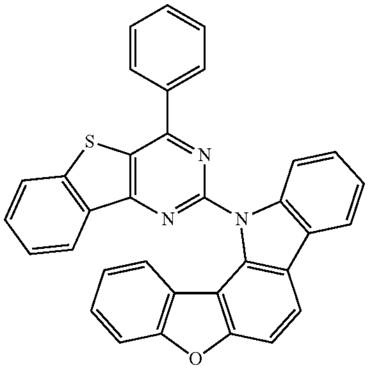
690
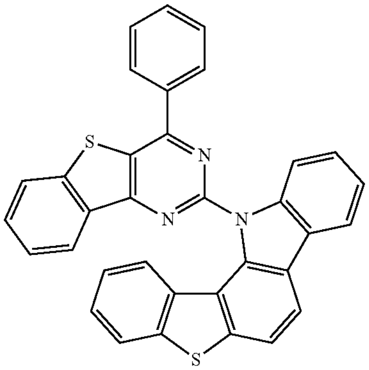
691
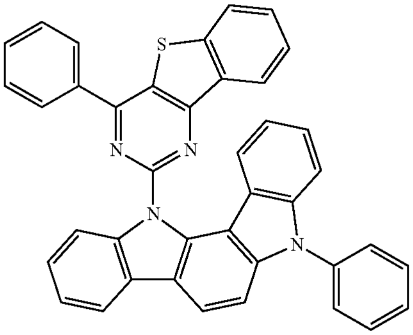
692
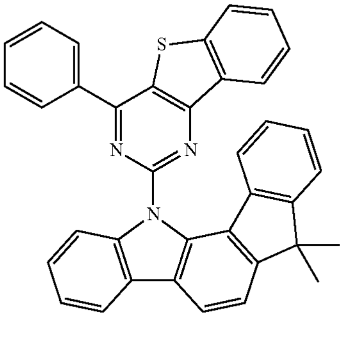
-continued
693
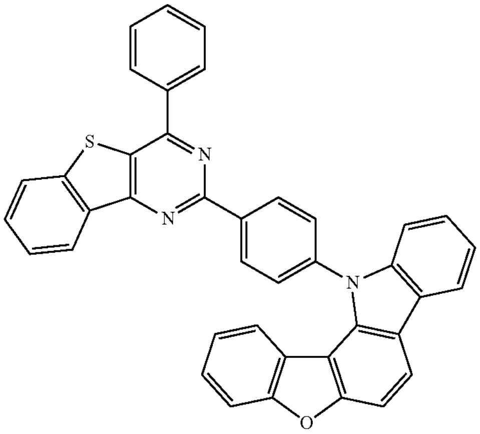
694
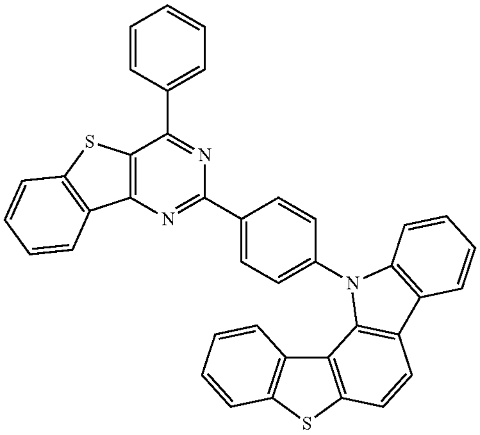
695
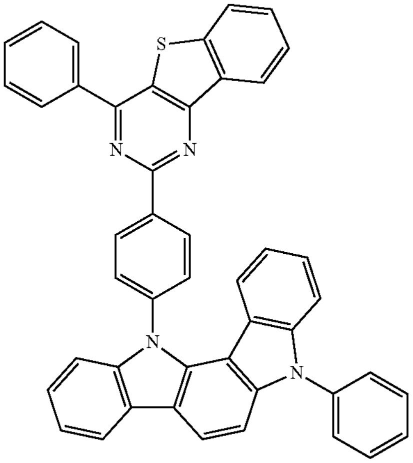

-continued
696
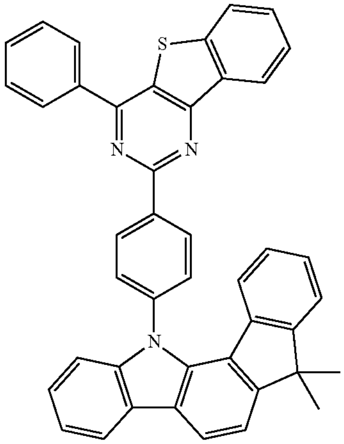
697
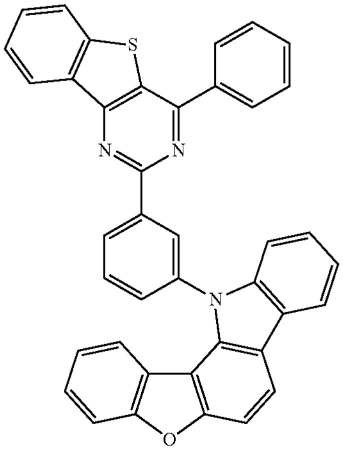
698
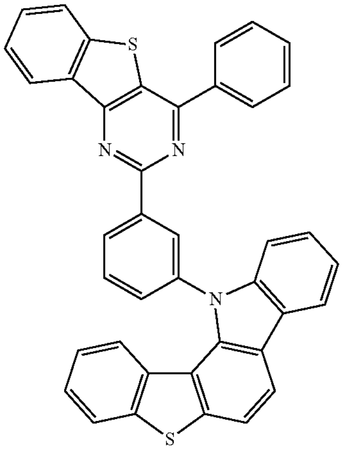
-continued
699
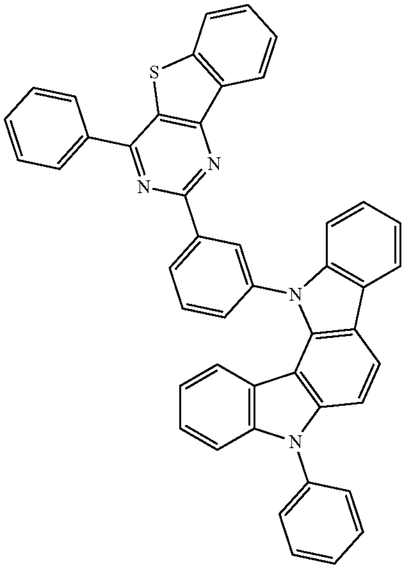
700
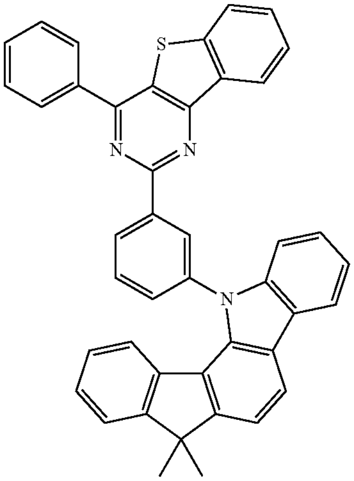
701
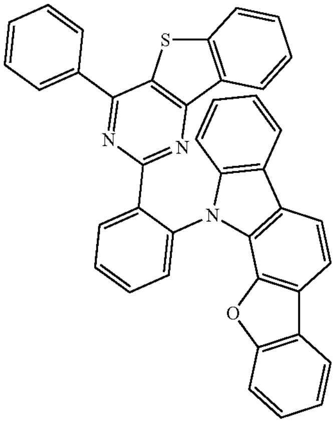

-continued
702
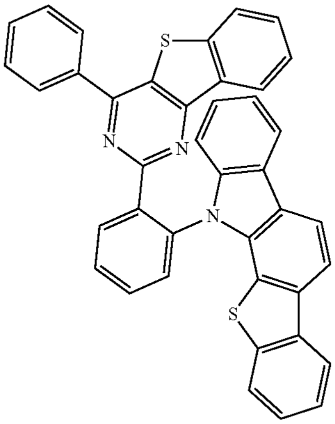
703
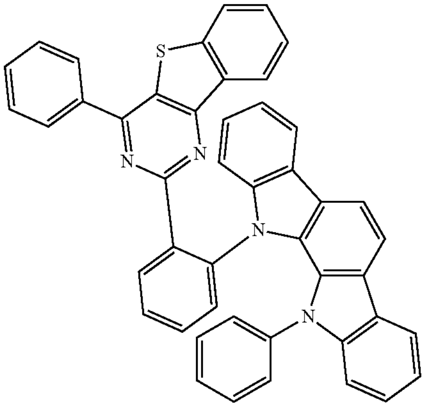
704
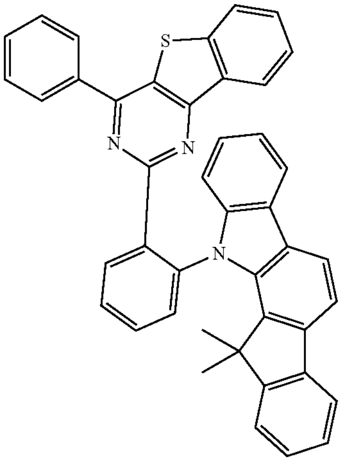
705
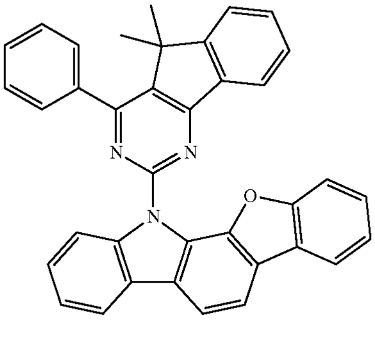
-continued
706
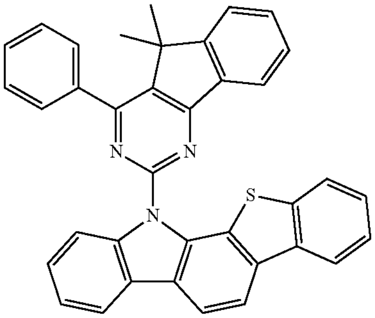
707
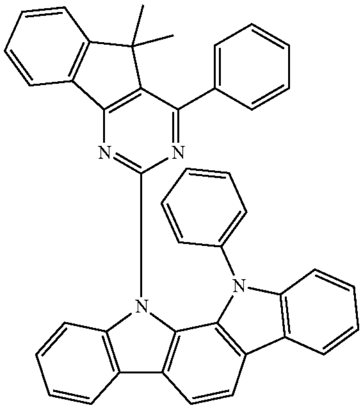
708
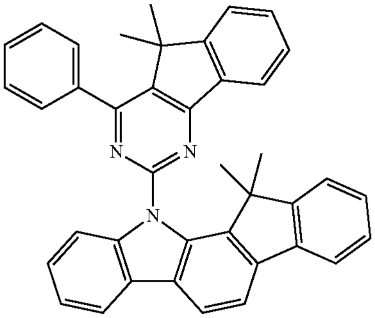
709
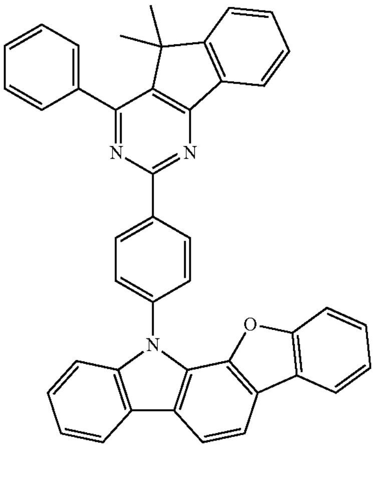

-continued
710
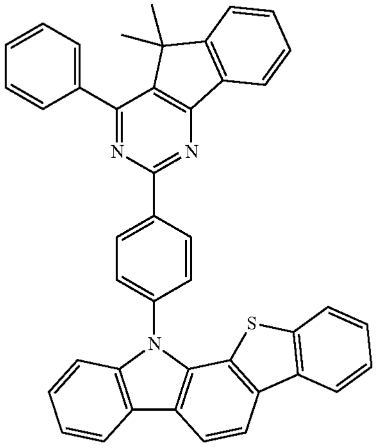
711
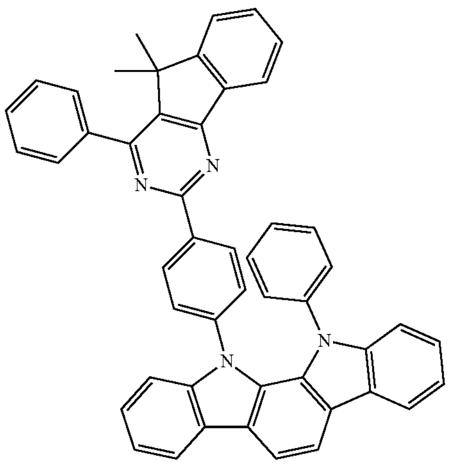
712
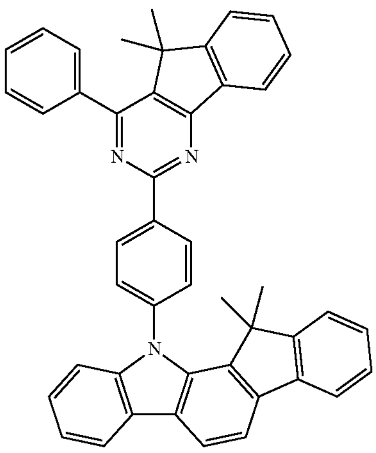
-continued
713
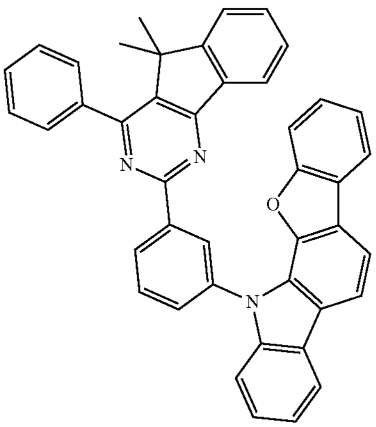
714
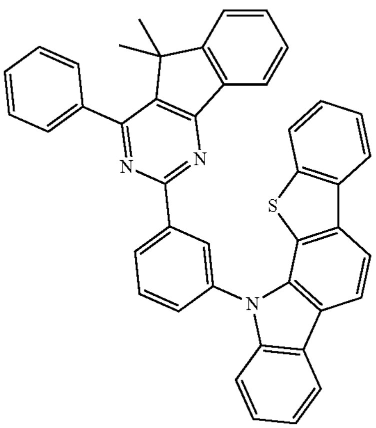
715
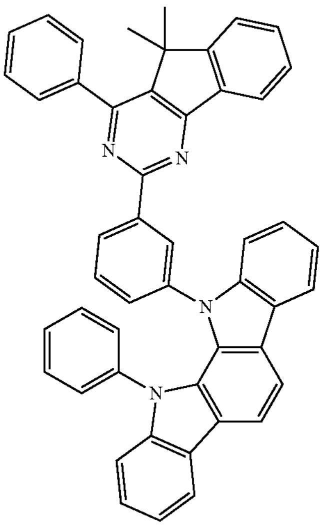

-continued
716
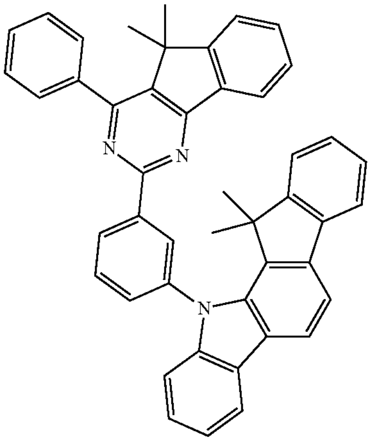
717
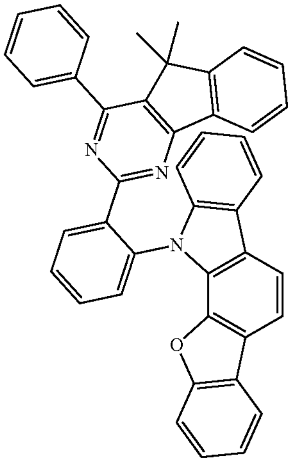
718
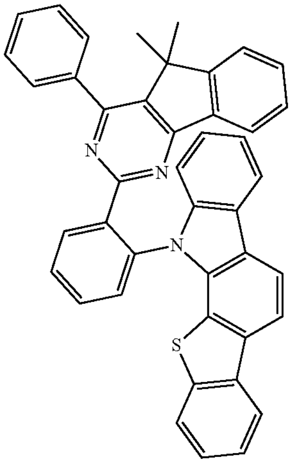
-continued
719
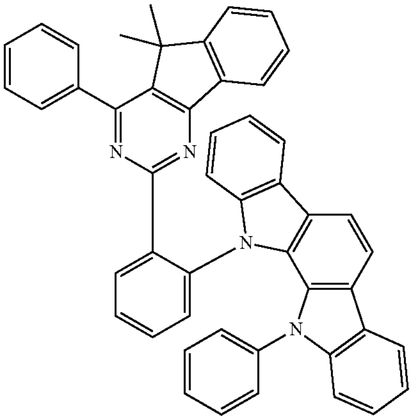
720
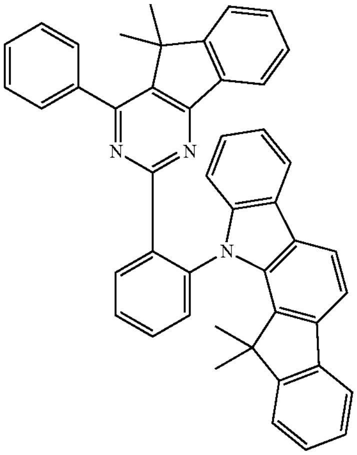
721
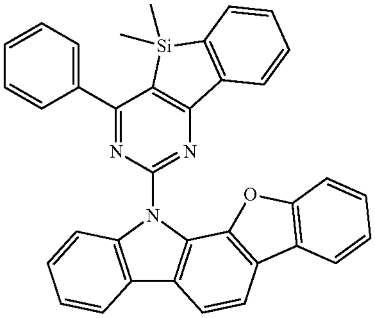
722
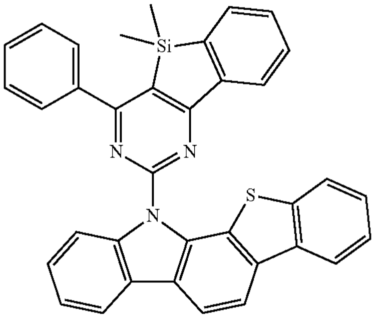

723
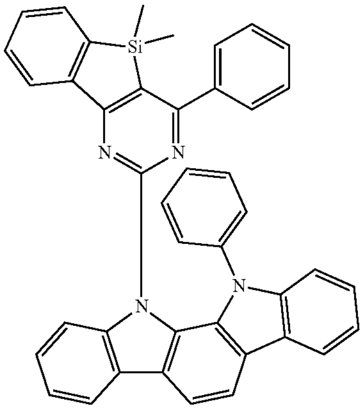
724
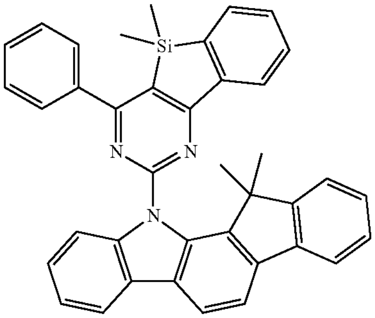
725
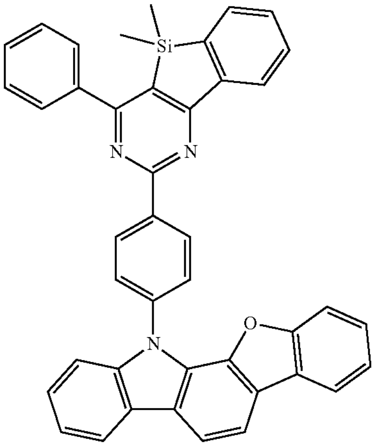
726
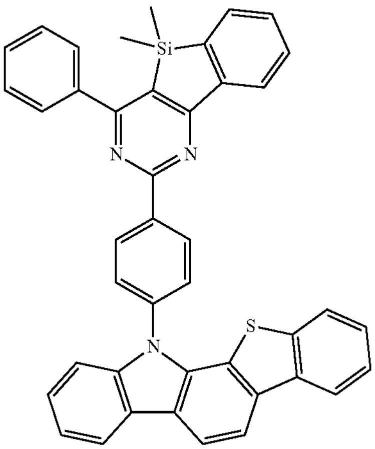
727
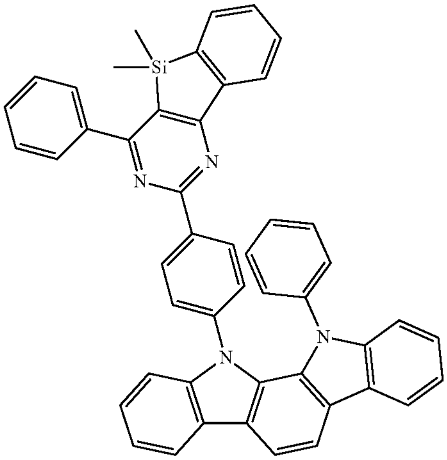
728
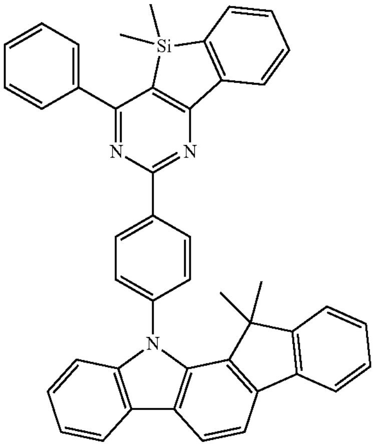
729
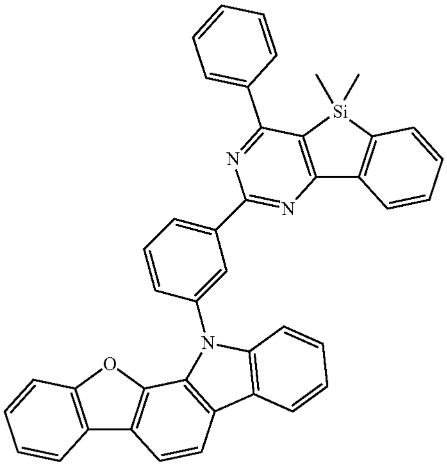

-continued
730
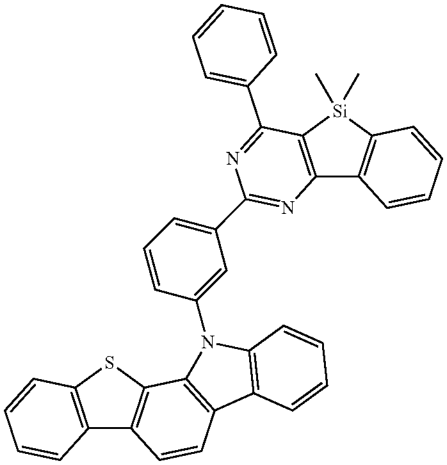
731
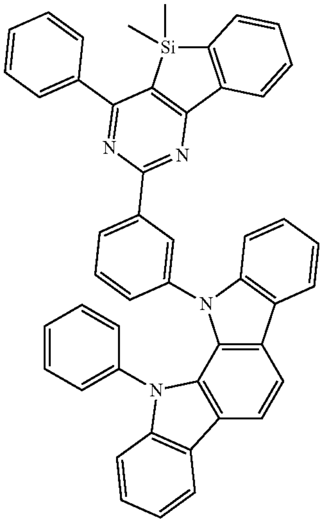
732
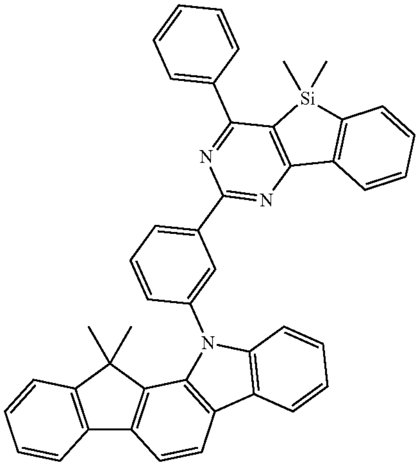
-continued
733
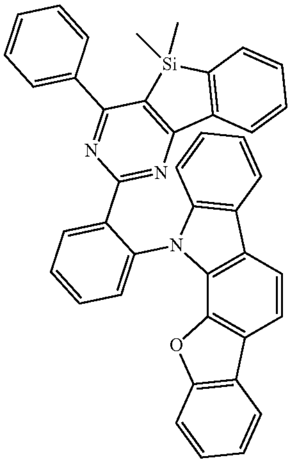
734
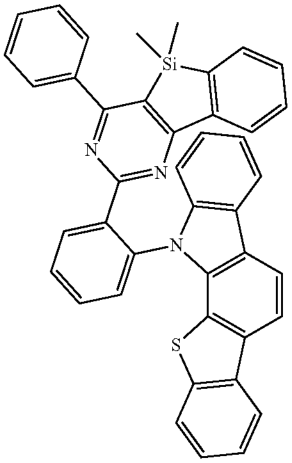
735
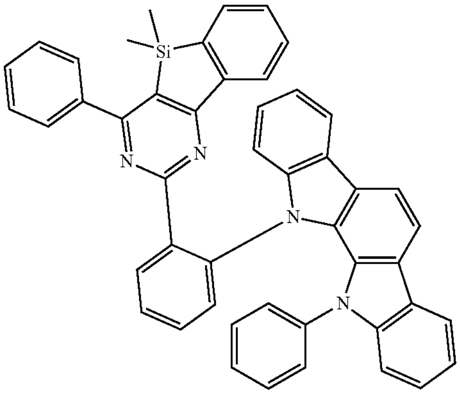

-continued
736
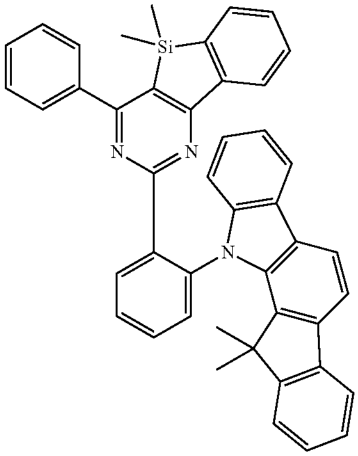
2390
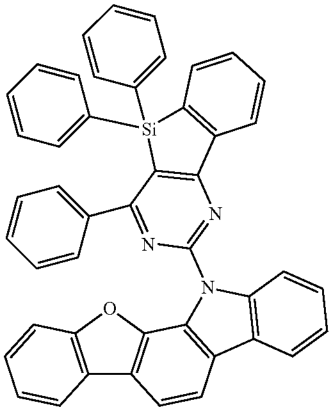
737
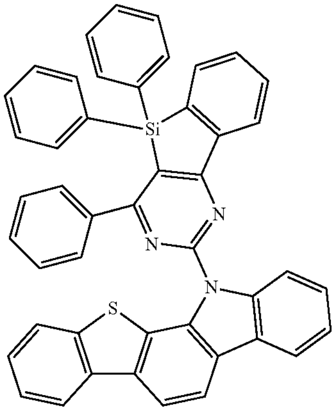
-continued
738
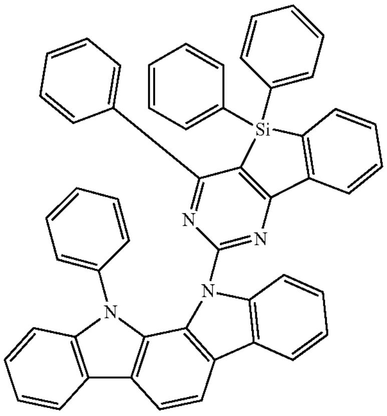
739
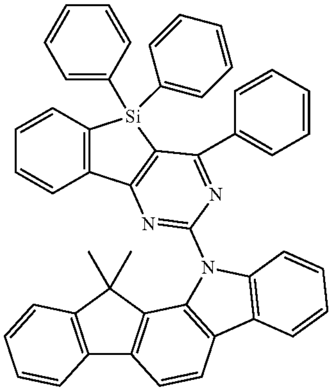
740
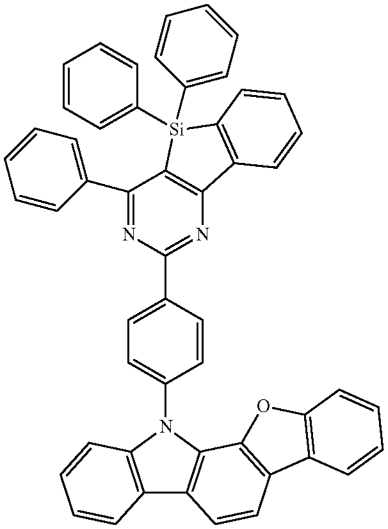

-continued
741
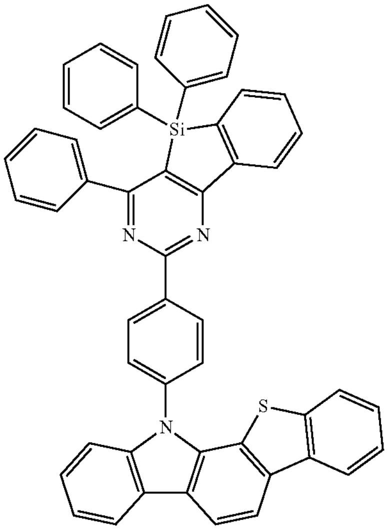
742
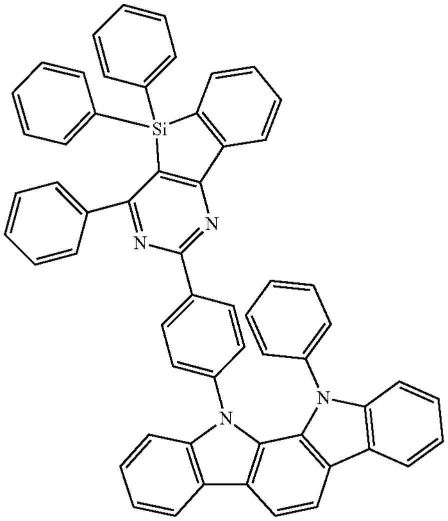
743
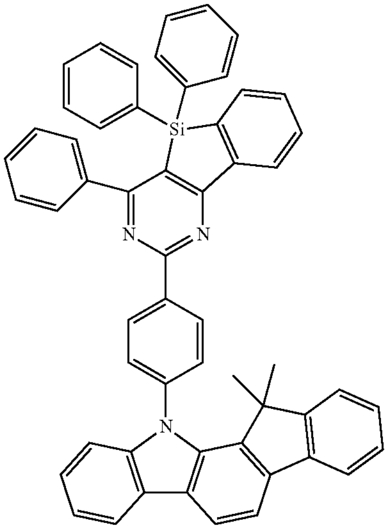
-continued
744
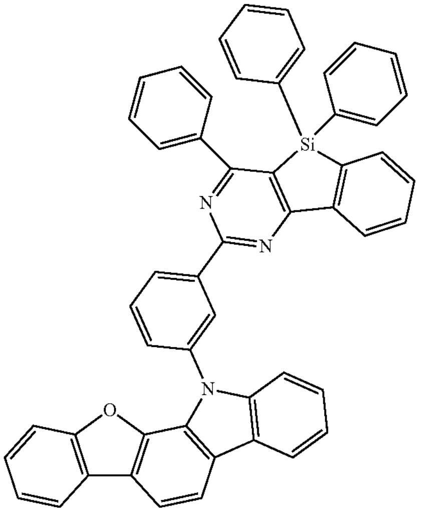
745
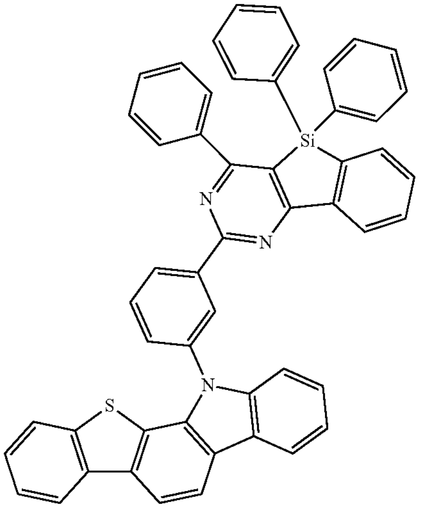
746
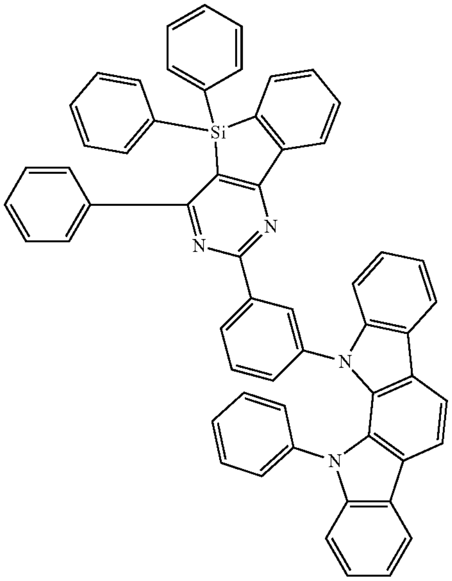

-continued
747
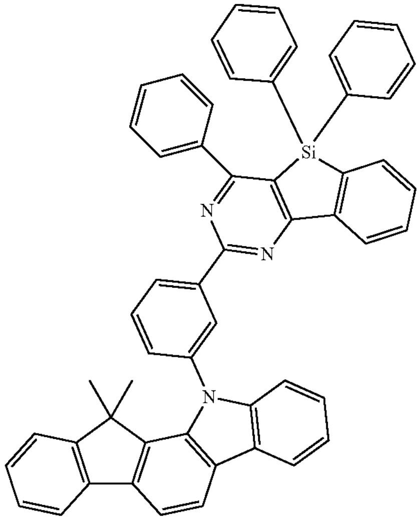
748
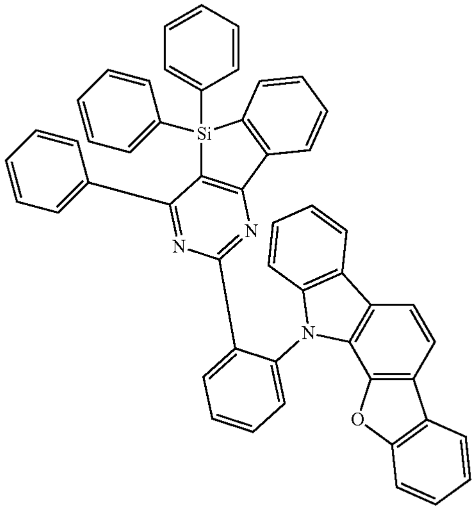
749
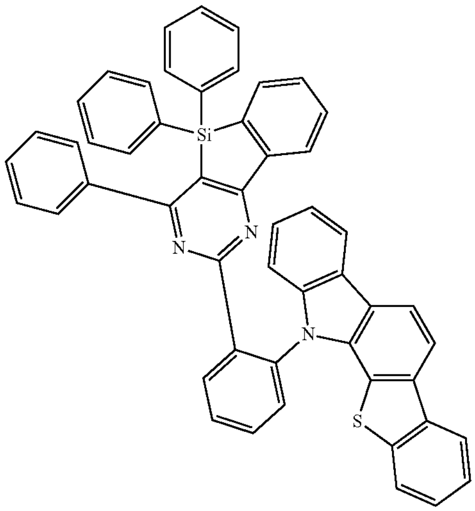
-continued
750
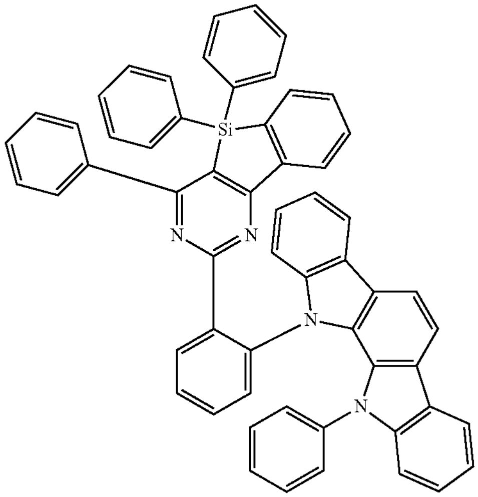
751
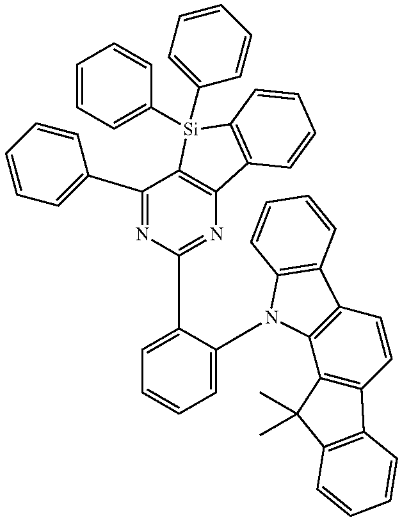
752
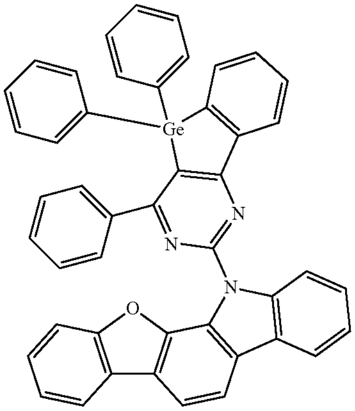

-continued
753
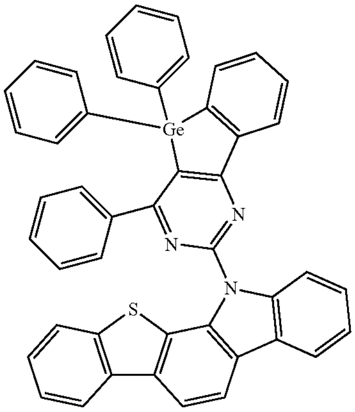
754
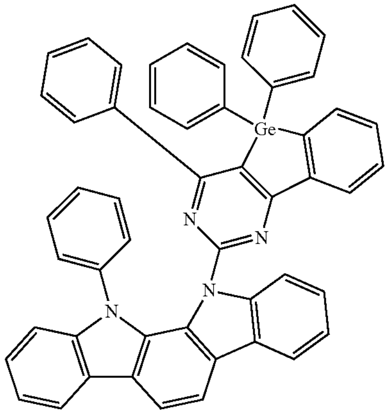
755
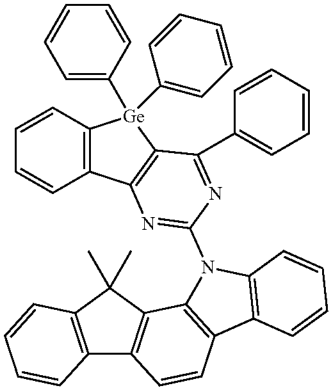
-continued
756
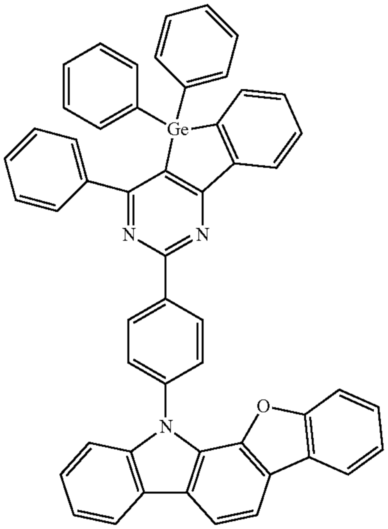
757
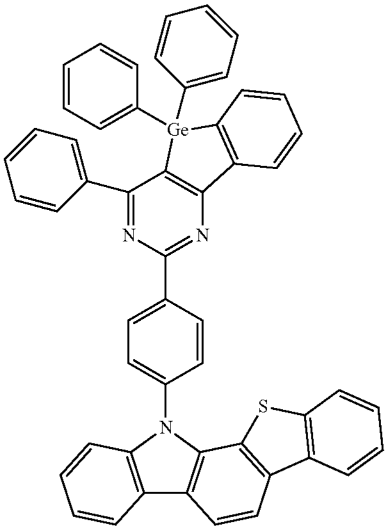
758
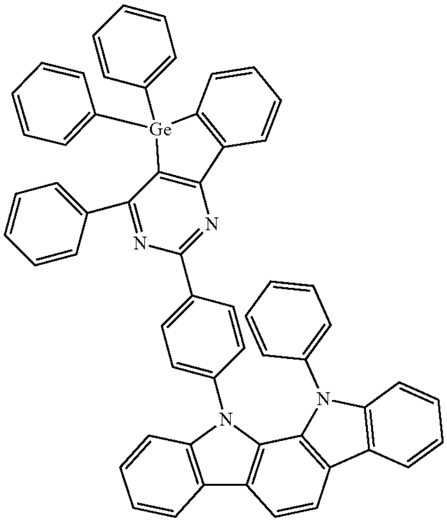

-continued
759
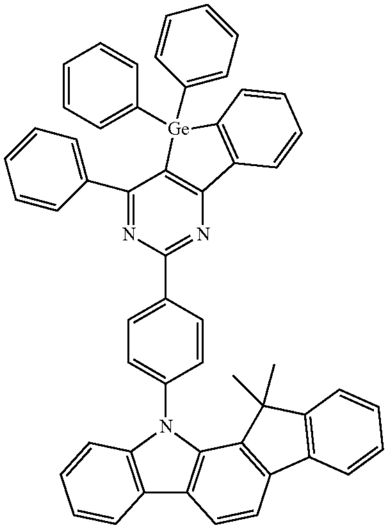
760
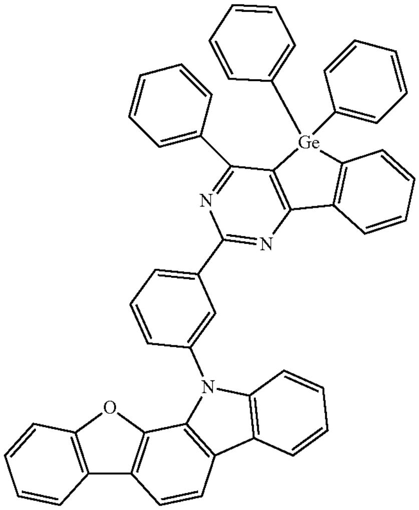
761
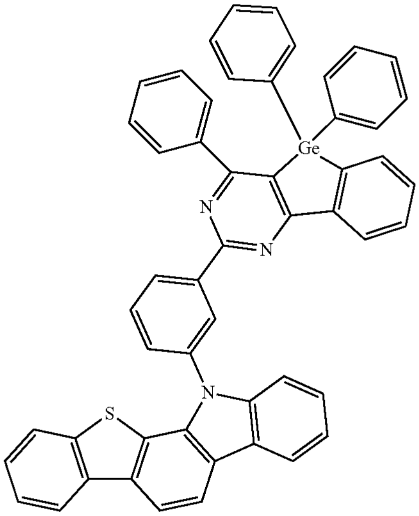
-continued
762
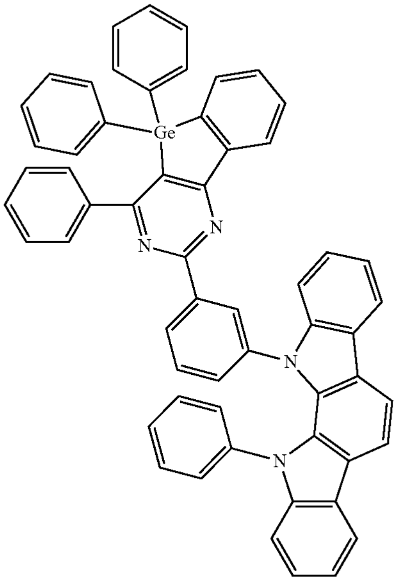
763
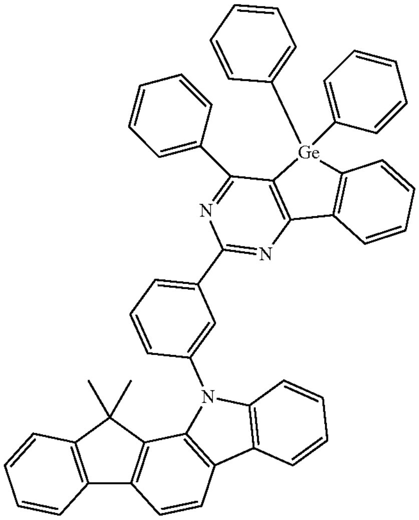
764
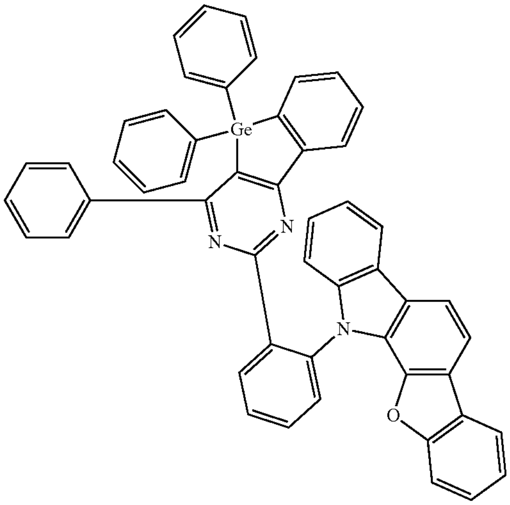

-continued
765
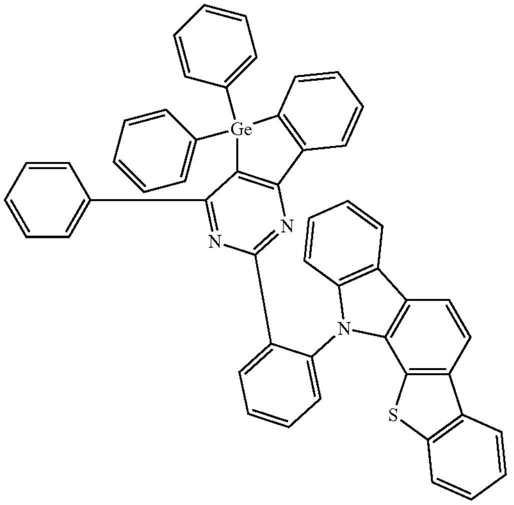
766
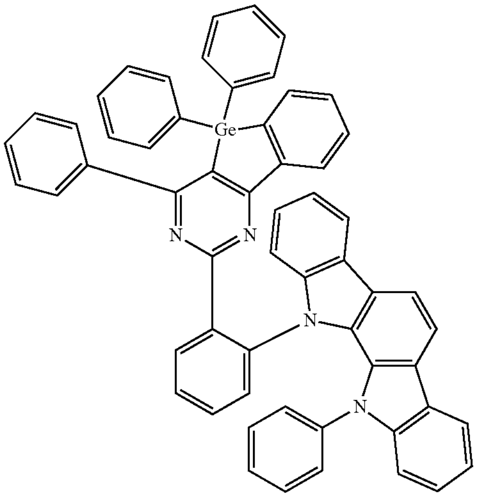
767
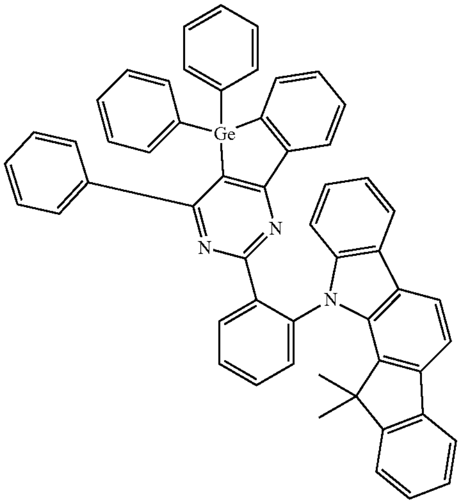
-continued
768
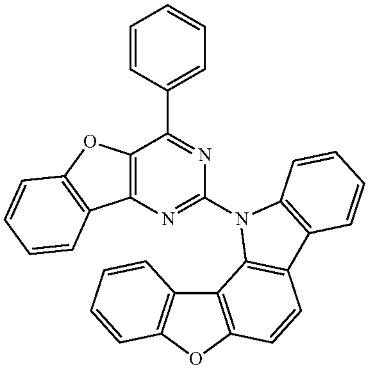
769
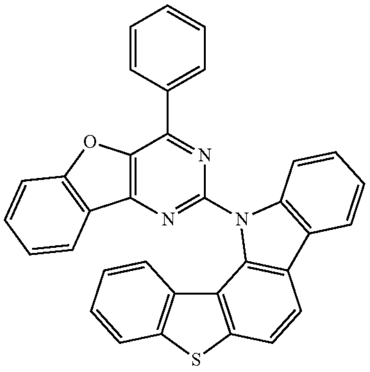
770
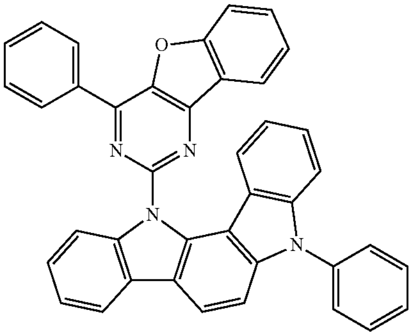
771
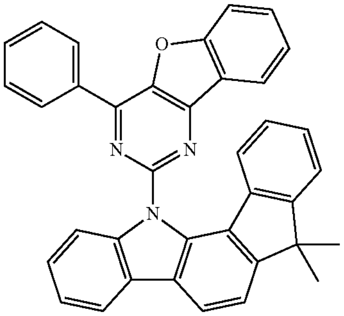

-continued
772
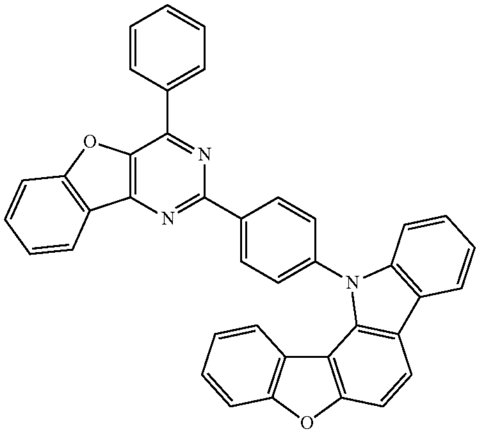
773
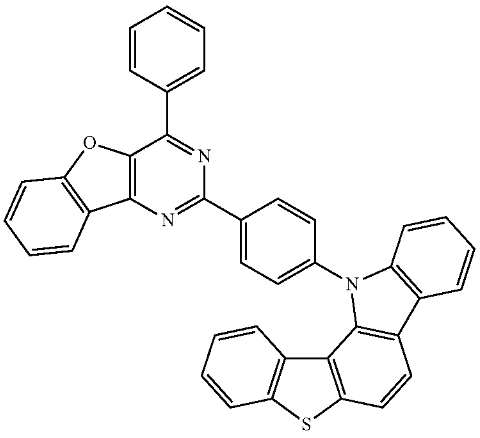
774
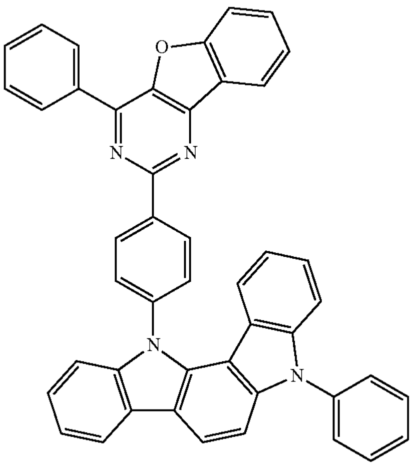
-continued
775
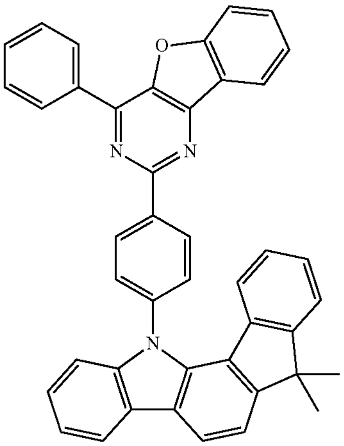
776
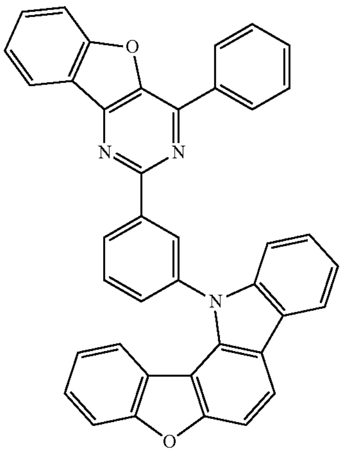
777
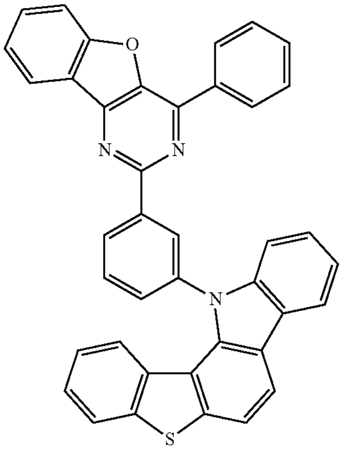

-continued
778
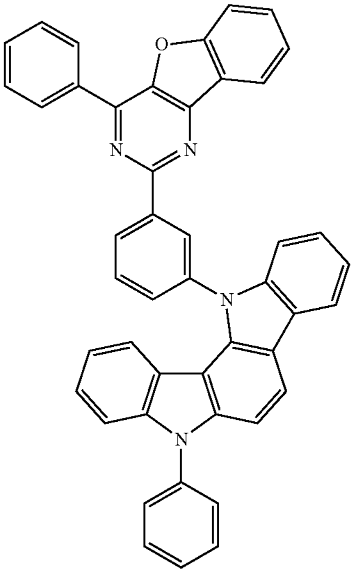
779
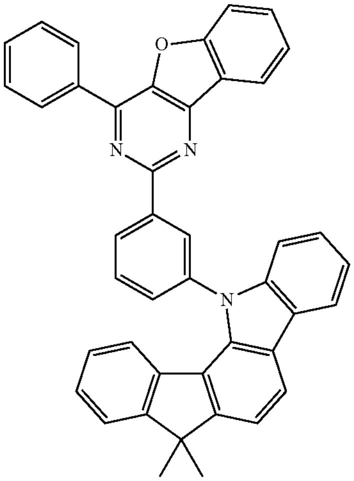
780
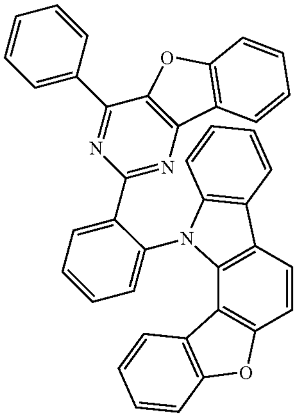
-continued
781
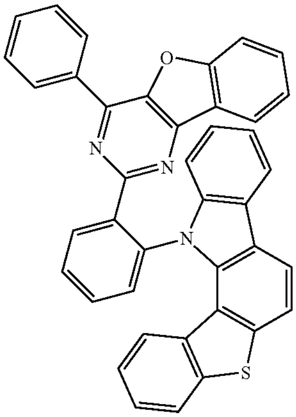
782
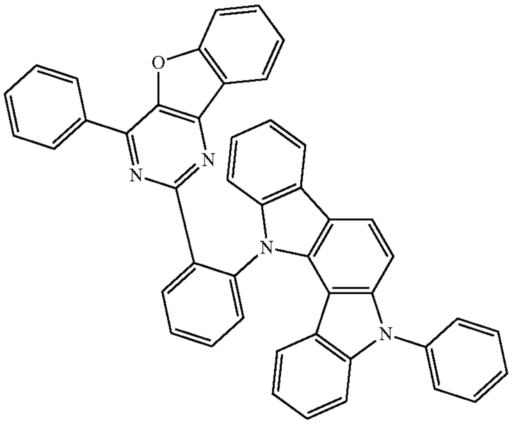
783
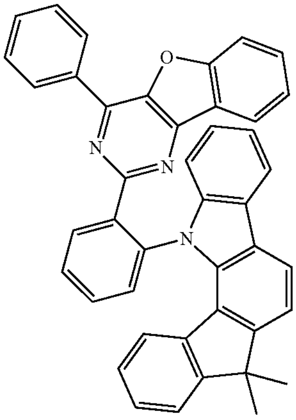

-continued
784
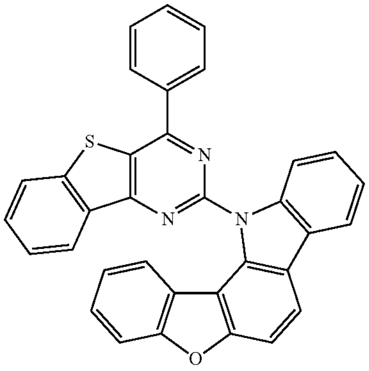
785
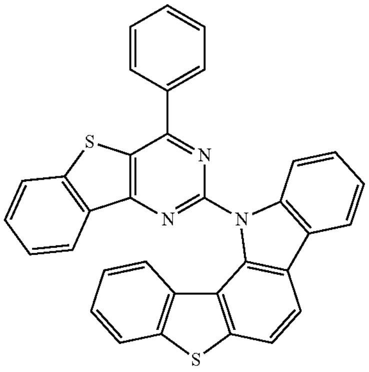
786
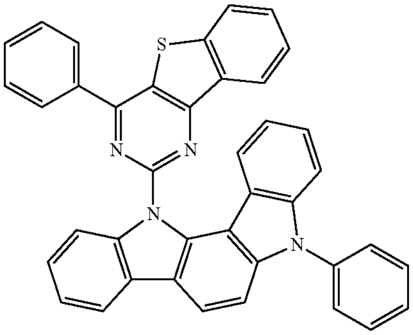
787
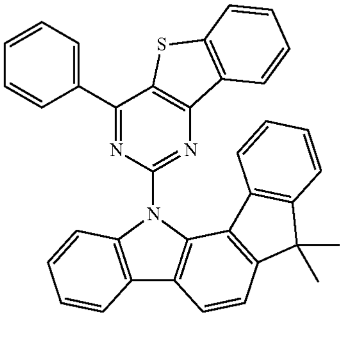
-continued
788
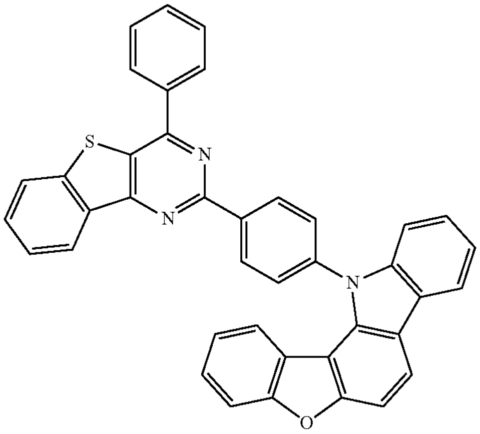
789
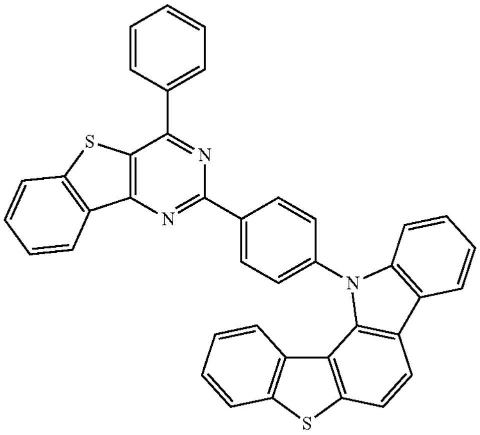
790
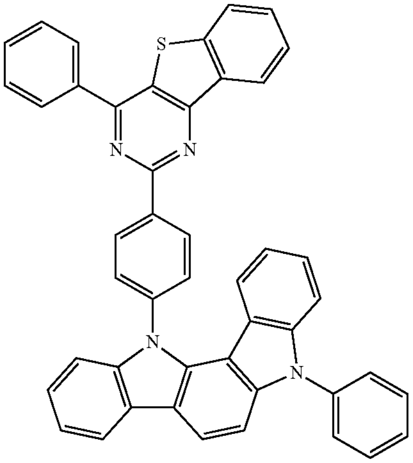

-continued
791
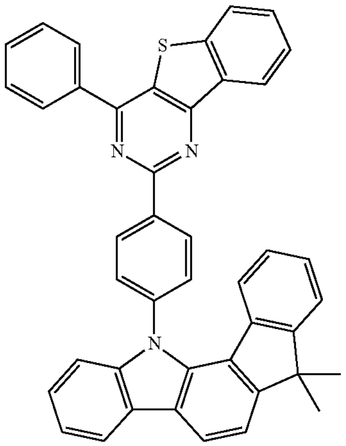
792
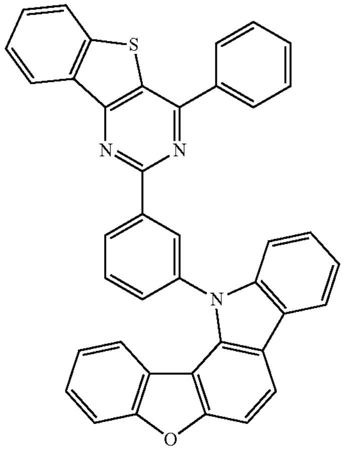
793
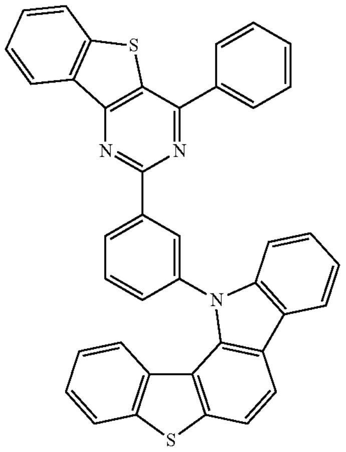
-continued
794
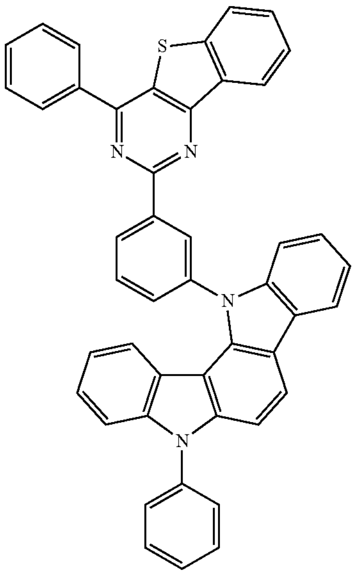
795
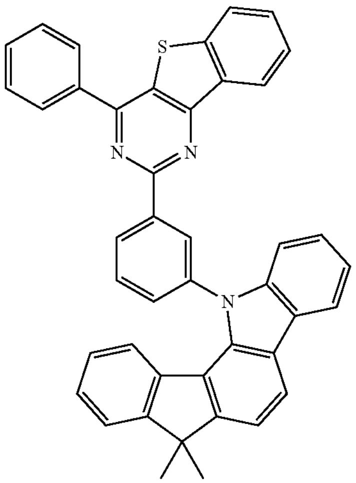
796
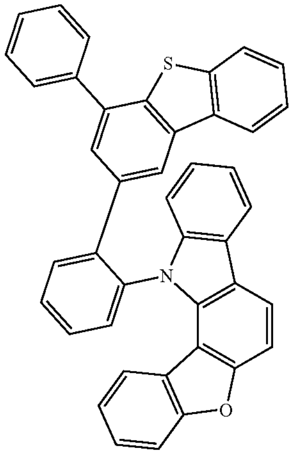

-continued
797
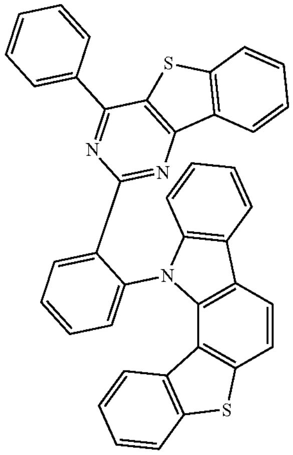
798
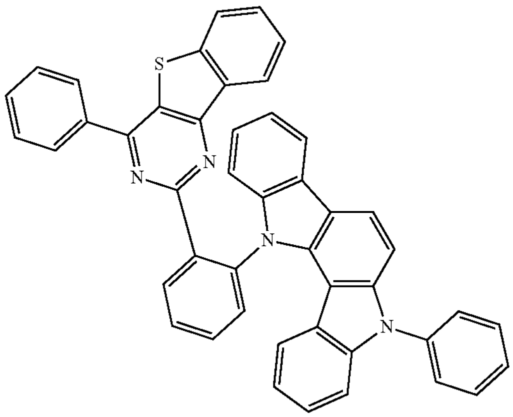
799
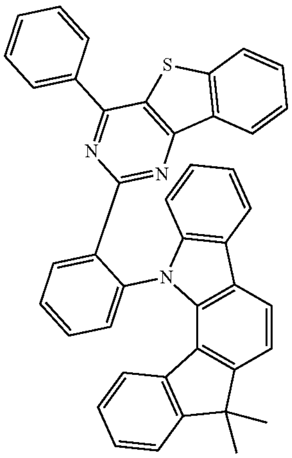
-continued
800
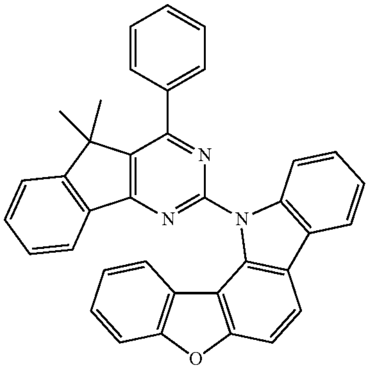
801
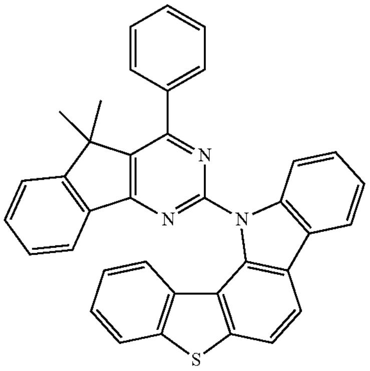
802
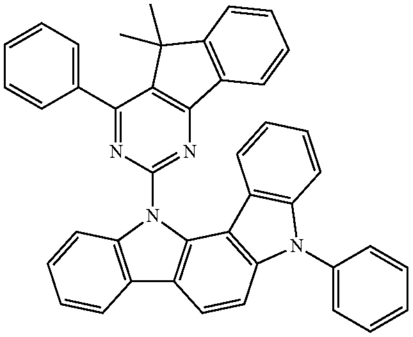
803
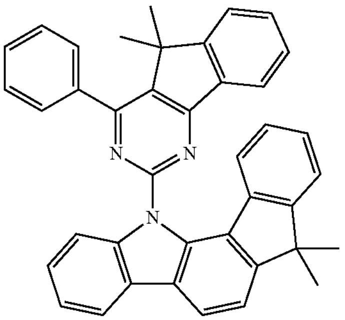

-continued
804
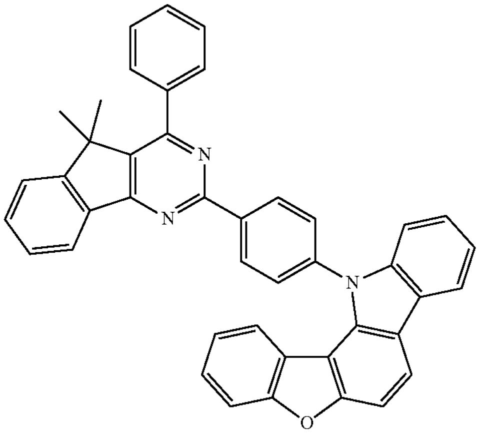
805
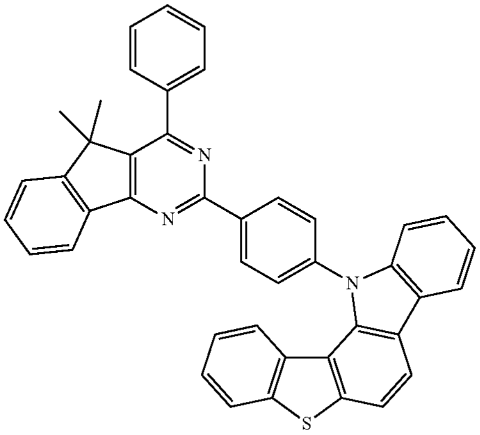
806
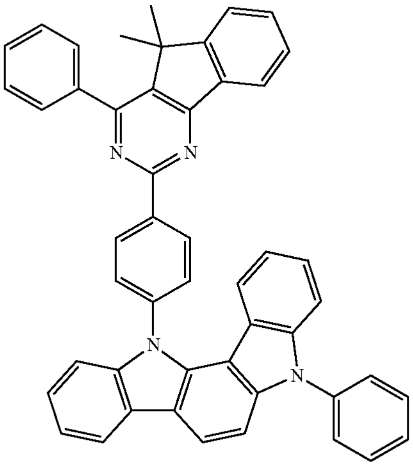
-continued
807
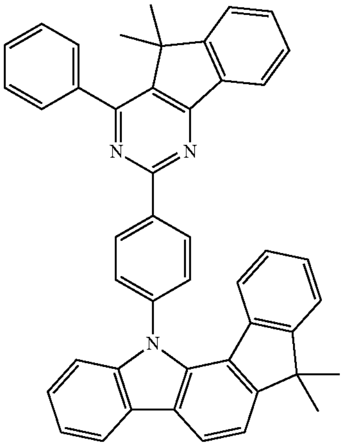
808
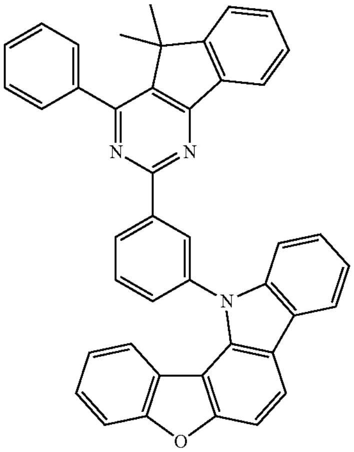
809
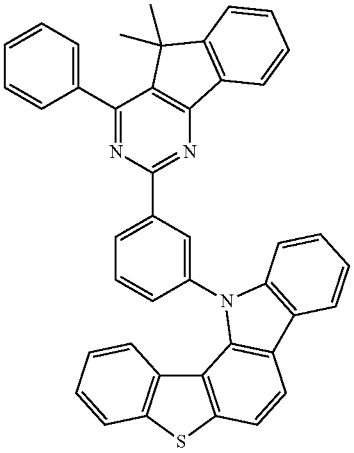

-continued
810
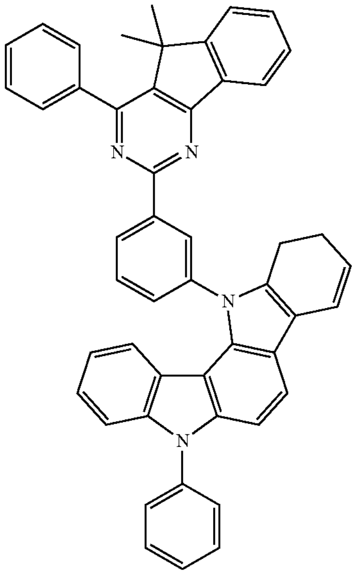
811
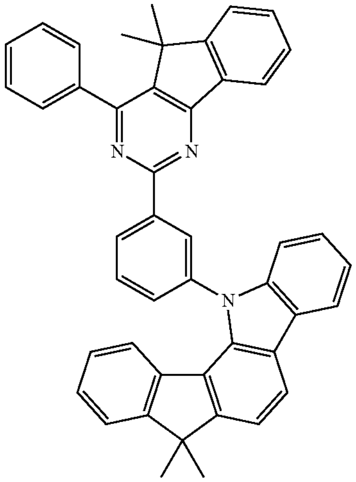
812
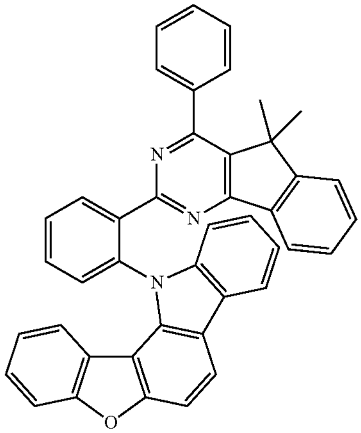
-continued
813
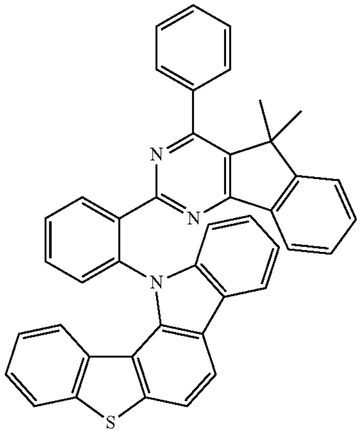
814
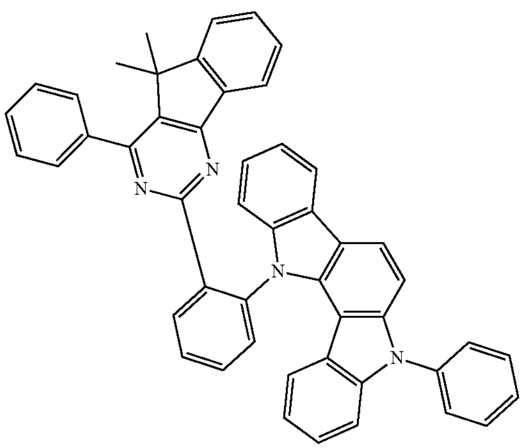
815
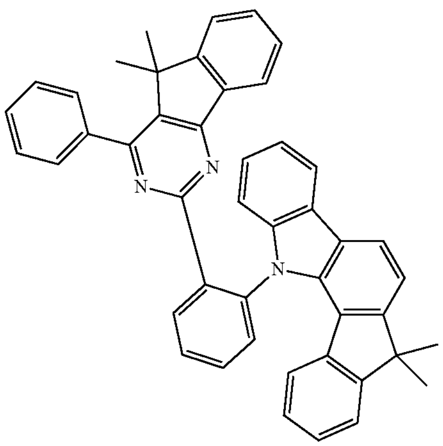

-continued
816
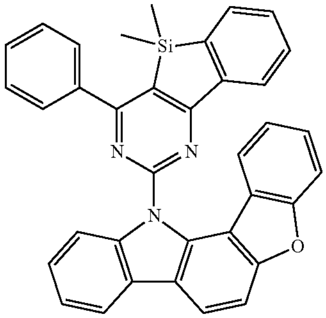
817
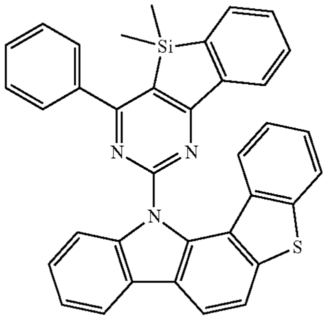
818
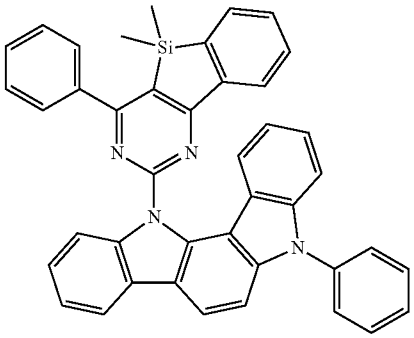
819
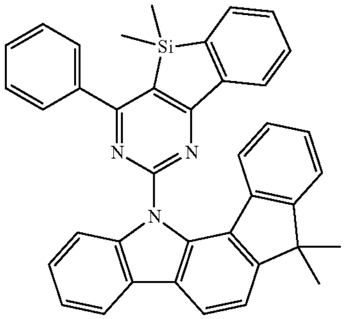
-continued
820
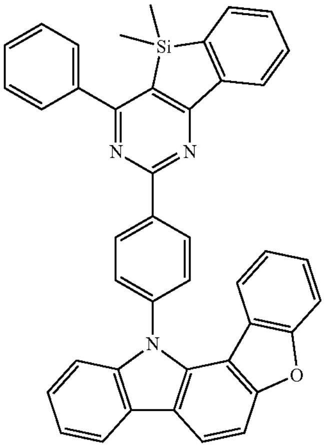
821
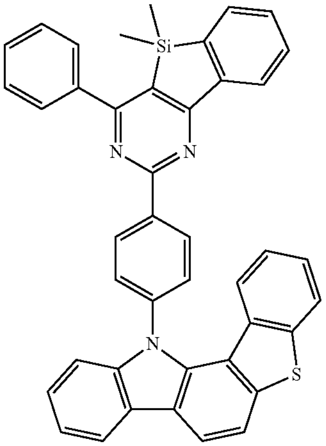
822
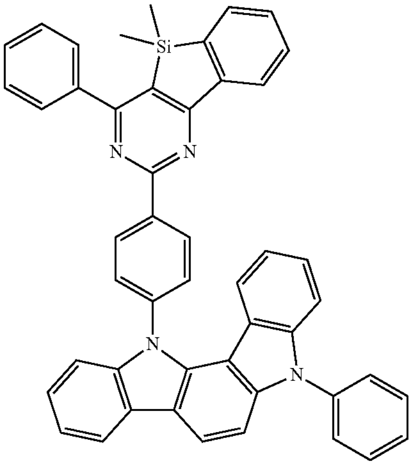

-continued
823
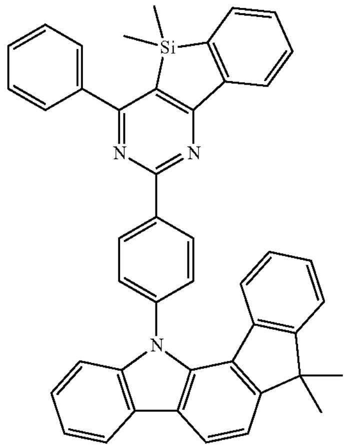
824
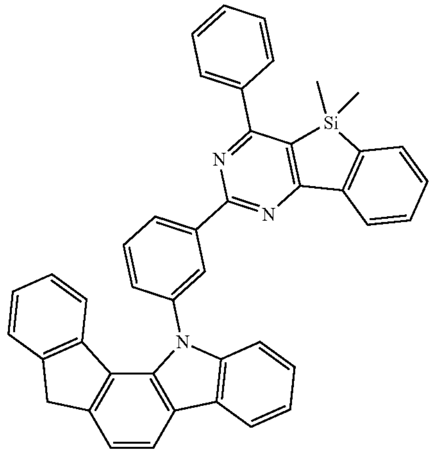
825
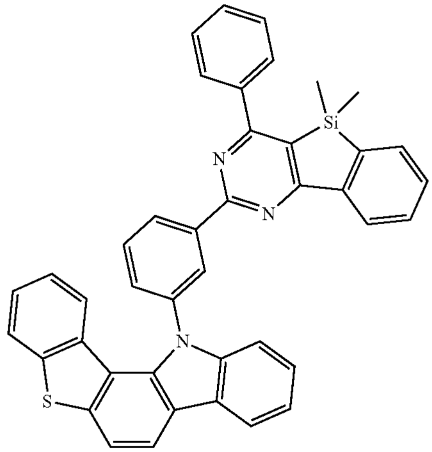
-continued
826
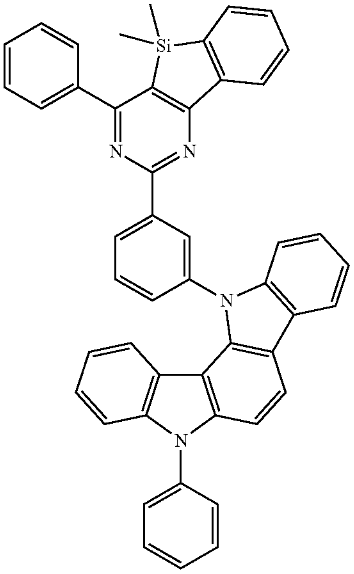
827
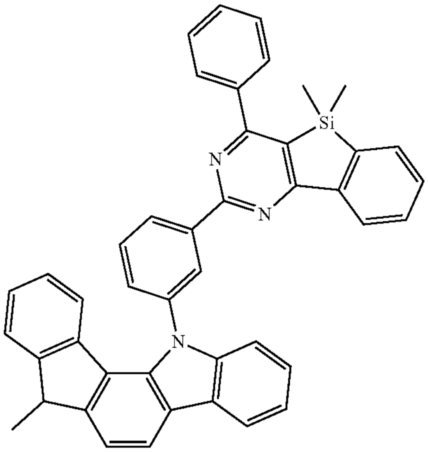
828
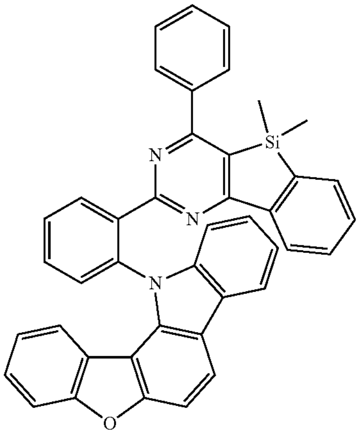

-continued
829
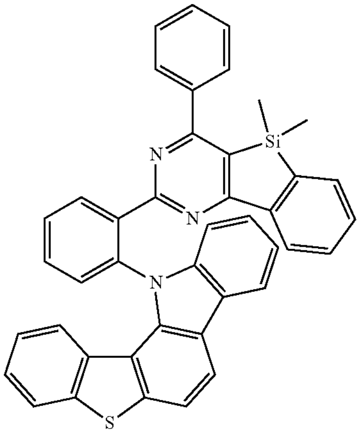
830
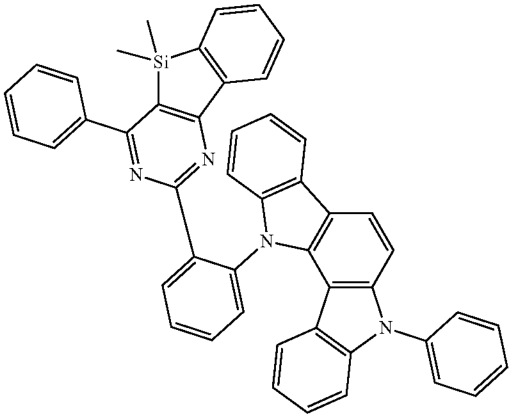
831
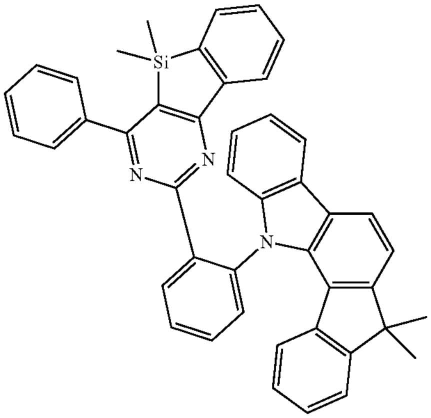
832
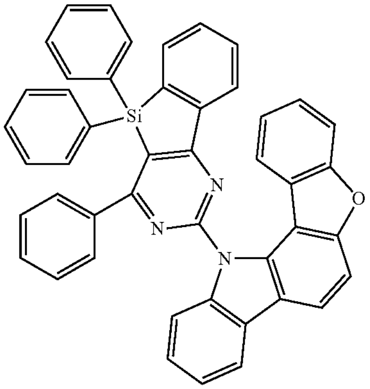
833
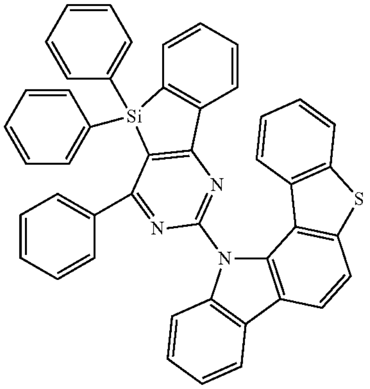
834
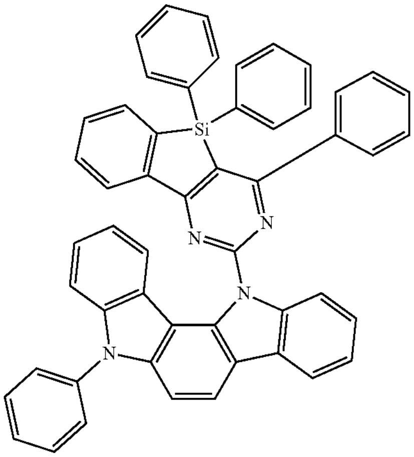
835
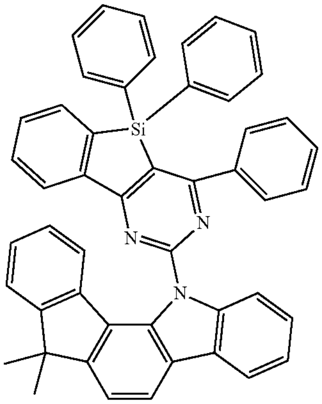

-continued
836
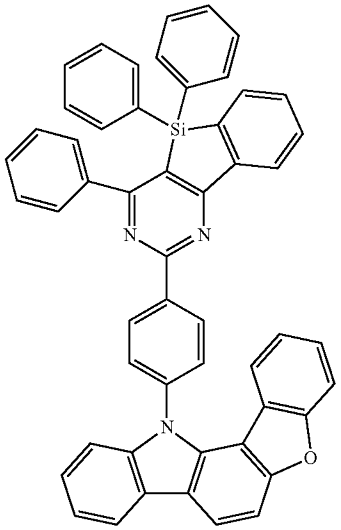
837
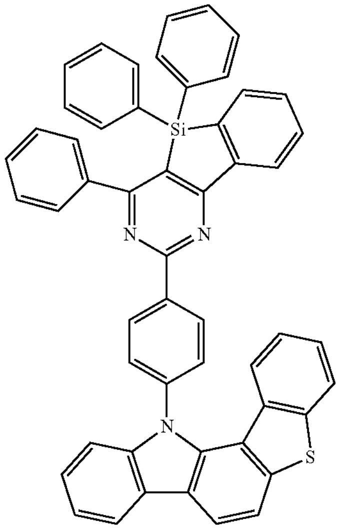
838
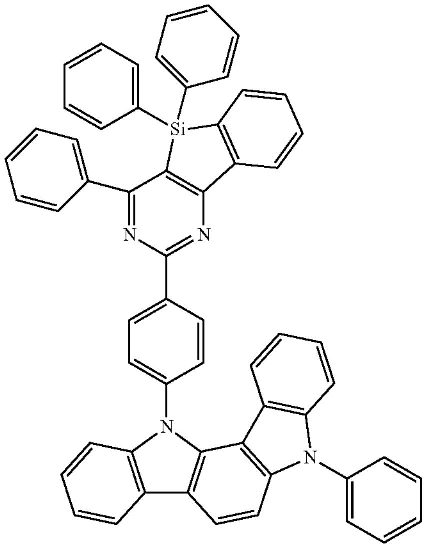
-continued
839
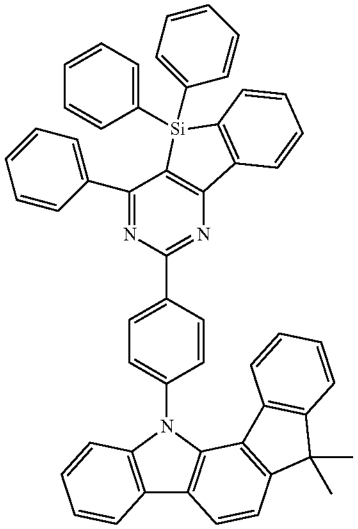
840
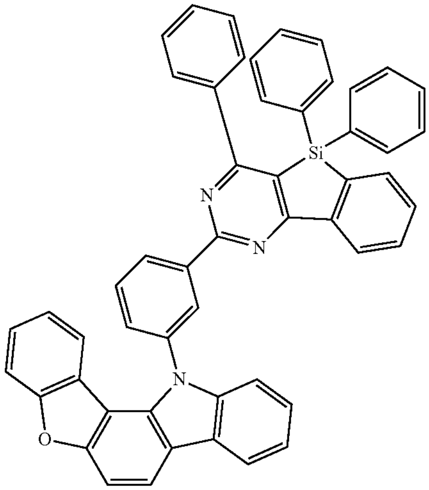
841
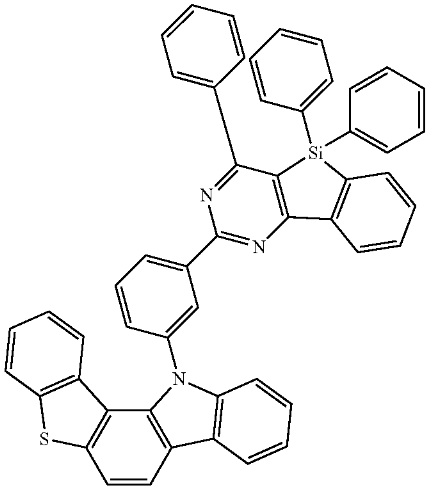

-continued
842
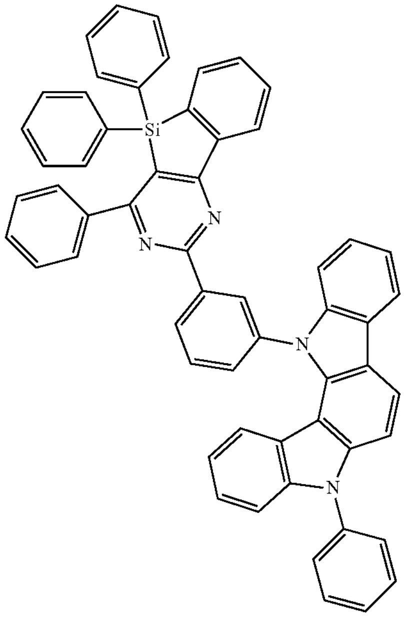
843
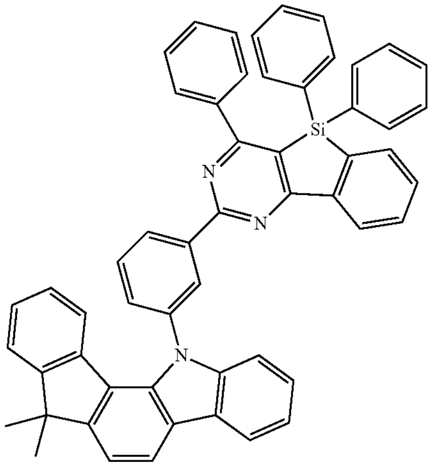
844
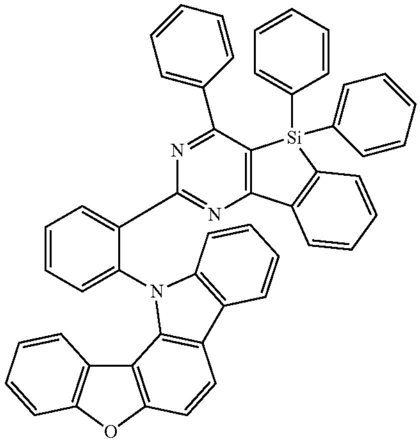
-continued
845
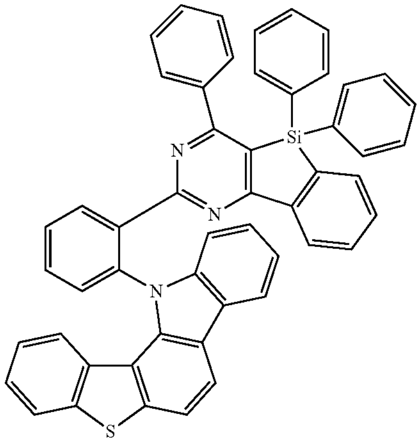
846
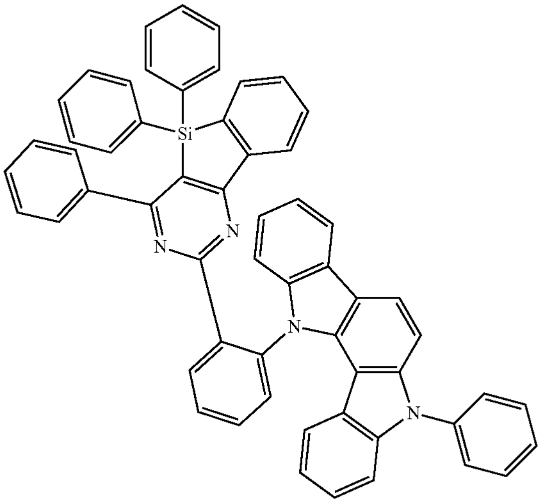
847
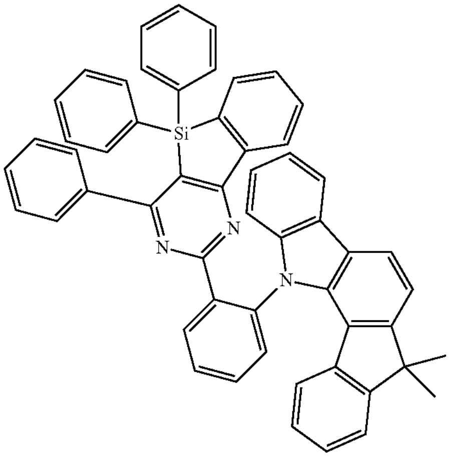

-continued
848
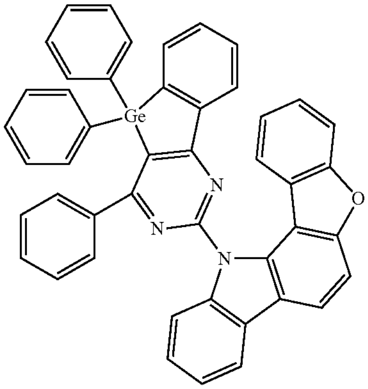
849
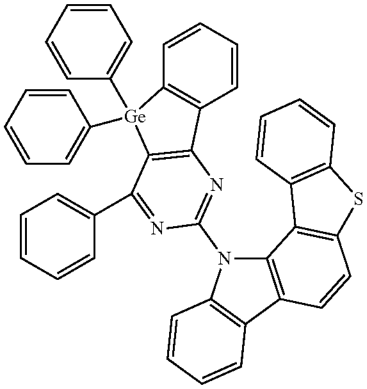
850
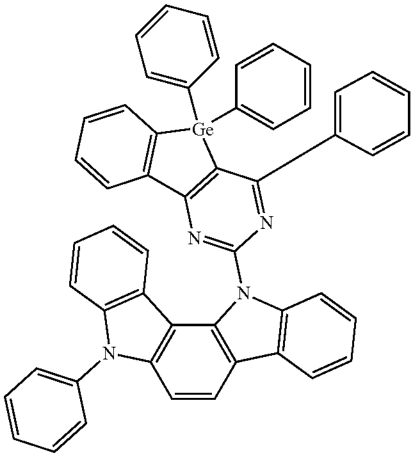
851
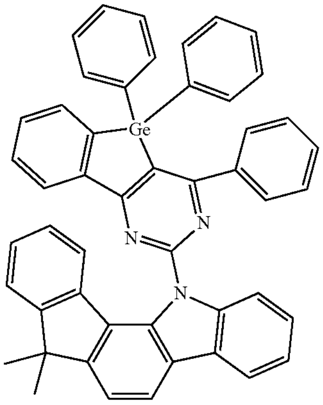
-continued
852
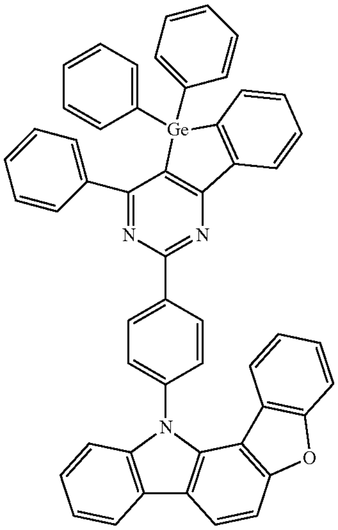
853
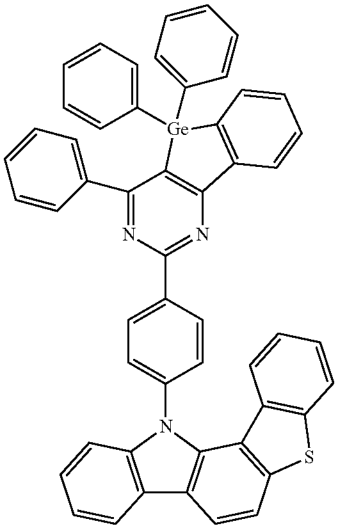
854
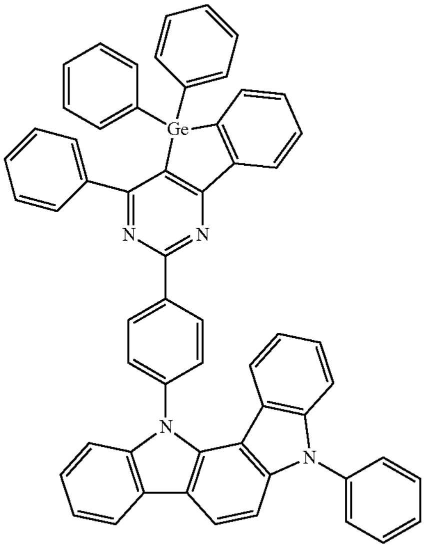

-continued
855
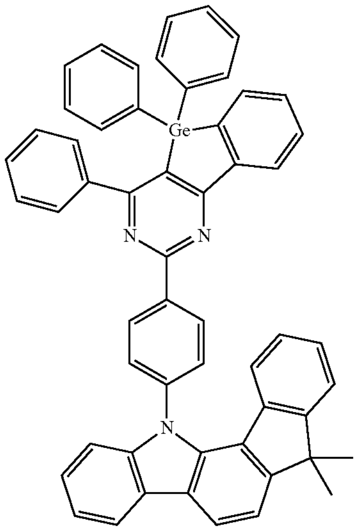
856
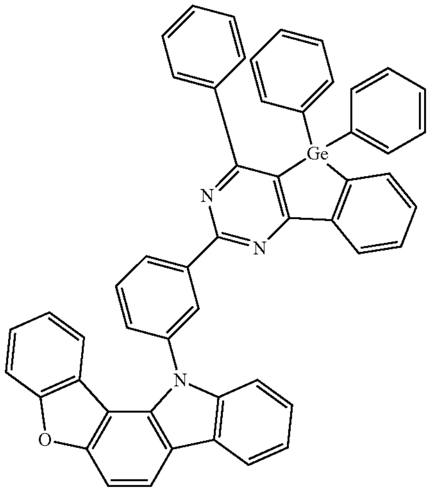
857
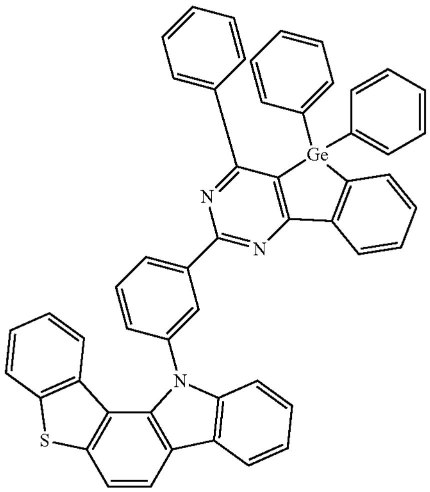
-continued
858
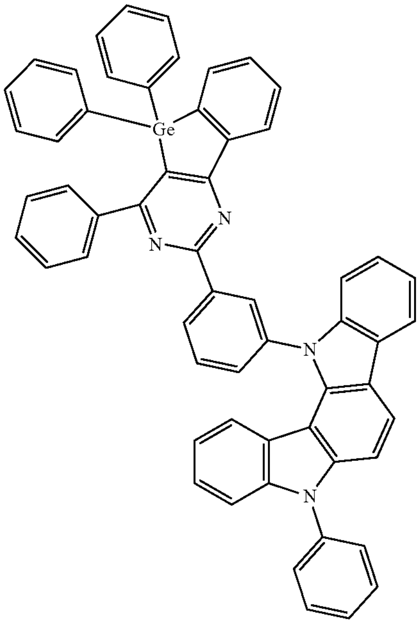
859
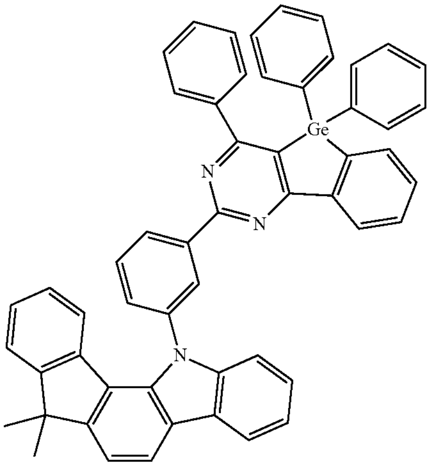
860
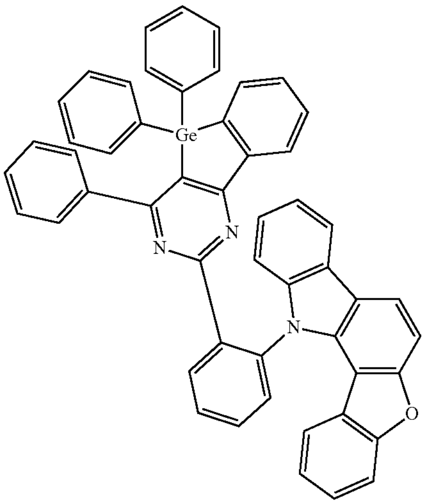

-continued
861
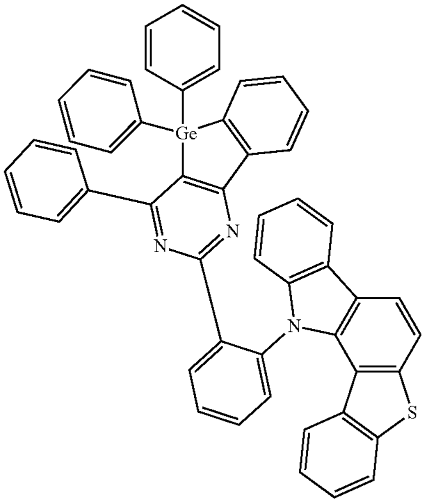
862
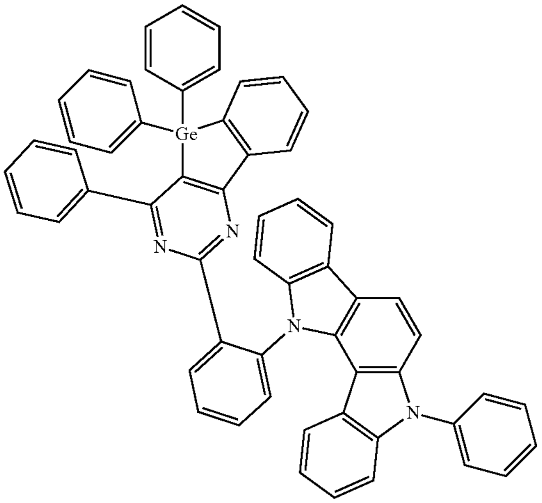
863
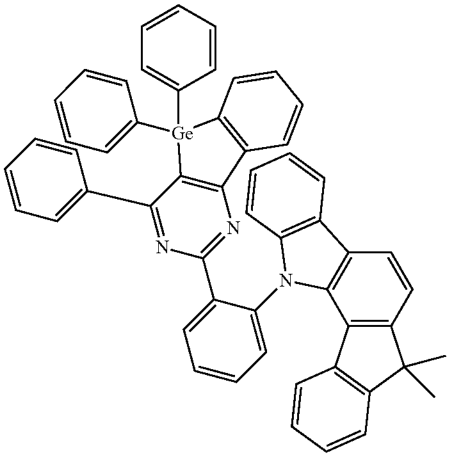
-continued
864
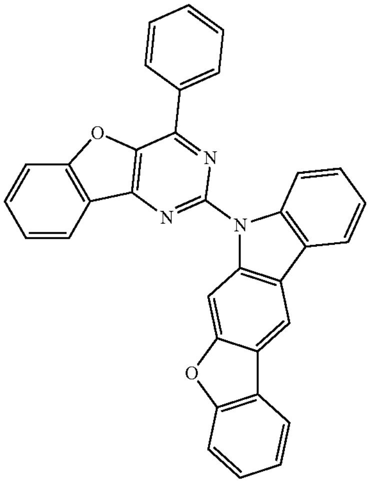
865
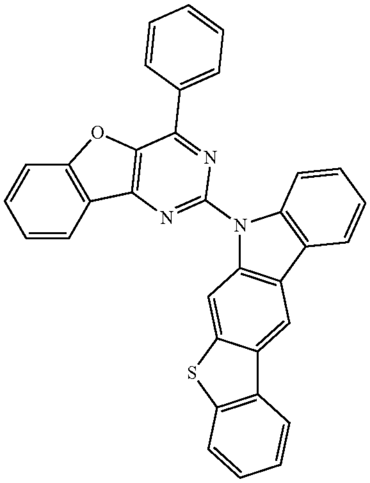
866
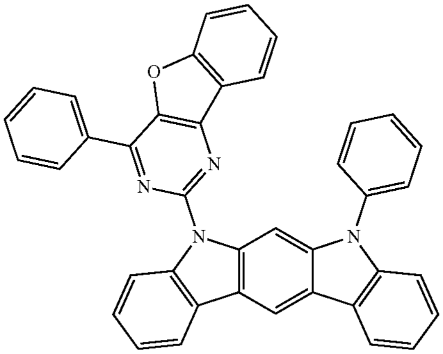

-continued
867
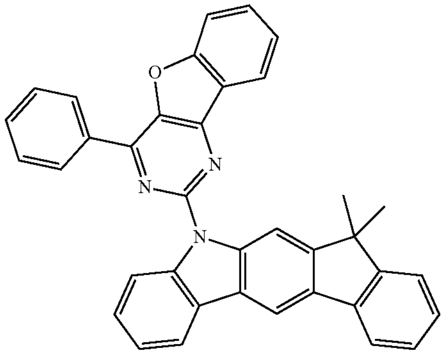
868
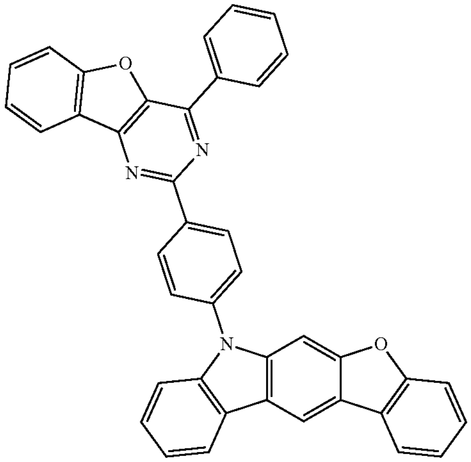
869
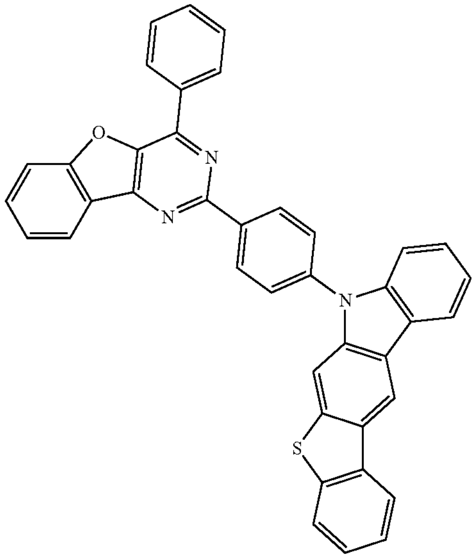
-continued
870
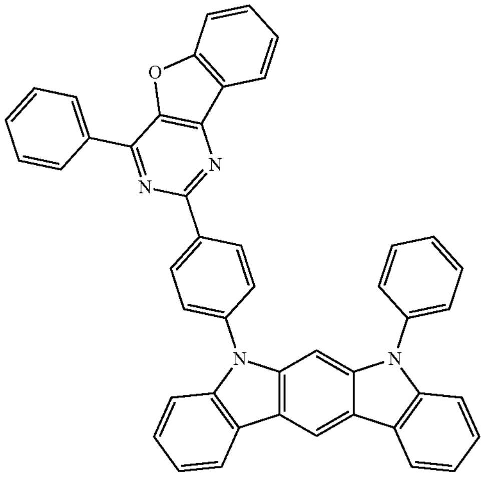
871
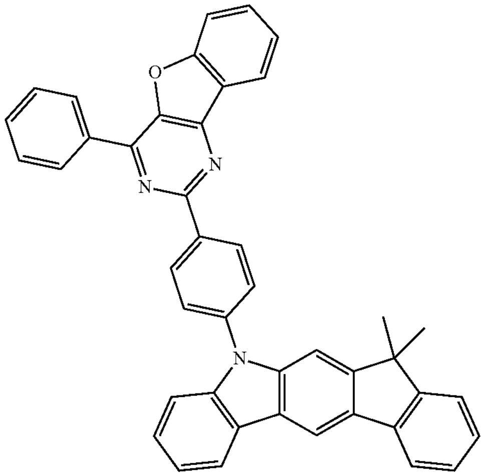
872
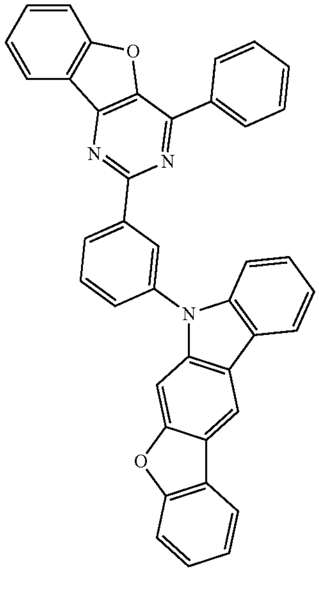

-continued
873
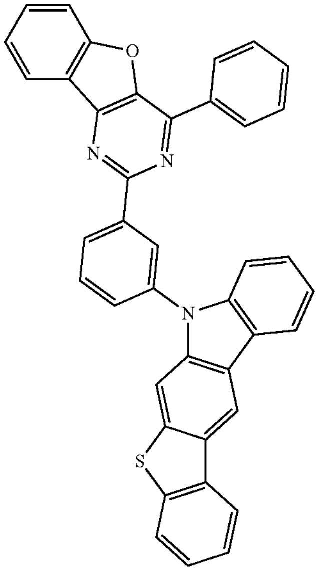
874
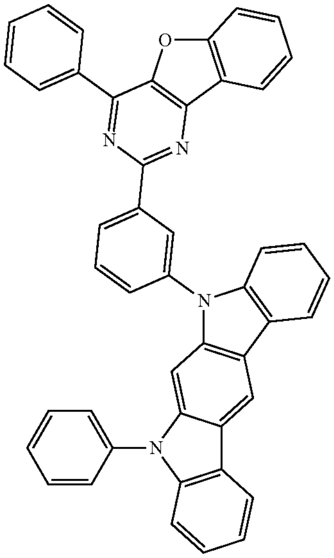
-continued
875
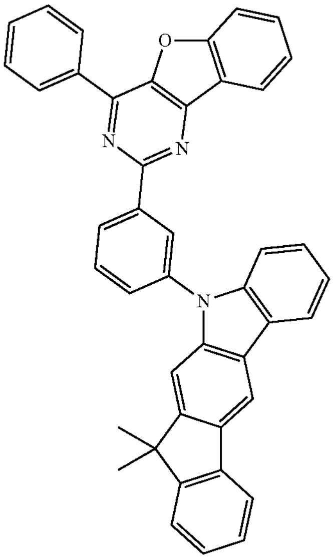
876
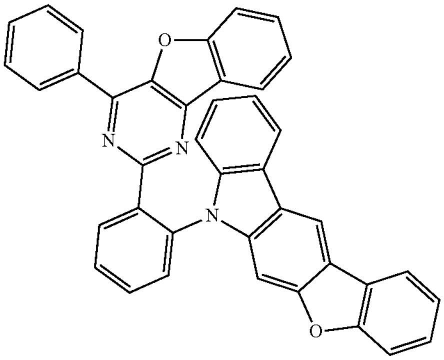
877
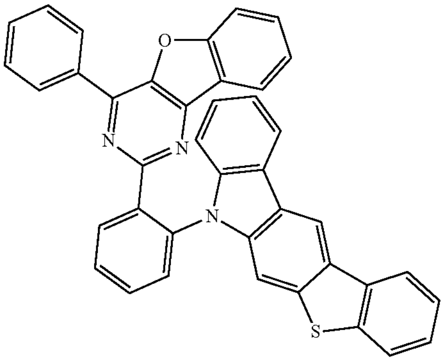
878
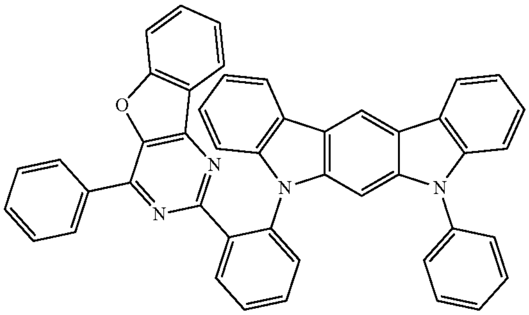

-continued
879
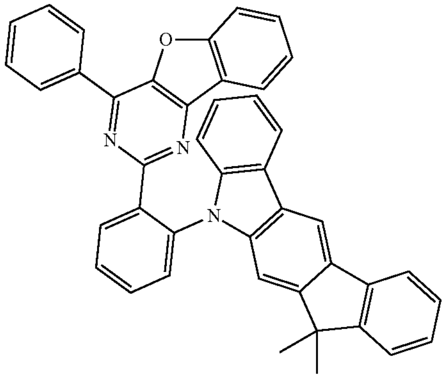
880
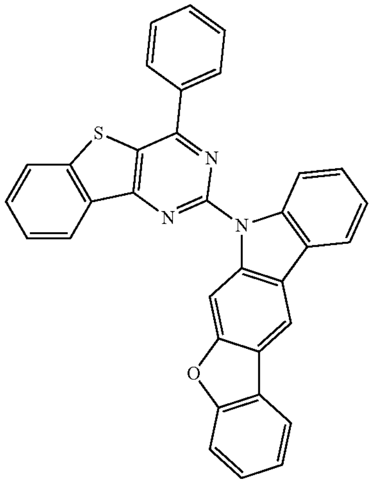
881
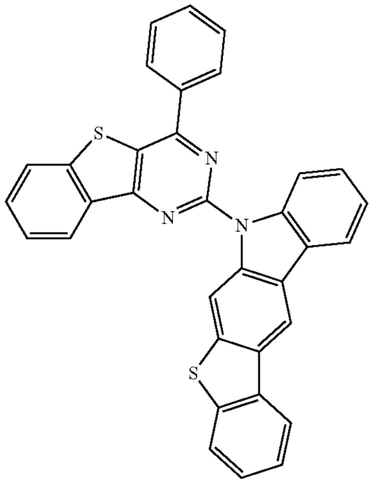
-continued
882
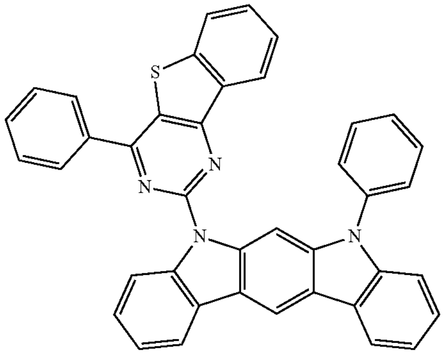
883
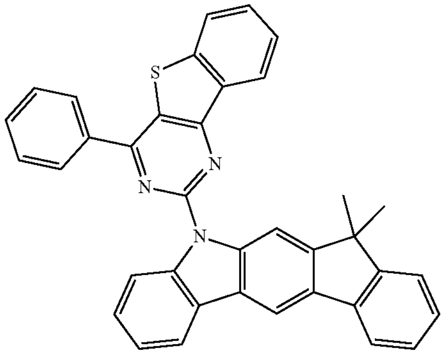
884
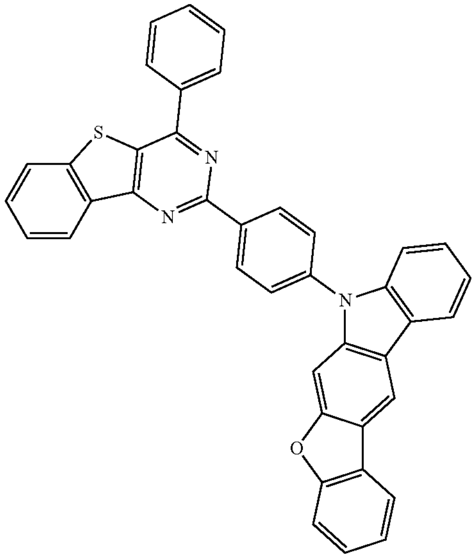

-continued
885
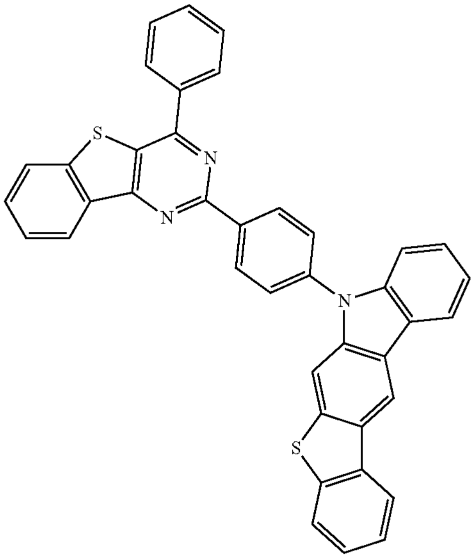
886
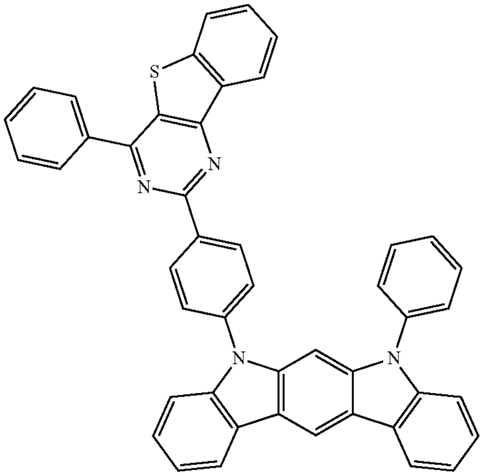
887
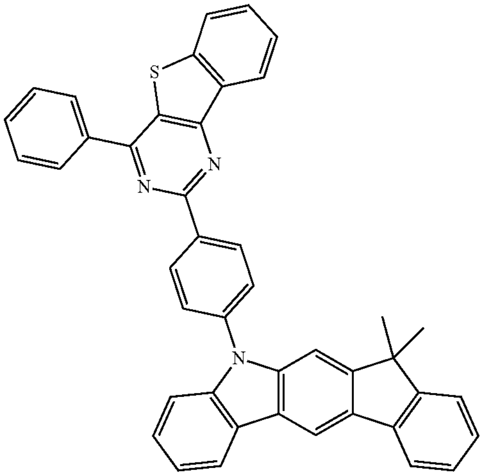
-continued
888
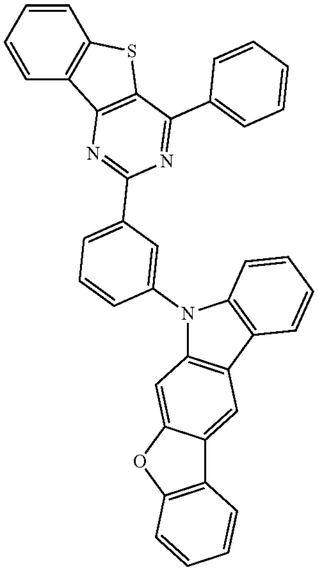
889
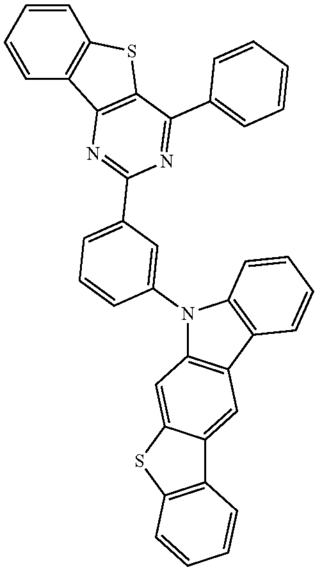

-continued
890
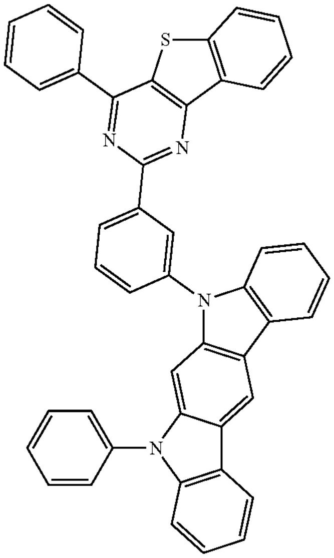
891
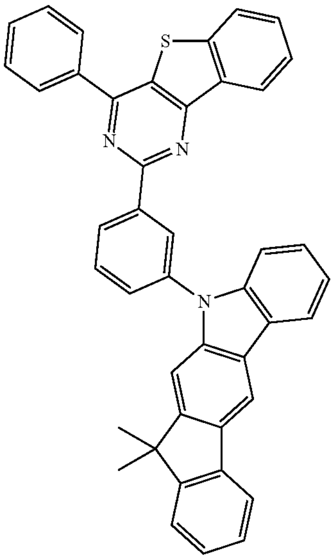
892
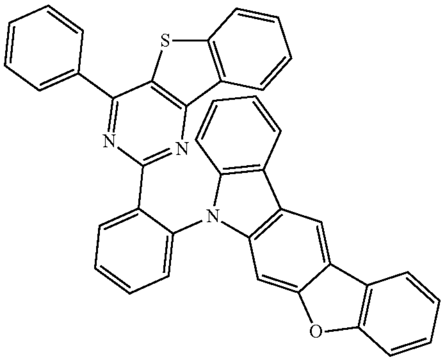
-continued
893
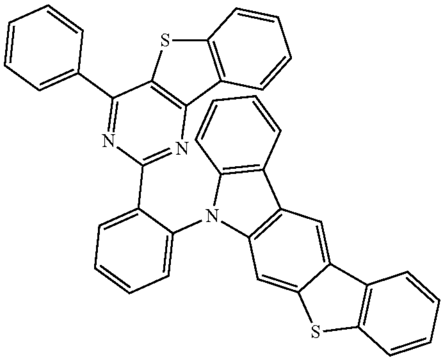
894
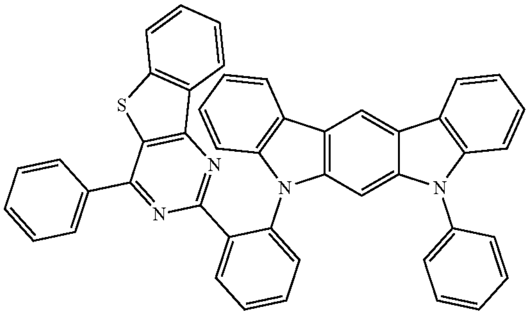
895
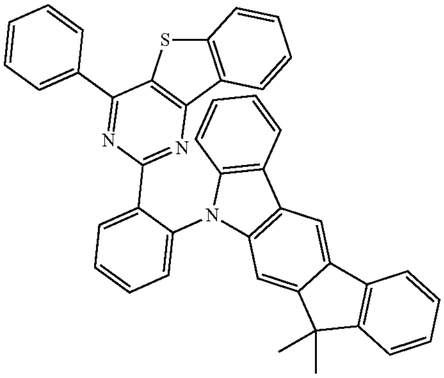
896
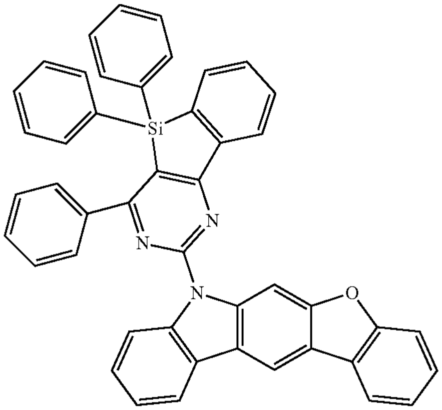

-continued
897
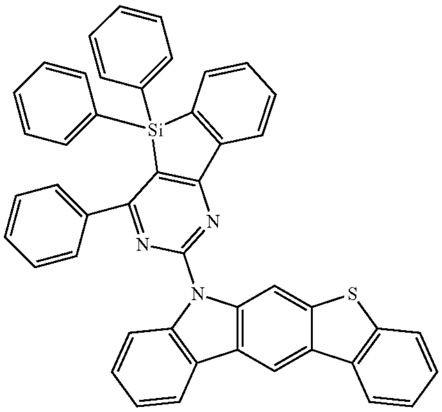
898
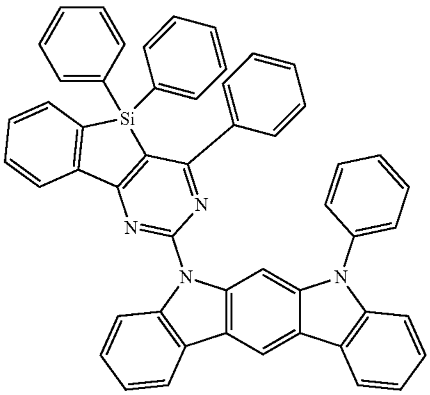
899
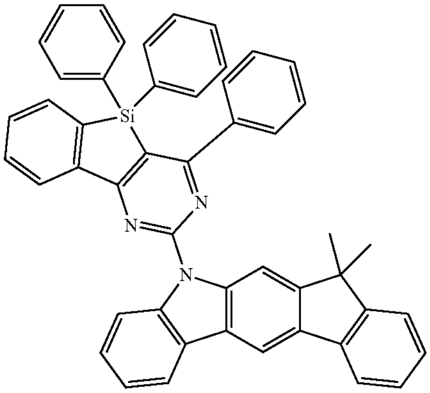
-continued
900
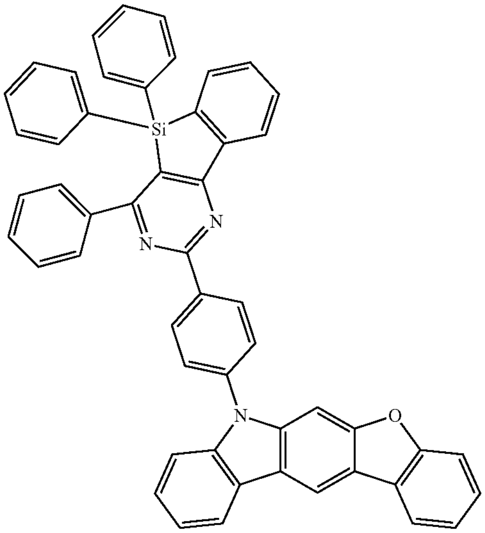
901
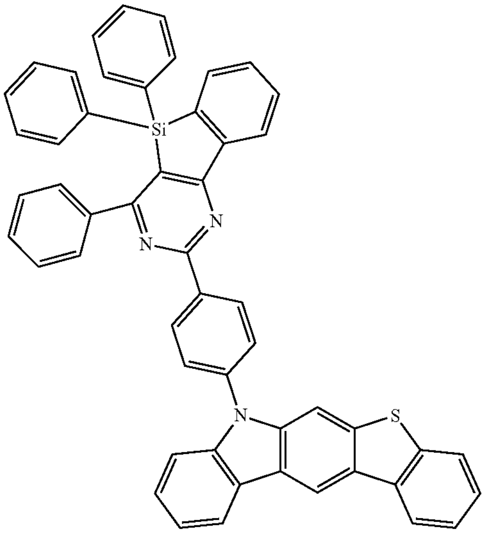
902
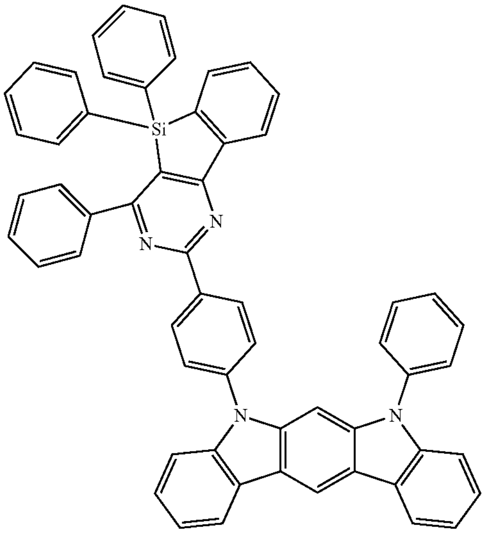

-continued
903
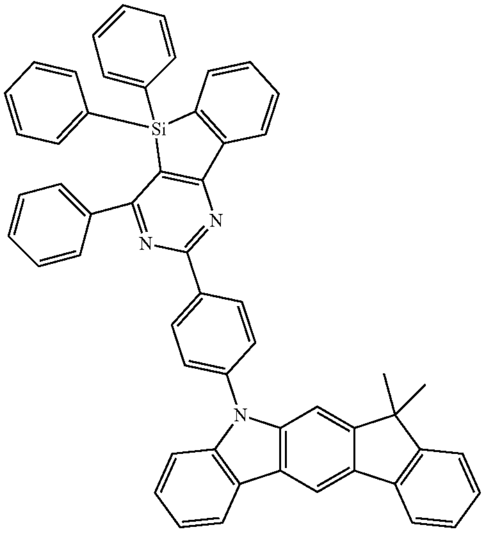
904
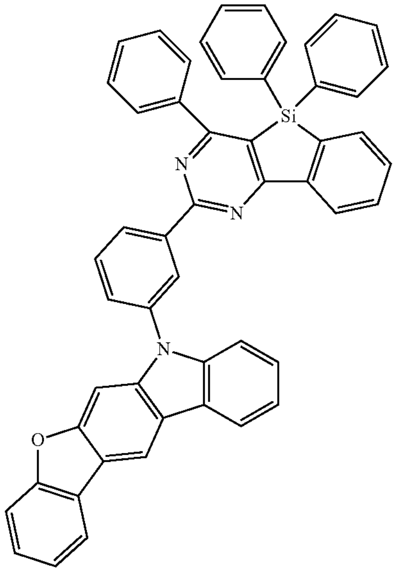
-continued
905
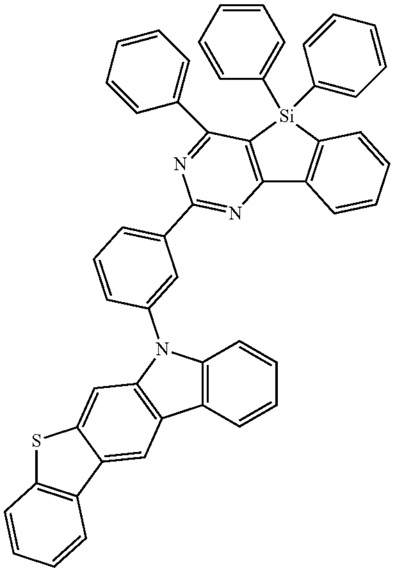
906
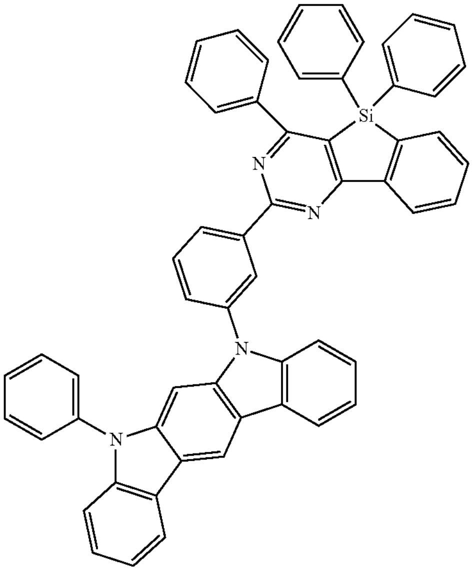

-continued
907
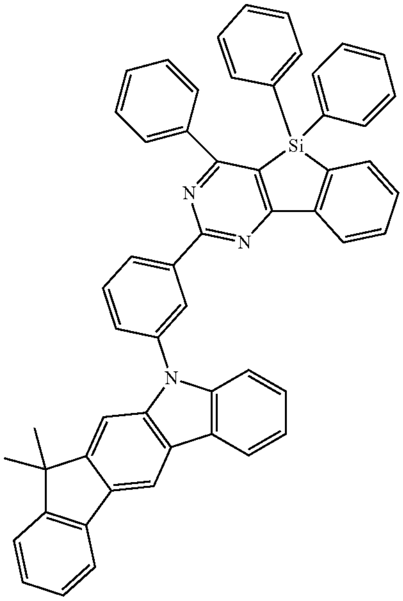
908
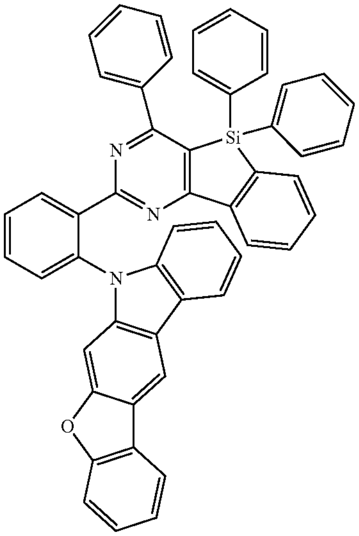
-continued
909
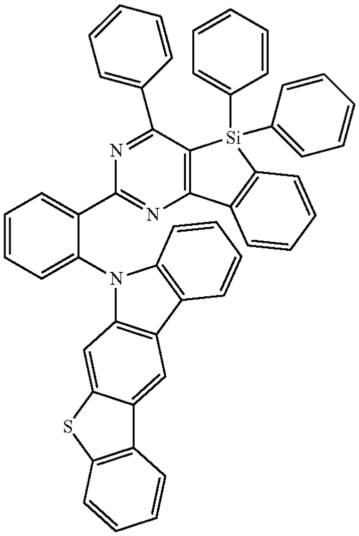
910
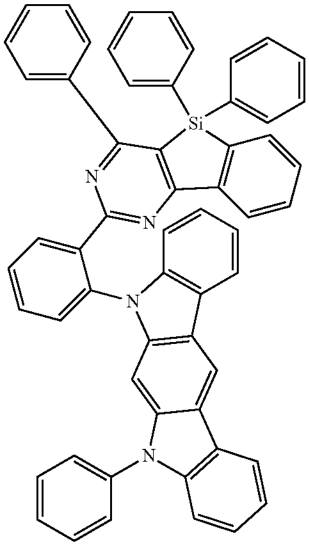
911
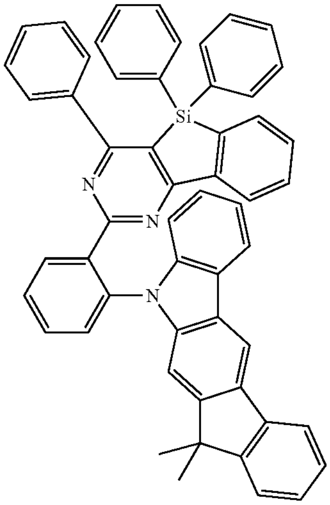

-continued
912
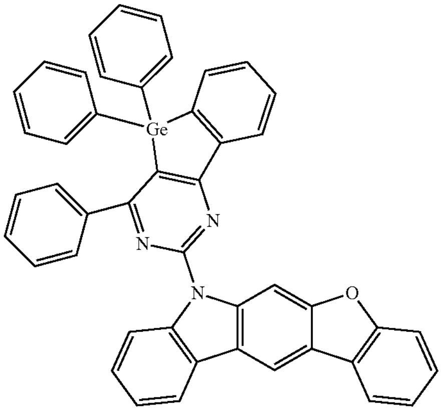
913
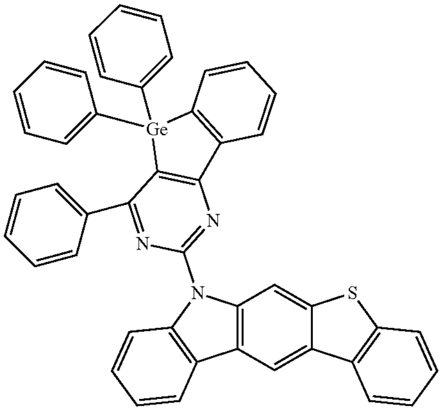
914
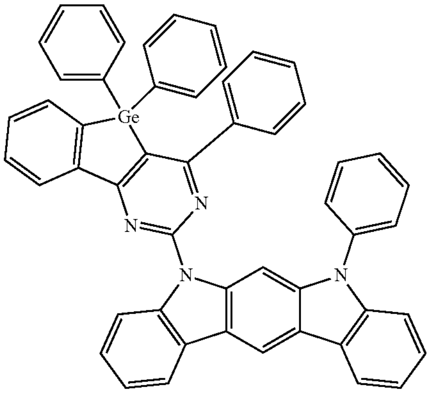
915
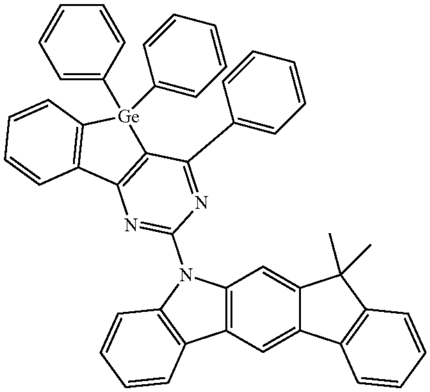
-continued
916
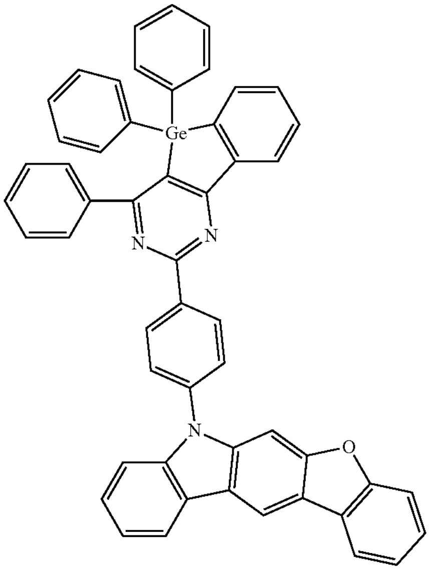
917
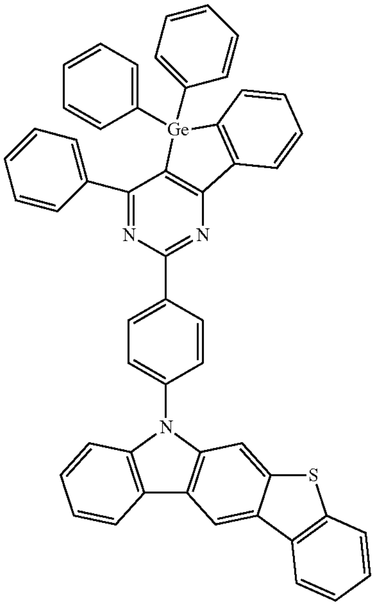

-continued
918
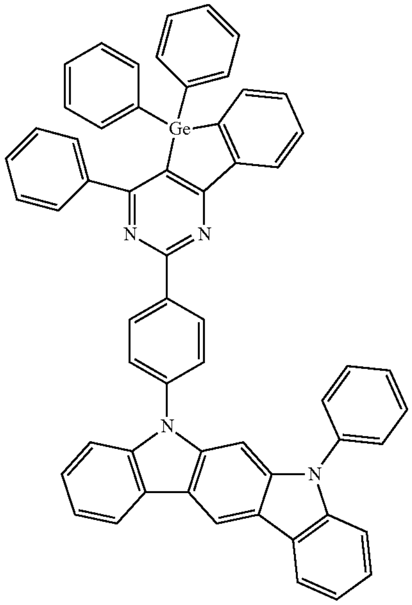
919
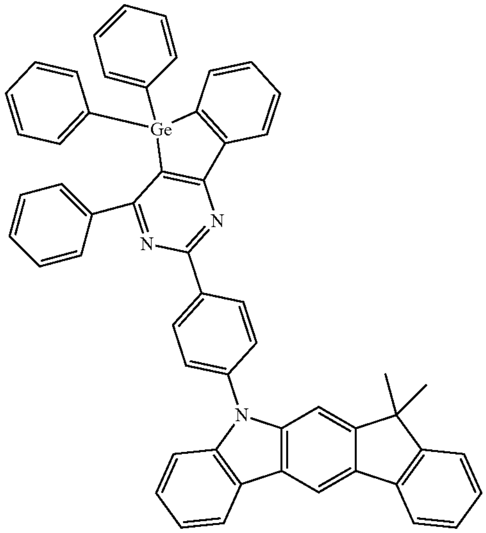
-continued
920
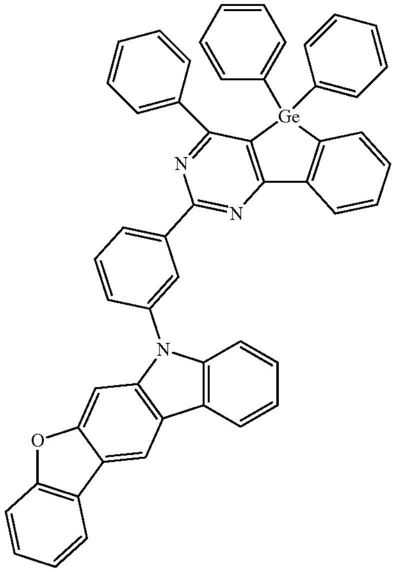
921
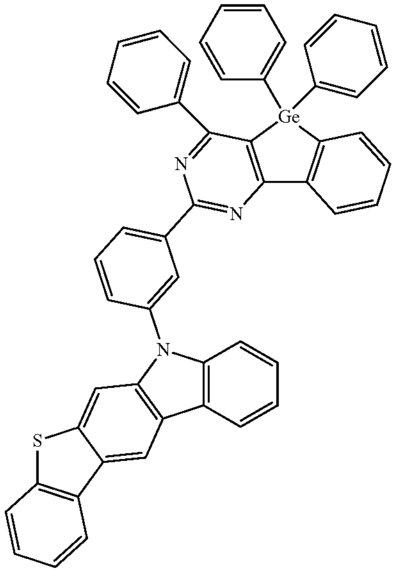

-continued
922
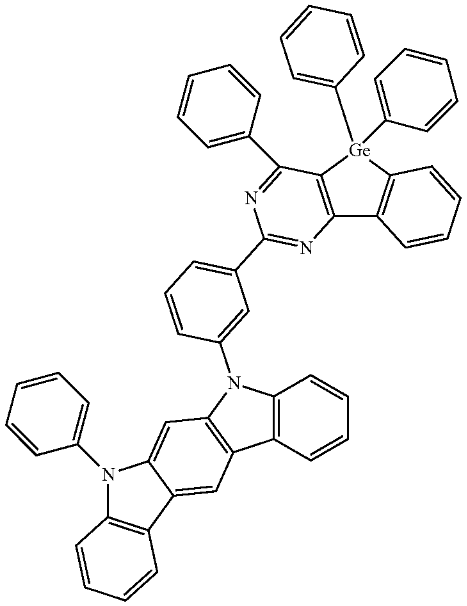
923
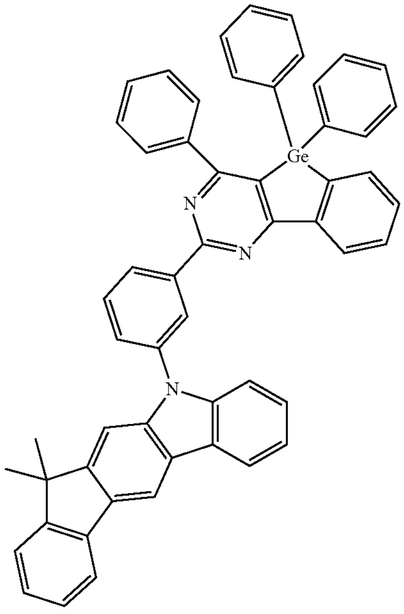
-continued
924
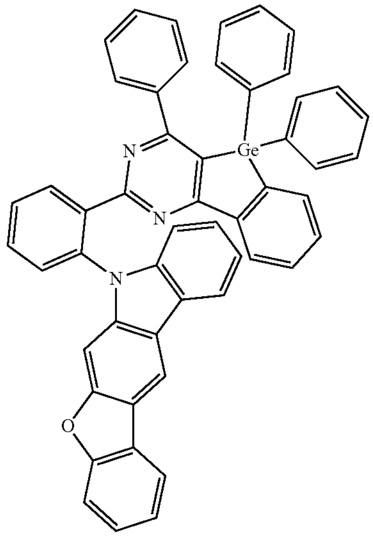
925
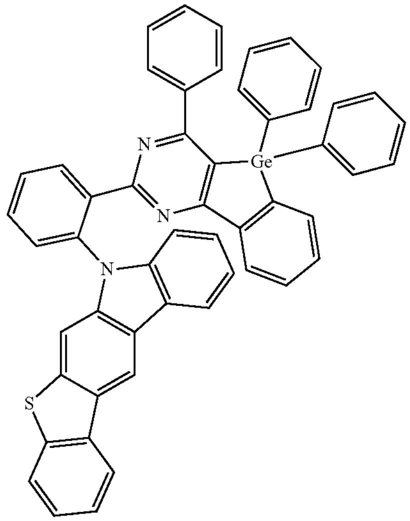
926
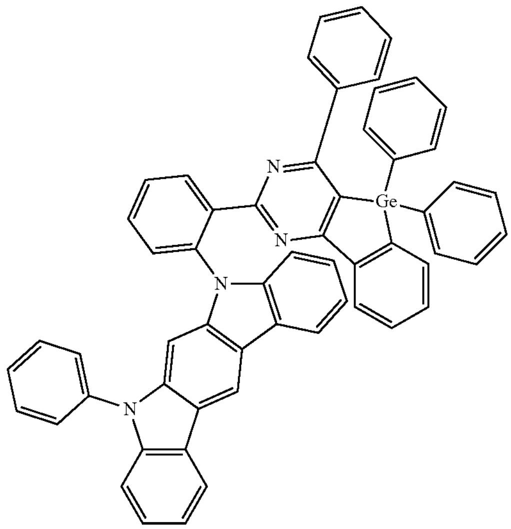

-continued
927
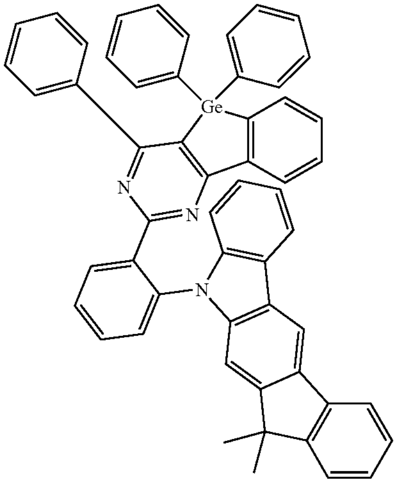
928
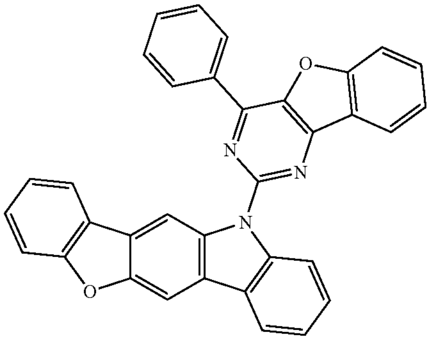
929
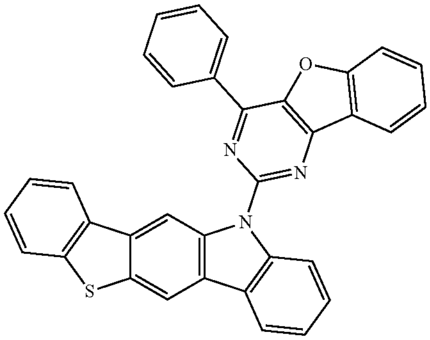
930
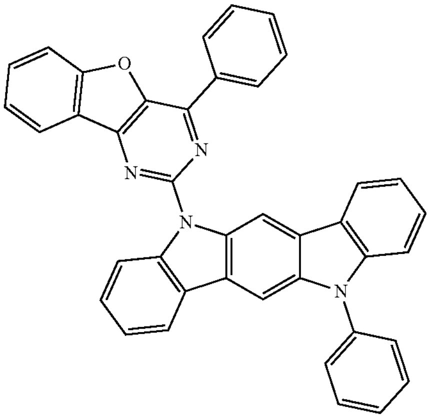
-continued
931
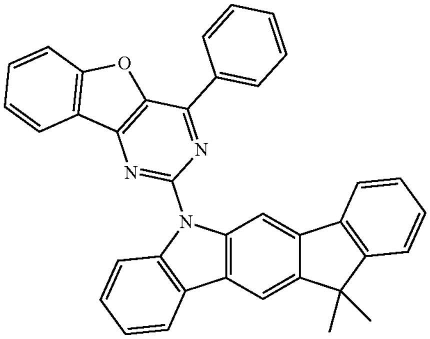
932
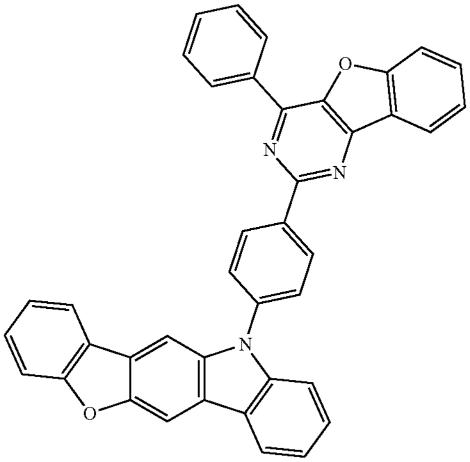
933
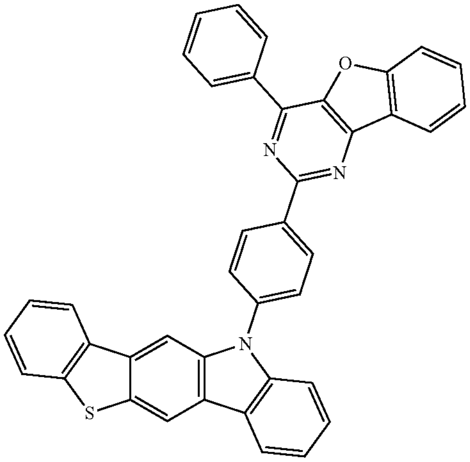

-continued
934
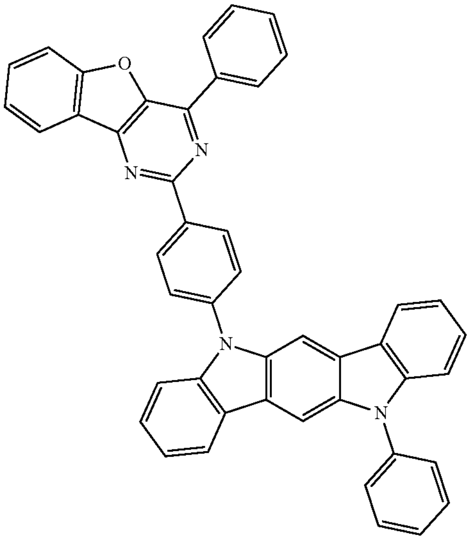
935
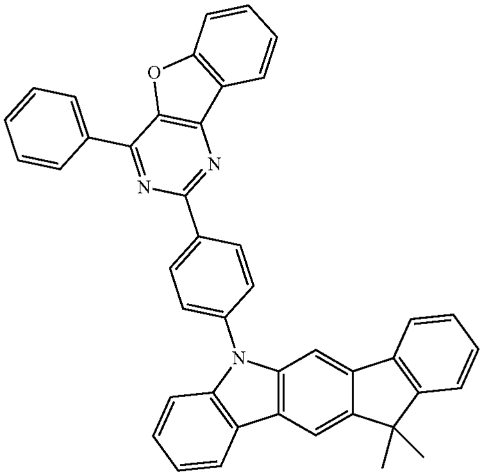
936
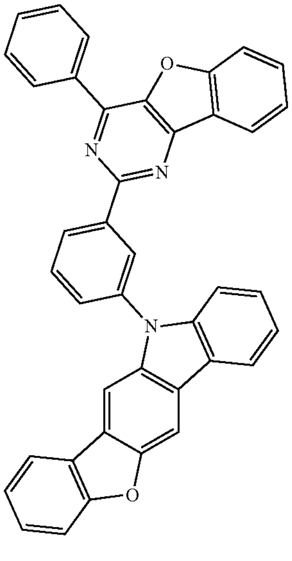
-continued
937
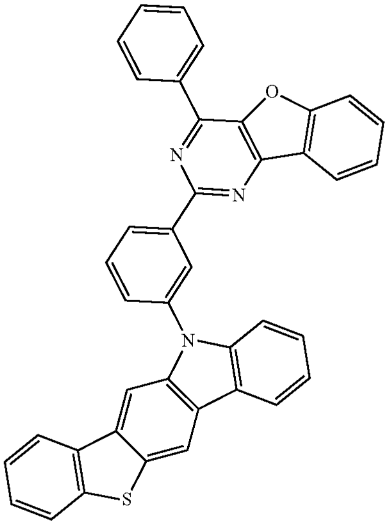
938
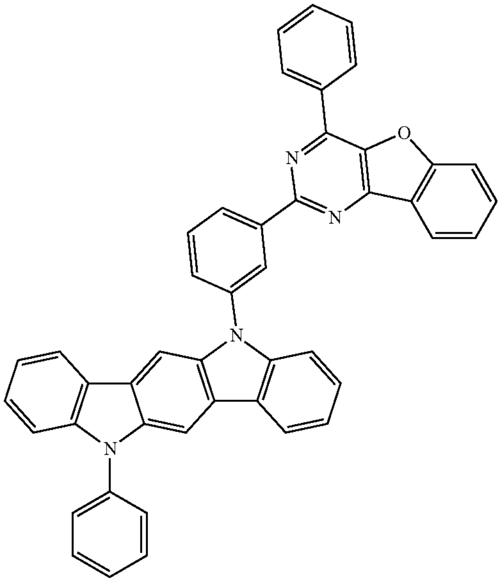
939
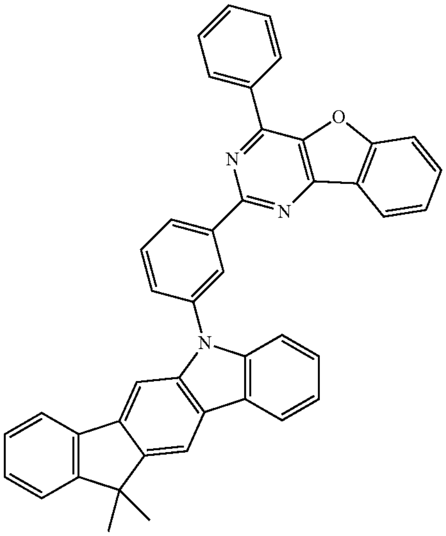

-continued
940
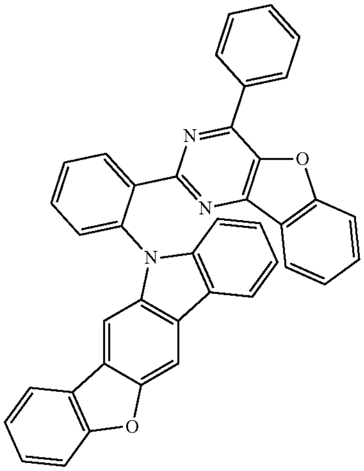
941
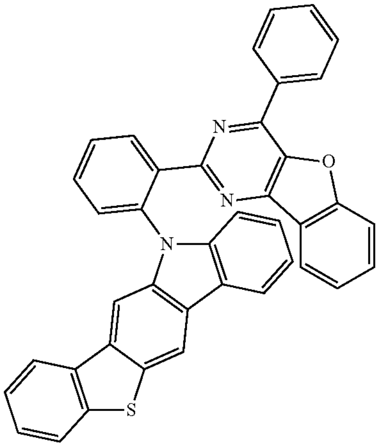
942
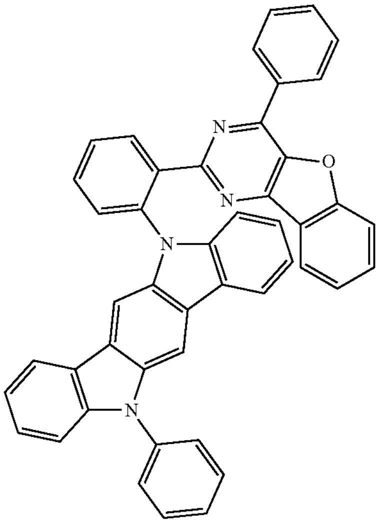
-continued
943
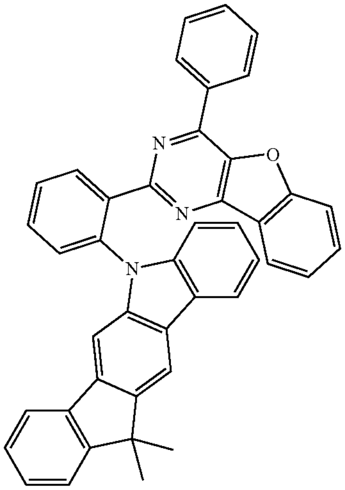
944
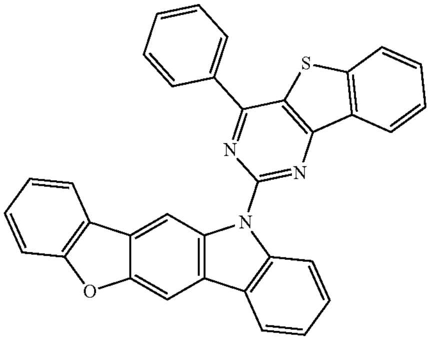
945
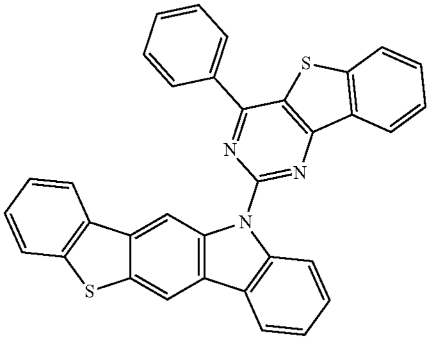
946
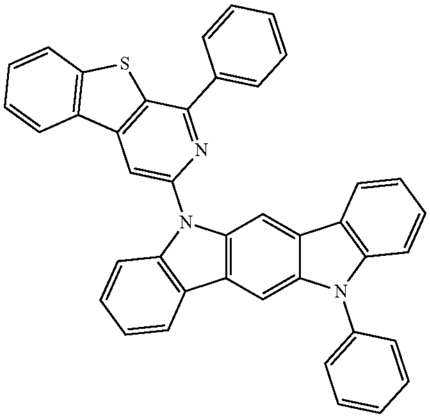

-continued
947
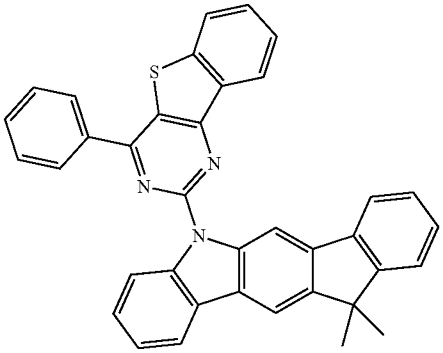
948
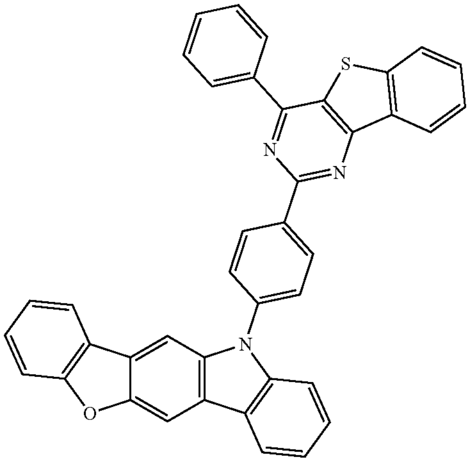
949
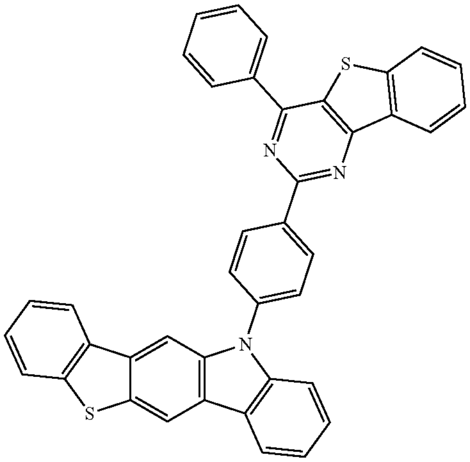
-continued
950
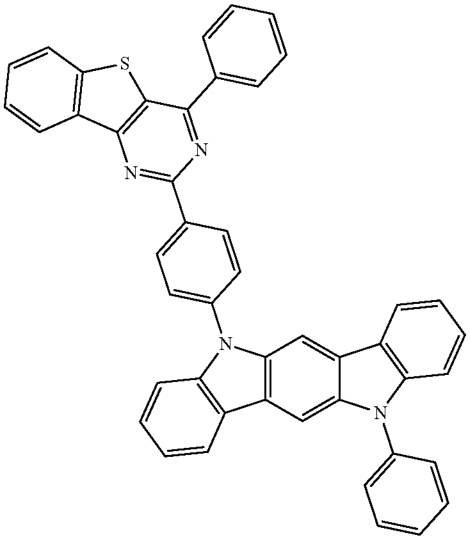
951
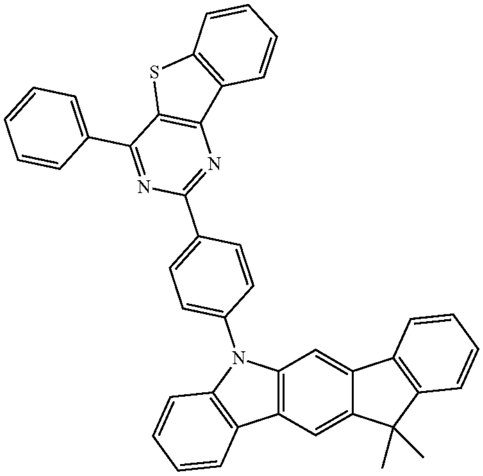
952
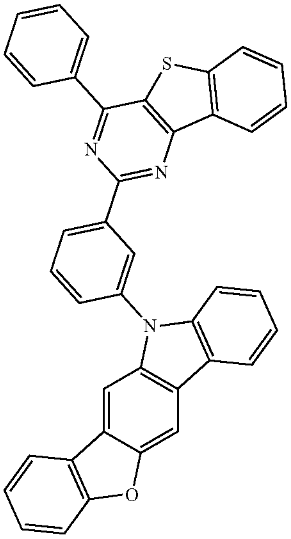

-continued
953
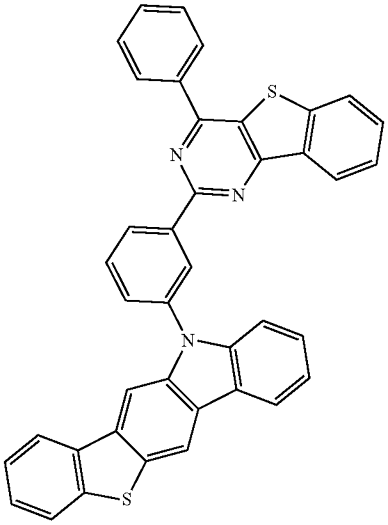
954
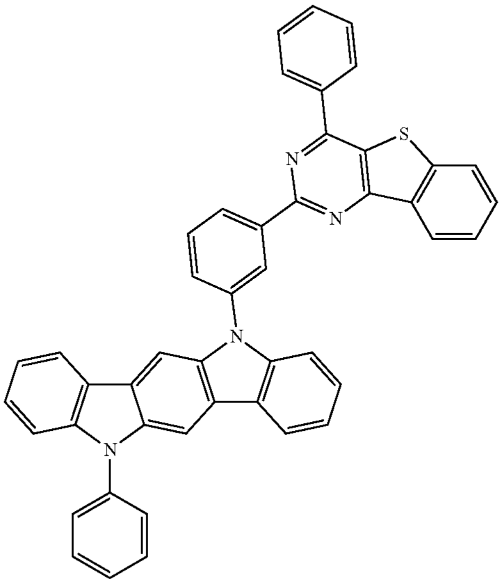
955
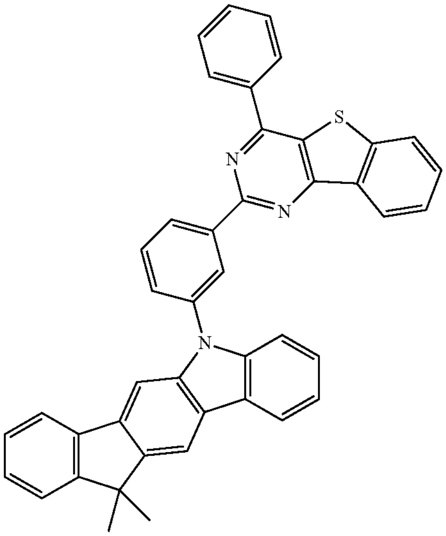
-continued
956
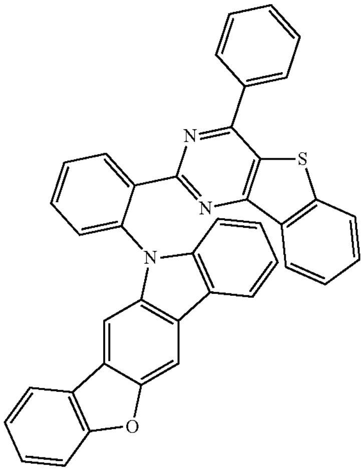
957
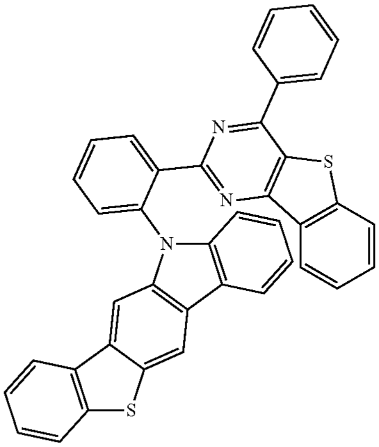
958
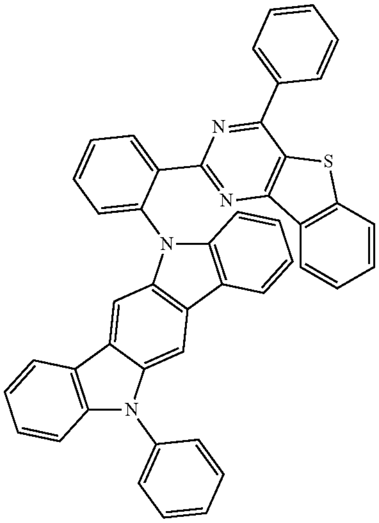

-continued
959
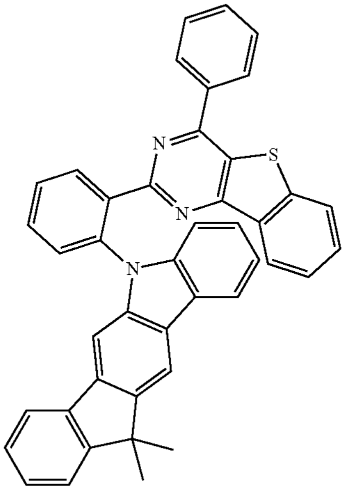
960
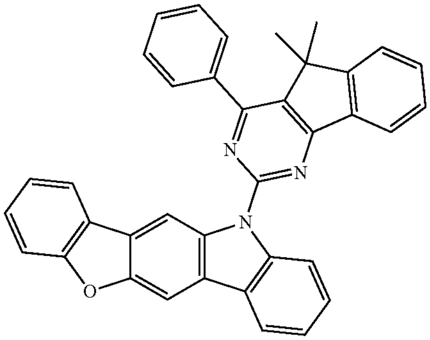
961
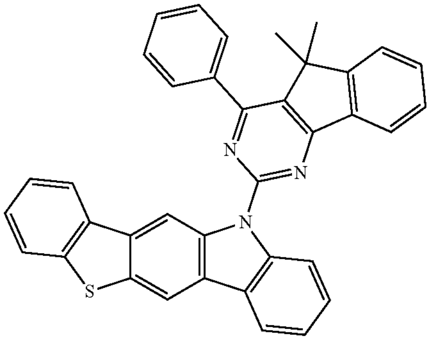
962
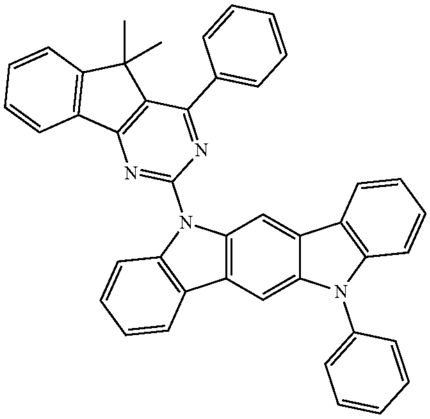
-continued
963
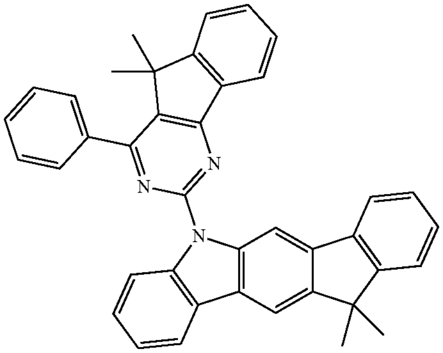
964
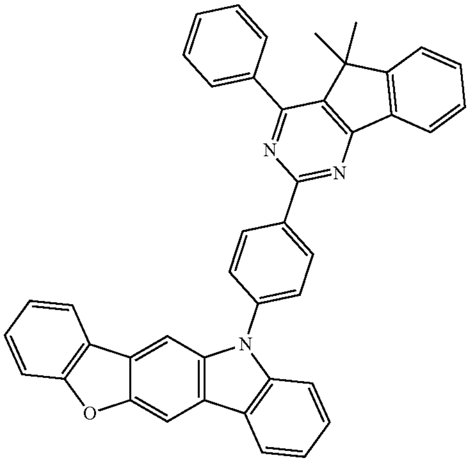
965
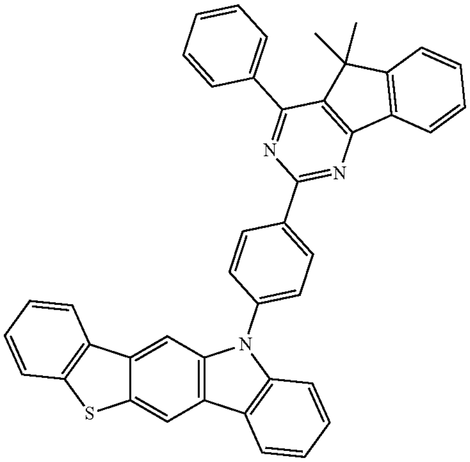

-continued
966
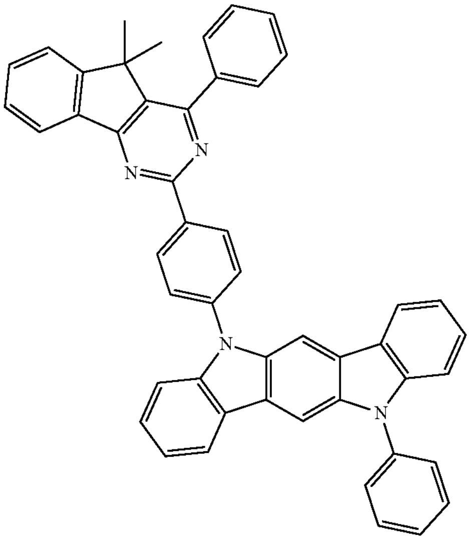
967
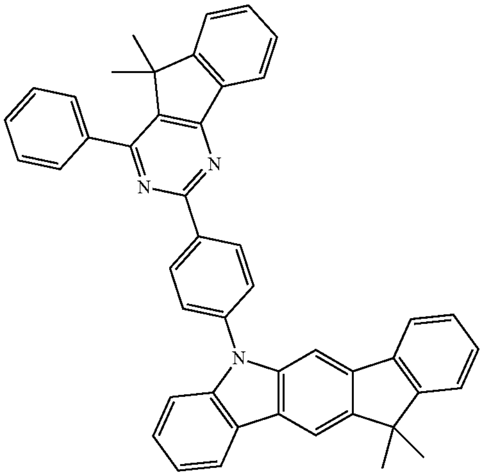
968
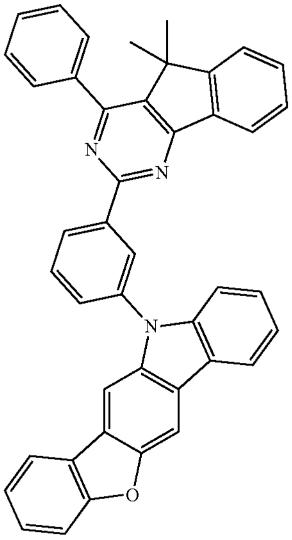
-continued
969
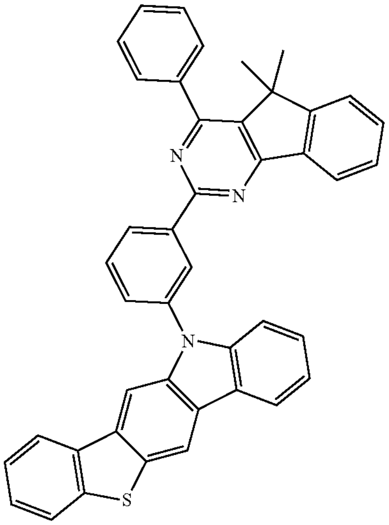
970
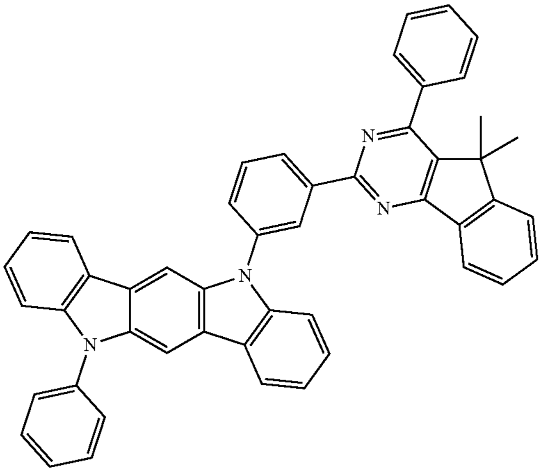
971
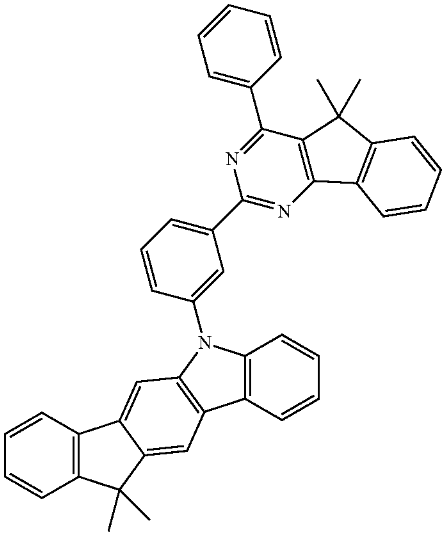

-continued
972
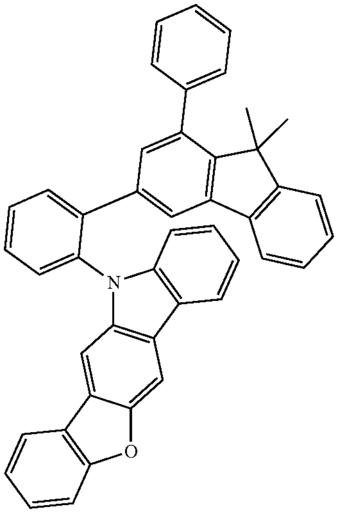
973
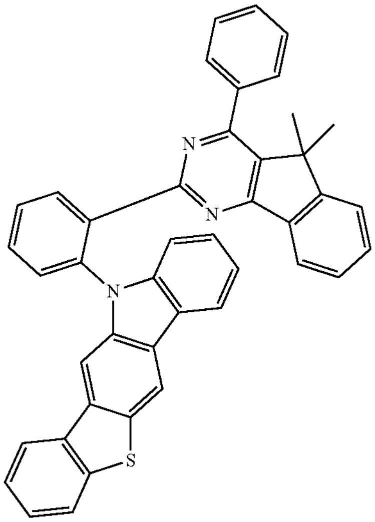
974
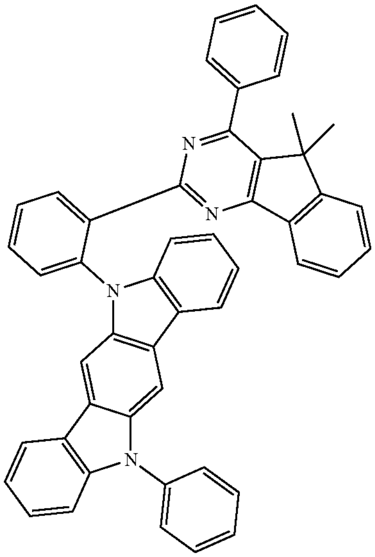
-continued
975
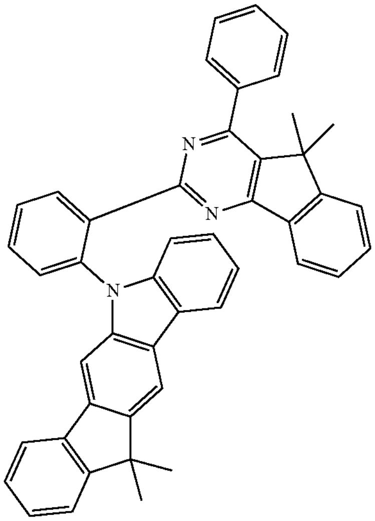
976
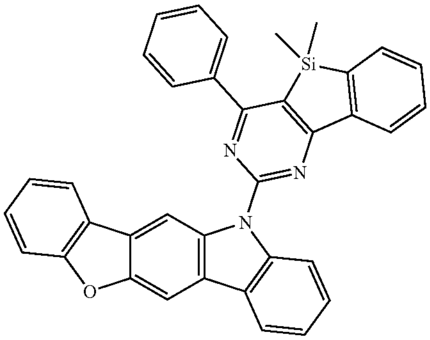
977
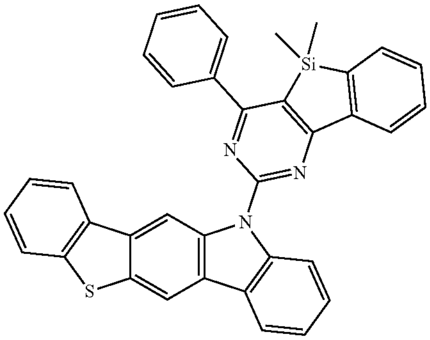
978
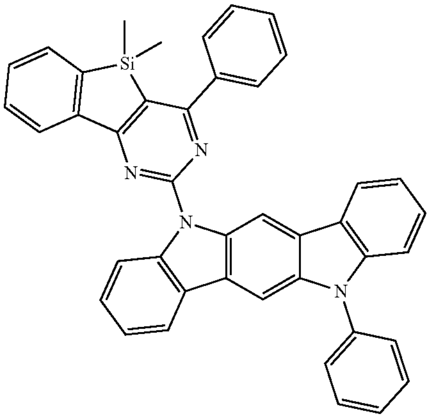

-continued
979
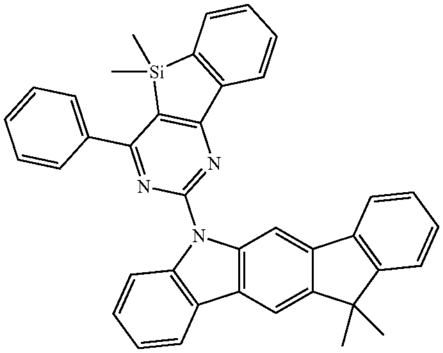
980
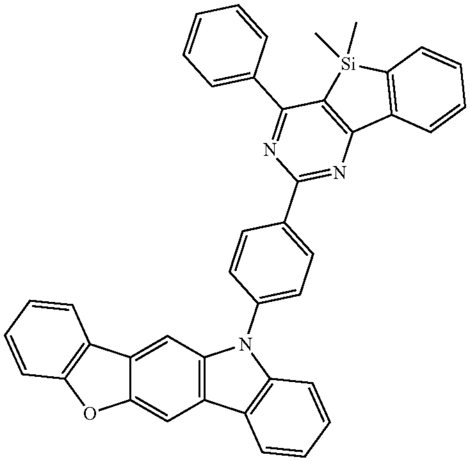
981
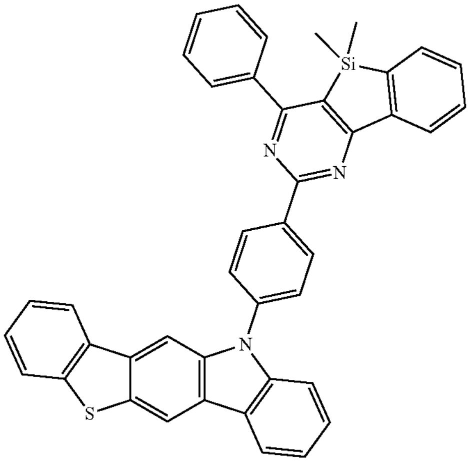
-continued
982
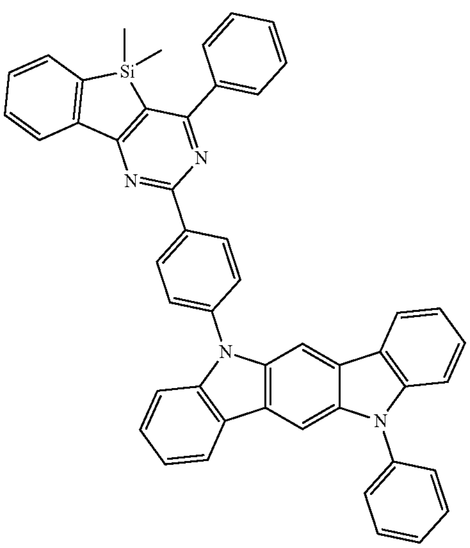
983
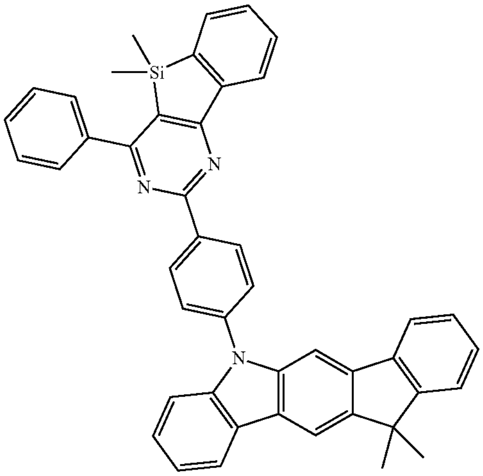
984
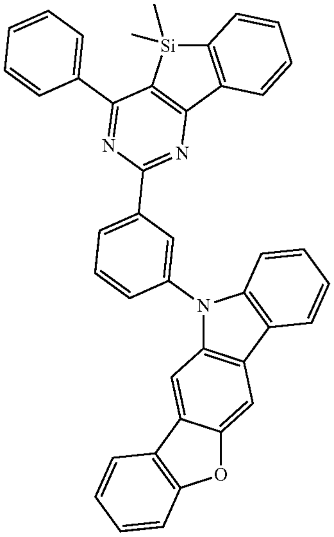

-continued
985
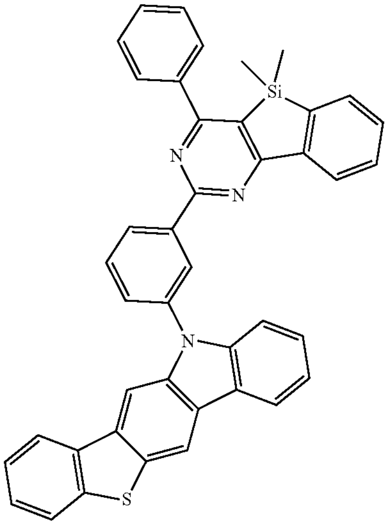
986
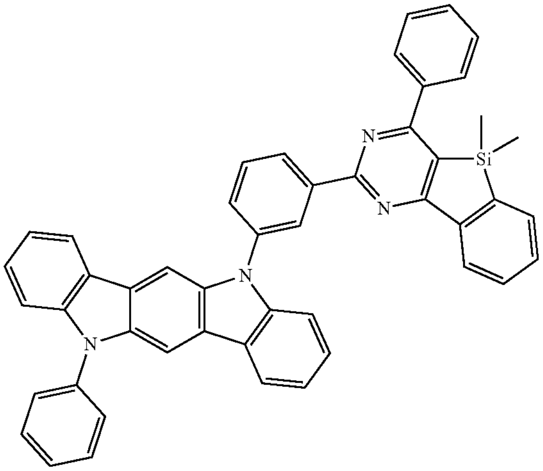
987
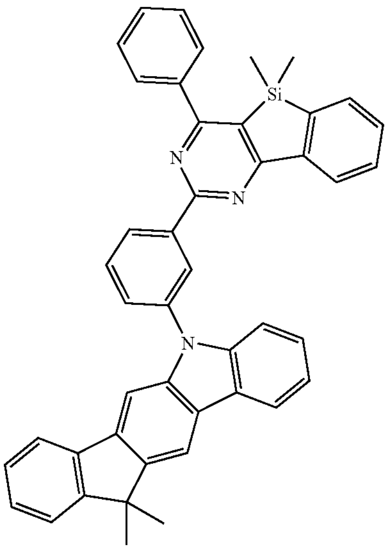
-continued
988
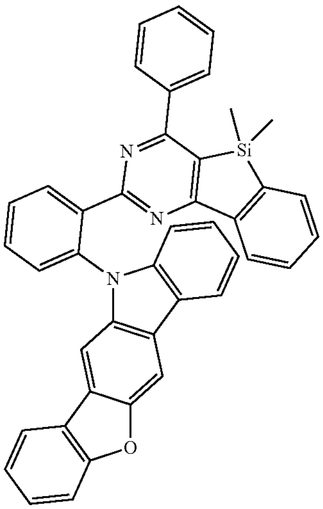
989
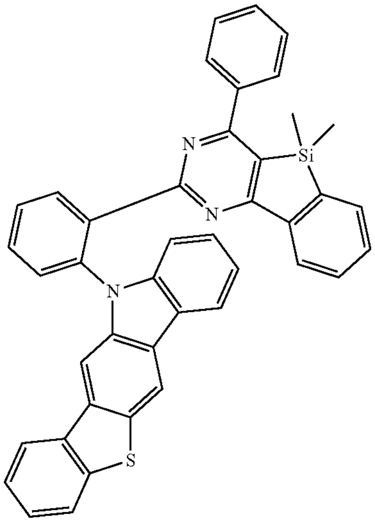
990
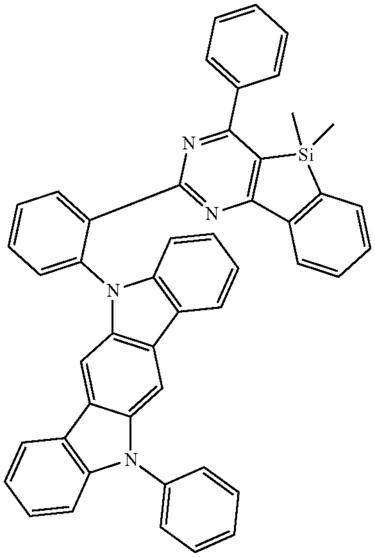

-continued
991
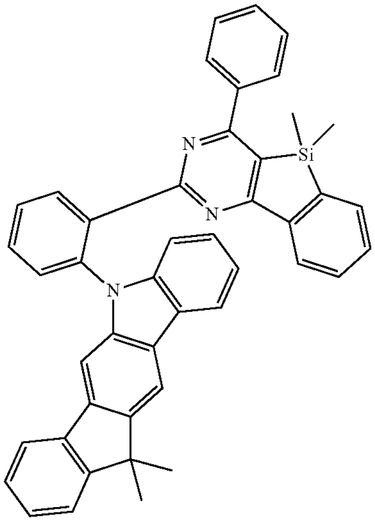
992
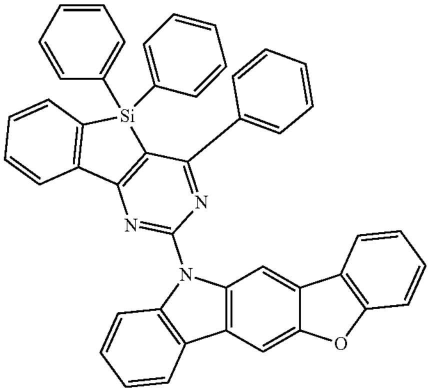
993
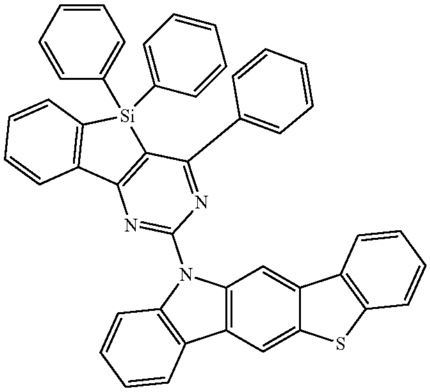
-continued
994
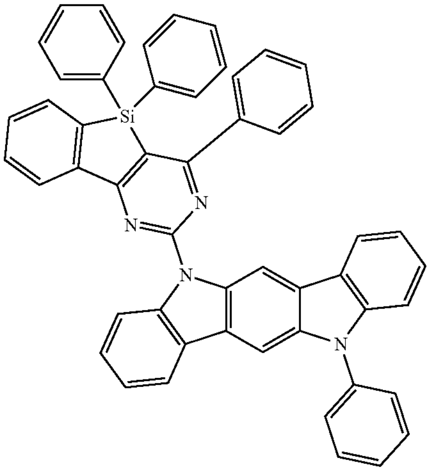
995
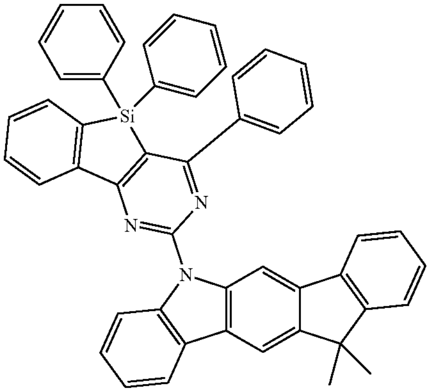
996
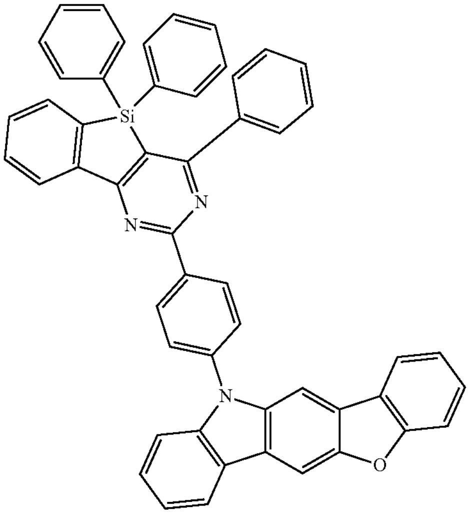

997
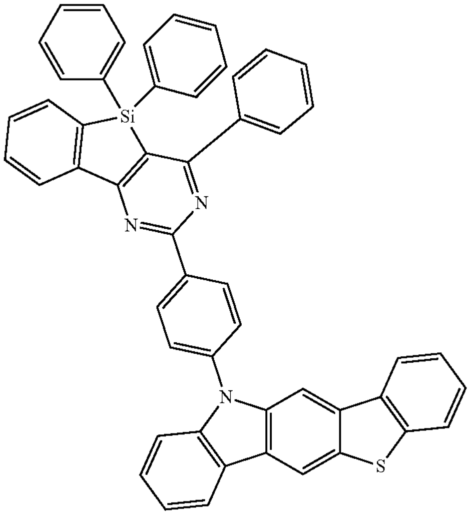
998
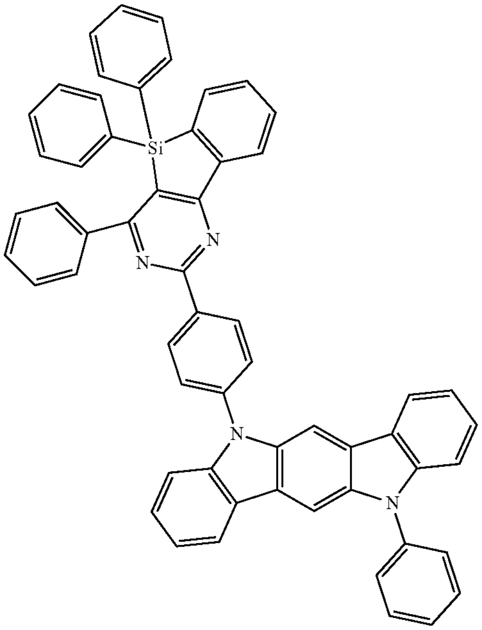
999
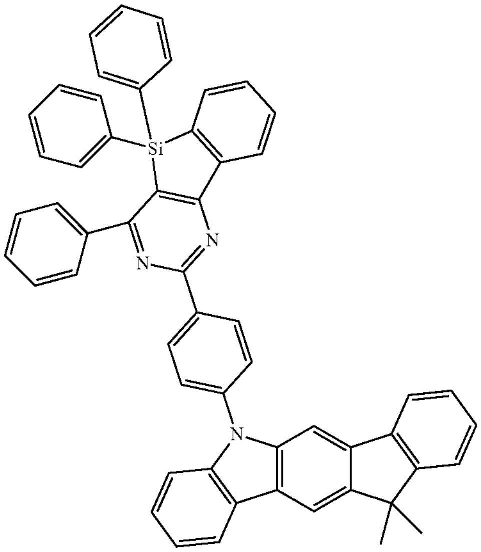
1000
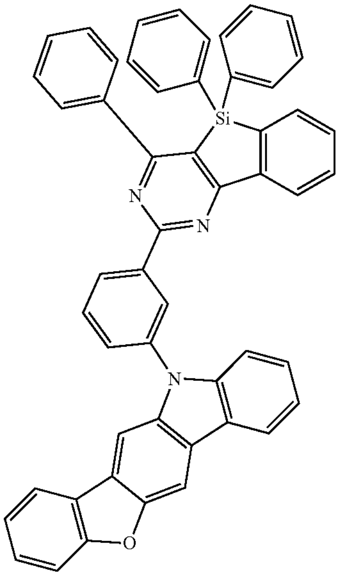

1001
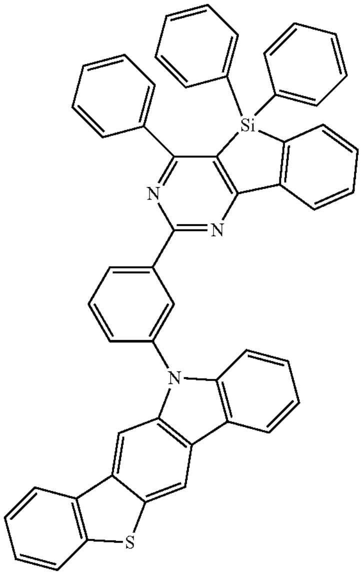
1002
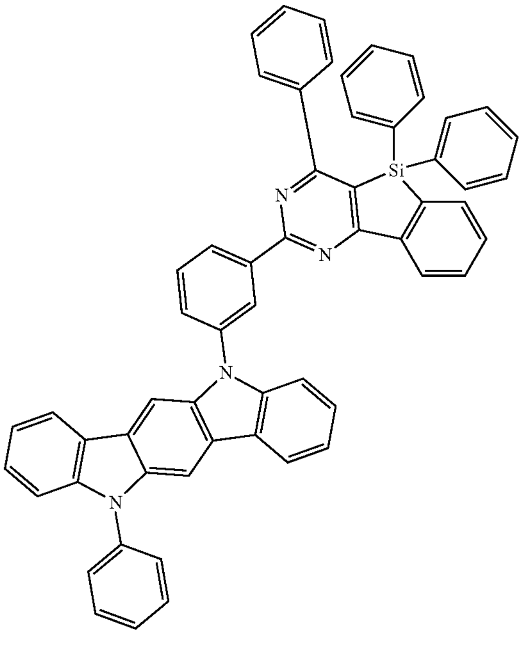
1003
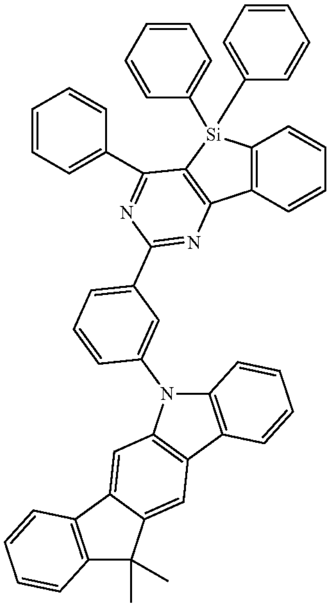
1004
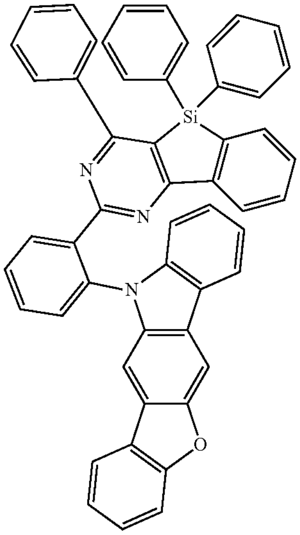

-continued
1005
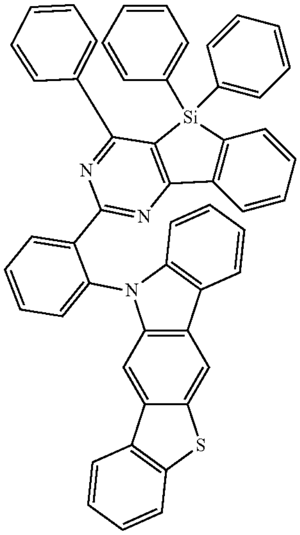
1006
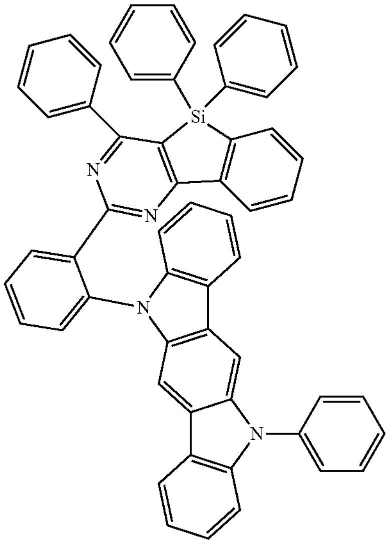
1007
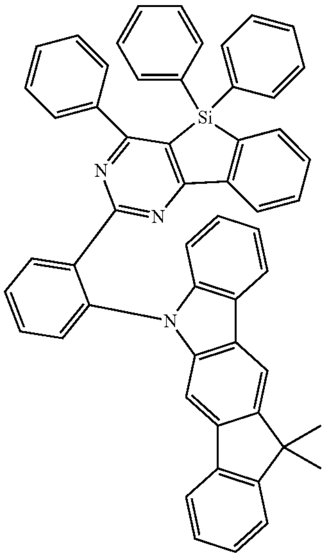
-continued
1008
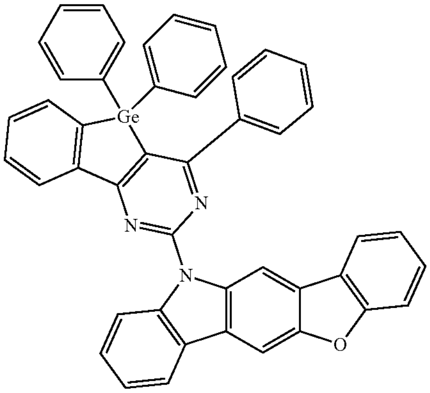
1009
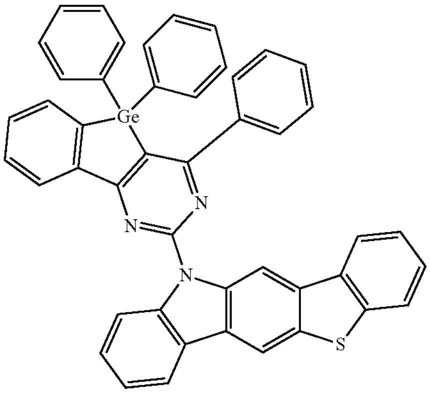
1010
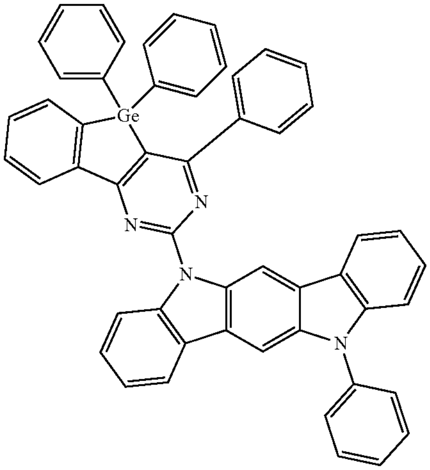
1011
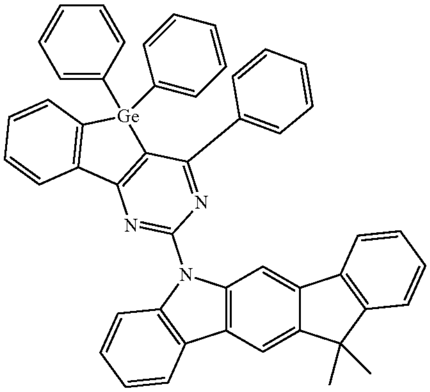

-continued
1012
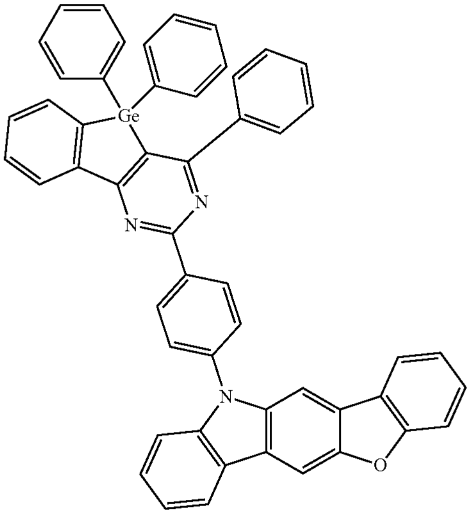
1013
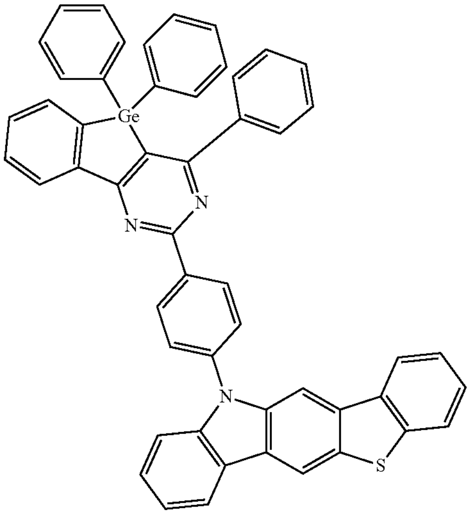
-continued
1014
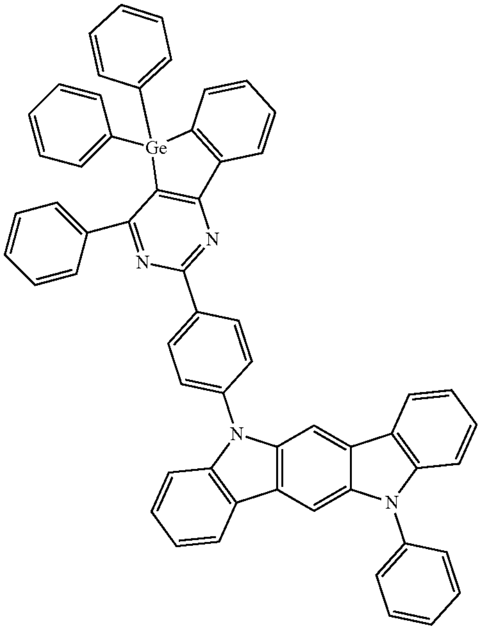
1015
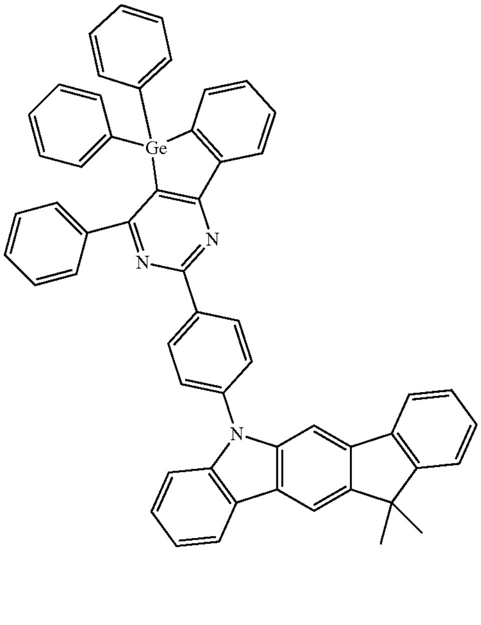

-continued
1016
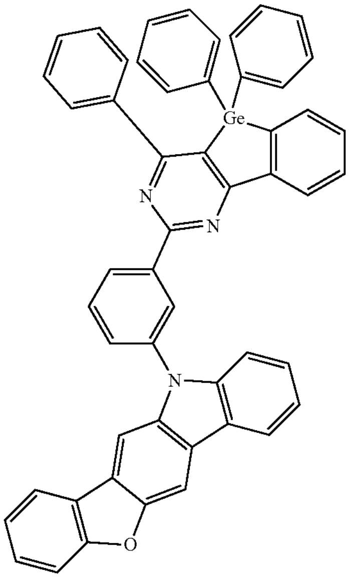
1017
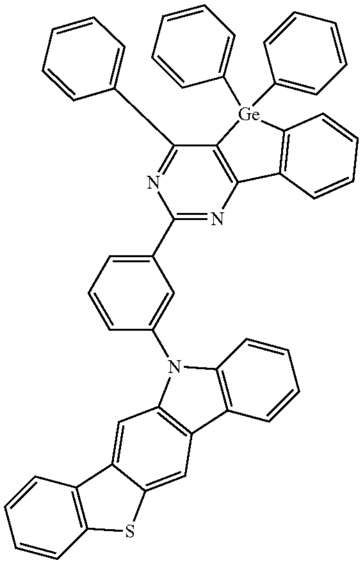
-continued
1018
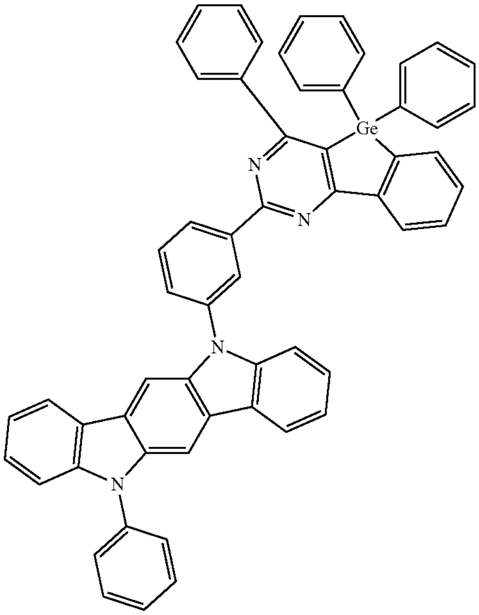
1019
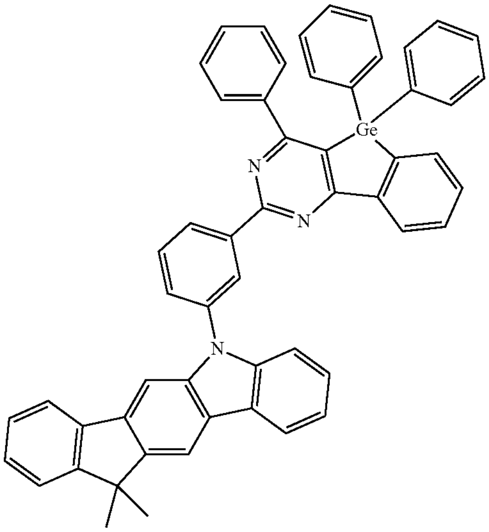

-continued
1020
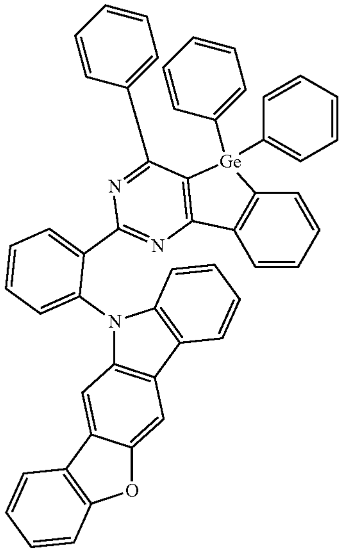
1021
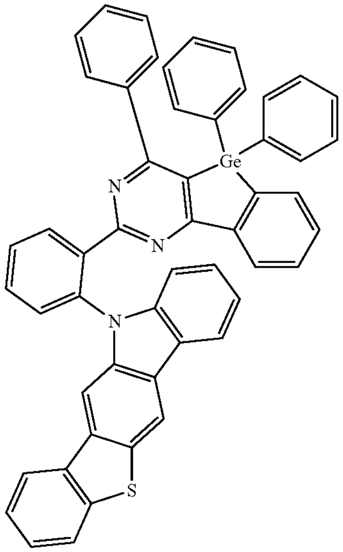
1022
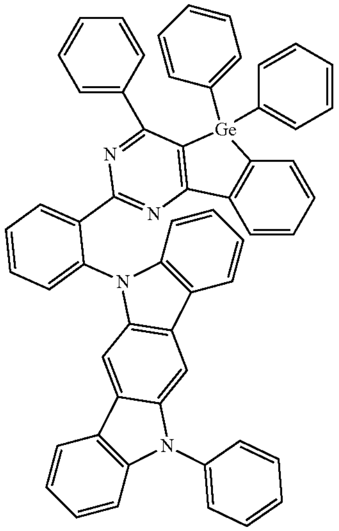
-continued
1023
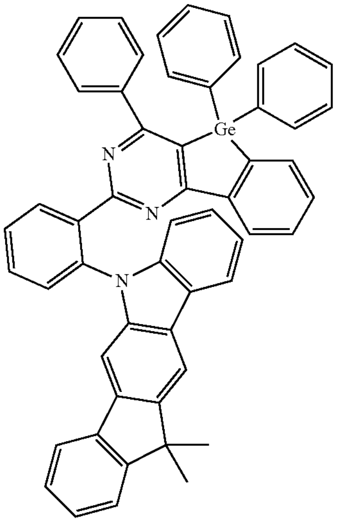
1024
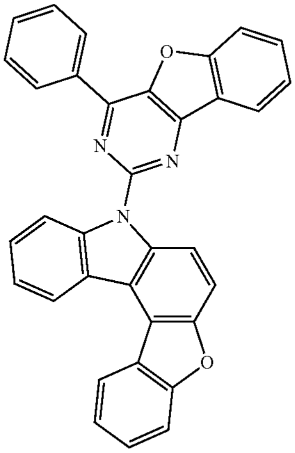
1025
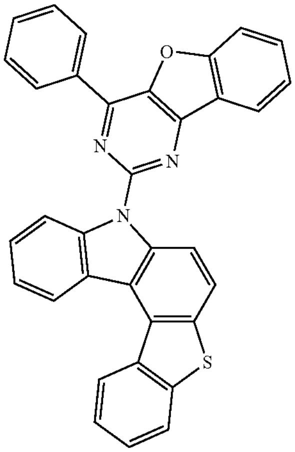

-continued
1026
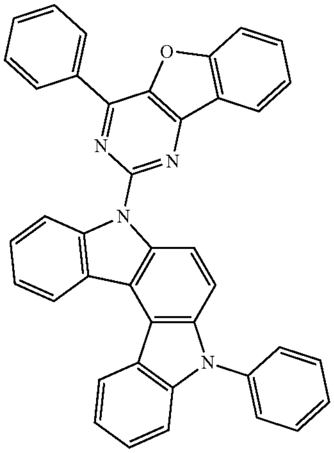
1027
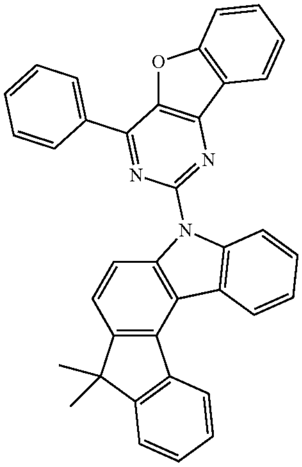
1028
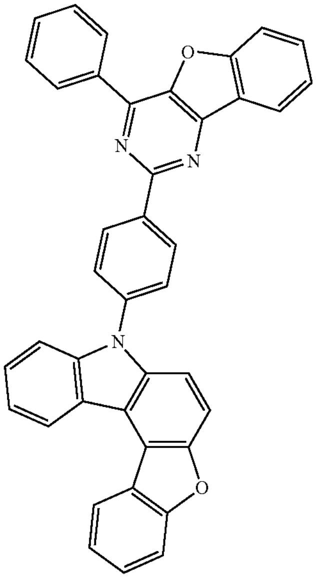
-continued
1029
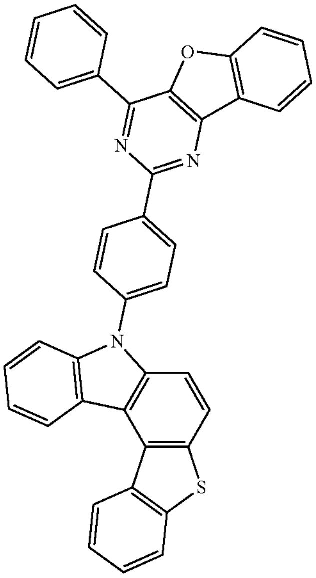
1030
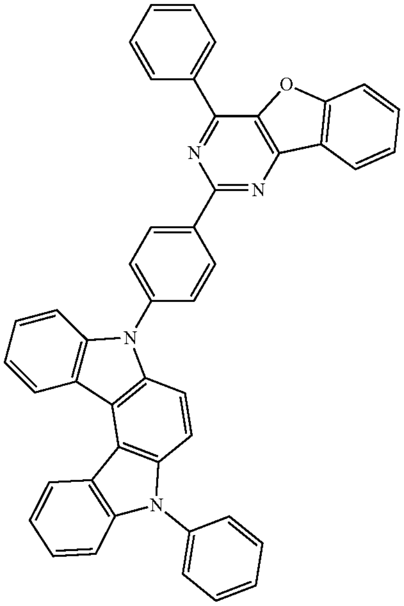

-continued
1031
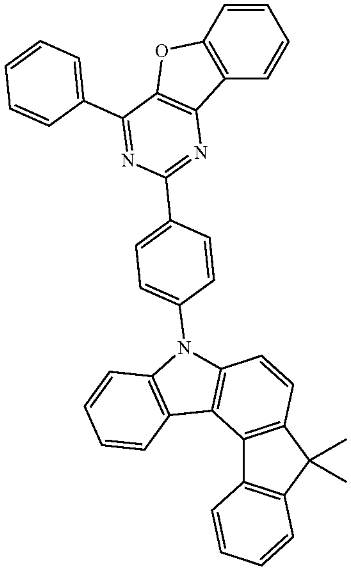
1032
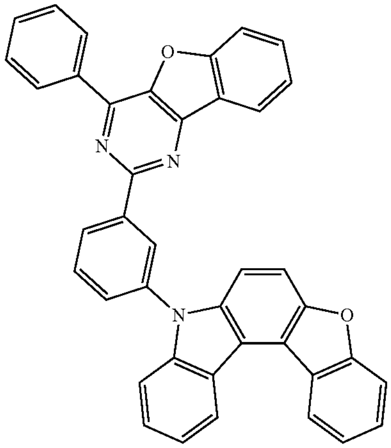
1033
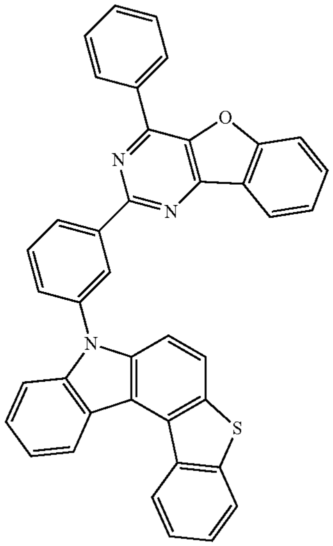
-continued
1034
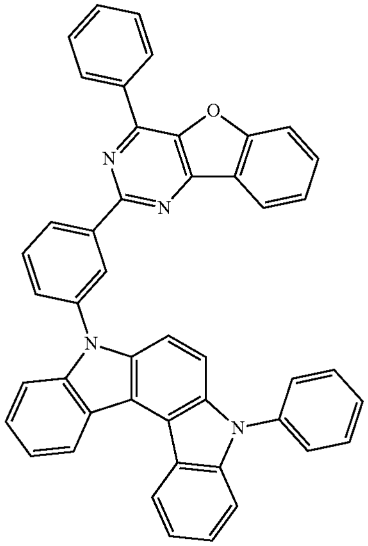
1035
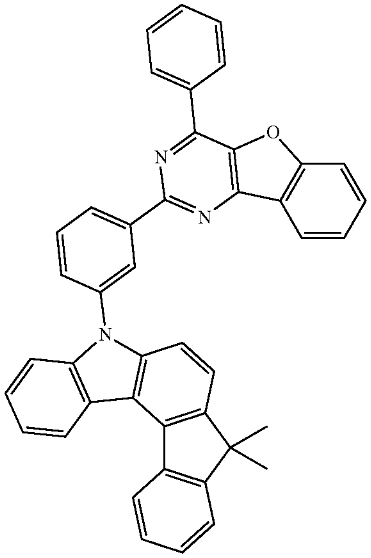
1036
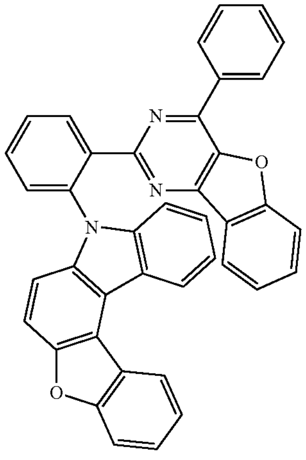

-continued
1037
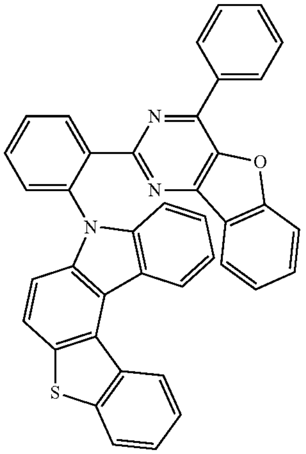
1038
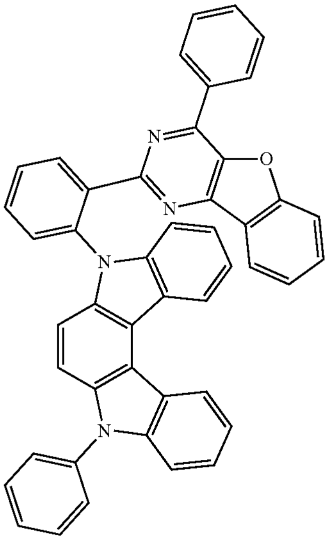
1039
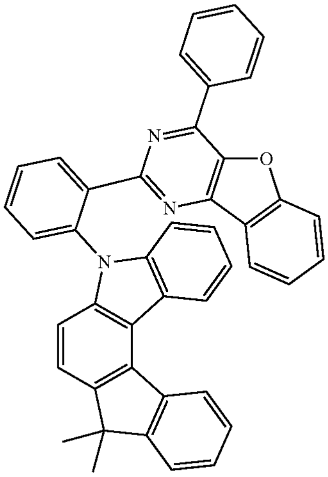
1040
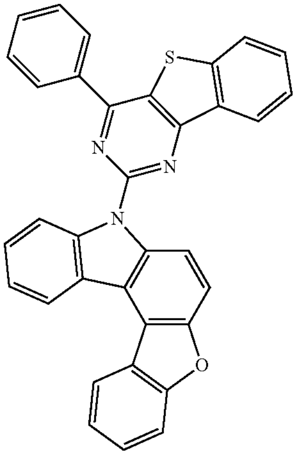
1041
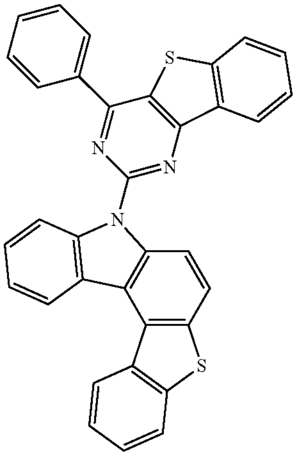
1042
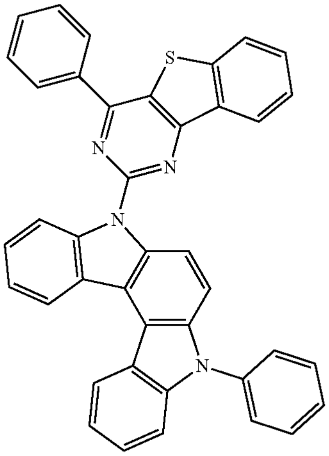

-continued
1043
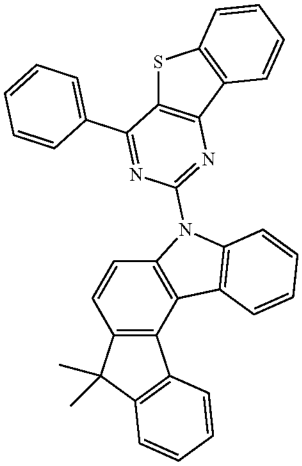
1044
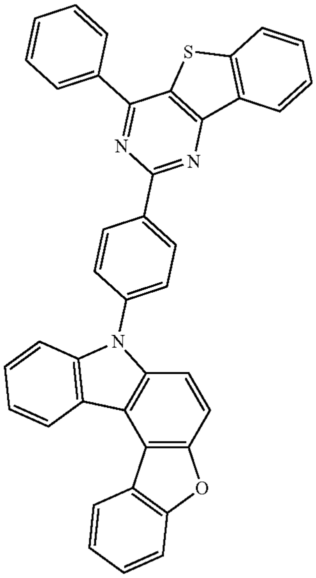
1045
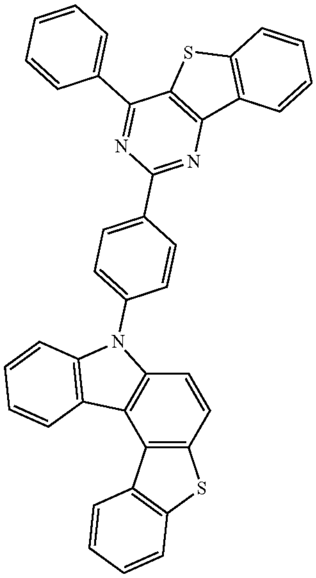
-continued
1046
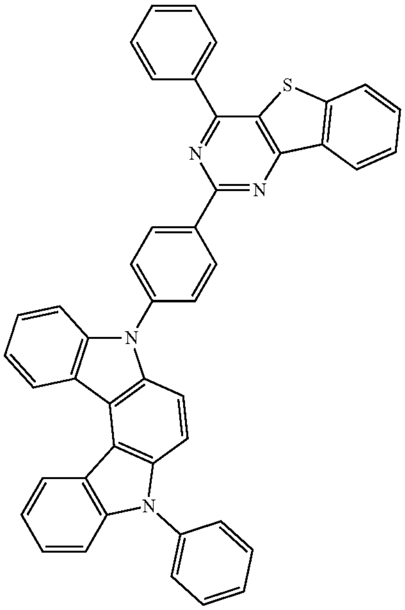
1047
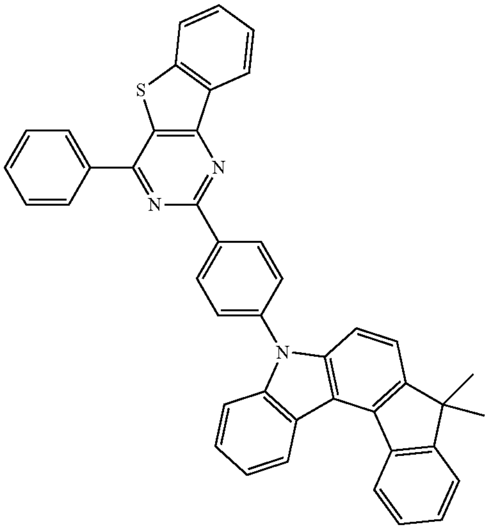
1048
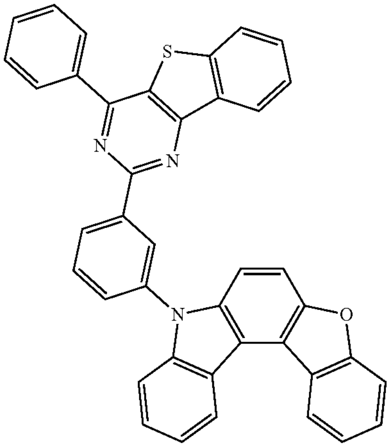

-continued
1049
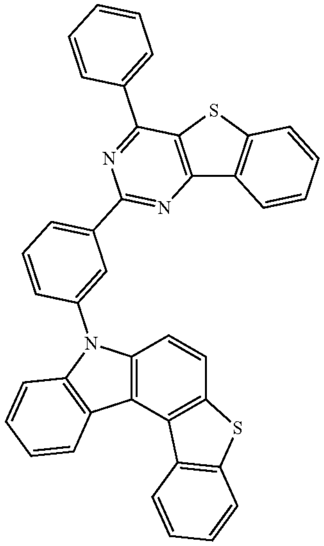
1050
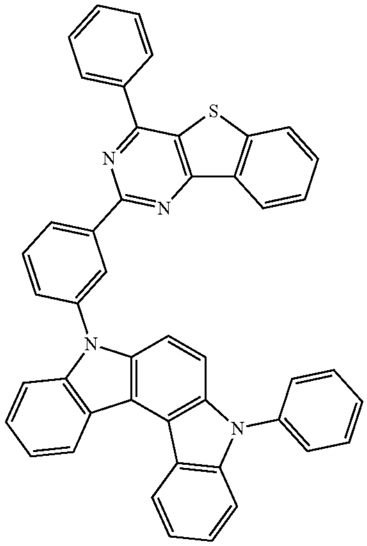
1051
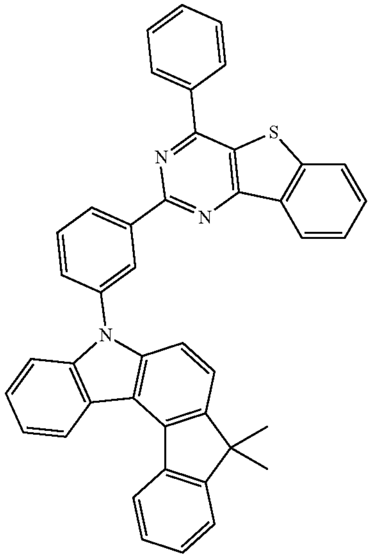
-continued
1052
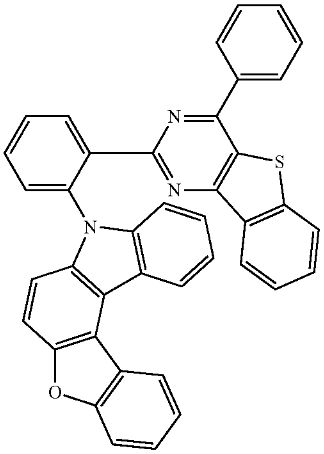
1053
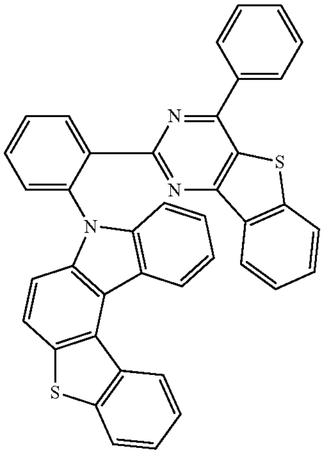
1054
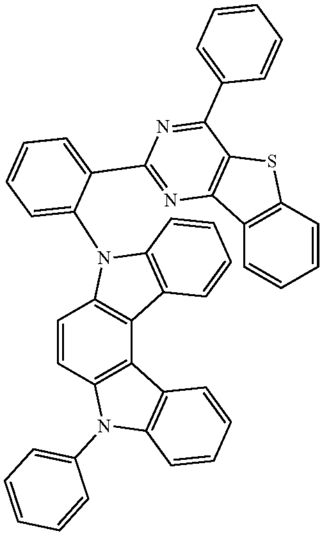

-continued
1055
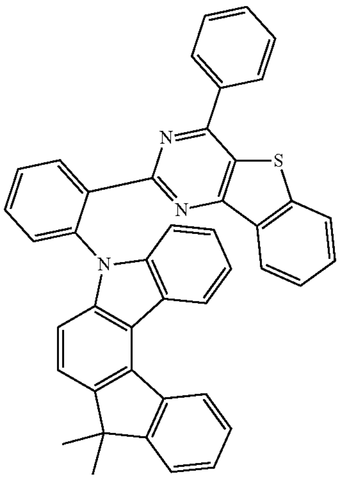
1056
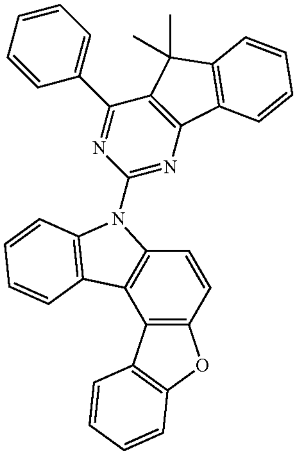
1057
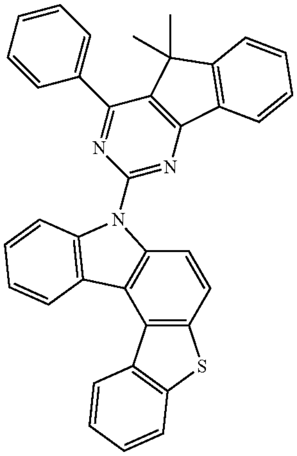
-continued
1058
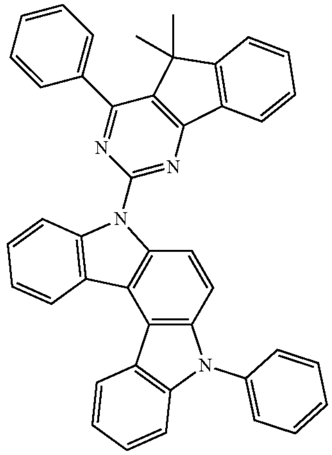
1059
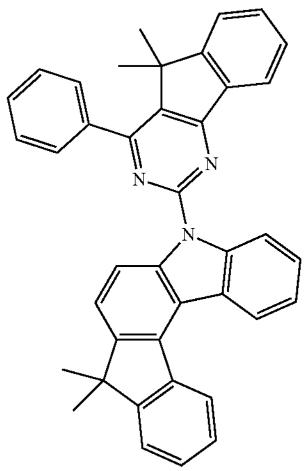
1060
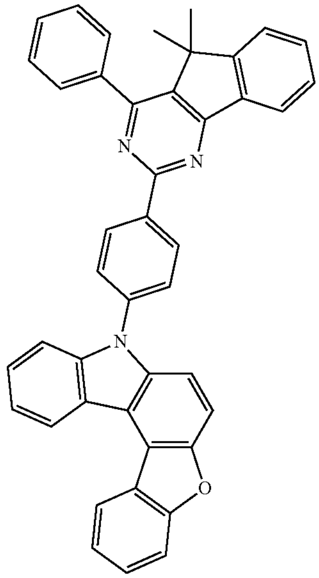

1061
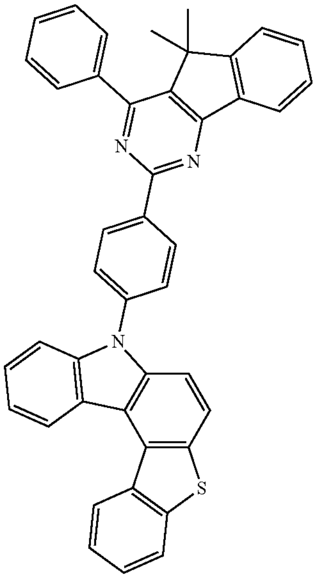
1062
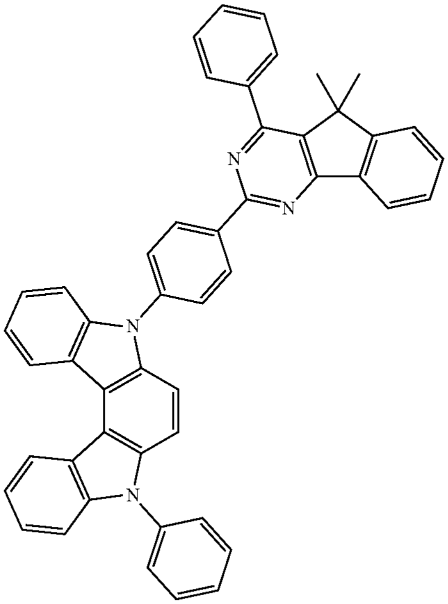
1063
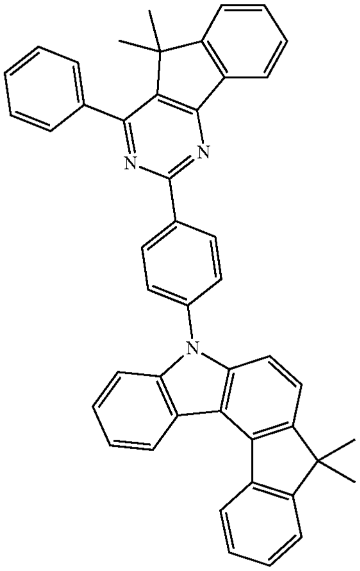
1064
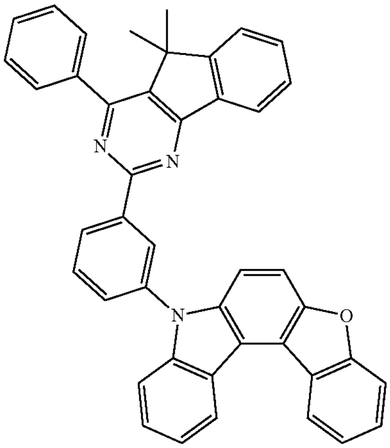
1065
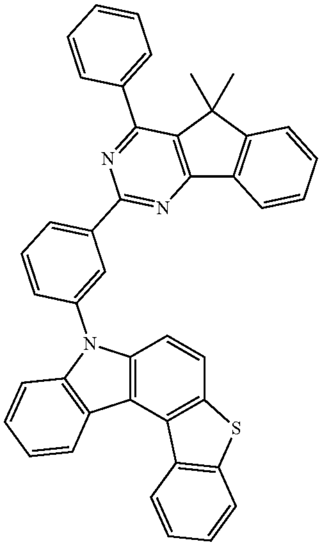

-continued
1066
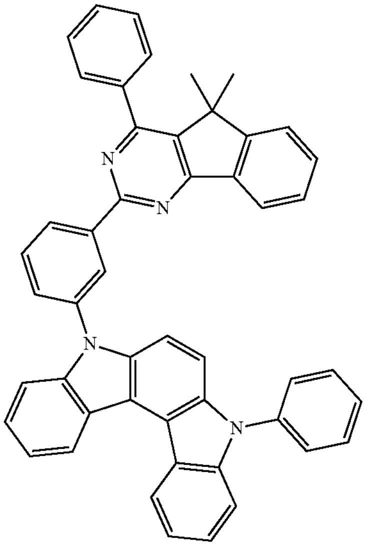
1067
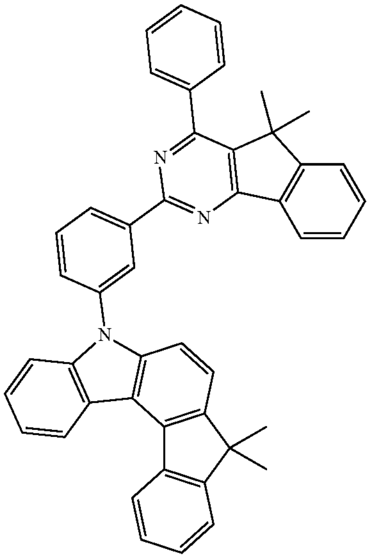
1068
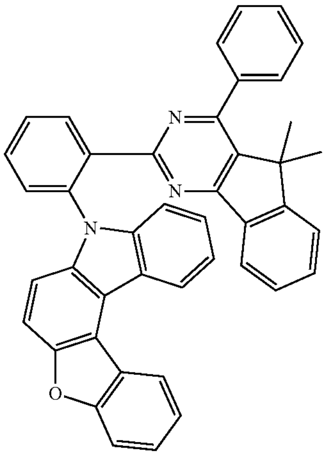
-continued
1069
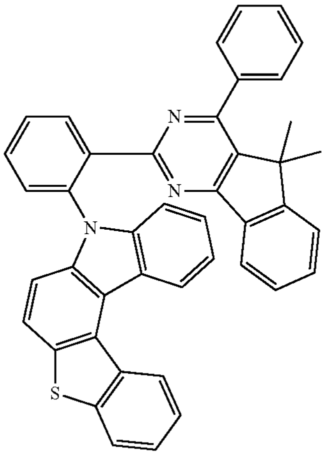
1070
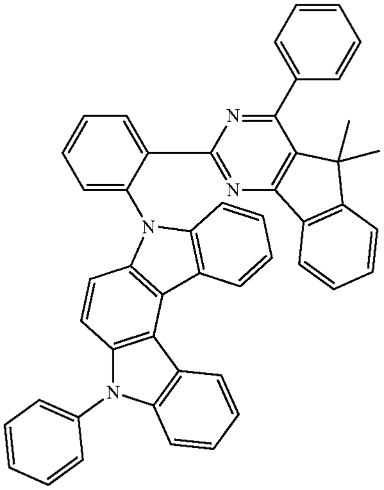
1071
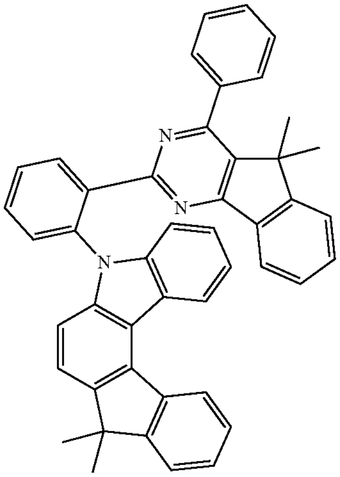

-continued
1072
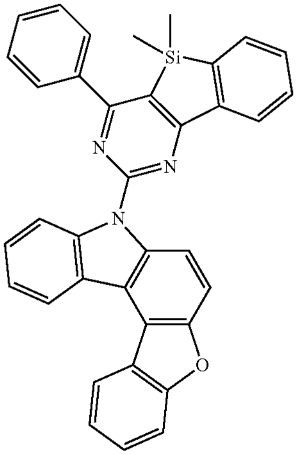
1073
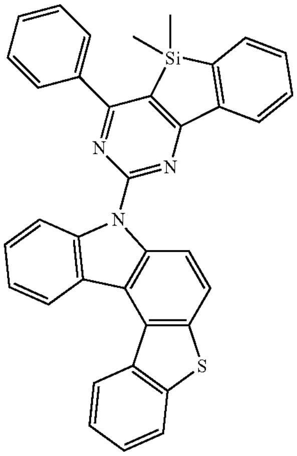
1074
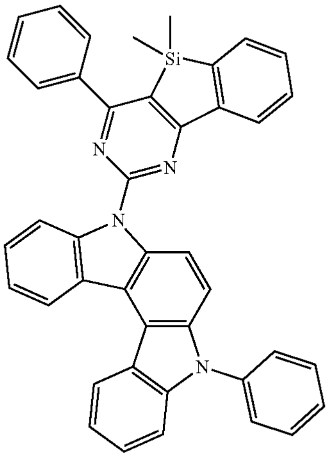
-continued
1075
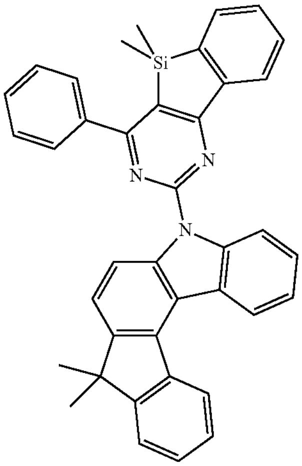
1076
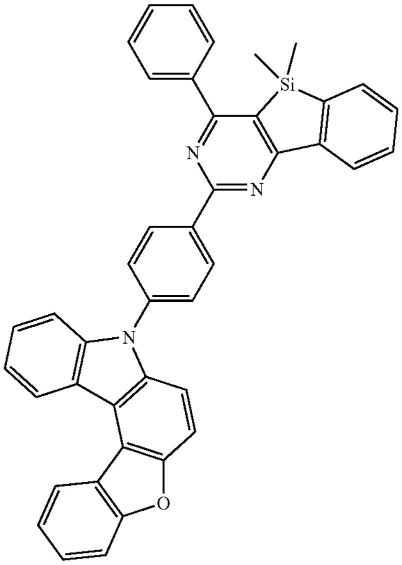
1077
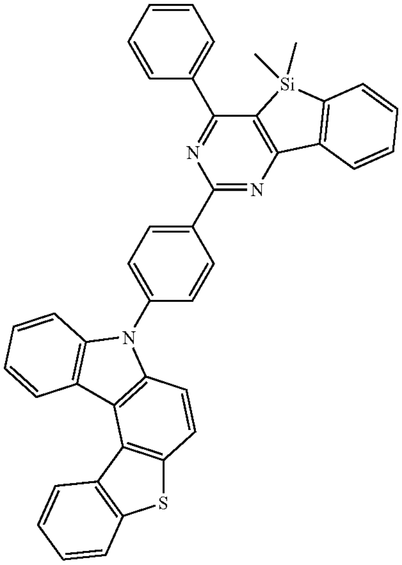

-continued
1078
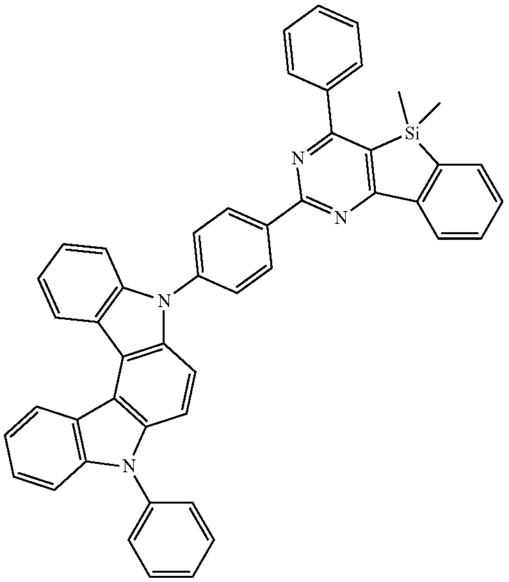
1079
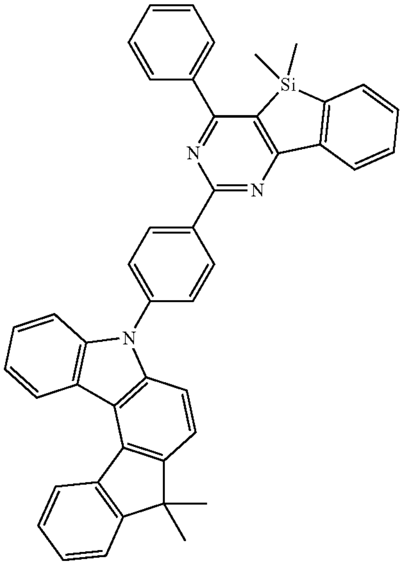
1080
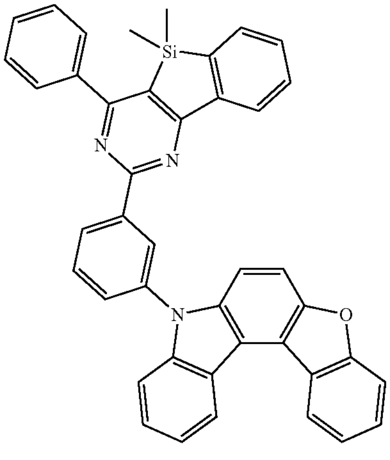
-continued
1081
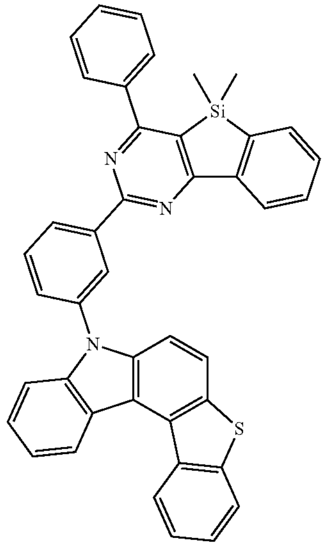
1082
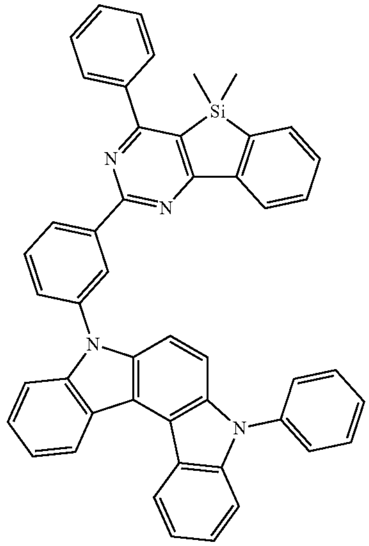
1083
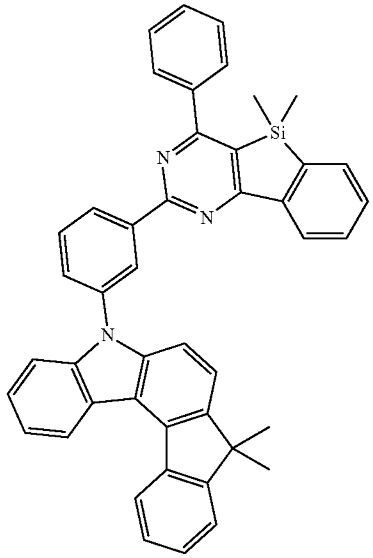

-continued
1084
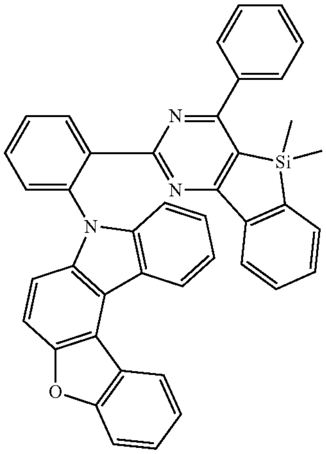
1085
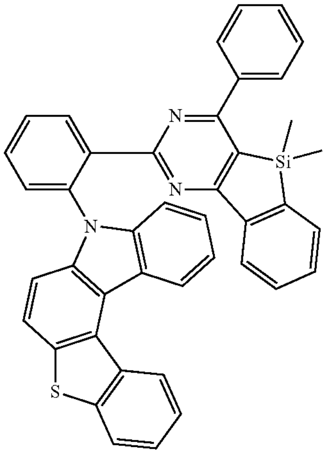
1086
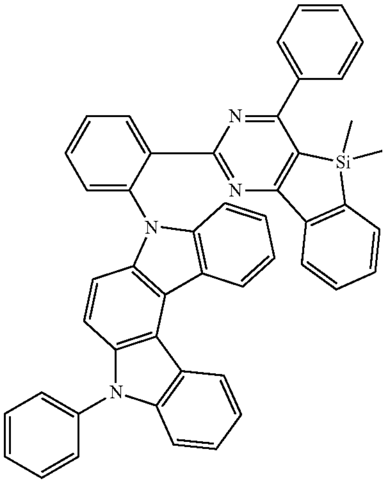
-continued
1087
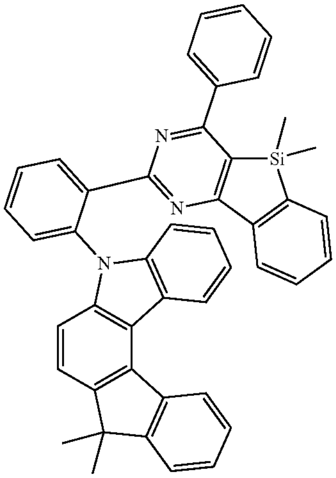
1088
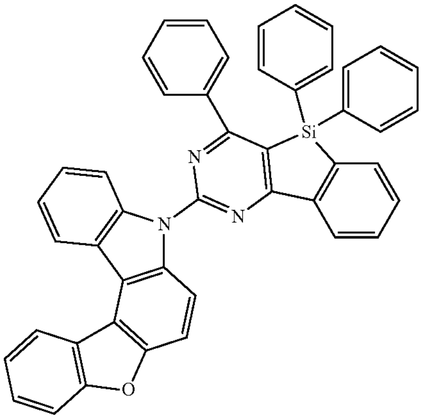
1089
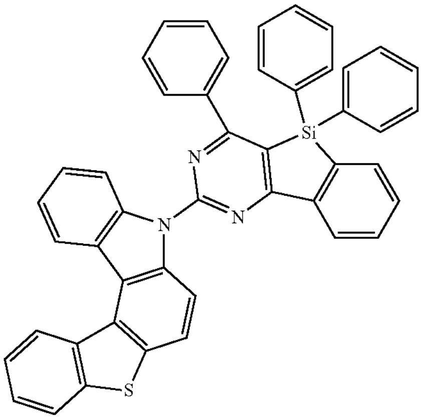

-continued
1090
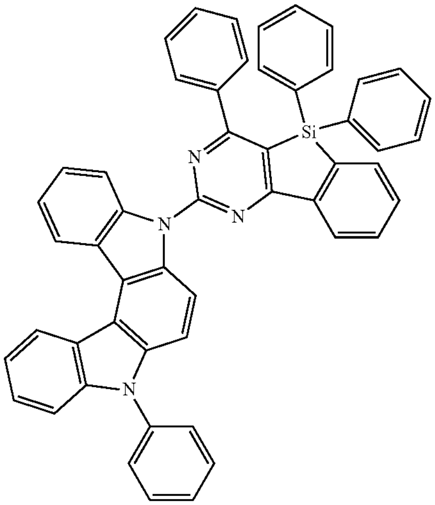
1091
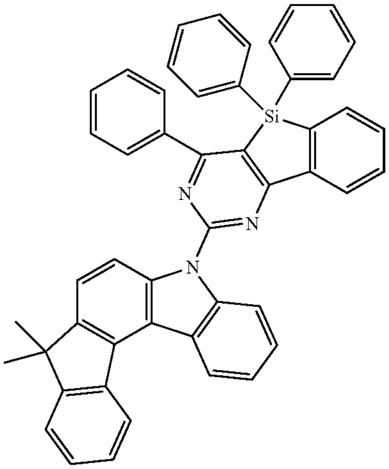
1092
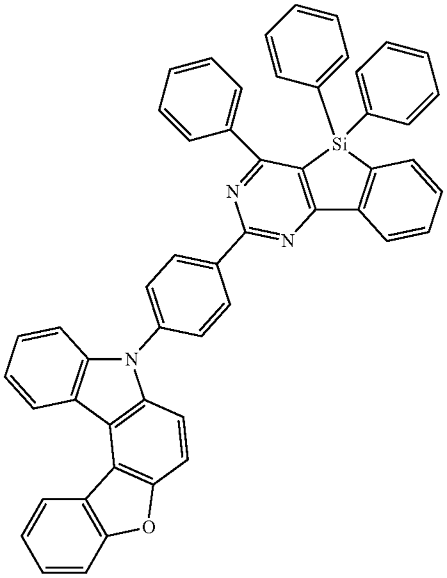
-continued
1093
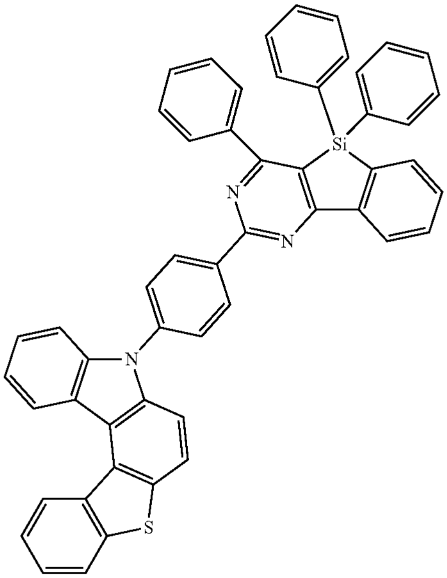
1094
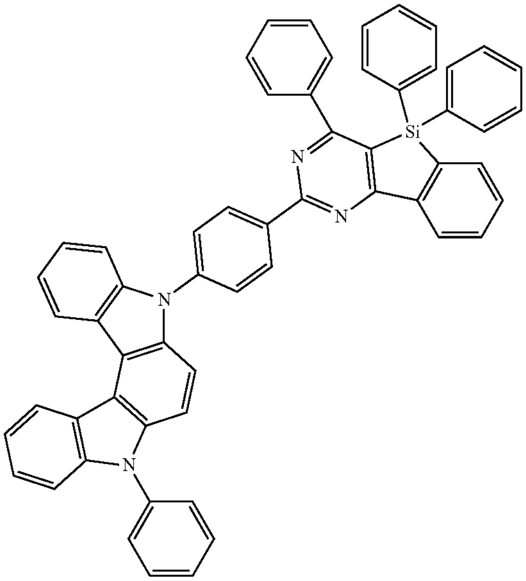

-continued
1095
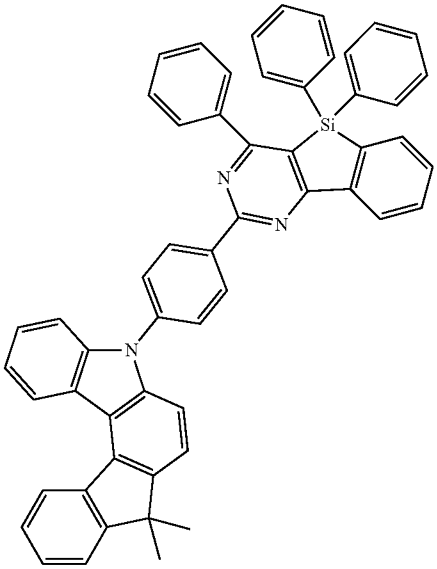
1096
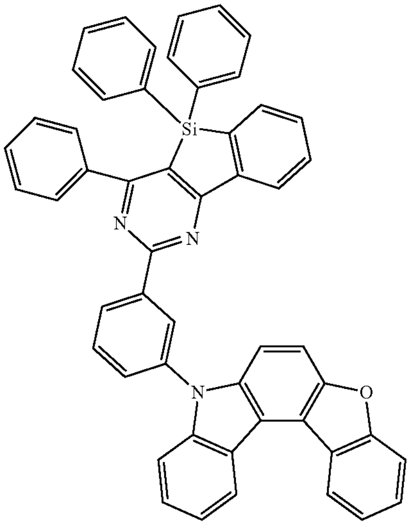
1097
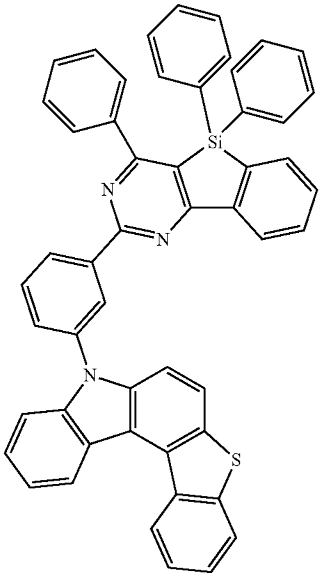
-continued
1098
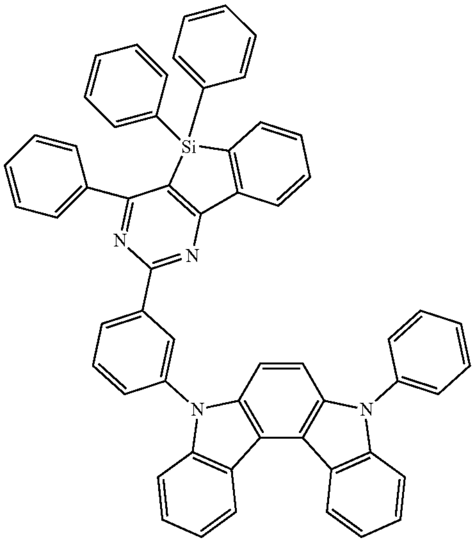
1099
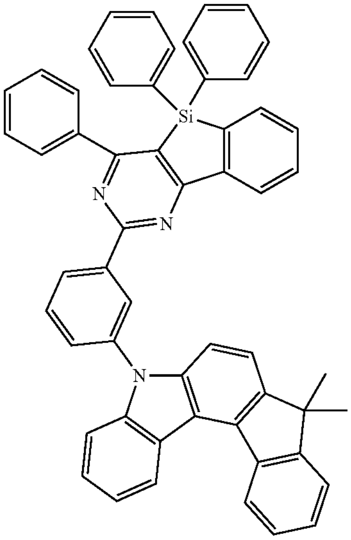
1100
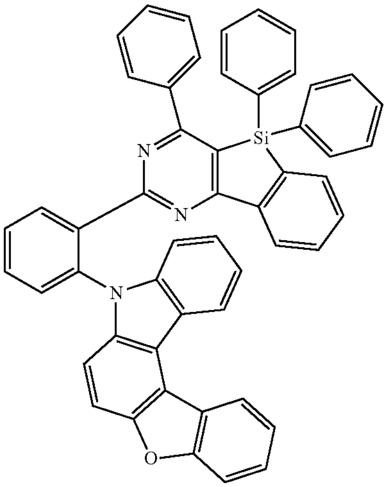

-continued
1101
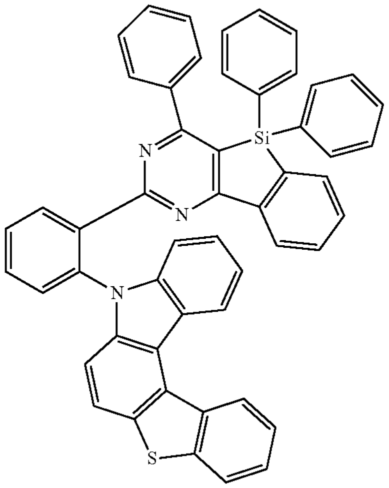
1102
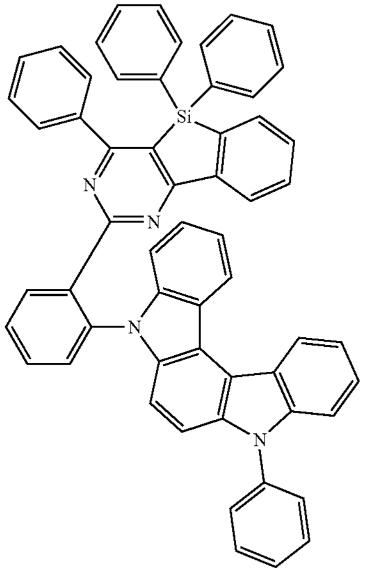
1103
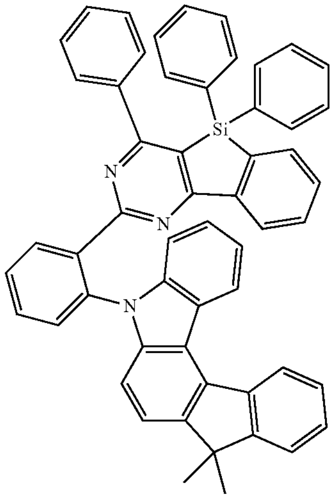
-continued
1104
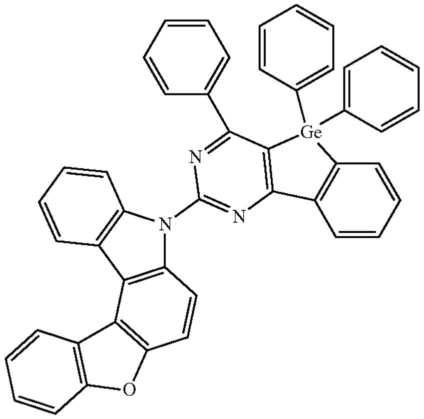
1105
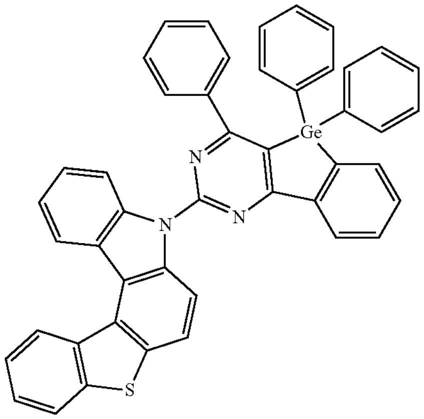
1106
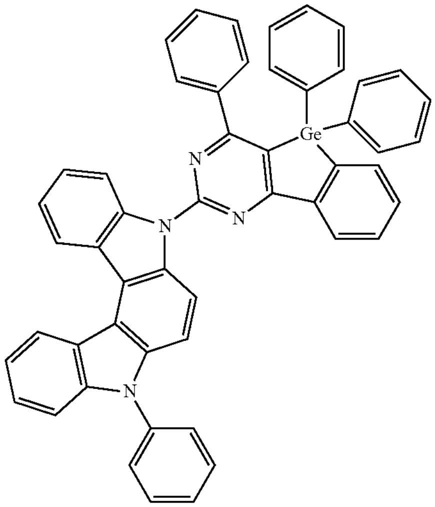

1107
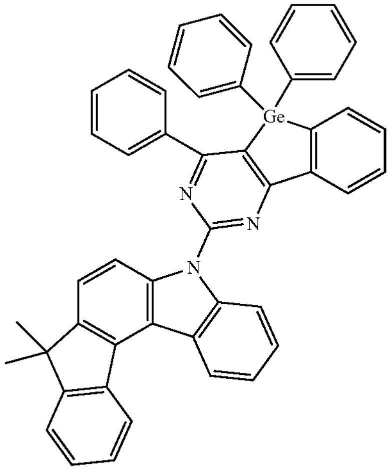
1108
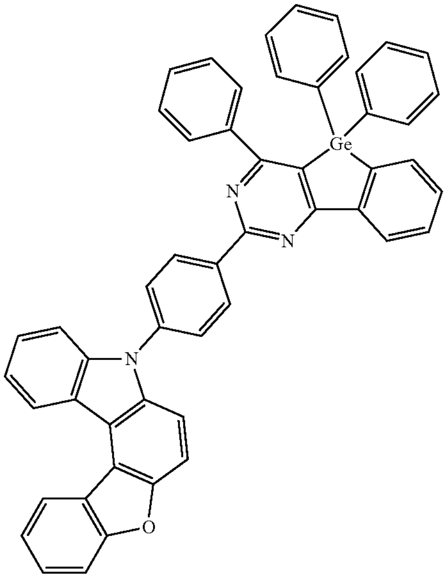
1109
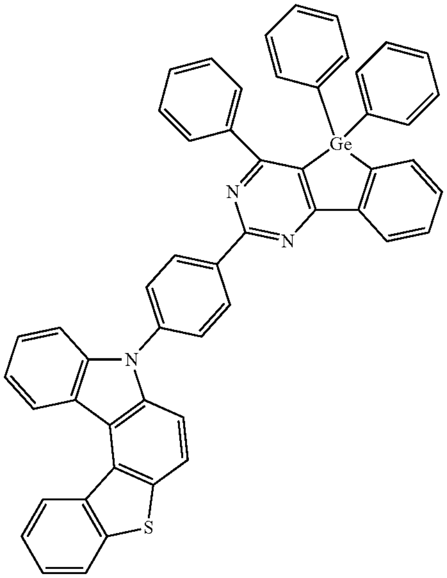
1110
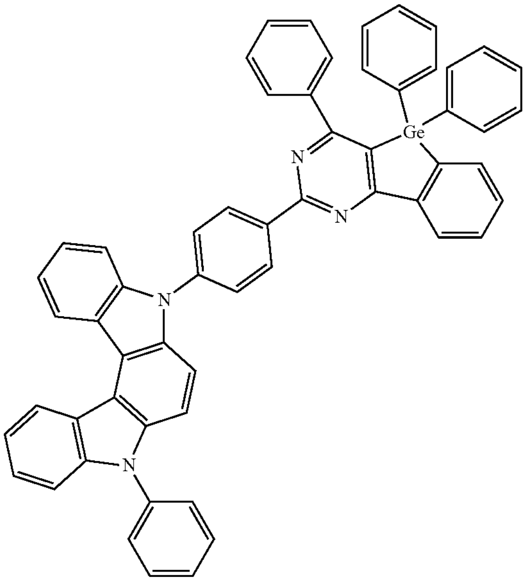
1111
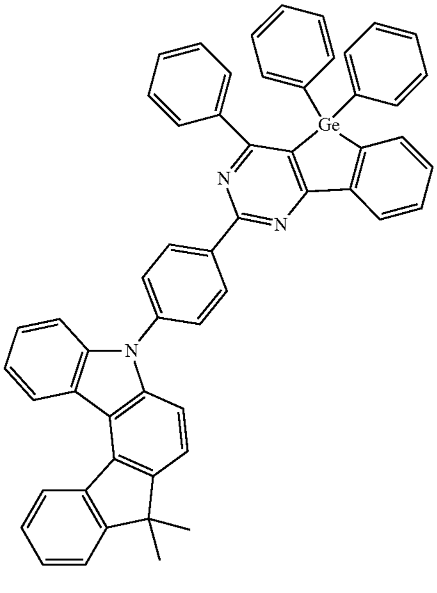

-continued
1112
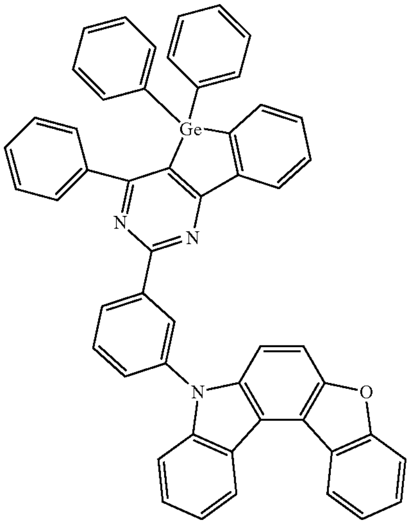
1113
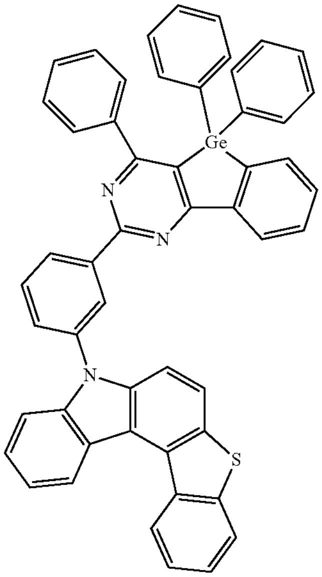
1114
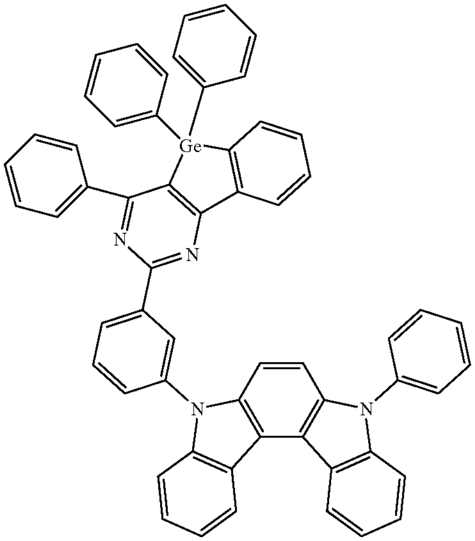
-continued
1115
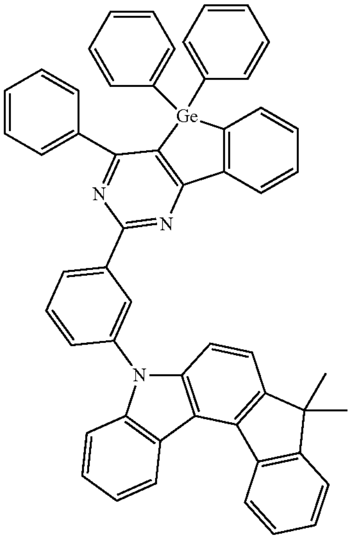
1116
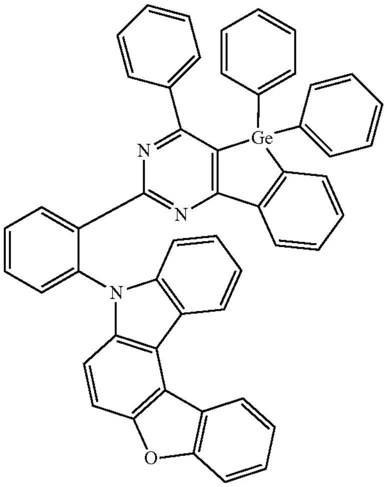
1117
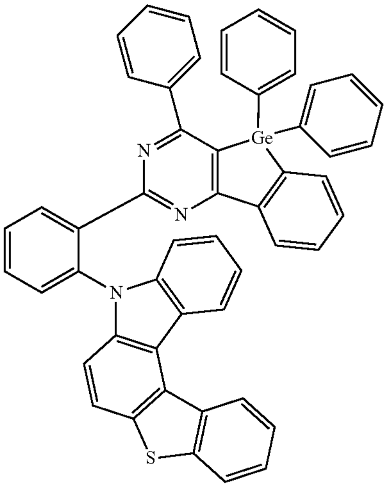

-continued
1118
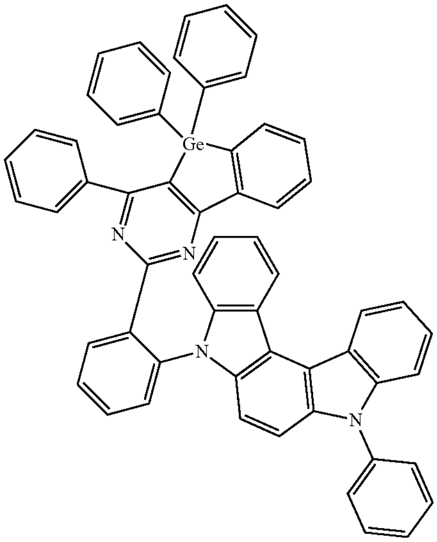
1119
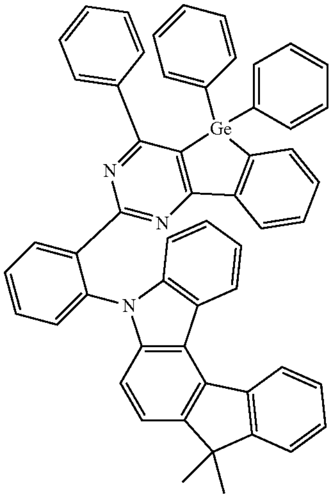
1120
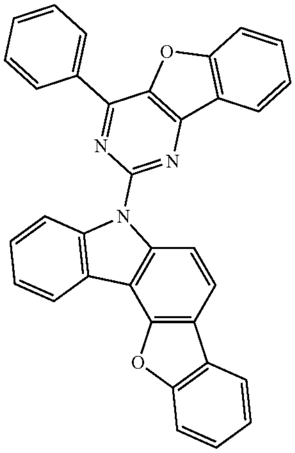
-continued
1121
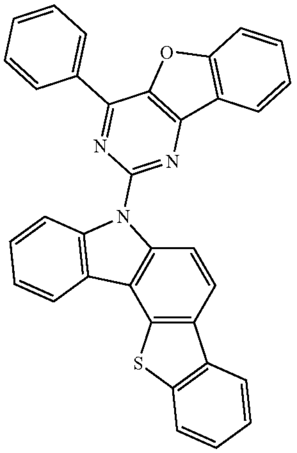
1122
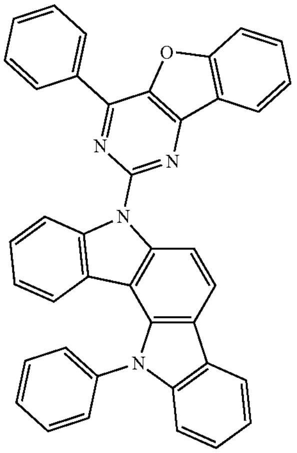
1123
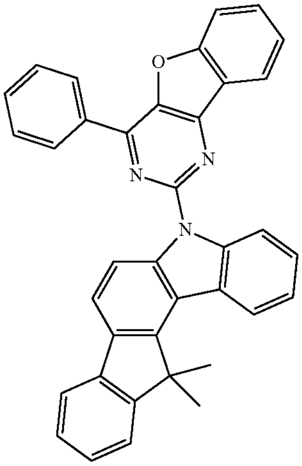

-continued
1124
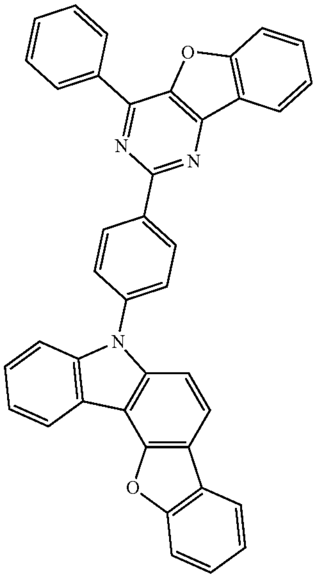
1125
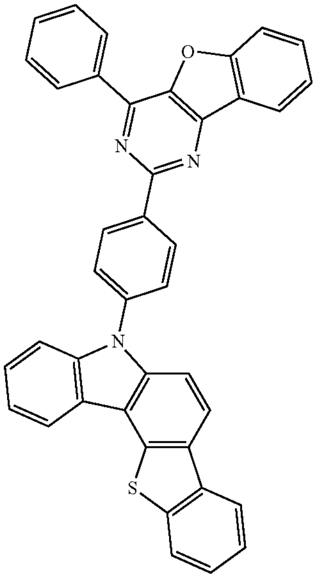
-continued
1126
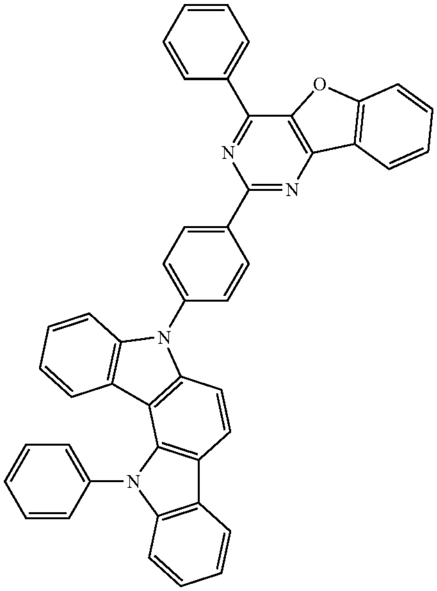
1127
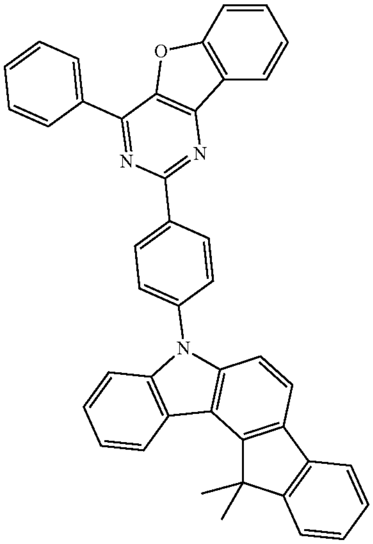
1128
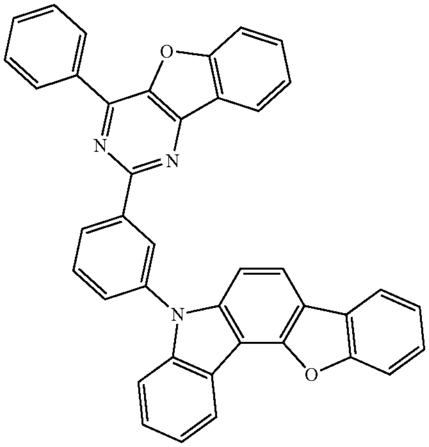

-continued
1129
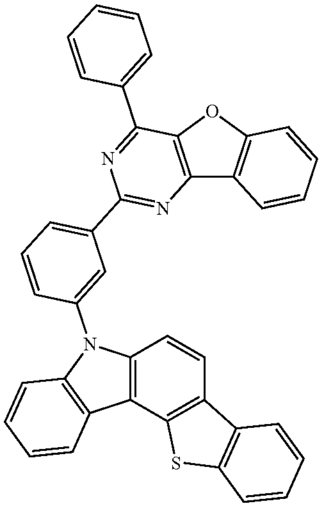
1130
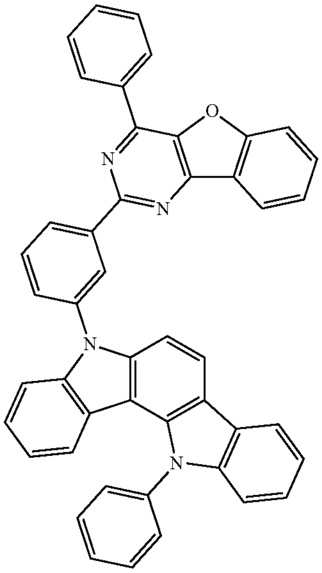
1131
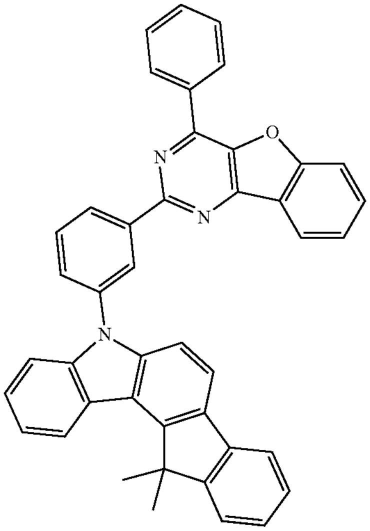
-continued
1132
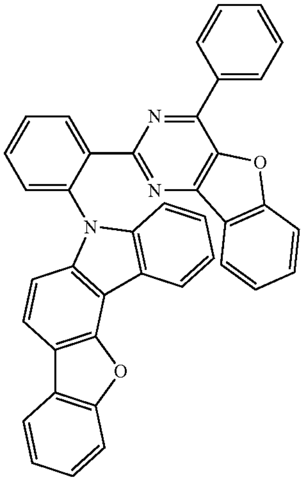
1133
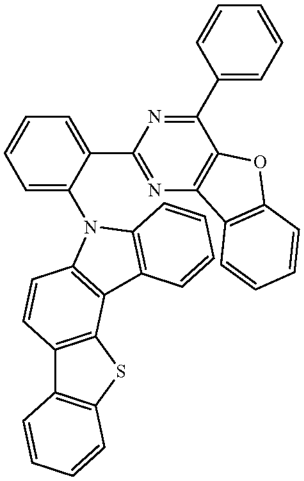
1134
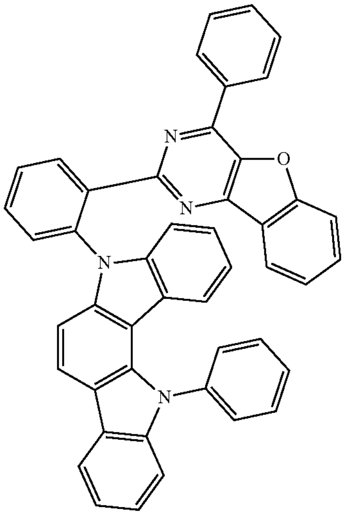

-continued
1135
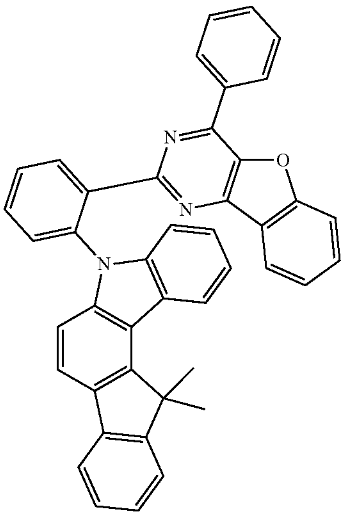
1136
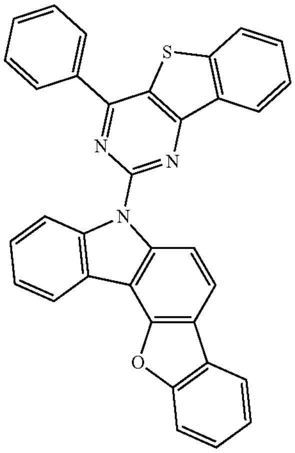
1137
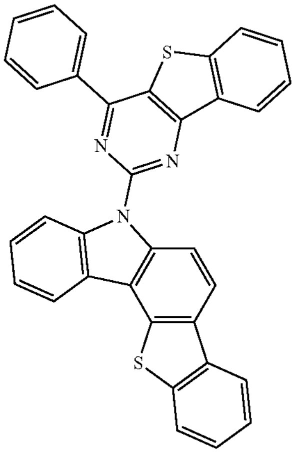
-continued
1138
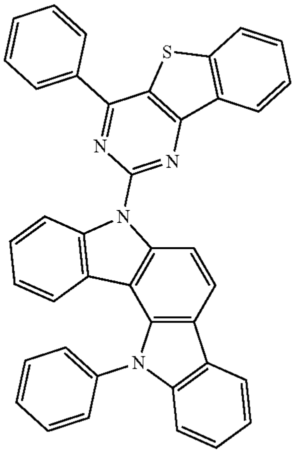
1139
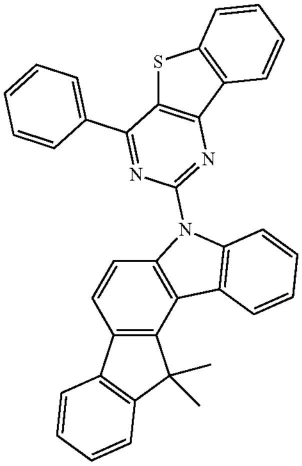
1140
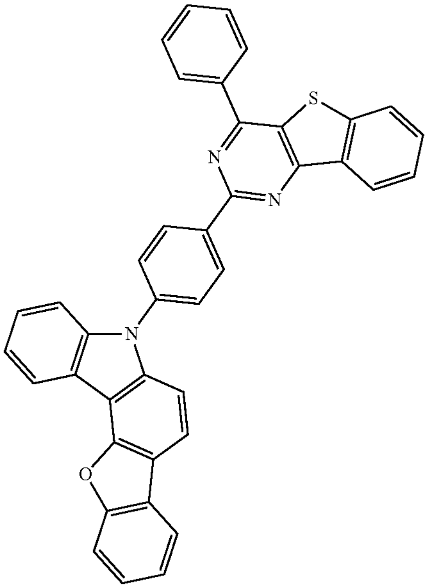

-continued
1141
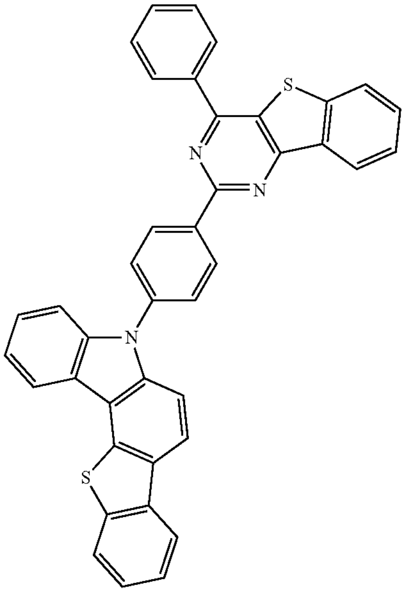
1142
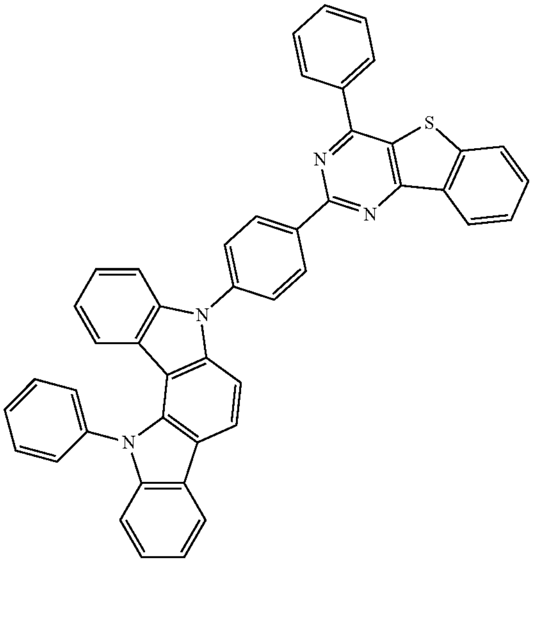
-continued
1143
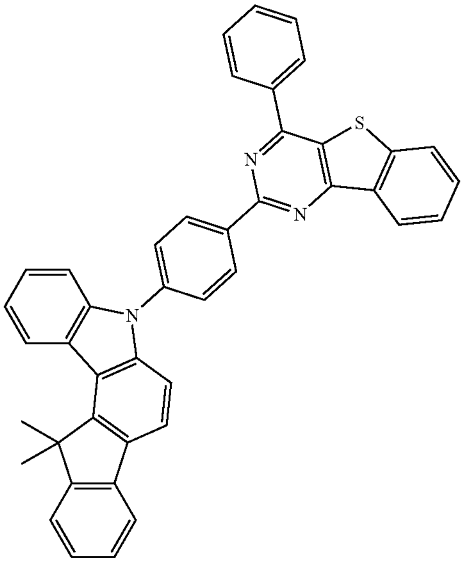
1144
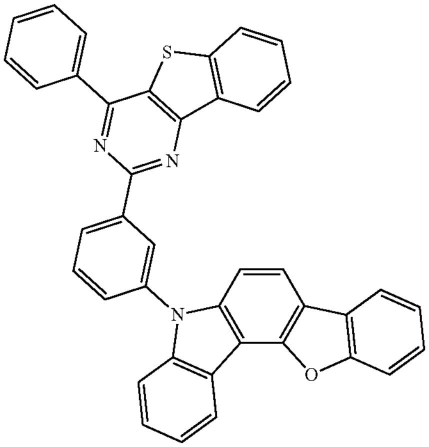
1145
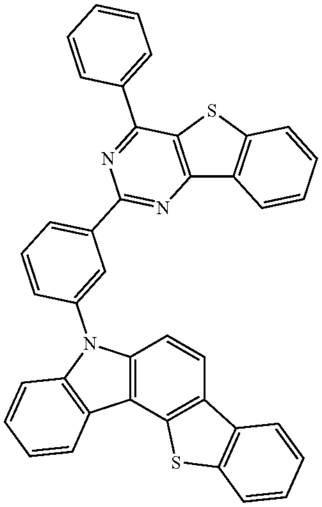

-continued
1146
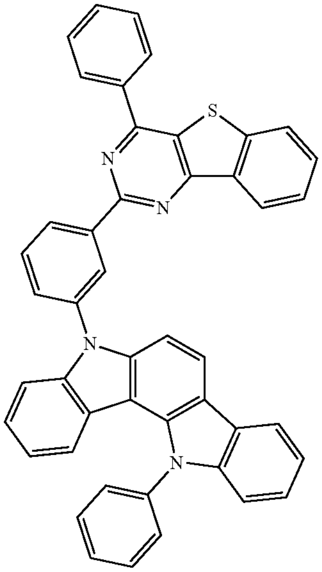
1147
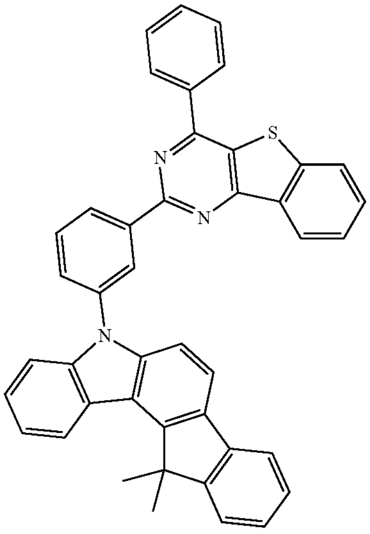
1148
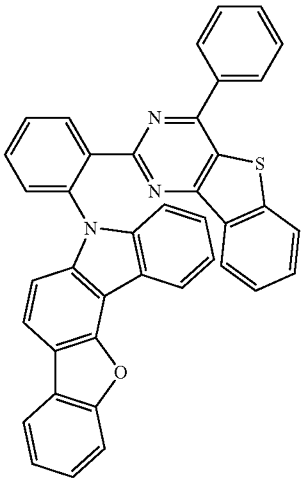
-continued
1149
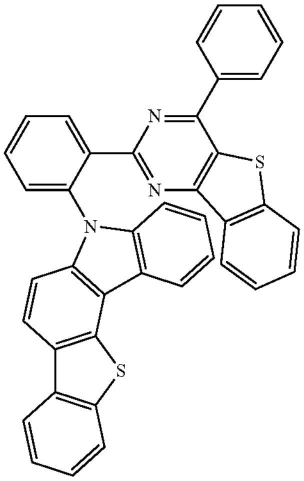
1150
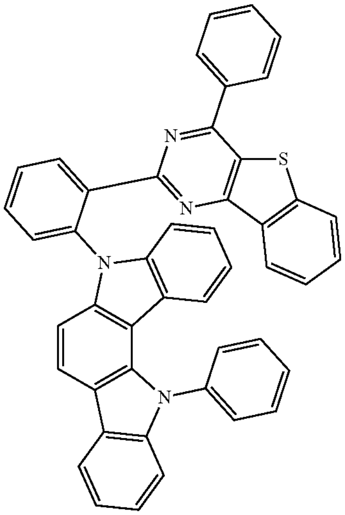
1151
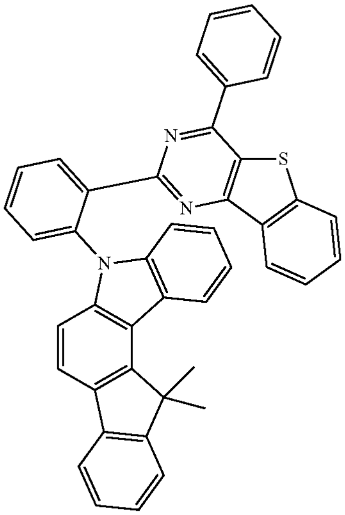

-continued
1152
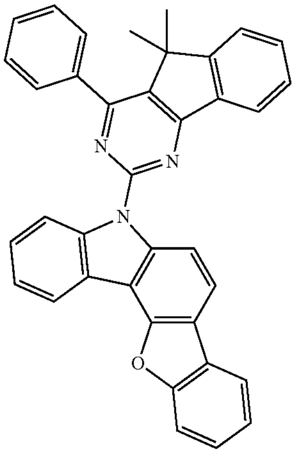
1153
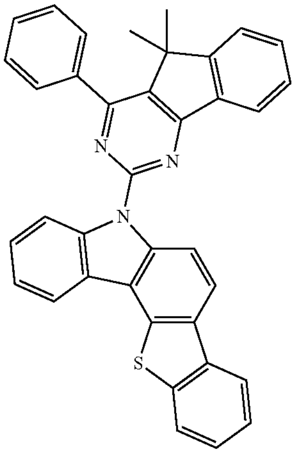
1154
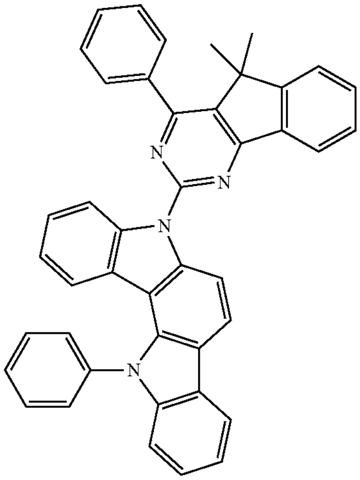
-continued
1155
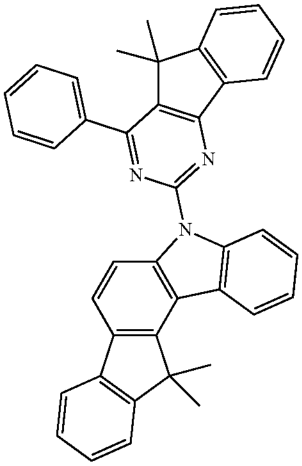
1156
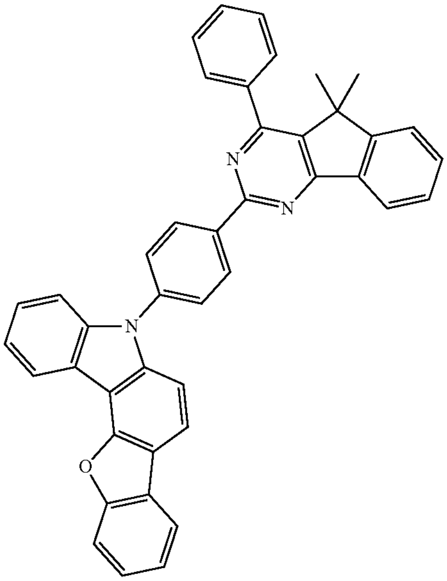
1157
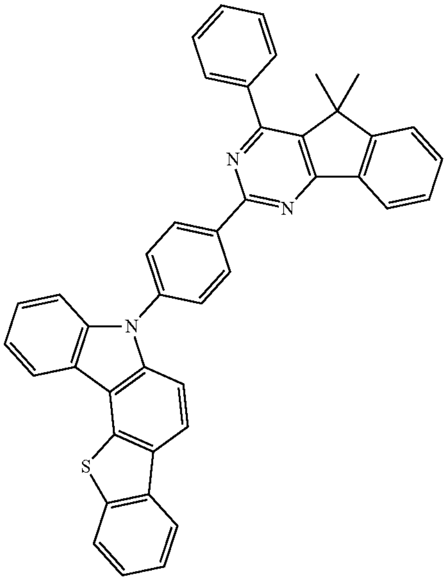

-continued
1158
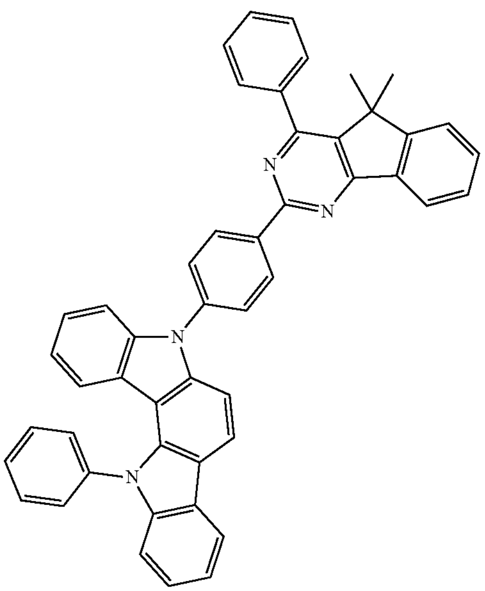
1159
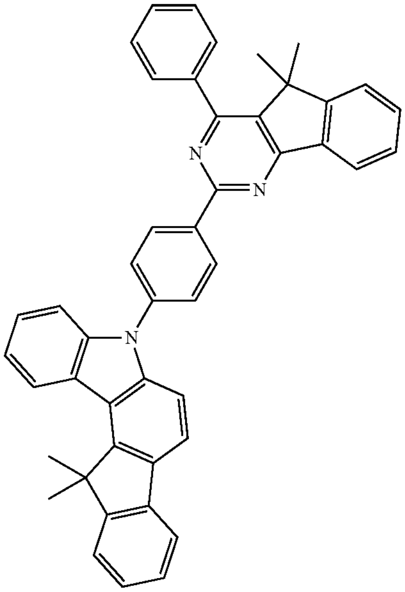
1160
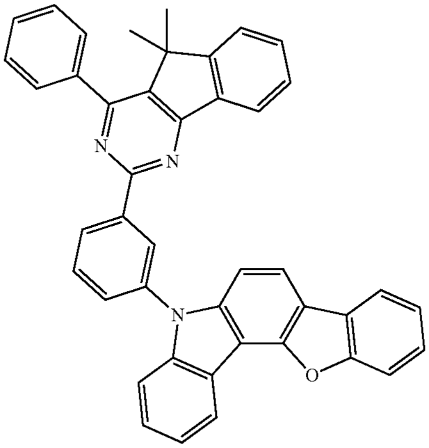
-continued
1161
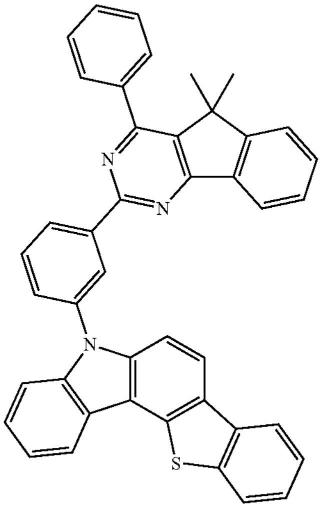
1162
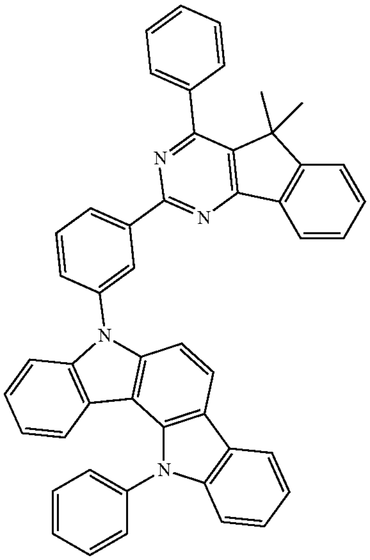
1163
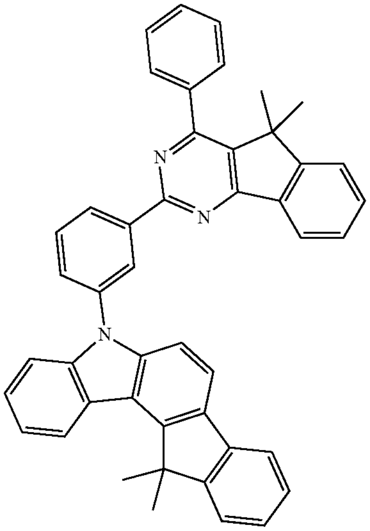

-continued
1164
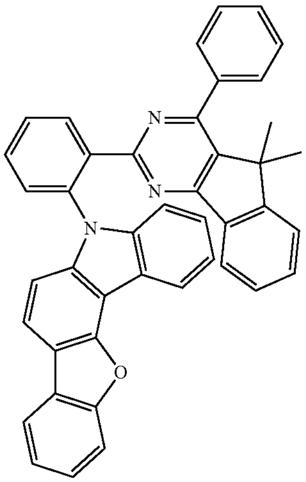
1165
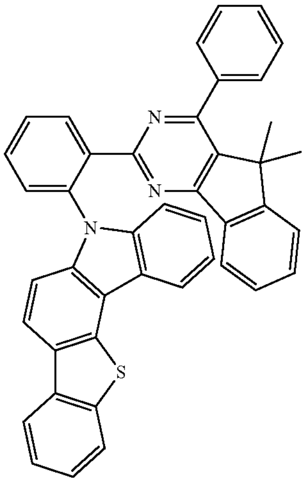
1166
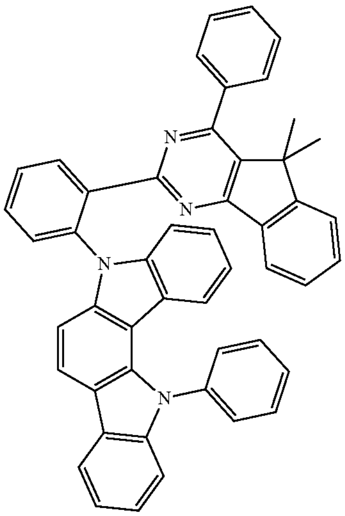
-continued
1167
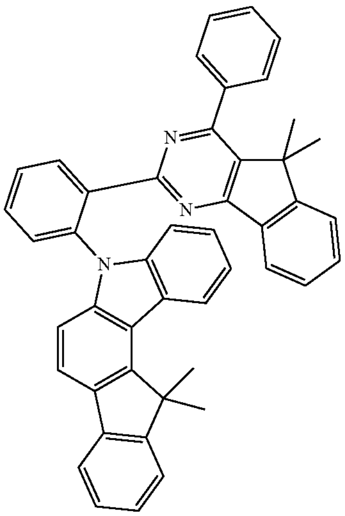
1168
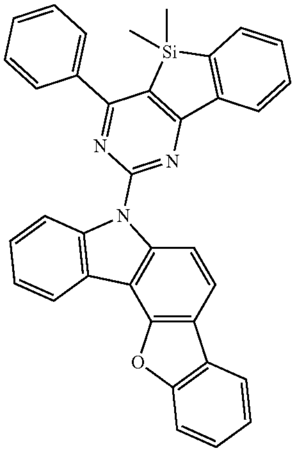
1169
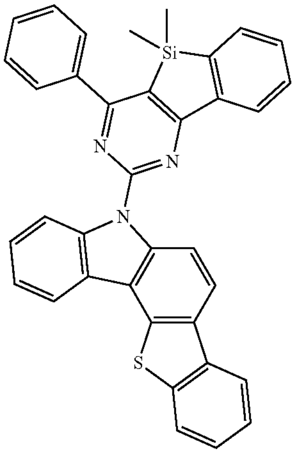

-continued
1170
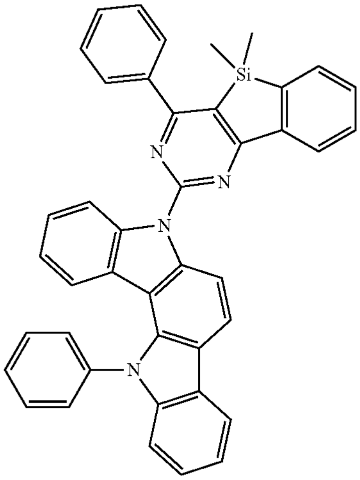
1171
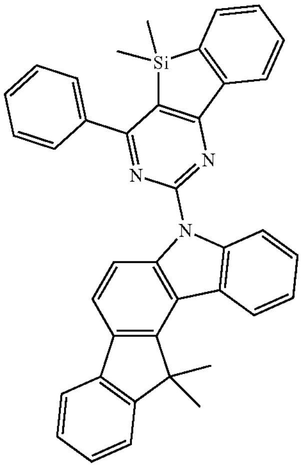
1172
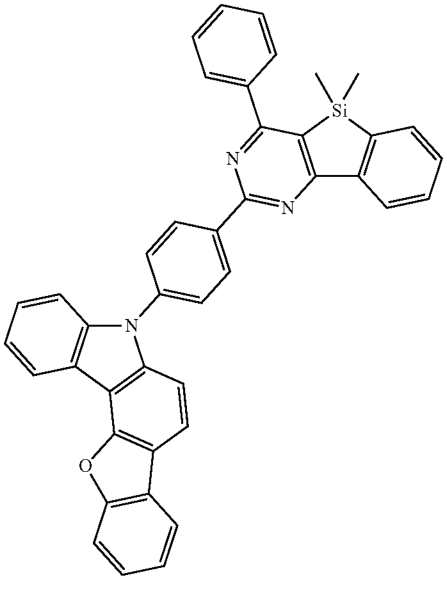
-continued
1173
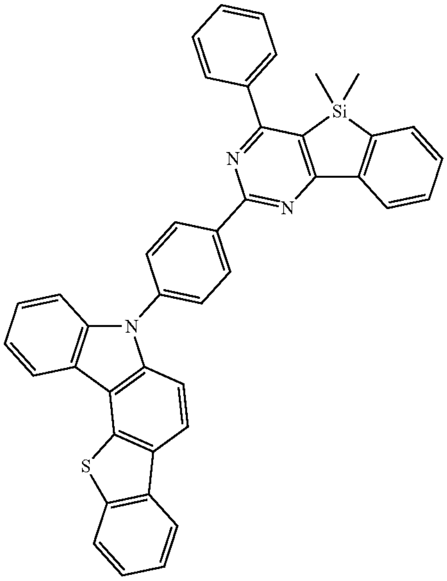
1174
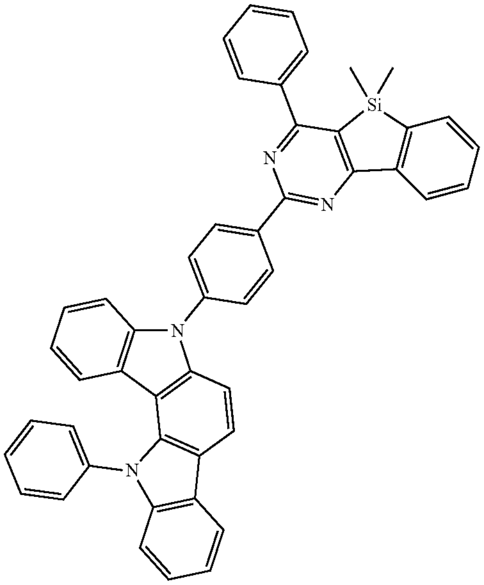

-continued
1175
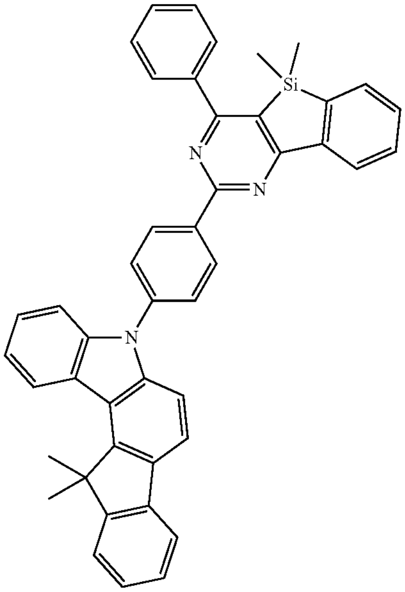
1176
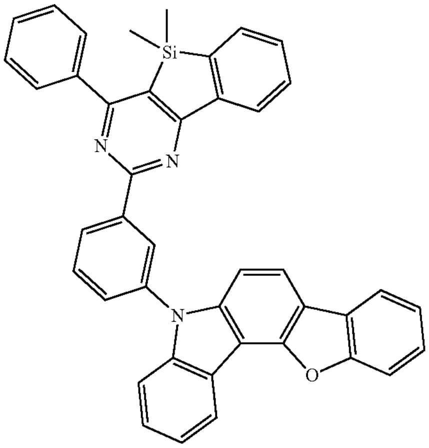
1177
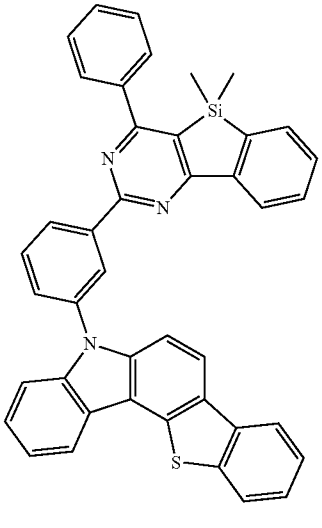
-continued
1178
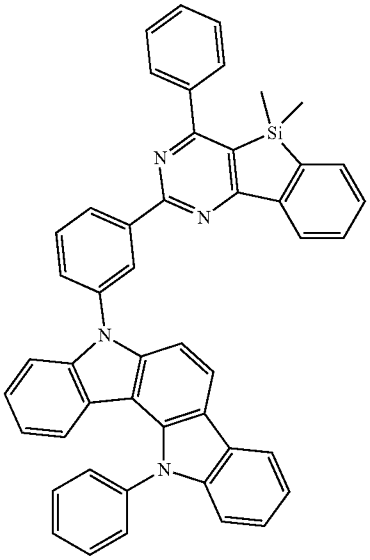
1179
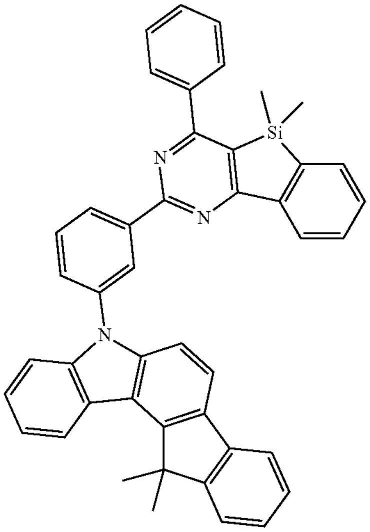
1180
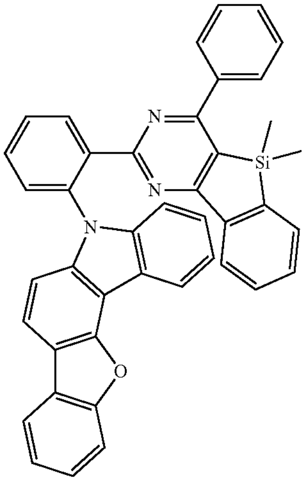

-continued
1181
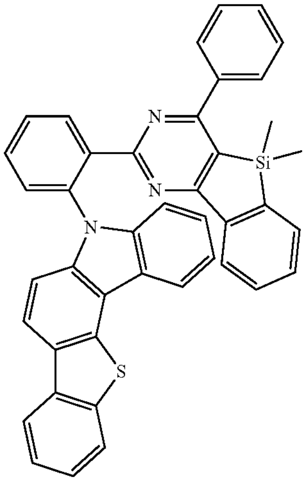
1182
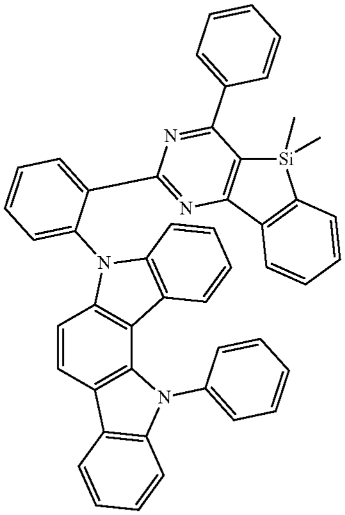
1183
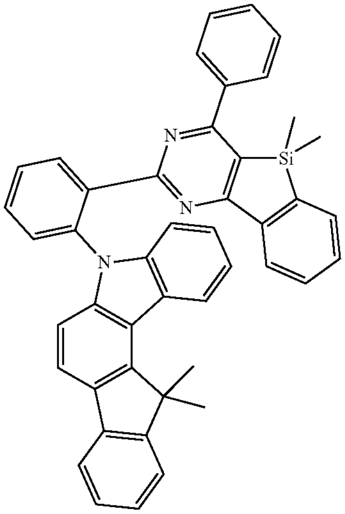
-continued
1184
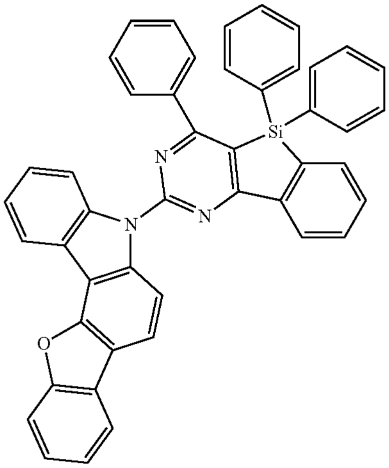
1185
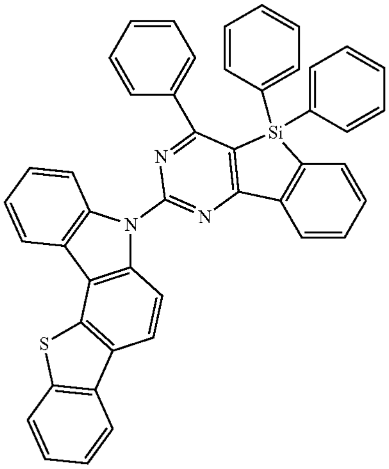
1186
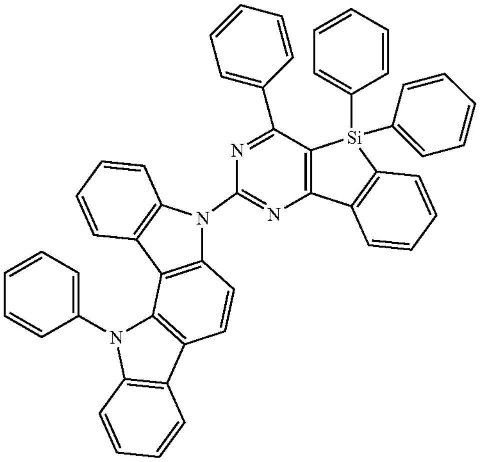

1187
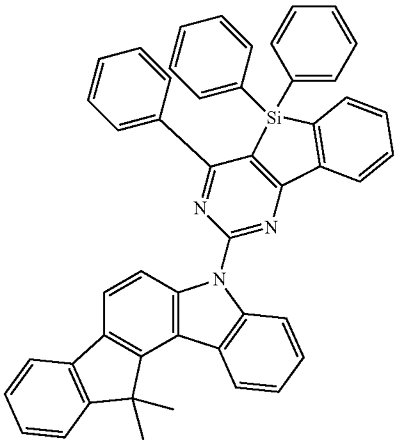
1188
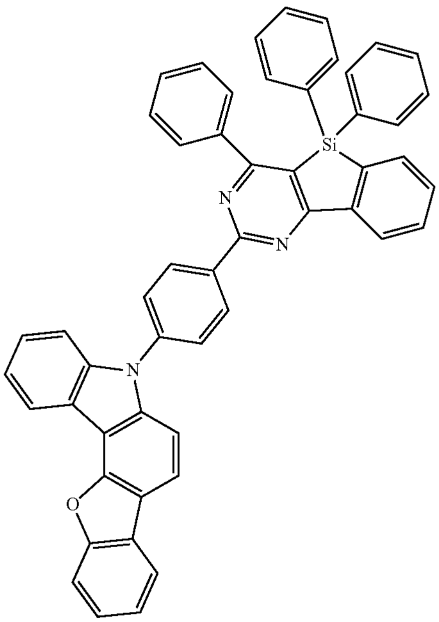
1189
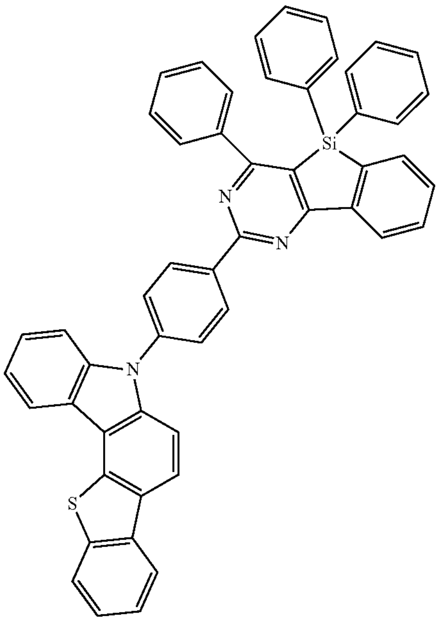
1190
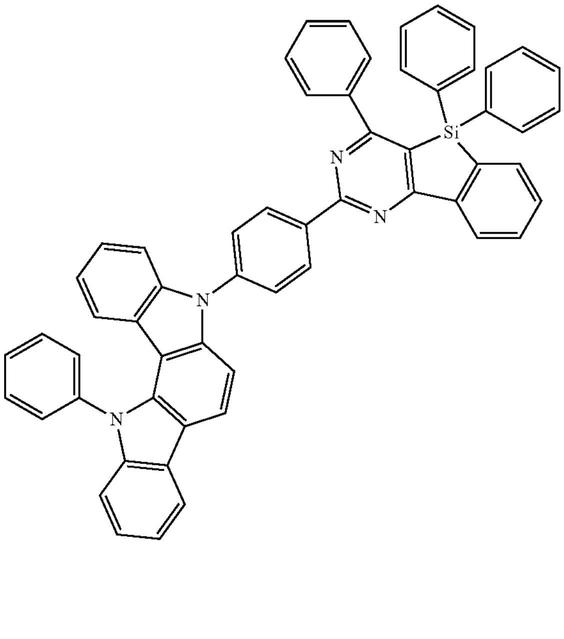

-continued
1191
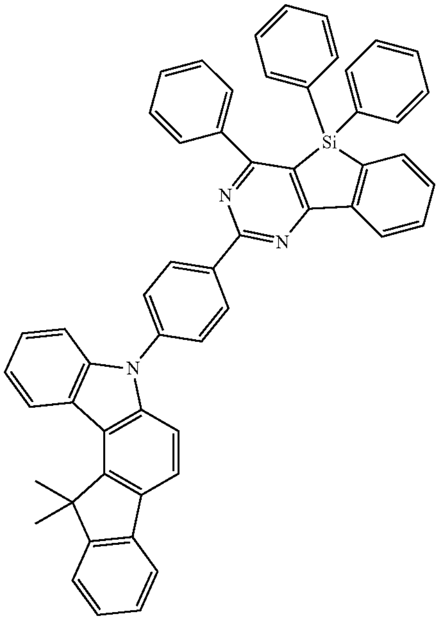
1192
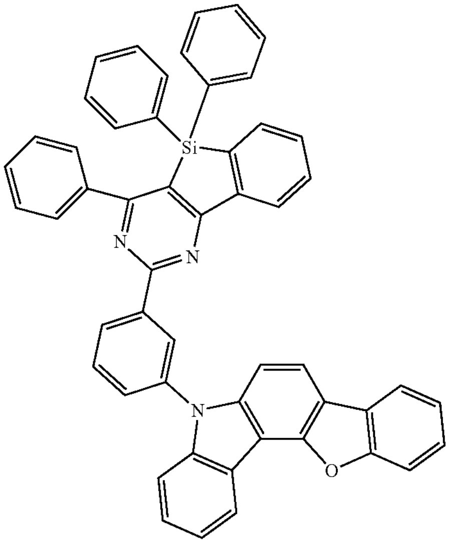
-continued
1193
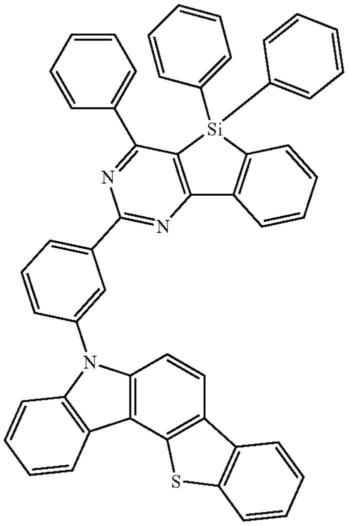
1194
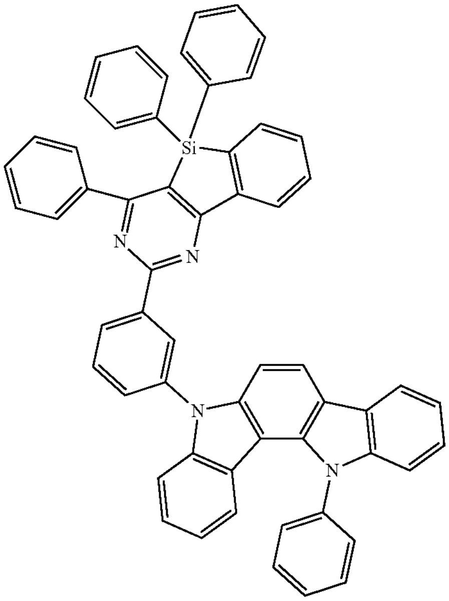
1195
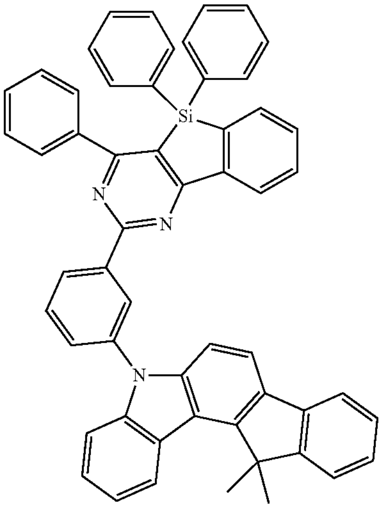

-continued
1196
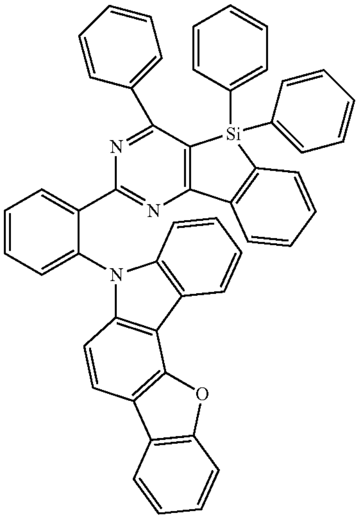
1197
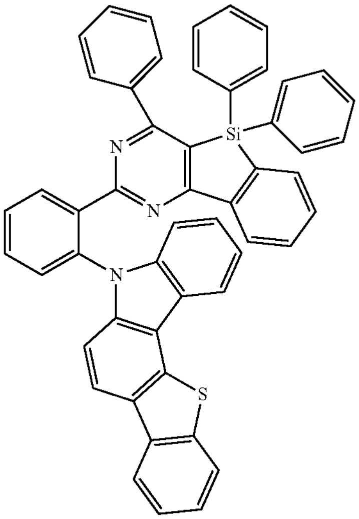
1198
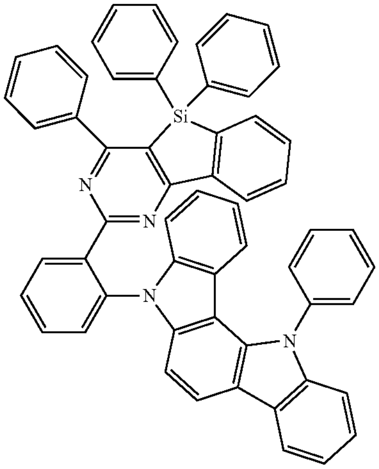
-continued
1199
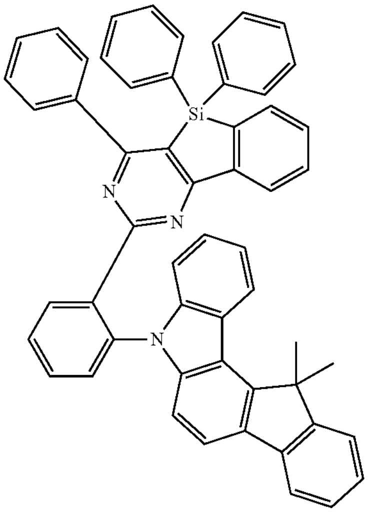
1200
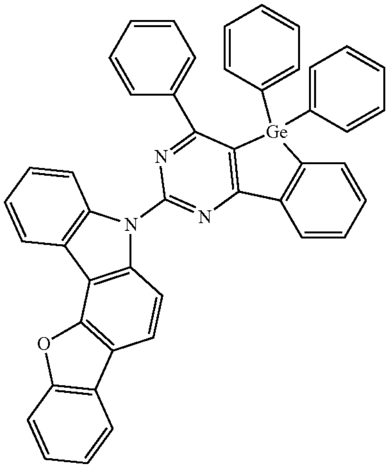
1201
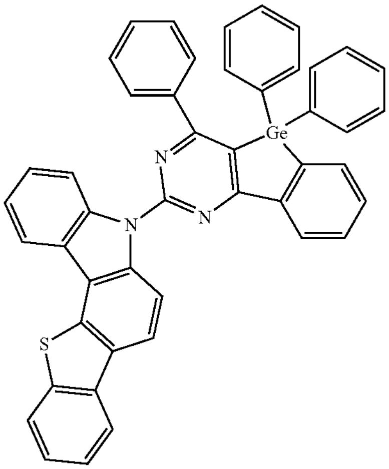

-continued
1202
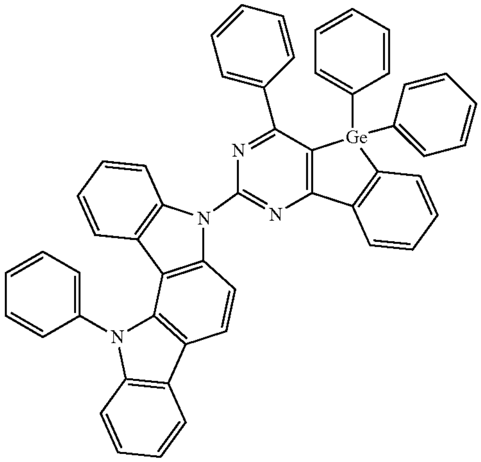
1203
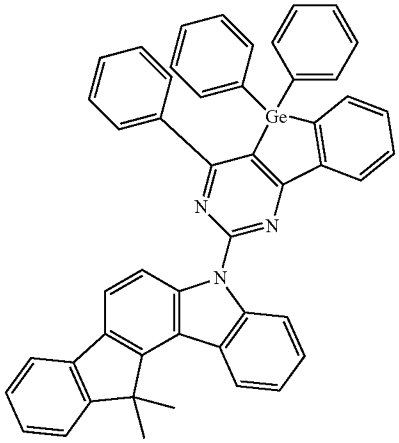
1204
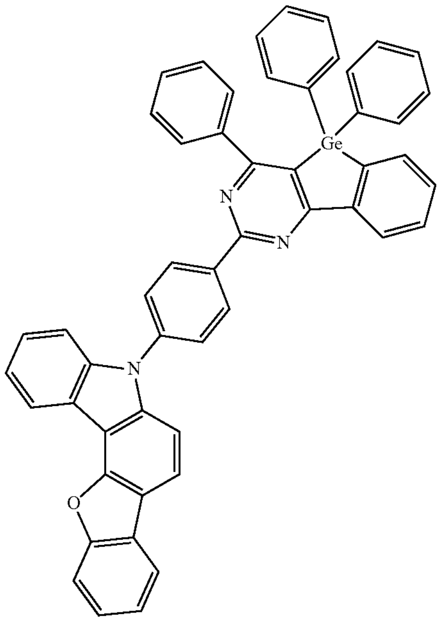
-continued
1205
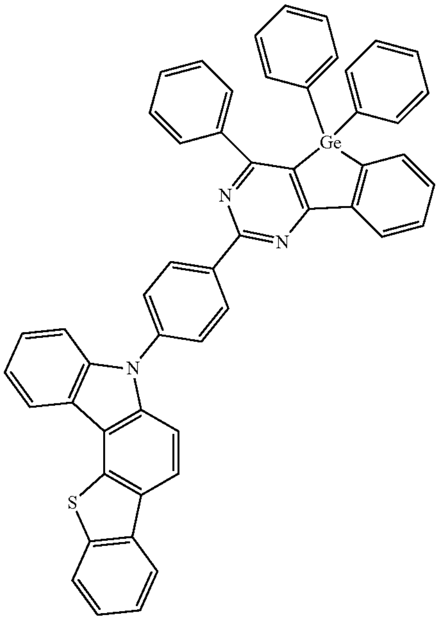
1206
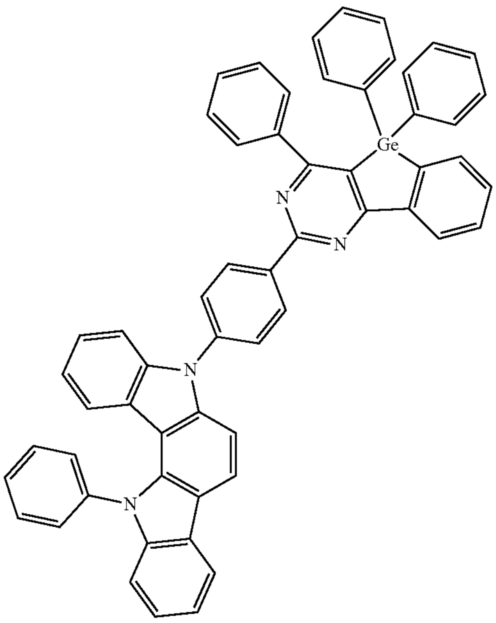

-continued
1207
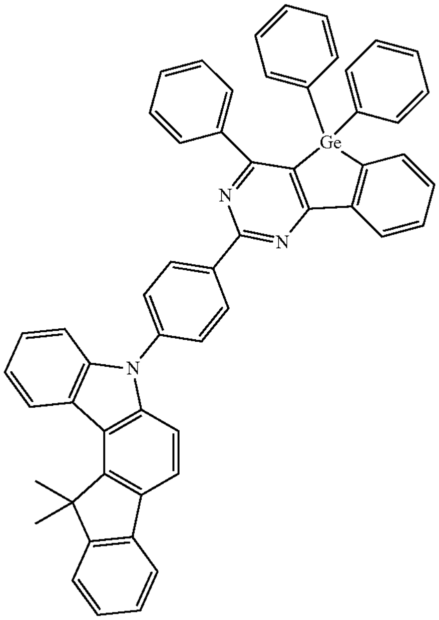
1208
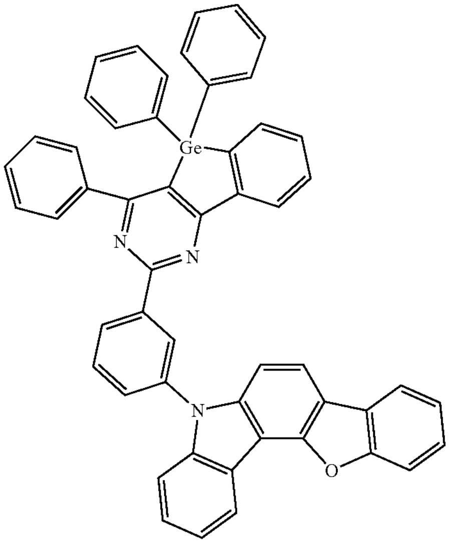
-continued
1209
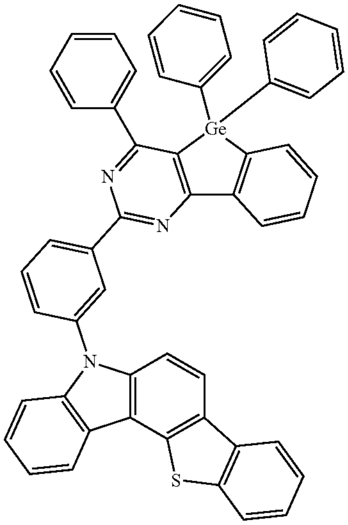
1210
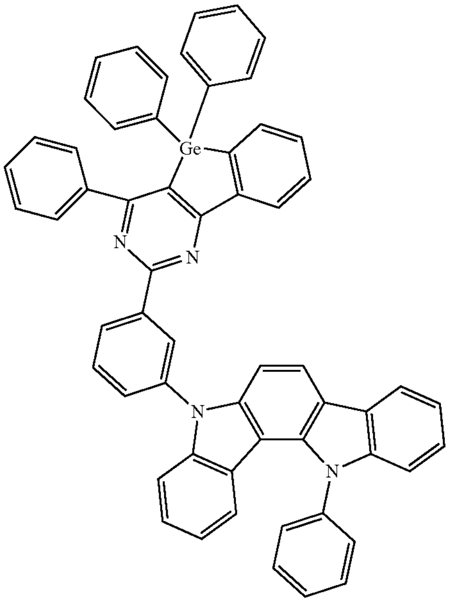
1211
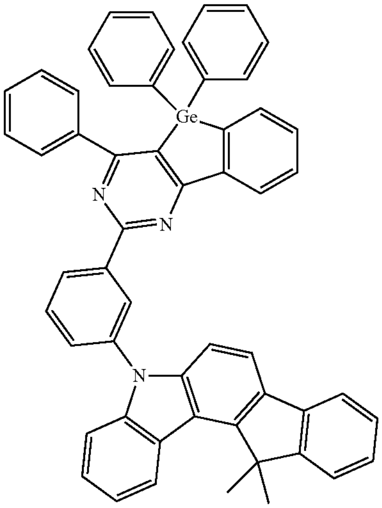

-continued
1212
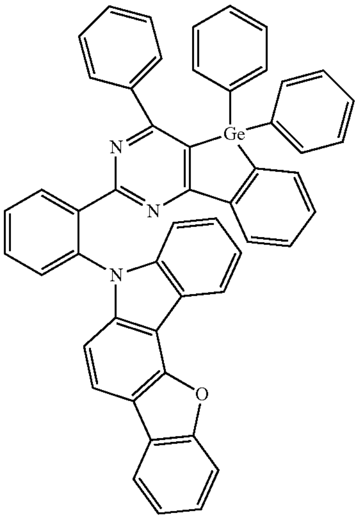
1213
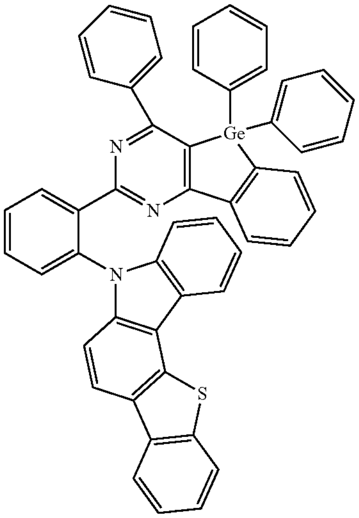
1214
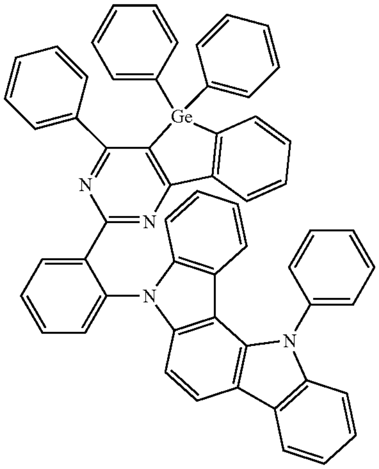
-continued
1215
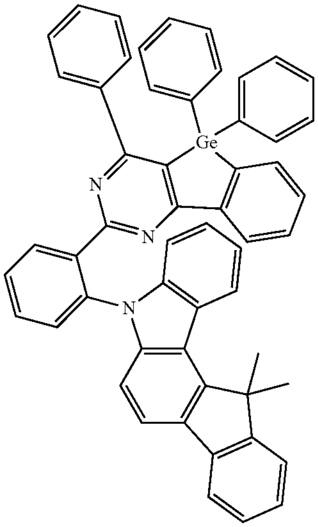
1216
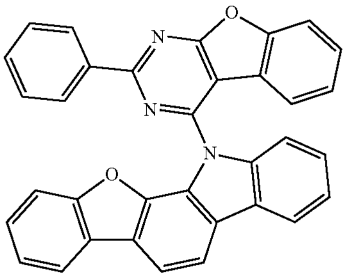
1217
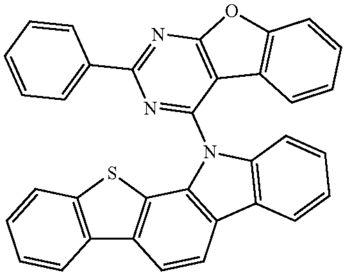
1218
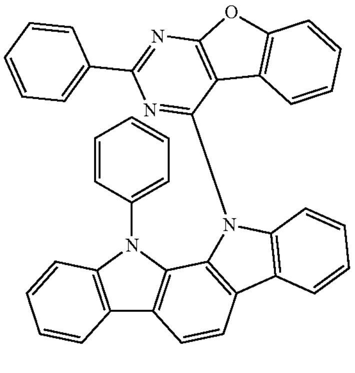

1219
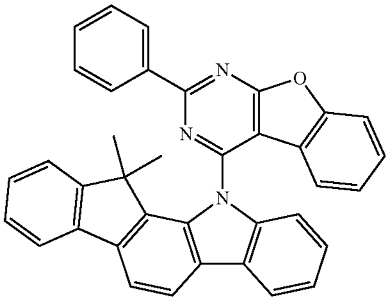
1220
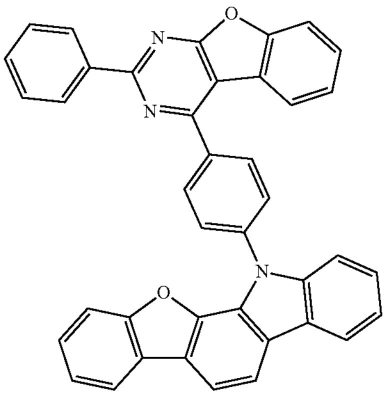
1221
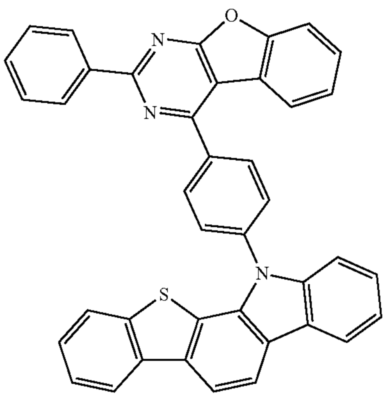
1222
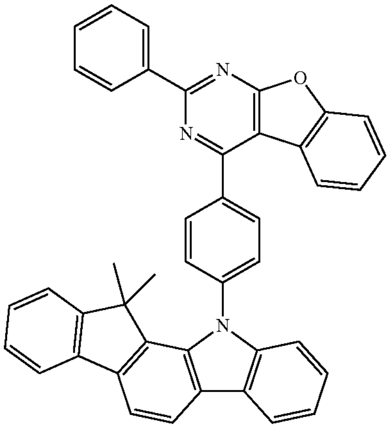
1223
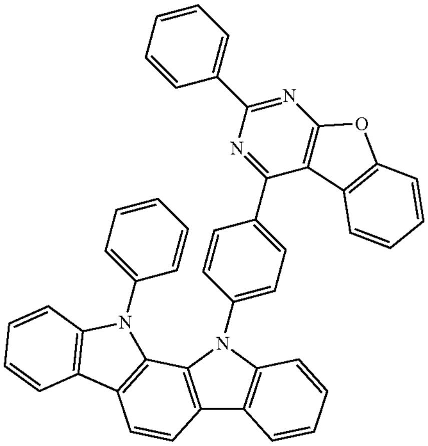
1224
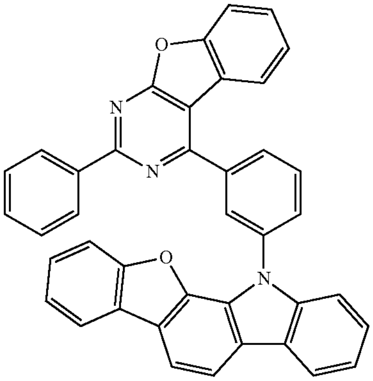
1225
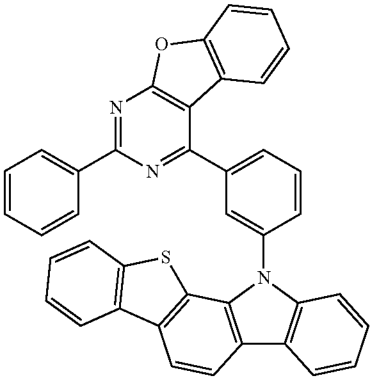
1226
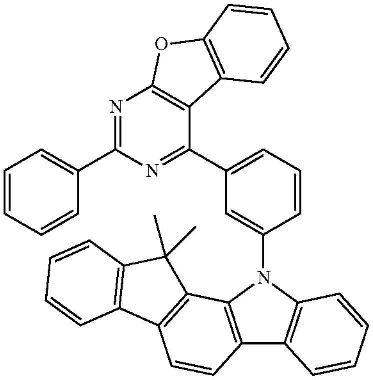

-continued
1227
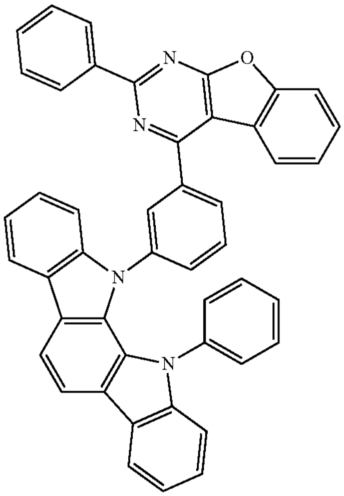
1228
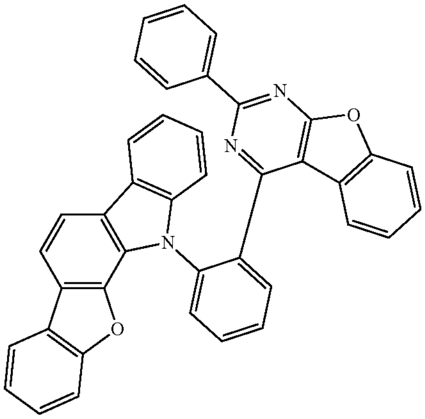
1229
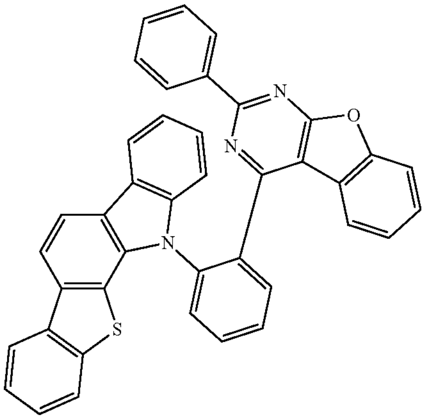
-continued
1230
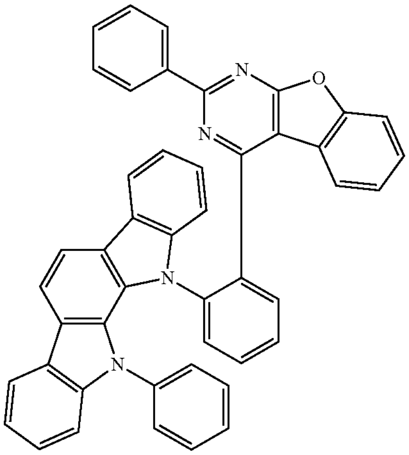
1231
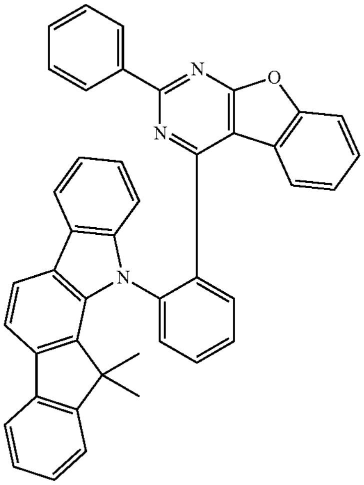
1232
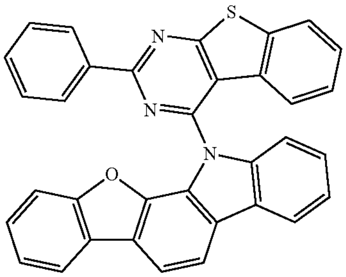
1233
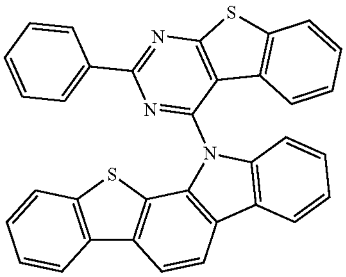

-continued
1234
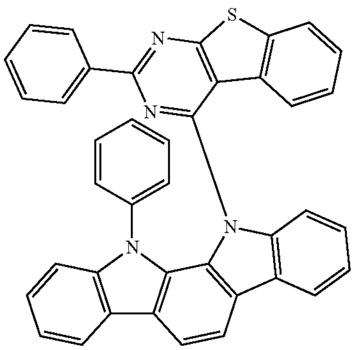
1235
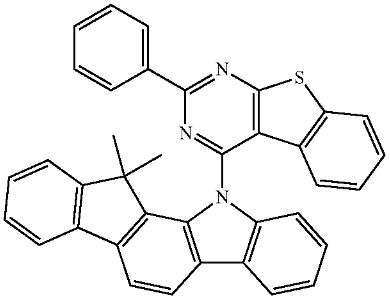
1236
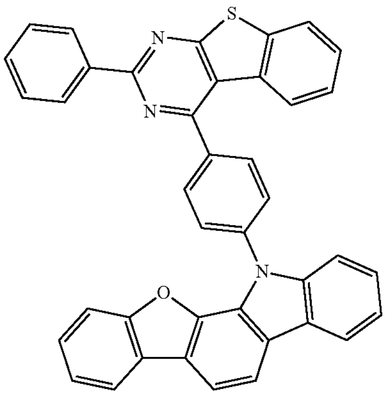
1237
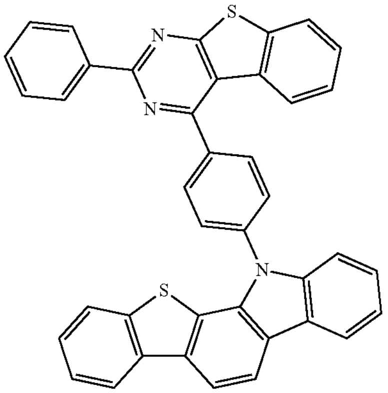
-continued
1238
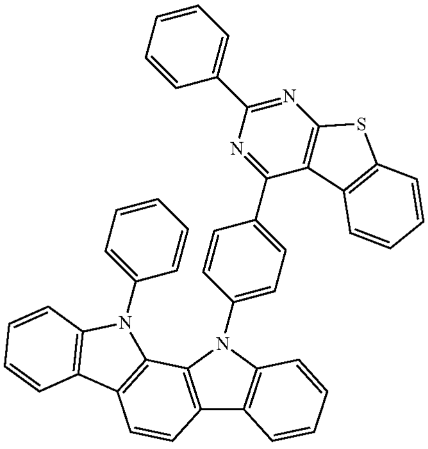
1239
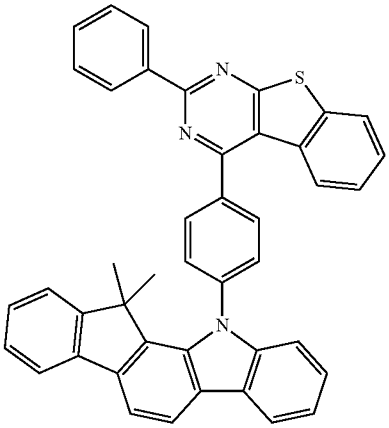
1240
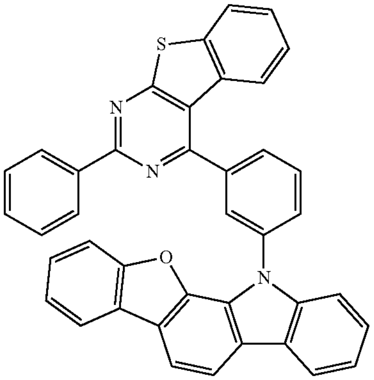
1241
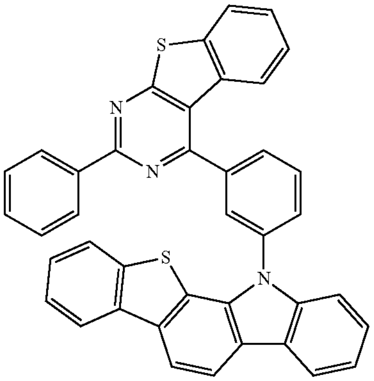

-continued
1242
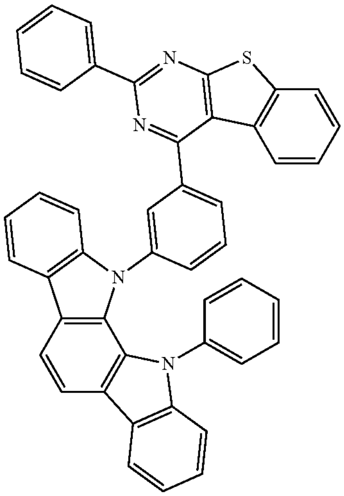
1243
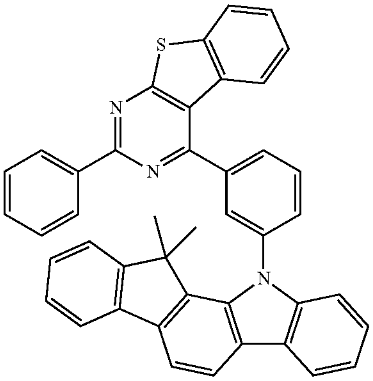
1244
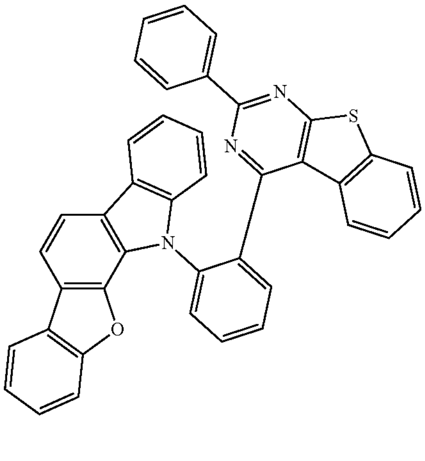
-continued
1245
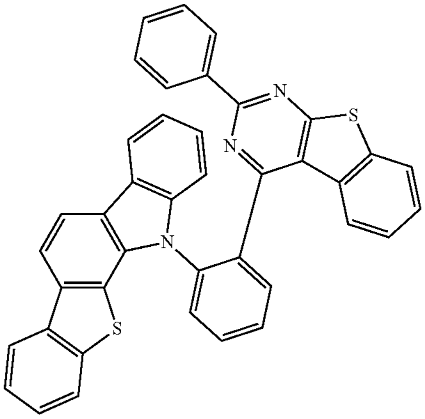
1246
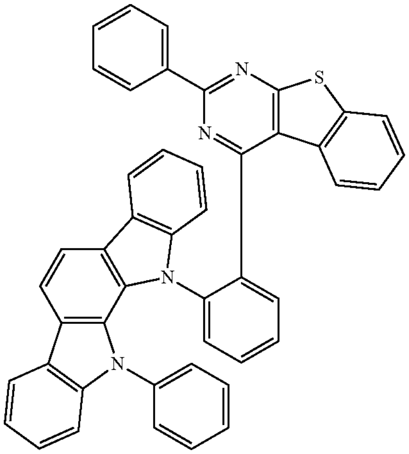
1247
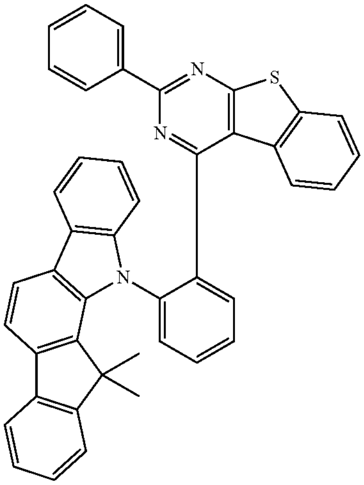

1248
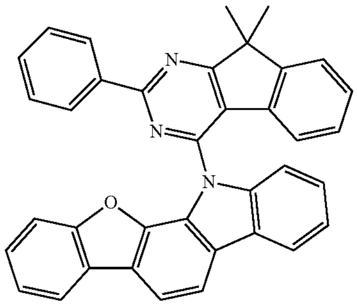
1249
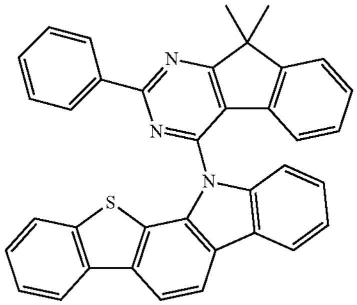
1250
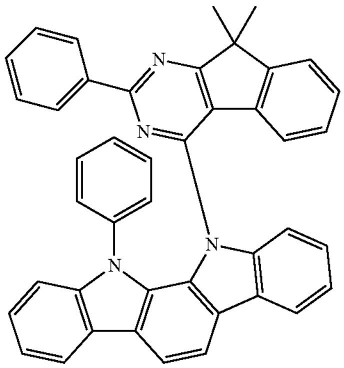
1251
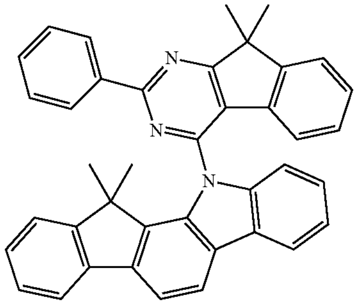
-continued
1252
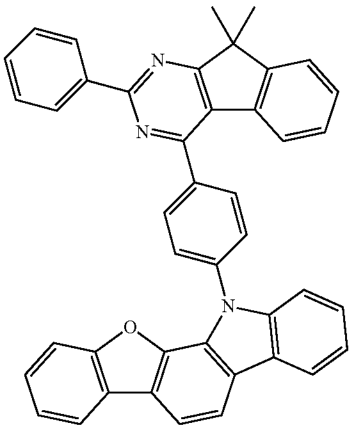
1253
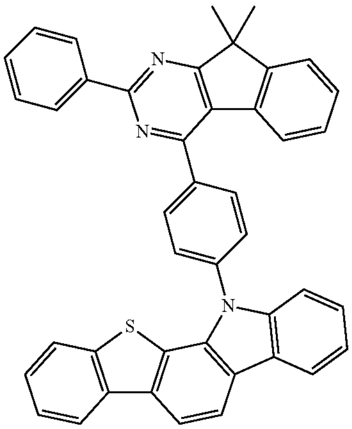
1254
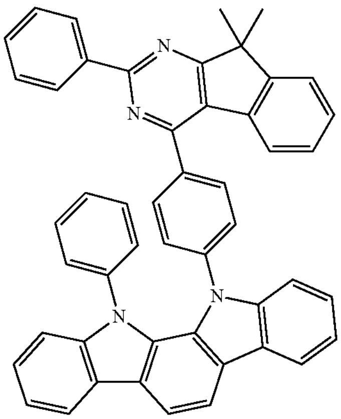

-continued
1255
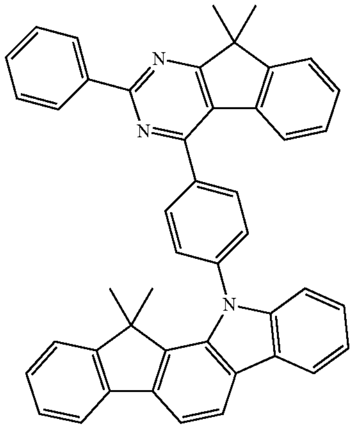
1256
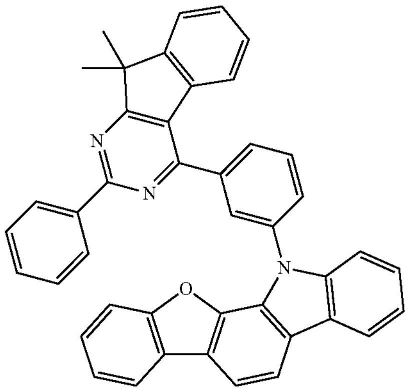
1257
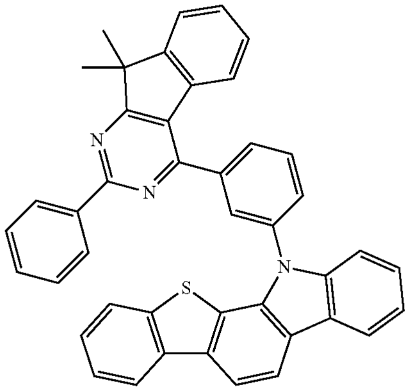
-continued
1258
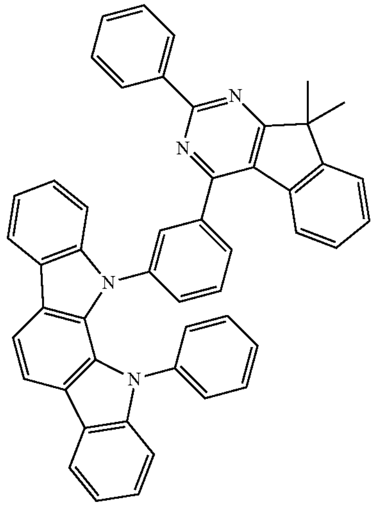
1259
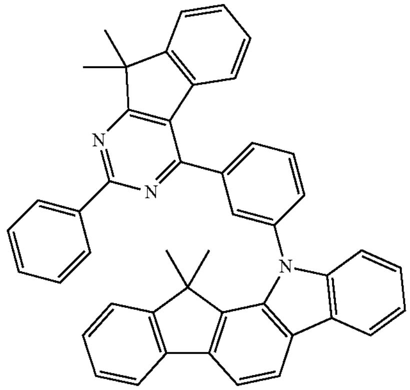
1260
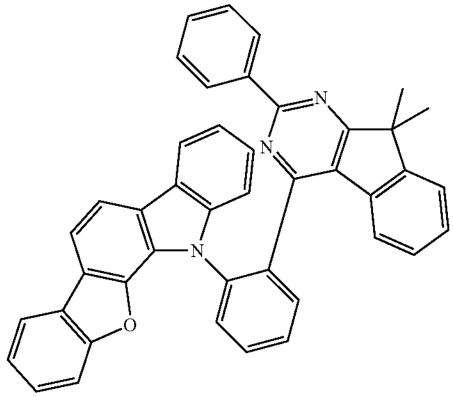

-continued
1261
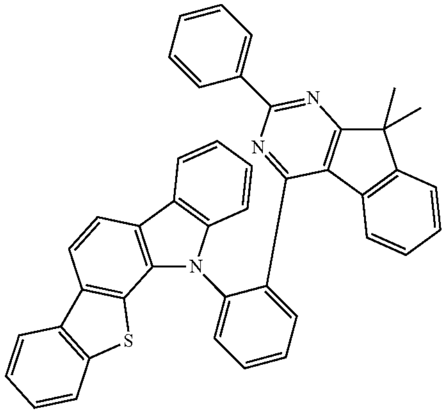
1262
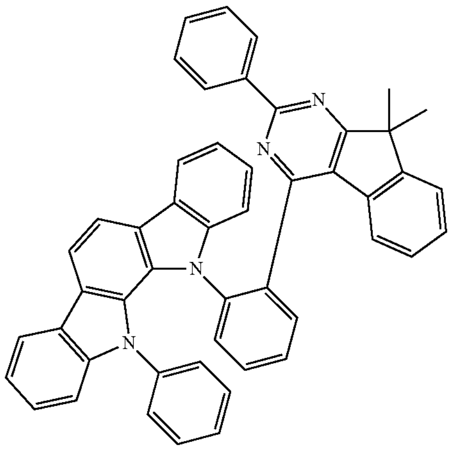
1263
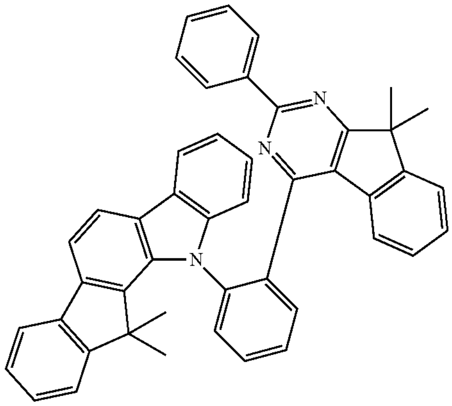
1264
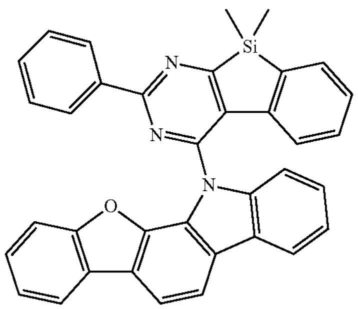
-continued
1265
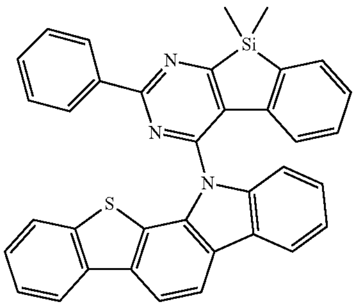
1266
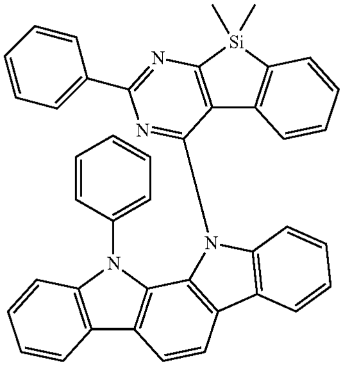
1267
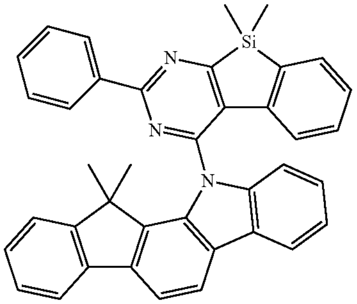
1268
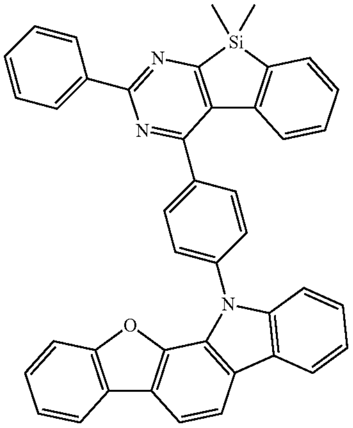

-continued
1269
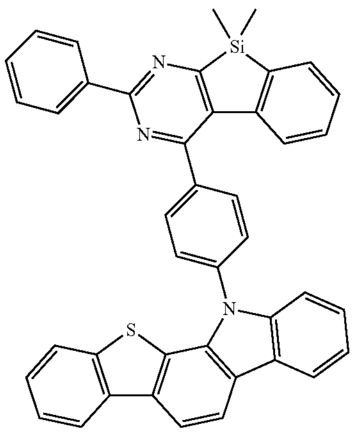
1270
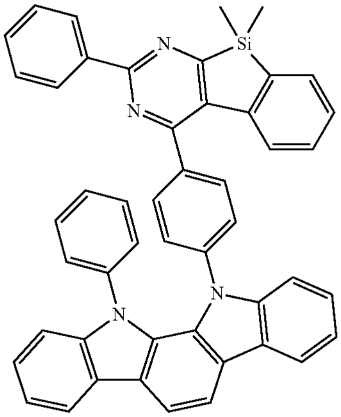
1271
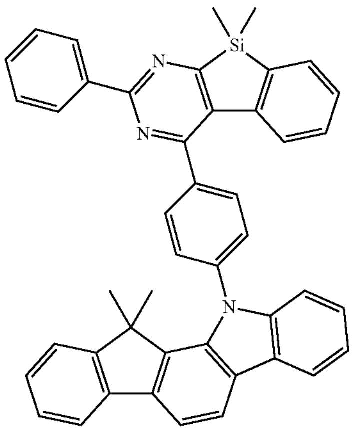
-continued
1272
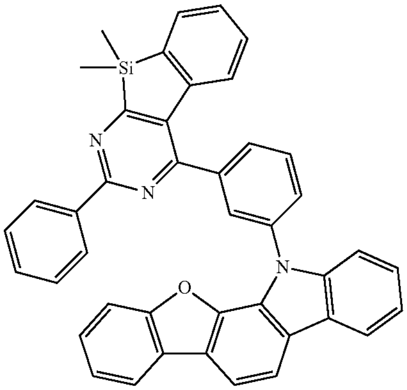
1273
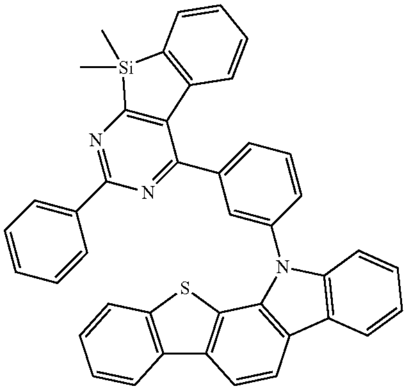
1274
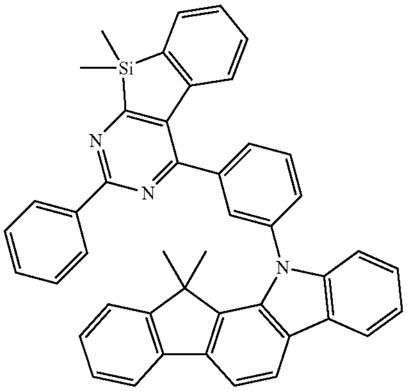

-continued
1275
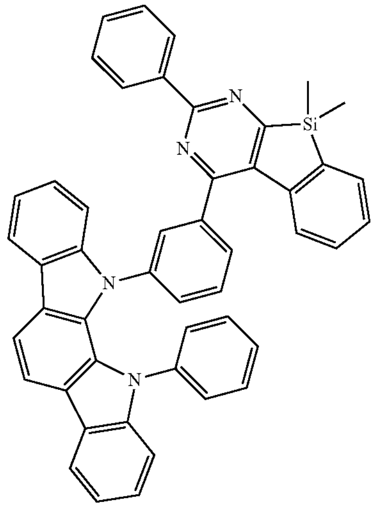
1276
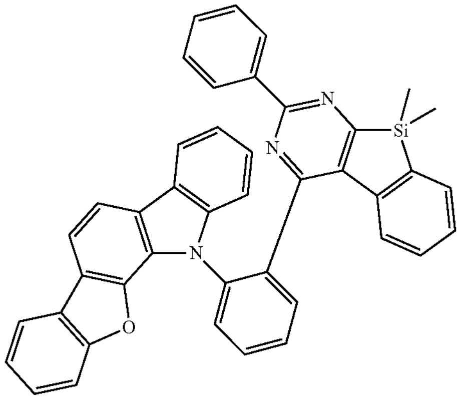
1277
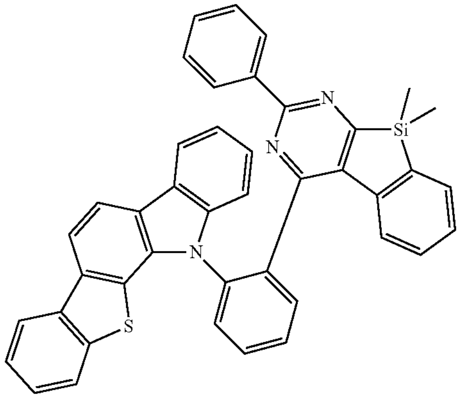
-continued
1278
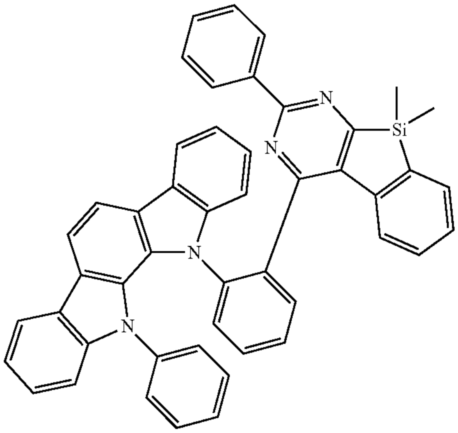
1279
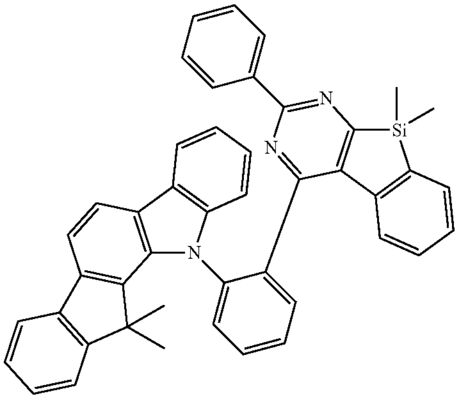
1280
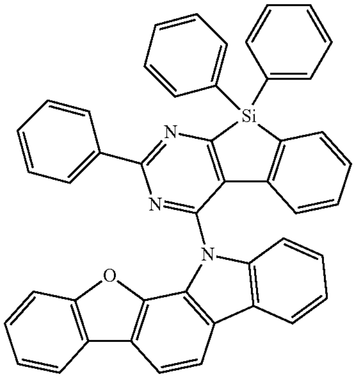
1281
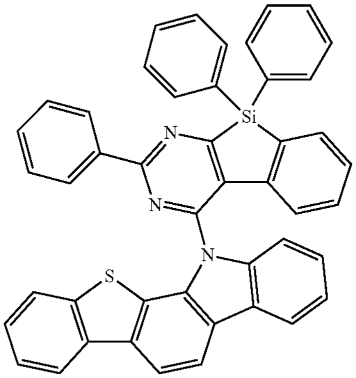

-continued
1282
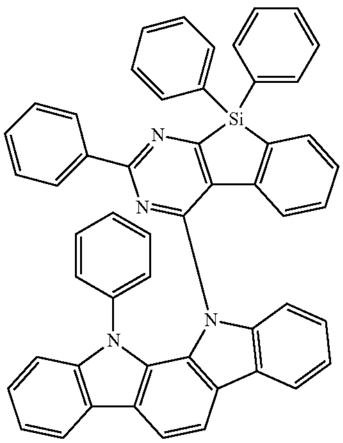
1283
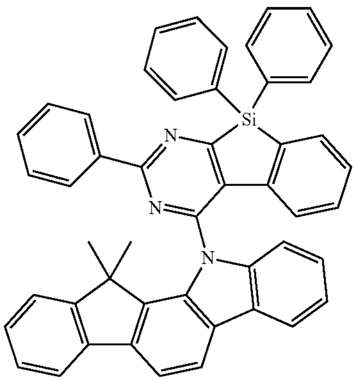
1284
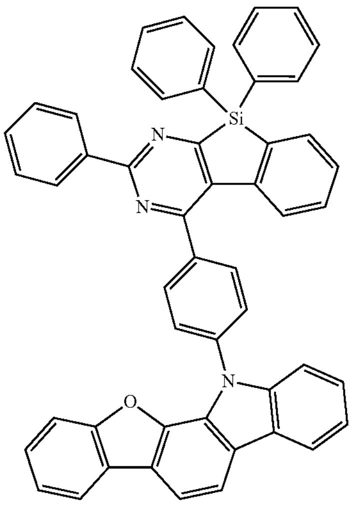
-continued
1285
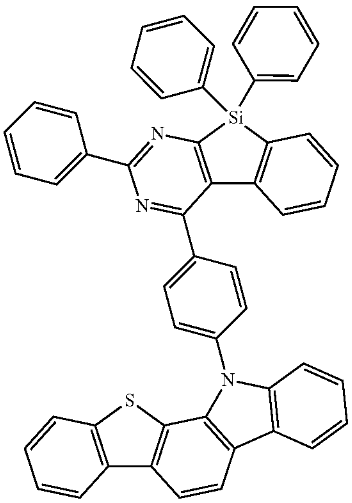
1286
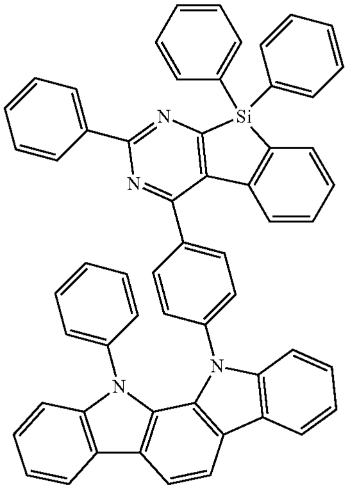
1287
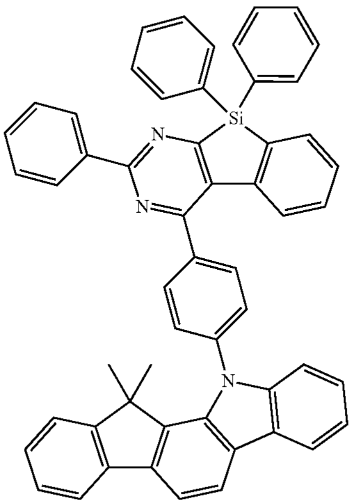

-continued
1288
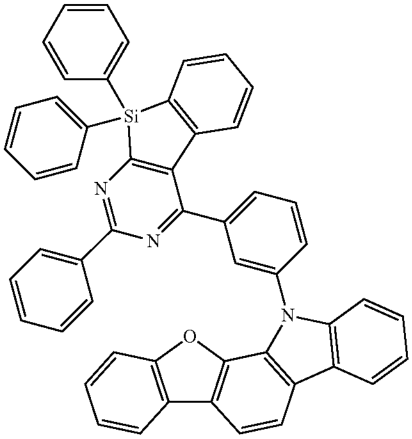
1289
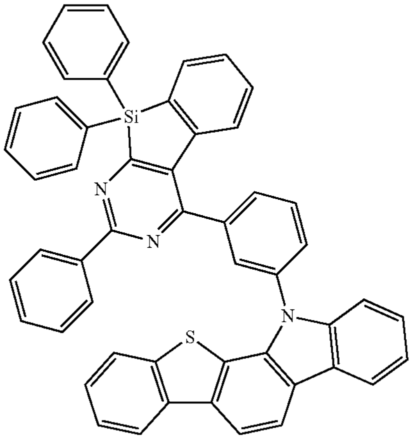
1290
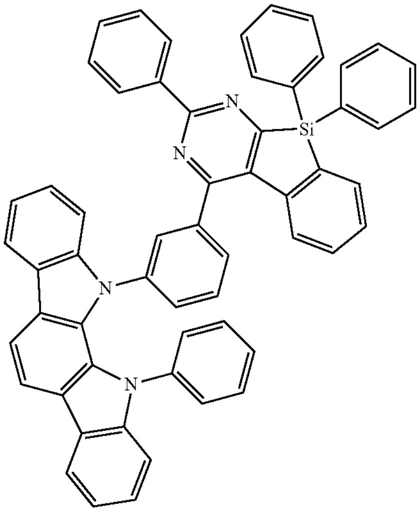
-continued
1291
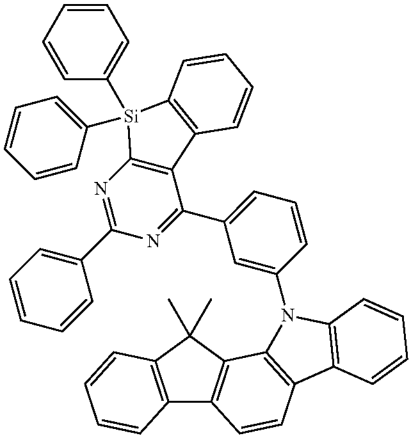
1292
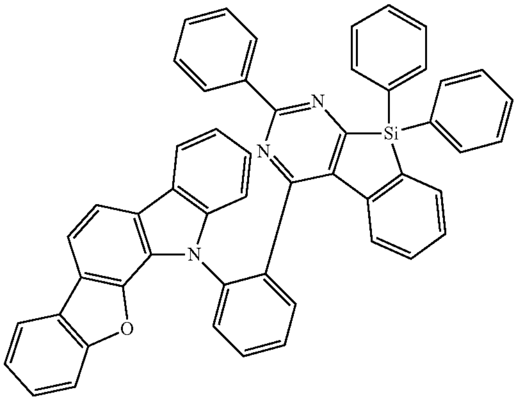
1293
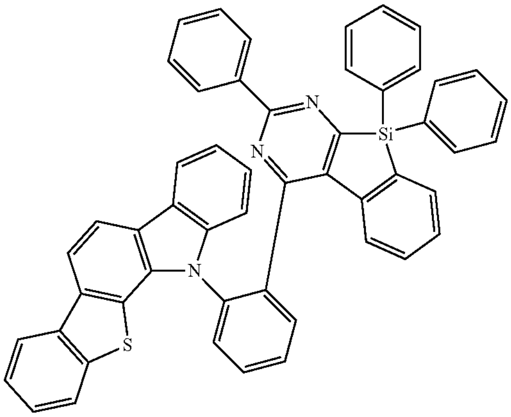

-continued
1294
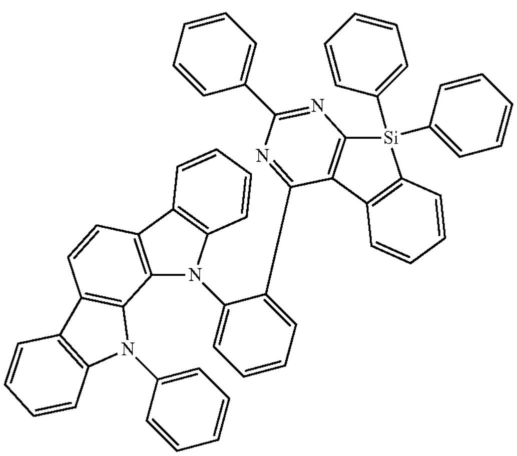
1295
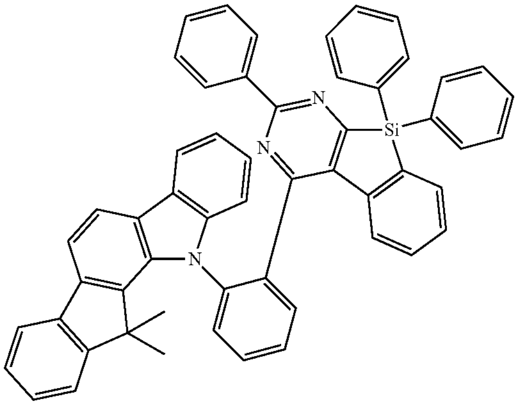
1296
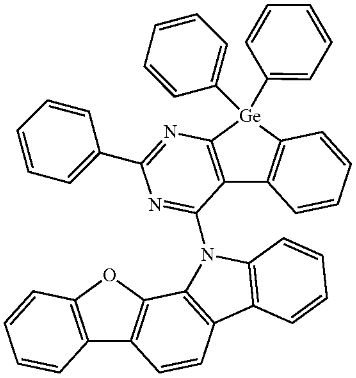
1297
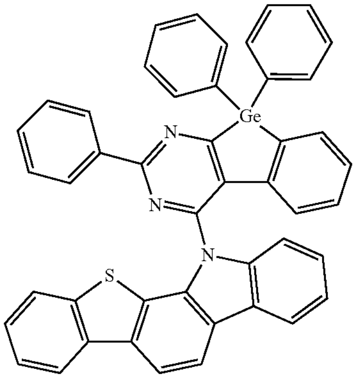
-continued
1298
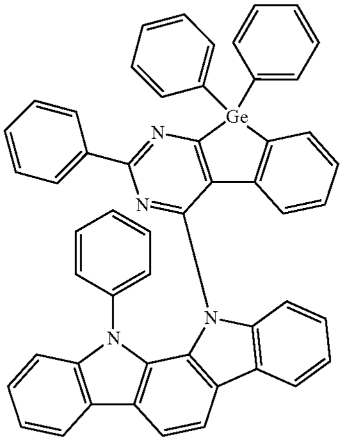
1299
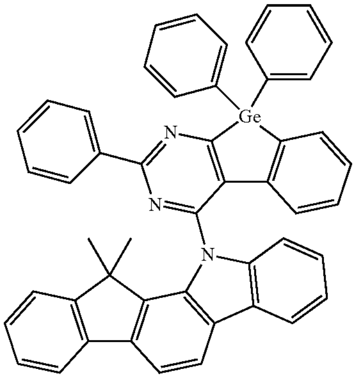
1300
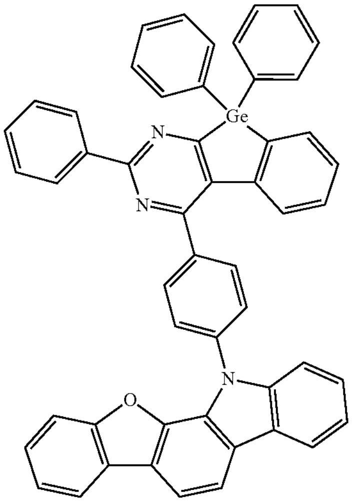

-continued
1301
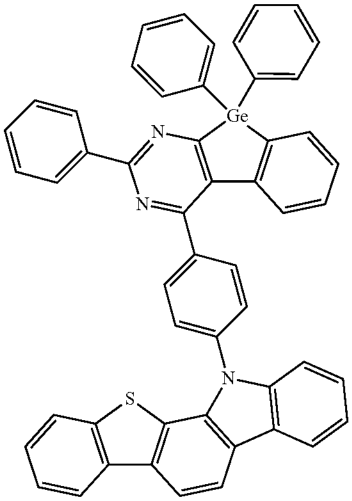
1302
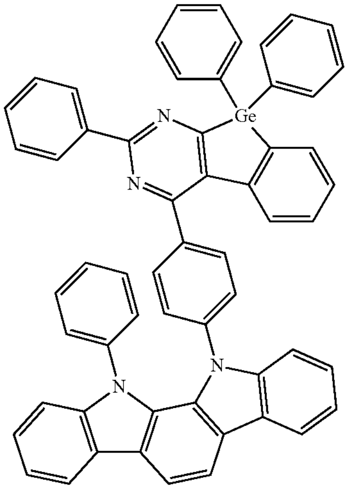
1303
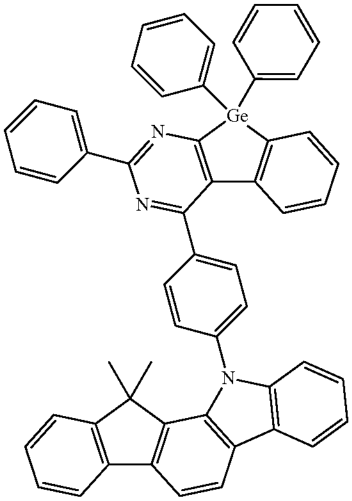
-continued
1304
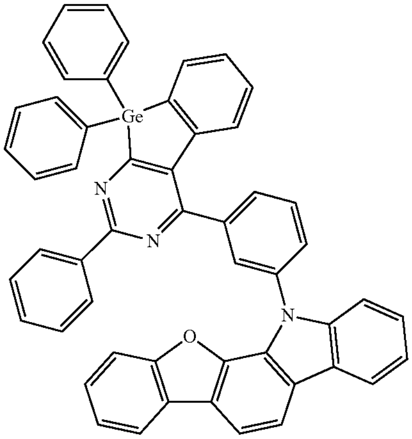
1305
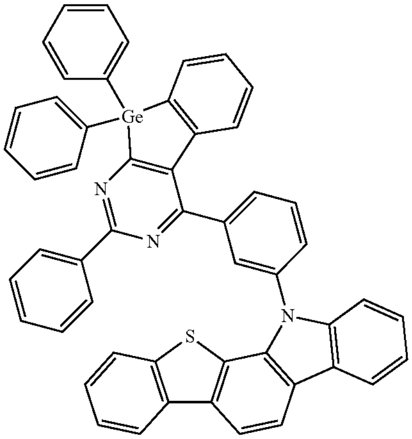
1306
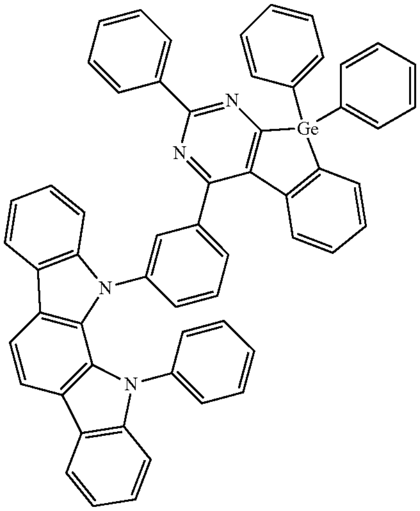

-continued
1307
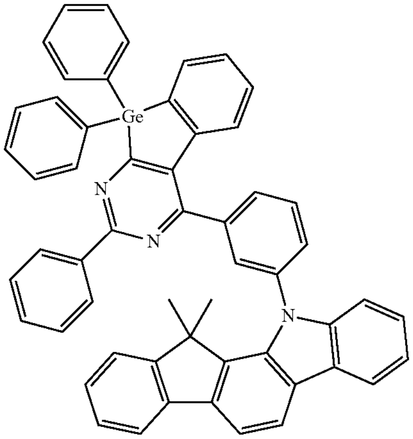
1308
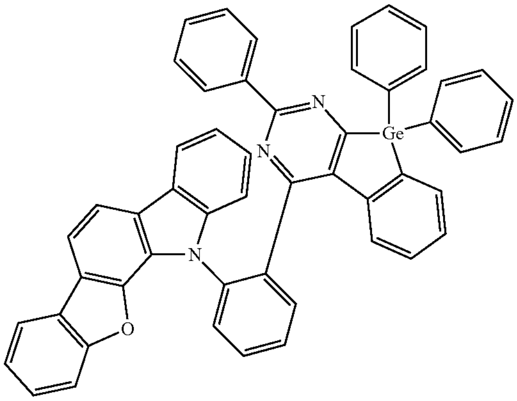
1309
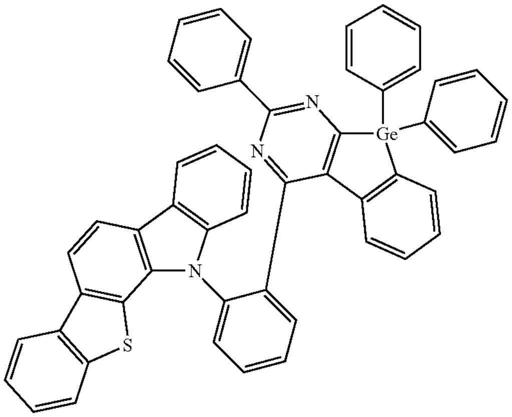
-continued
1310
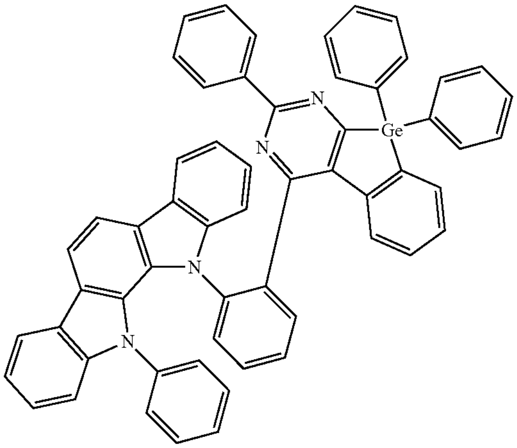
1311
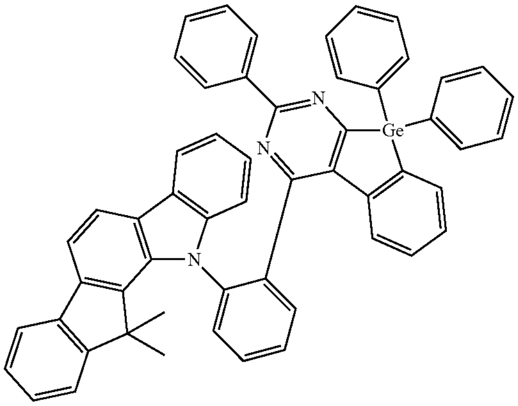
1312
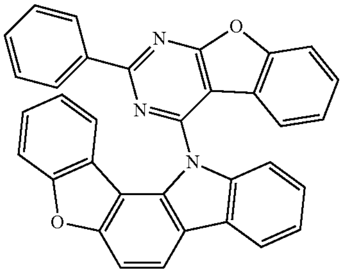
1313
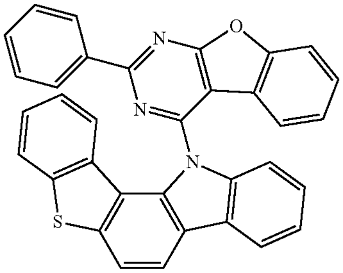

-continued
1314
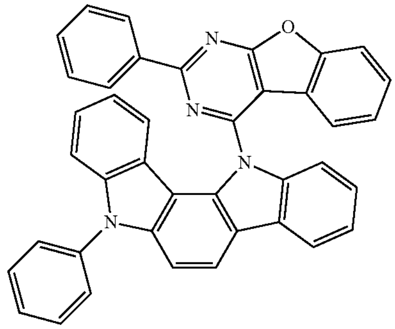
1315
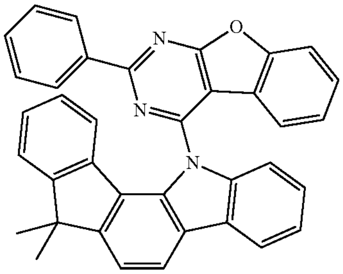
1316
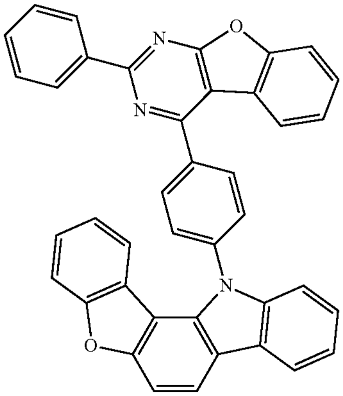
1317
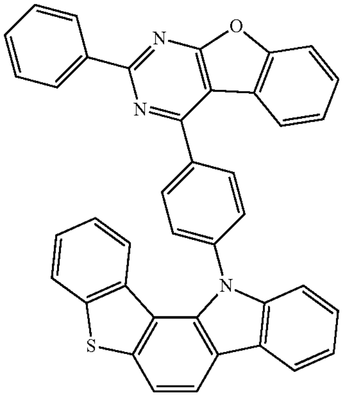
-continued
1318
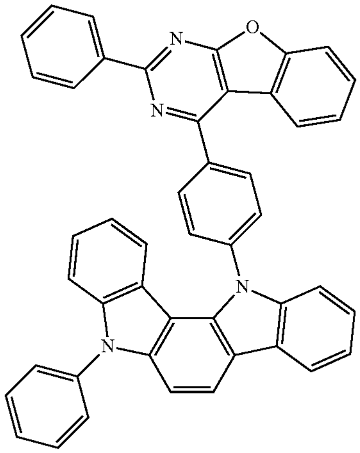
1319
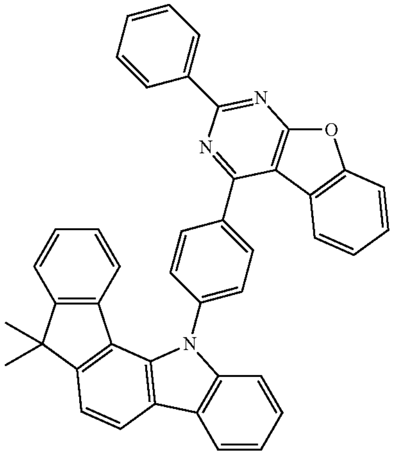
1320
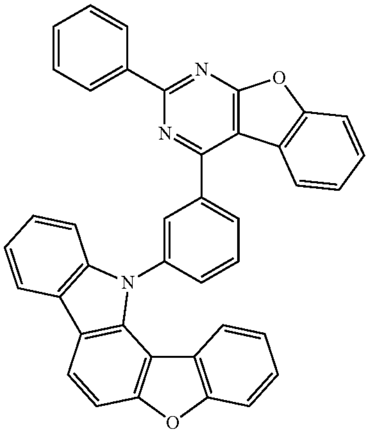

-continued
1321
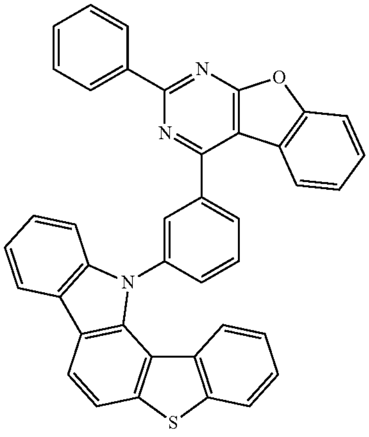
1322
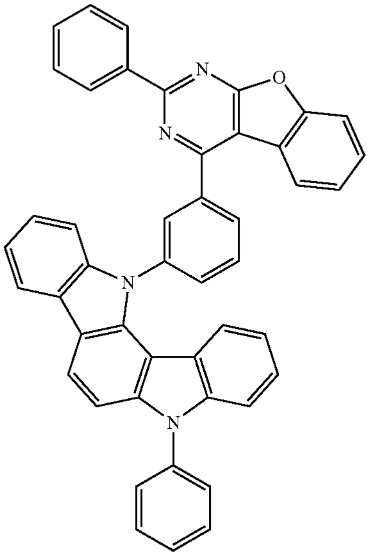
1323
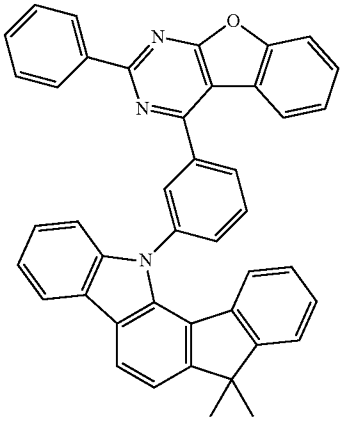
-continued
1324
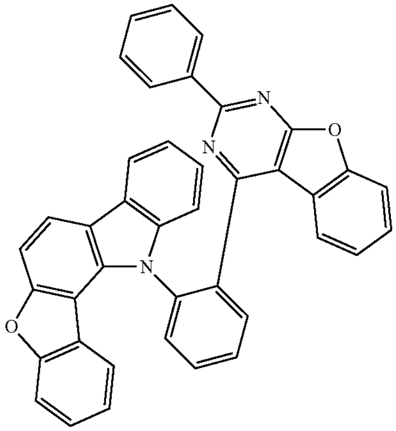
1325
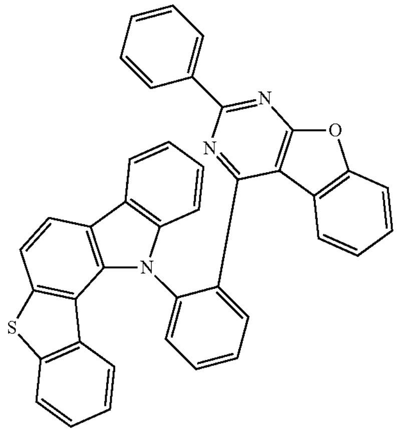
1326
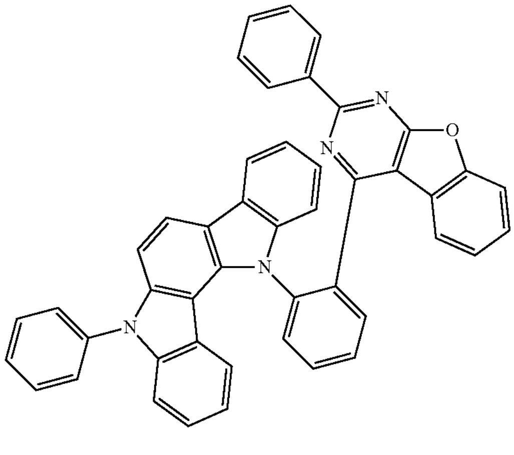

-continued
1327
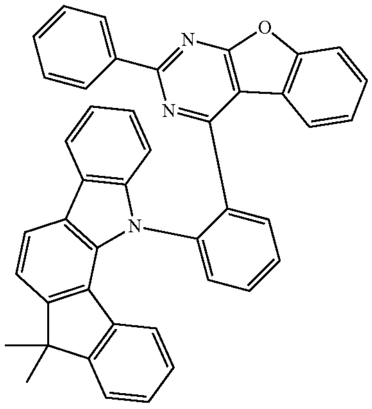
1328
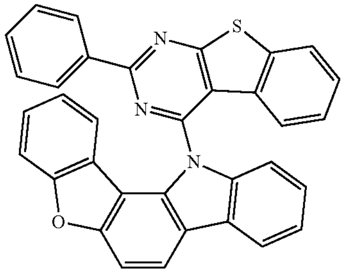
1329
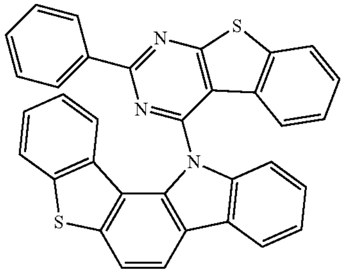
1330
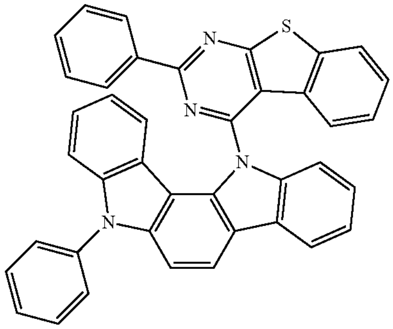
1331
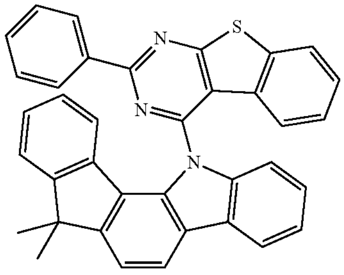
-continued
1332
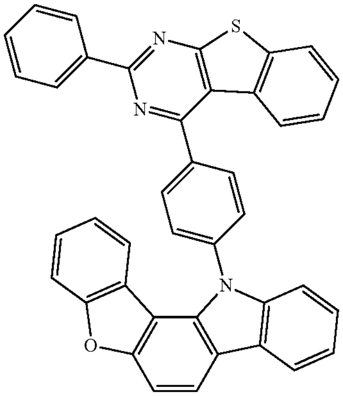
1333
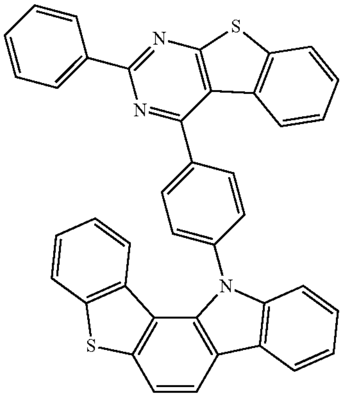
1334
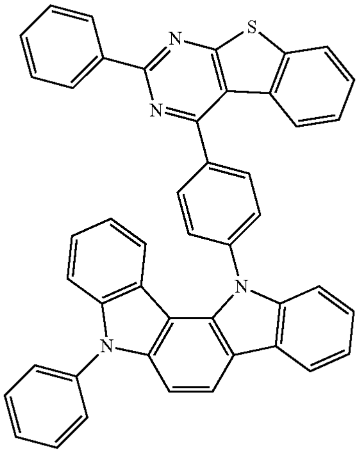

-continued
1335
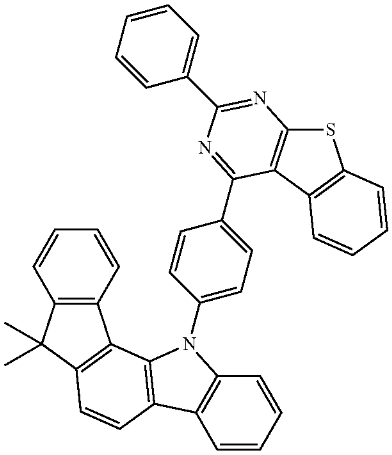
1336
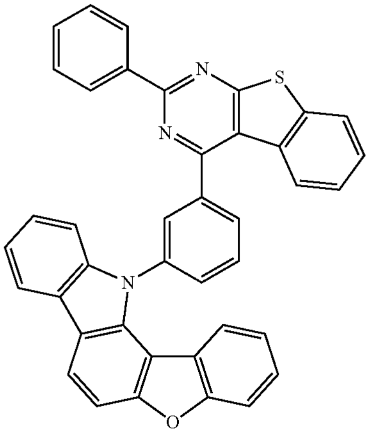
1337
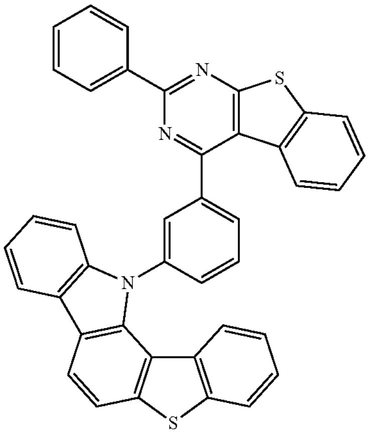
-continued
1338
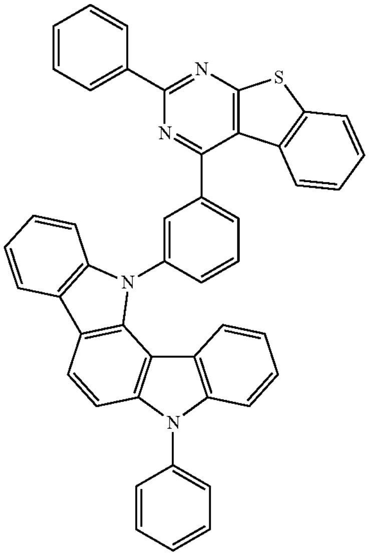
1339
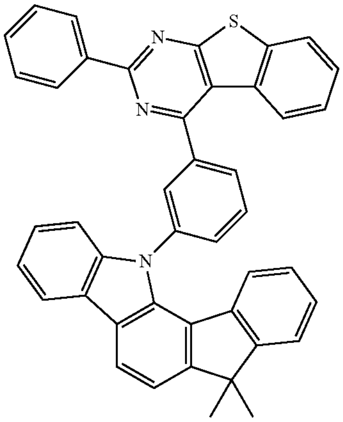
1340
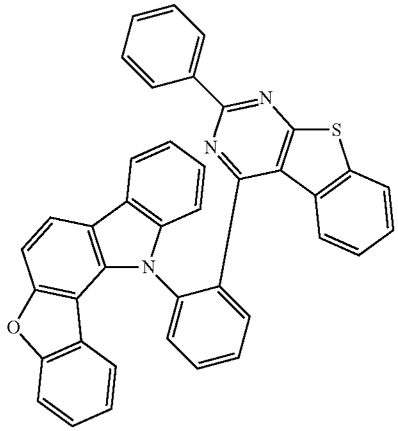

-continued
1341
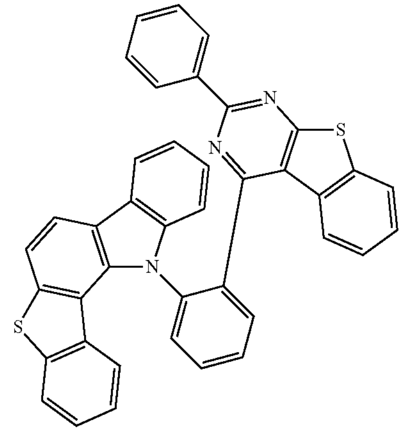
1342
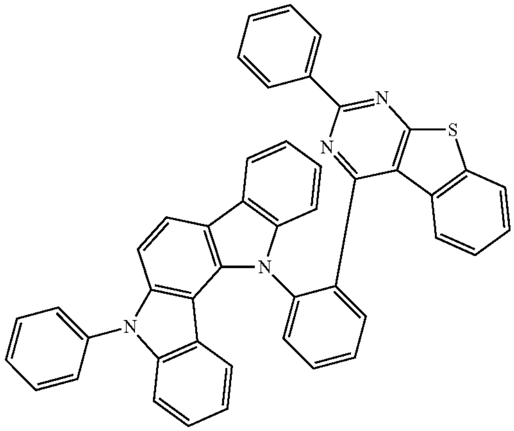
1343
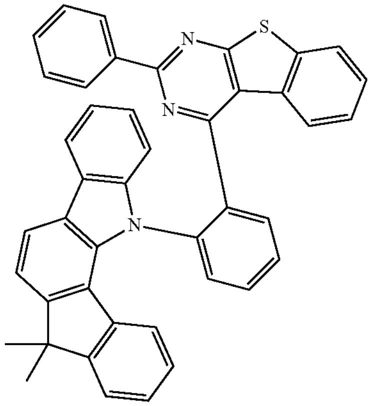
1344
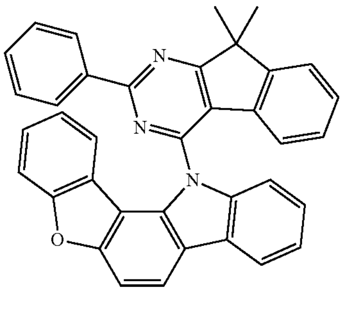
-continued
1345
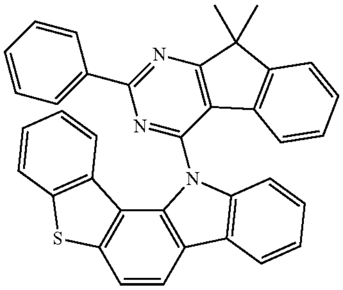
1346
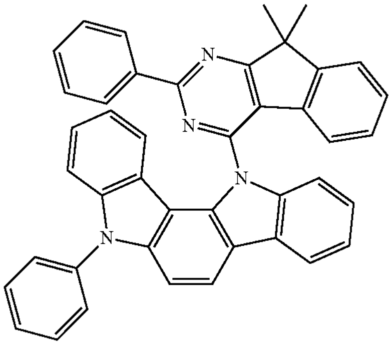
1347
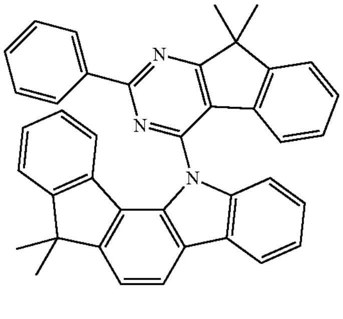
1348
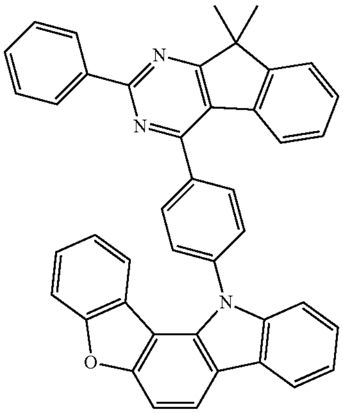

-continued
1349
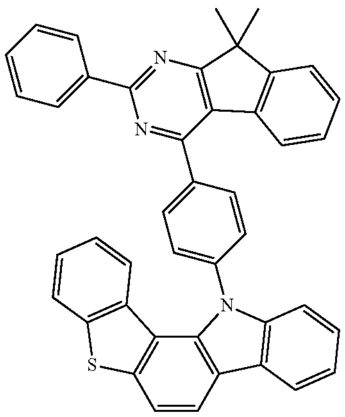
1350
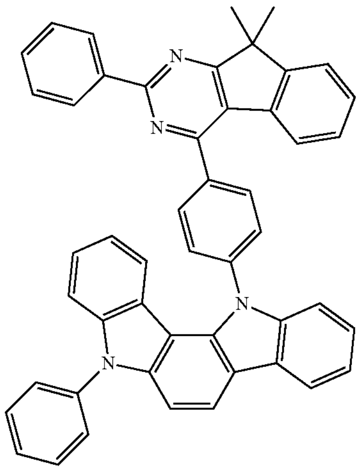
1351
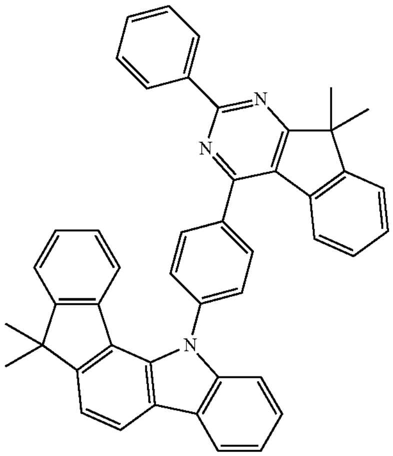
-continued
1352
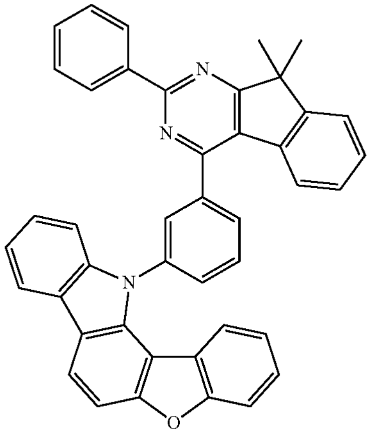
1353
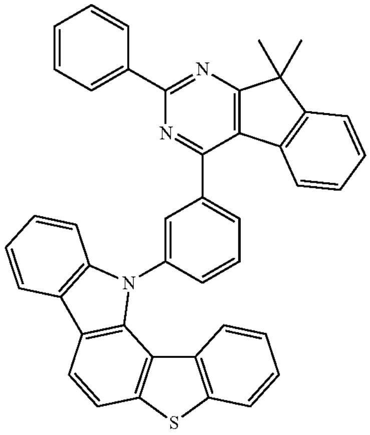
1354
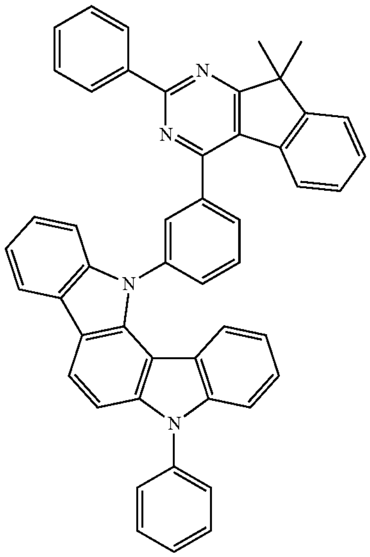

-continued
1355
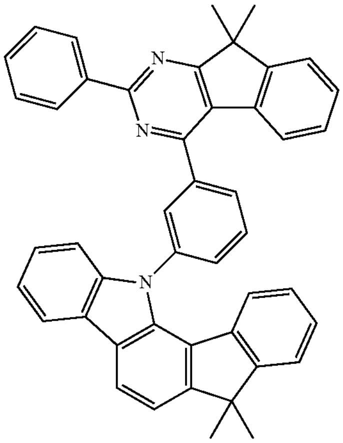
1356
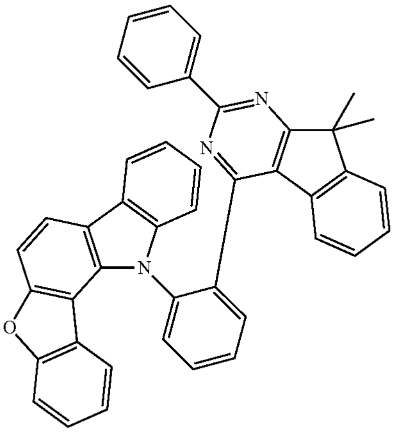
1357
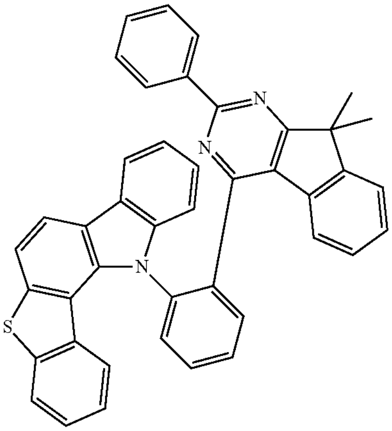
-continued
1358
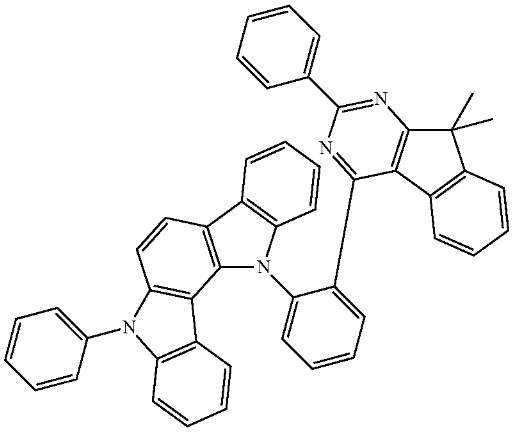
1359
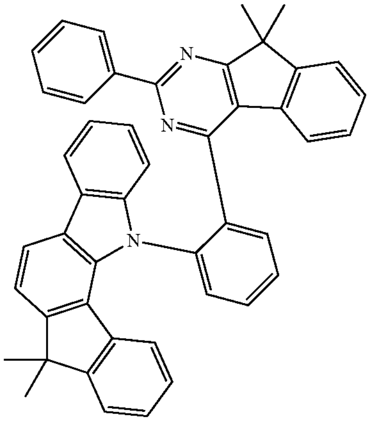
1360
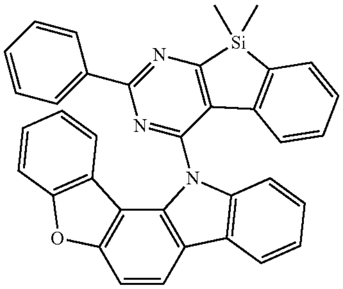
1361
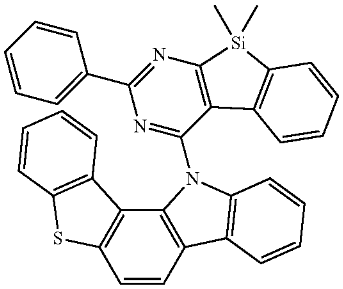

-continued
1362
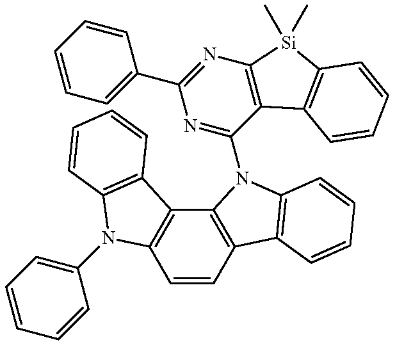
1363
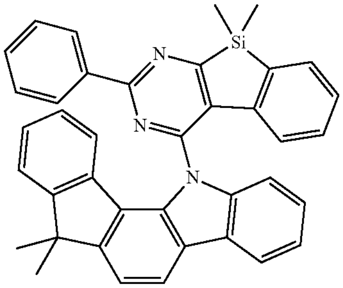
1364
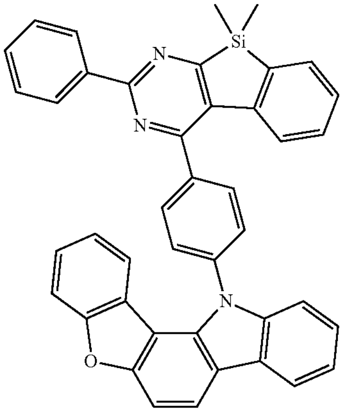
1365
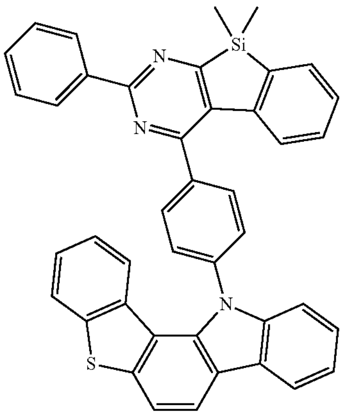
-continued
1366
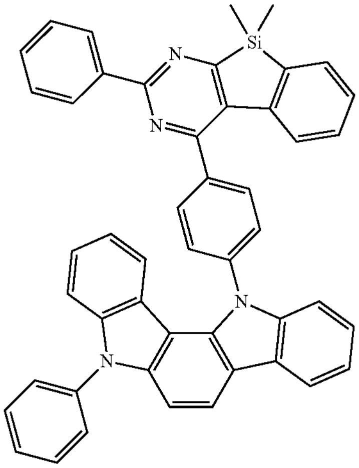
1367
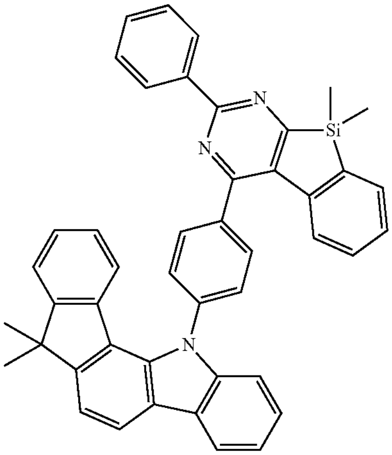
1368
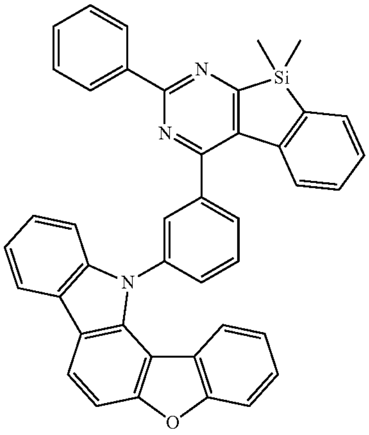

1369
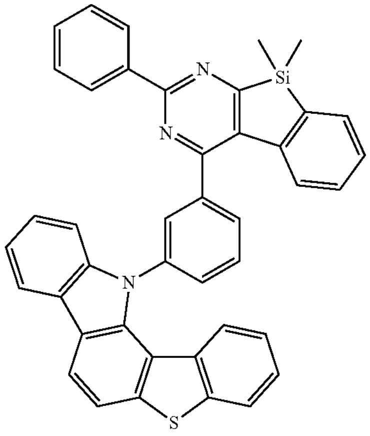
1370
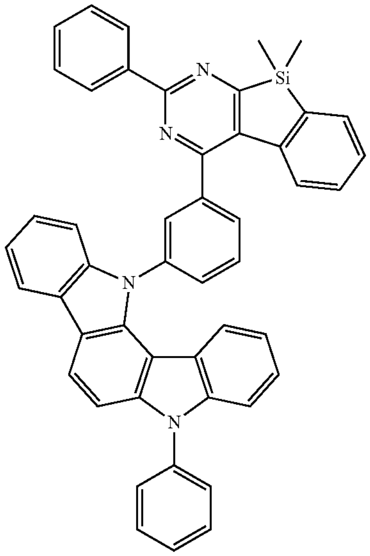
1371
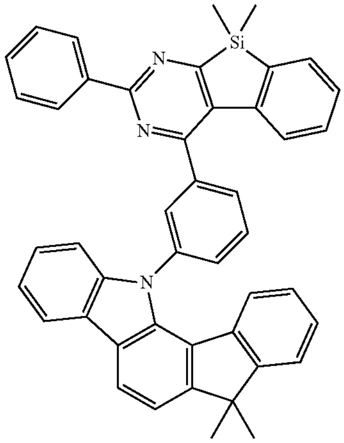
1372
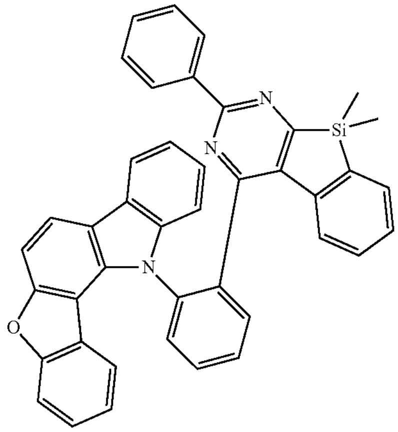
1373
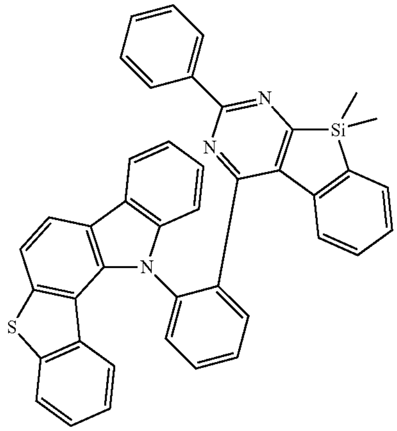
1374
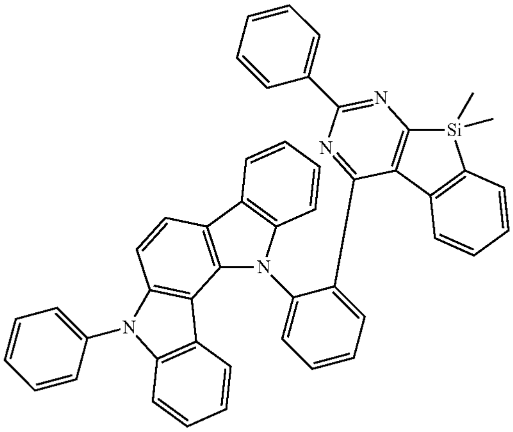

1375
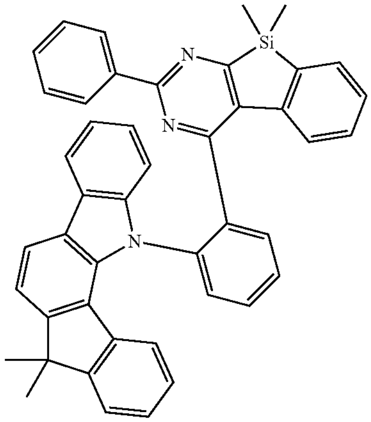
1376
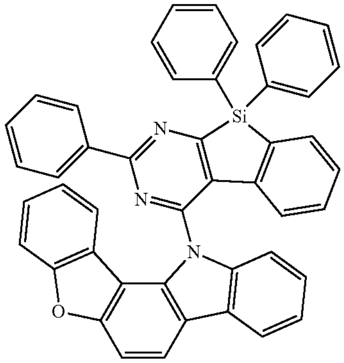
1377
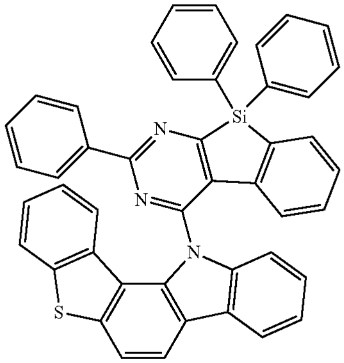
1378
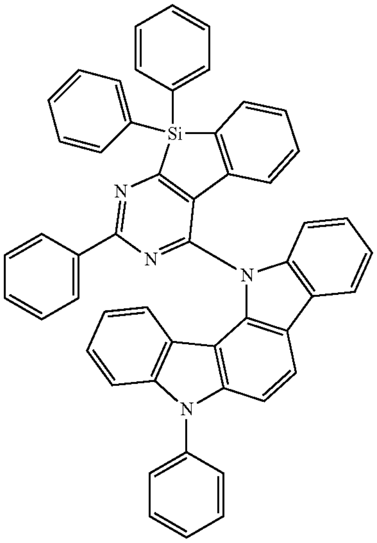
1379
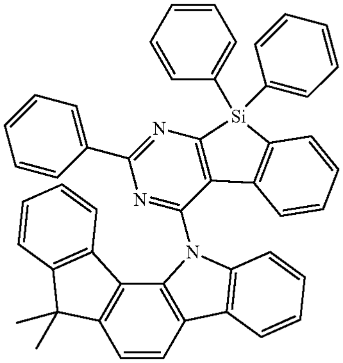
1380
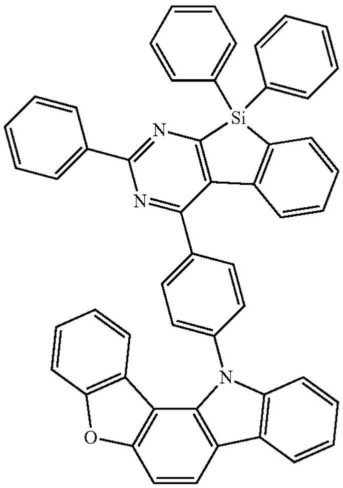

-continued
1381
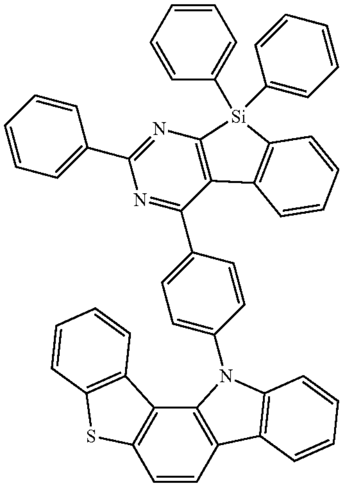
1382
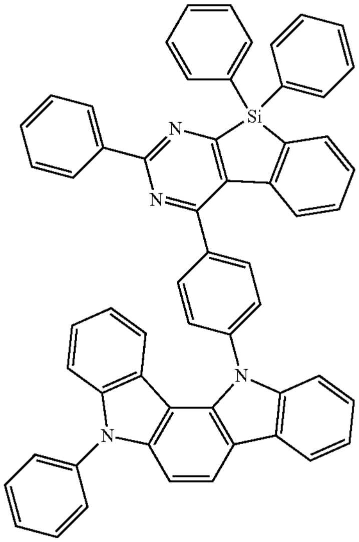
1383
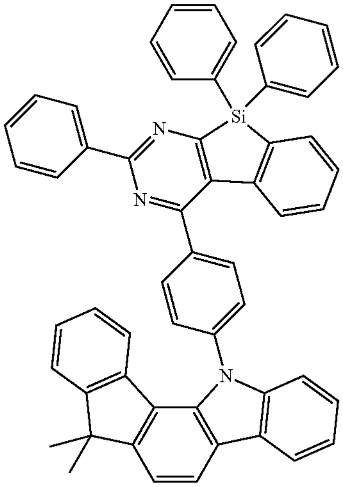
-continued
1384
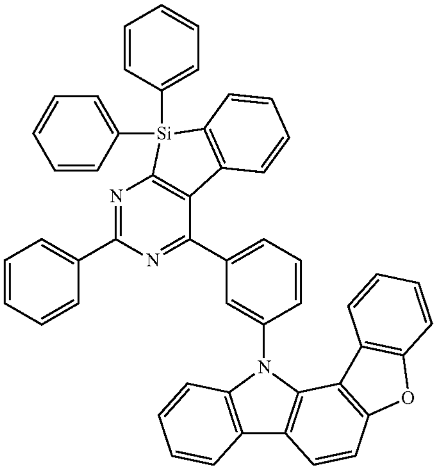
1385
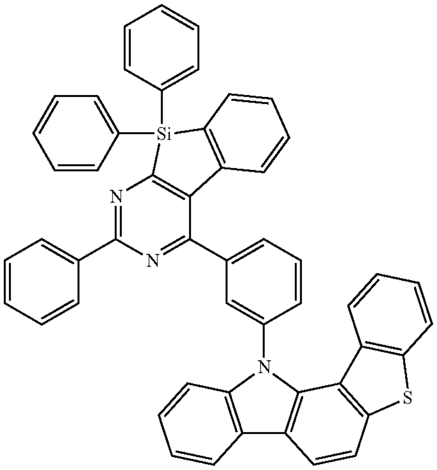
1386
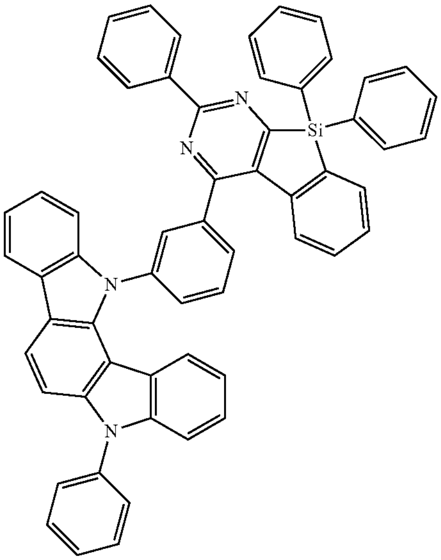

-continued
1387
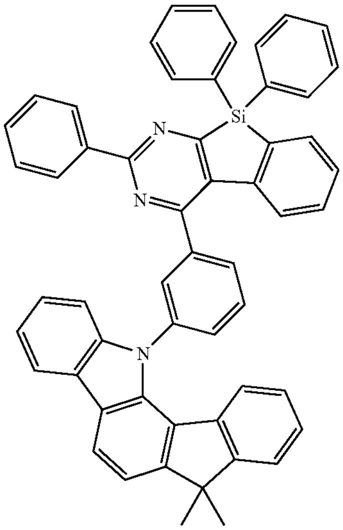
1388
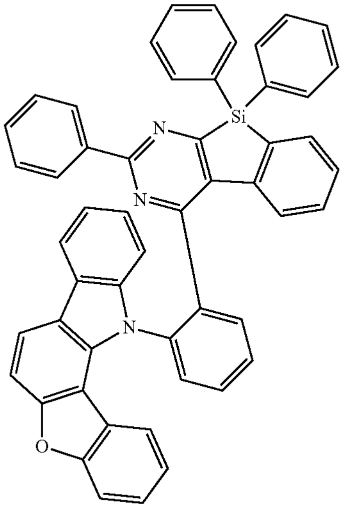
1389
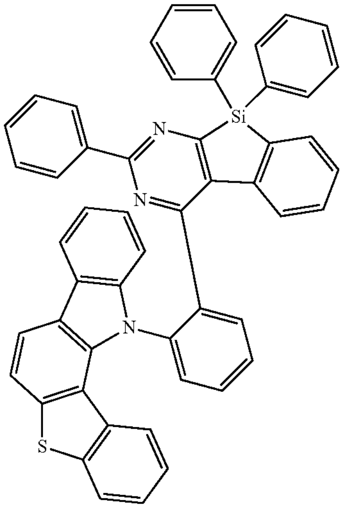
-continued
1390
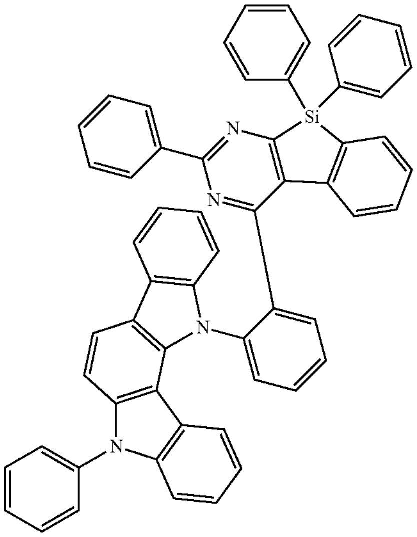
1391
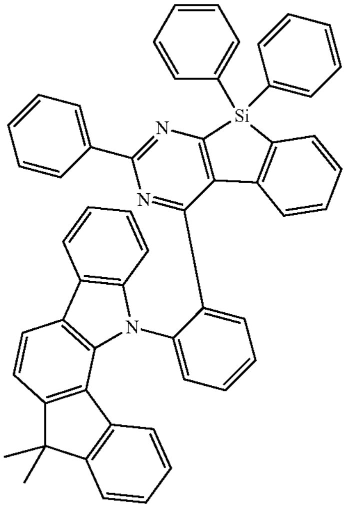
1392
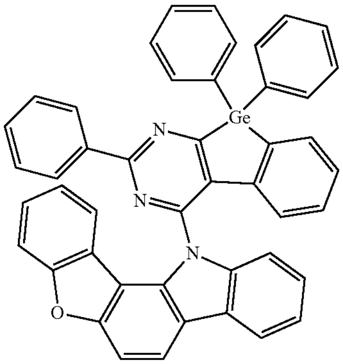

-continued
1393
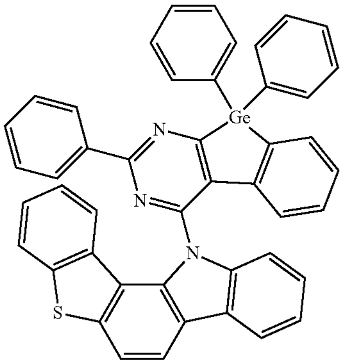
1394
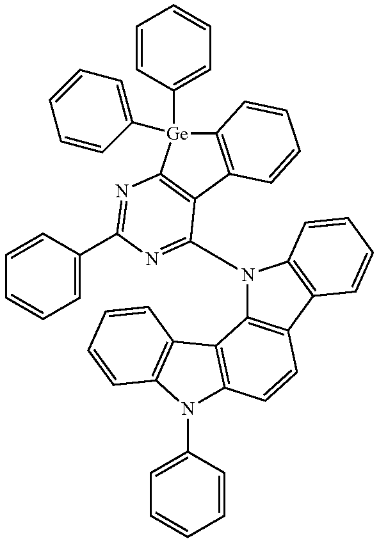
1395
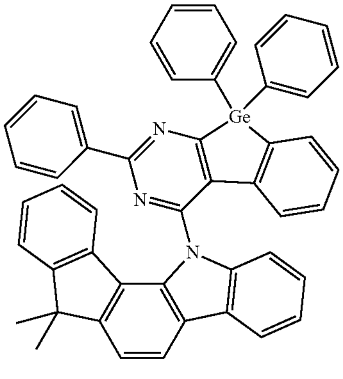
-continued
1396
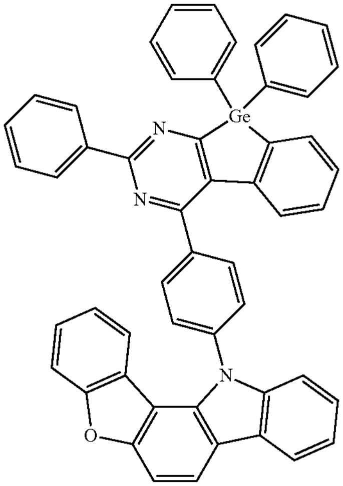
1397
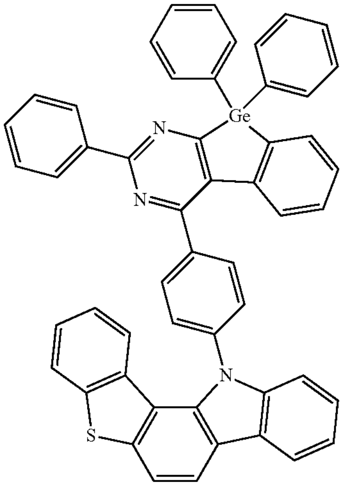
1398
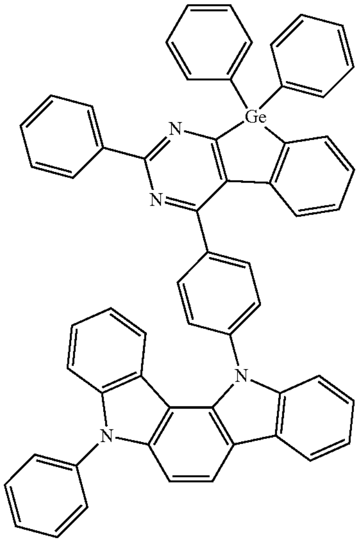

-continued
1399
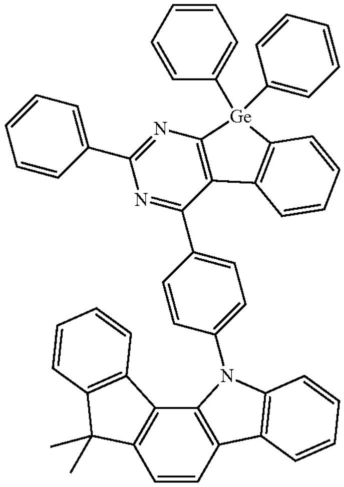
1400
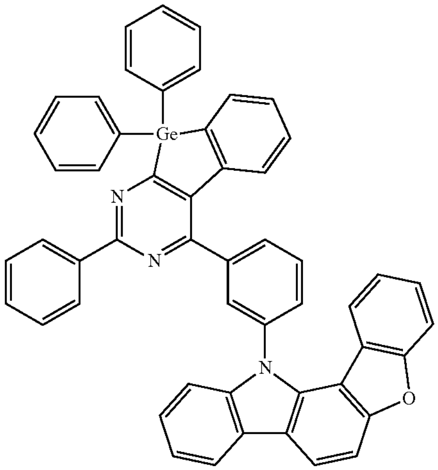
1401
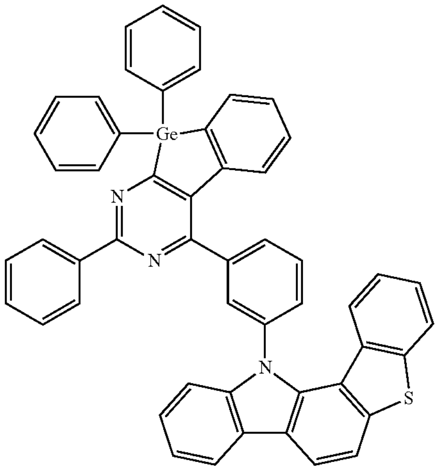
-continued
1402
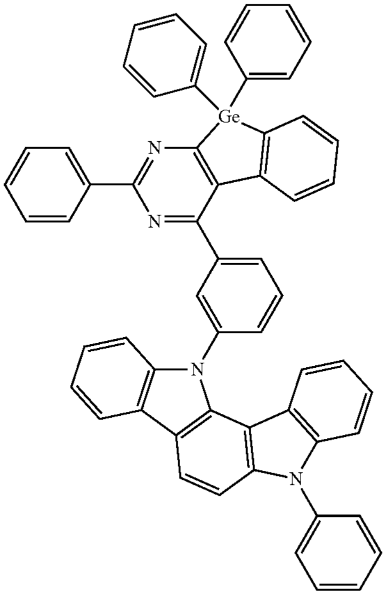
1403
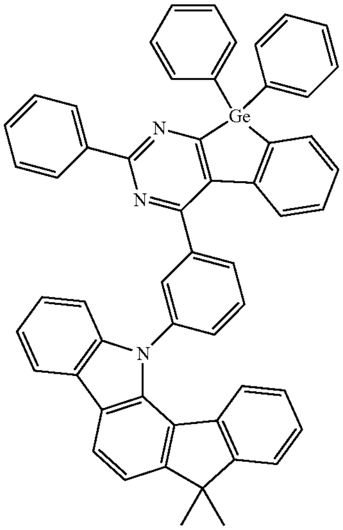
1404
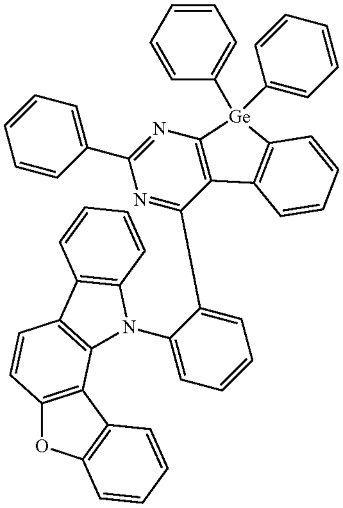

-continued
1405
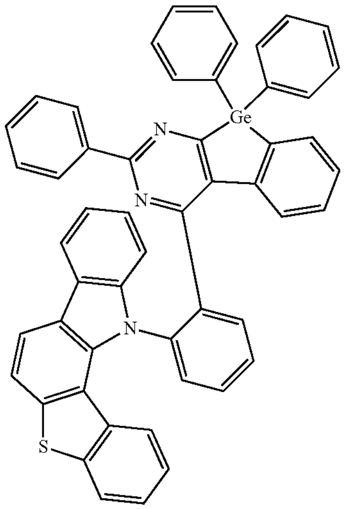
1406
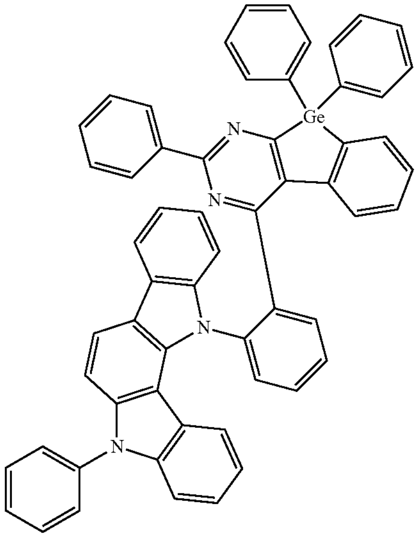
1407
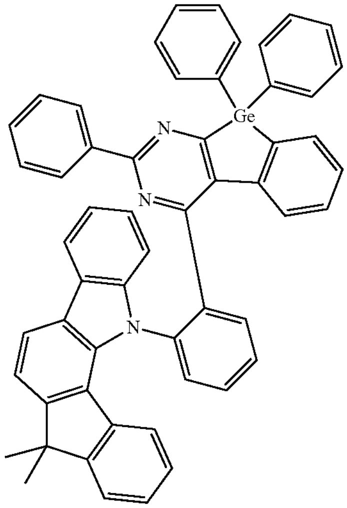
-continued
1408
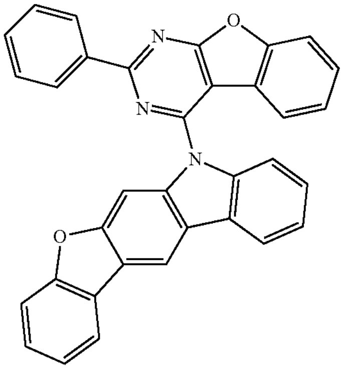
1409
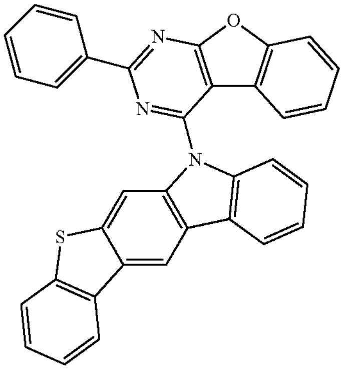
1410
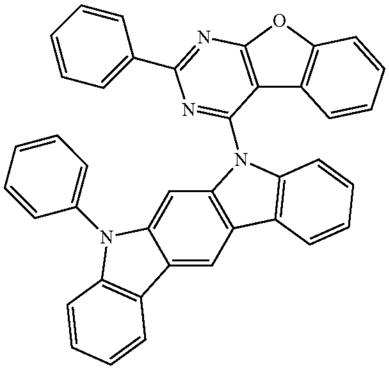
1411
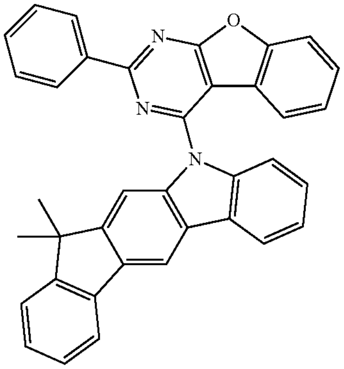

-continued
1412
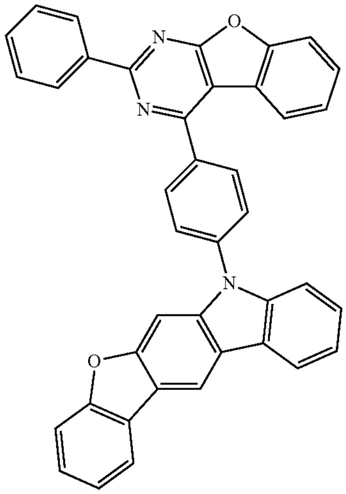
1413
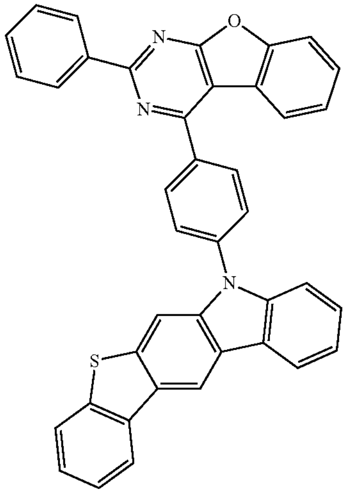
1414
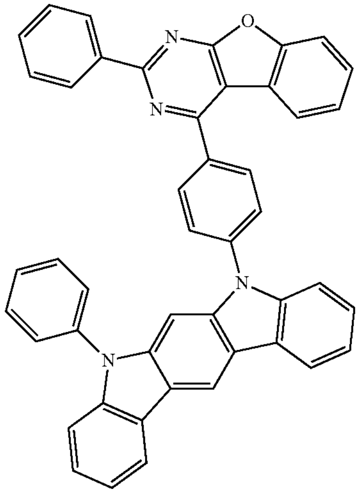
-continued
1415
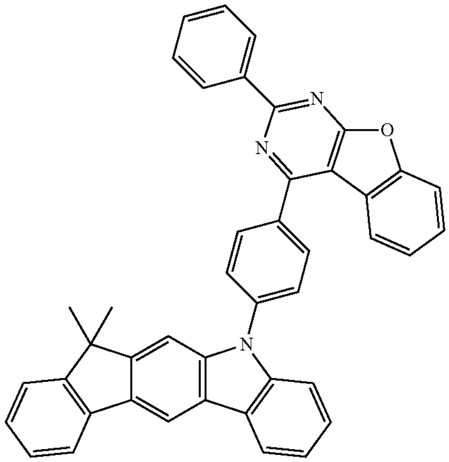
1416
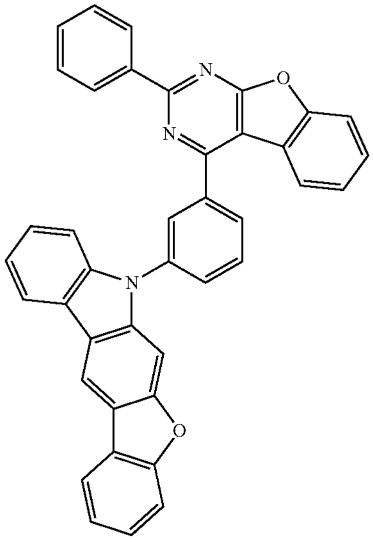
1417
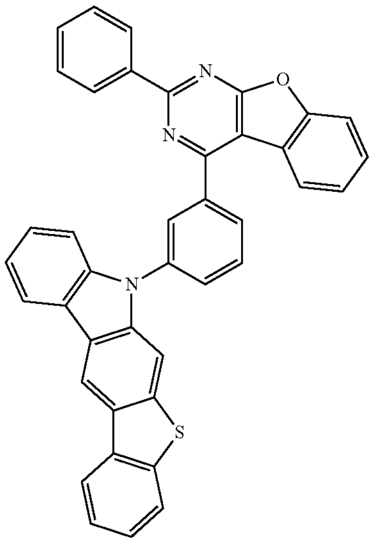

-continued
1418
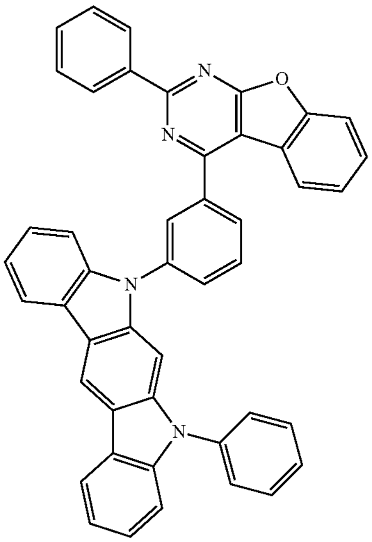
1419
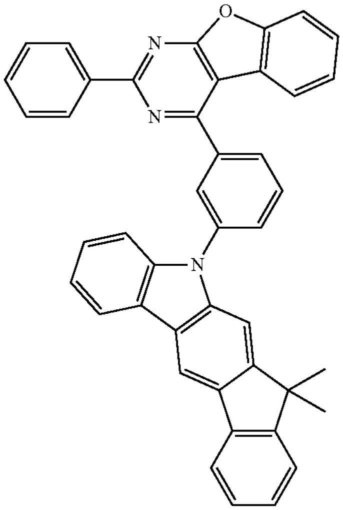
1420
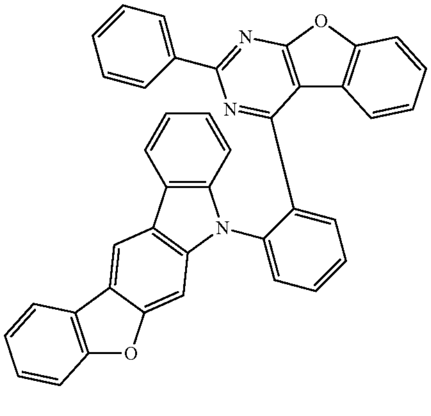
-continued
1421
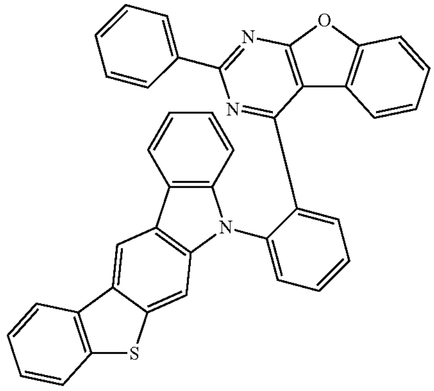
1422
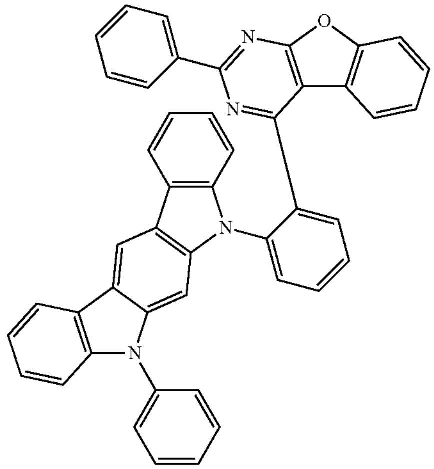
1423
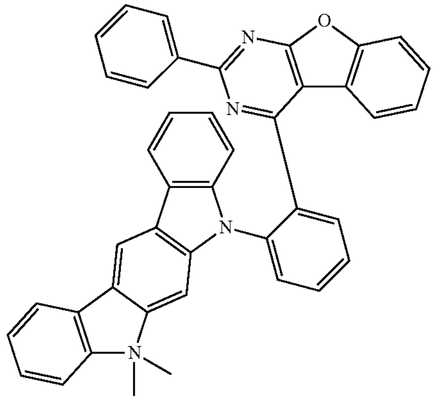
2391
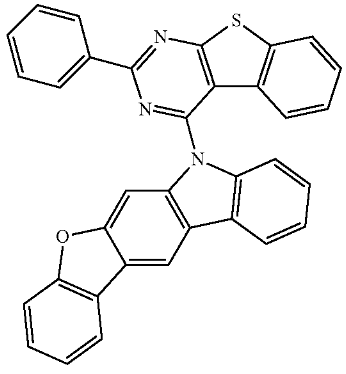

-continued
1424
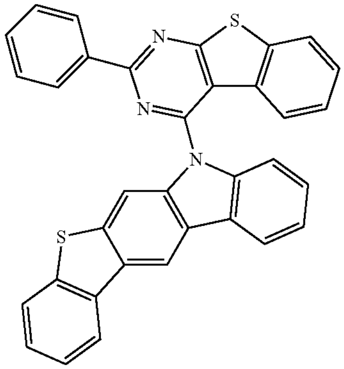
1425
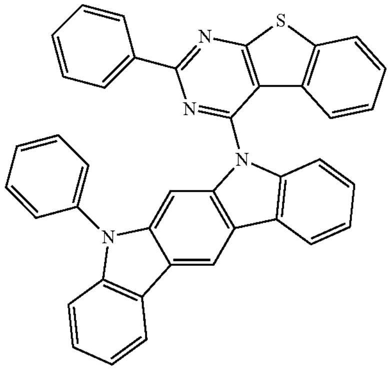
1426
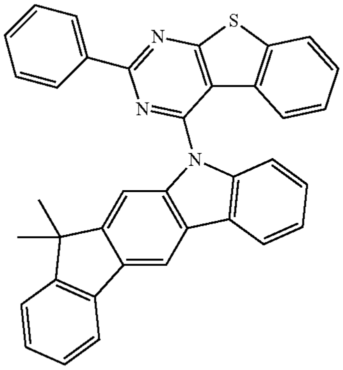
1427
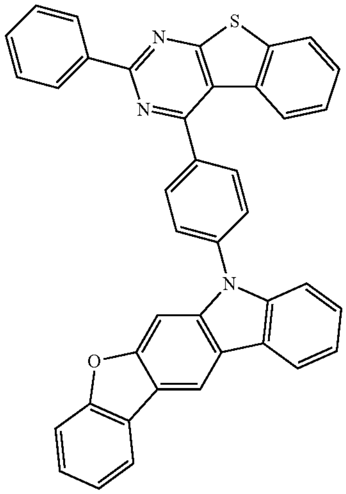
-continued
1428
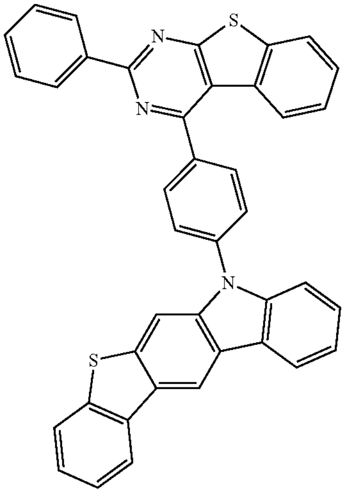
1429
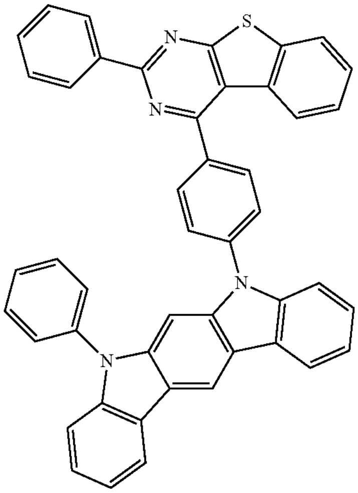
1430
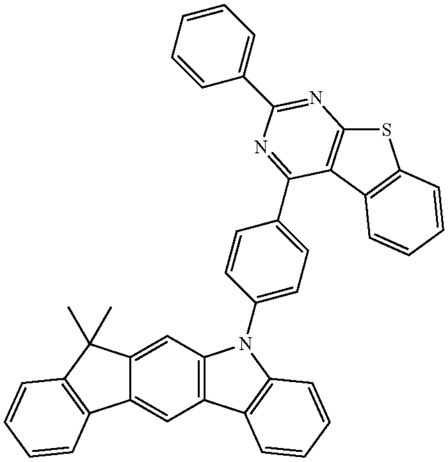

-continued
1431
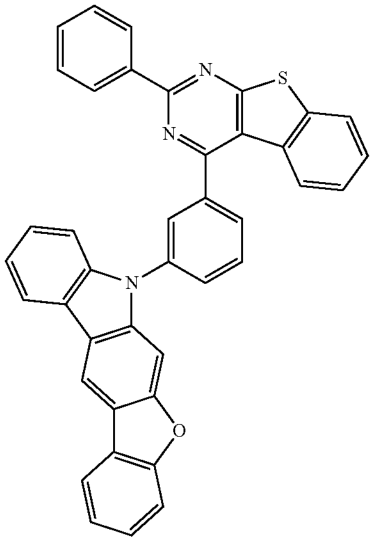
1432
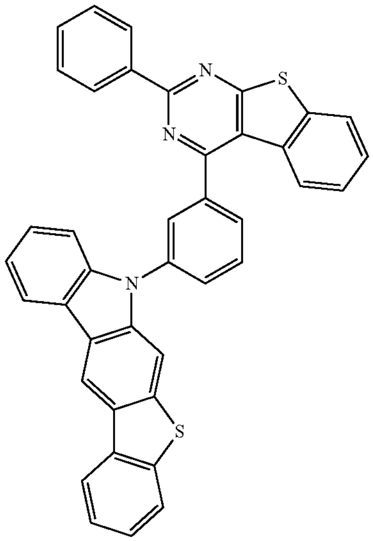
1433
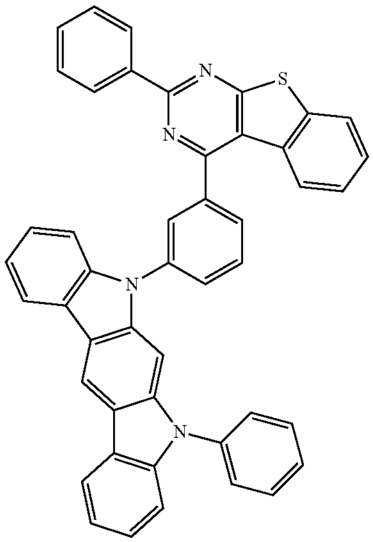
-continued
1434
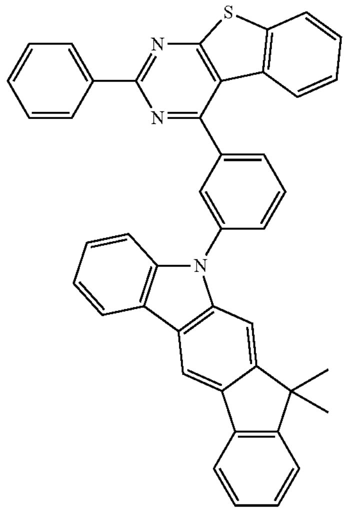
1435
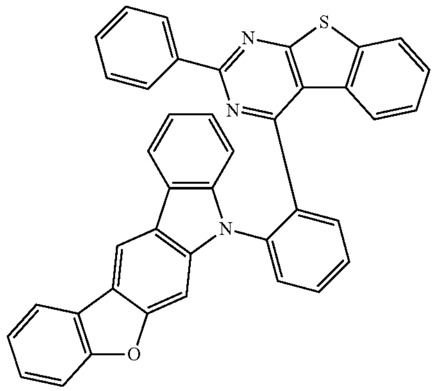
1436
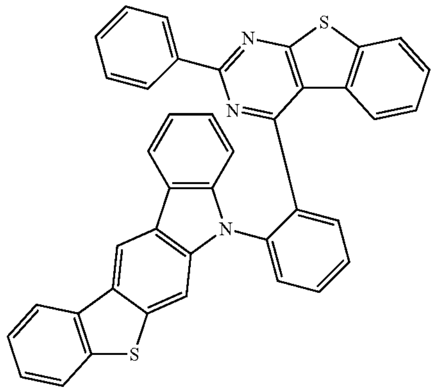

-continued
1437
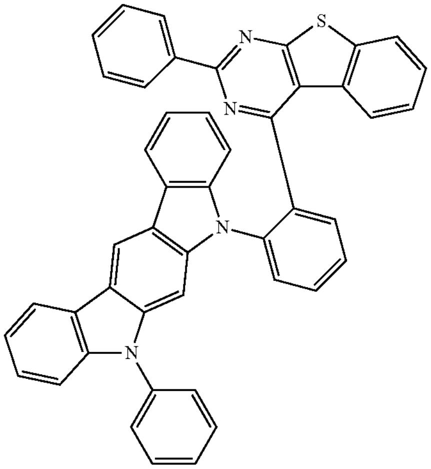
1438
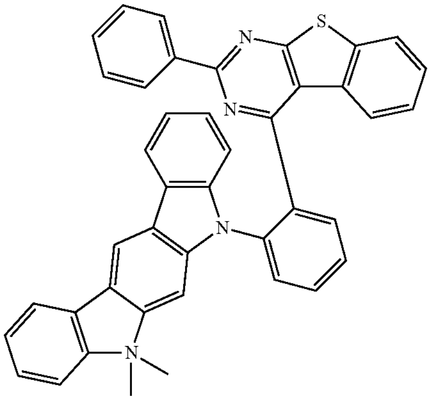
1439
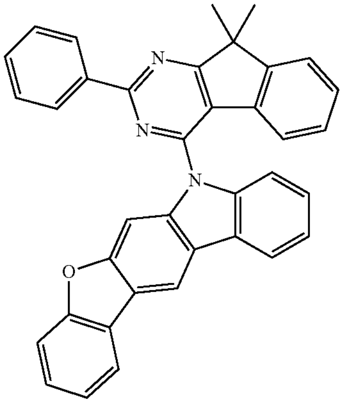
-continued
1440
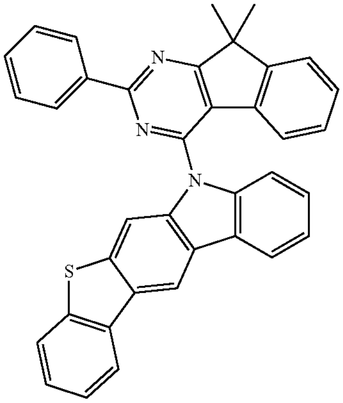
1441
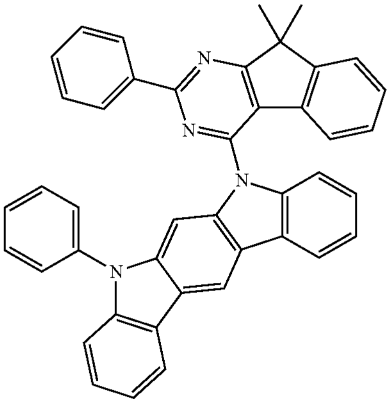
1442
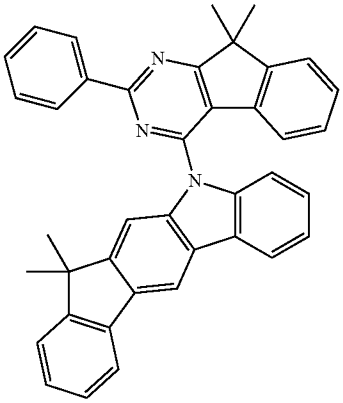

-continued
1443
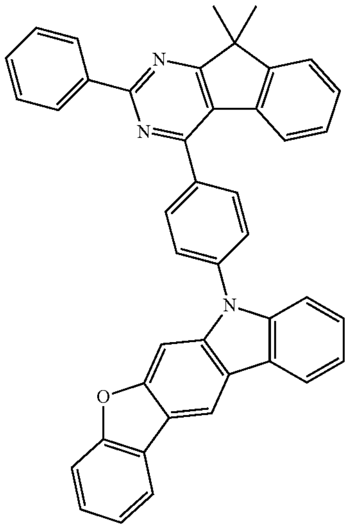
1444
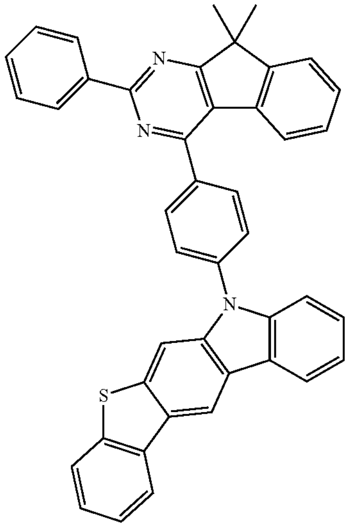
1445
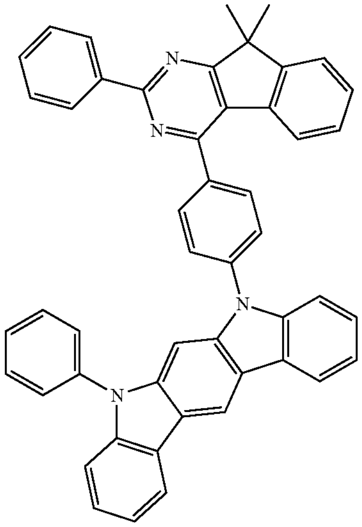
-continued
1446
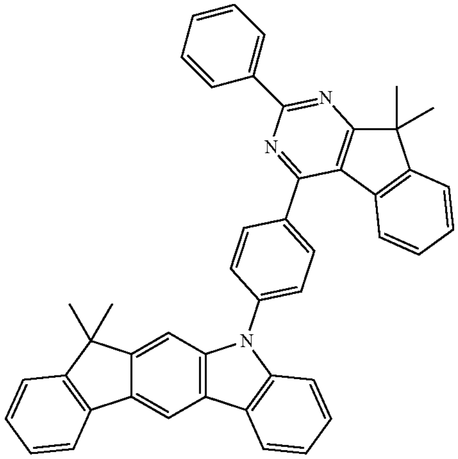
1447
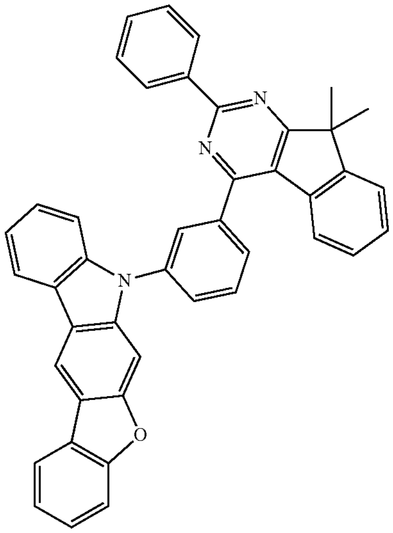
1448
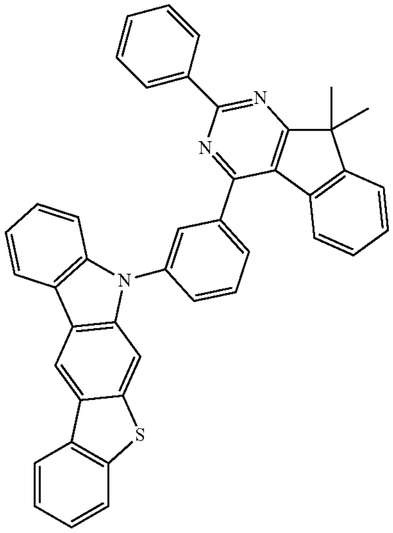

-continued
1449
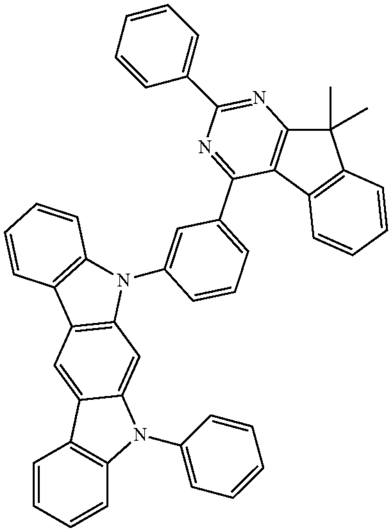
1450
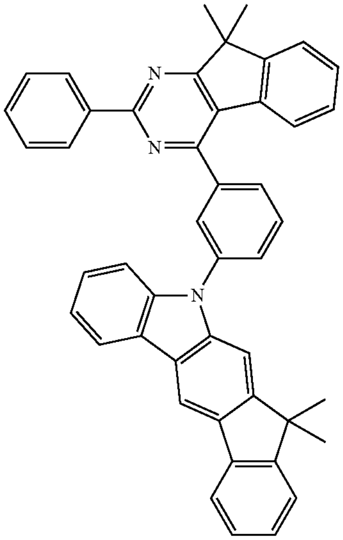
1451
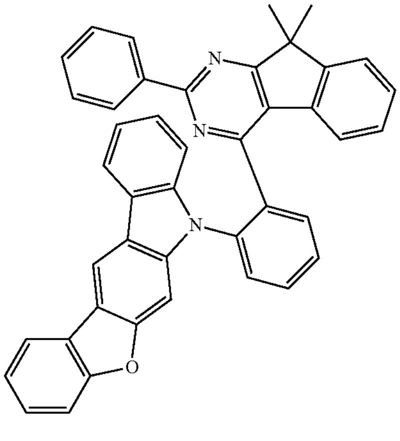
-continued
1452
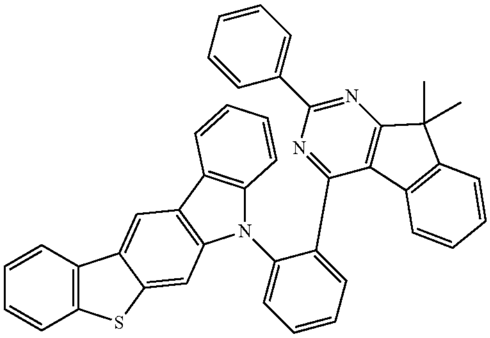
1453
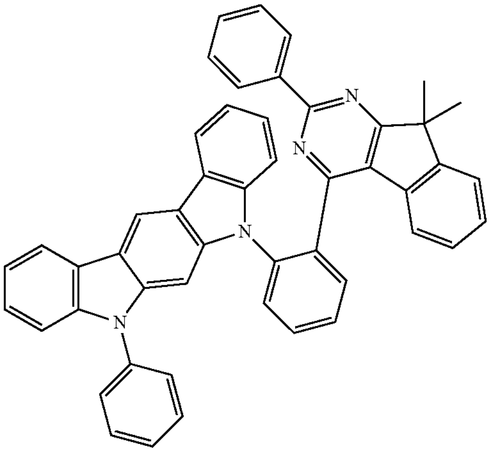
1454
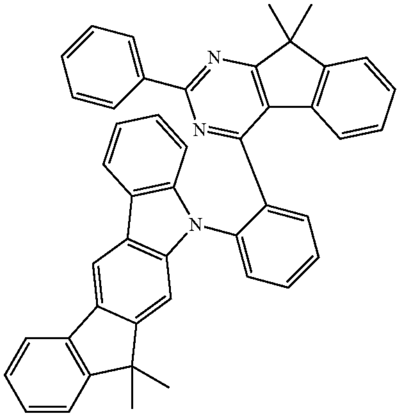

-continued
1455
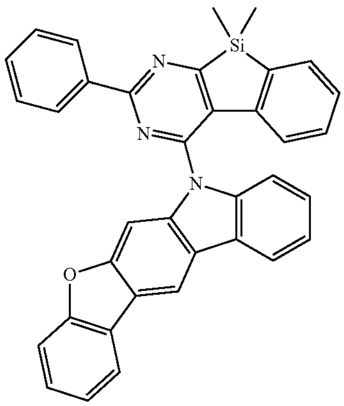
1456
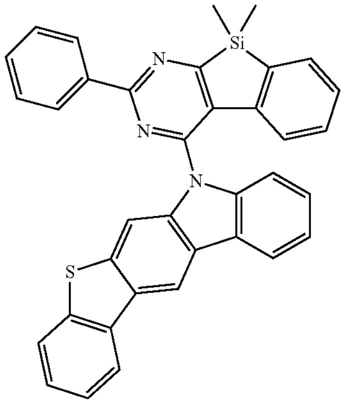
1457
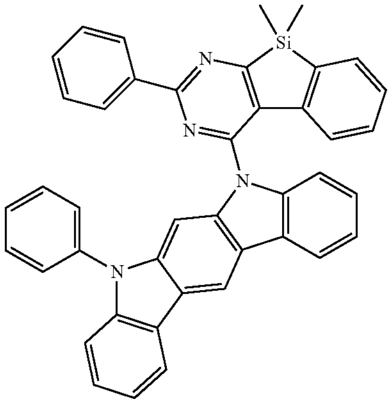
1458
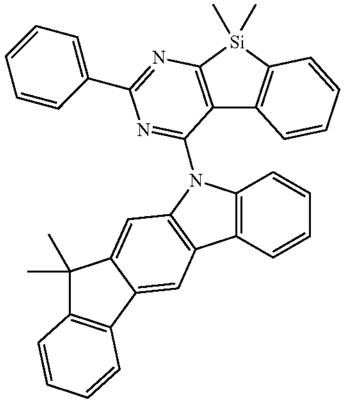
-continued
1459
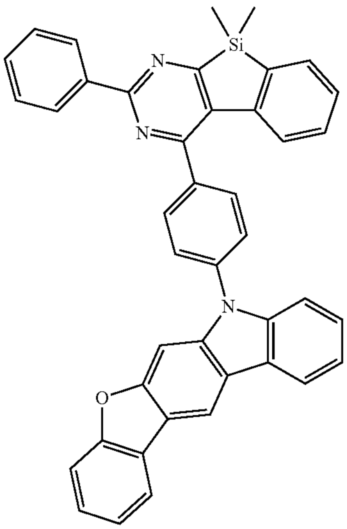
1460
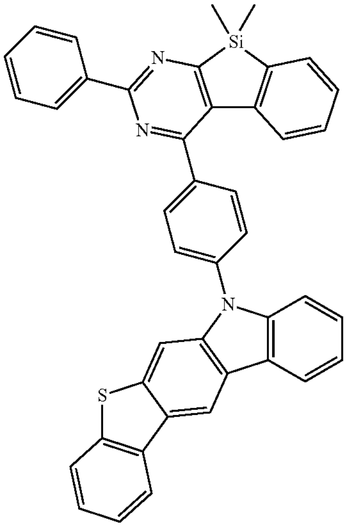
1461
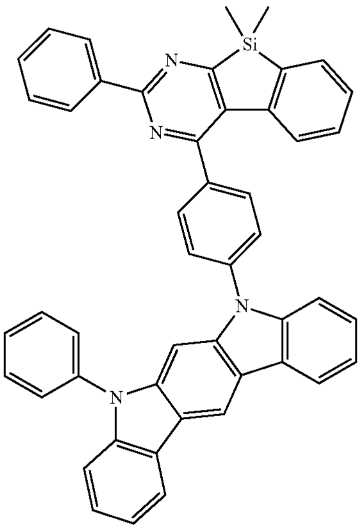

-continued
1462
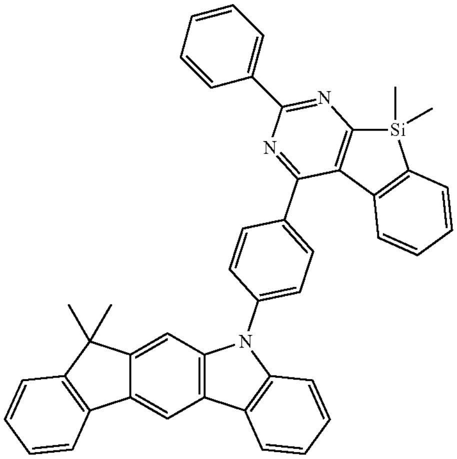
1463
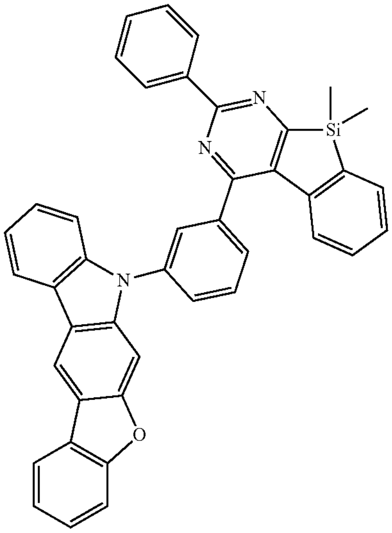
1464
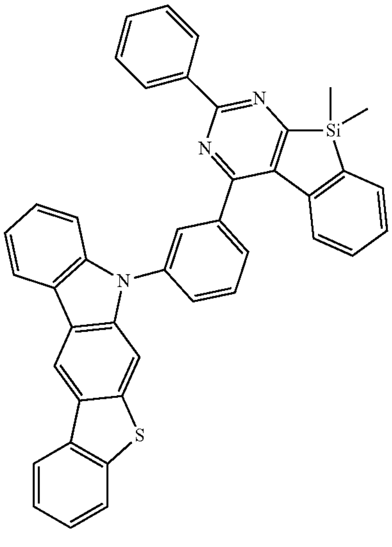
-continued
1465
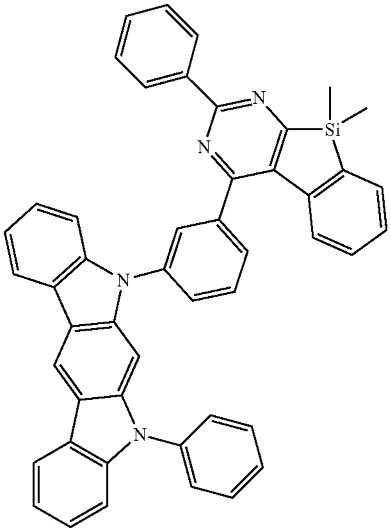
1466
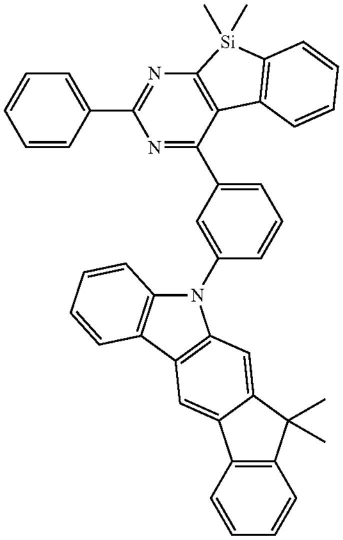
1467
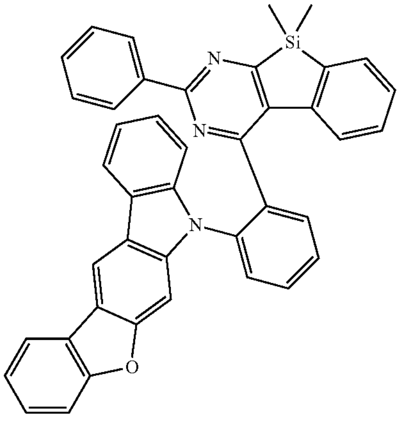

-continued
1468
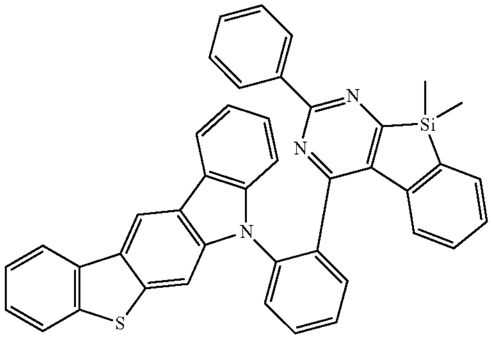
1469
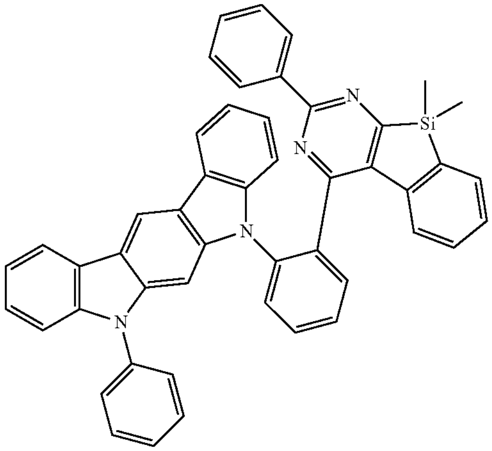
1470
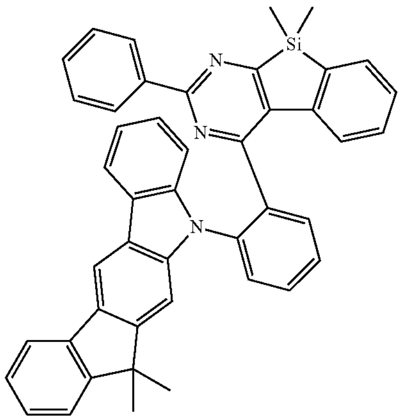
-continued
1471
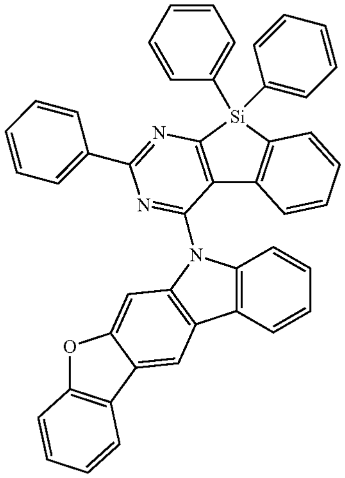
1472
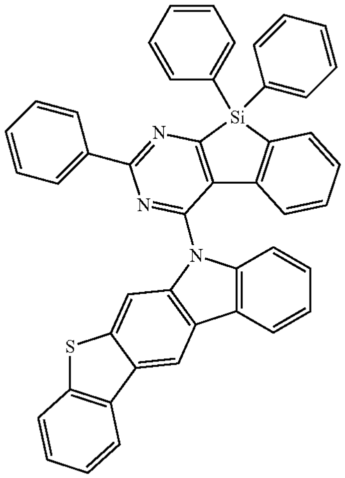
1473
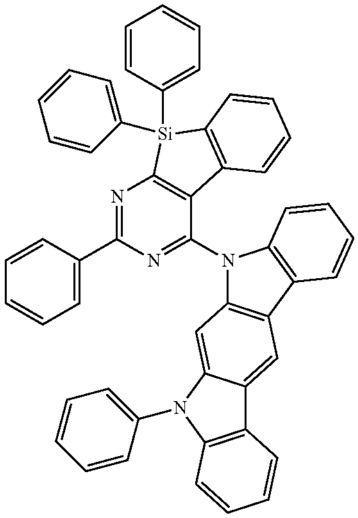

1474
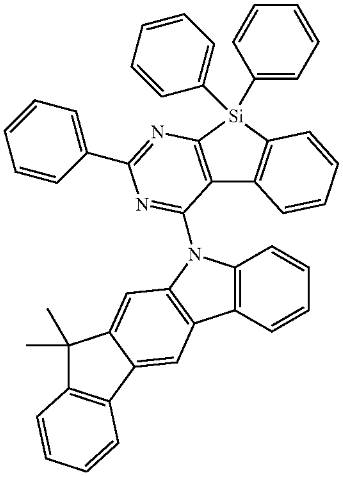
1475
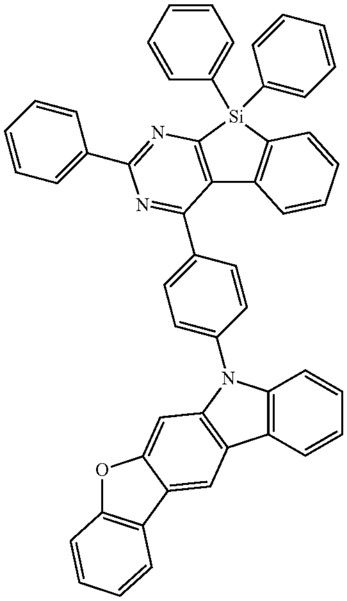
1476
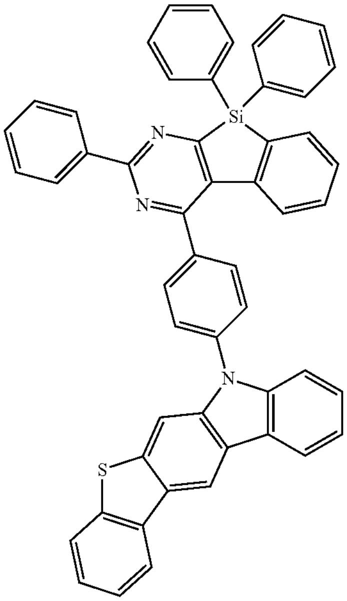
1477
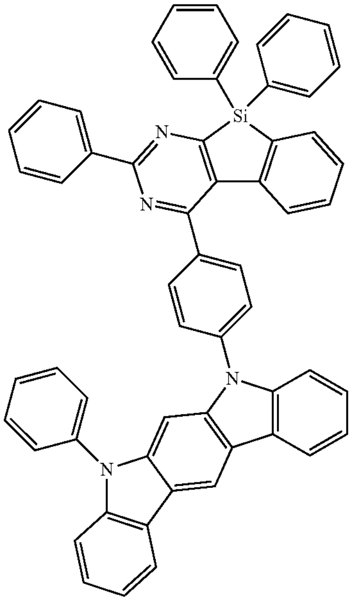

-continued
1478
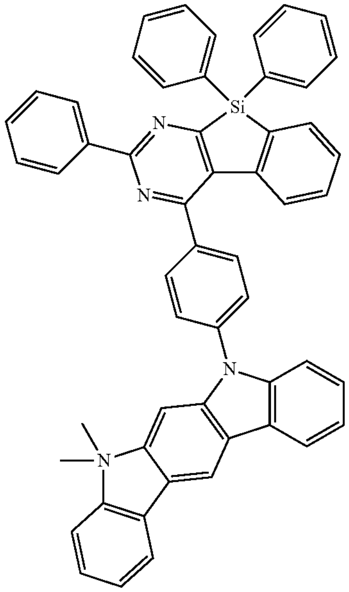
1479
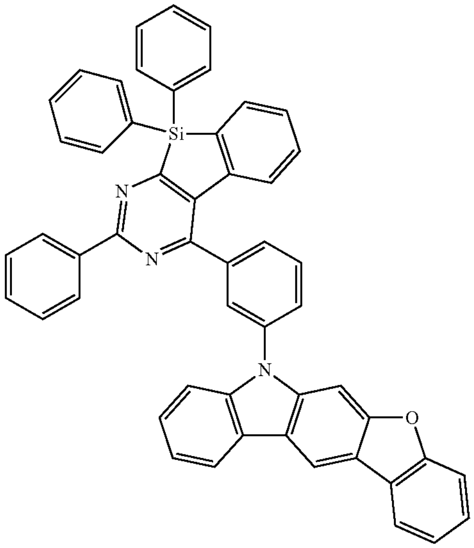
-continued
1480
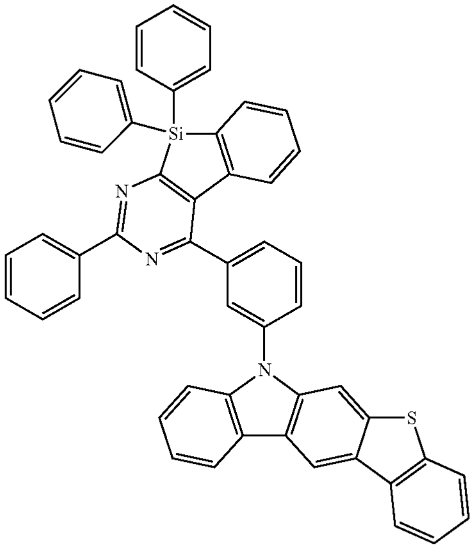
1481
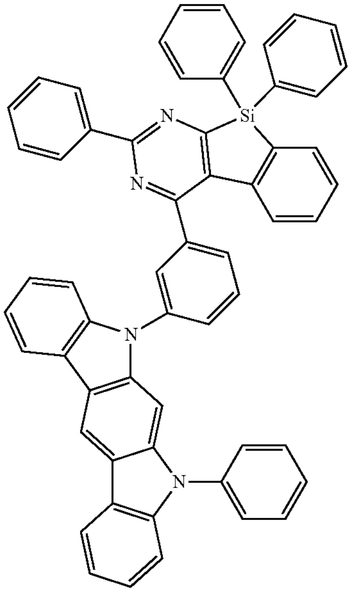

-continued
1482
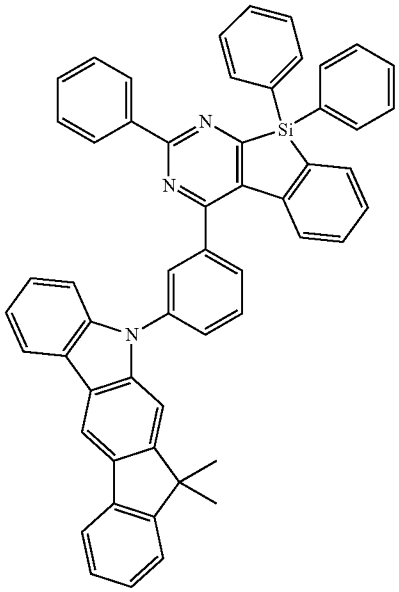
1483
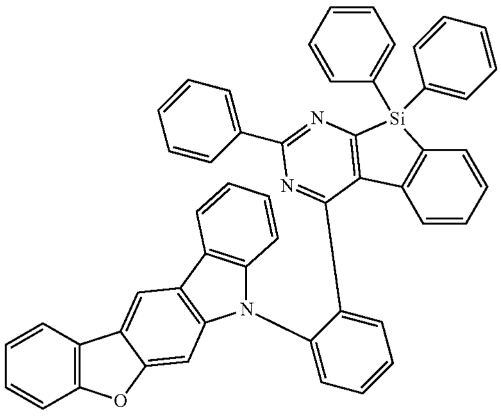
1484
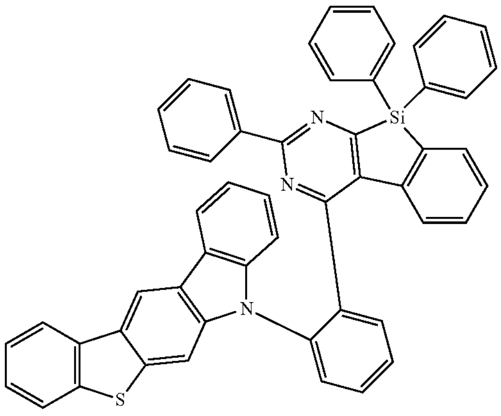
-continued
1485
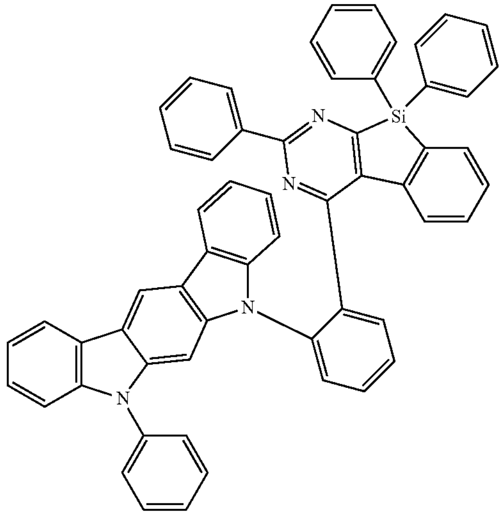
1486
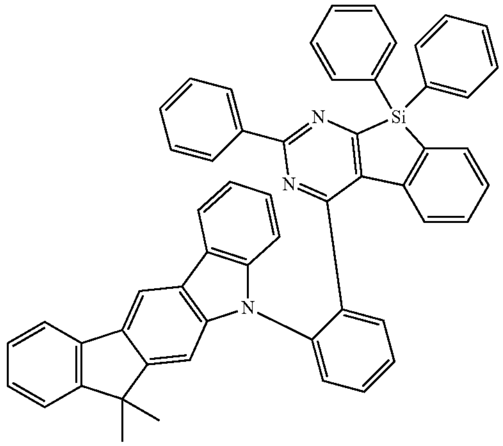
1487
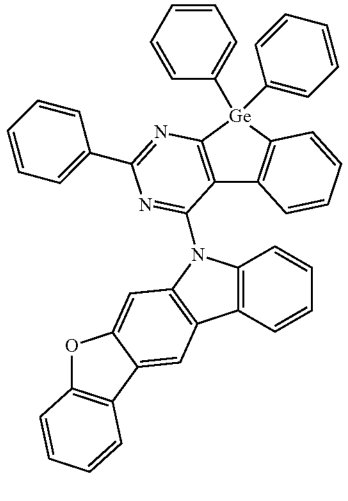

-continued
1488
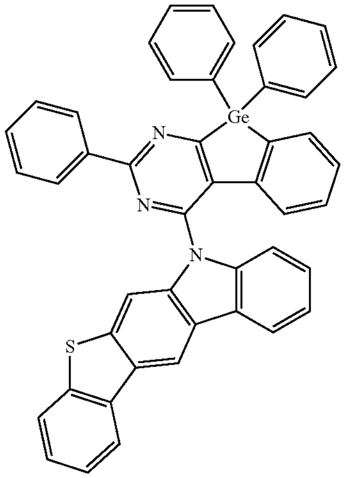
1489
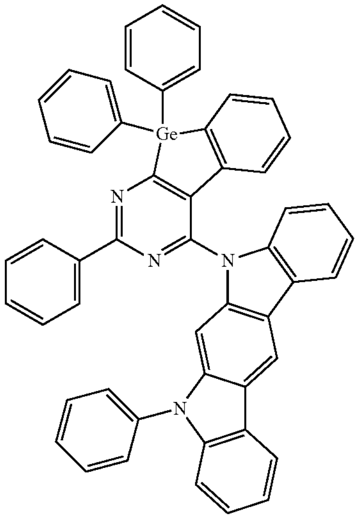
1490
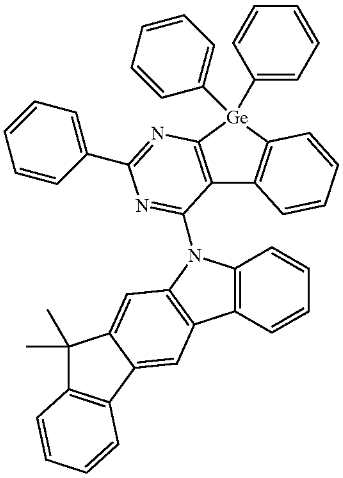
-continued
1491
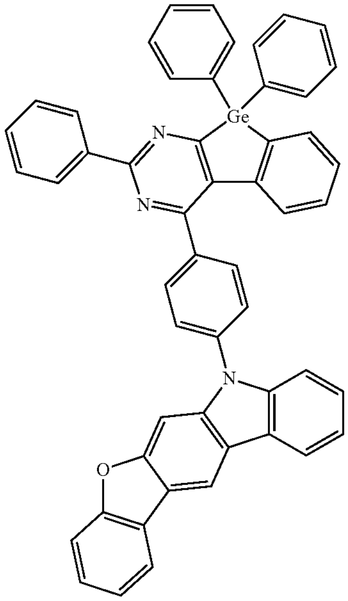
1492
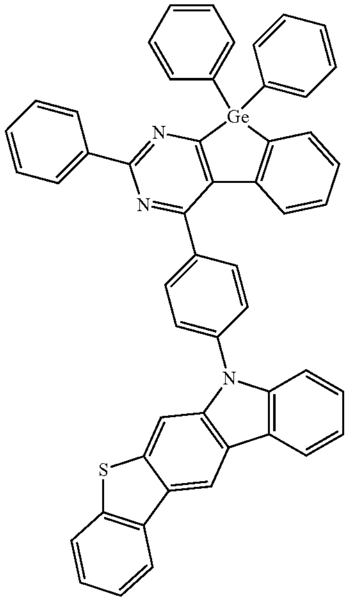

1493
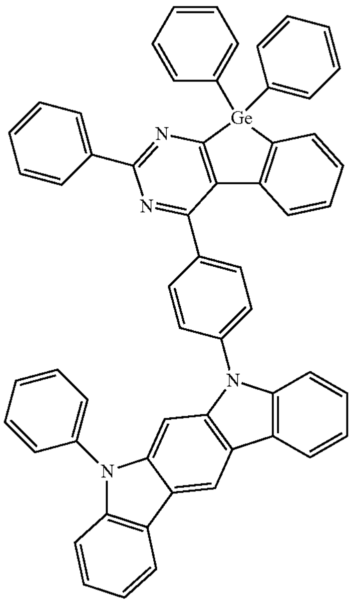
1494
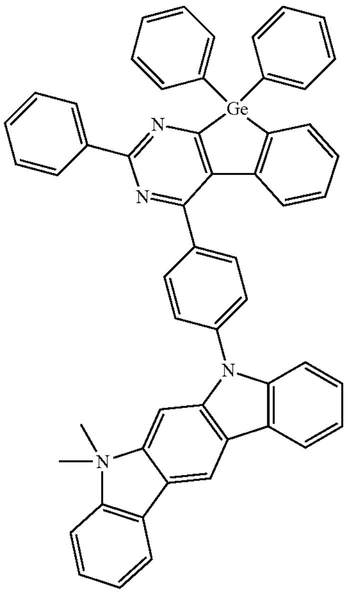
1495
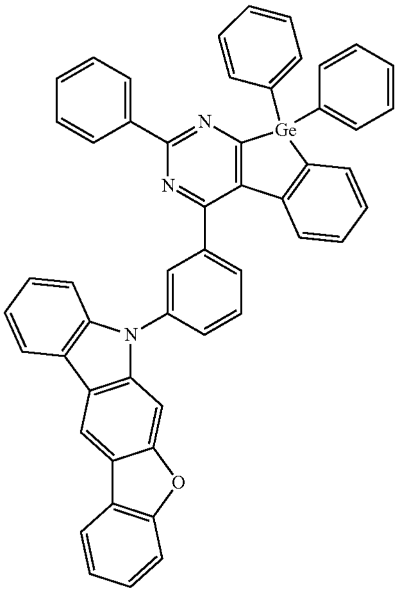
1496
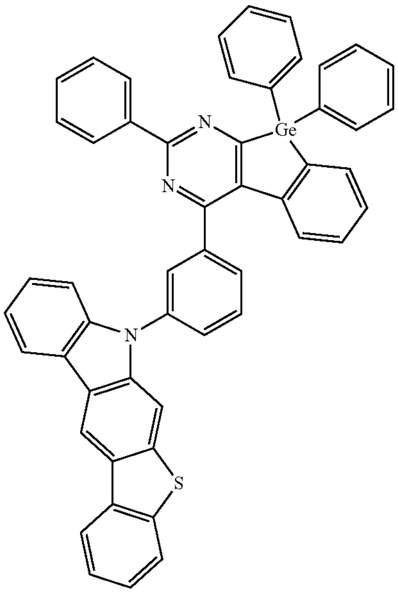

-continued
1497
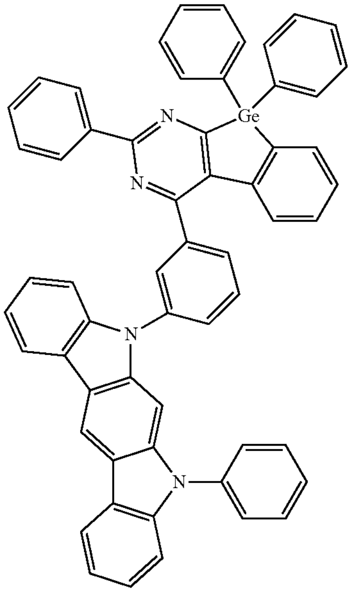
1498
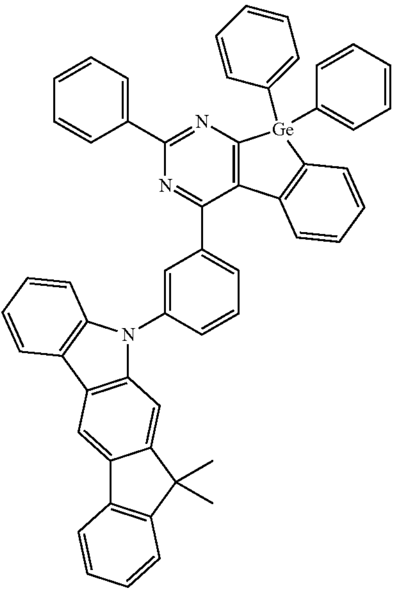
1499
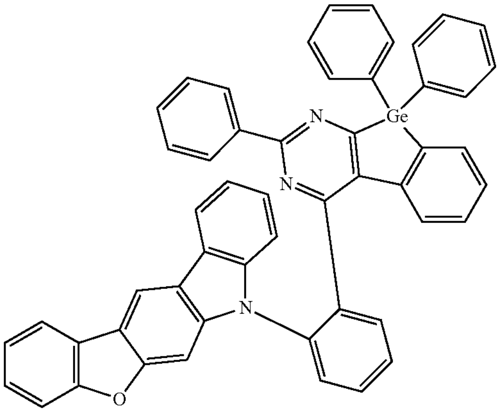
-continued
1500
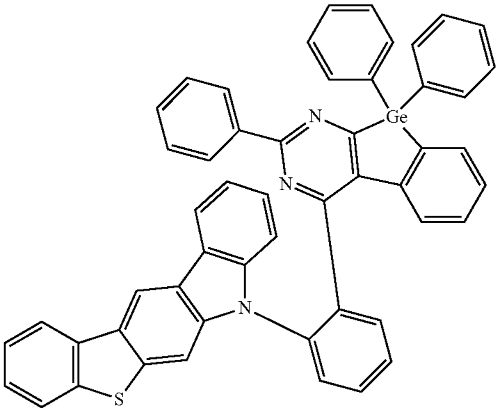
1501
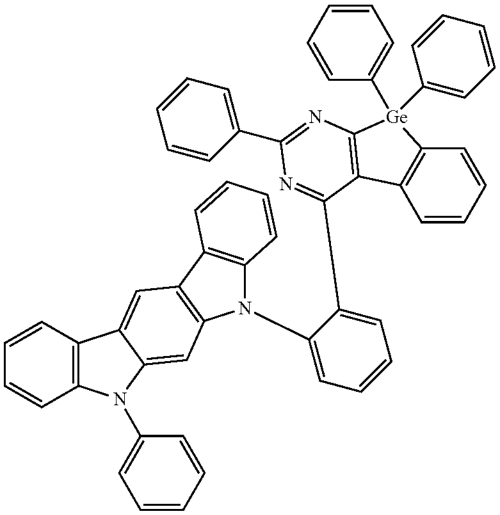
1502
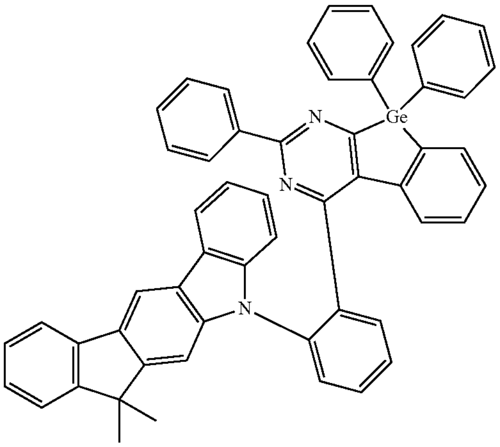

-continued
1503
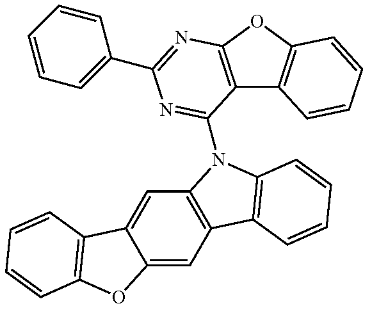
1504
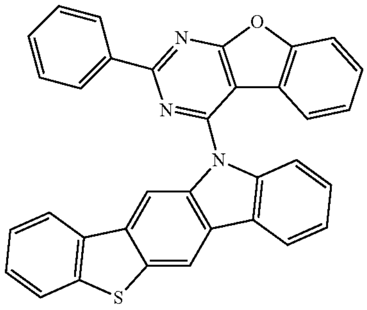
1505
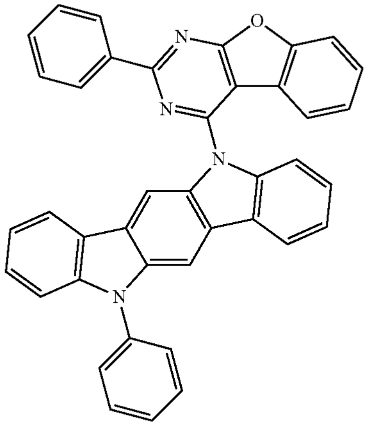
1506
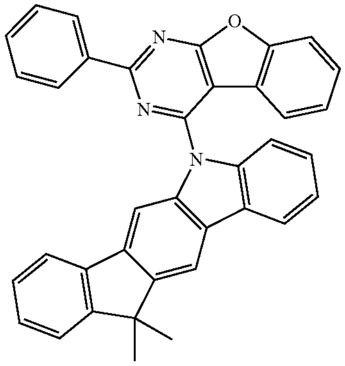
-continued
1507
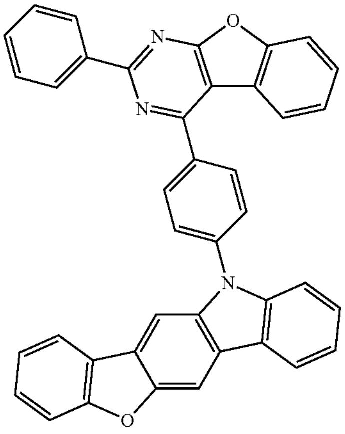
1508
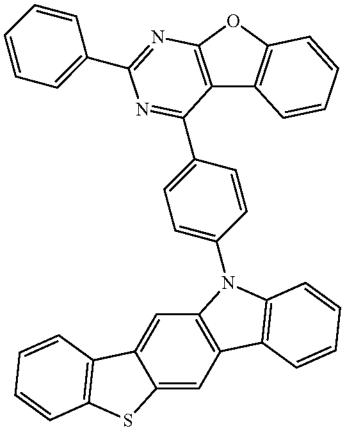
1509
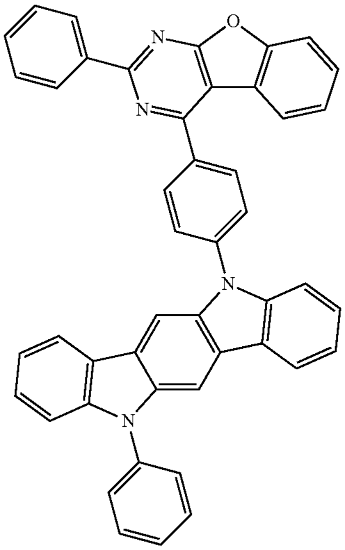

-continued
1510
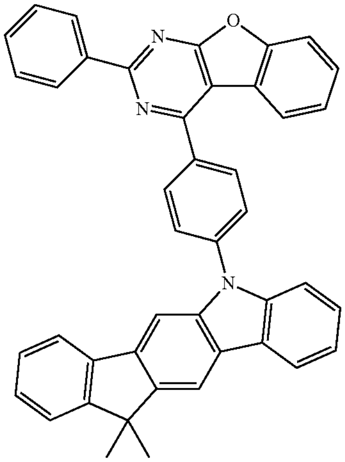
1511
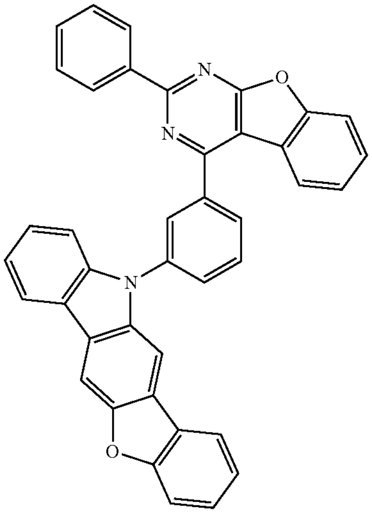
1512
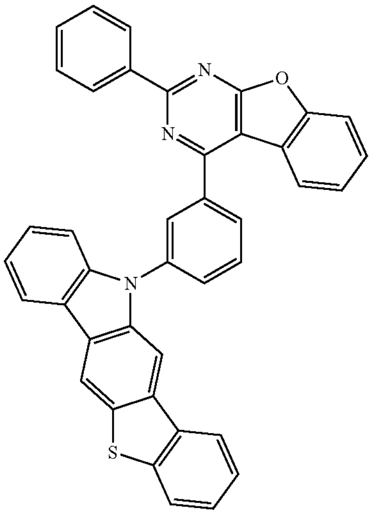
-continued
1513
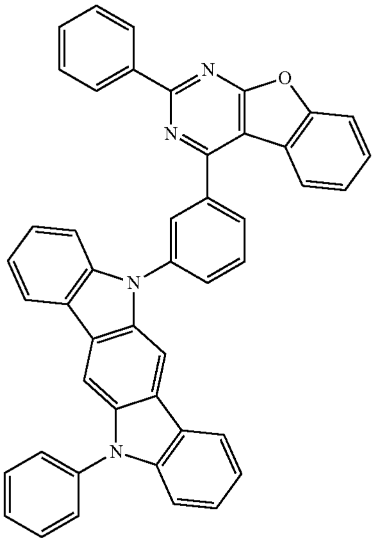
1514
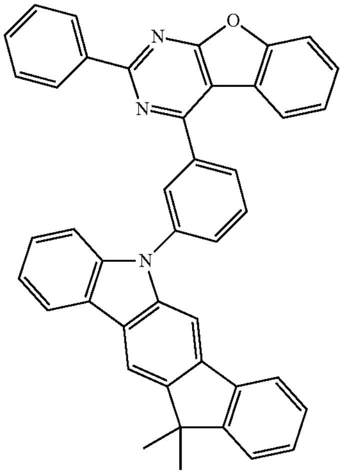
1515
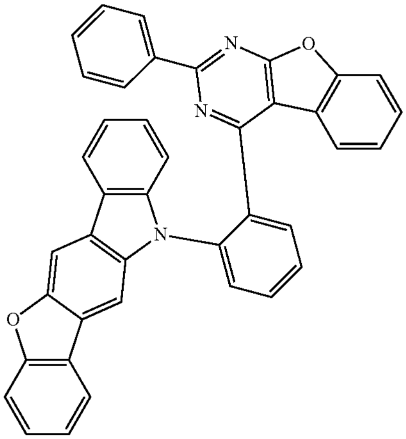

-continued
1516
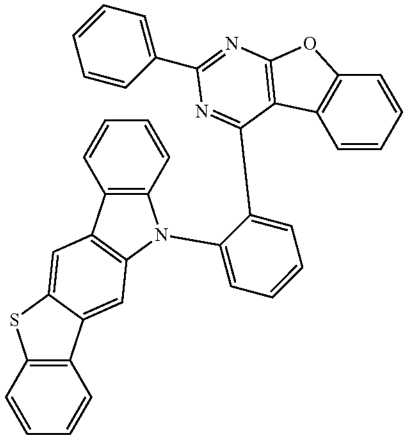
1517
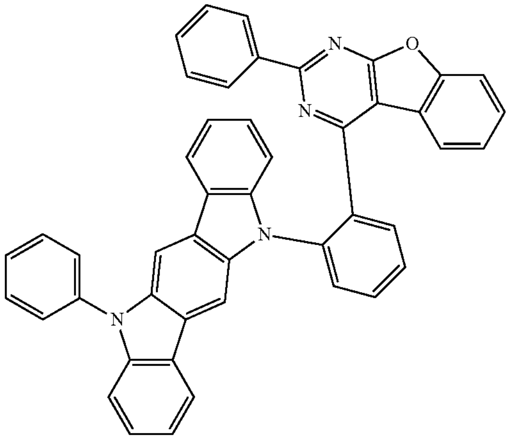
1518
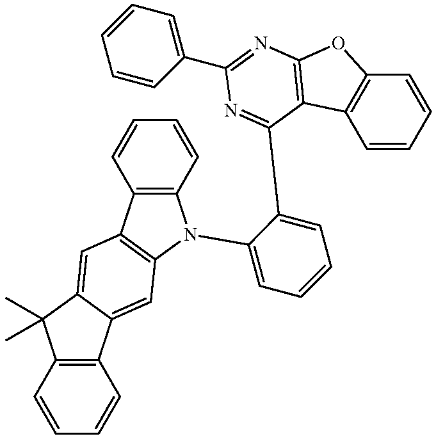
1519
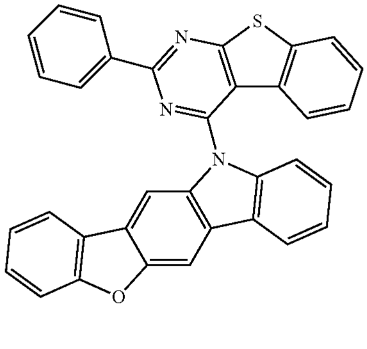
-continued
1520
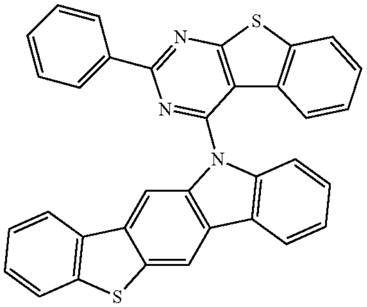
1521
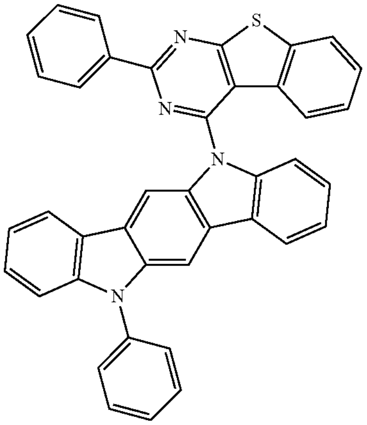
1522
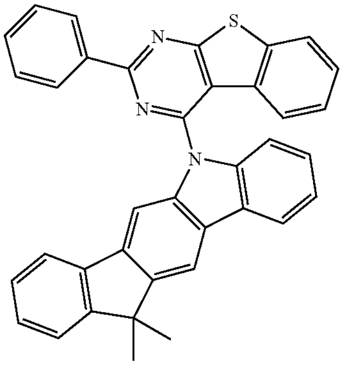
1523
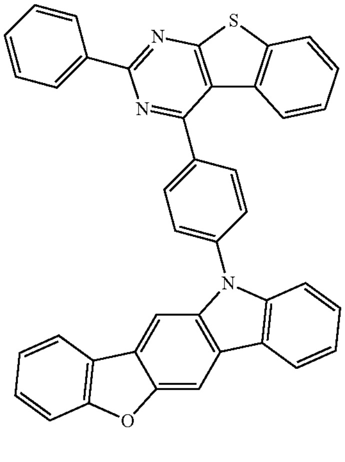

-continued
1524
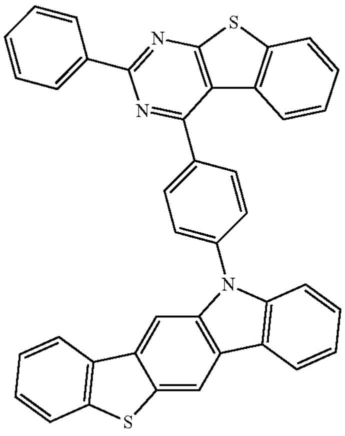
1525
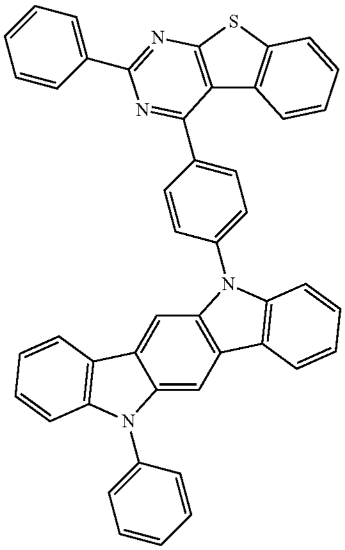
1526
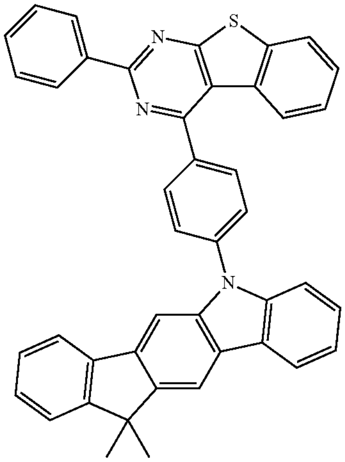
-continued
1527
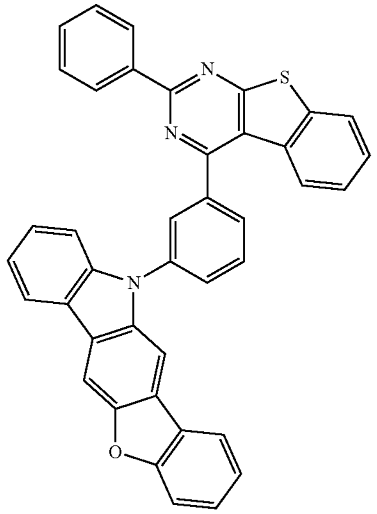
1528
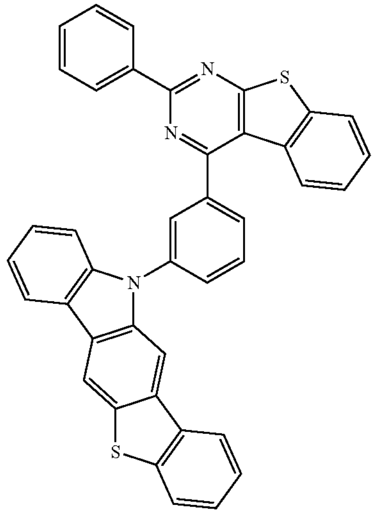
1529
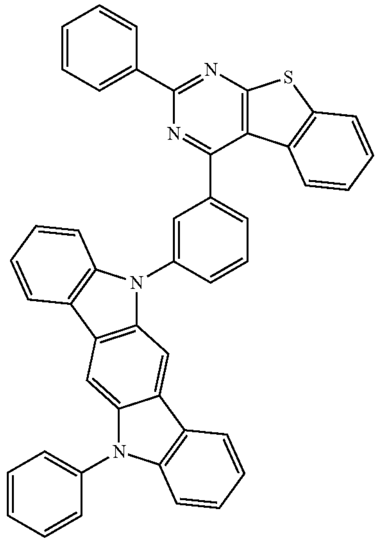

-continued
1530
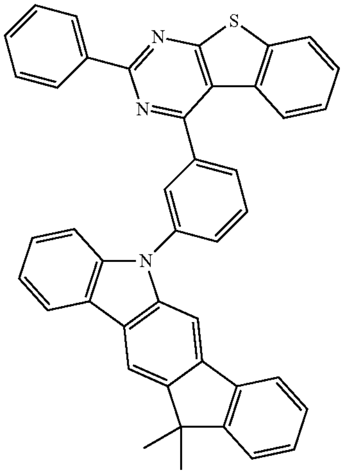
1531
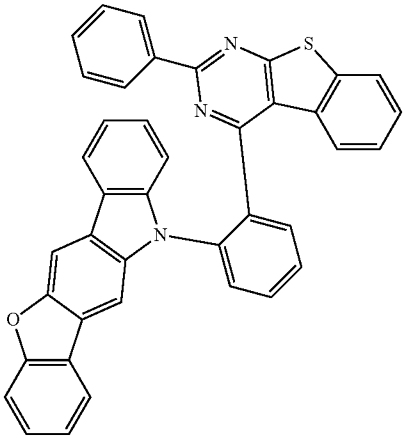
1532
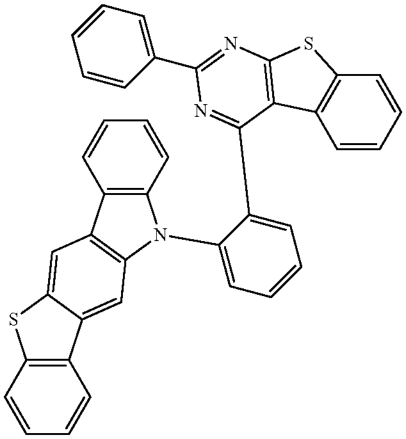
-continued
1533
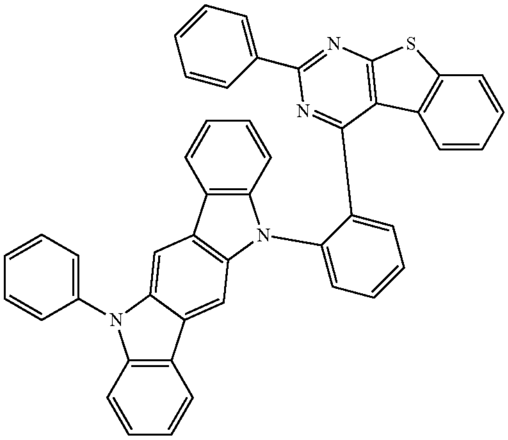
1534
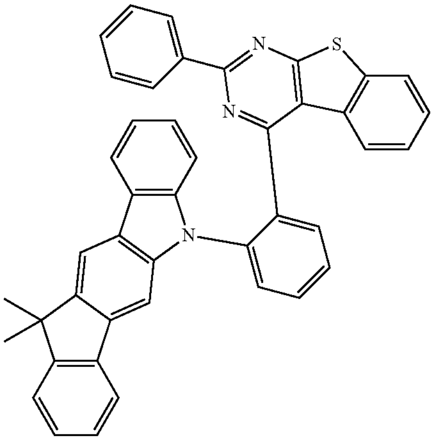
1535
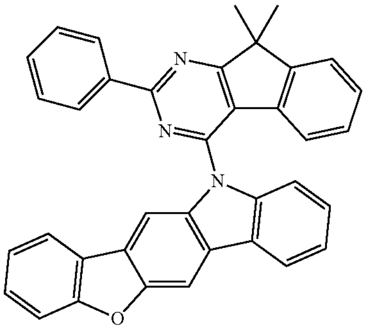
1536
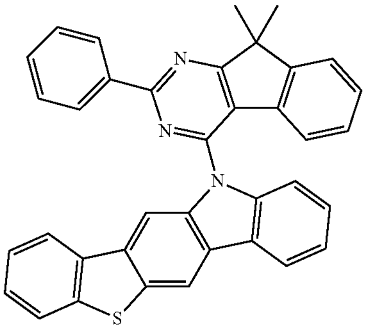

-continued
1537
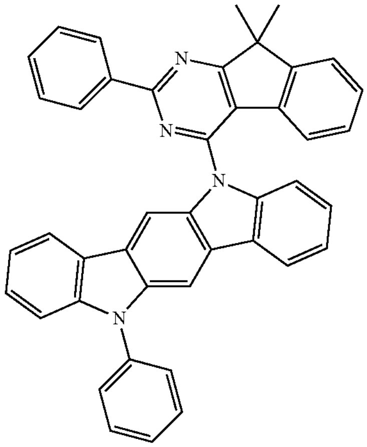
1538
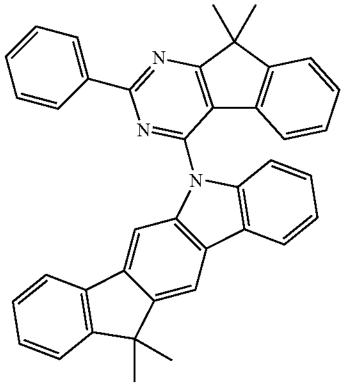
1539
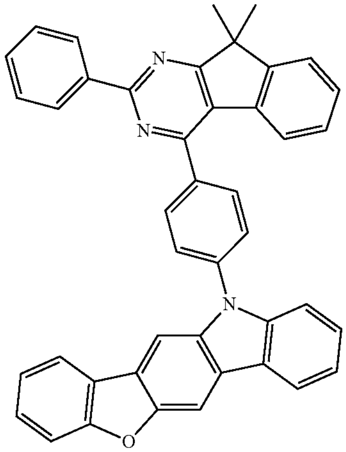
-continued
1540
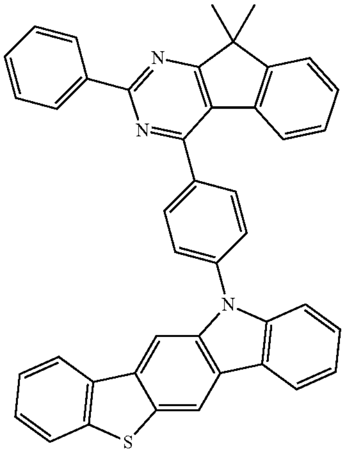
1541
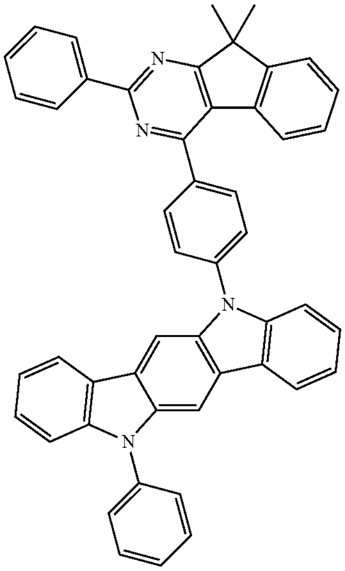
1542
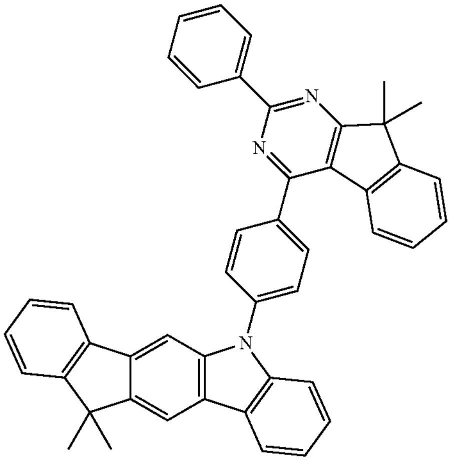

-continued
1543
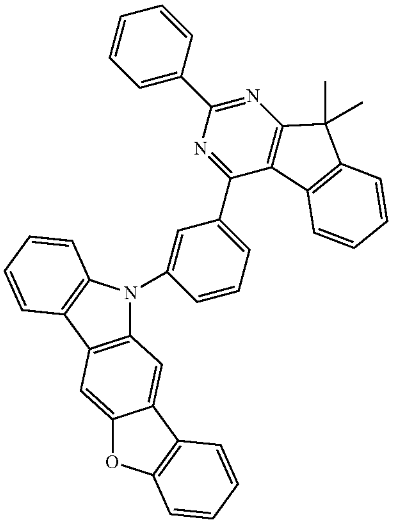
1544
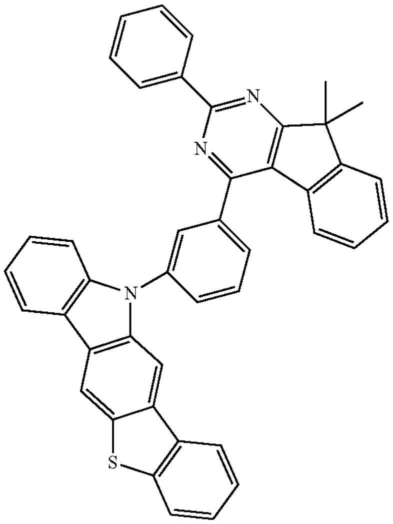
1545
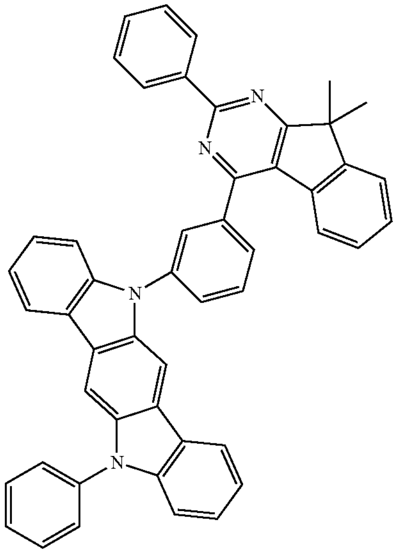
-continued
1546
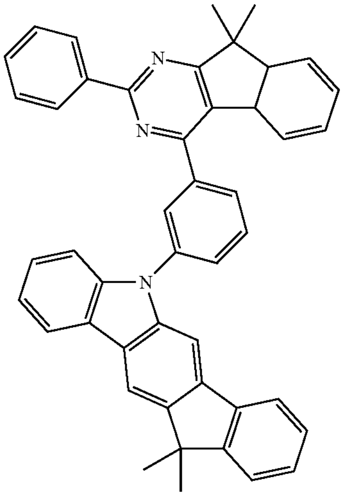
1547
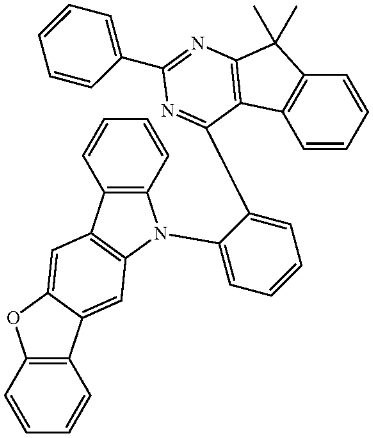
1548
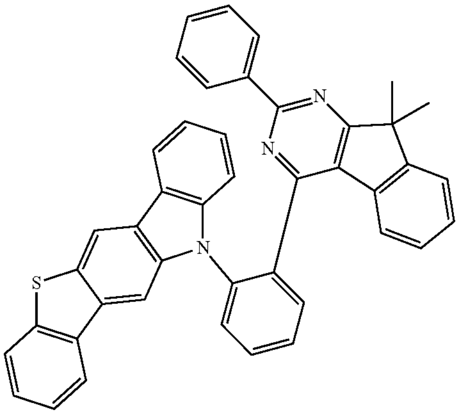

-continued
1549
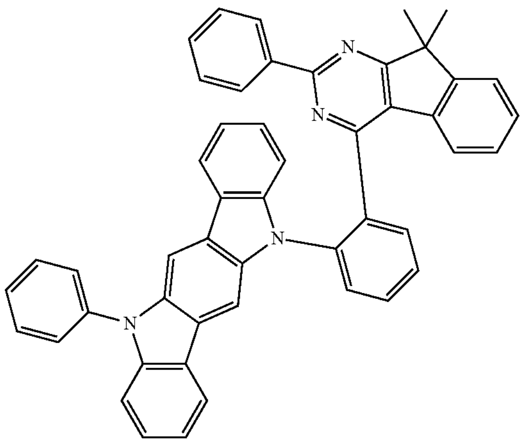
1550
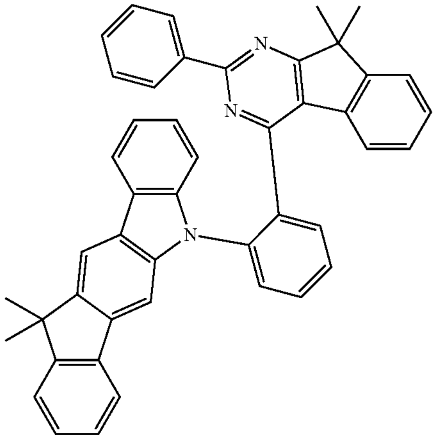
1551
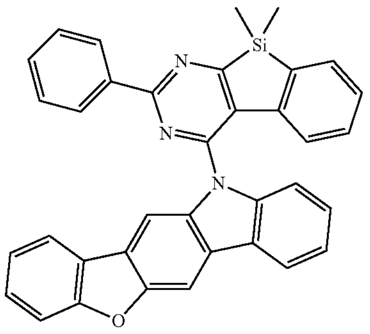
1552
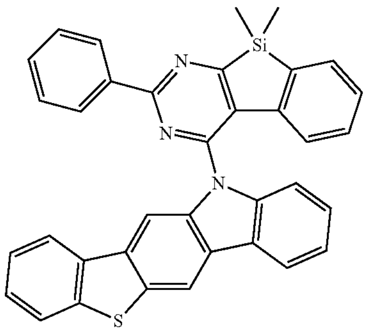
-continued
1553
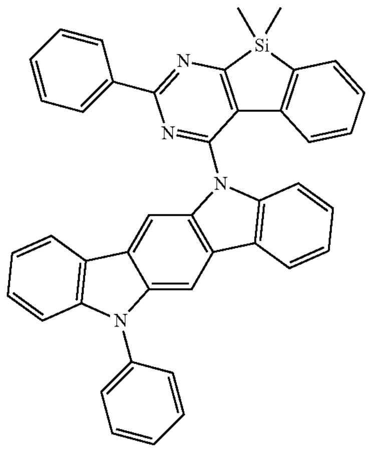
1554
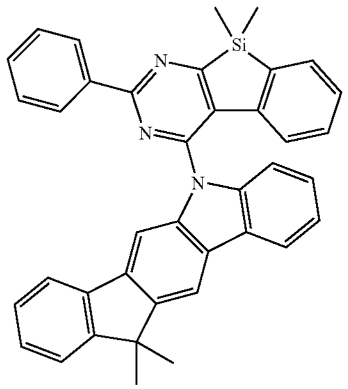
1555
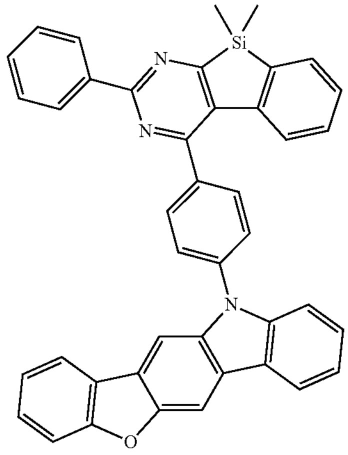

1556
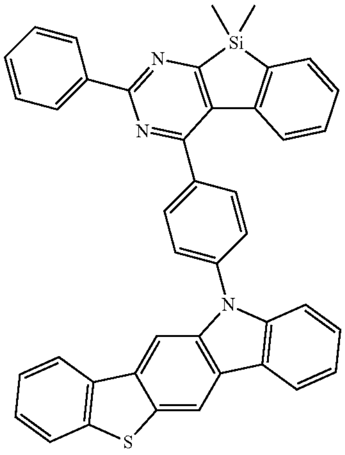
1557
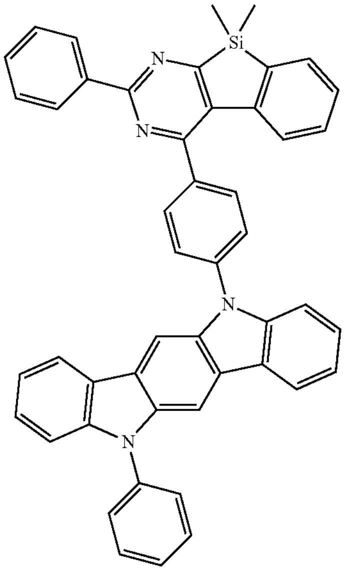
1558
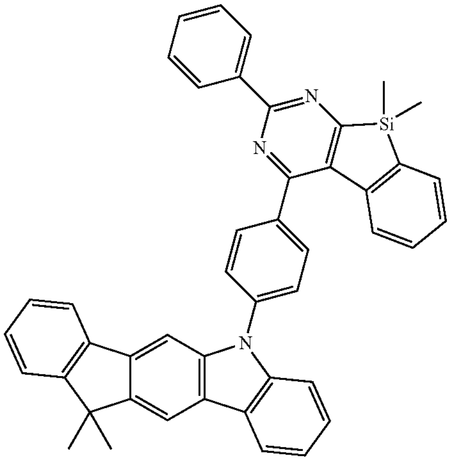
1559
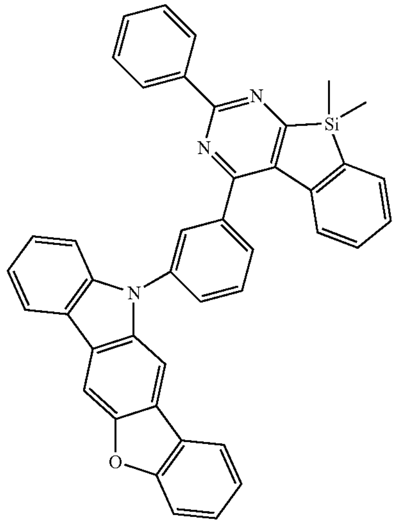
1560
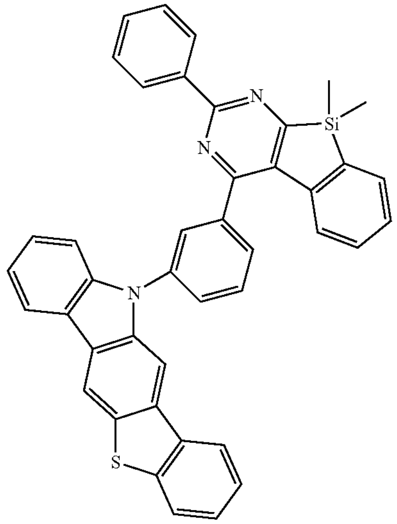
1561
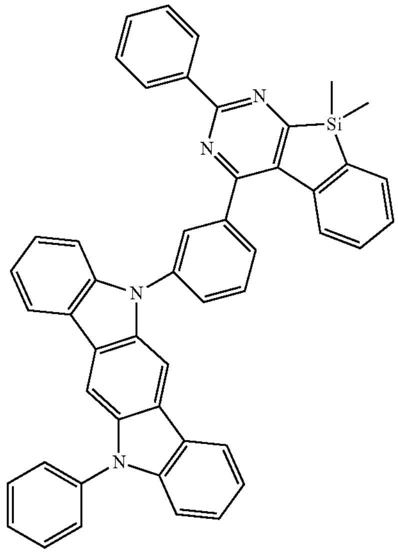

-continued
1562
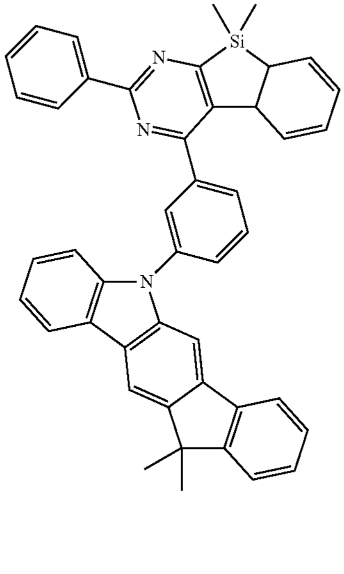
1563
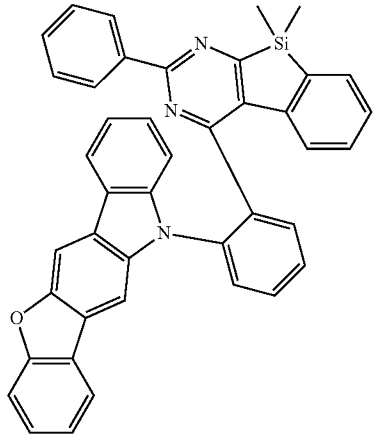
1564
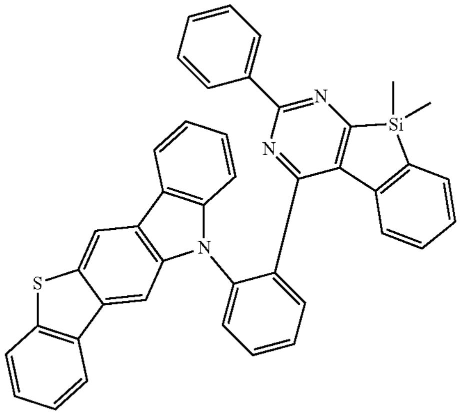
-continued
1565
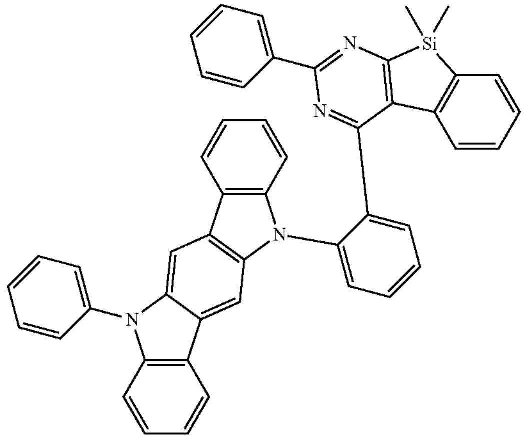
1566
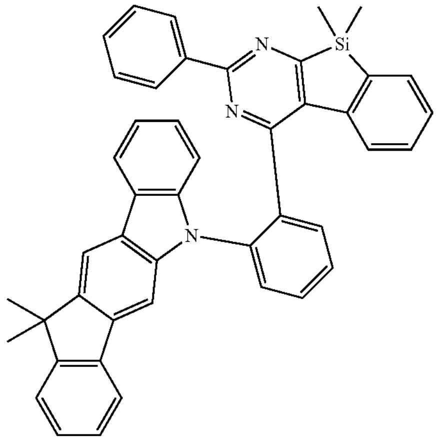
1567
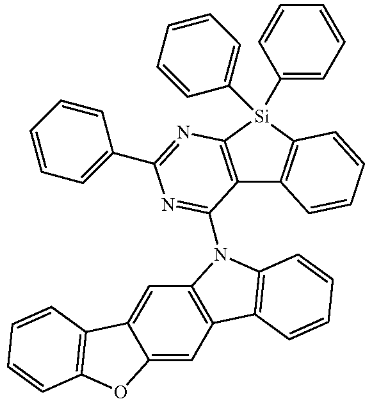

-continued
1568
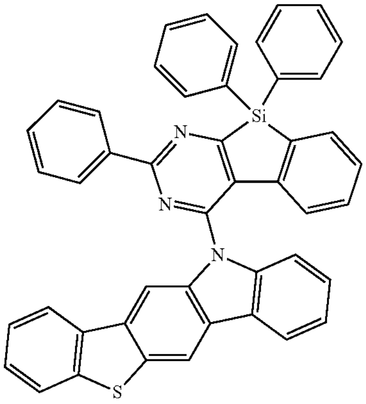
1569
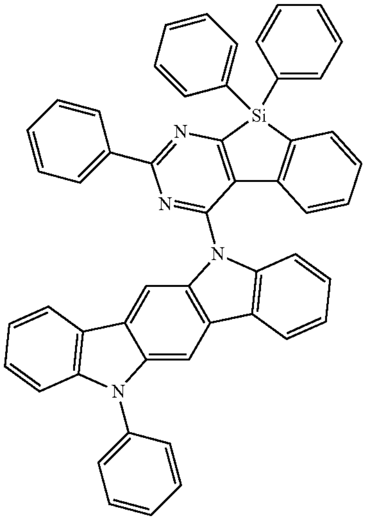
1570
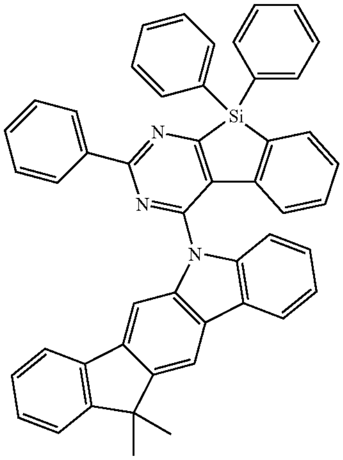
-continued
1571
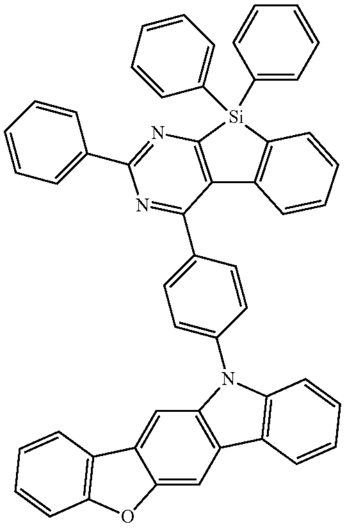
1572
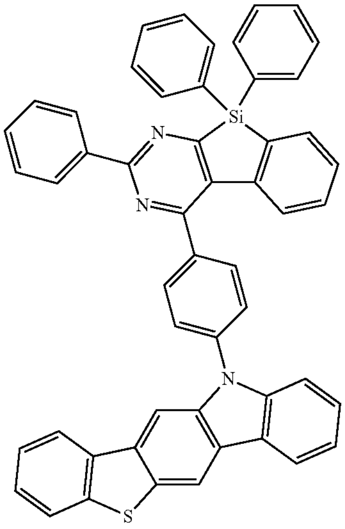
1573
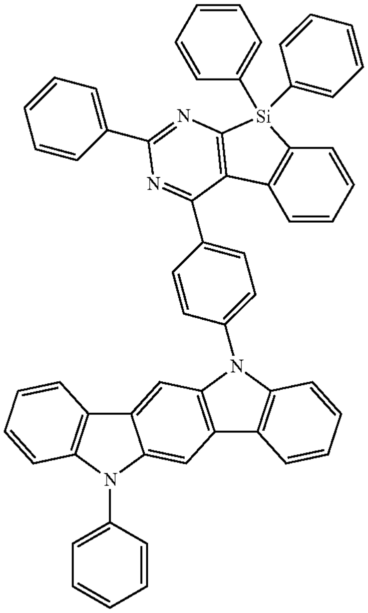

-continued
1574
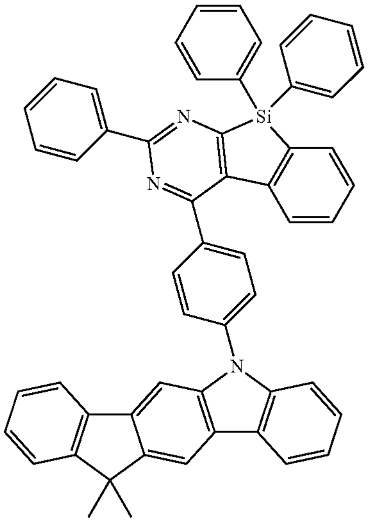
1575
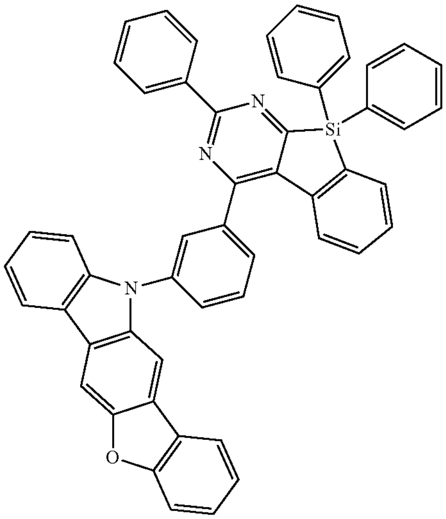
1576
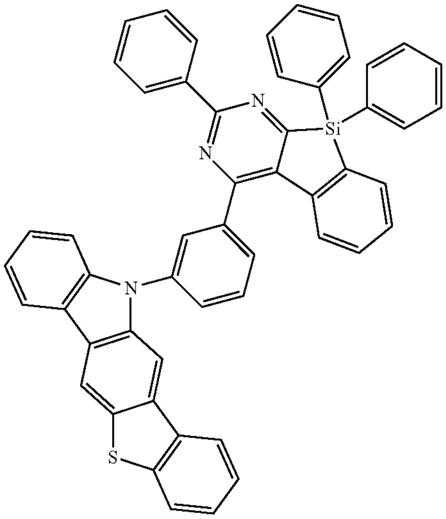
-continued
1577
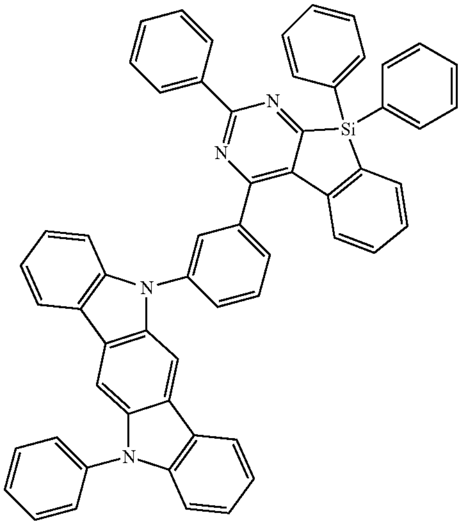
1578
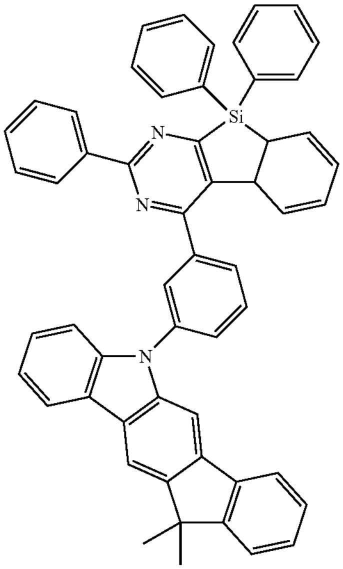
1579
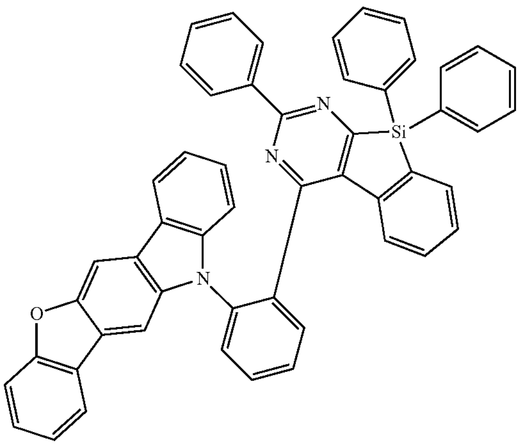

-continued
1580
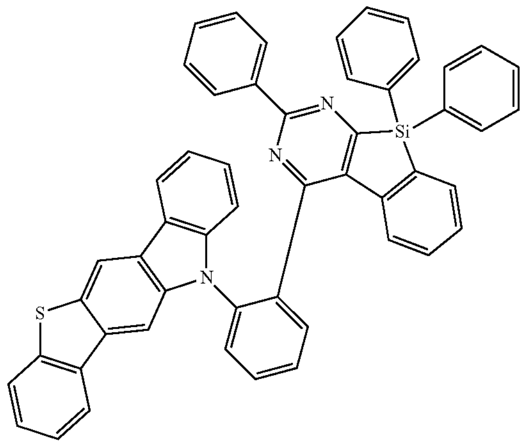
1581
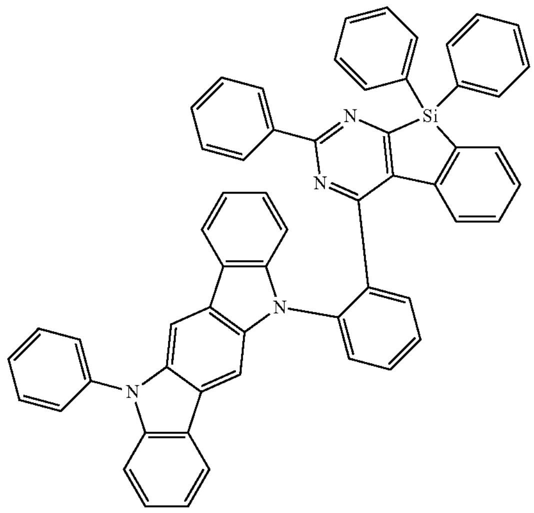
1582
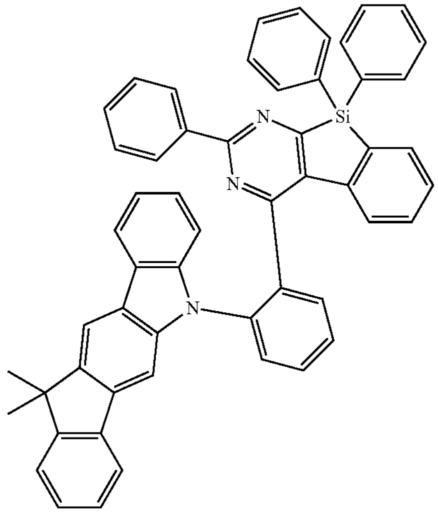
-continued
1583
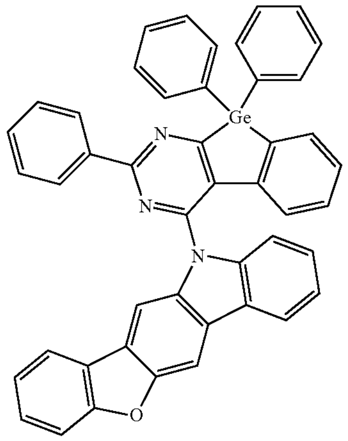
1584
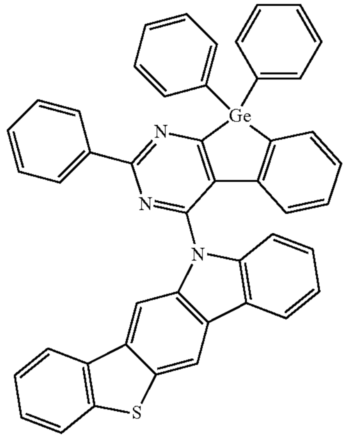
1585
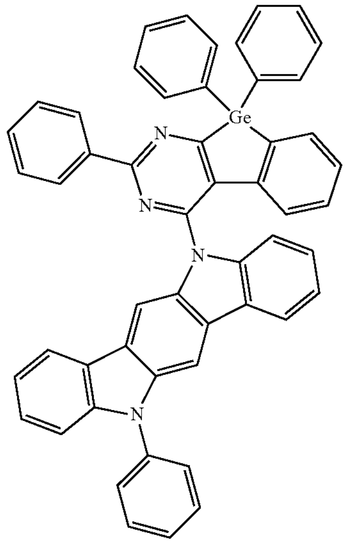

-continued
1586
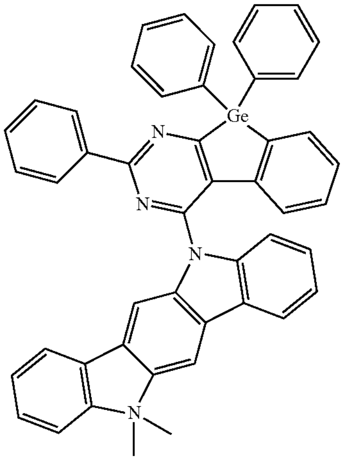
1587
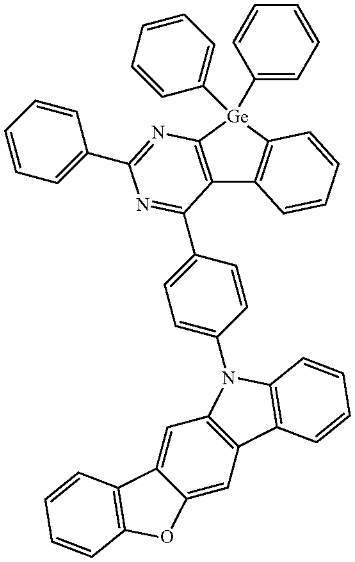
1588
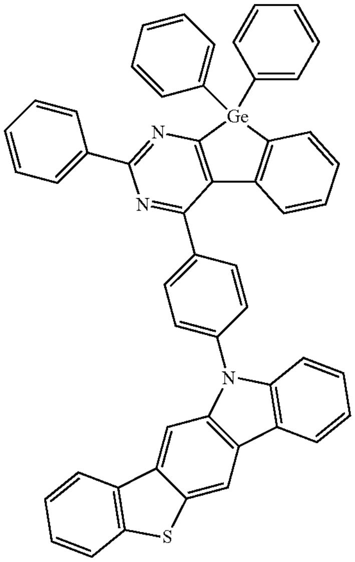
-continued
1589
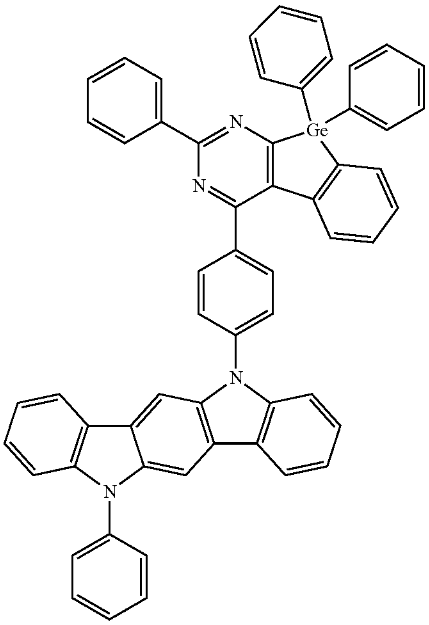
1590
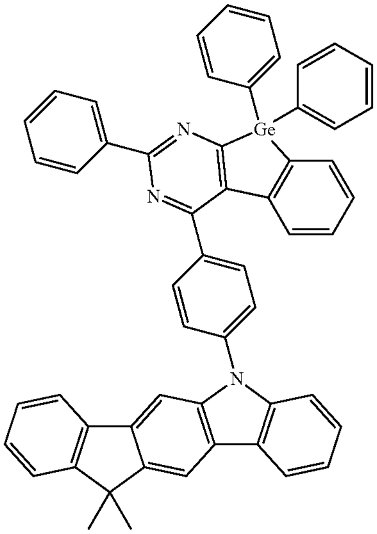

-continued
1591
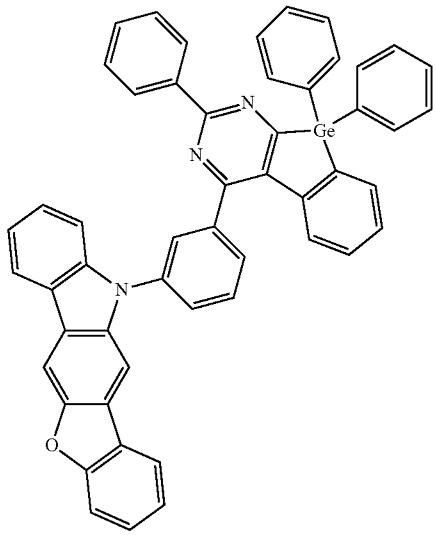
1592
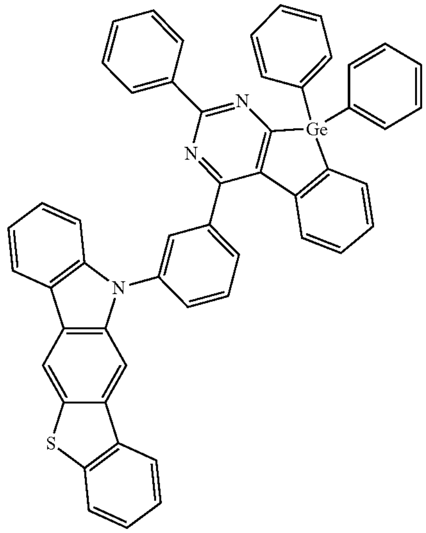
1593
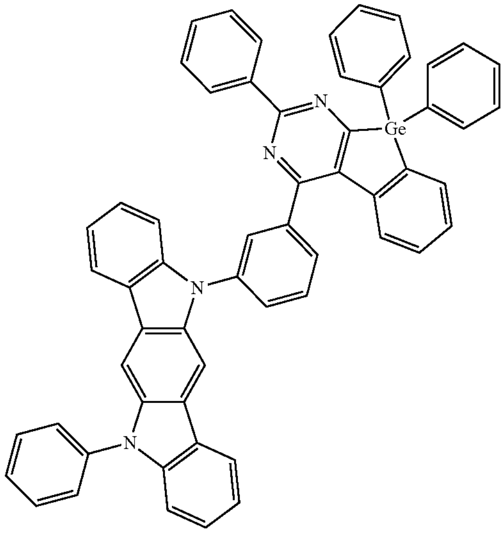
-continued
1594
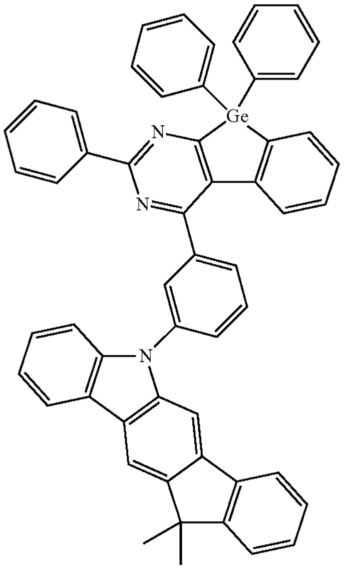
1595
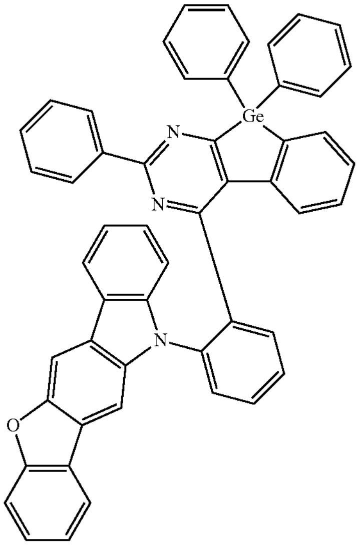
1596
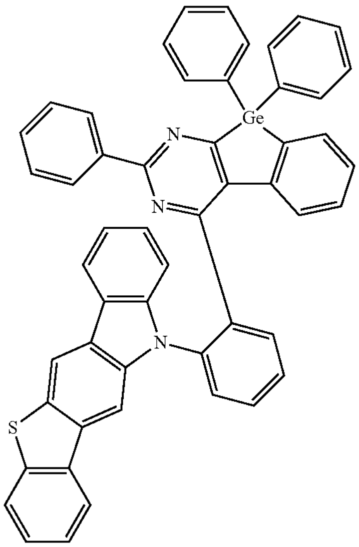

1597
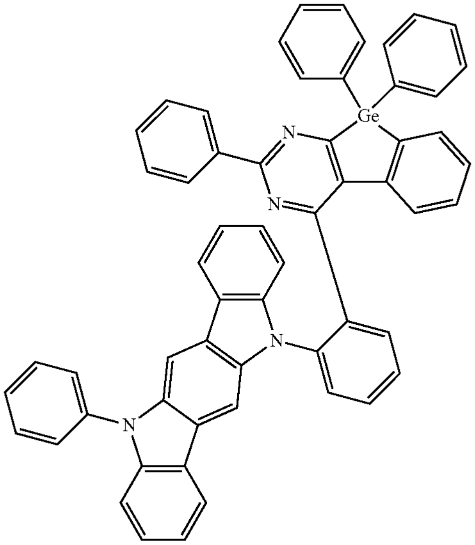
1598
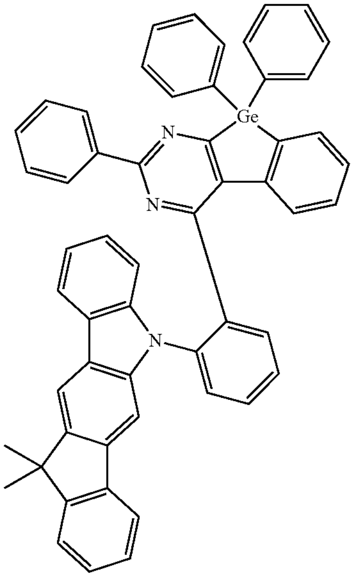
2392
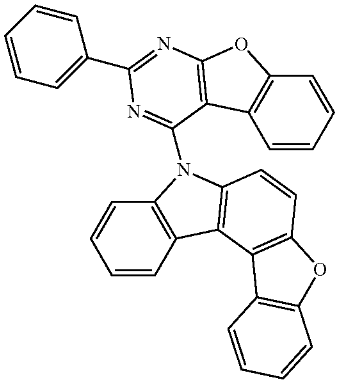
2393
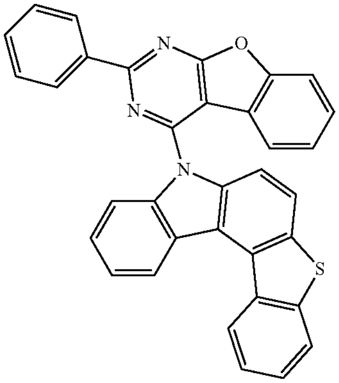
2394
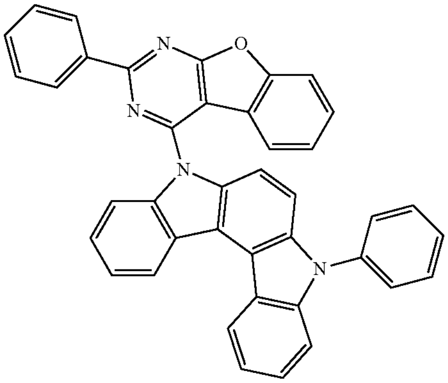
2395
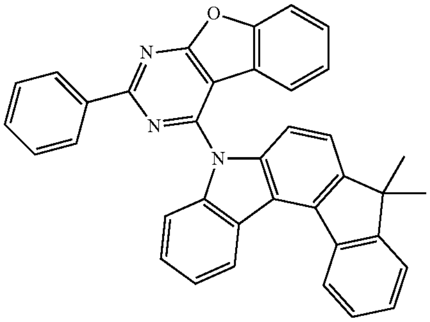
2396
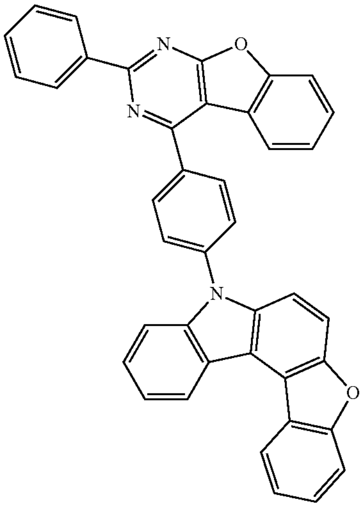

-continued
2397
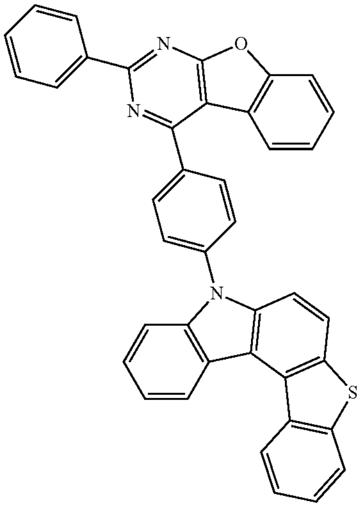
2398
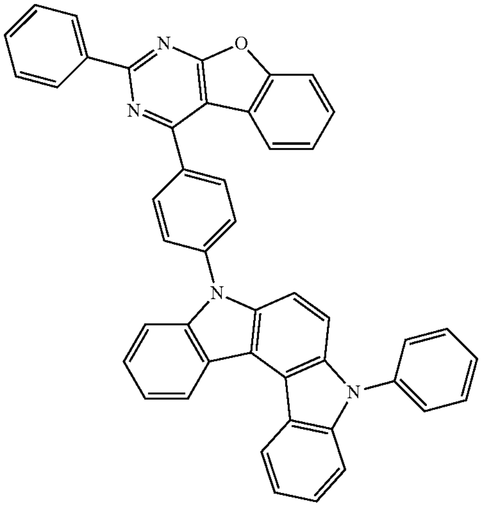
2399
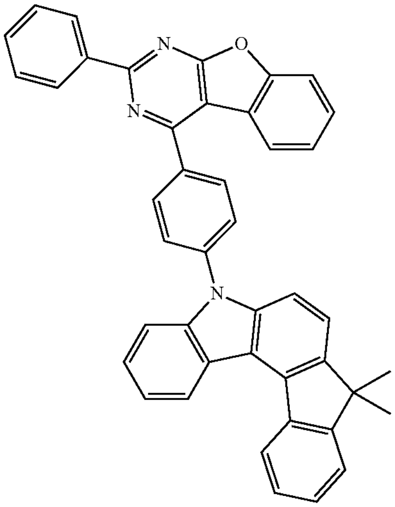
-continued
2400
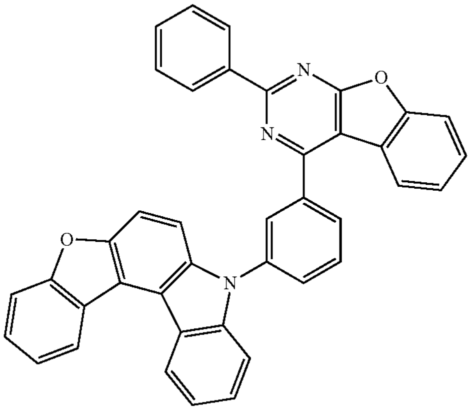
1599
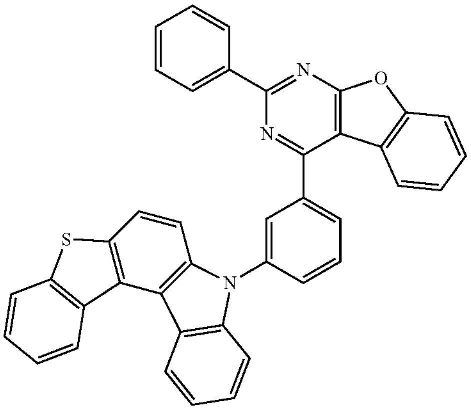
1600
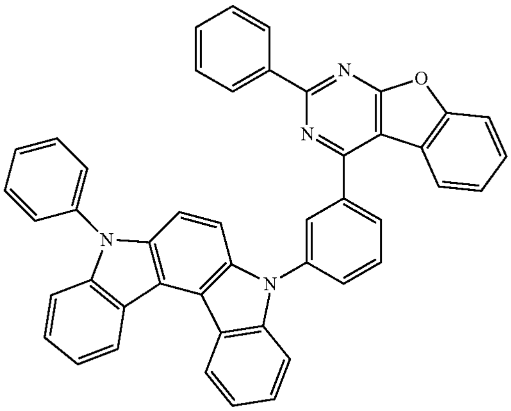

-continued
1601
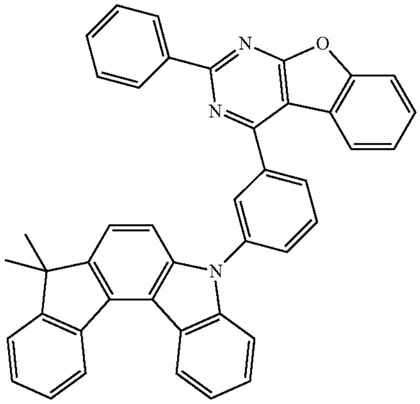
1602
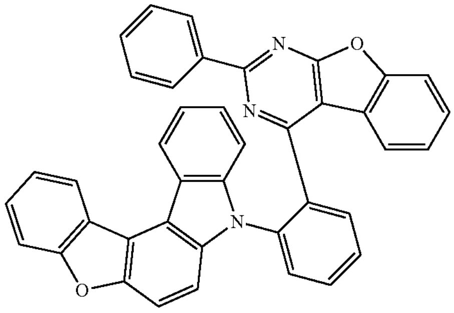
1603
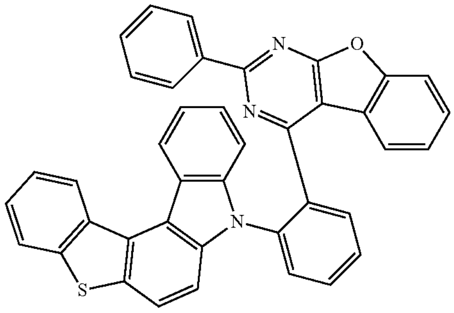
1604
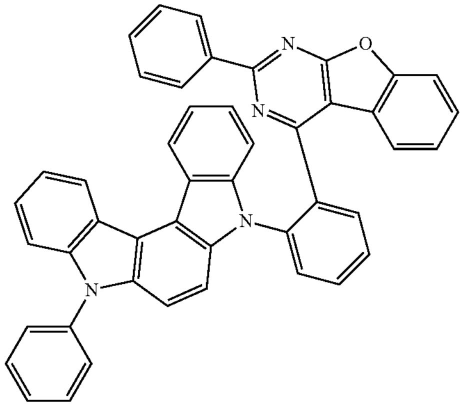
-continued
1605
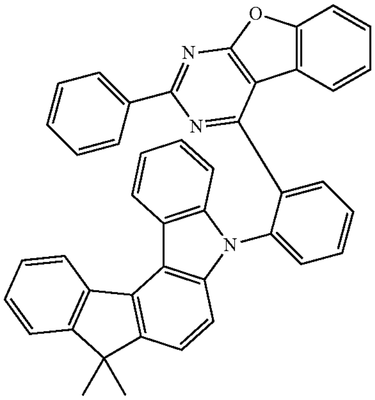
1606
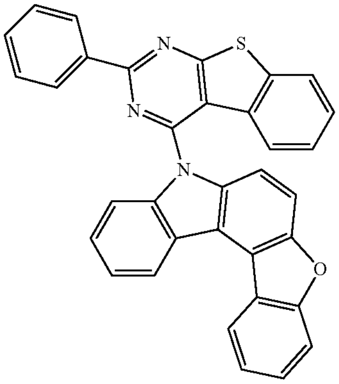
1607
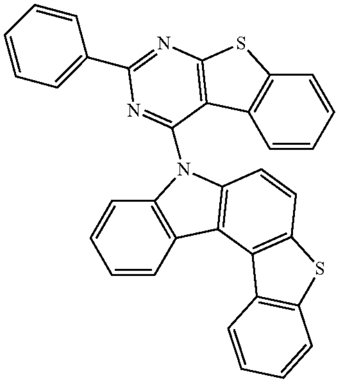
1608
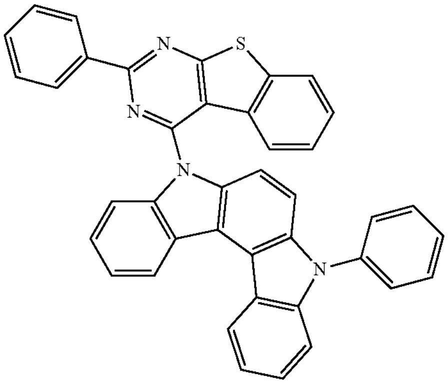

-continued
1609
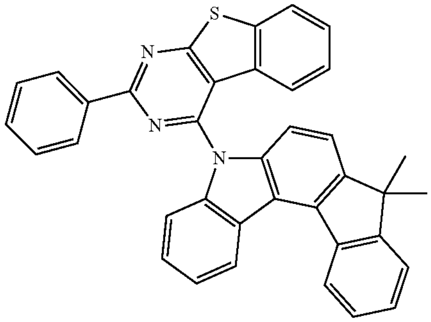
1610
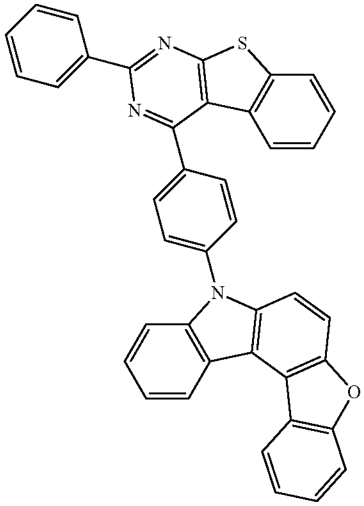
1611
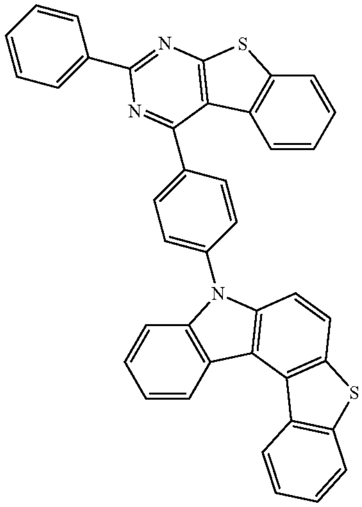
-continued
1612
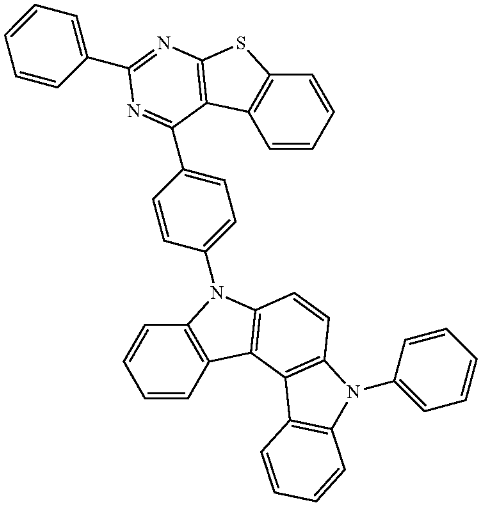
1613
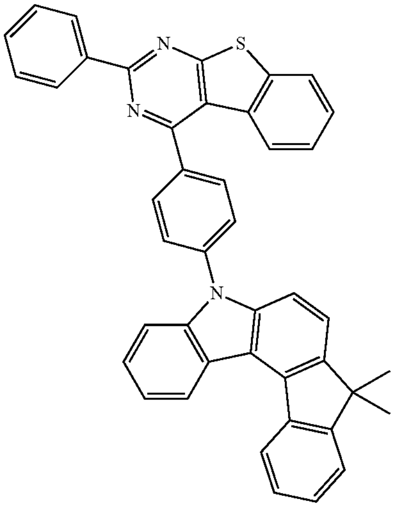
1614
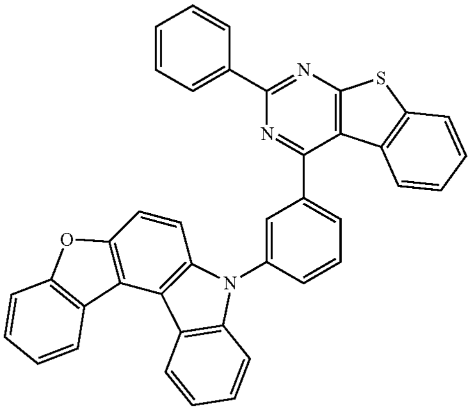

-continued
1615
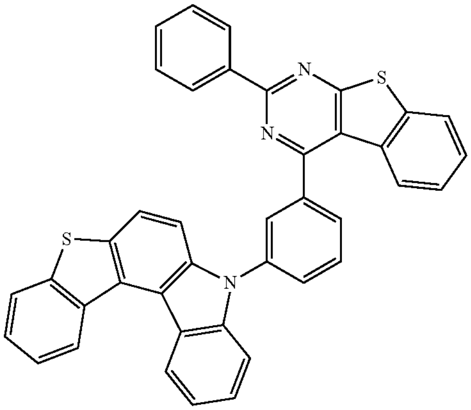
1616
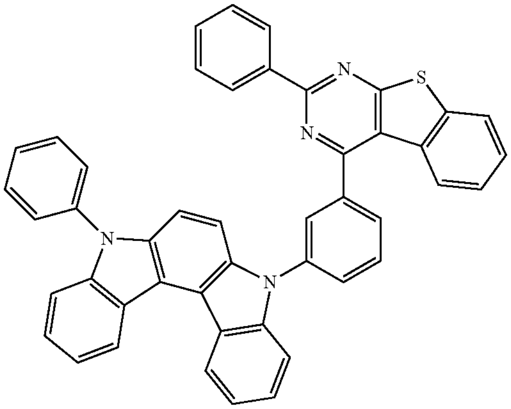
1617
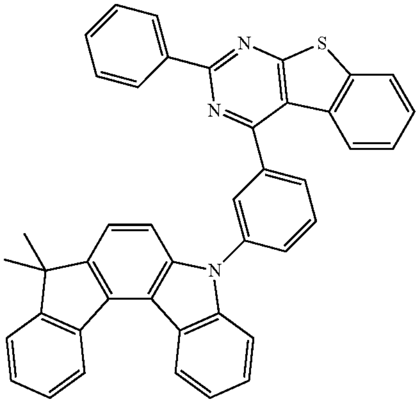
1618
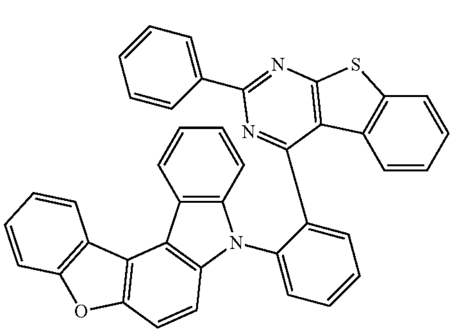
-continued
1619
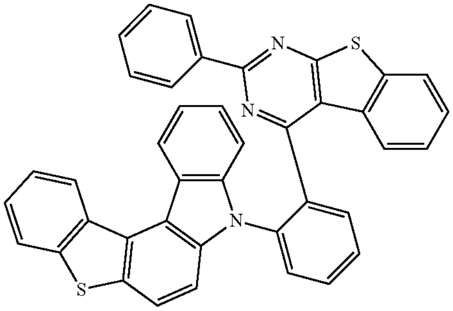
1620
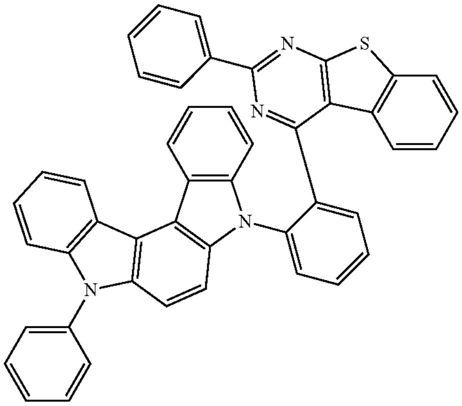
1621
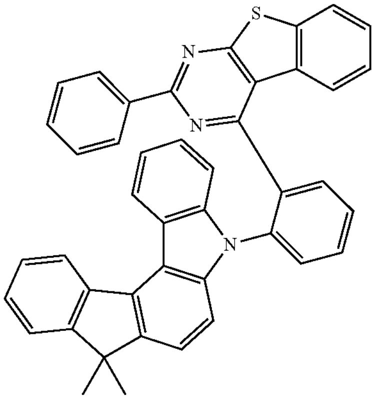
1622
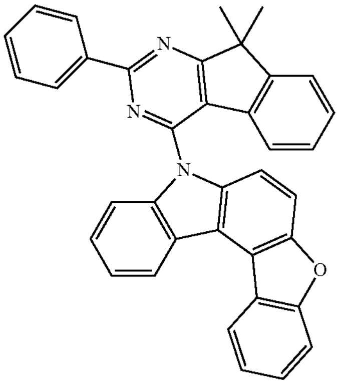

-continued
1623
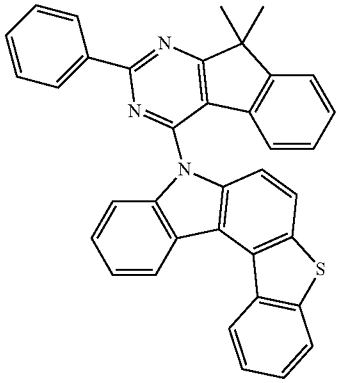
1624
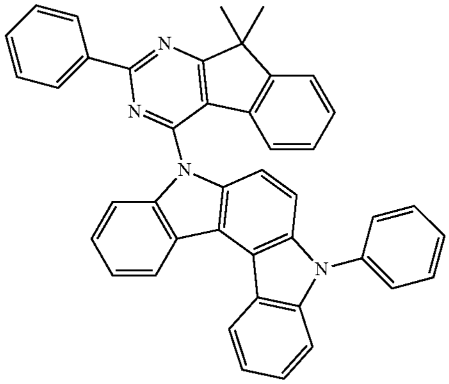
1625
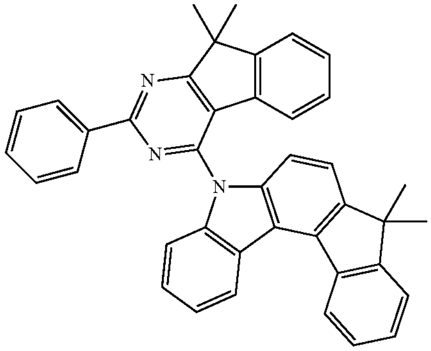
1626
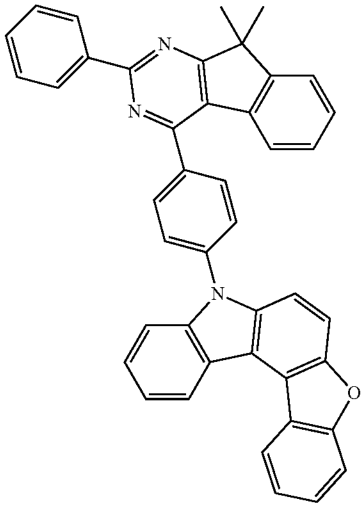
-continued
1627
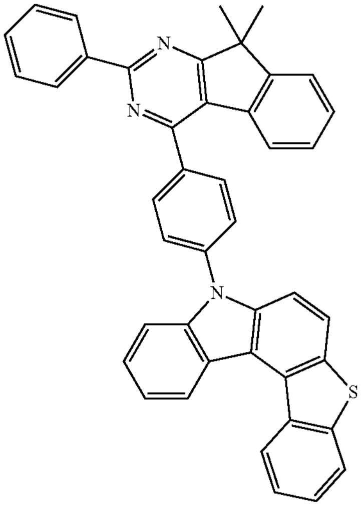
1628
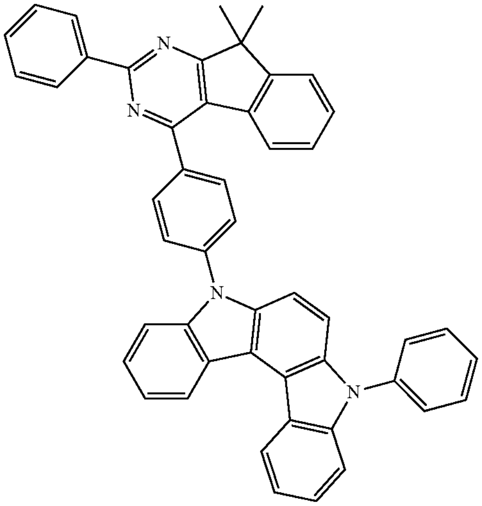
1629
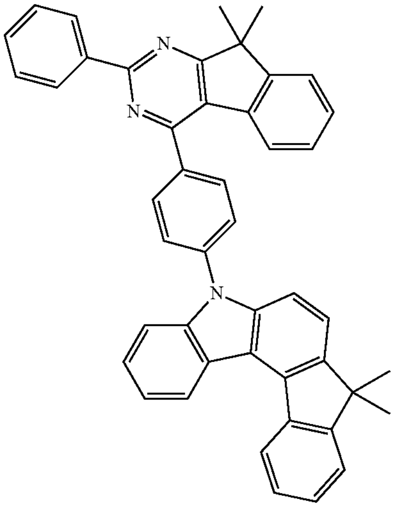

-continued
1630
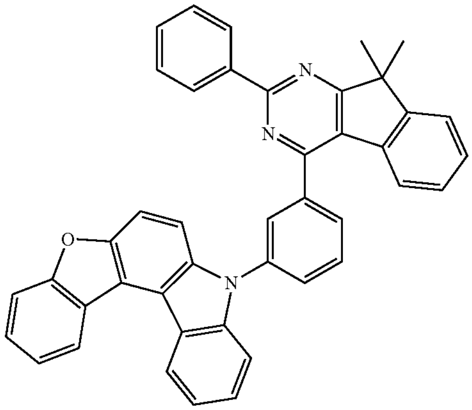
1631
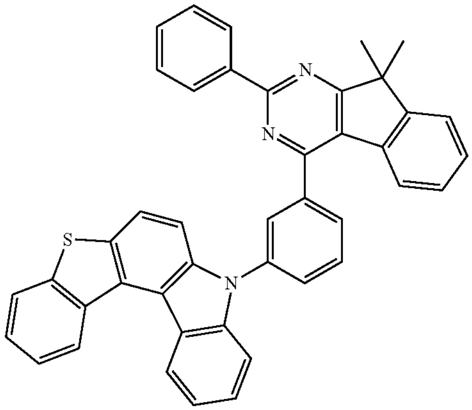
1632
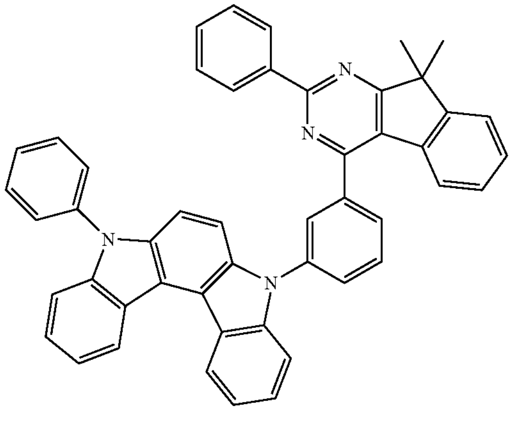
-continued
1633
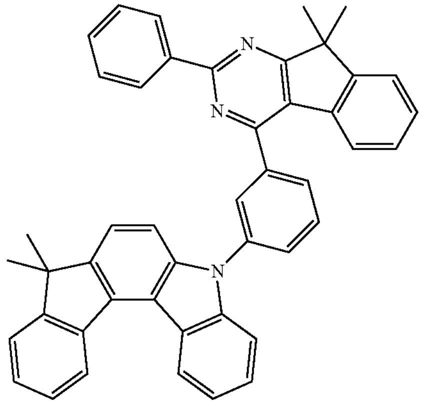
1634
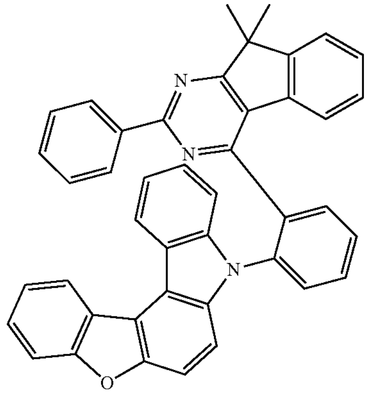
1635
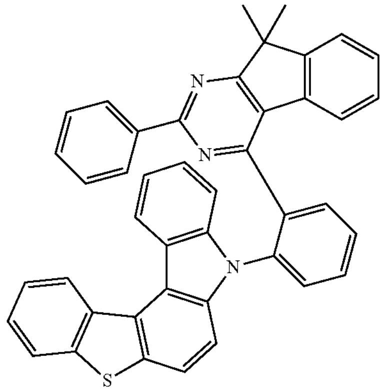

-continued
1636
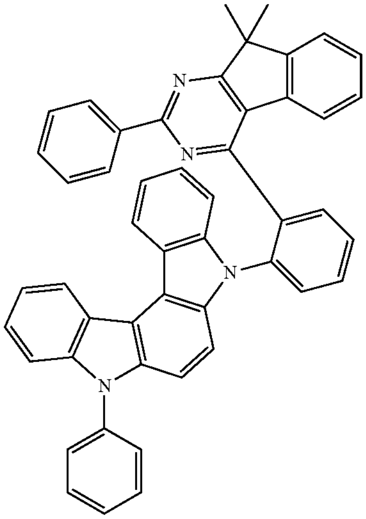
1637
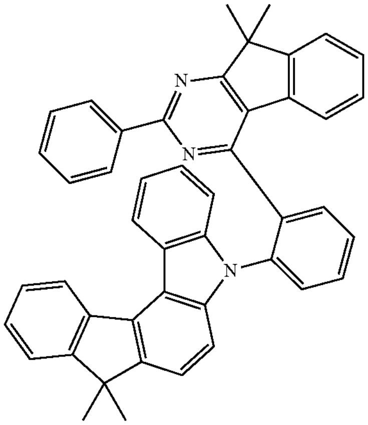
1638
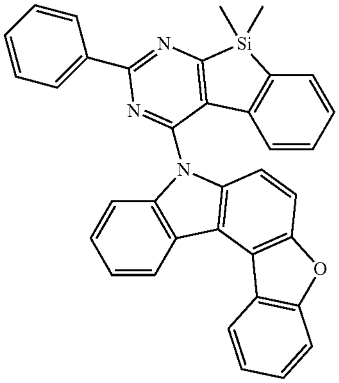
-continued
1639
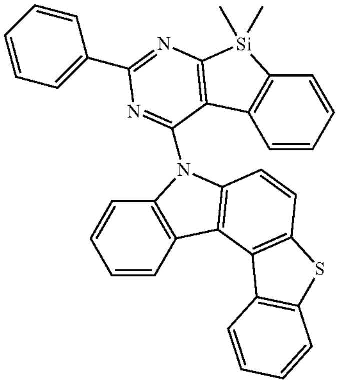
1640
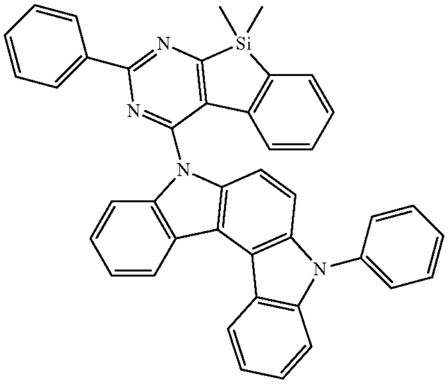
1641
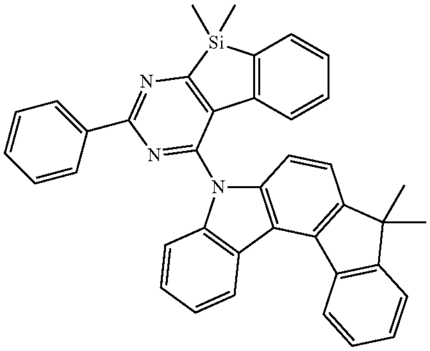
1642
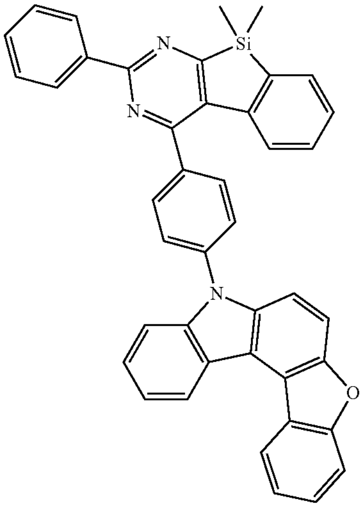

-continued
1643
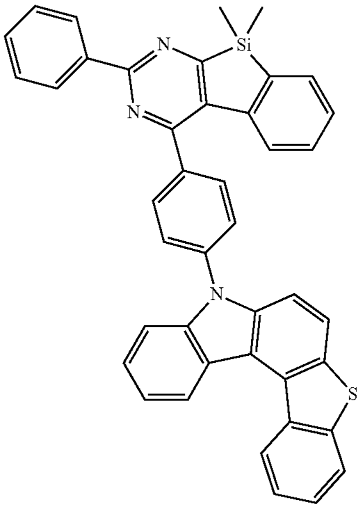
1644
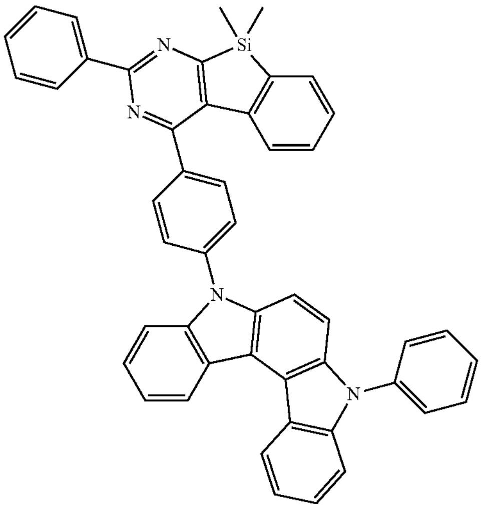
1645
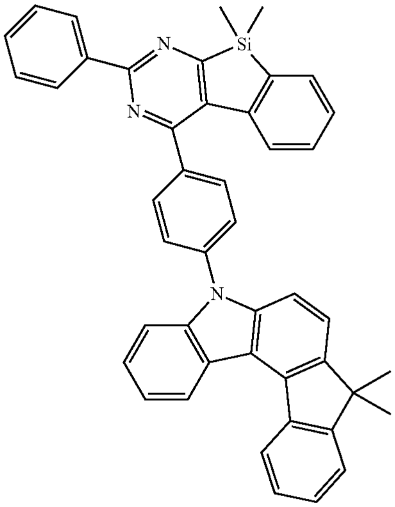
-continued
1646
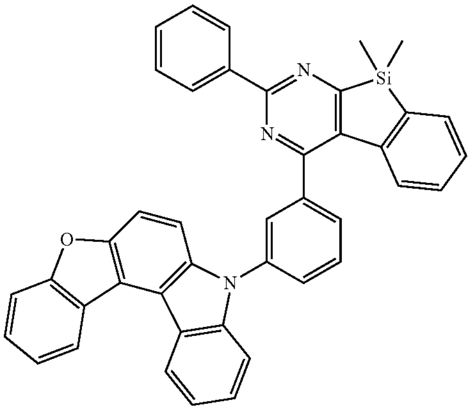
1647
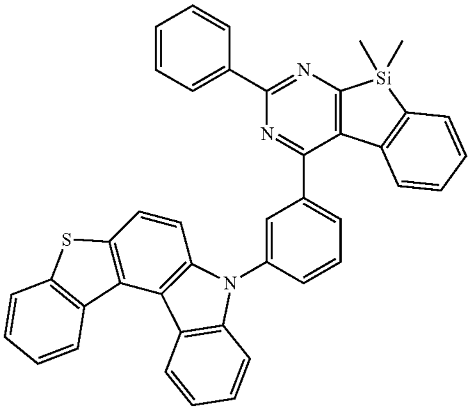
1648
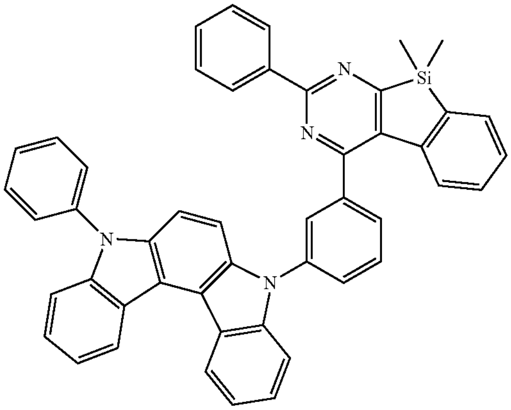

-continued
1649
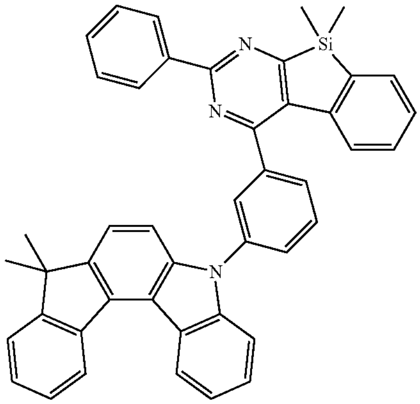
1650
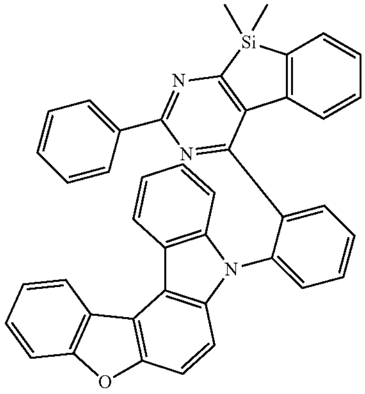
1651
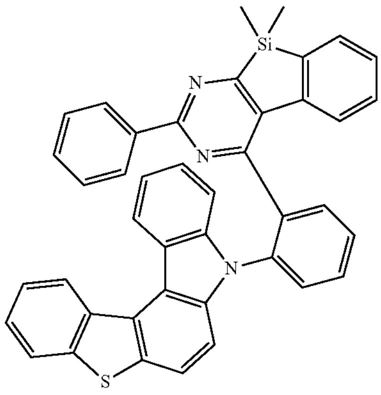
-continued
1652
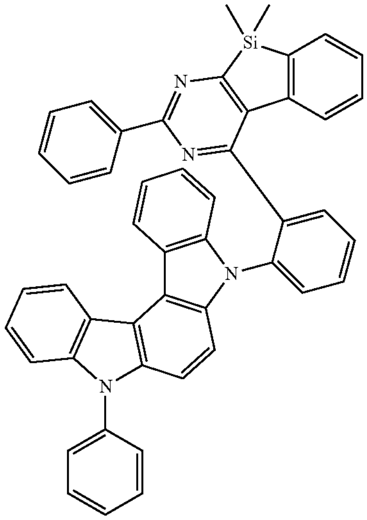
1653
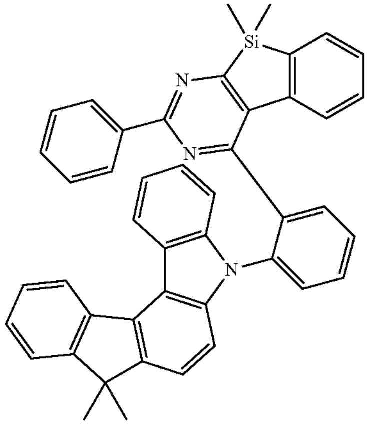
1654
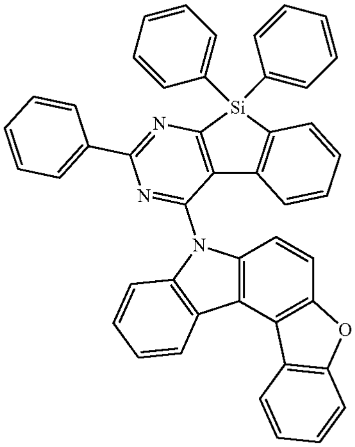

-continued
1655
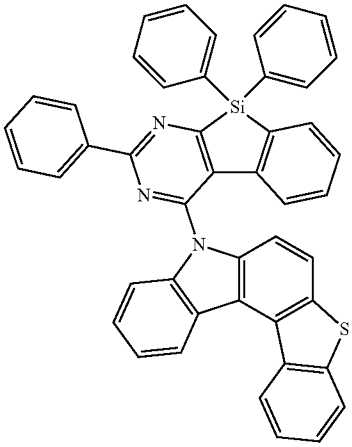
1656
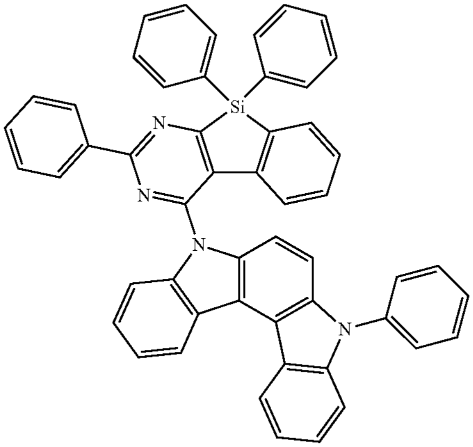
1657
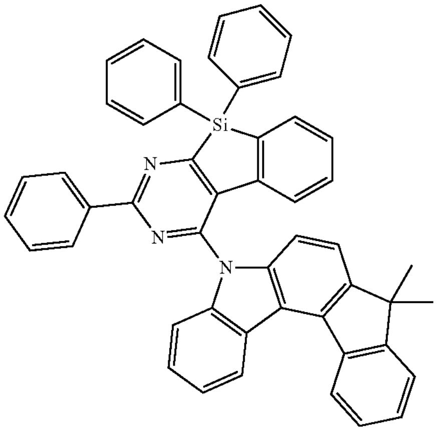
-continued
1658
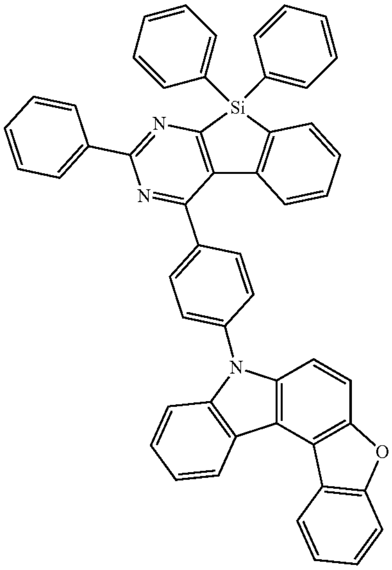
1659
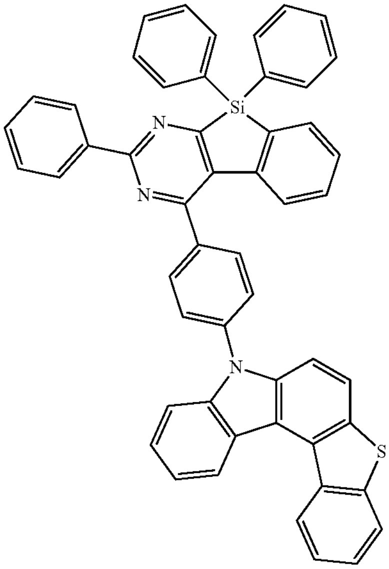

-continued
1660
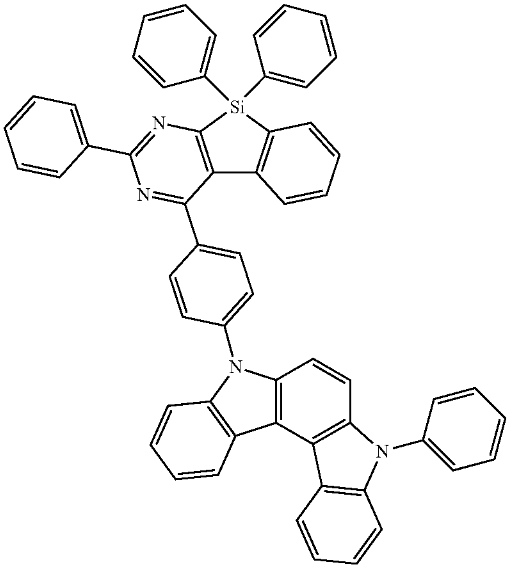
1661
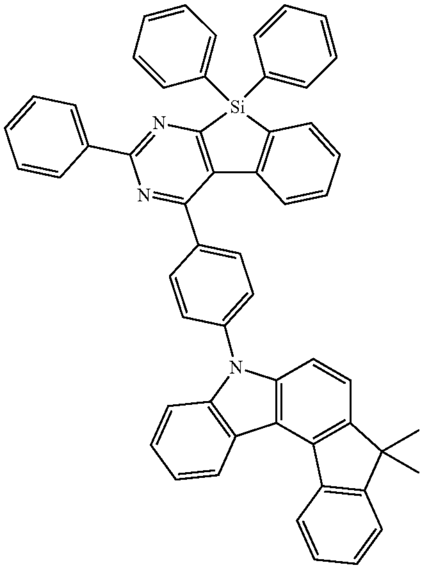
1662
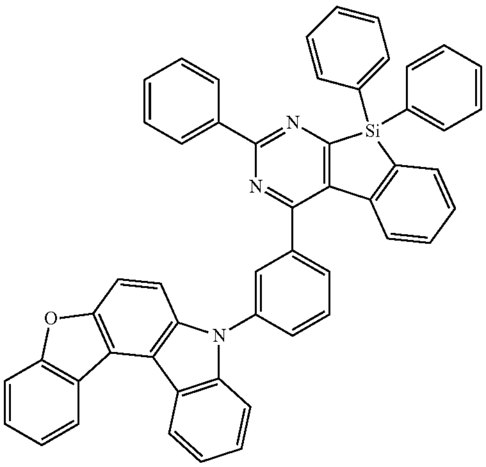
-continued
1663
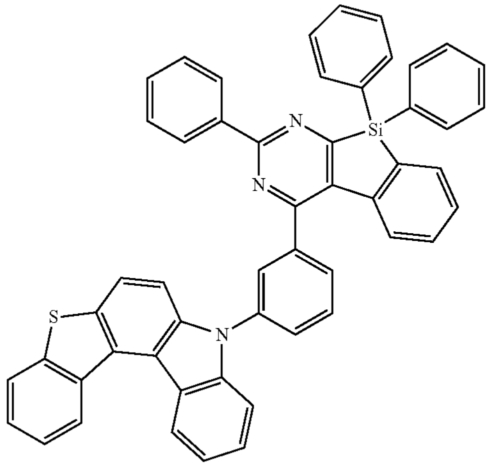
1664
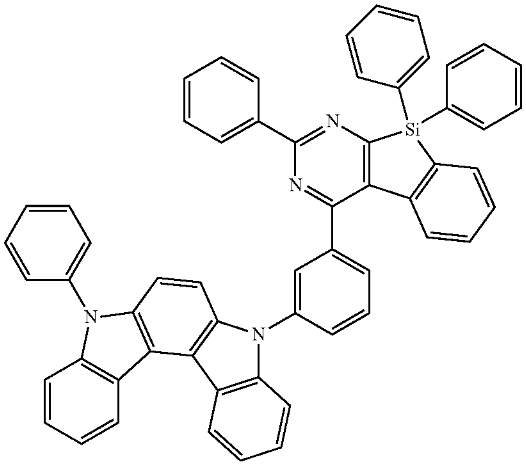
1665
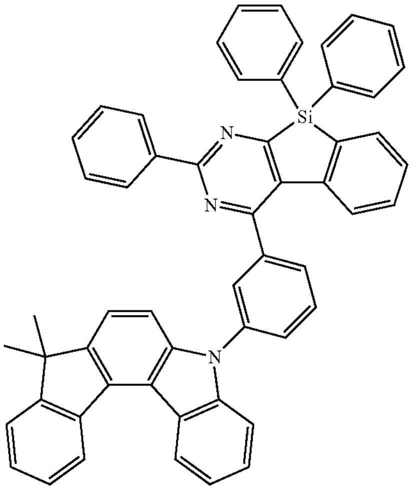

-continued
1666
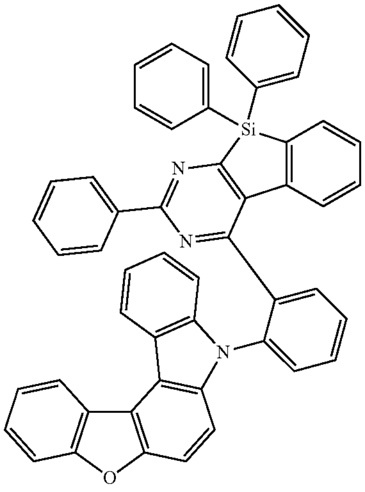
1667
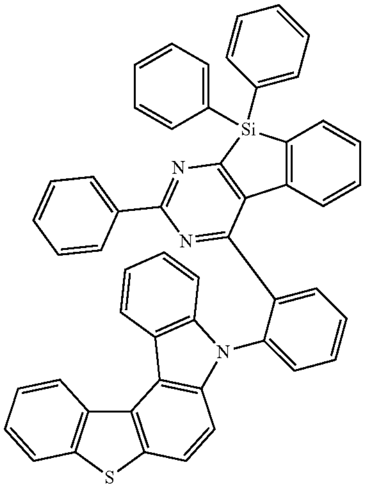
1668
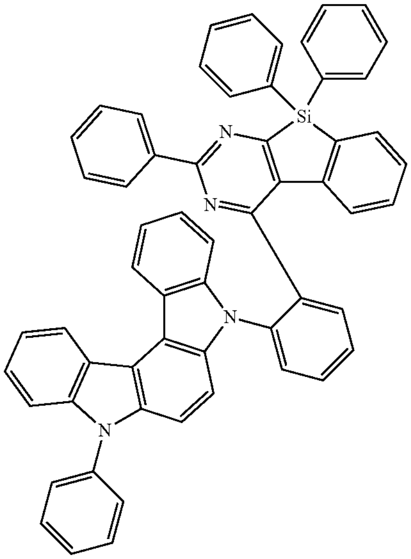
-continued
1669
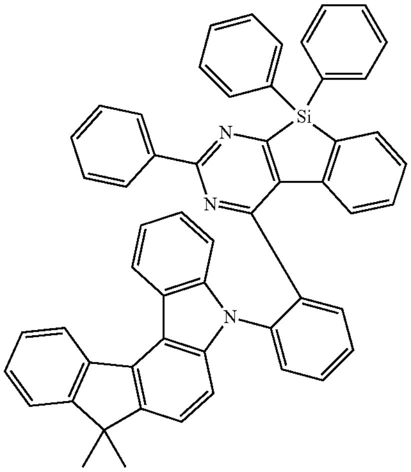
1670
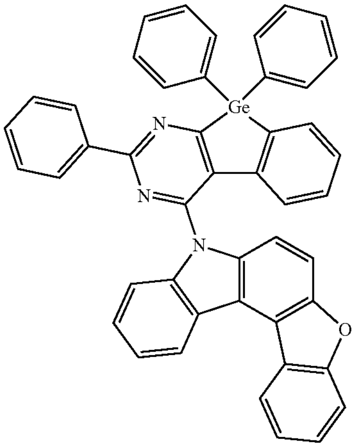
1671
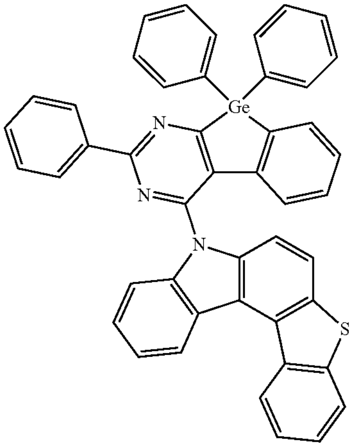

-continued
1672
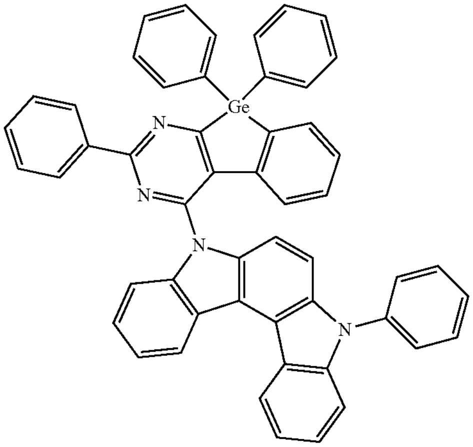
1673
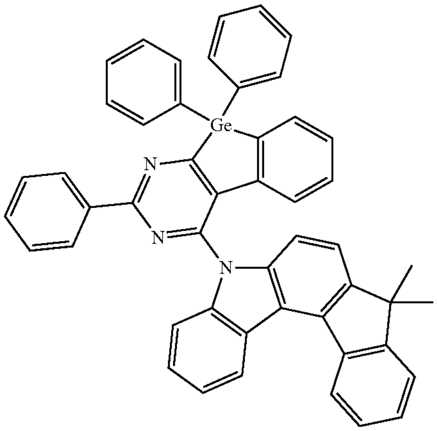
1674
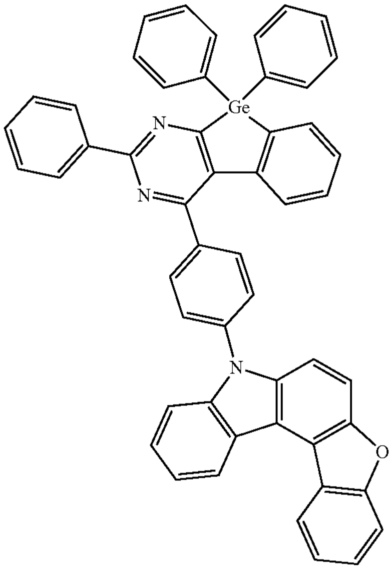
-continued
1675
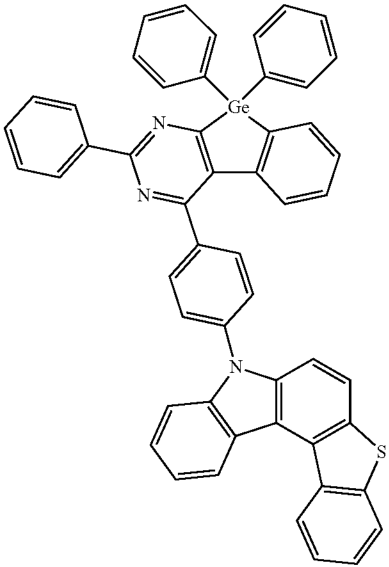
1676
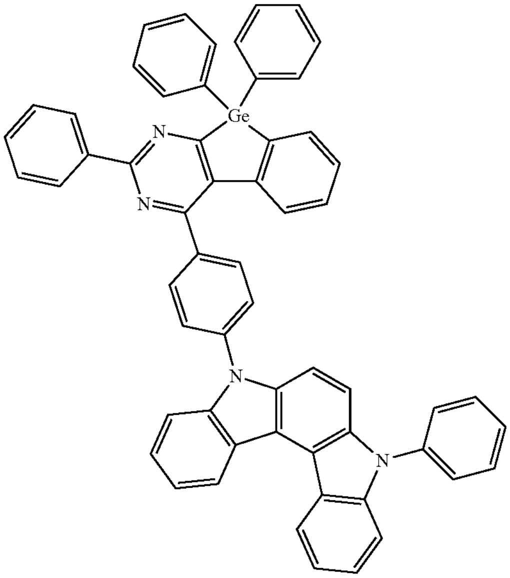

-continued
1677
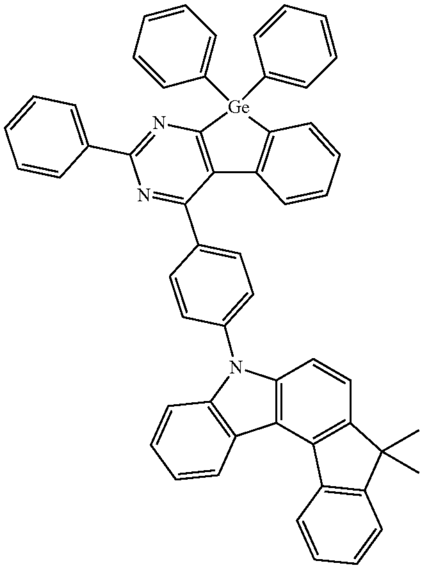
1678
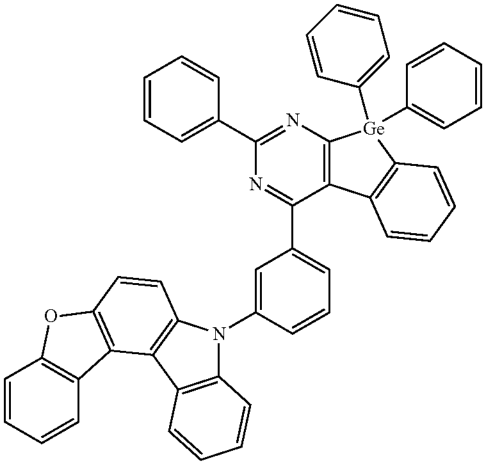
1679
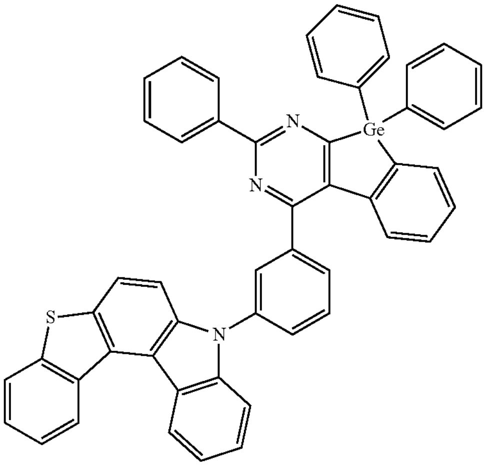
-continued
1680
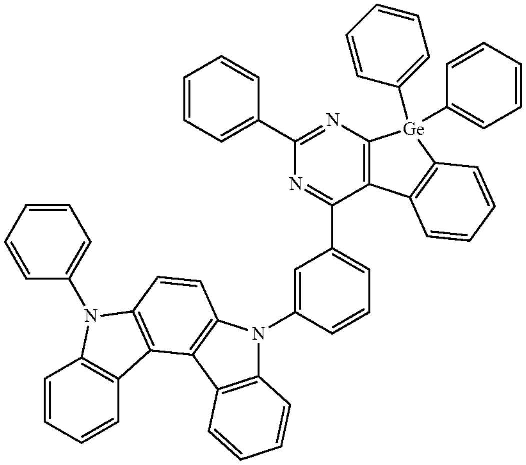
1681
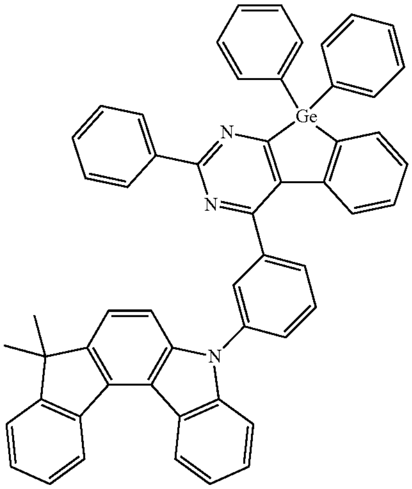
1682
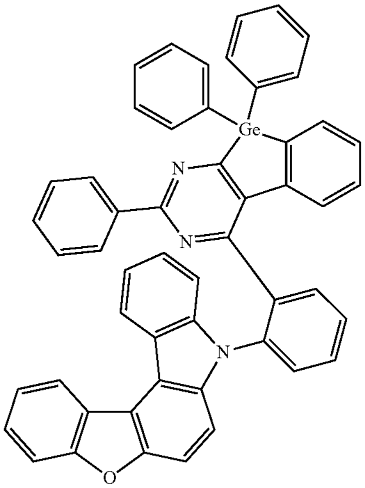

-continued
1683
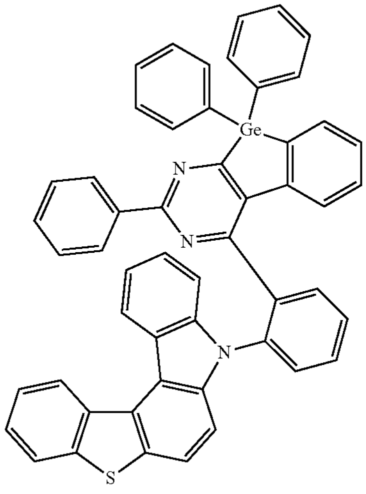
1684
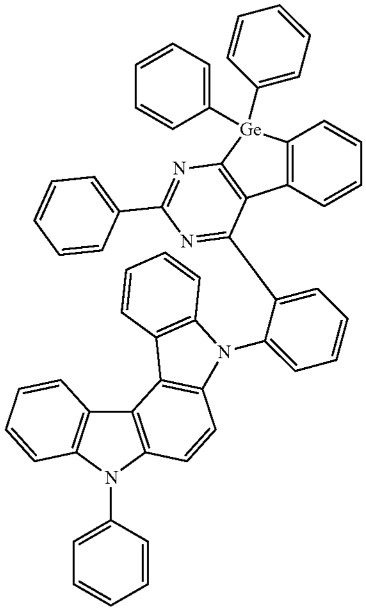
1685
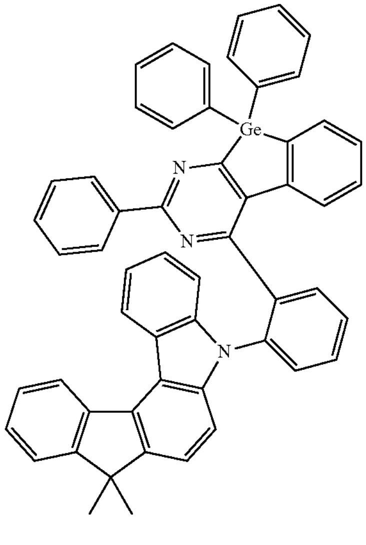
-continued
1686
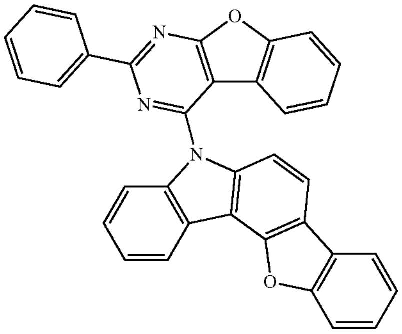
1687
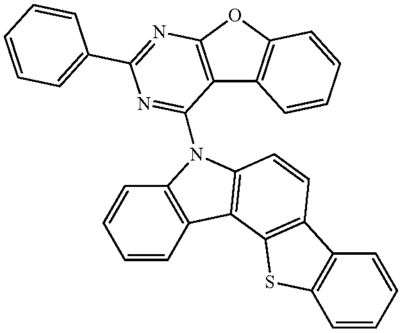
1688
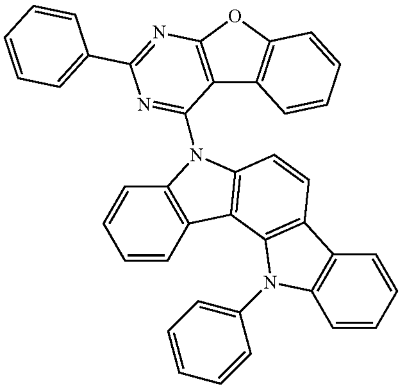
1689
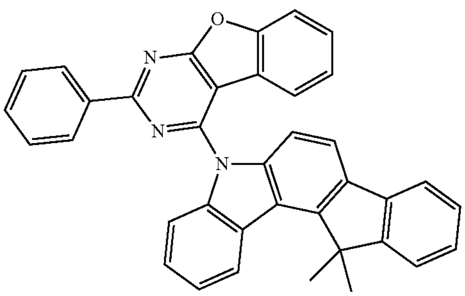

-continued
1690
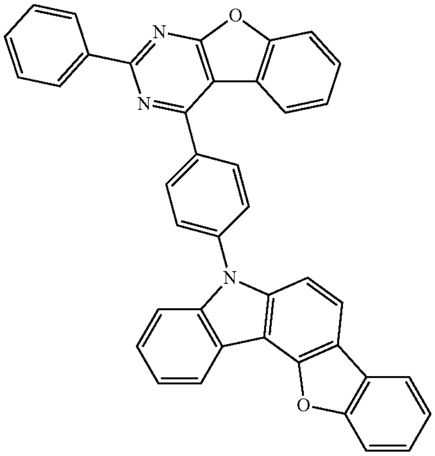
lp;2p
1691
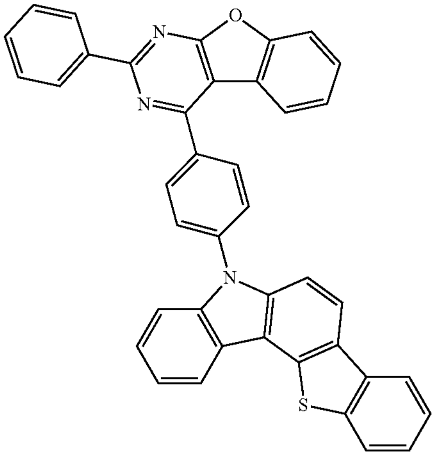
1692
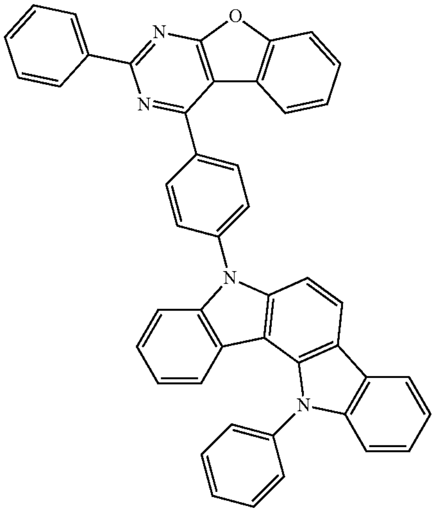
-continued
1693
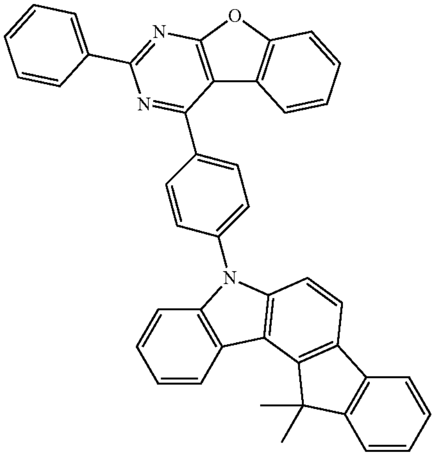
1694
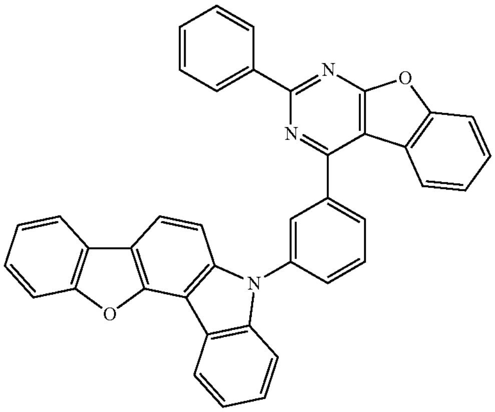
1695
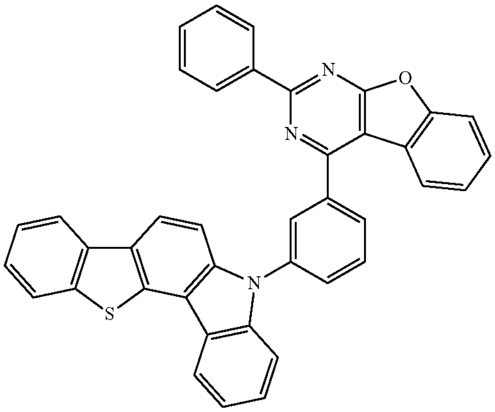

-continued
1696
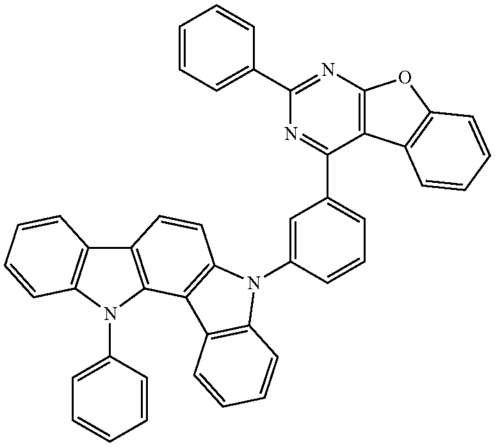
1697
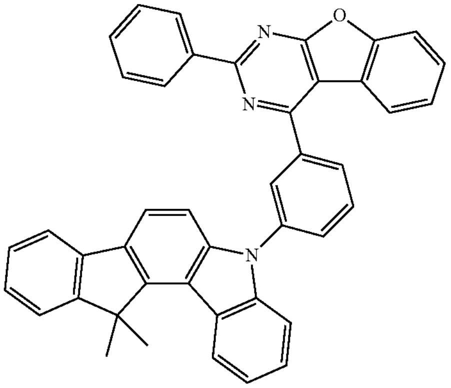
1698
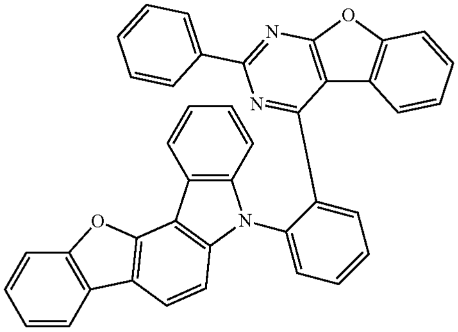
1699
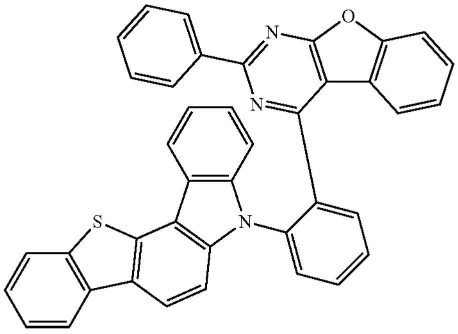
-continued
1700
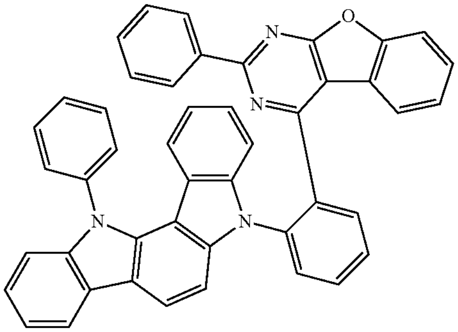
1701
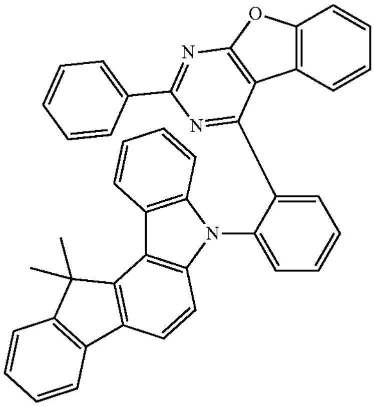
1702
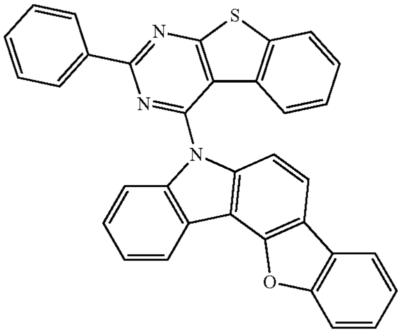
1703
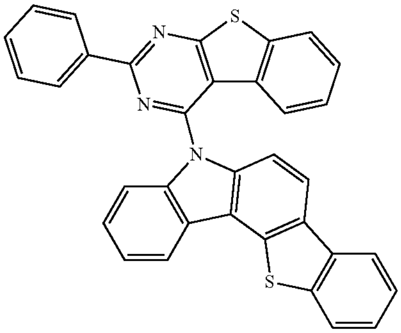

-continued
1704
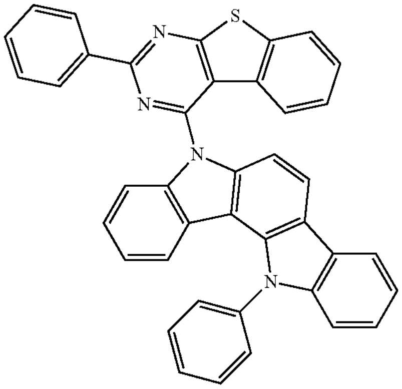
1705
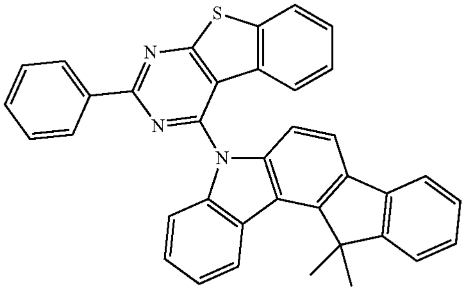
1706
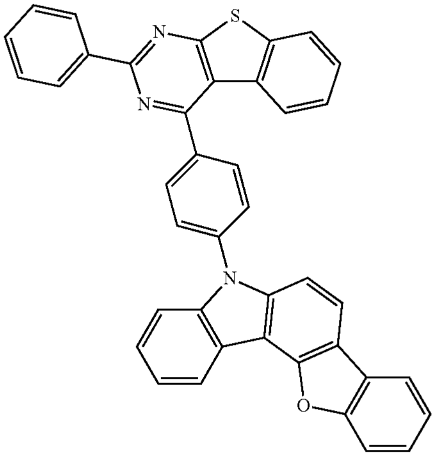
1707
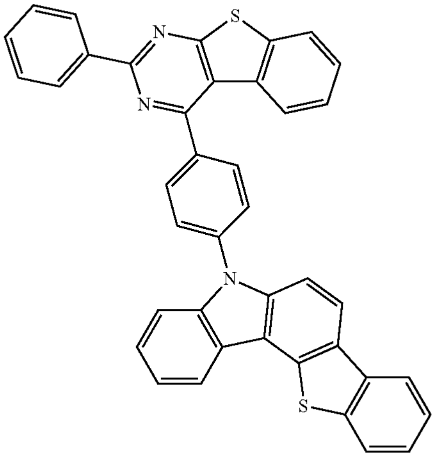
-continued
1708
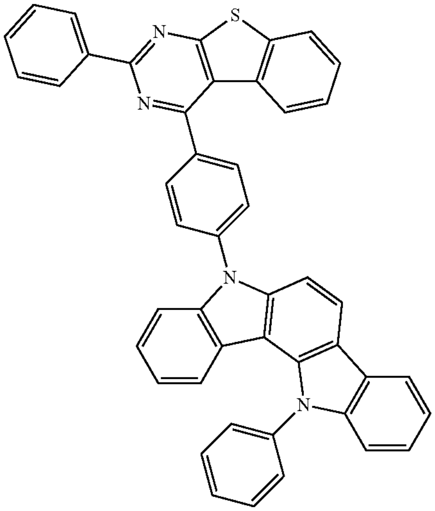
1709
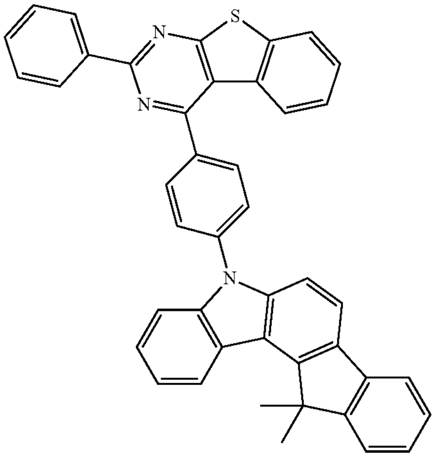
1710
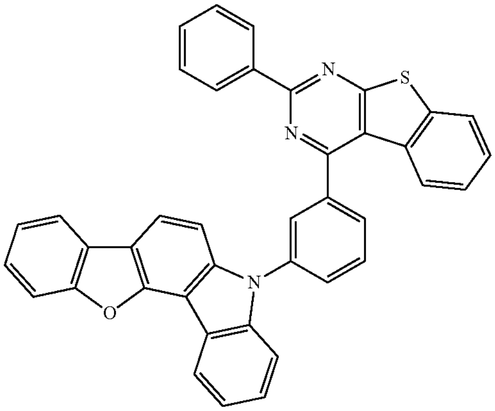

-continued
1711
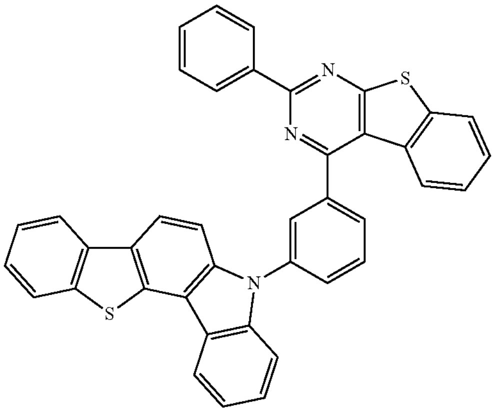
1712
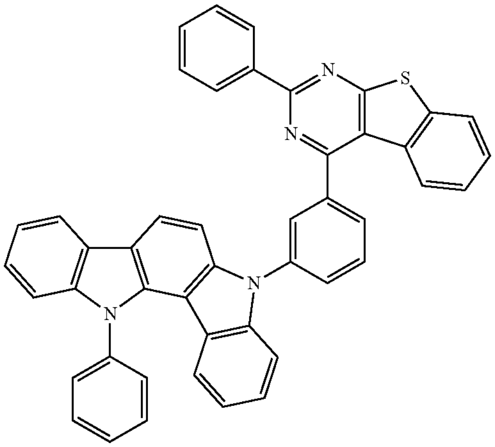
1713
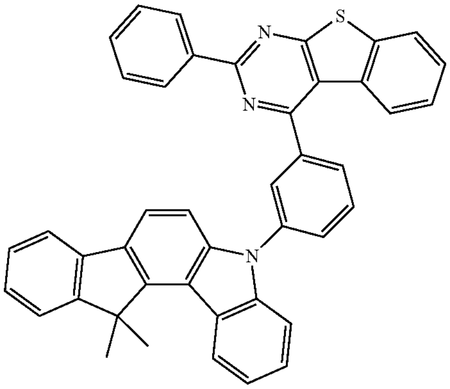
1714
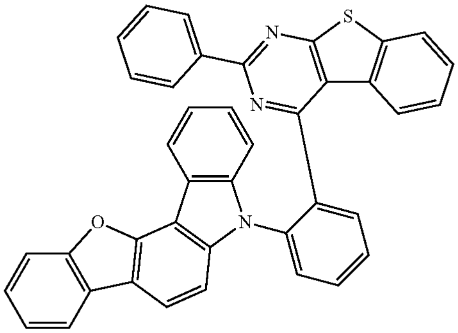
-continued
1715
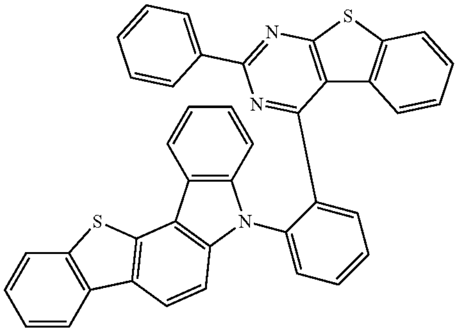
1716
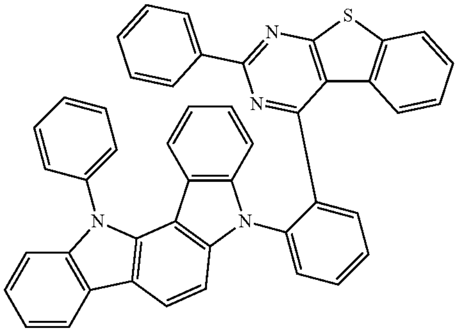
1717
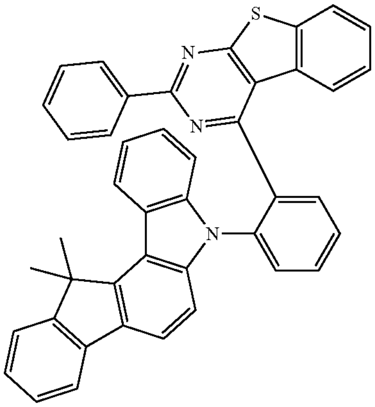
1718
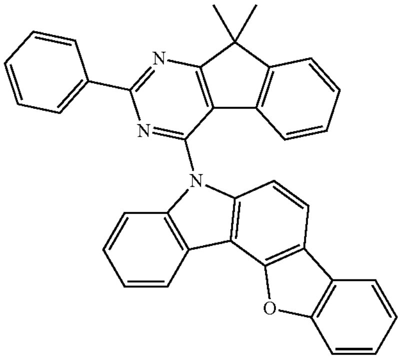

-continued
1719
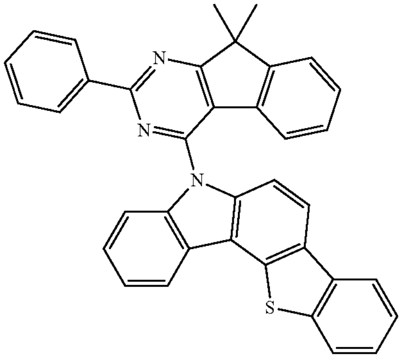
1720
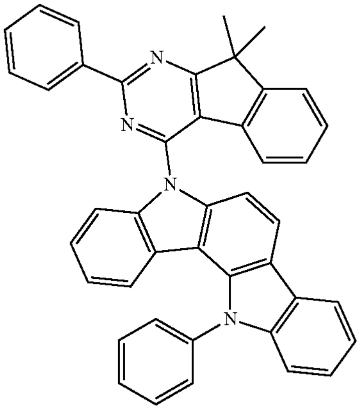
1721
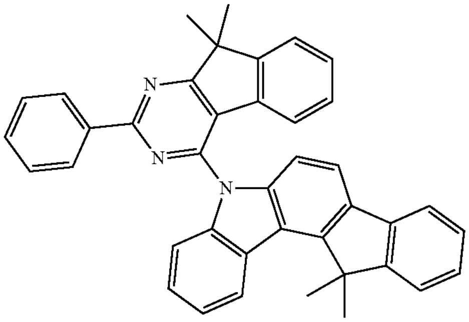
1722
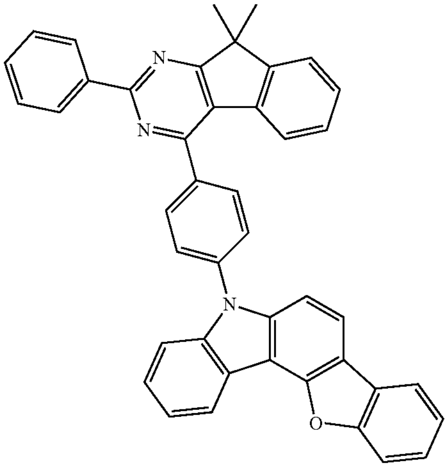
-continued
1723
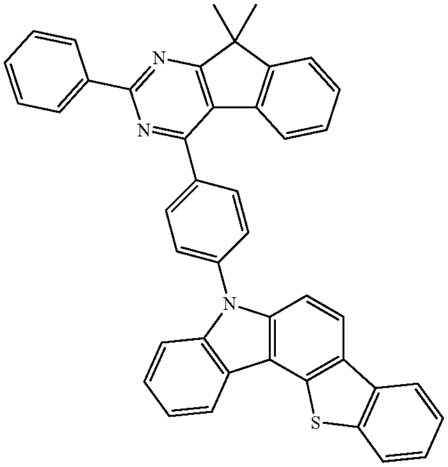
1724
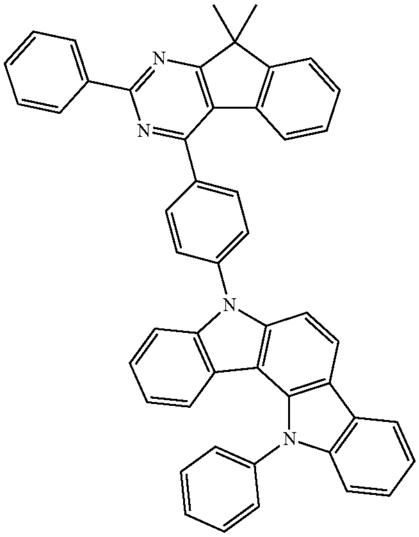
1725
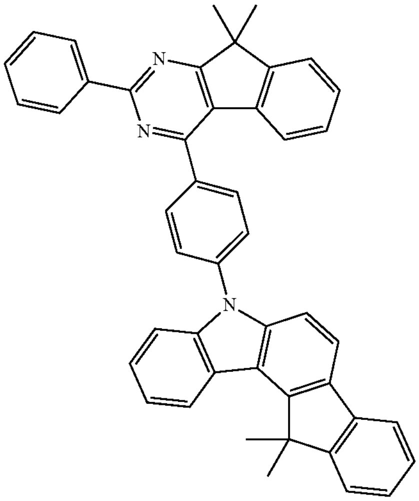

1726
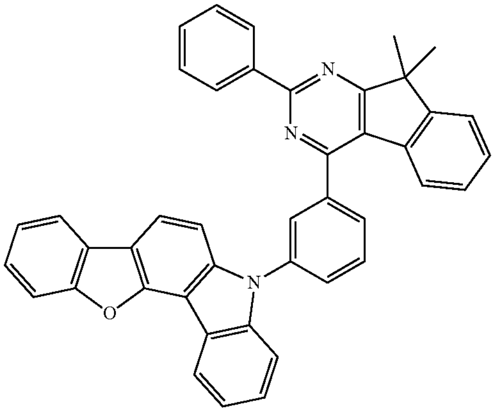
1727
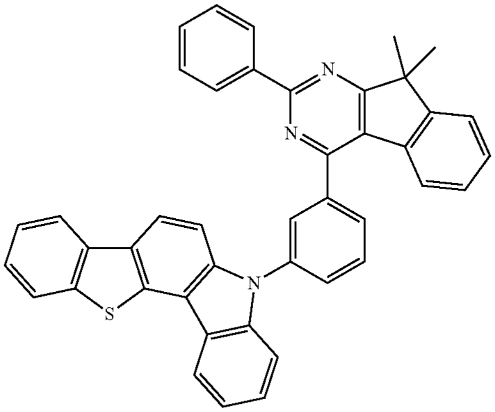
1728
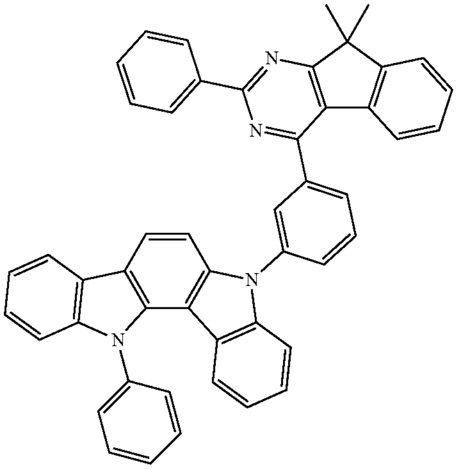
1729
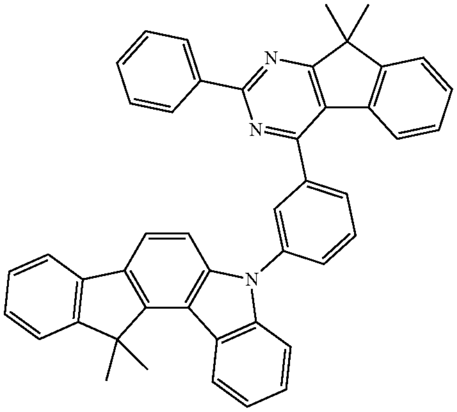
1730
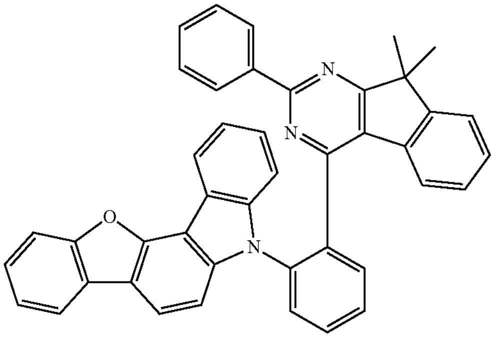
1731
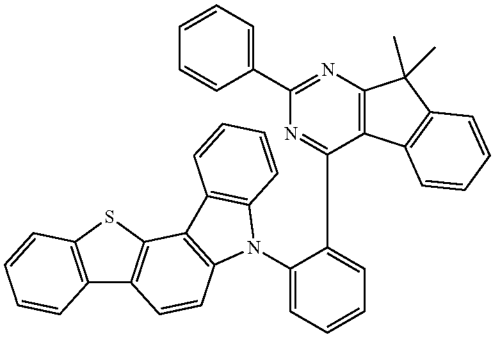
1732
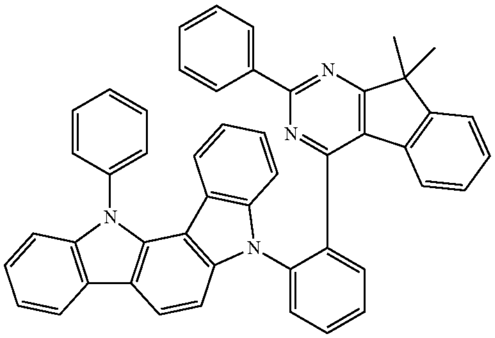

-continued
1733
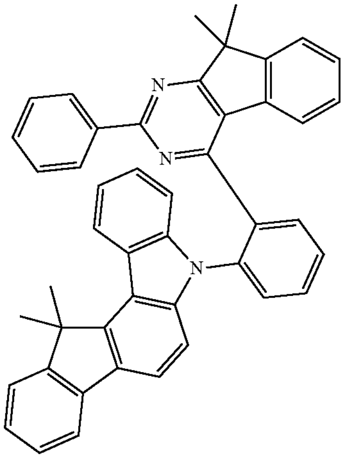
1734
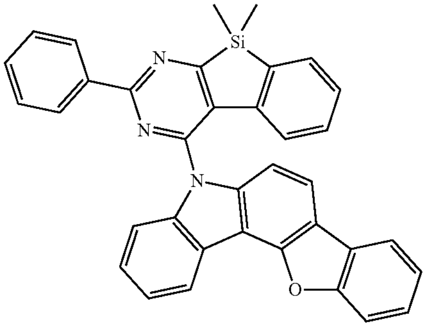
1735
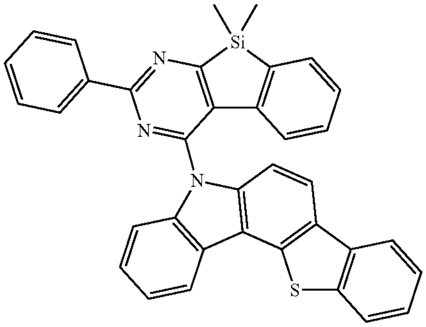
1736
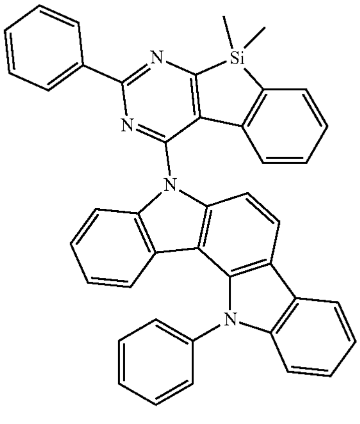
-continued
1737
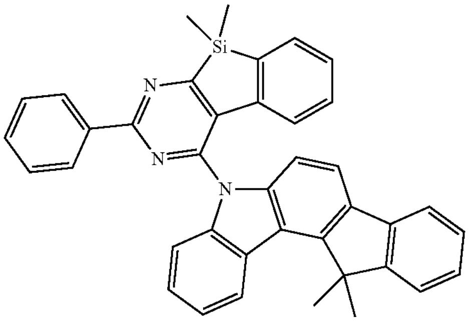
1738
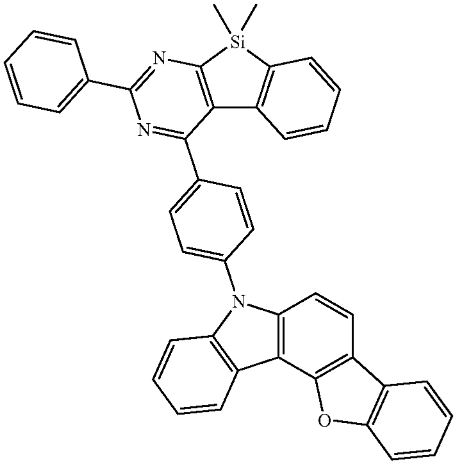
1739
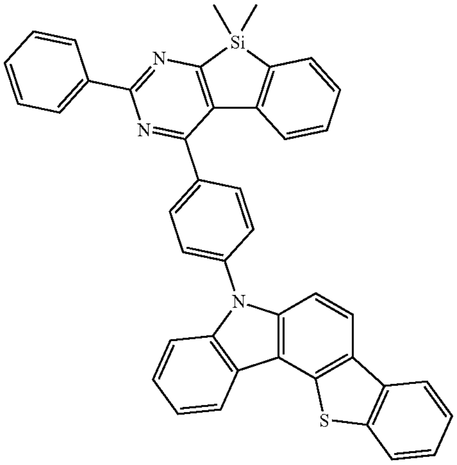

-continued
1740
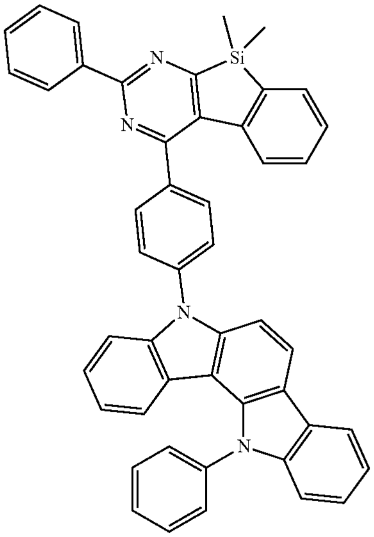
1741
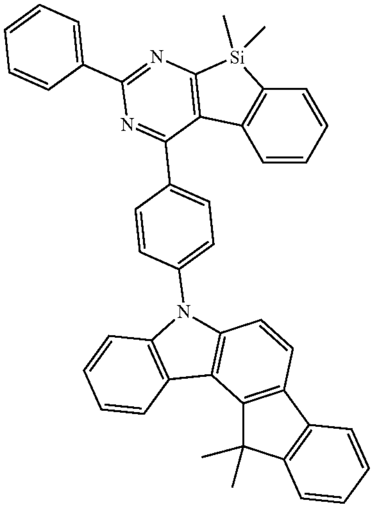
1742
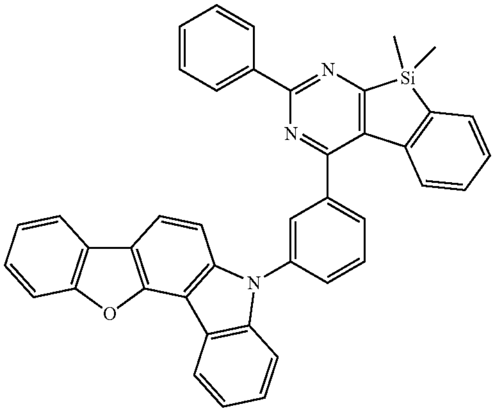
-continued
1743
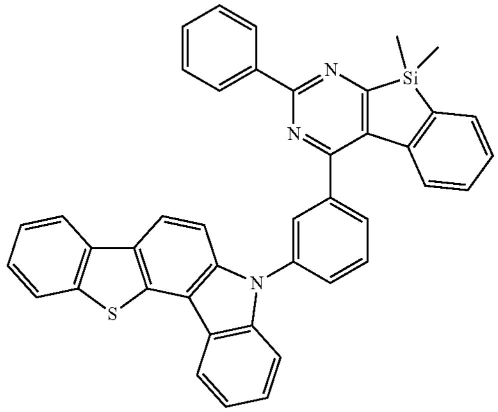
1744
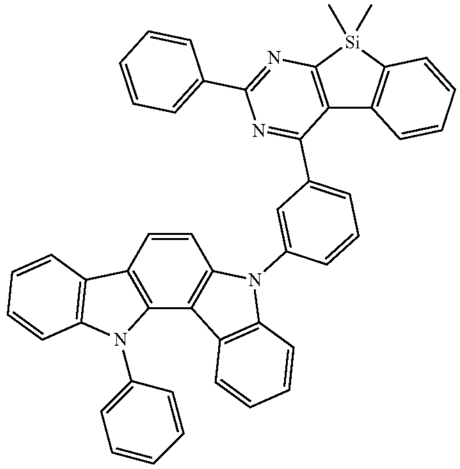
1745
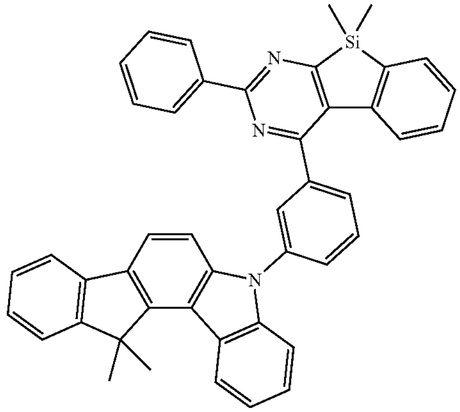

-continued
1746
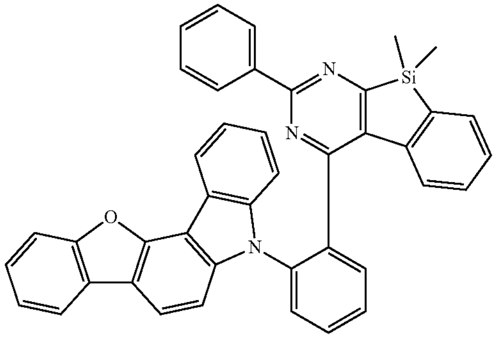
1747
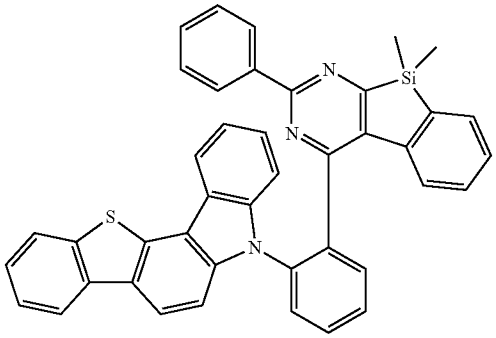
1748
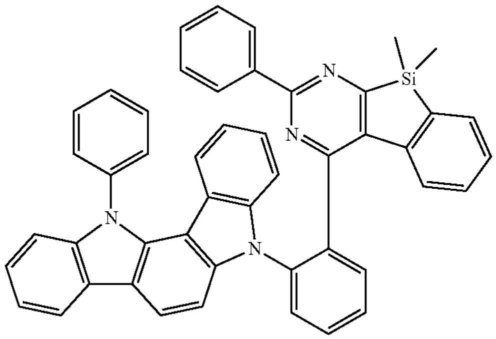
1749
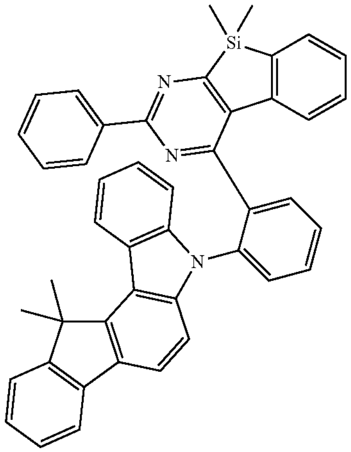
-continued
1750
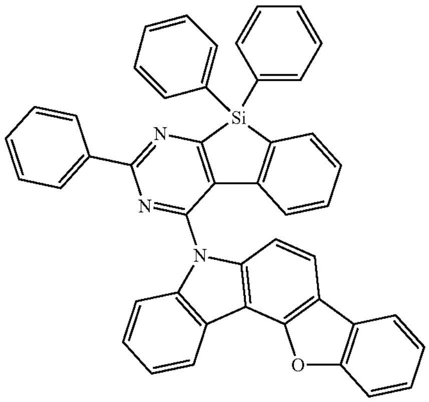
1751
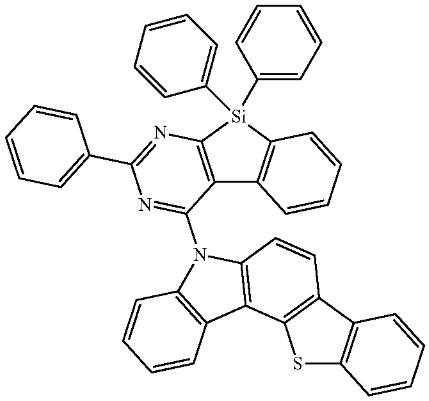
1752
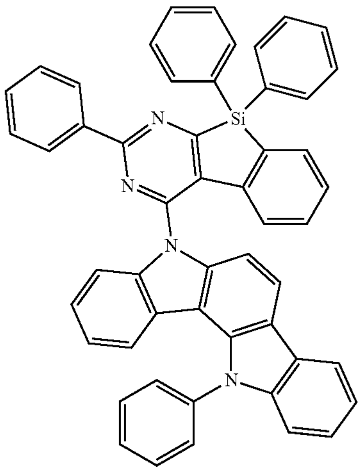

-continued
1753
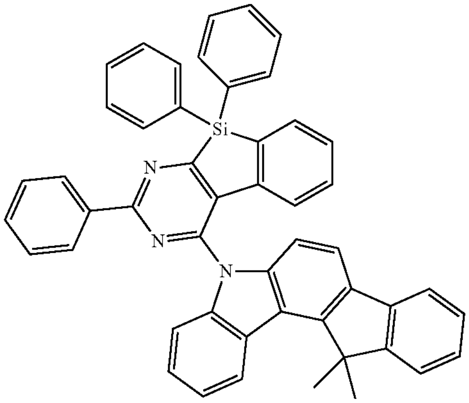
1754
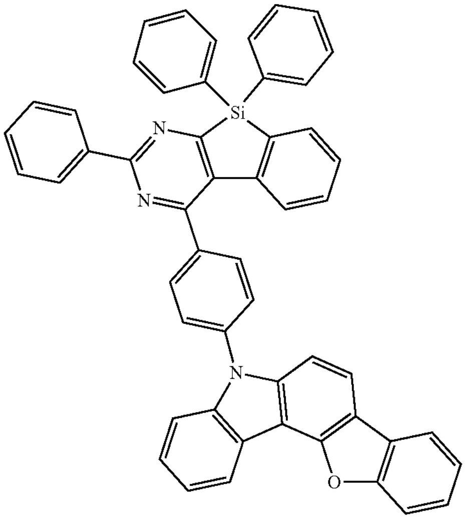
1755
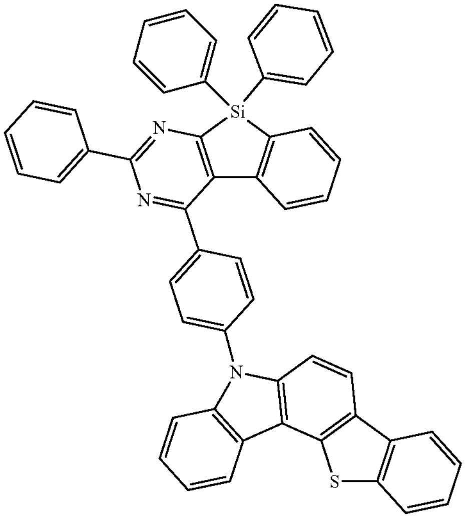
-continued
1756
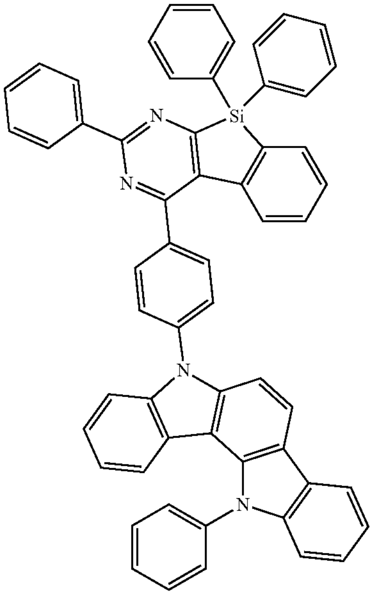
1757
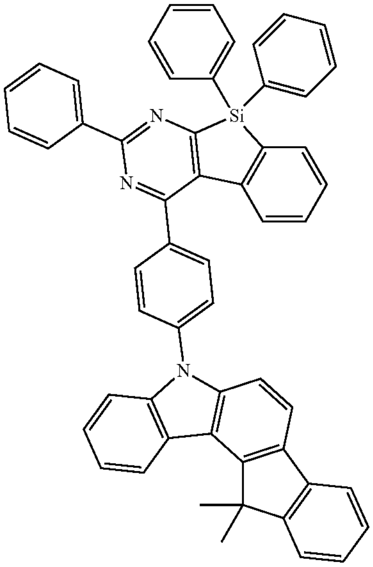
1758
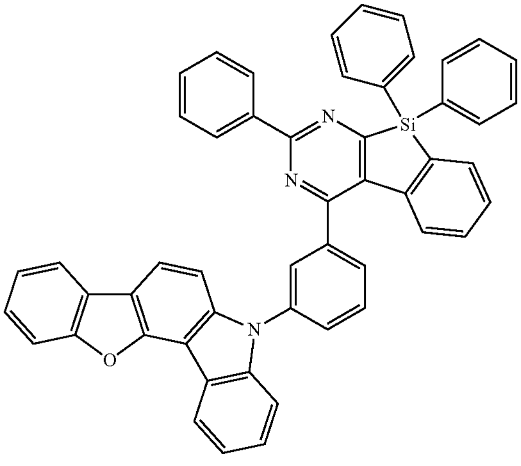

-continued
1759
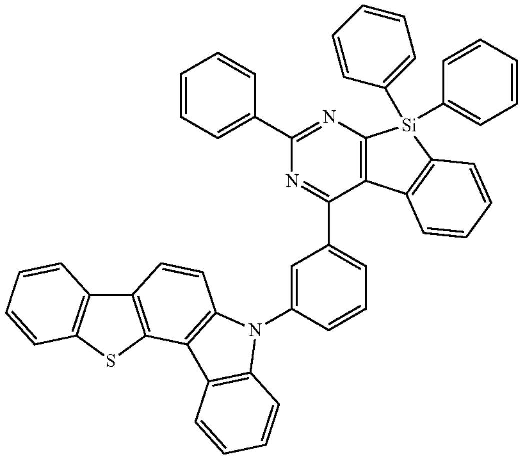
1760
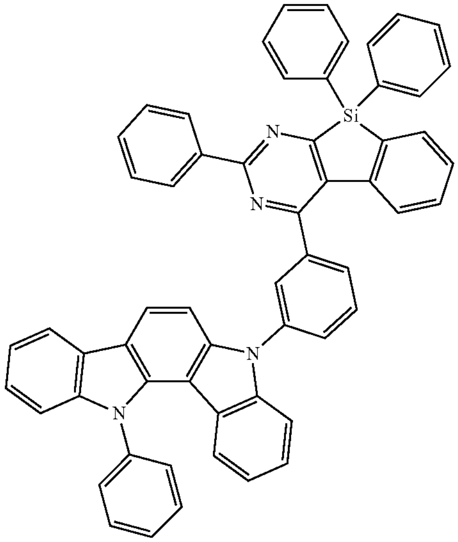
1761
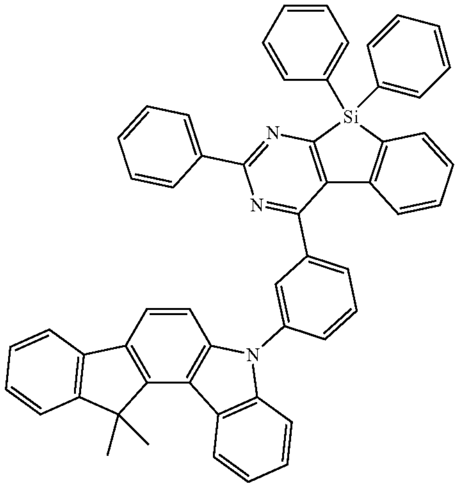
-continued
1762
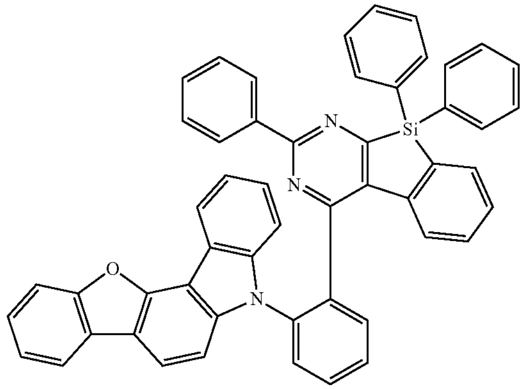
1763
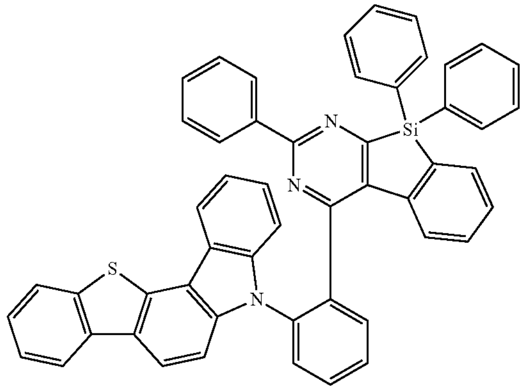
1764
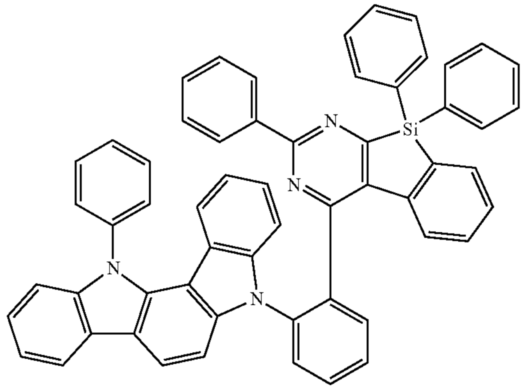

1765
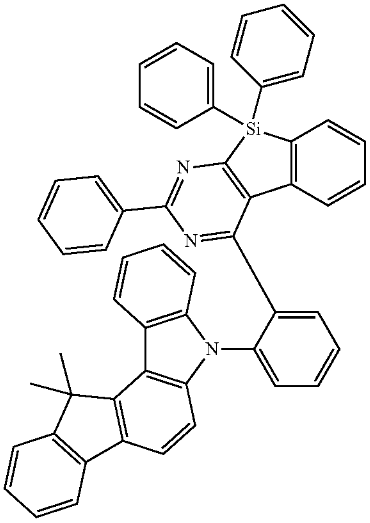
1766
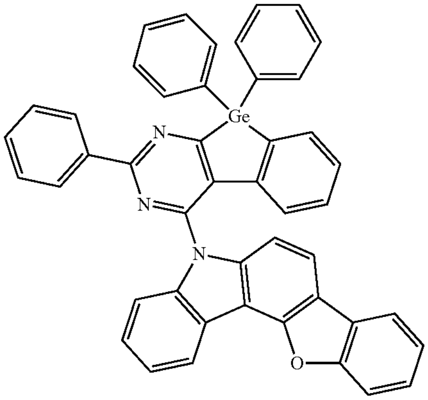
1767
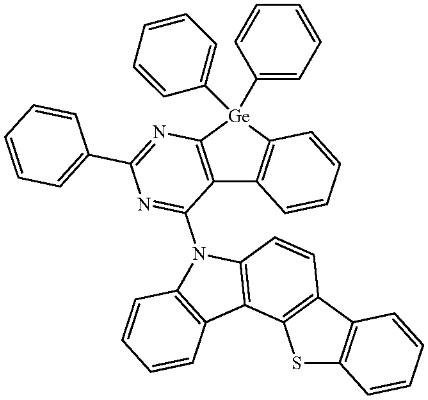
1768
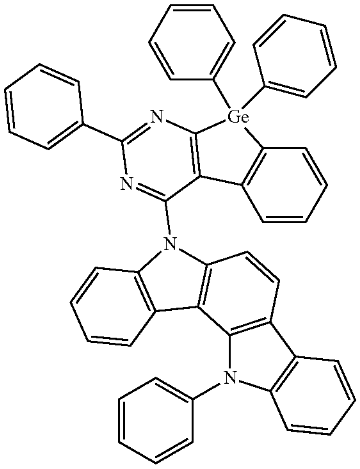
1769
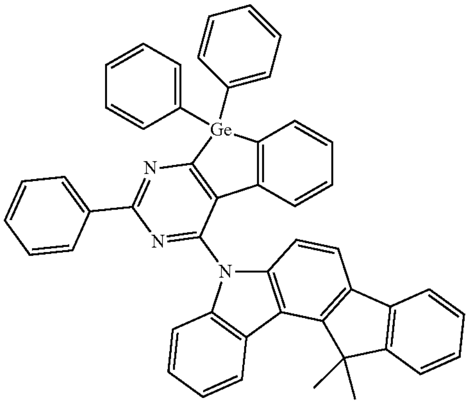
1770
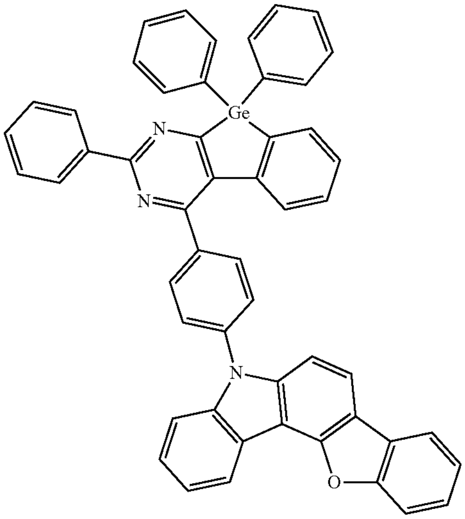

-continued
1771
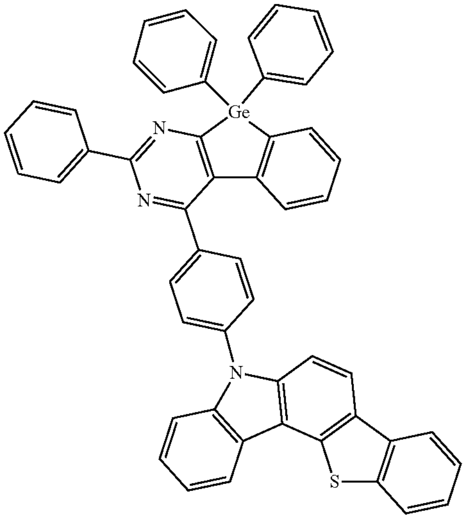
1772
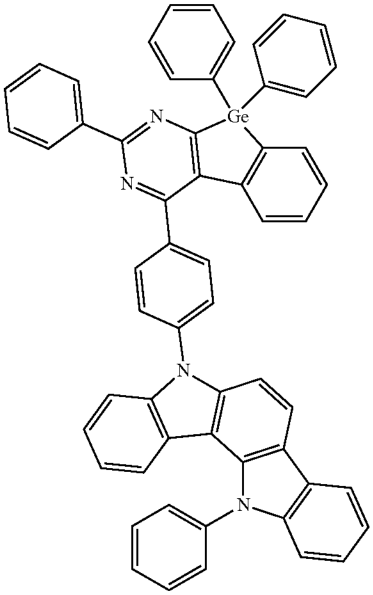
-continued
1773
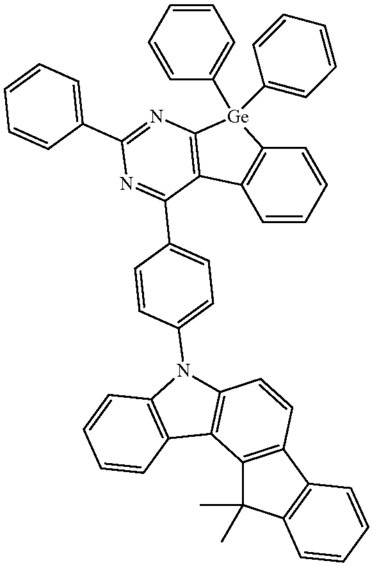
1774
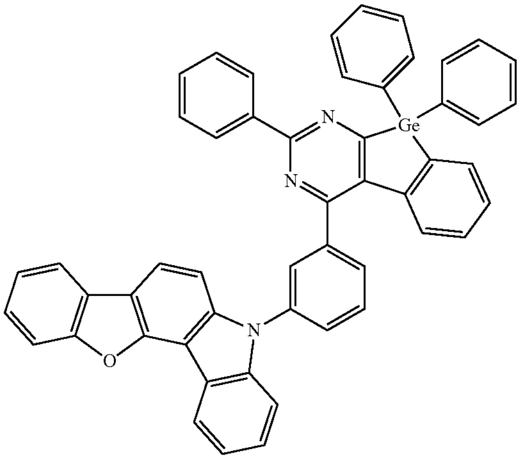
1775
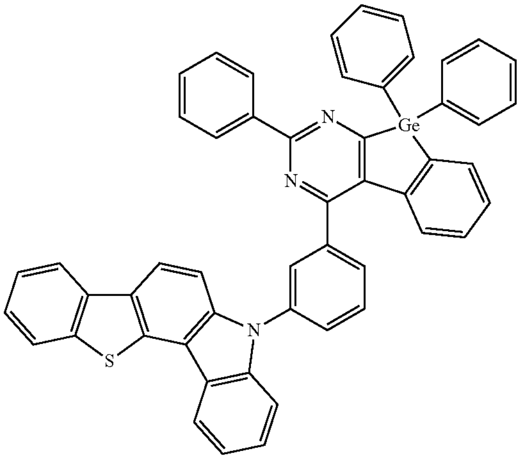

-continued
1776
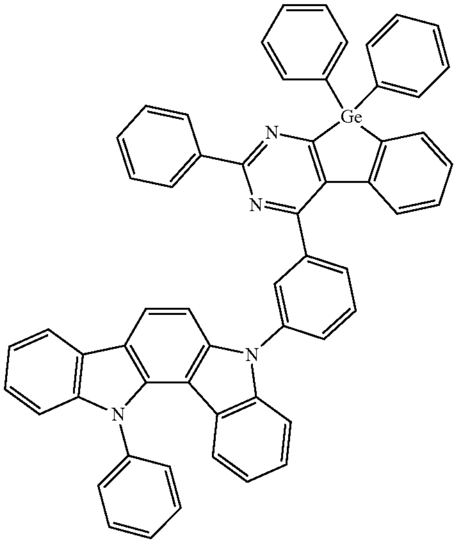
1777
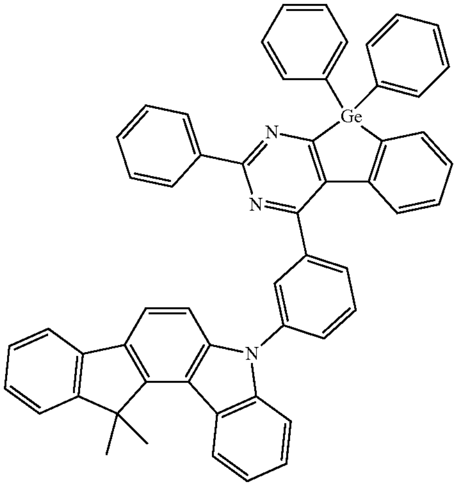
1778
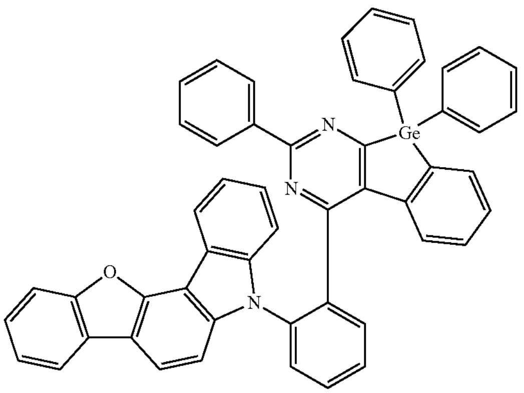
-continued
1779
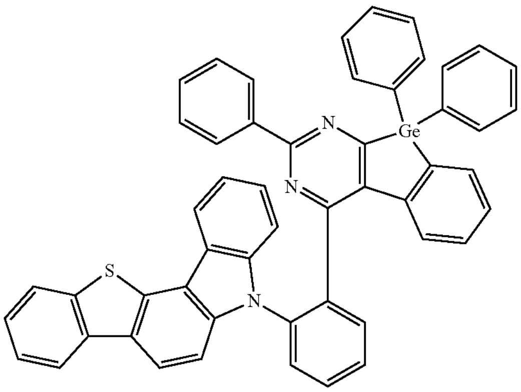
1780
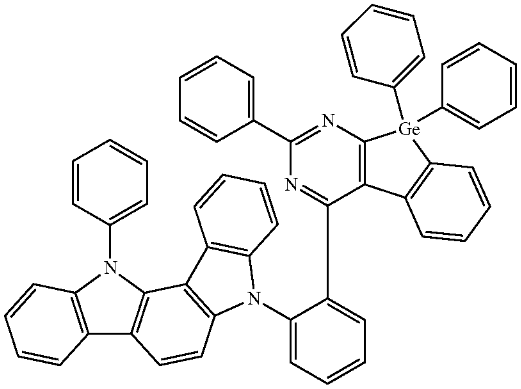
1781
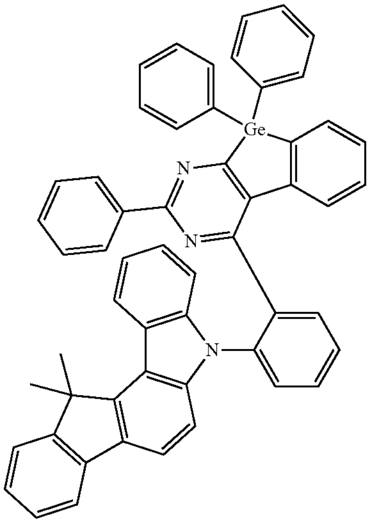

-continued
1782
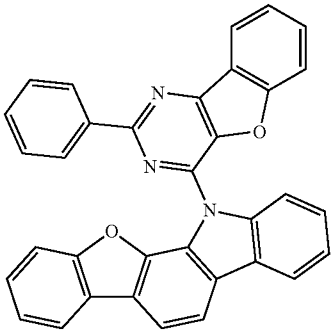
1783
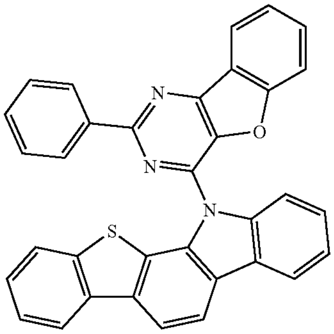
1784
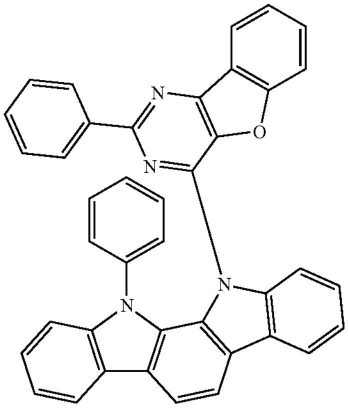
1785
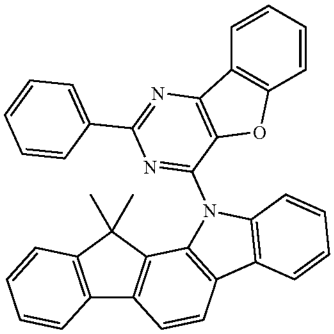
-continued
1786
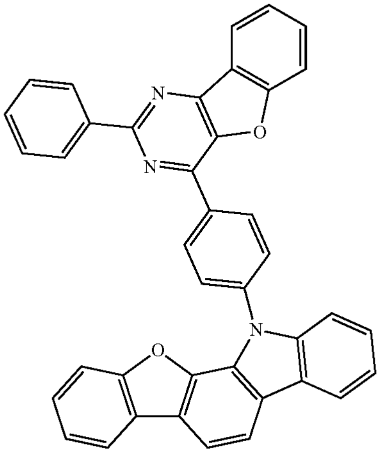
1787
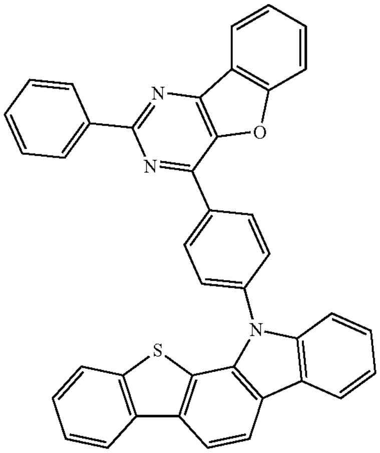
1788
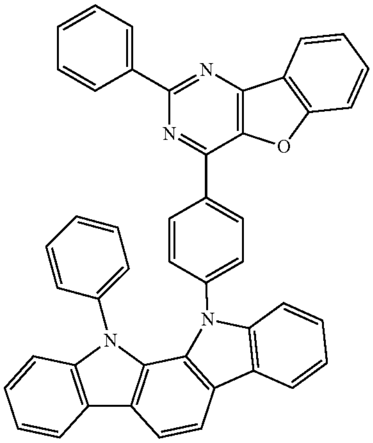

-continued
1789
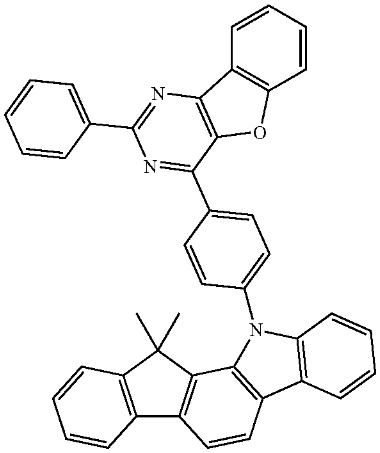
1790
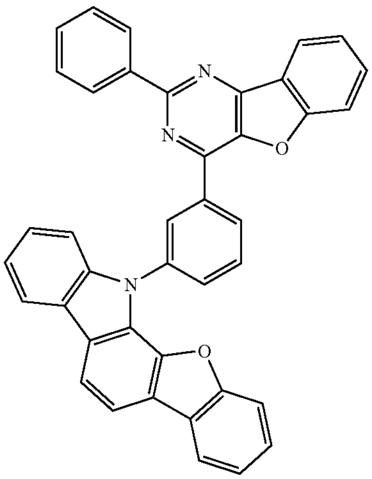
1791
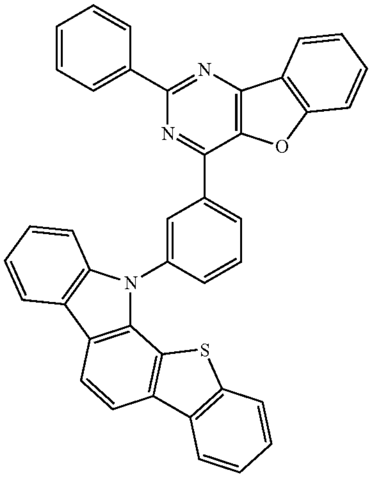
-continued
1792
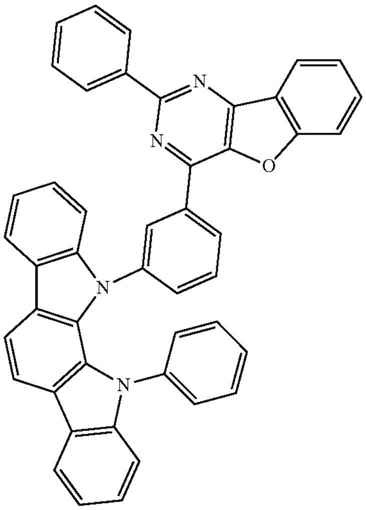
1793
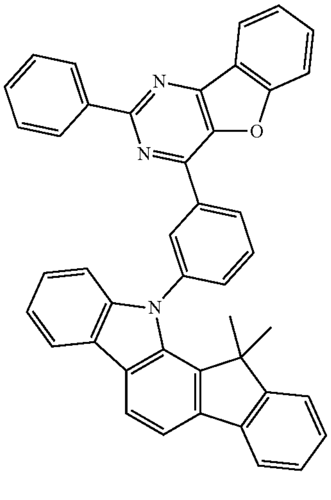
1794
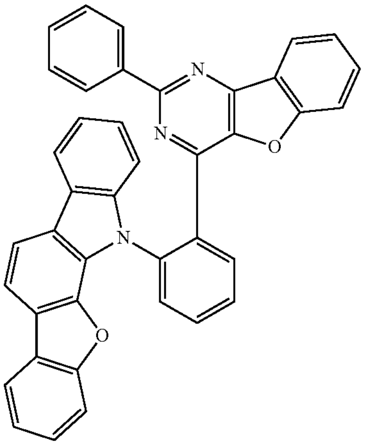

-continued
1795
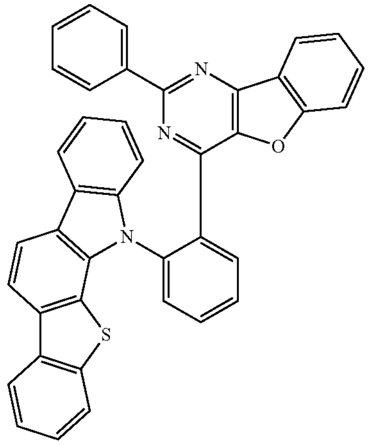
1796
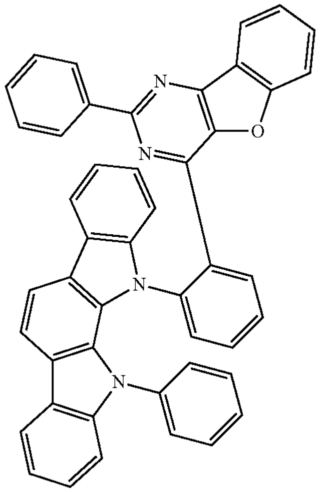
1797
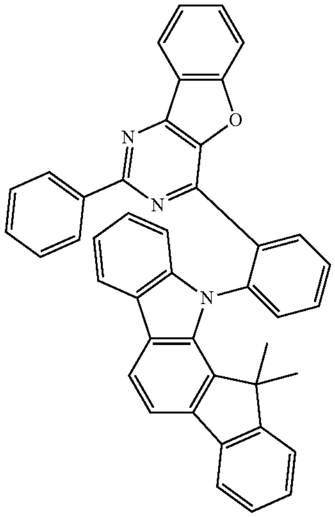
-continued
1798
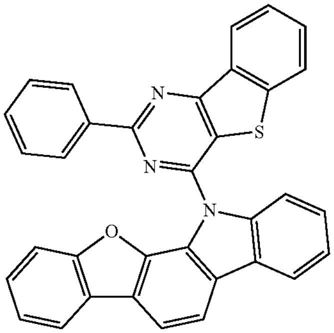
1799
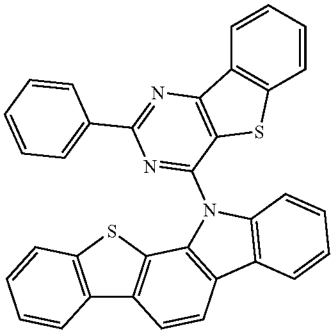
1800
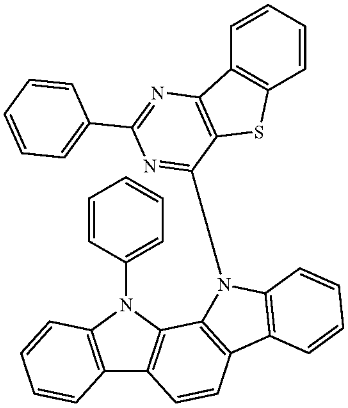
1801
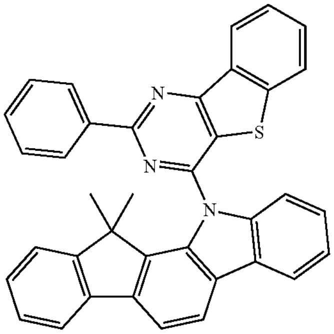

-continued
1802
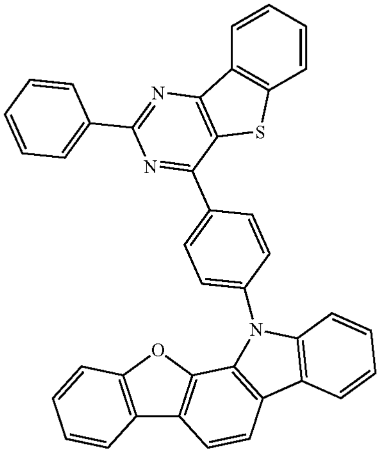
1803
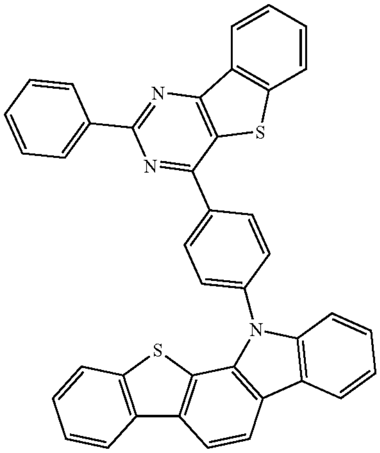
1804
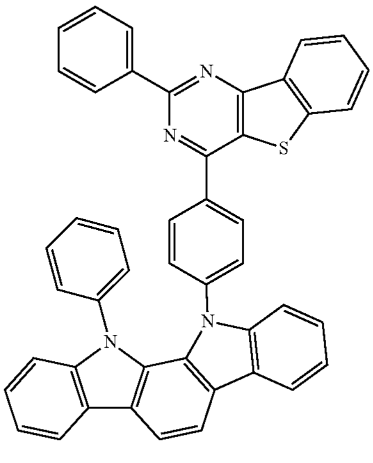
-continued
1805
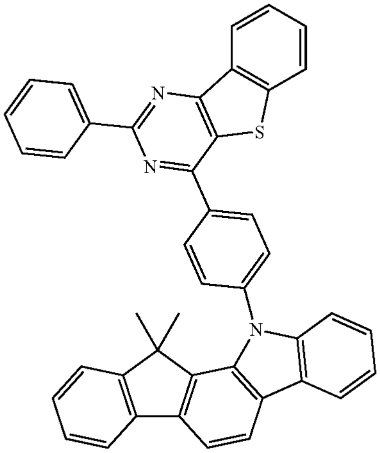
1806
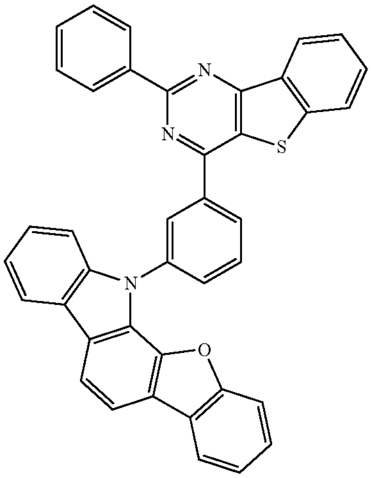
1807
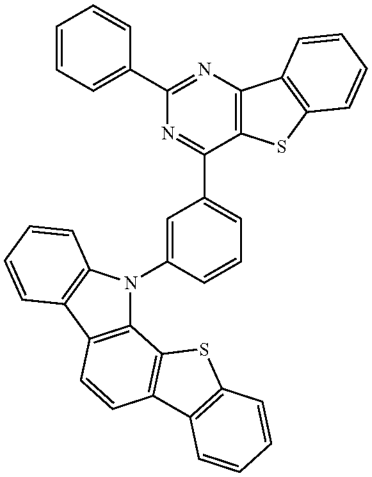

-continued
1808
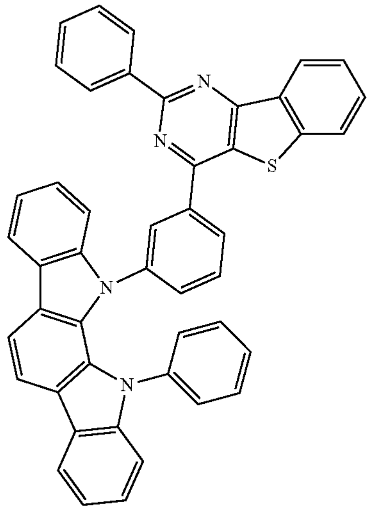
1809
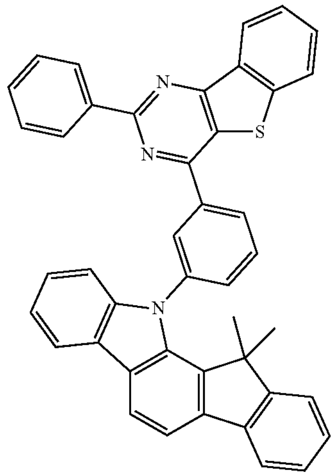
1810
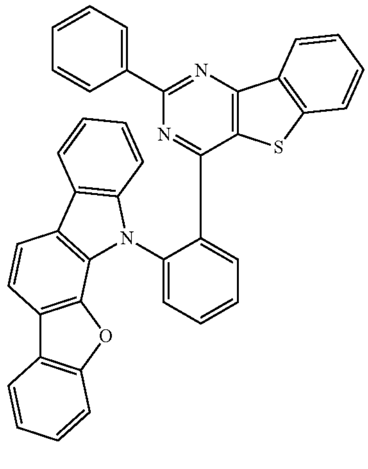
-continued
1811
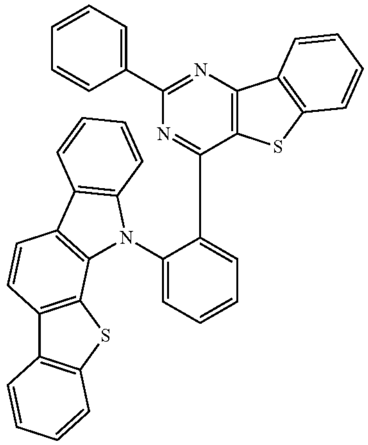
1812
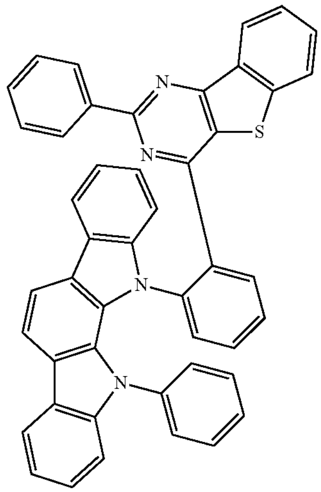
1813
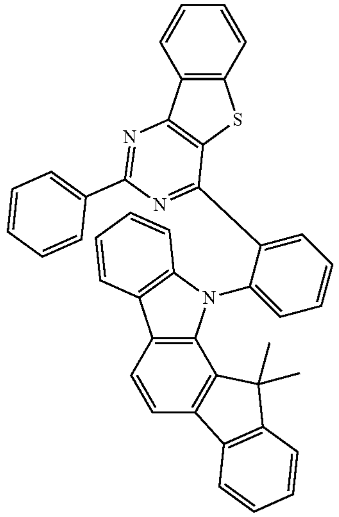

-continued
1814
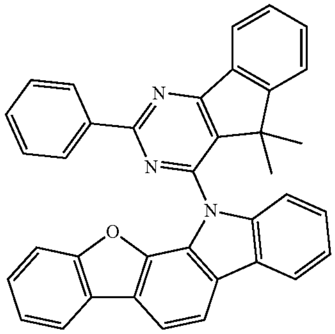
1815
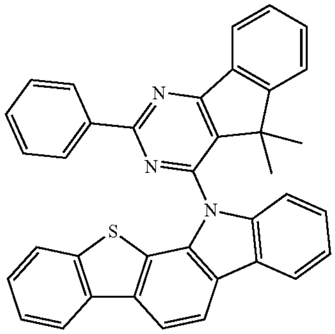
1816
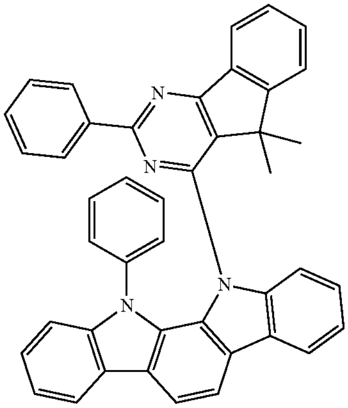
1817
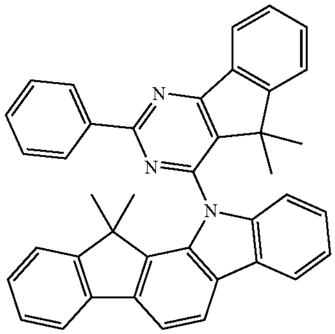
-continued
1818
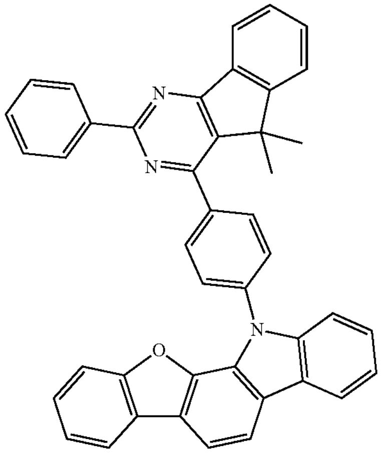
1819
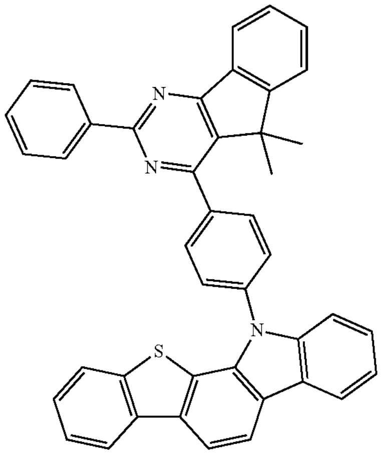
1820
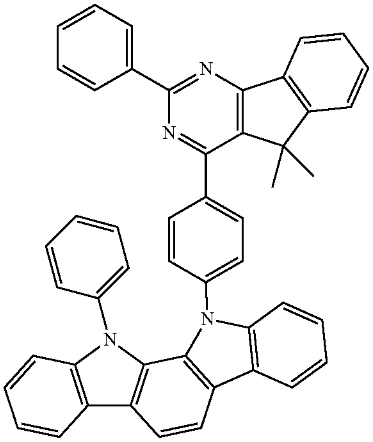

-continued
1821
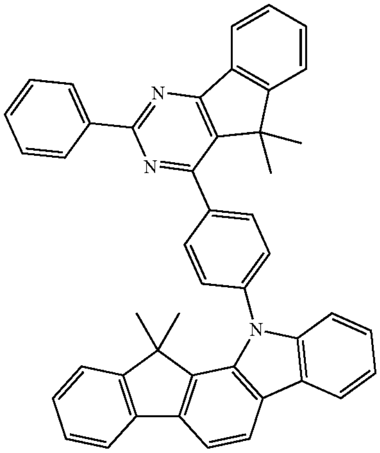
1822
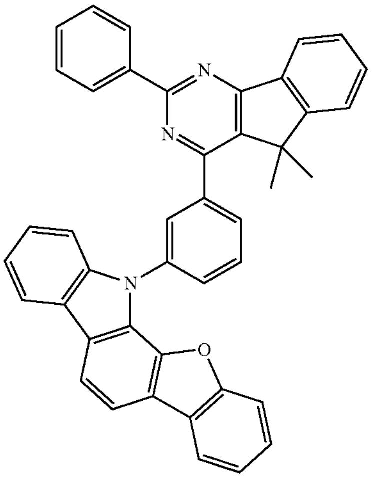
1823
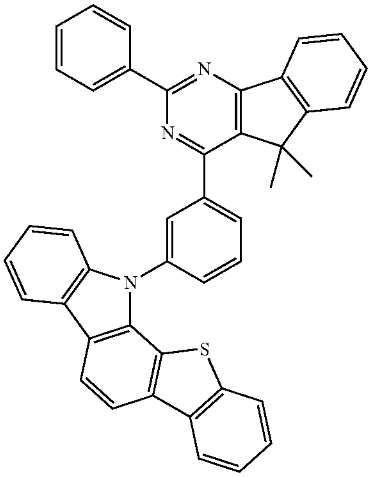
-continued
1824
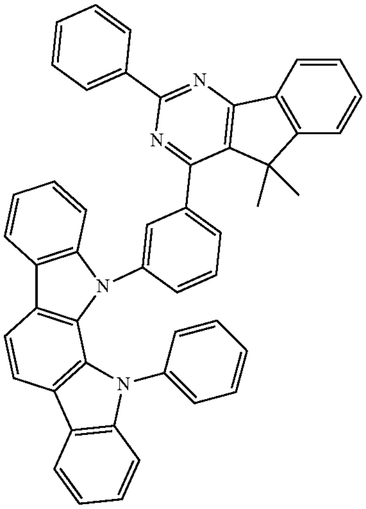
1825
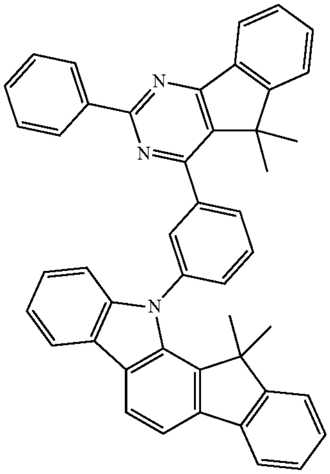
1826
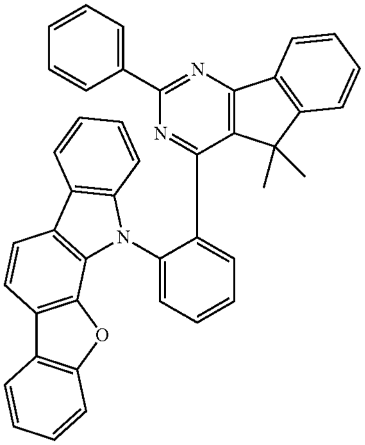

-continued
1827
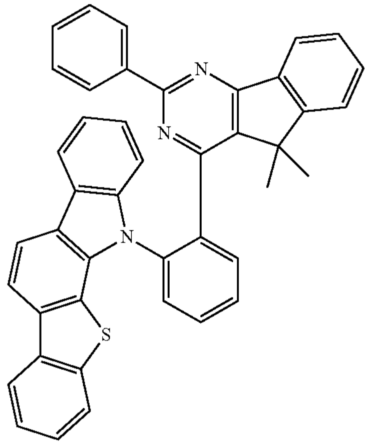
1828
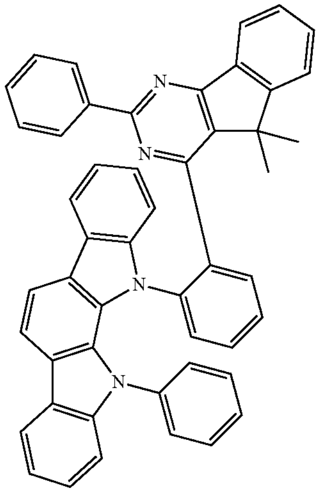
1829
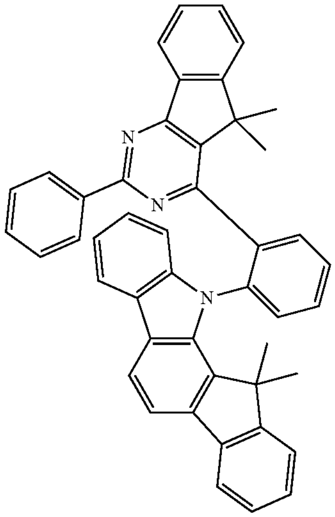
-continued
1830
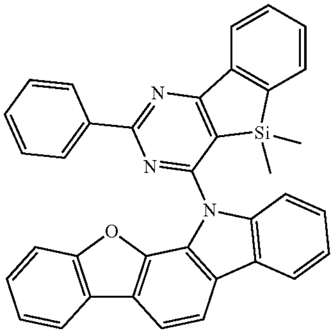
1831
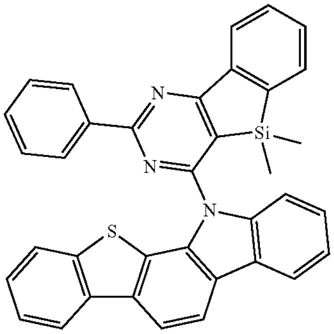
1832
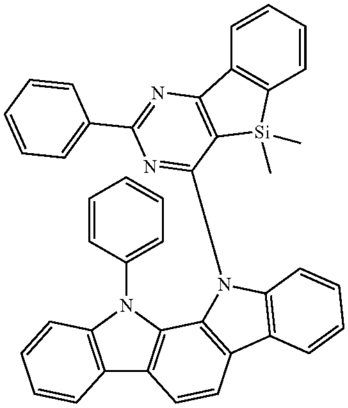
1833
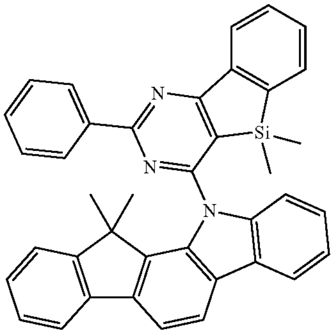

-continued
1834
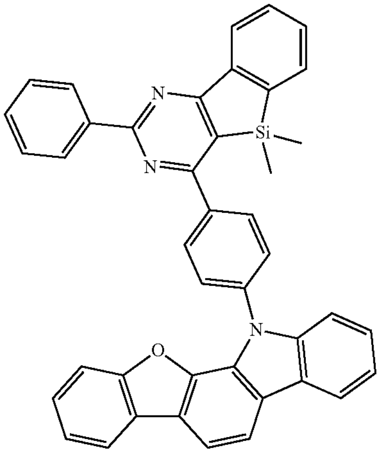
1835
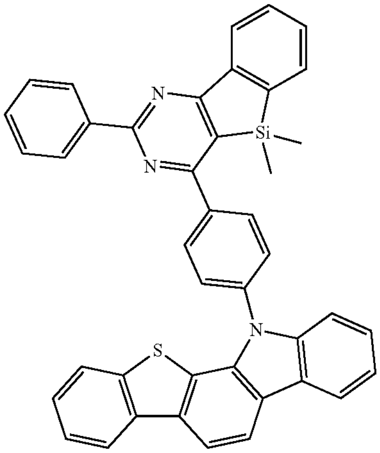
1836
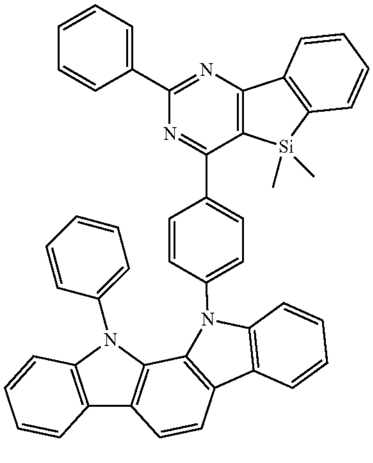
-continued
1837
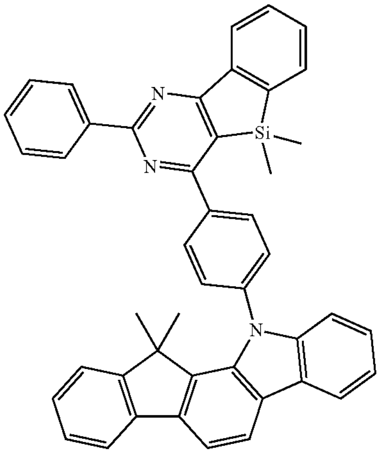
1838
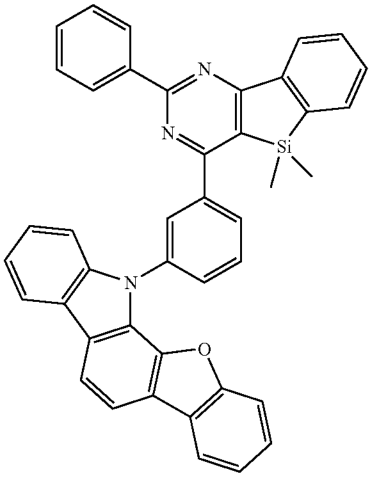
1839
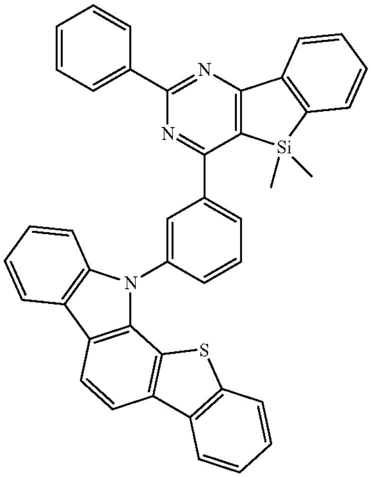

-continued
1840
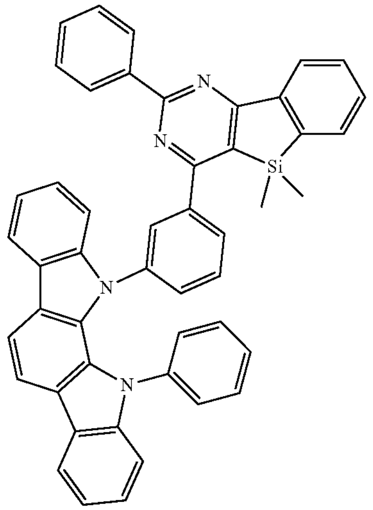
1841
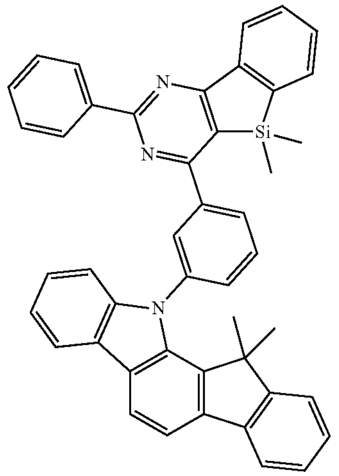
1842
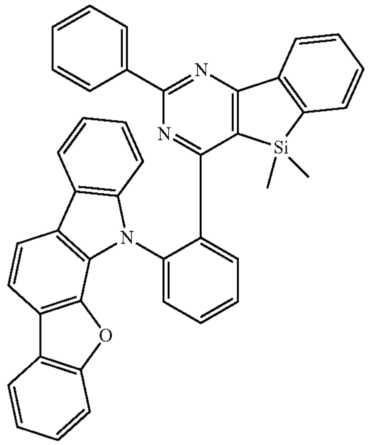
-continued
1843
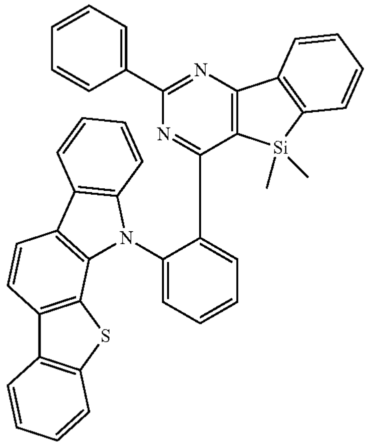
1844
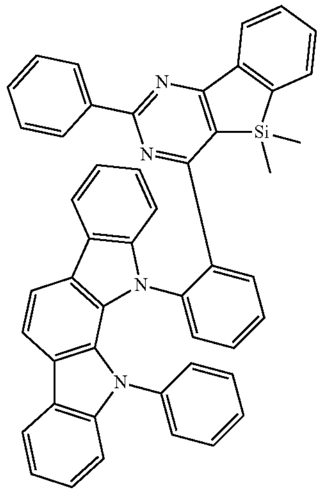
1845
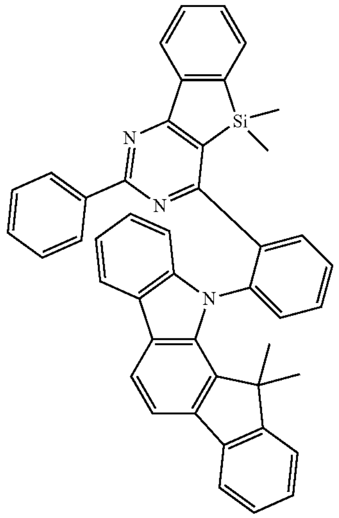

-continued
1846
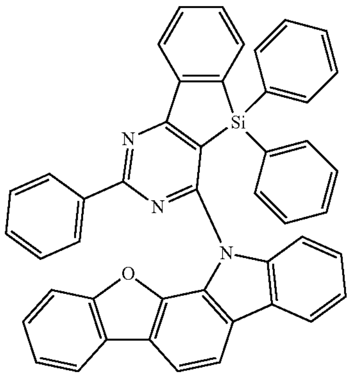
1847
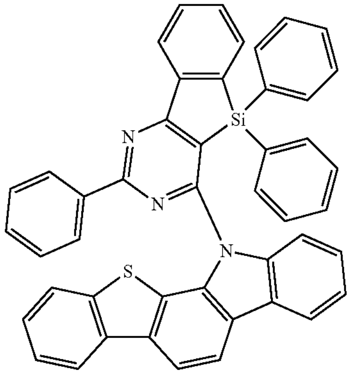
1848
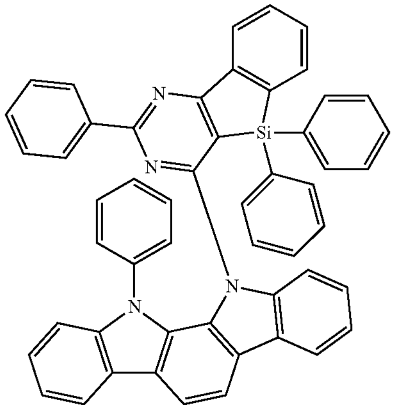
1849
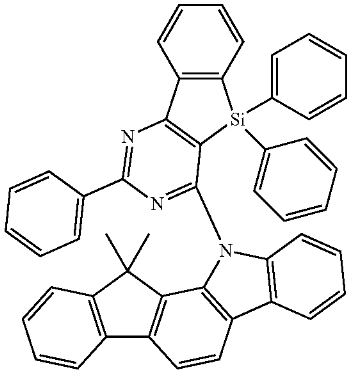
-continued
1850
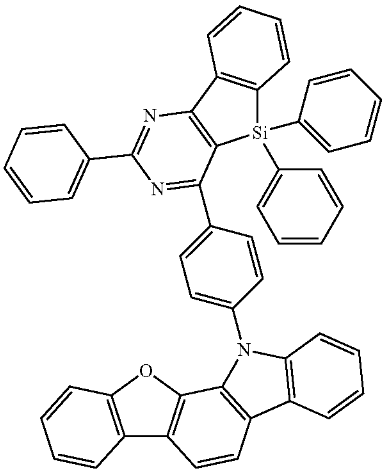
1851
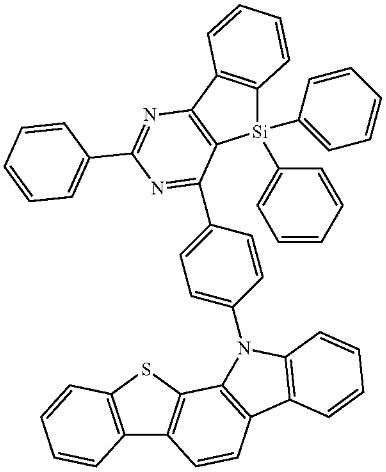
1852
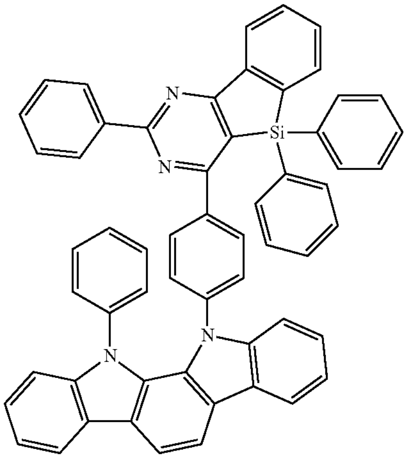

-continued
1853
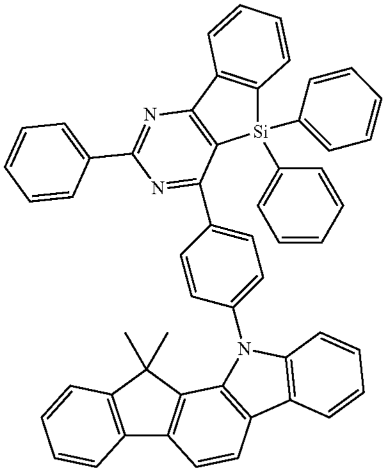
1854
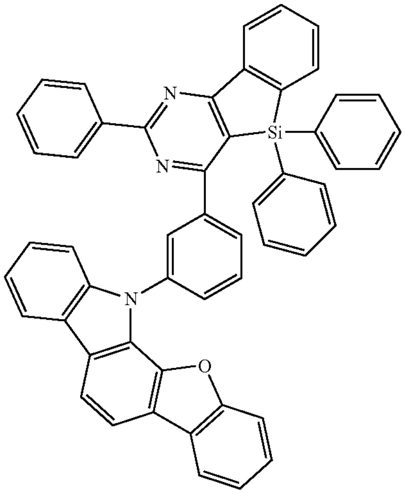
1855
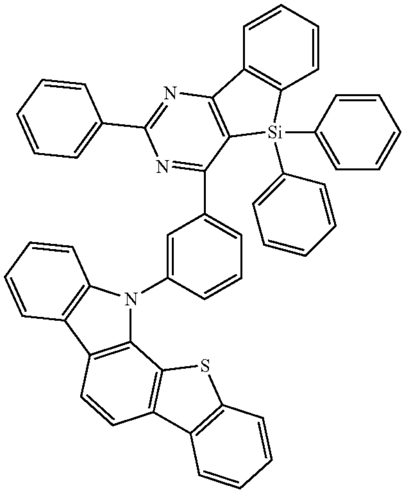
-continued
1856
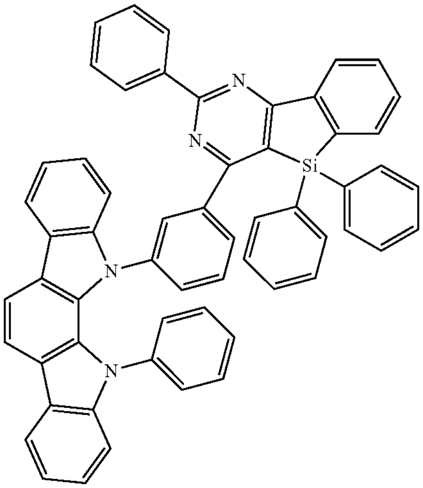
1857
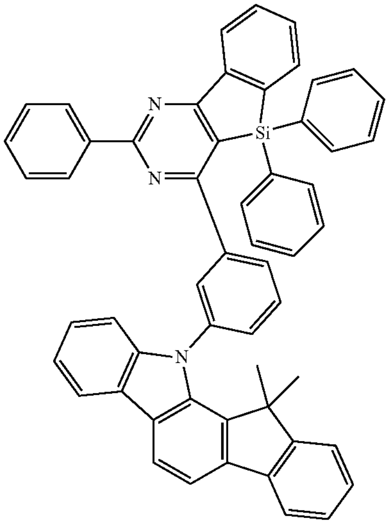
1858
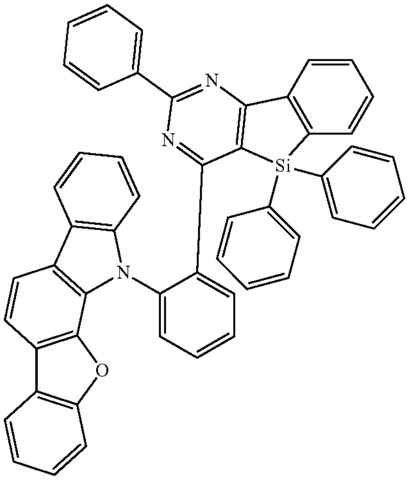

-continued
1859
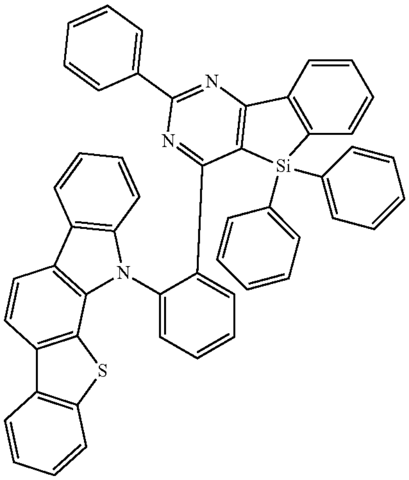
1860
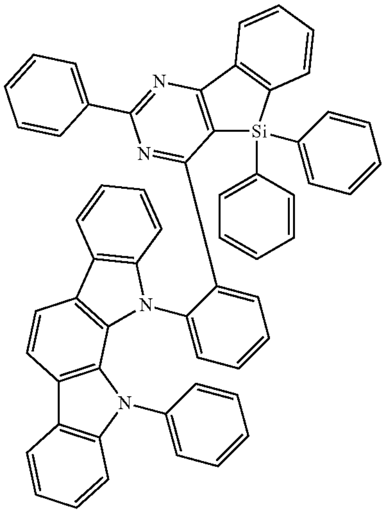
1861
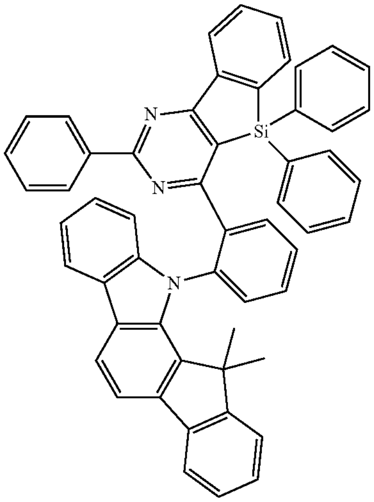
1862
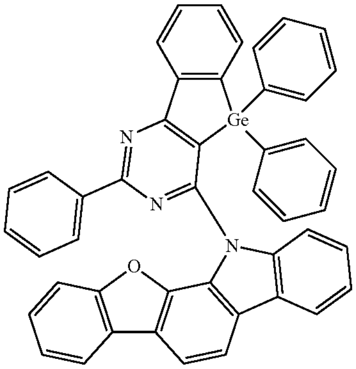
1863
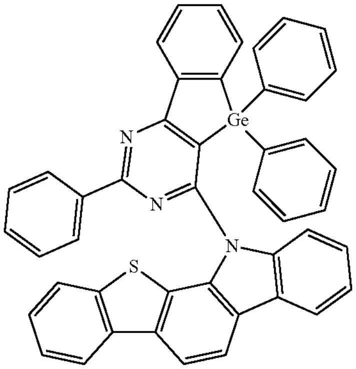
1864
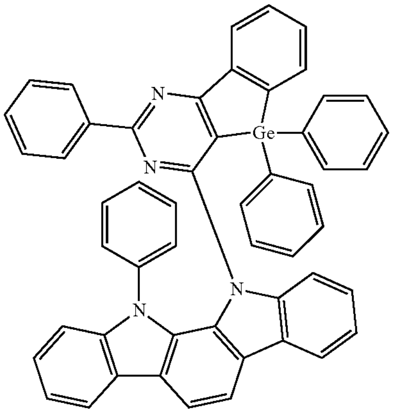
1865
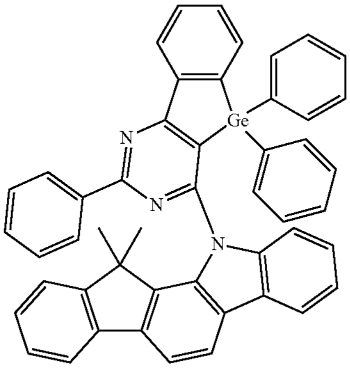

-continued
1866
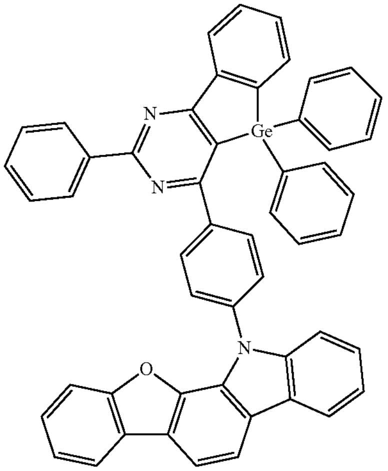
1867
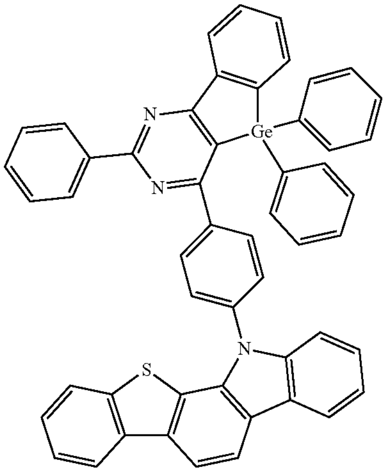
1868
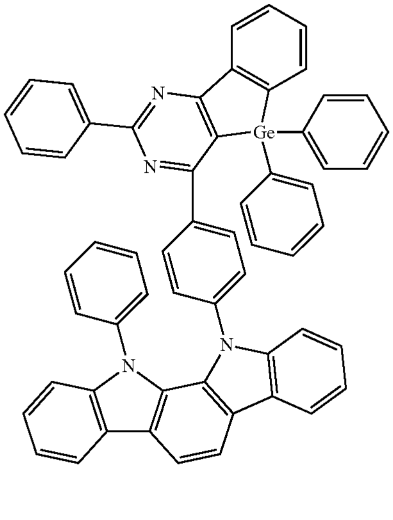
-continued
1869
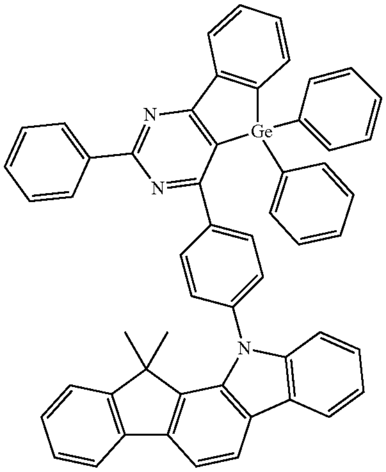
1870
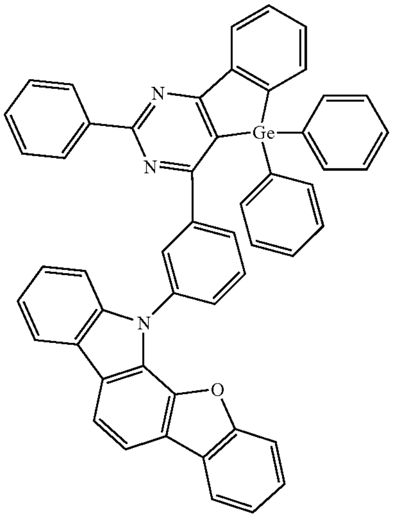
1871
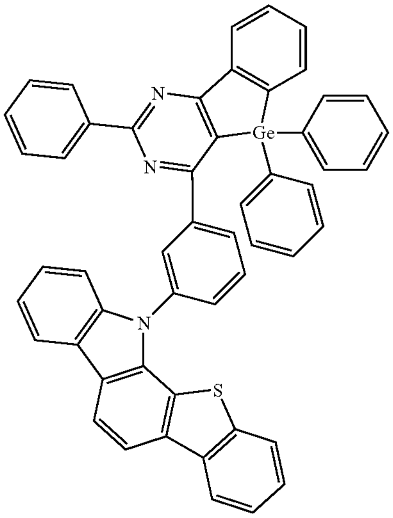

-continued
1872
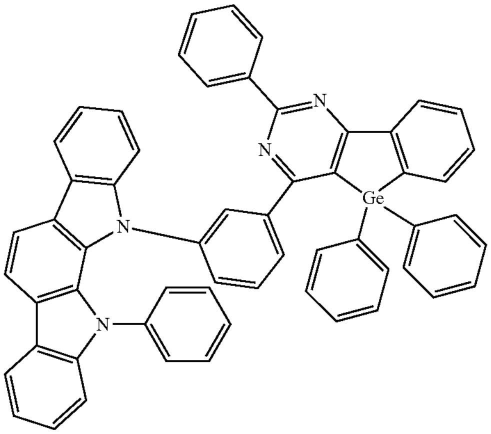
1873
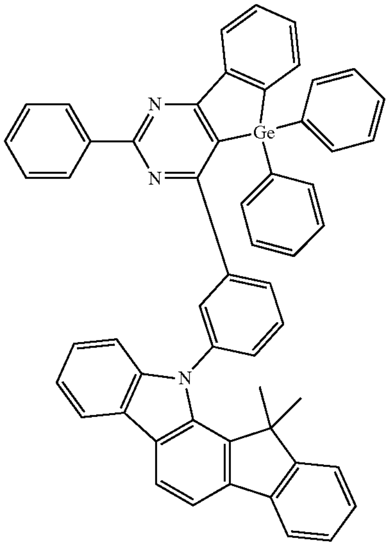
1874
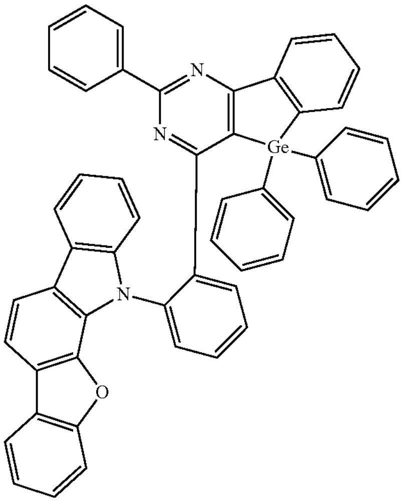
-continued
1875
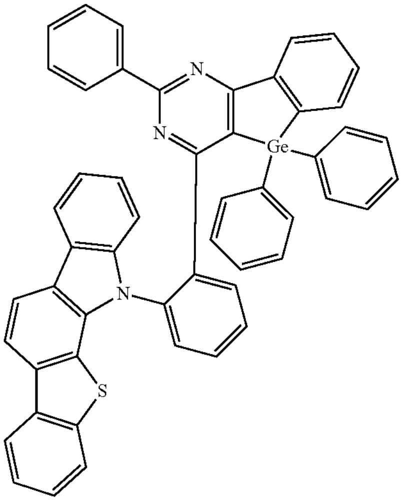
1876
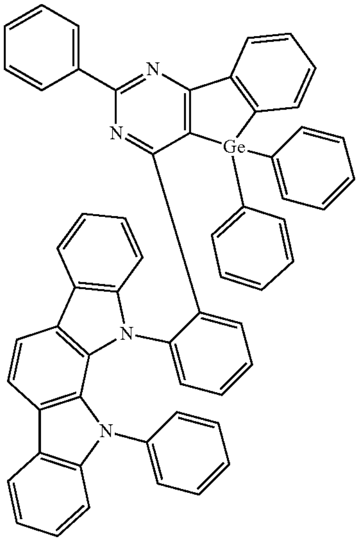
1877
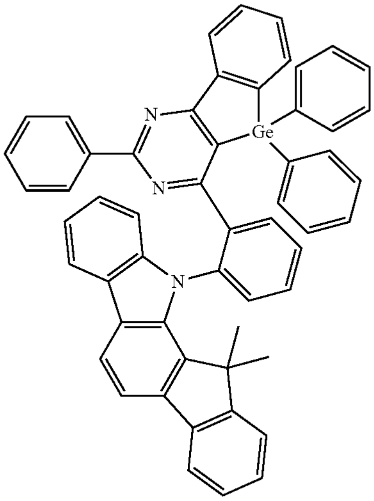

-continued
1878
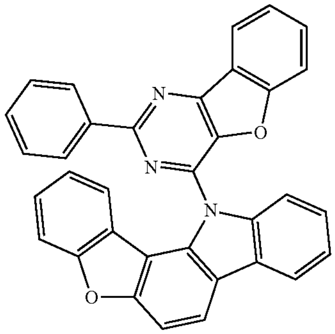
1879
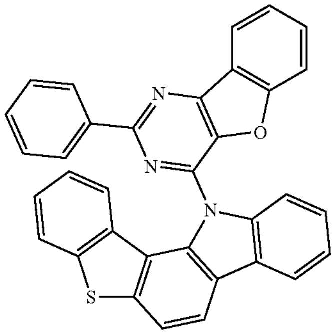
1880
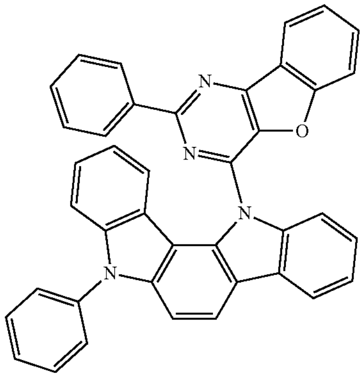
1881
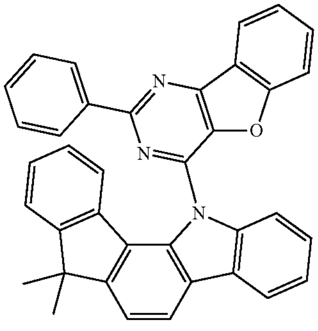
-continued
1882
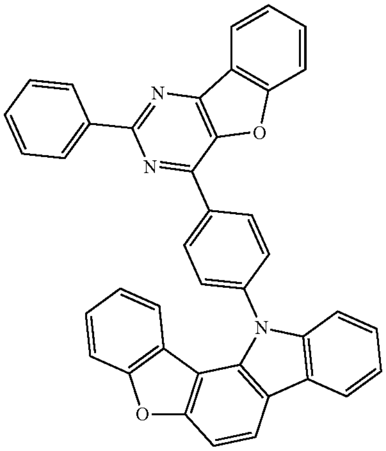
1883
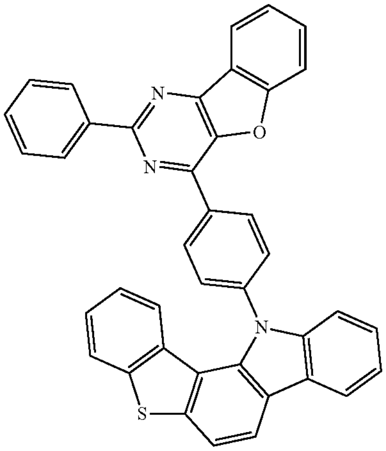
1884
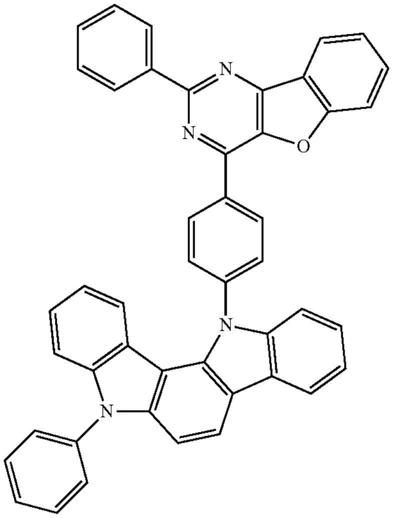

1885
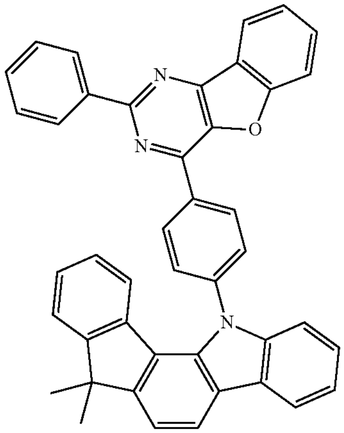
1886
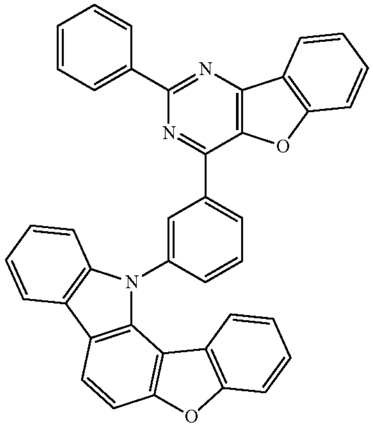
1887
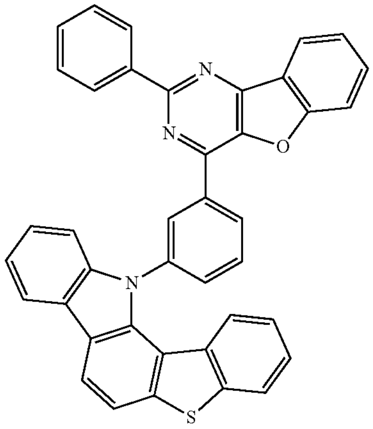
1888
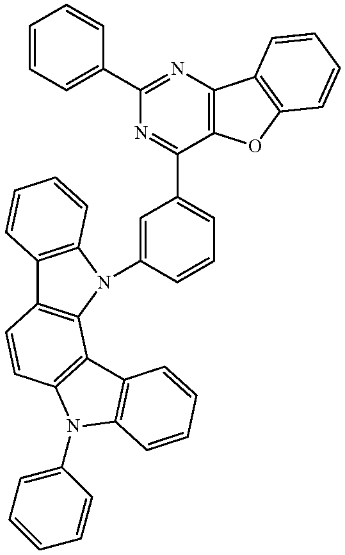
1889
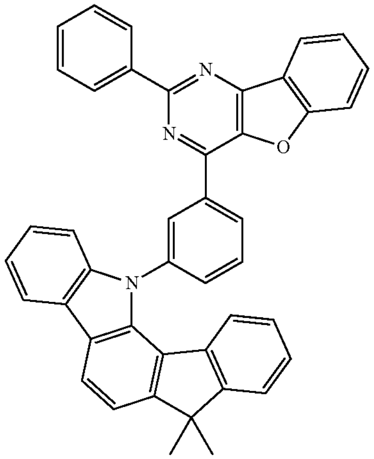
1890
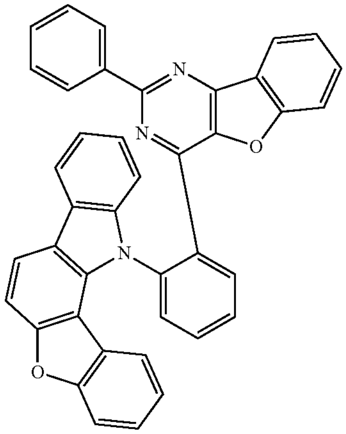

-continued
1891
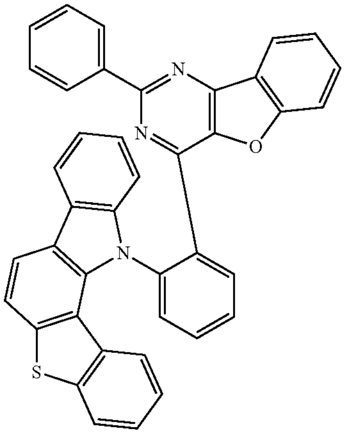
1892
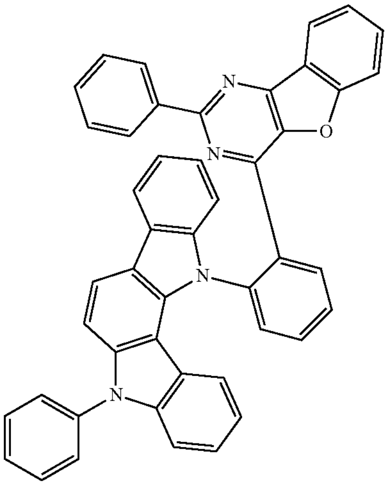
1893
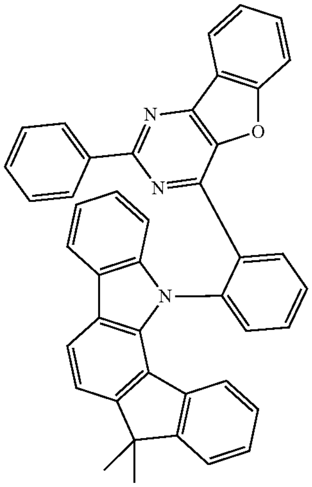
-continued
1894
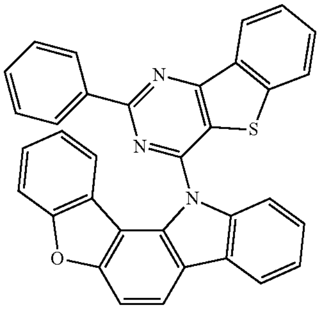
1895
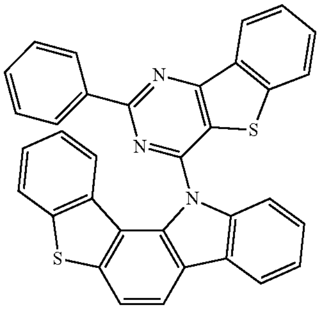
1896
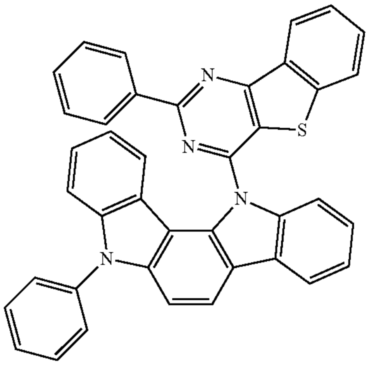
1897
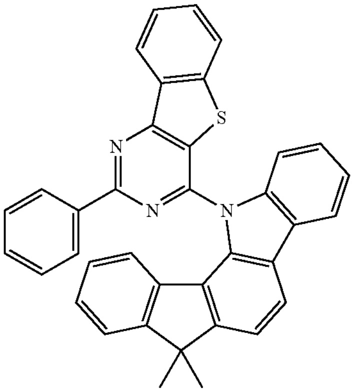

-continued
1898
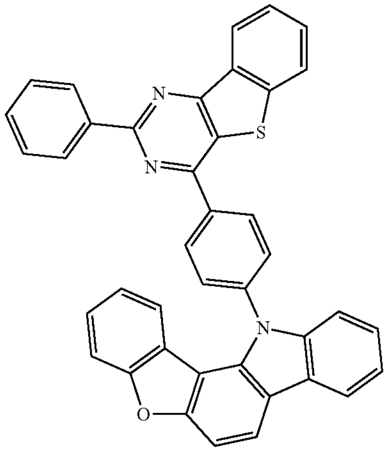
1899
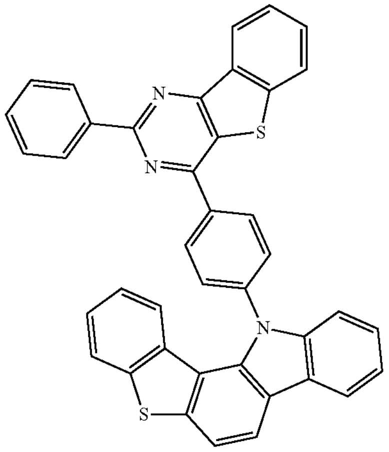
1900
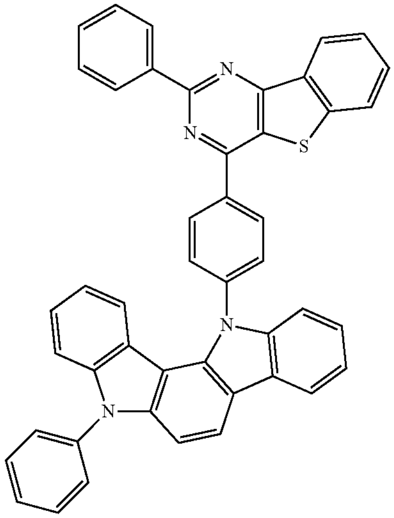
-continued
1901
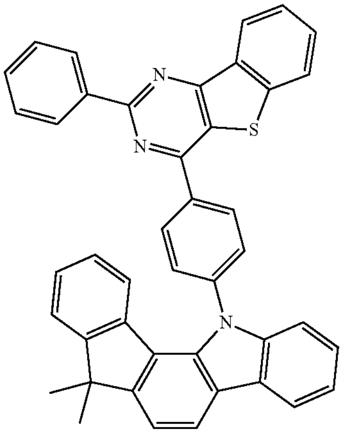
1902
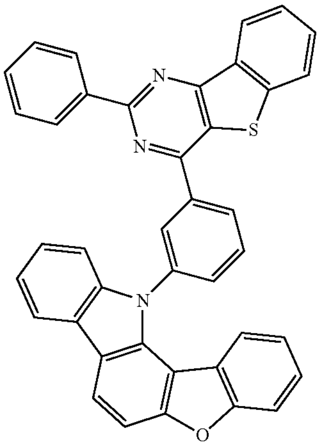
1903
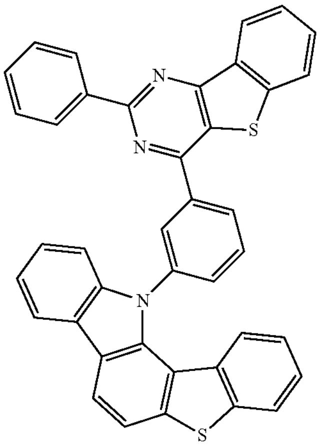

-continued
1904
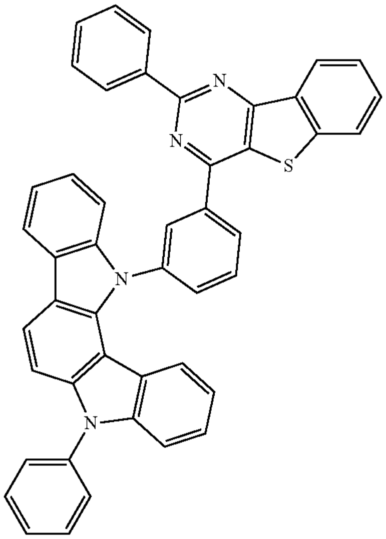
1905
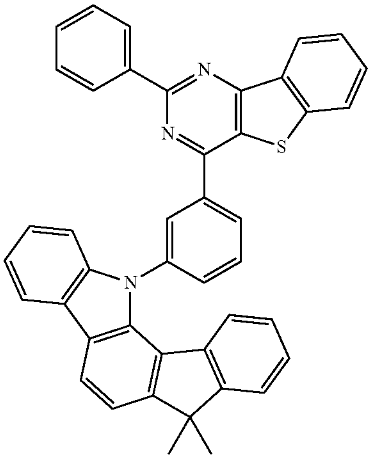
1906
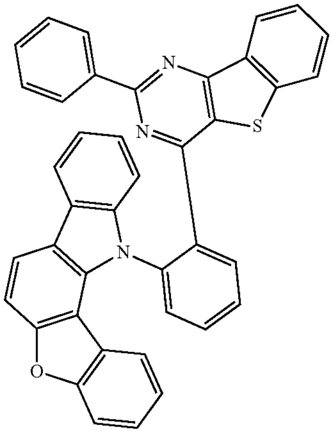
-continued
1907
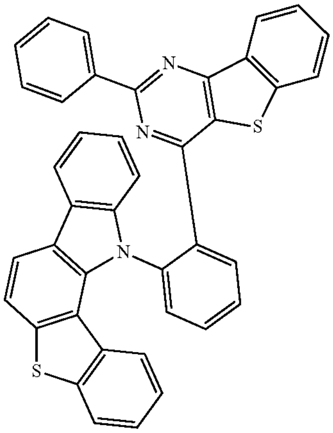
1908
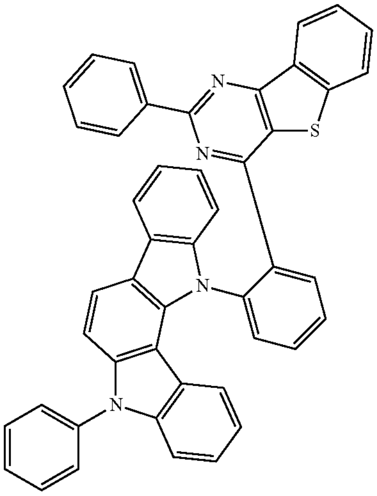
1909
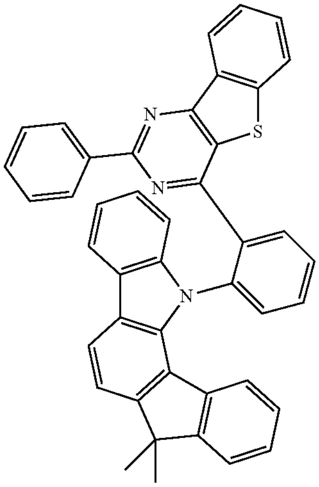

-continued
1910
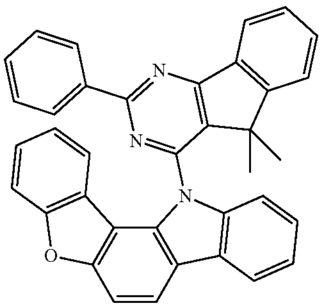
1911
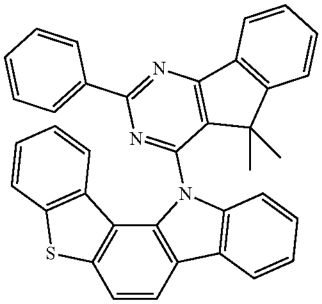
1912
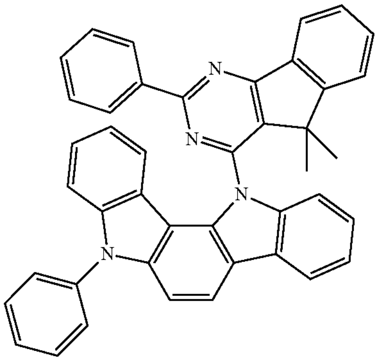
1913
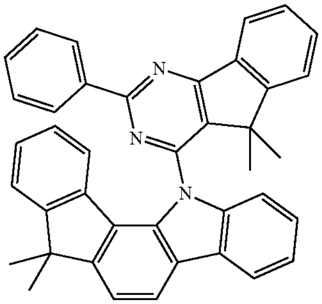
-continued
1914
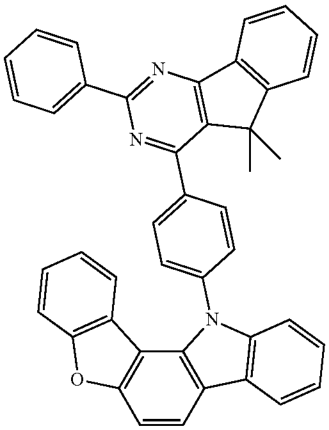
1915
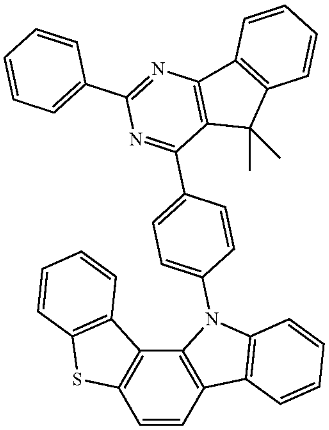
1916
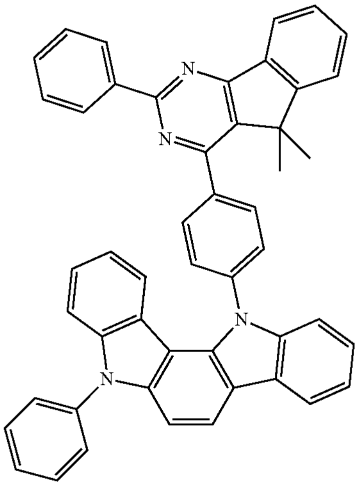

-continued
1917
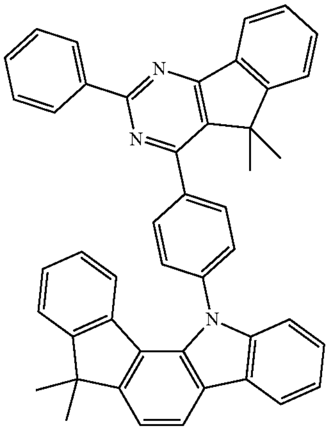
1918
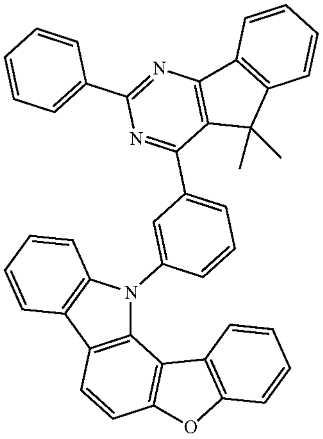
1919
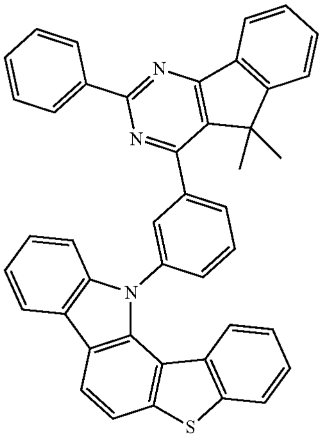
-continued
1920
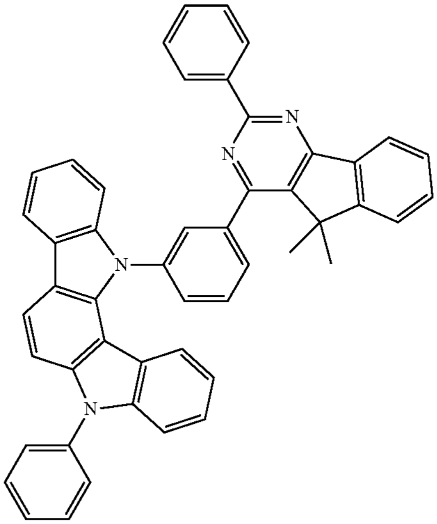
1921
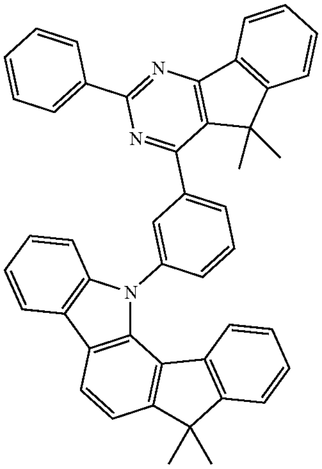
1922
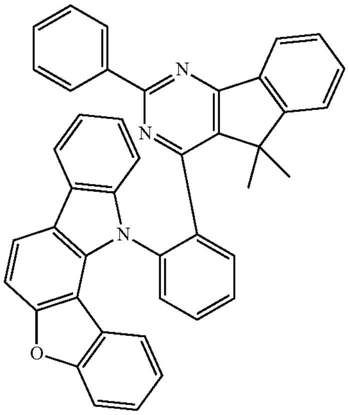

-continued
1923
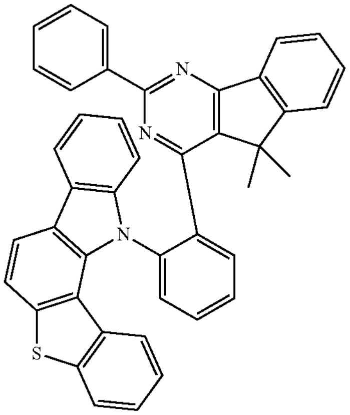
1924
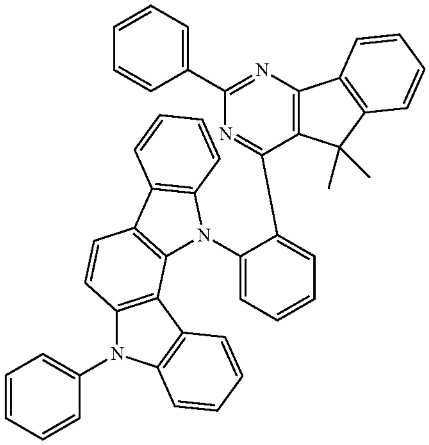
1925
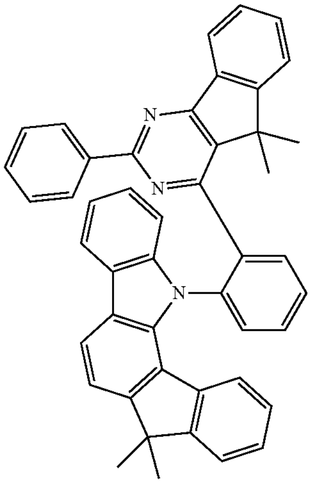
1926
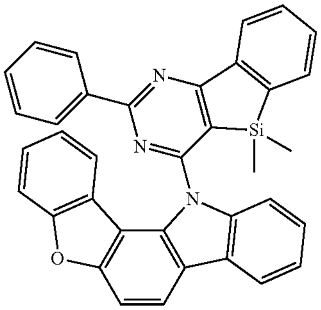
-continued
1927
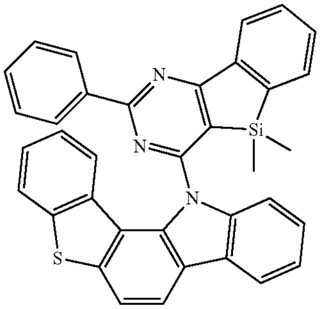
1928
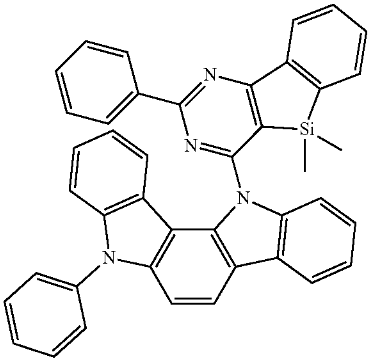
1929
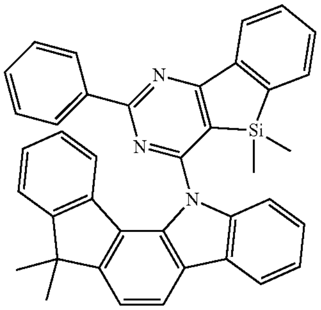
1930
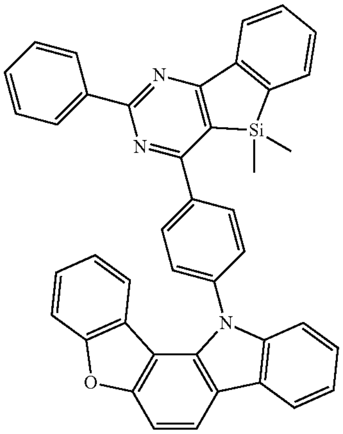

-continued
1931
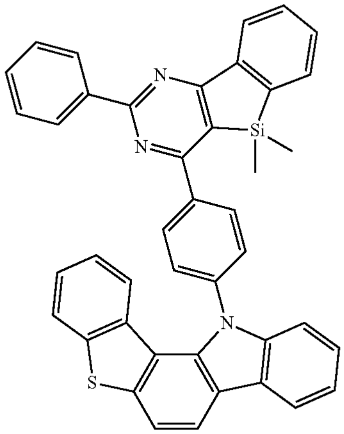
1932
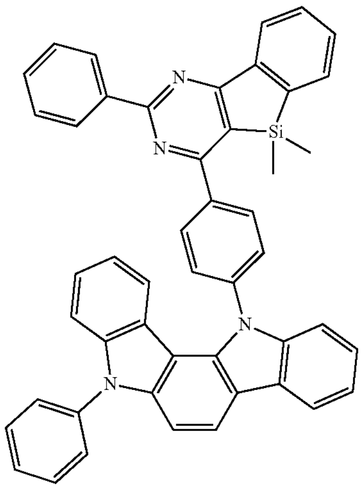
1933
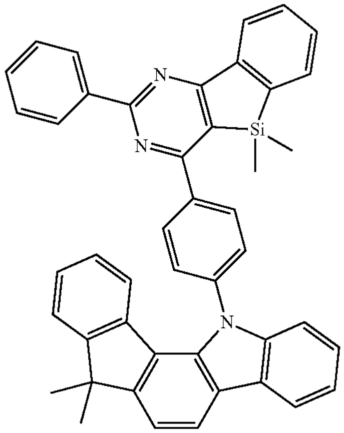
-continued
1934
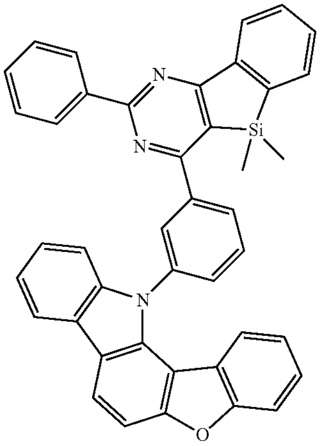
1935
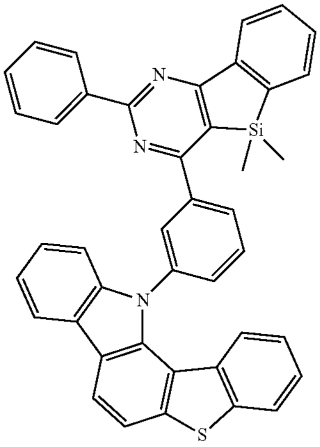
1936
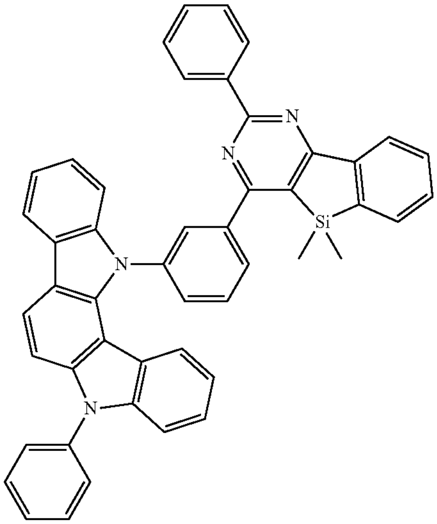

-continued
1937
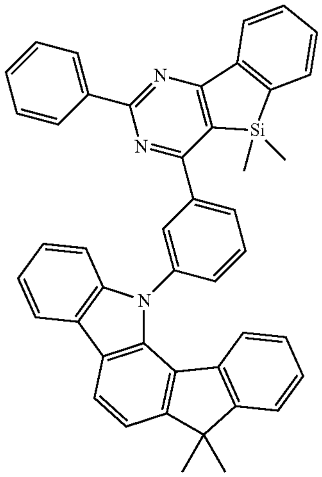
1938
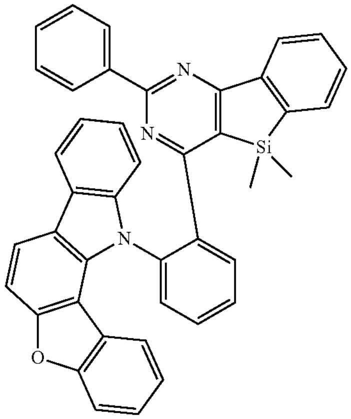
1939
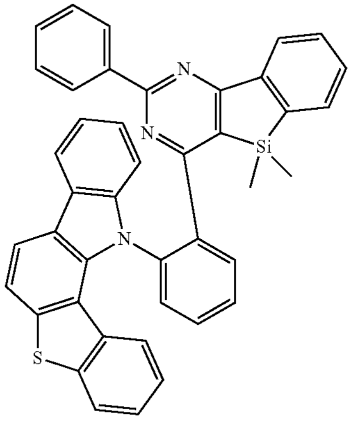
-continued
1940
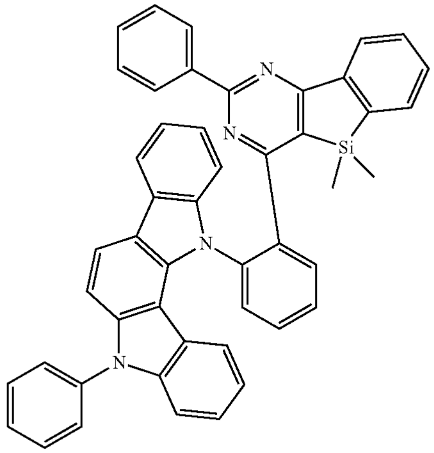
1941
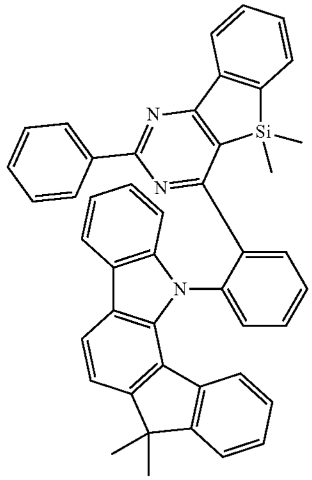
1942
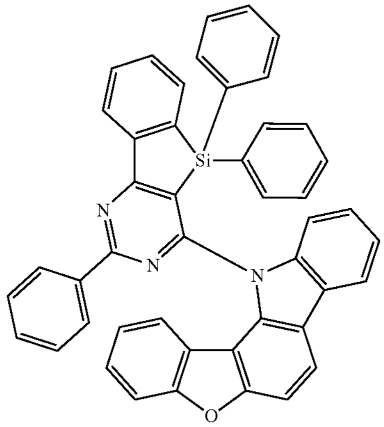

-continued
1943
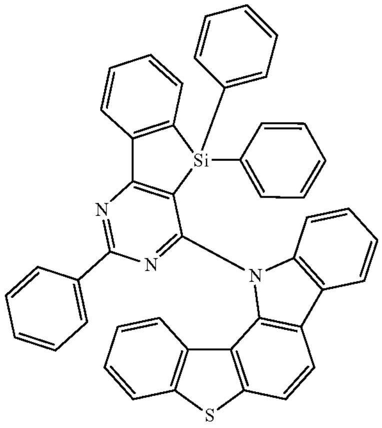
1944
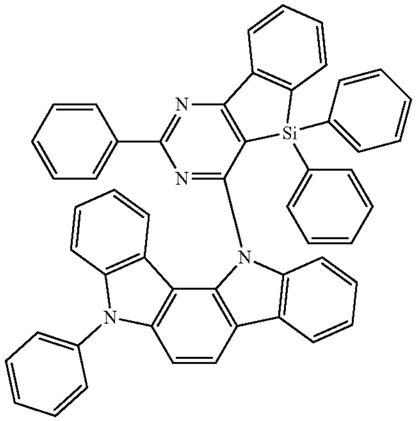
1945
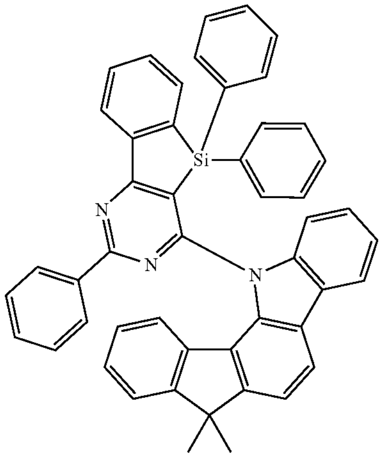
-continued
1946
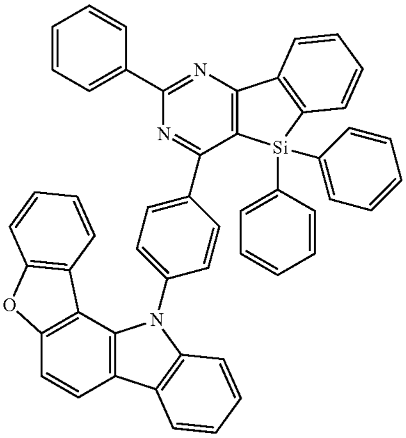
1947
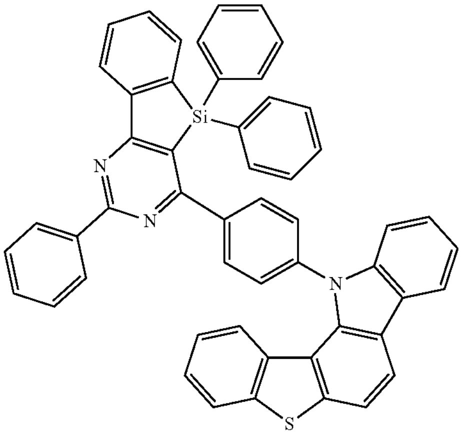
1948
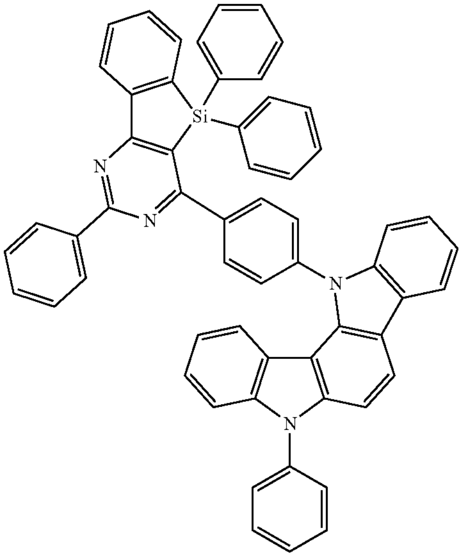

-continued
1949
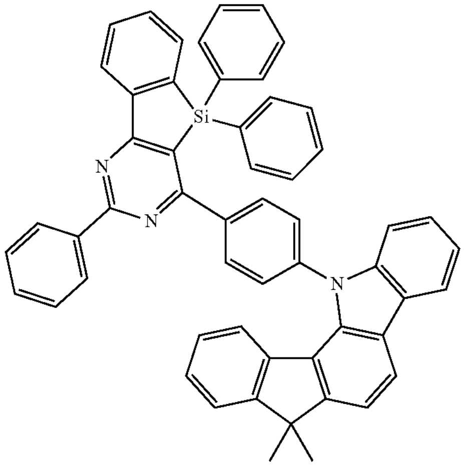
1950
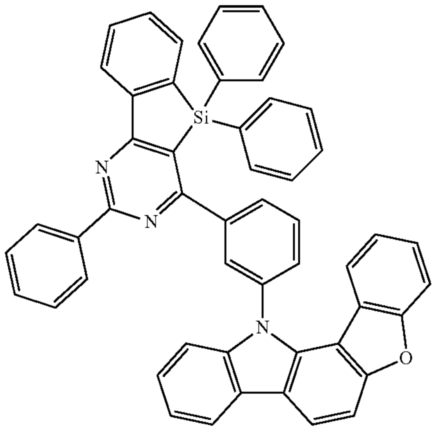
1951
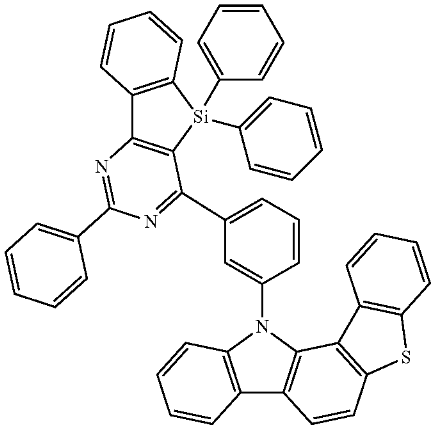
-continued
1952
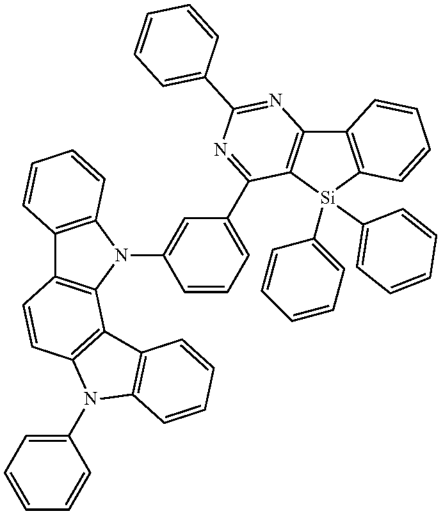
1953
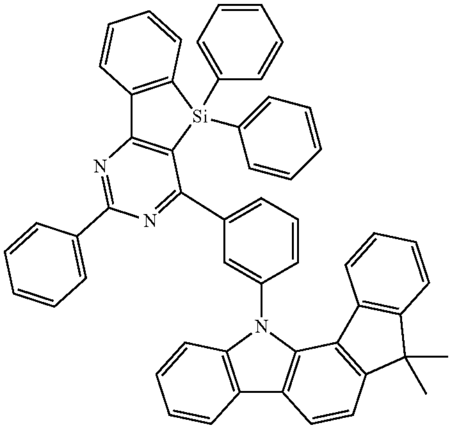
1954
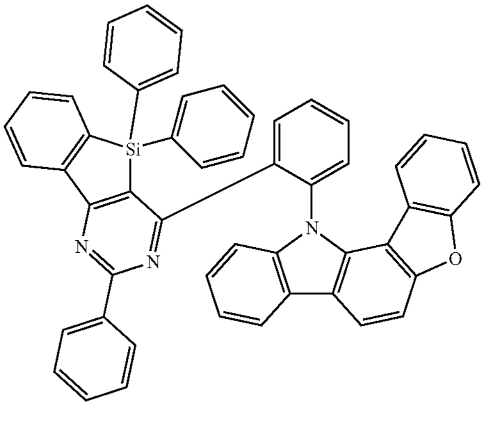

1955
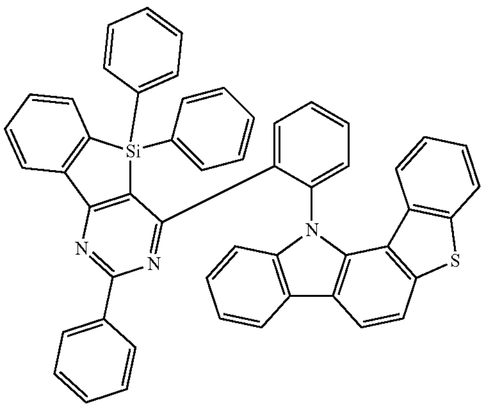
1956
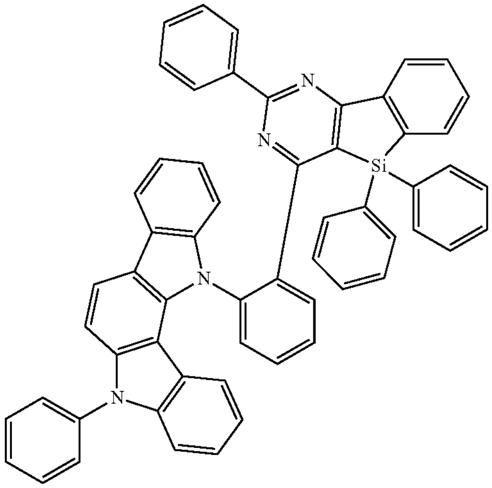
1957
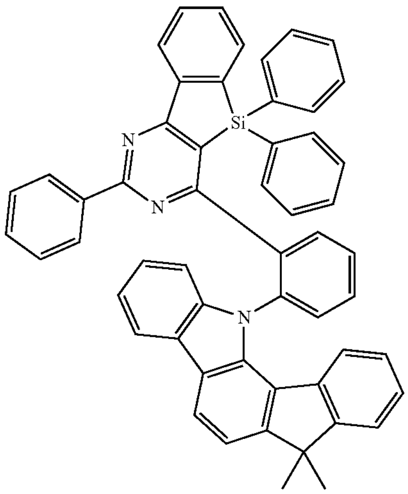
1958
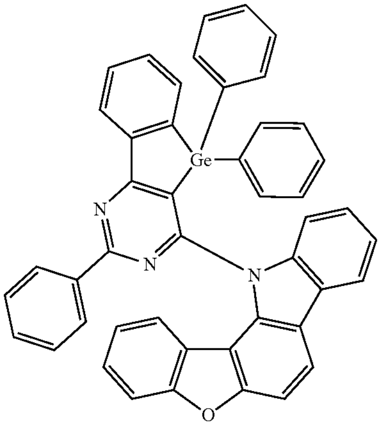
1959
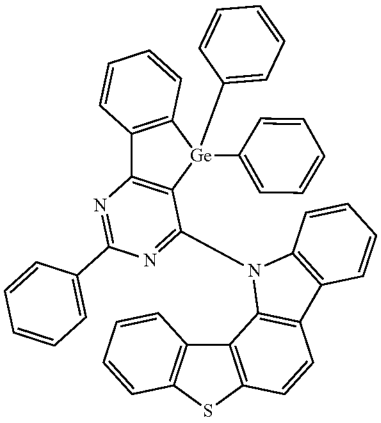
1960
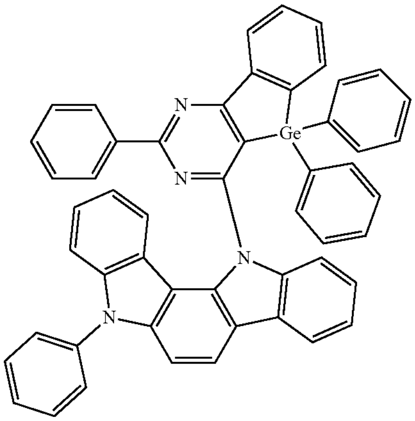

-continued
1961
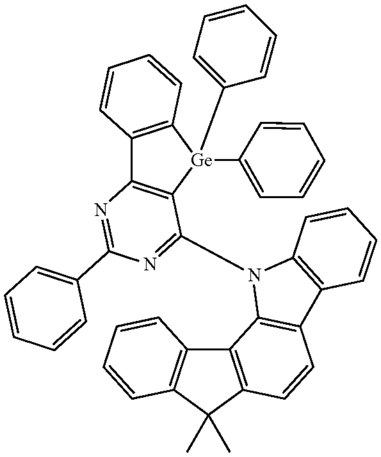
1962
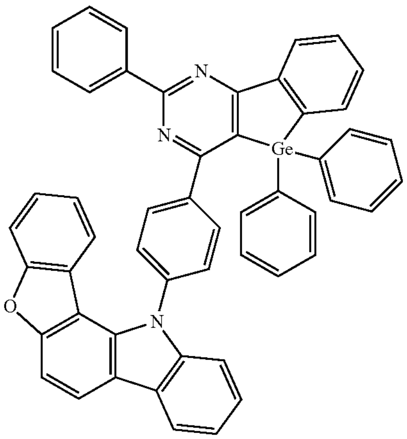
1963
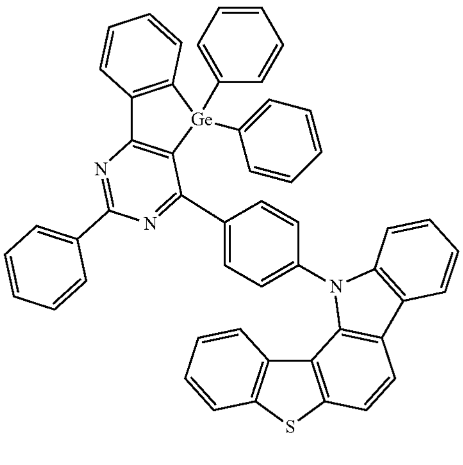
-continued
1964
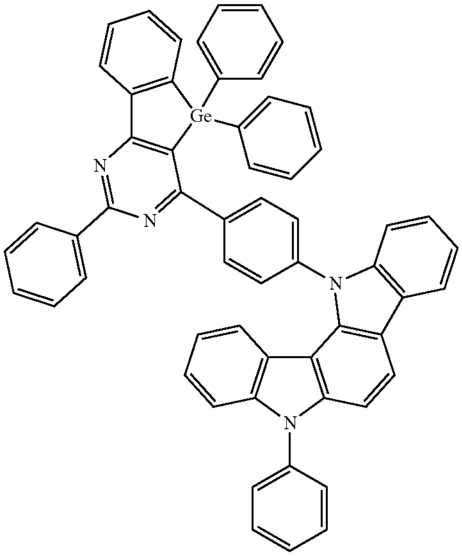
1965
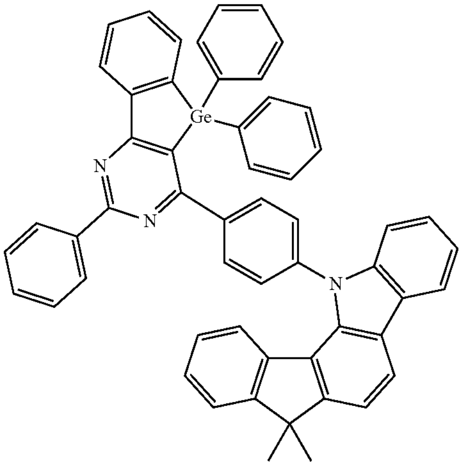
1966
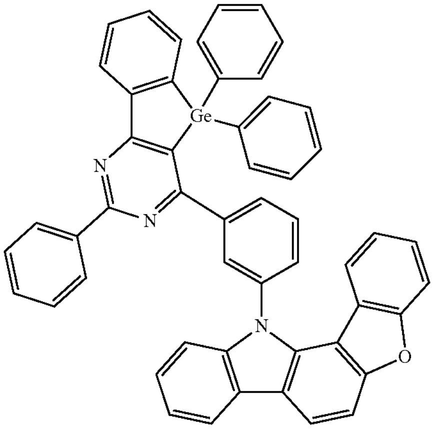

-continued
1967
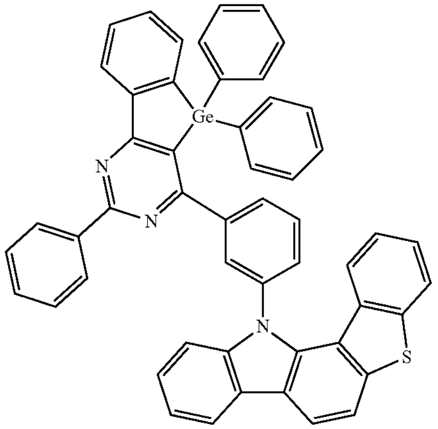
1968
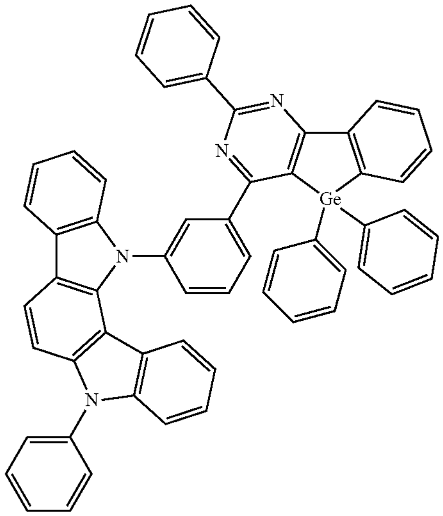
1969
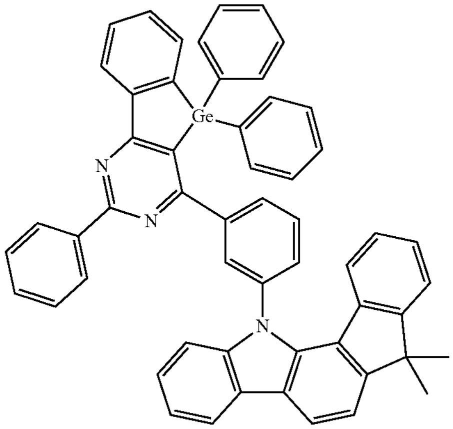
-continued
1970
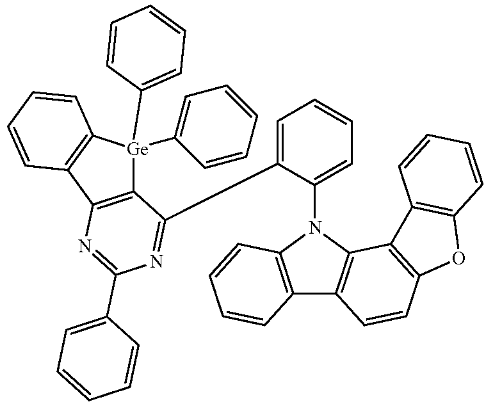
1971
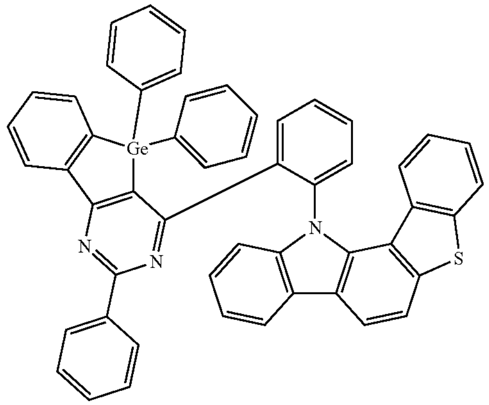
1972
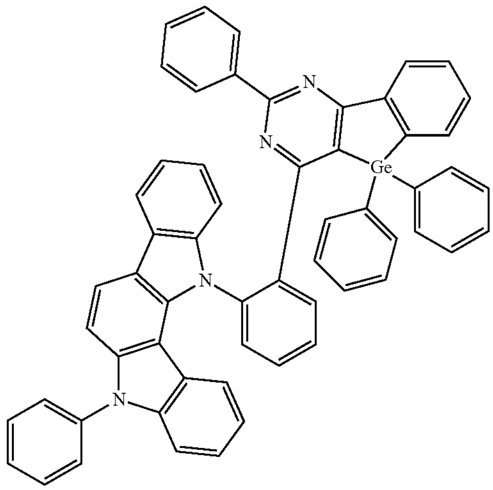

-continued
1973
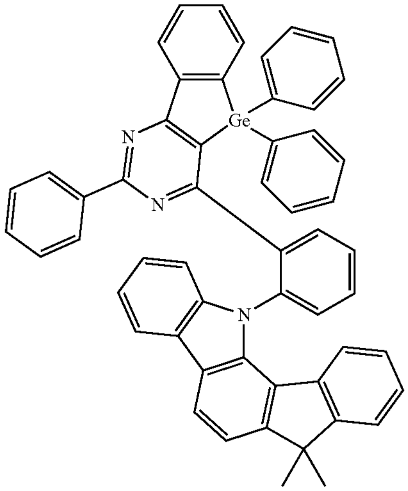
1974
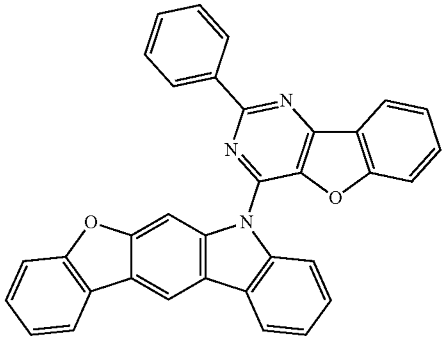
1975
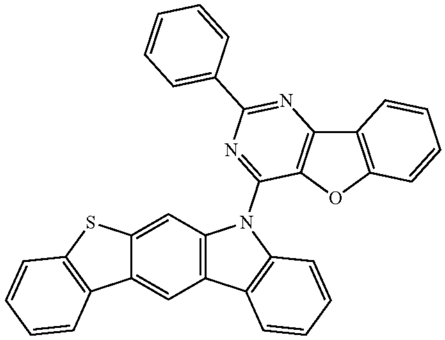
1976
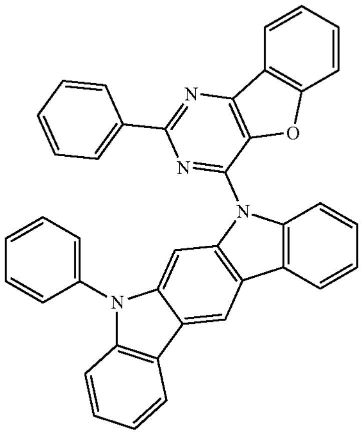
-continued
1977
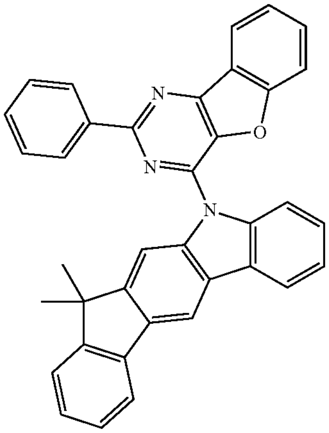
1978
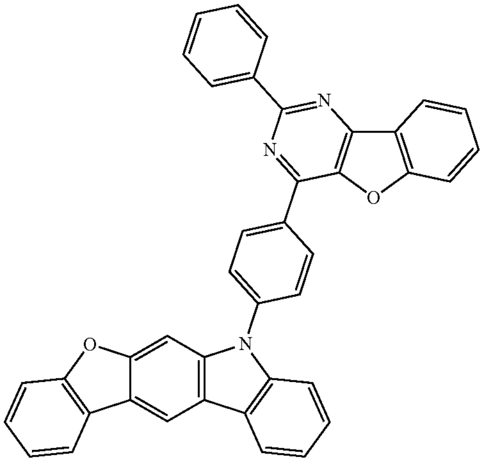
1979
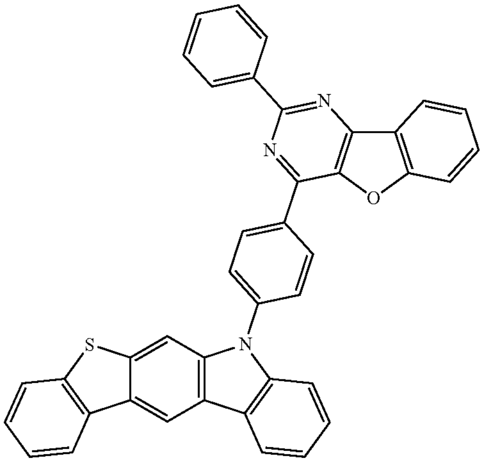

-continued
1980
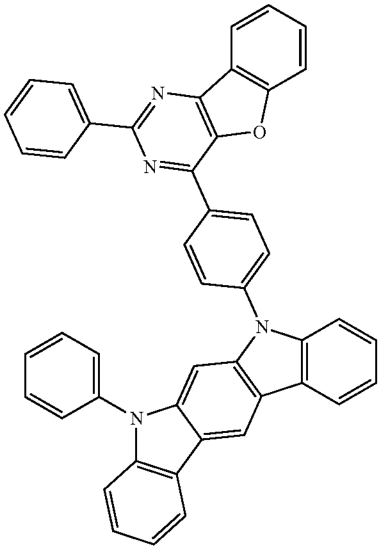
1981
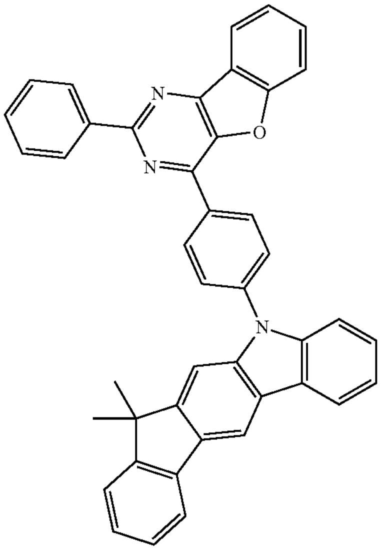
1982
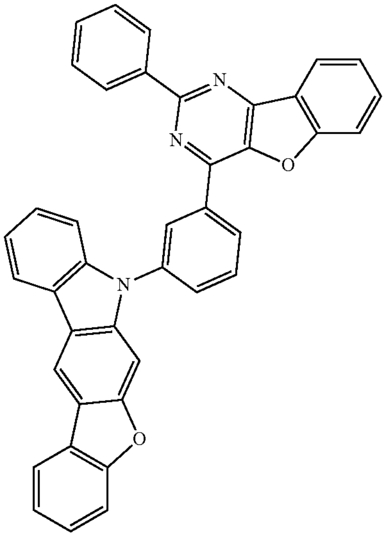
-continued
1983
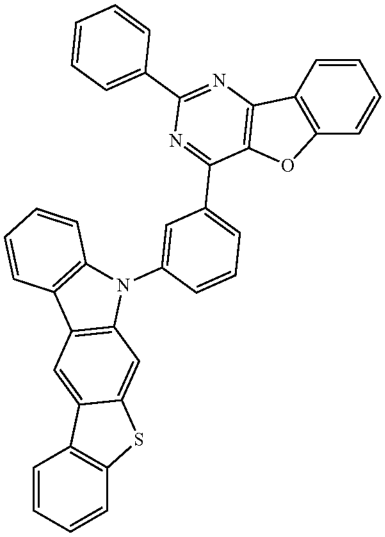
1984
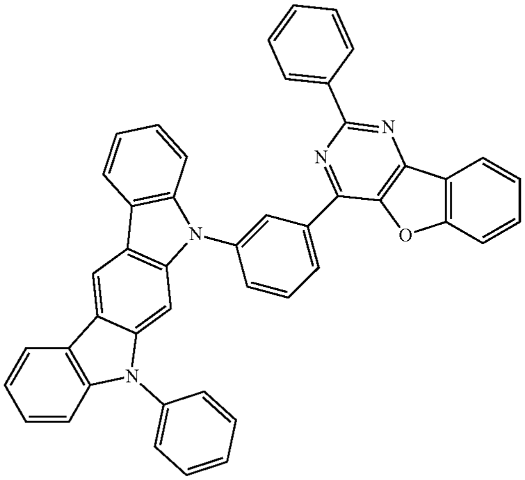
1985
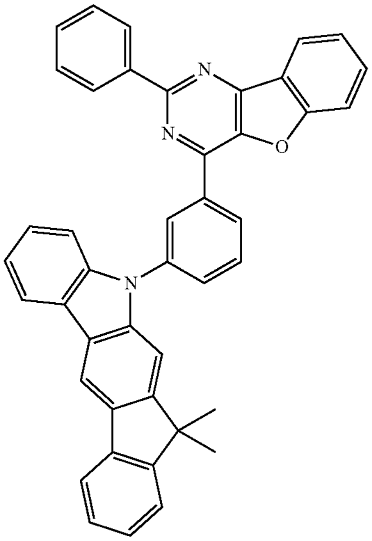

-continued
1986
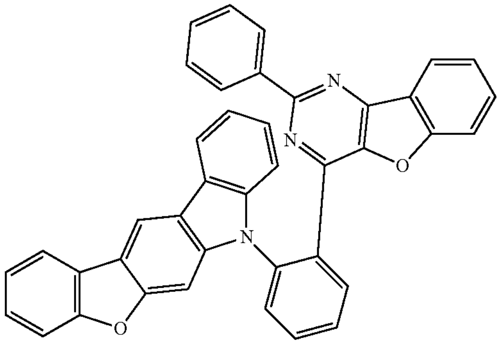
1987
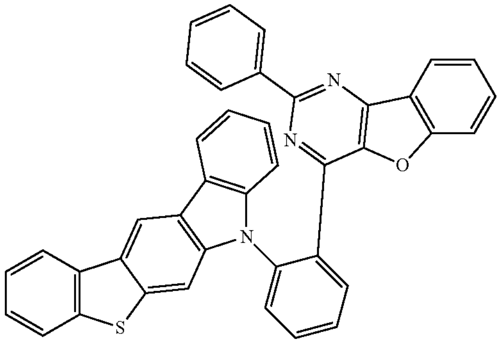
1988
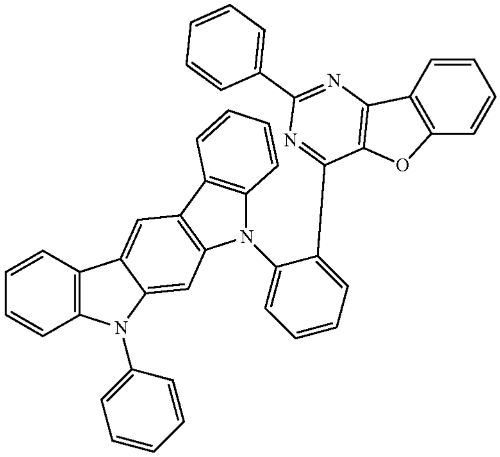
-continued
1989
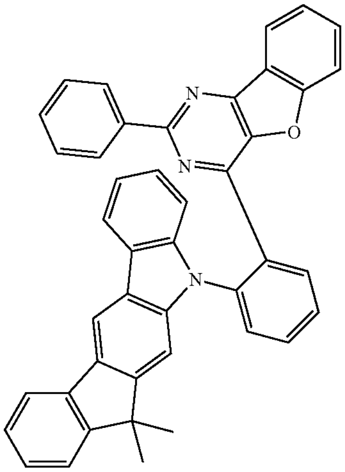
1990
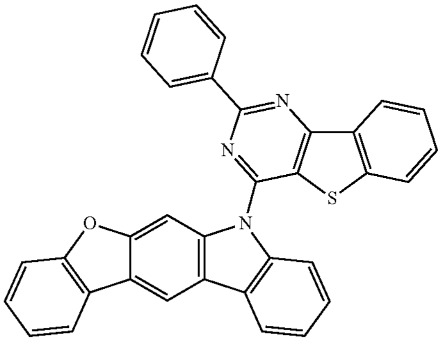
1991
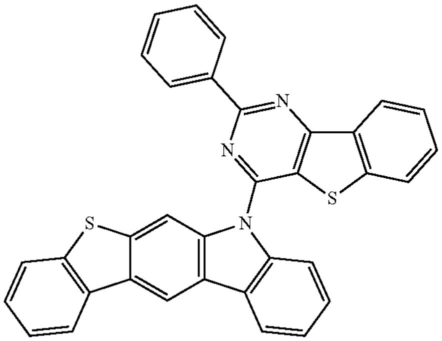
1992
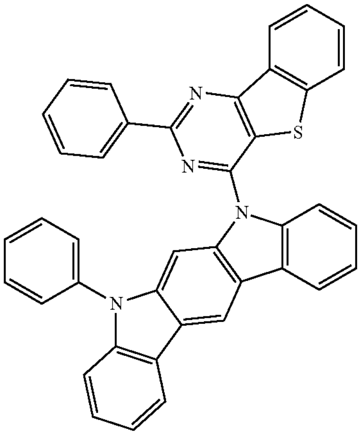

-continued
1993
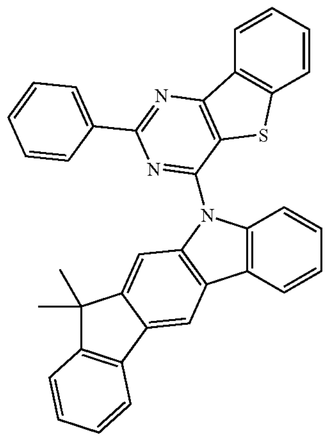
1994
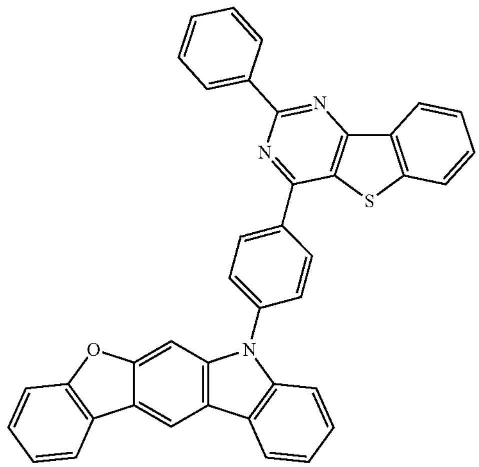
1995
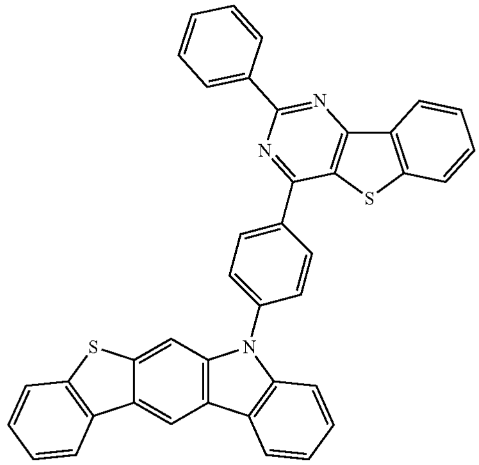
-continued
1996
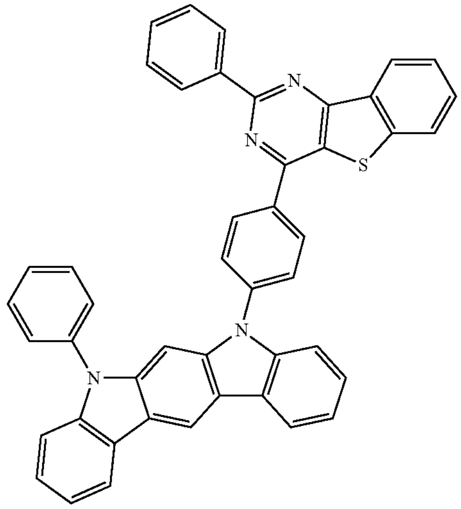
1997
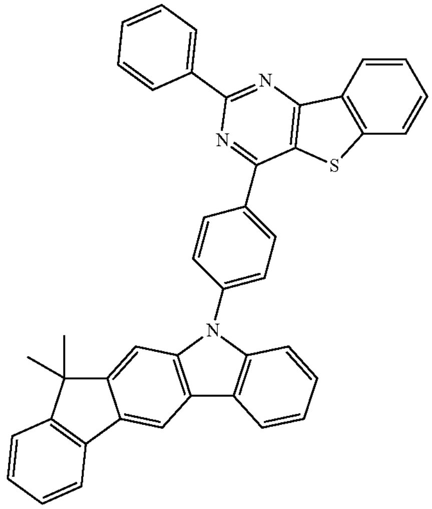
1998
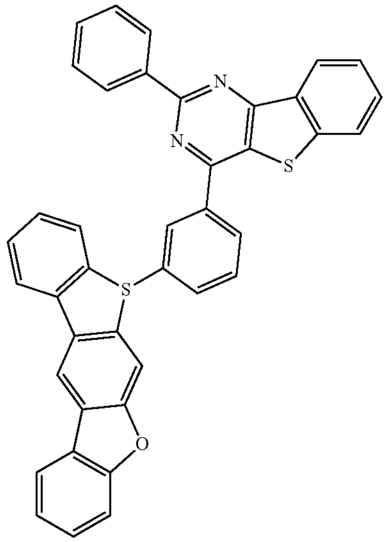

-continued
1999
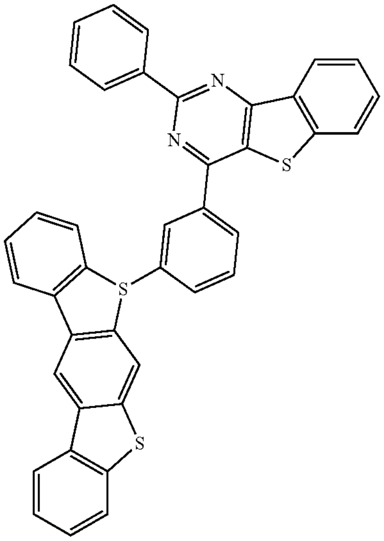
2000
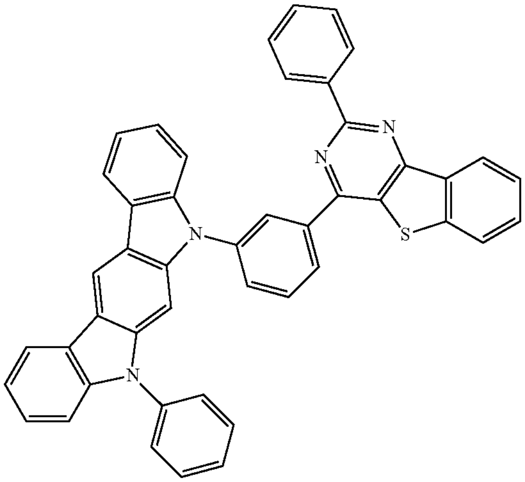
2001
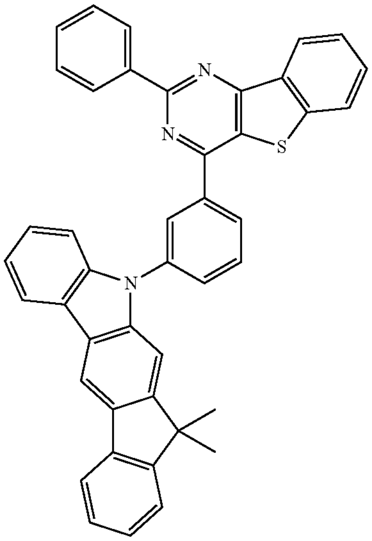
-continued
2002
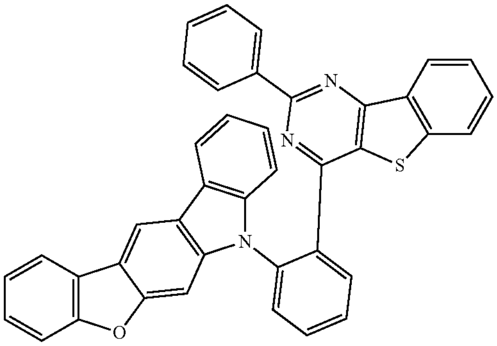
2003
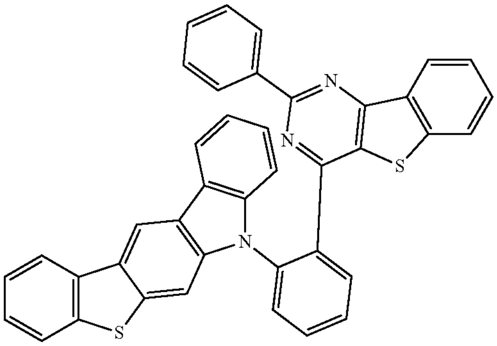
2004
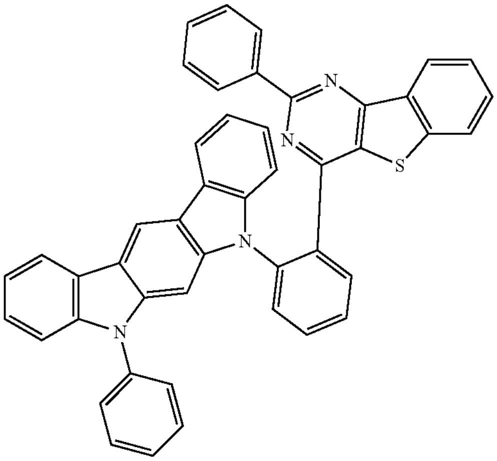

-continued
2005
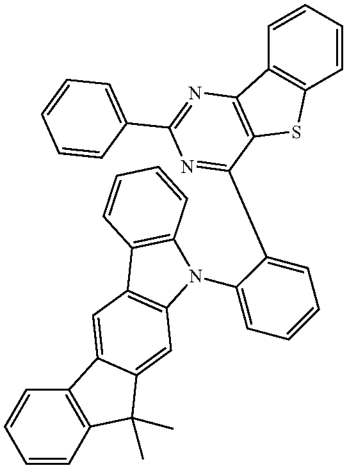
2006
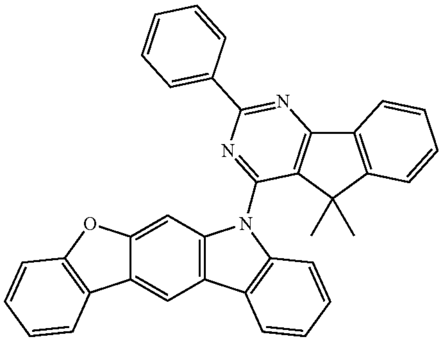
2007
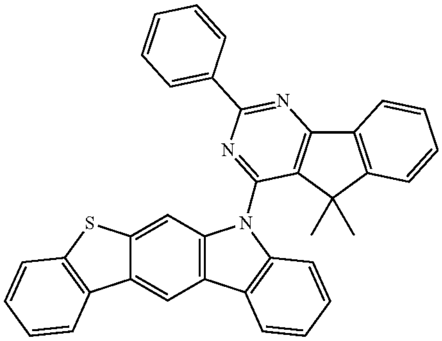
2008
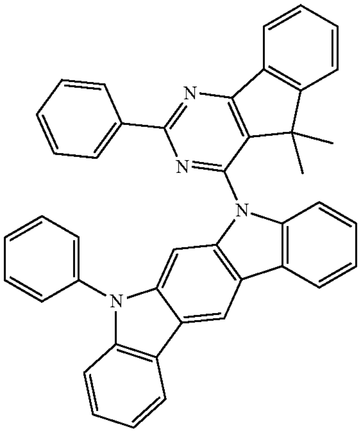
-continued
2009
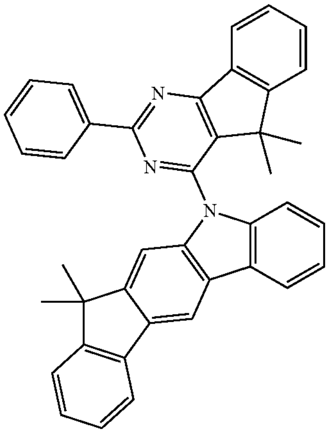
2010
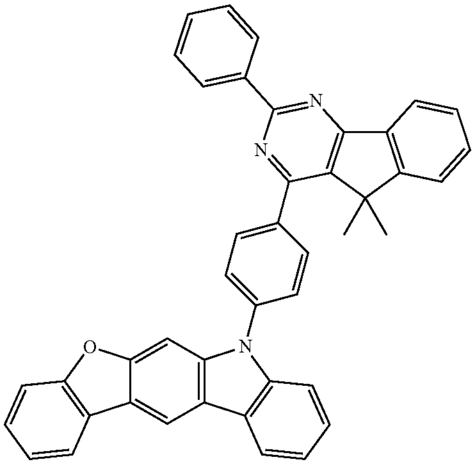
2011
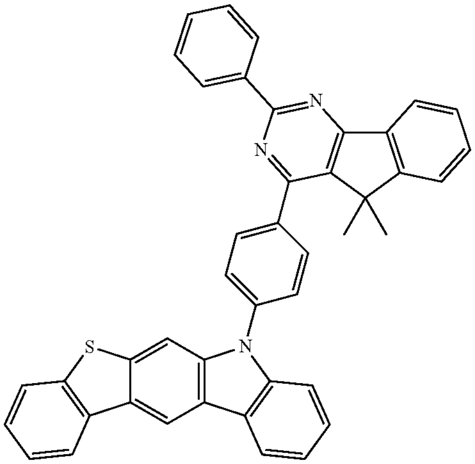

-continued
2012
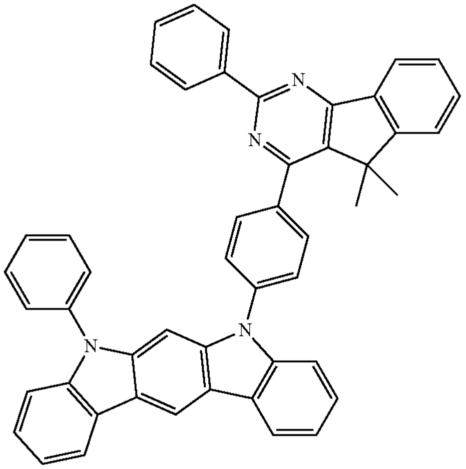
2013
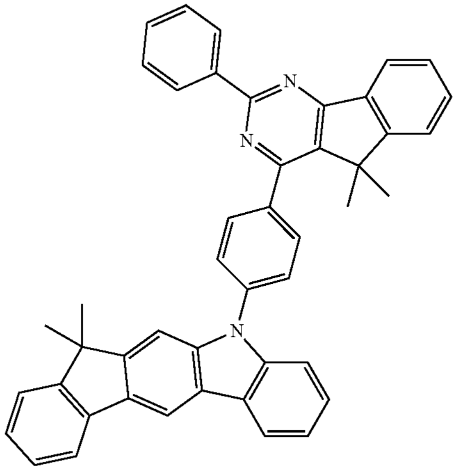
2014
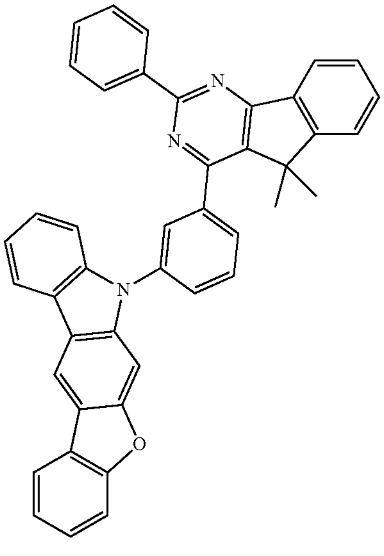
-continued
2015
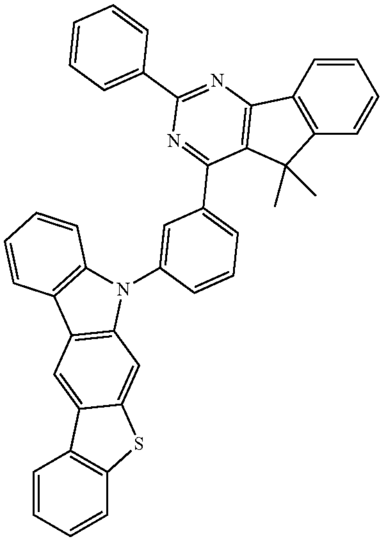
2016
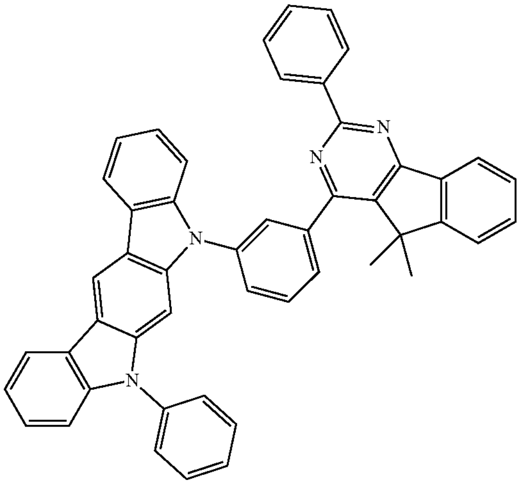
2017
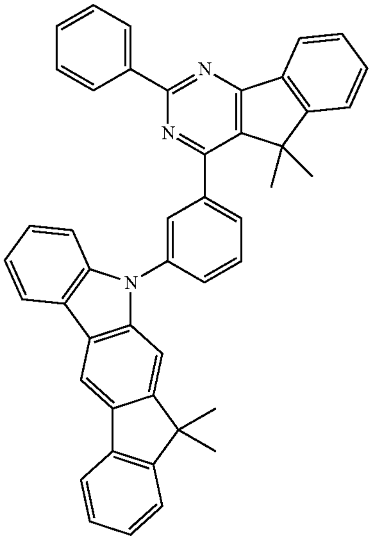

-continued
2018
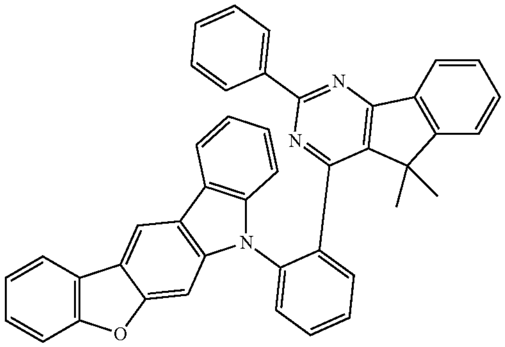
2019
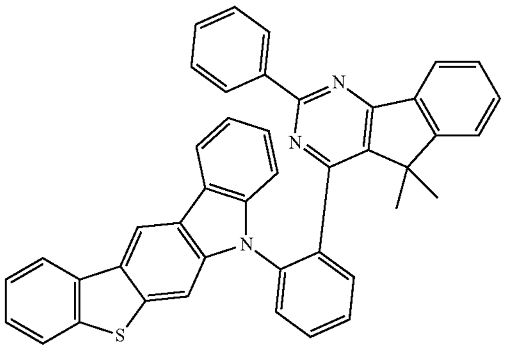
2020
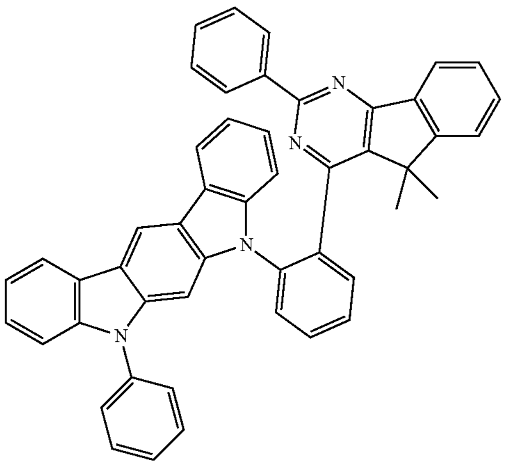
-continued
2021
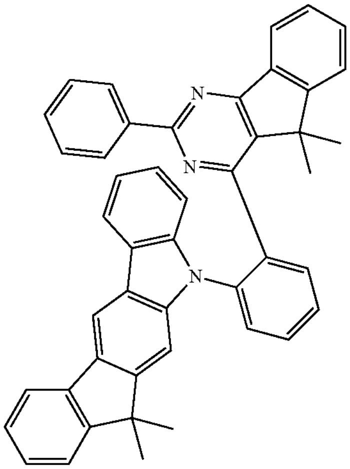
2022
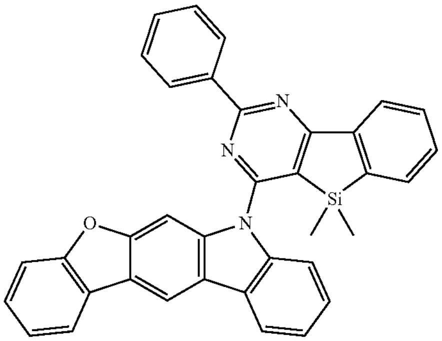
2023
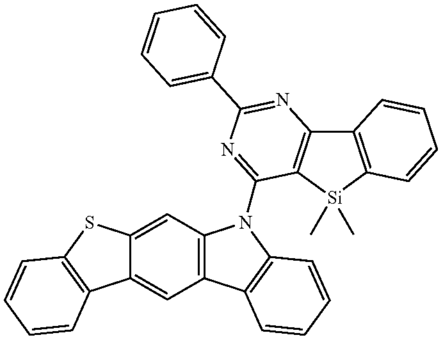
2024
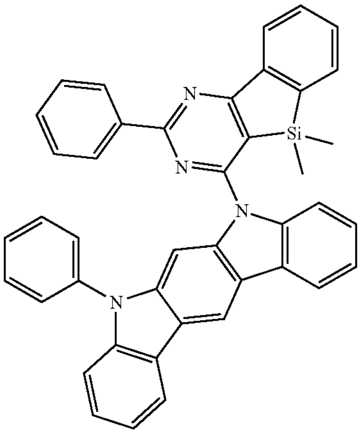

-continued
2025
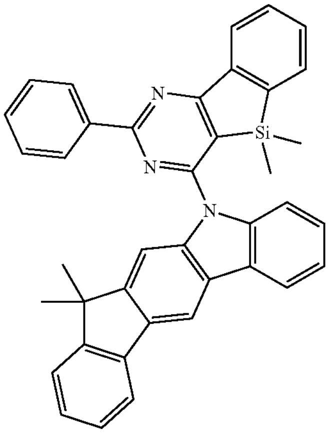
2026
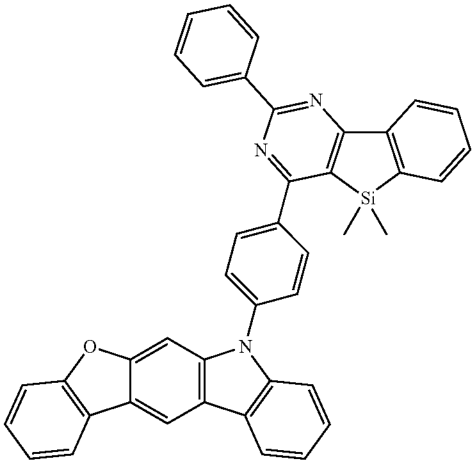
2027
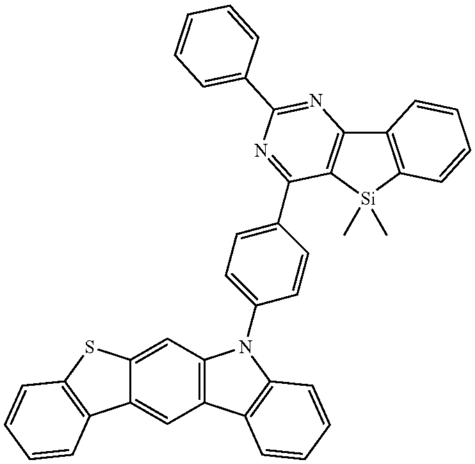
-continued
2028
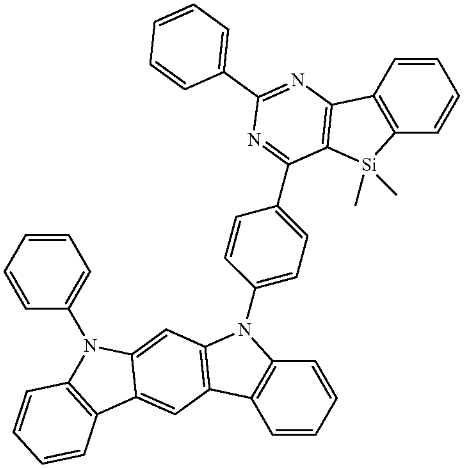
2029
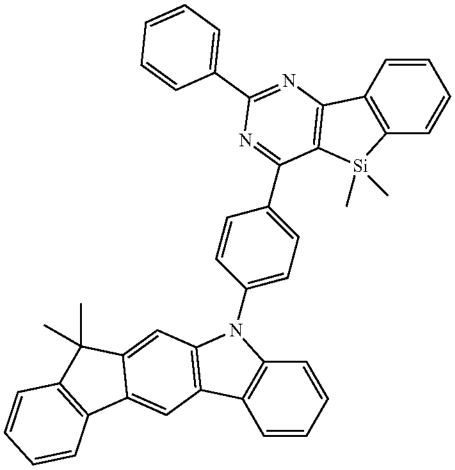
2030
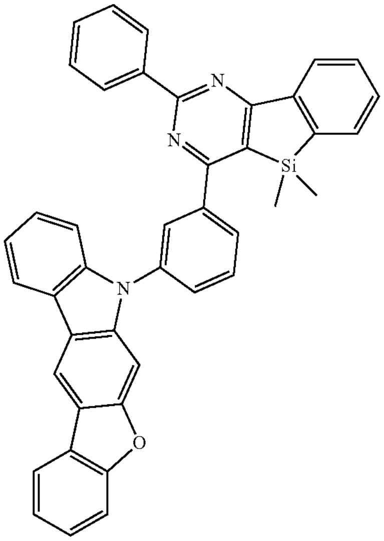

-continued
2031
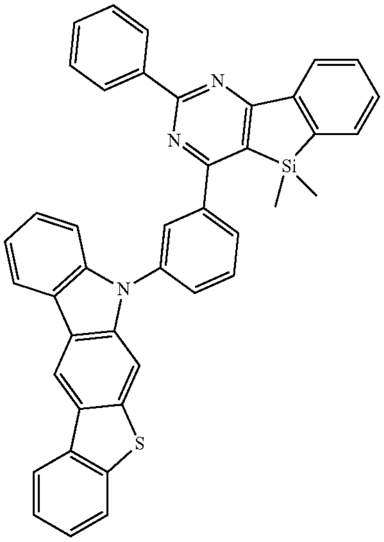
2032
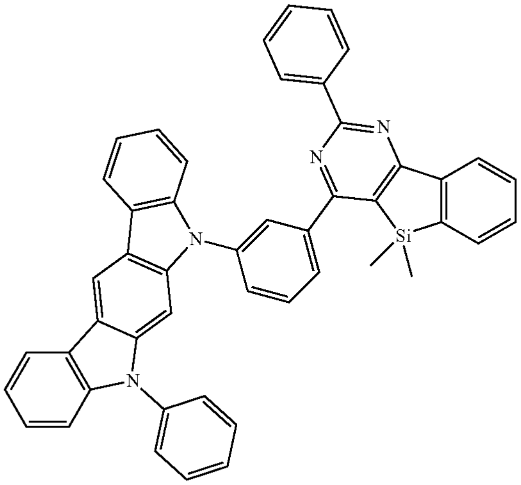
2033
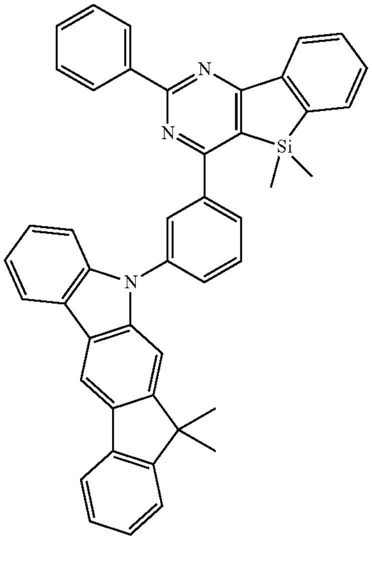
-continued
2034
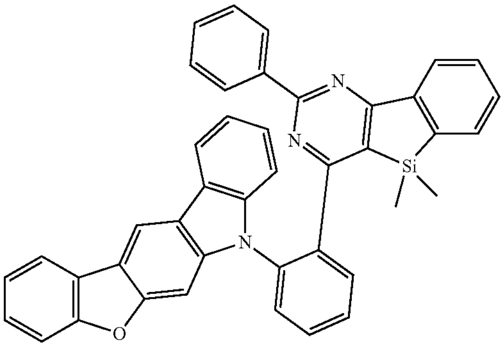
2035
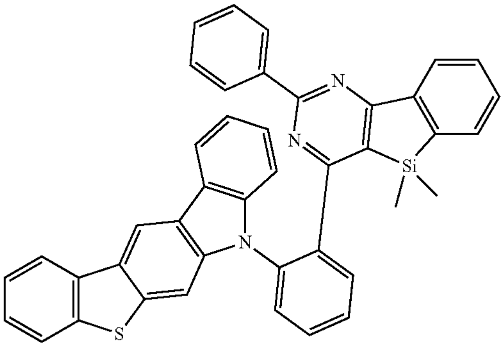
2036
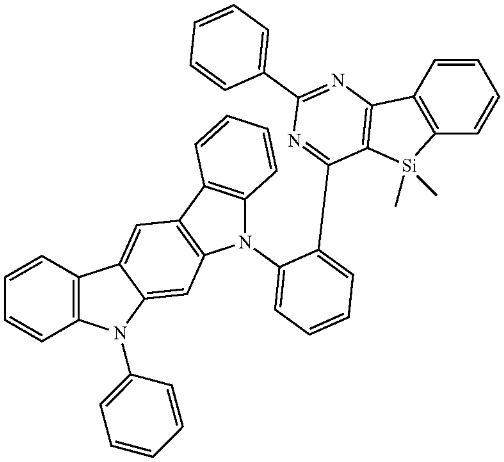
2037
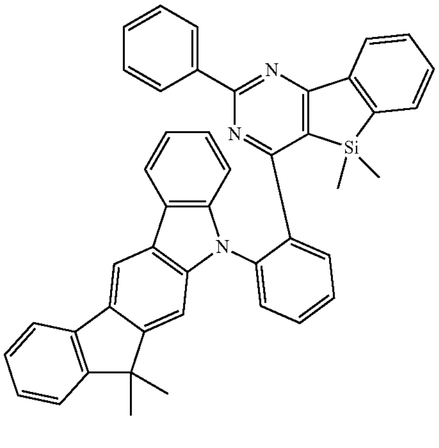

-continued
2038
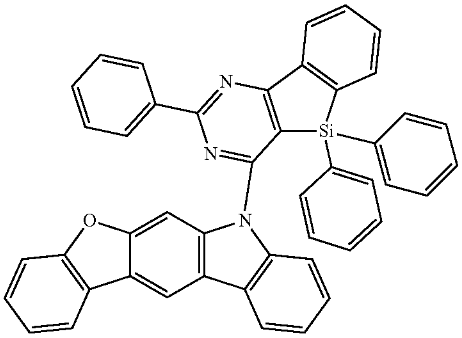
2039
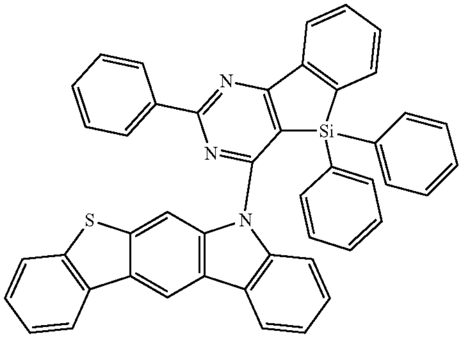
2040
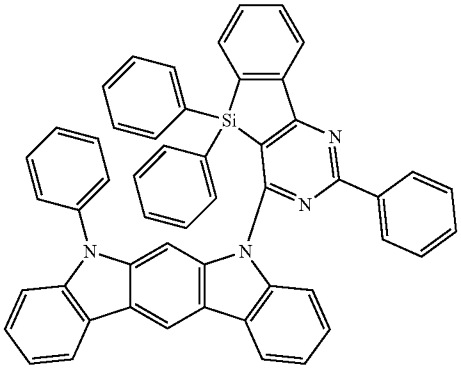
2041
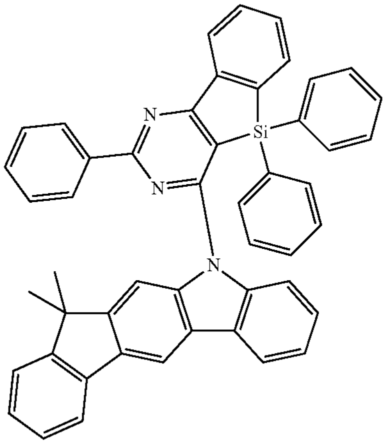
-continued
2042
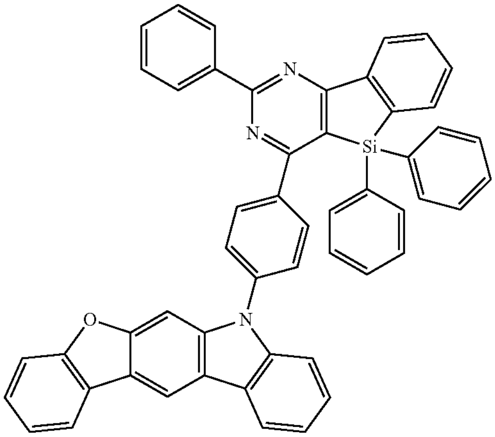
2043
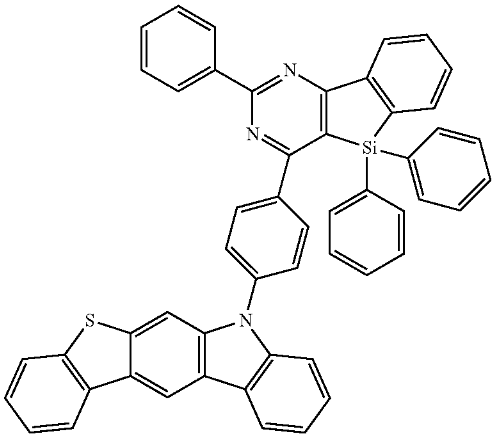
2044
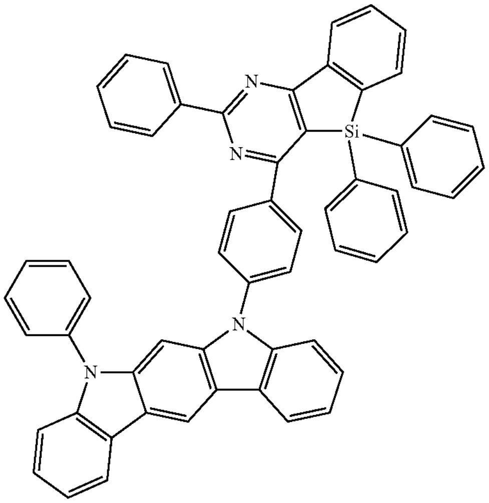

-continued
2045
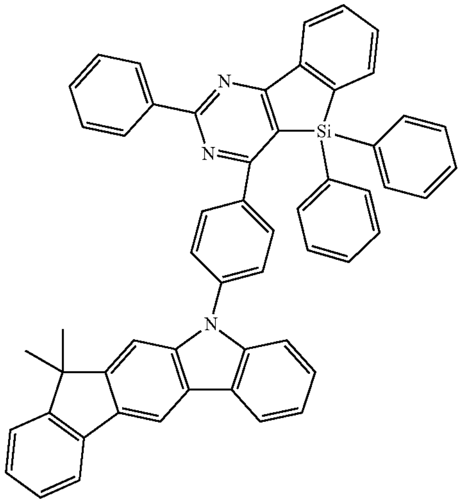
2046
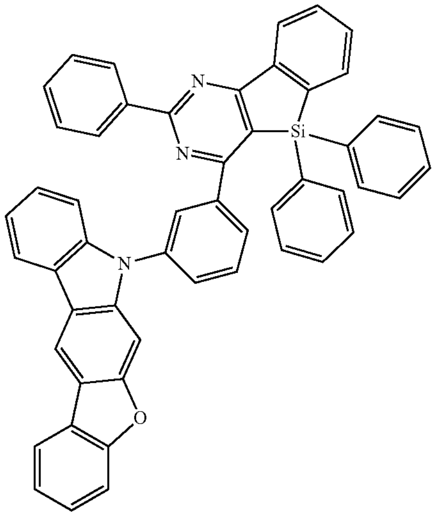
2047
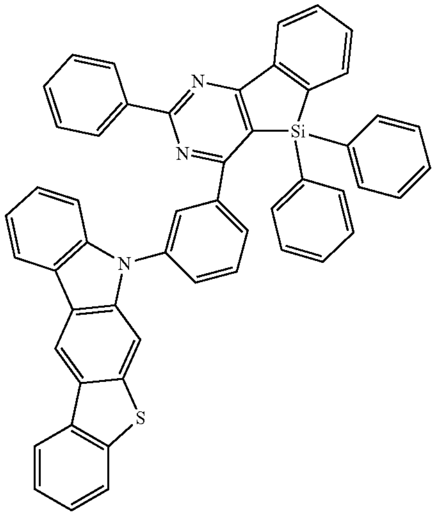
-continued
2048
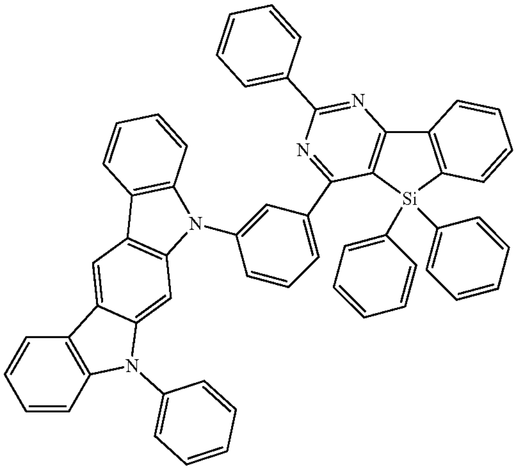
2049
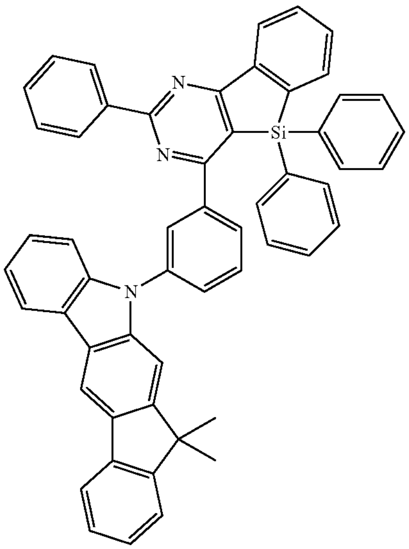
2050
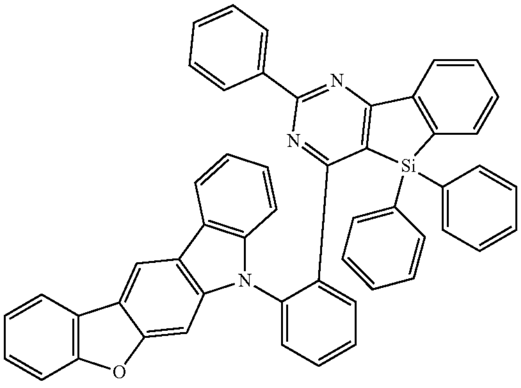

-continued
2051
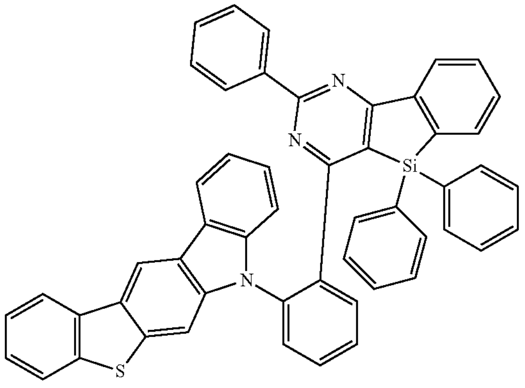
2052
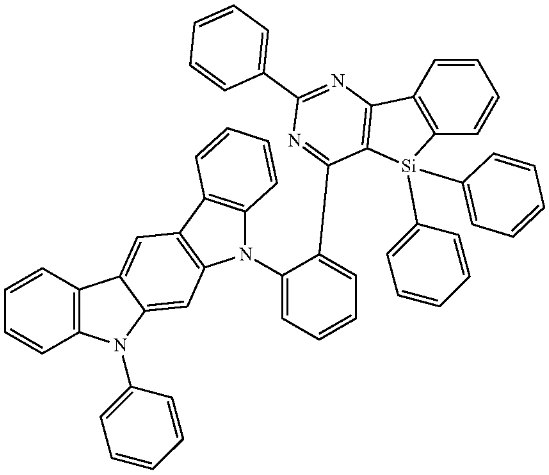
2053
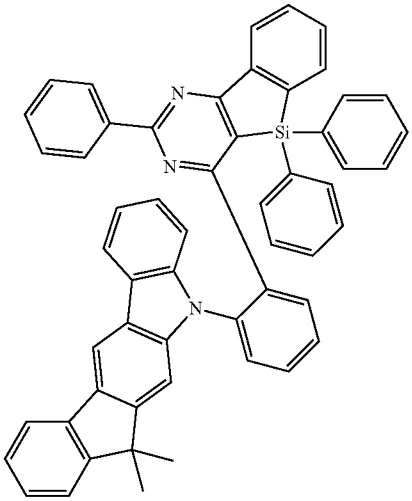
2054
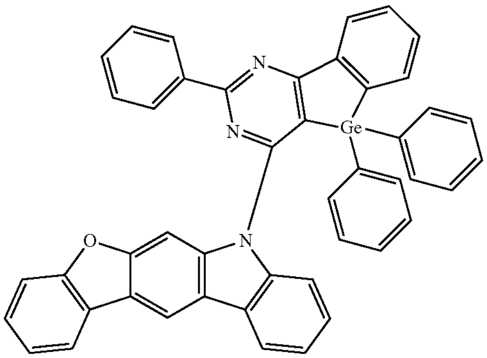
2055
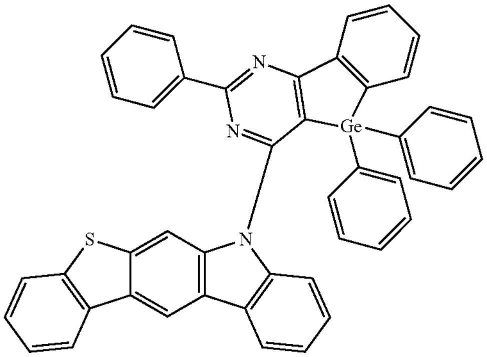
2056
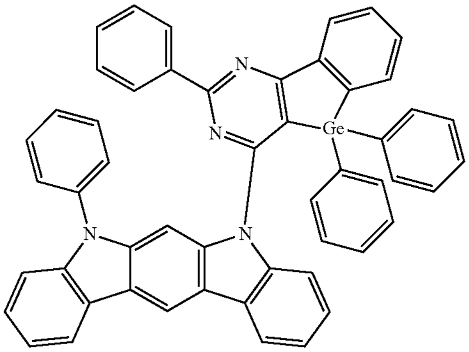
2057
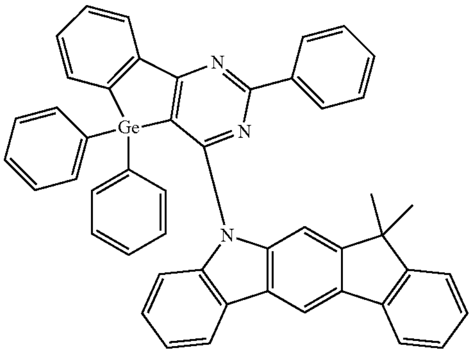

-continued
2058
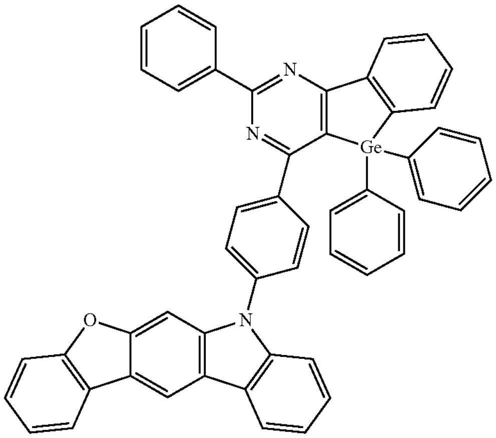
2059
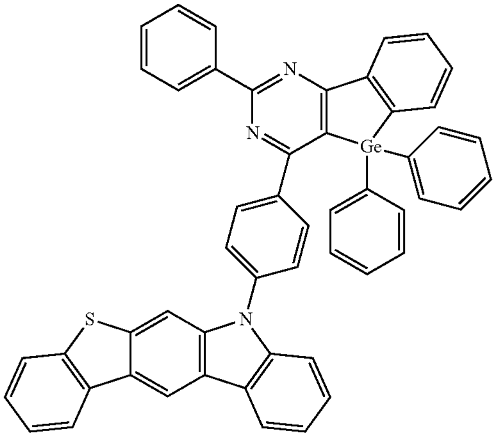
2060
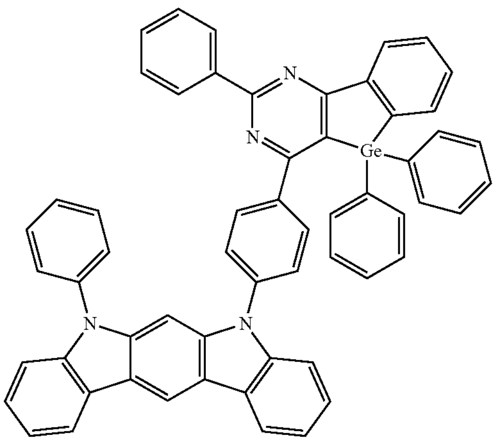
-continued
2061
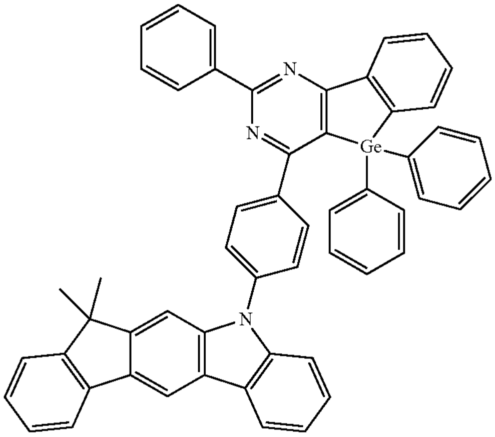
2062
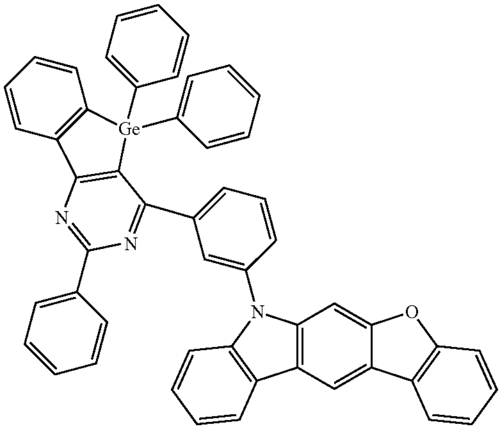
2063
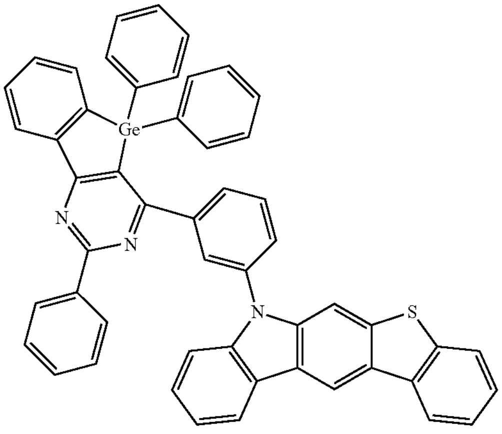

-continued
2064
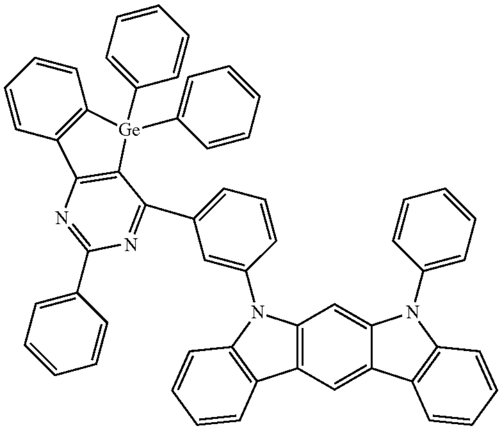
2065
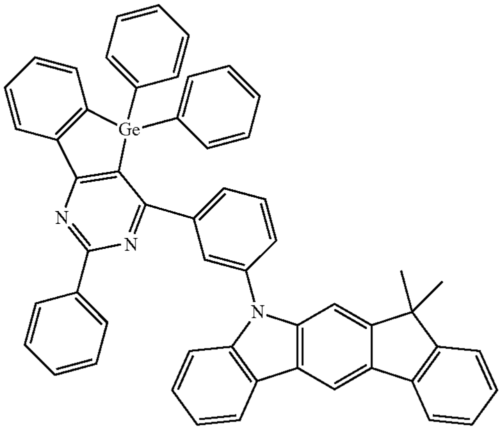
2066
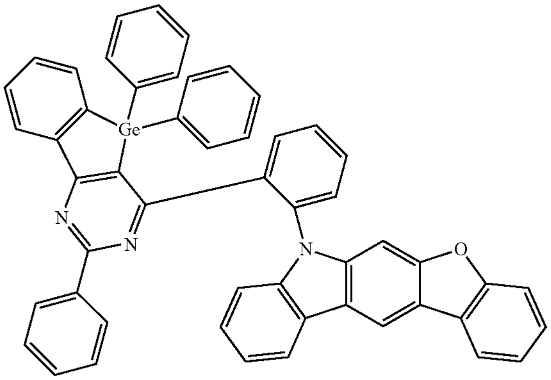
-continued
2067
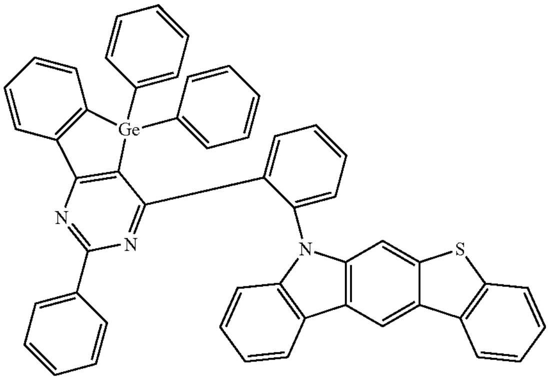
2068
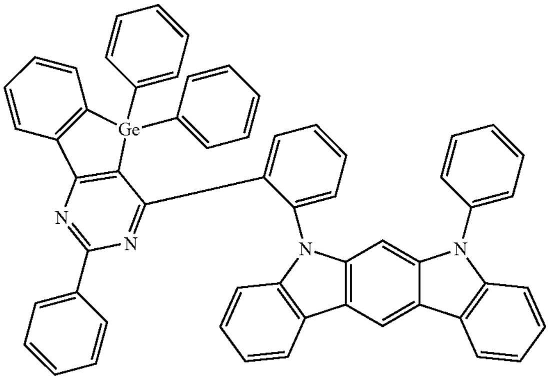
2069
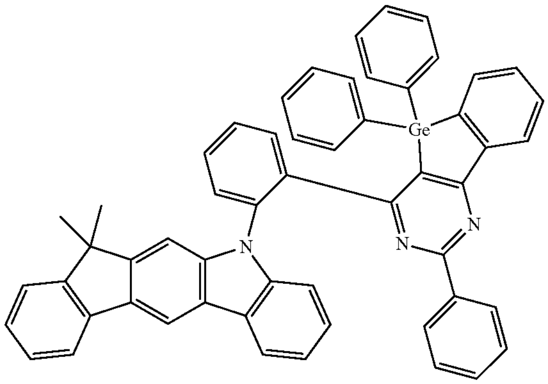
2070
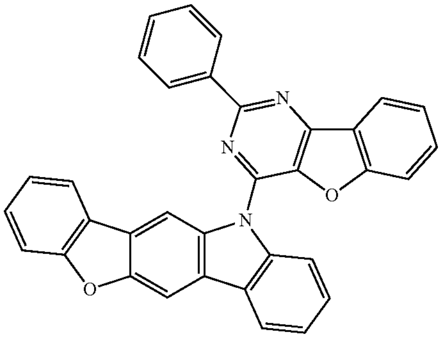

-continued
2071
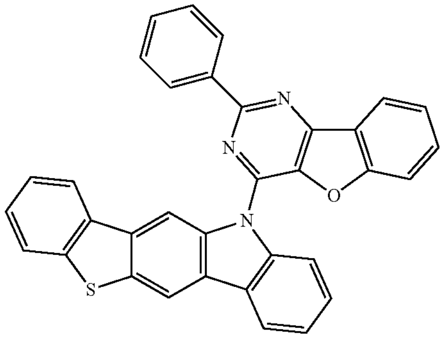
2072
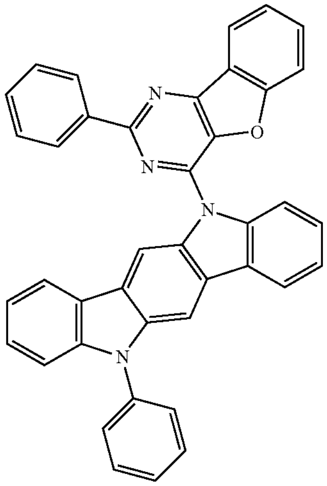
2073
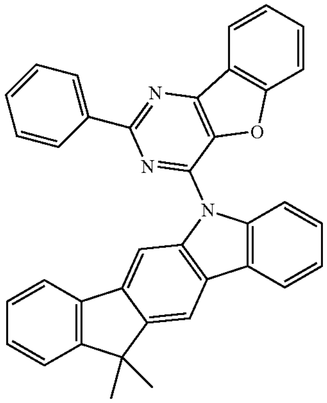
-continued
2074
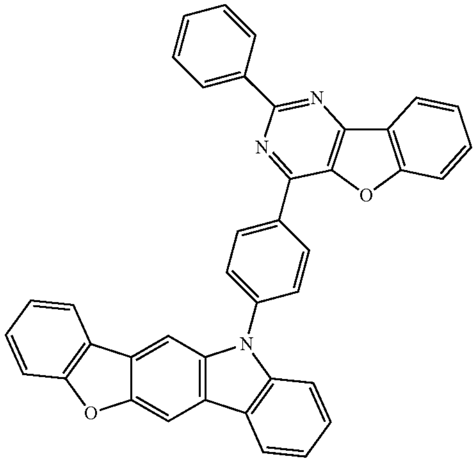
2075
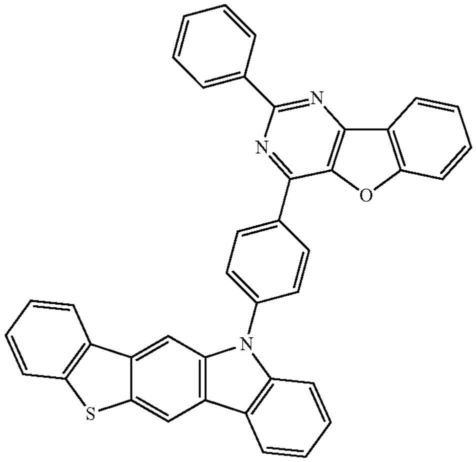
2076
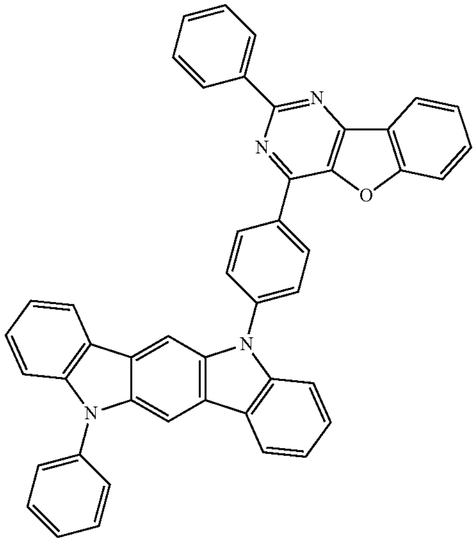

-continued
2077
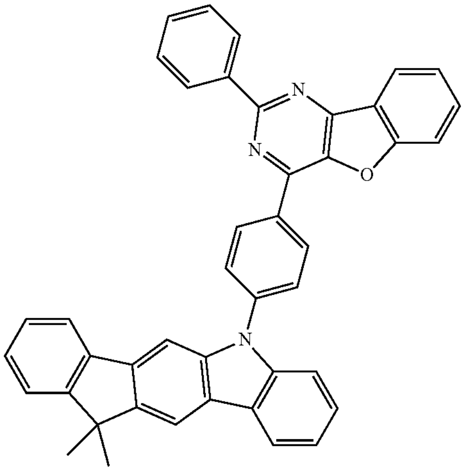
2078
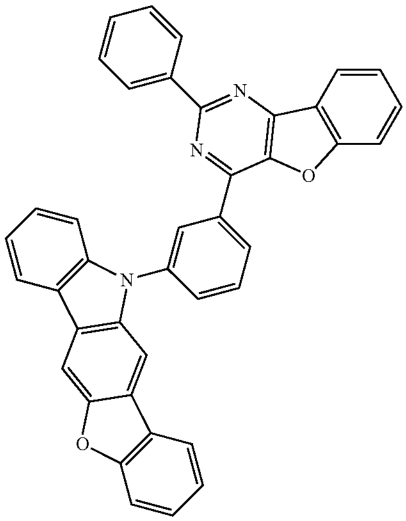
2079
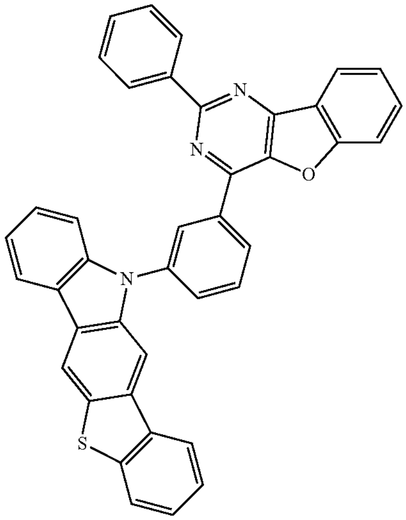
-continued
2080
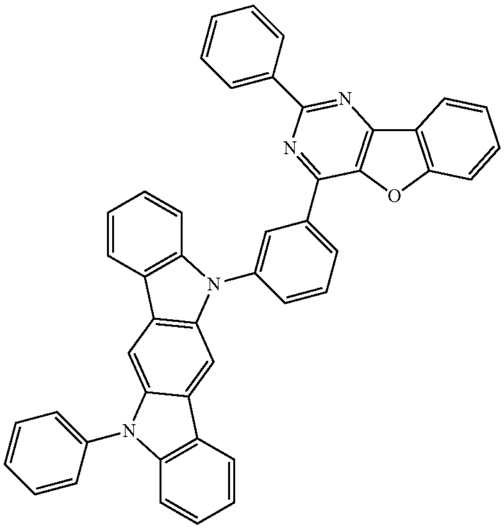
2081
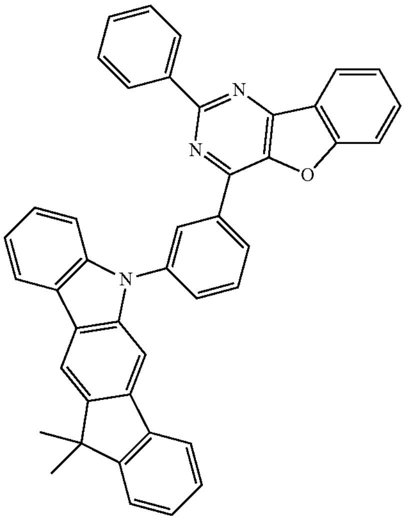
2082
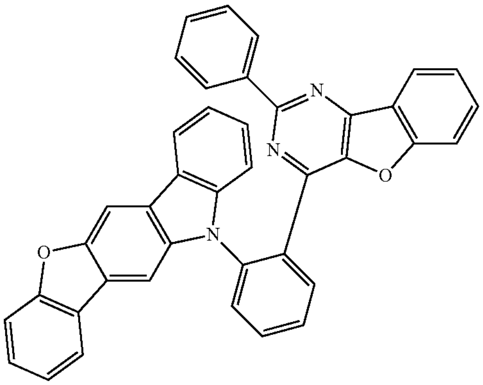

-continued
2083
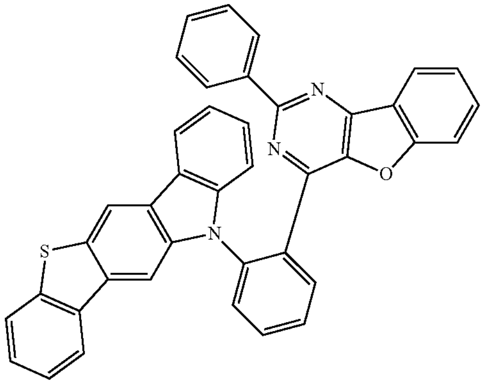
2084
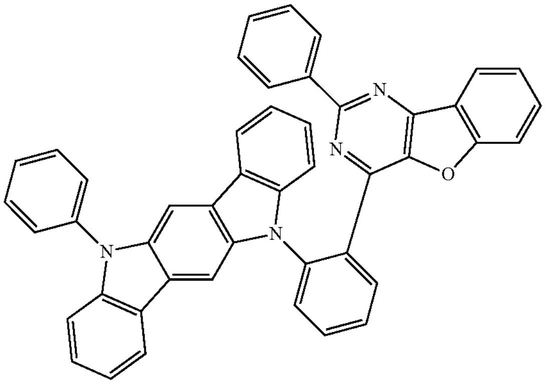
2085
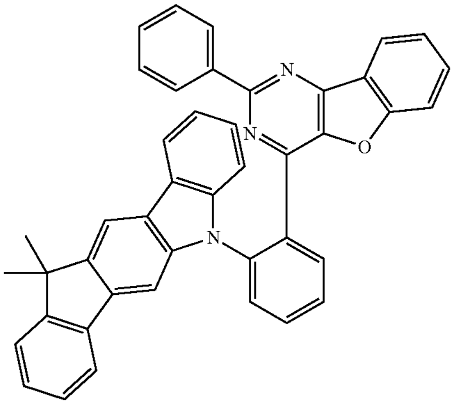
2086
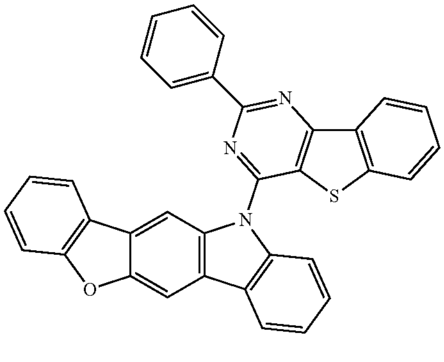
-continued
2087
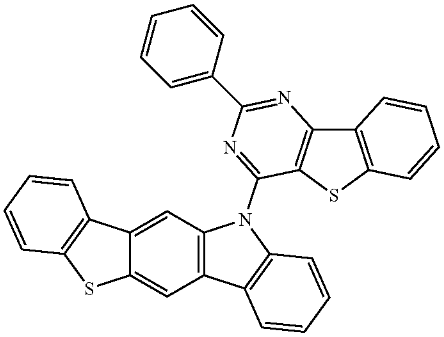
2088
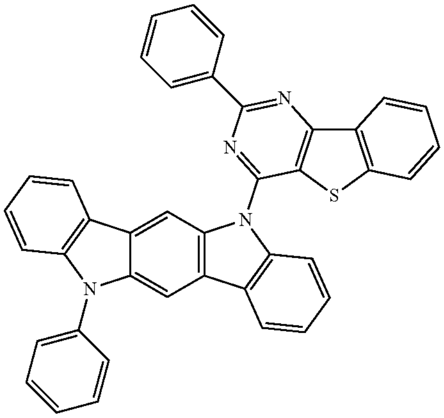
2089
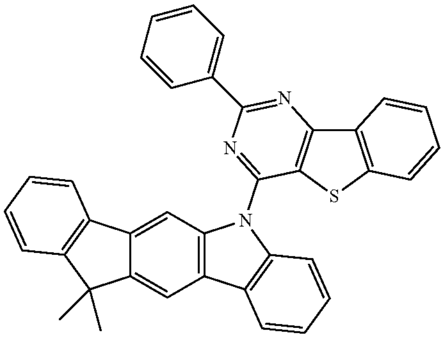
2090
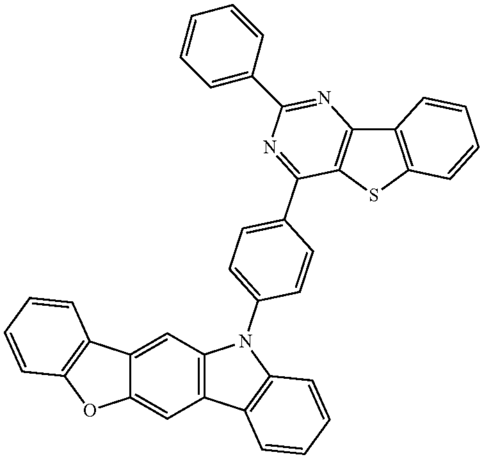

-continued
2091
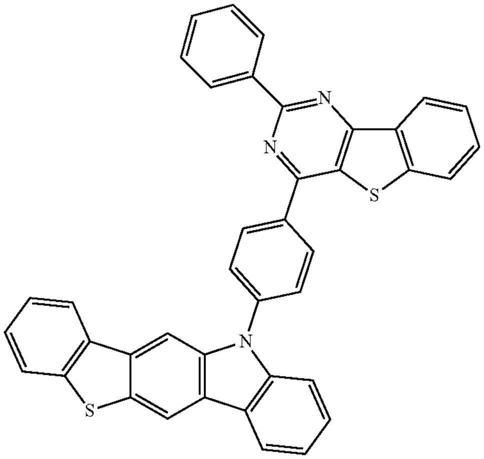
2092
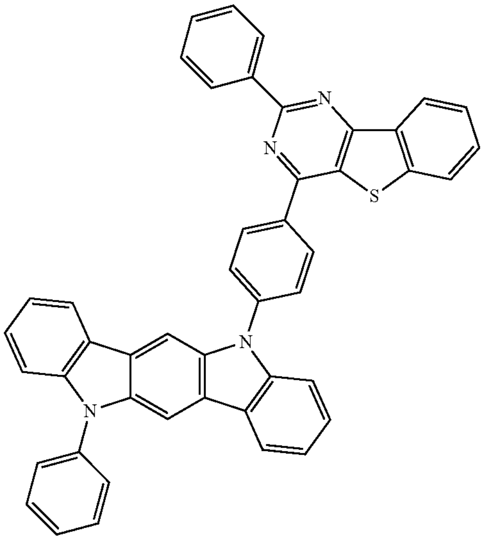
2093
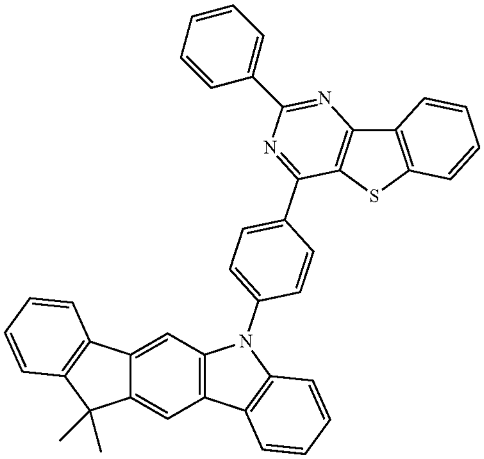
-continued
2094
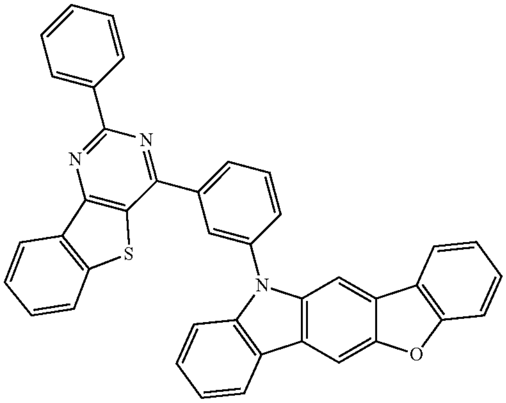
2095
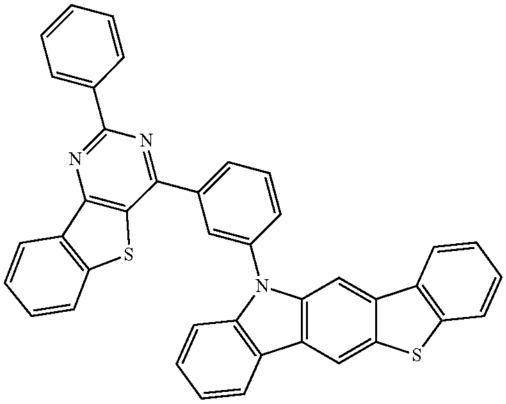
2096
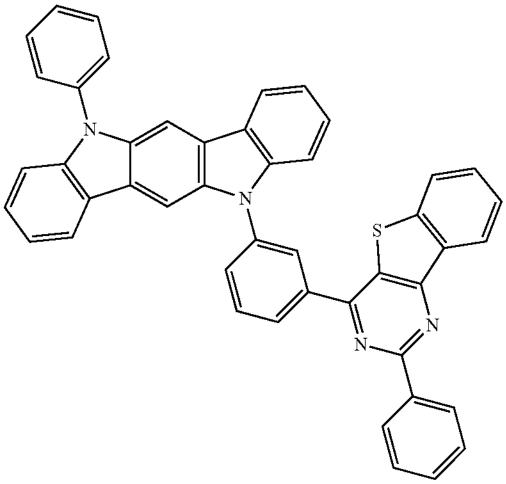

-continued
2097
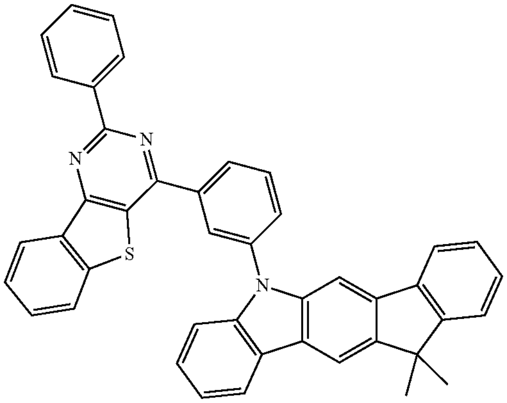
2098
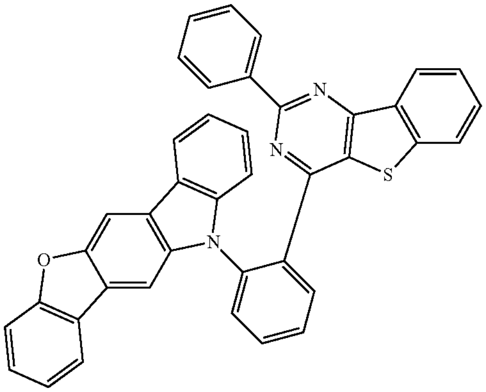
2099
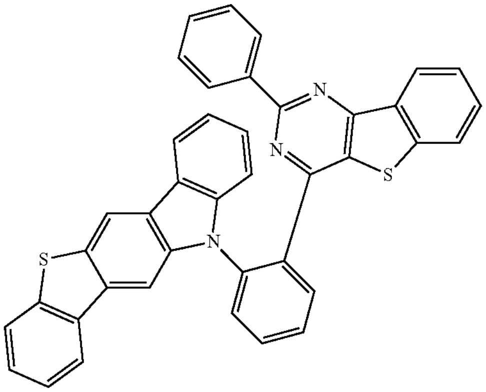
-continued
2100
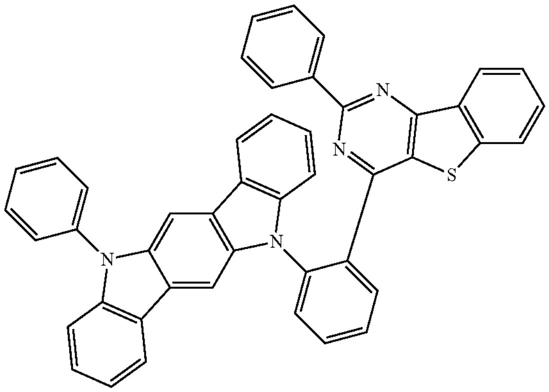
2101
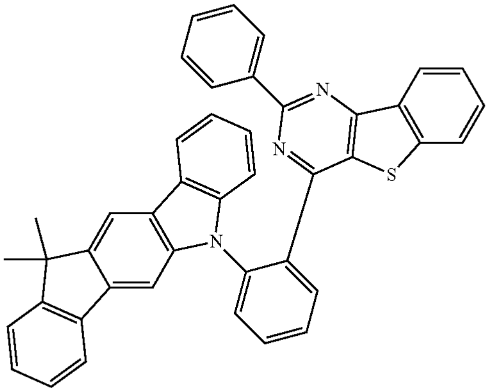
2102
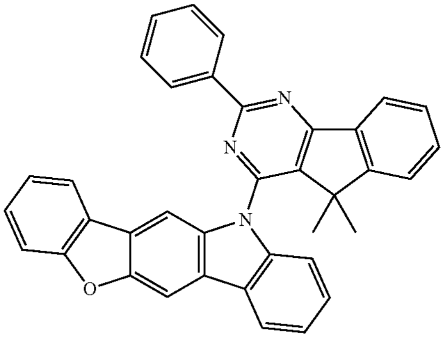
2103
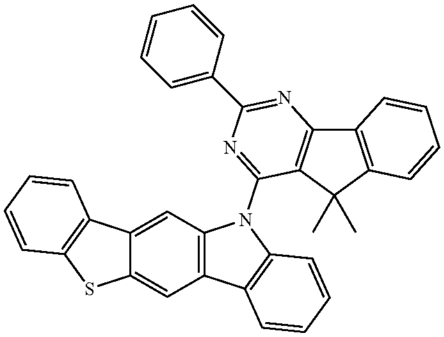

-continued
2104
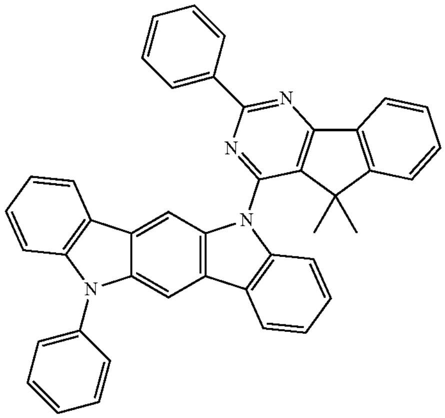
2105
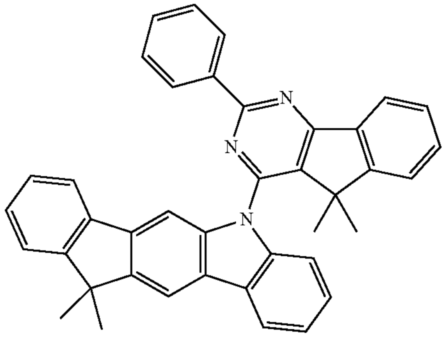
2106
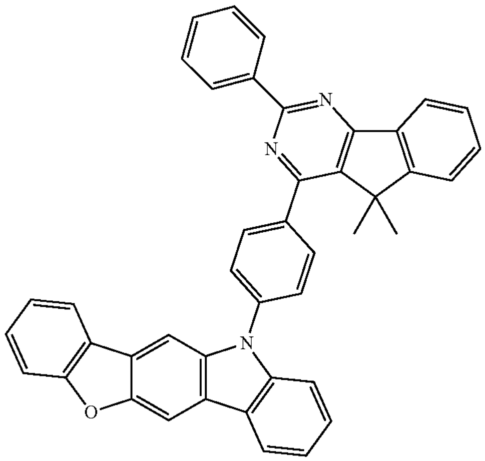
-continued
2107
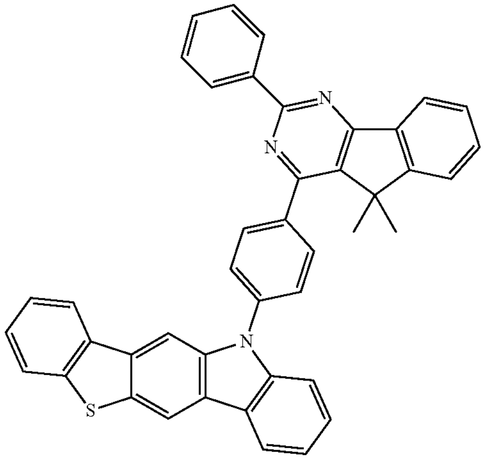
2108
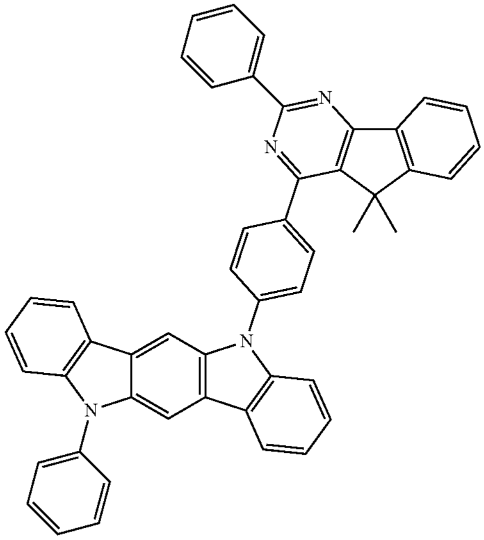
2109
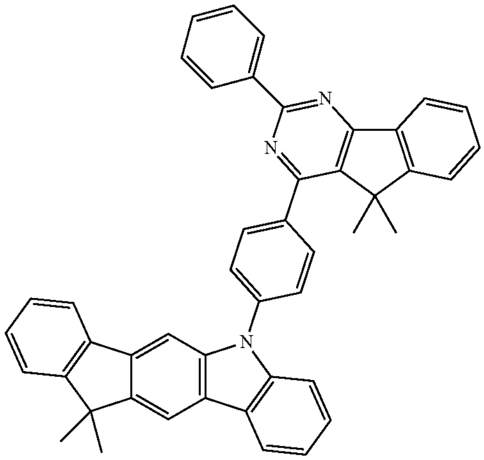

-continued
2110
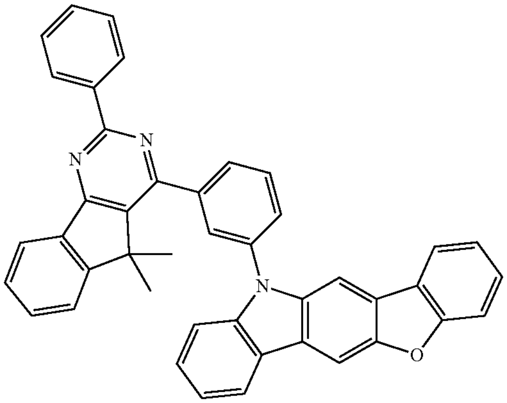
2111
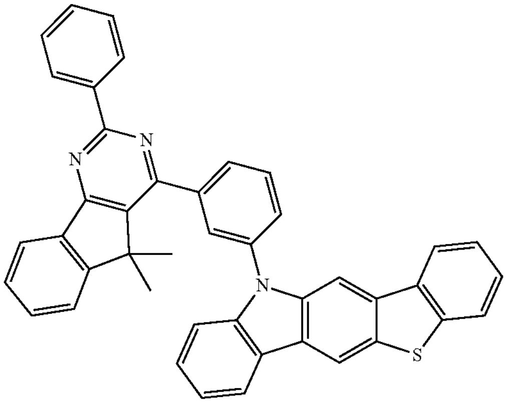
2112
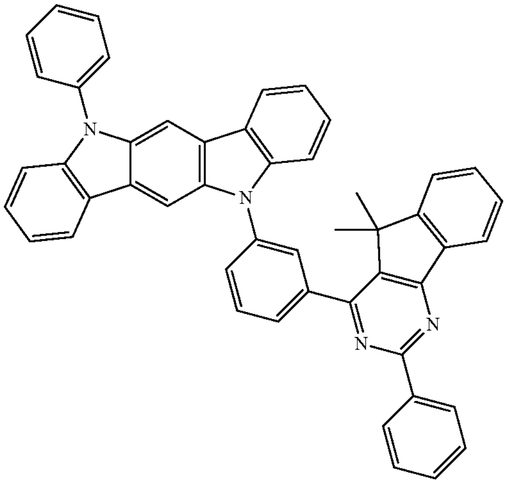
-continued
2113
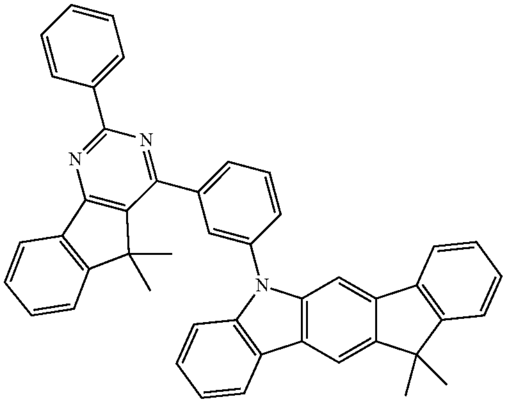
2114
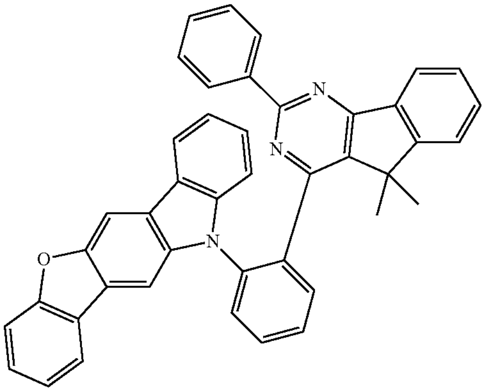
2115
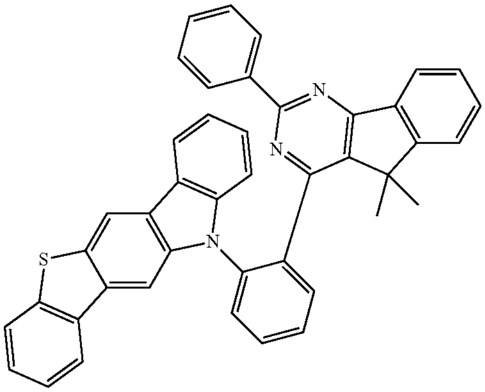

-continued
2116
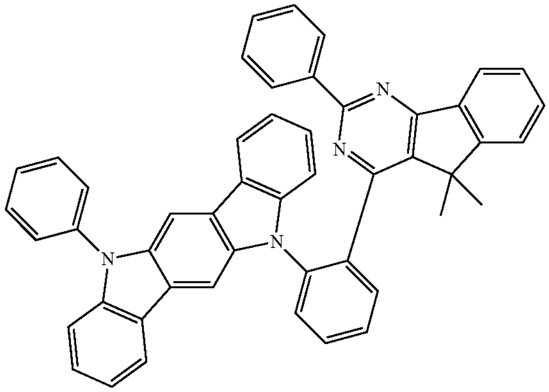
2117
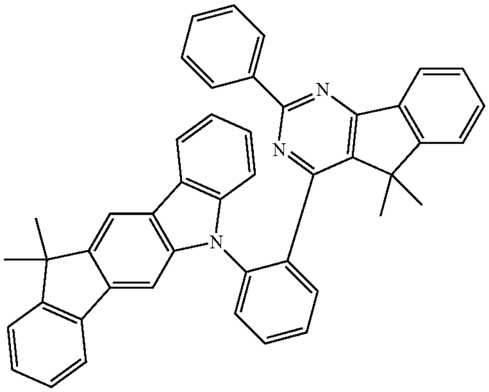
2118
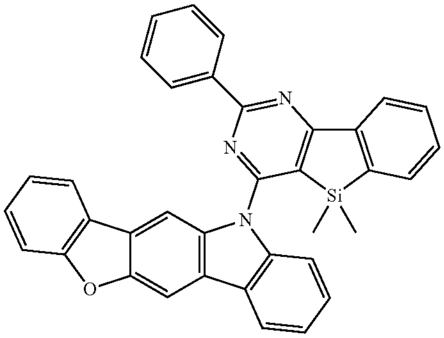
2119
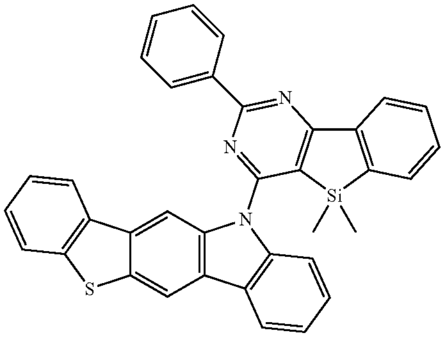
-continued
2120
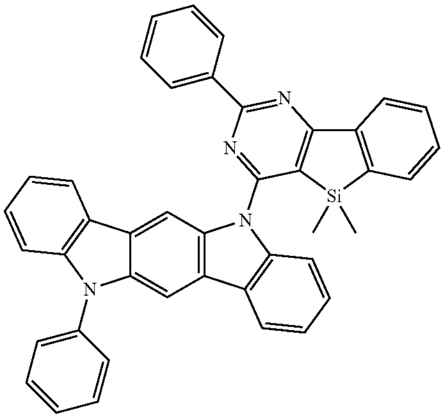
2121
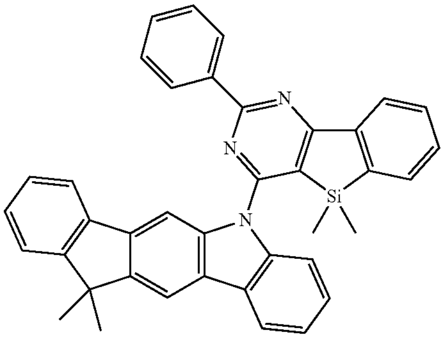
2122
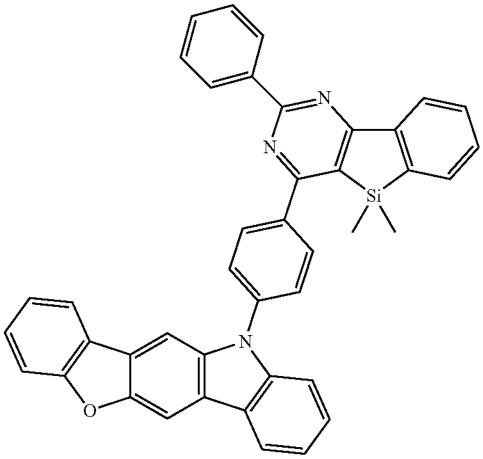

2123
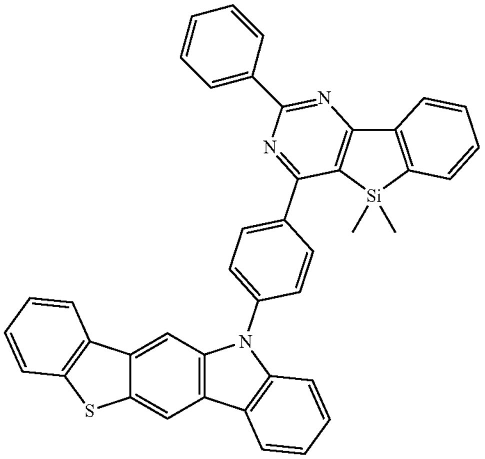
2124
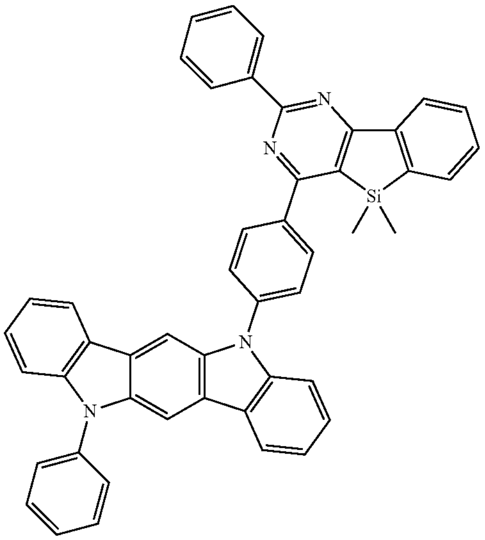
2125
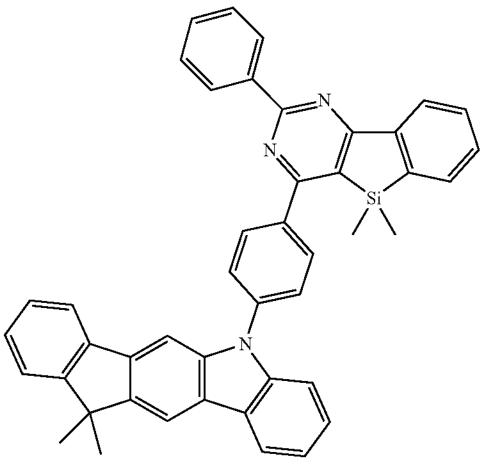
2126
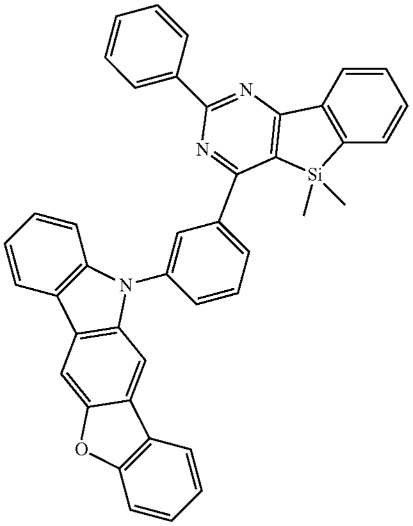
2127
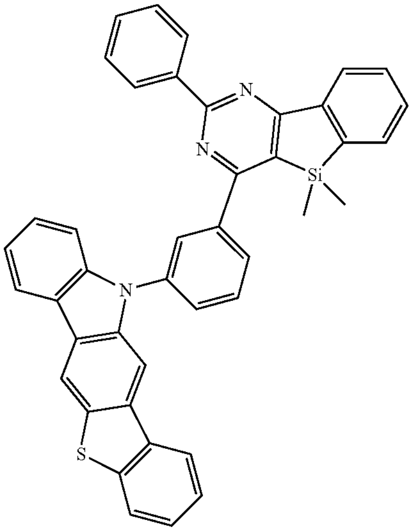
2128
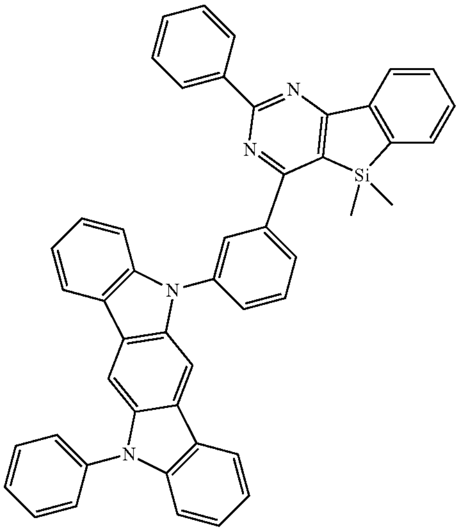

-continued
2129
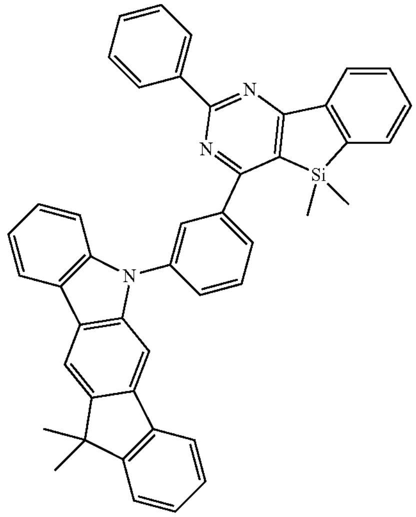
2130
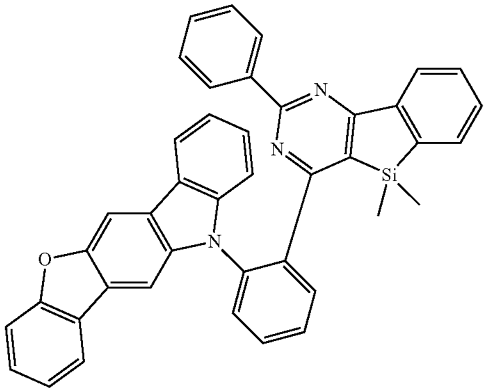
2131
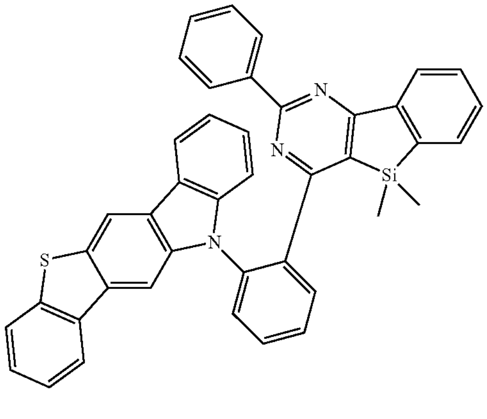
-continued
2132
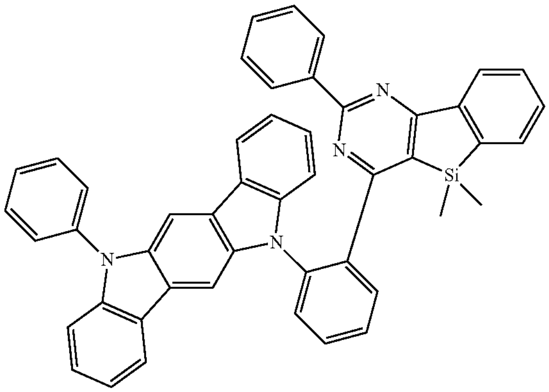
2133
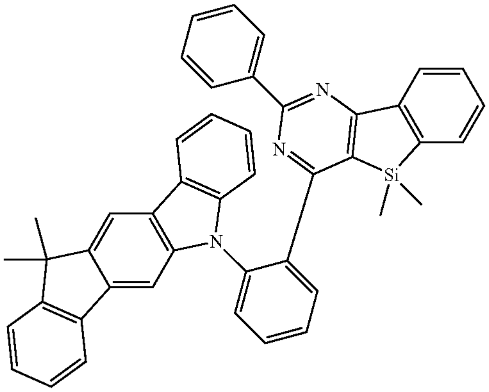
2134
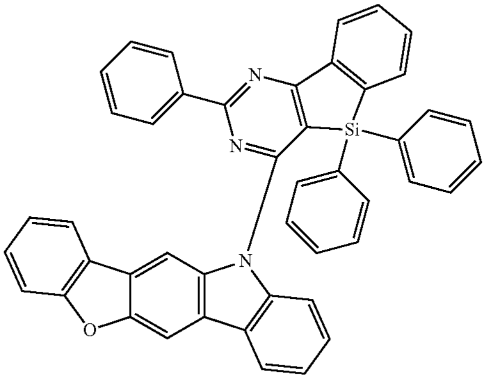
2135
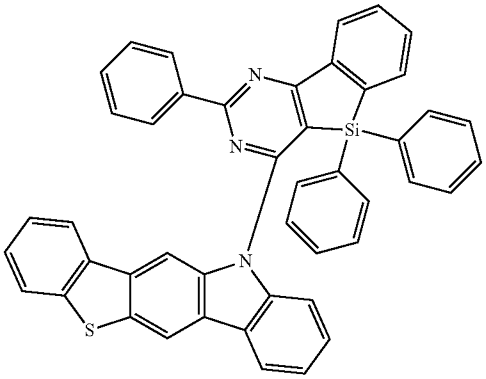

-continued
2136
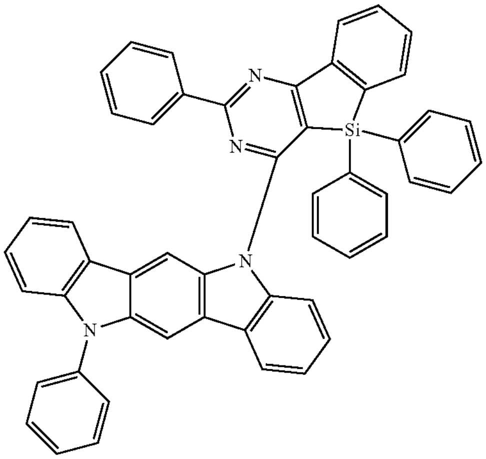
2137
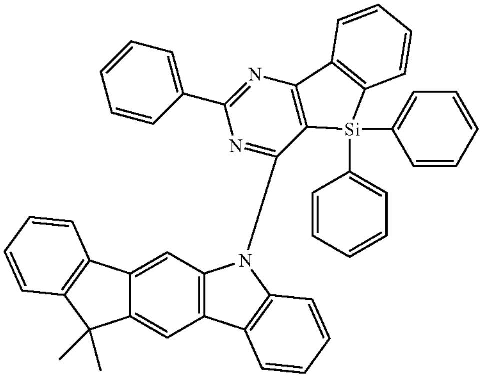
2138
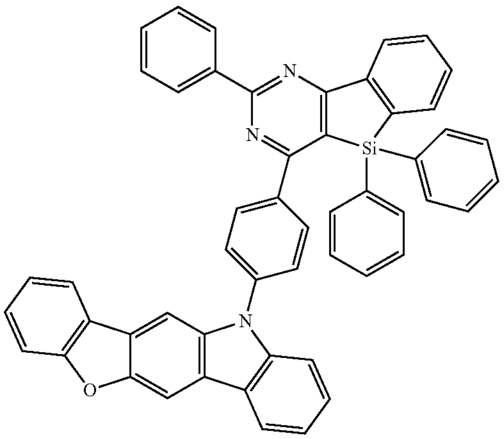
-continued
2139
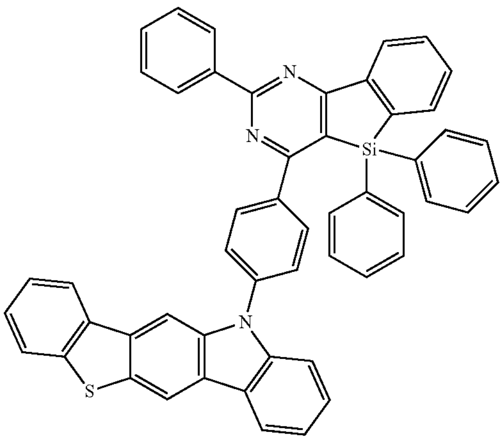
2140
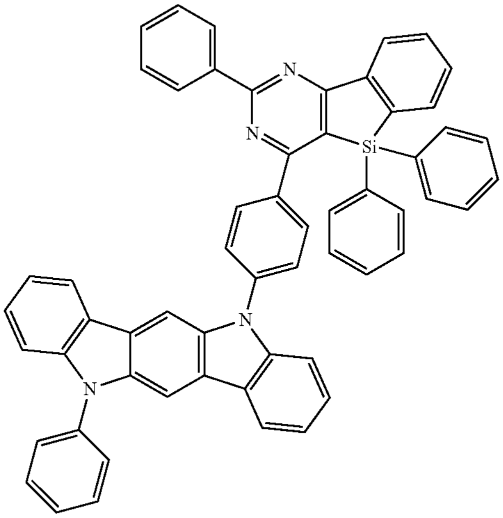
2141
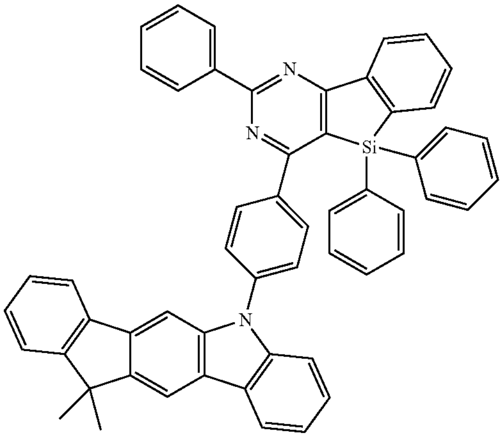

-continued
2142
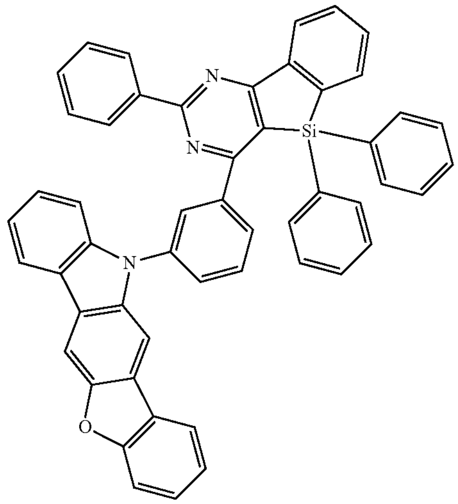
2143
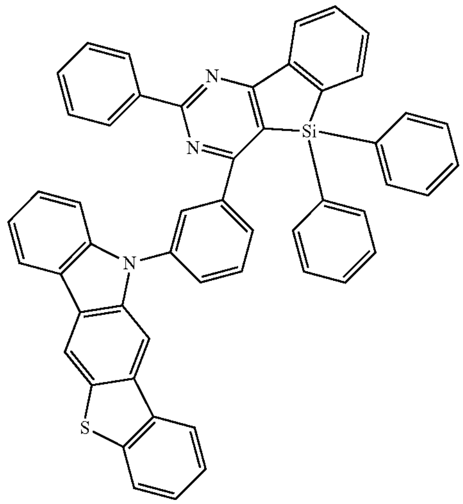
2144
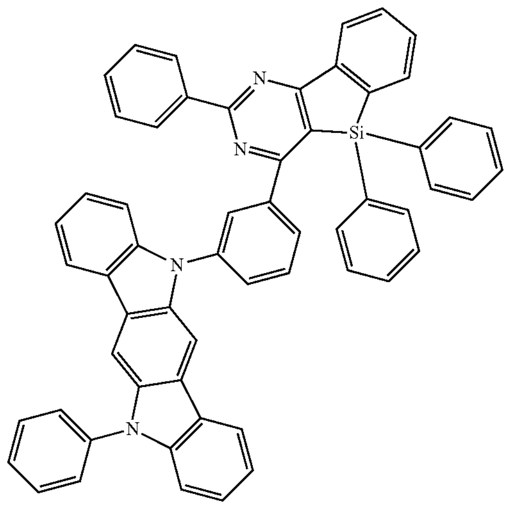
-continued
2145
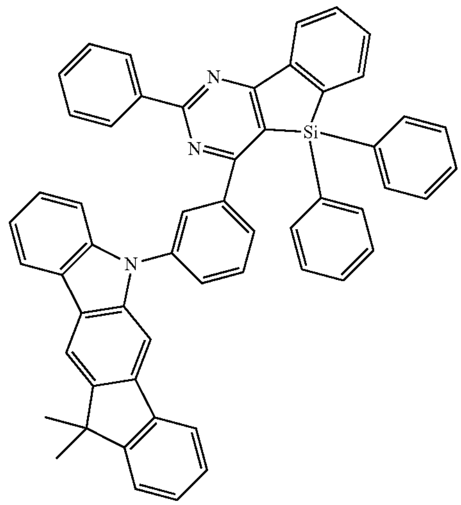
2146
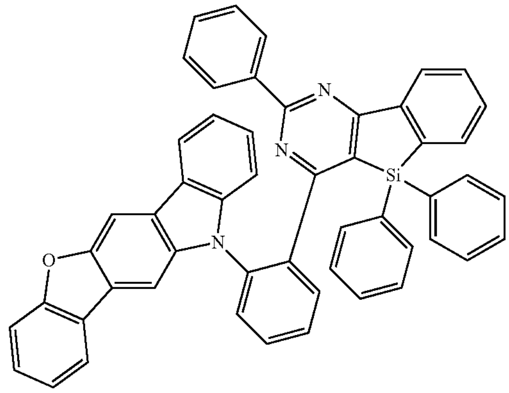
2147
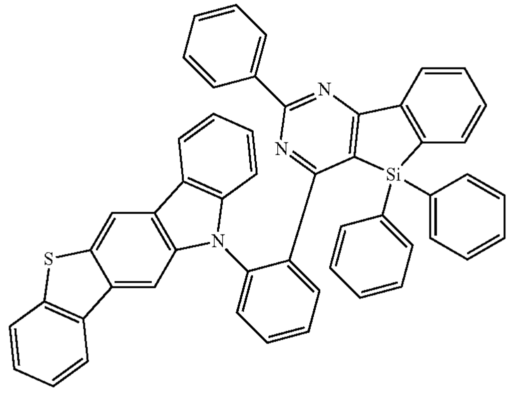

-continued
2148
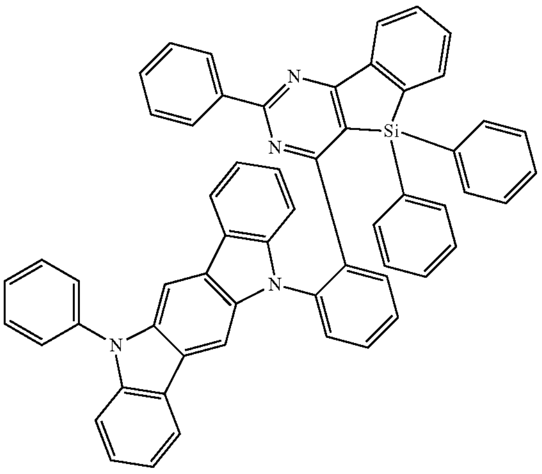
2149
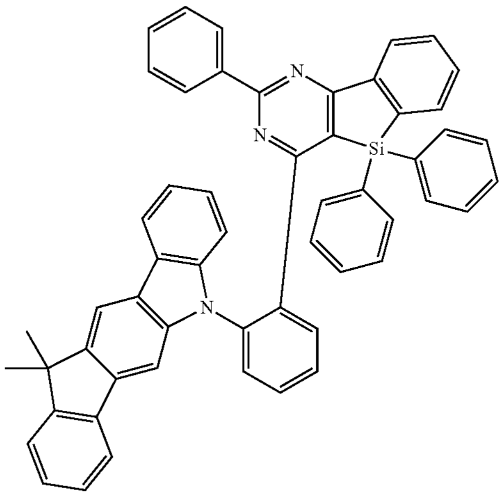
2150
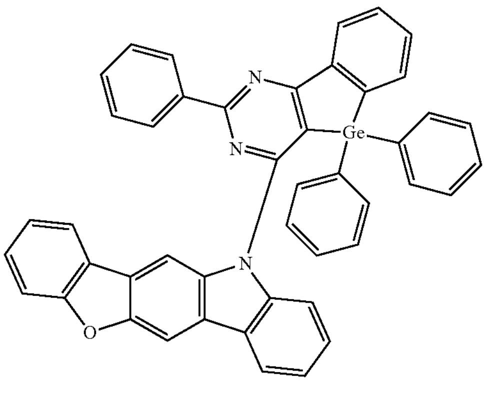
-continued
2151
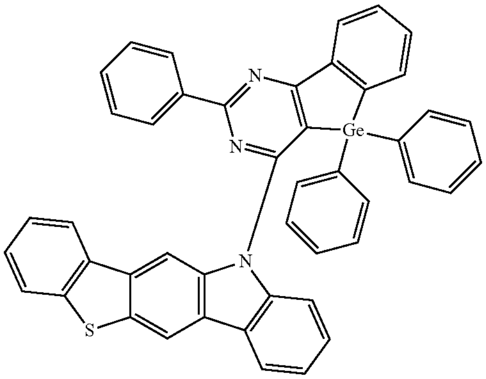
2152
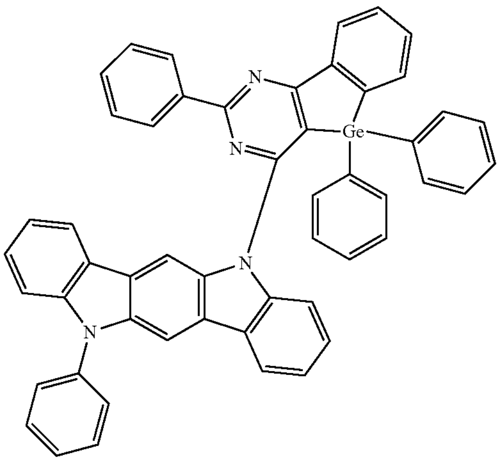
2153
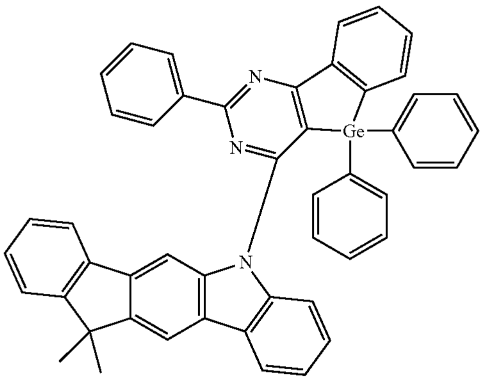

-continued
2154
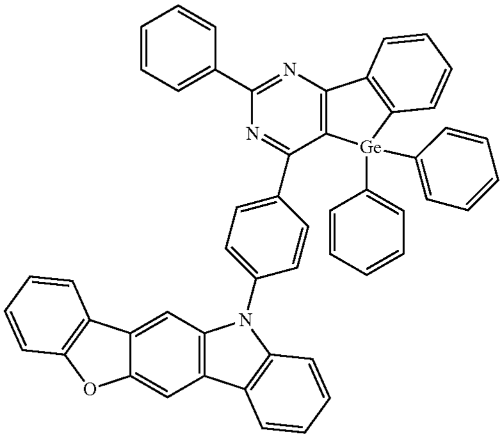
2155
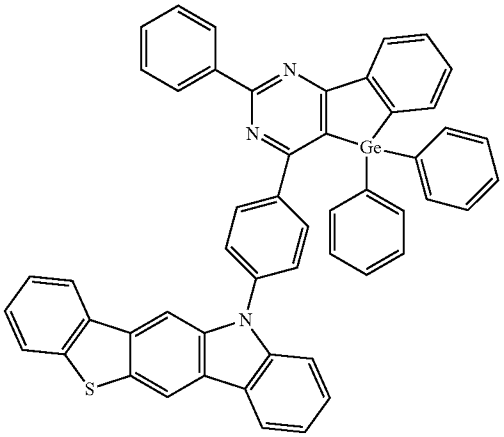
2156
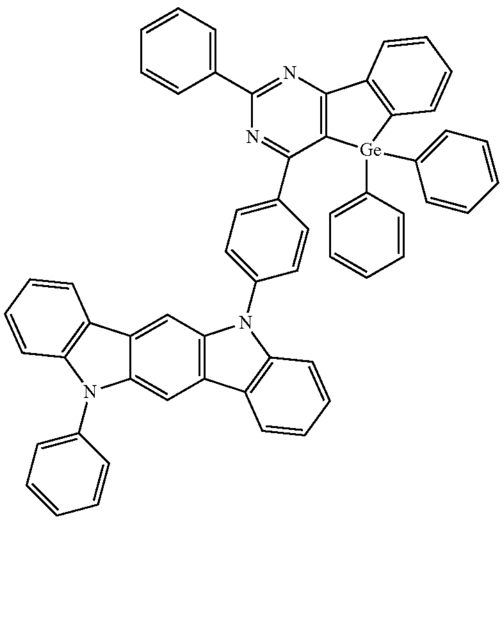
-continued
2157
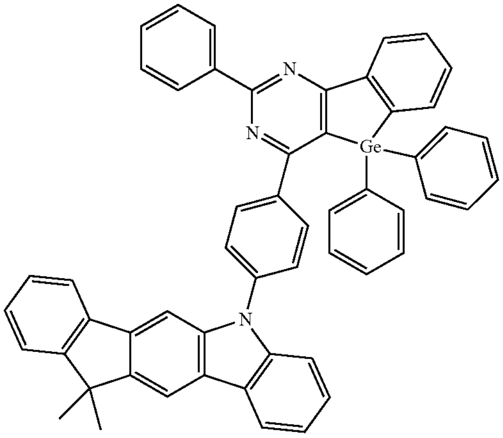
2158
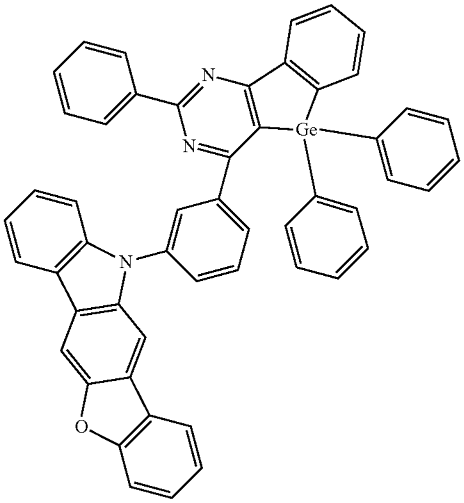
2159
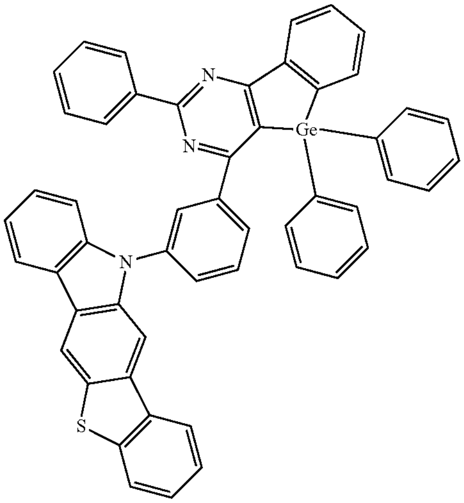

-continued
2160
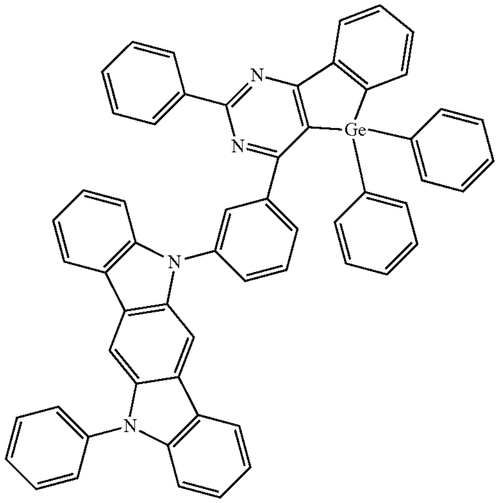
2161
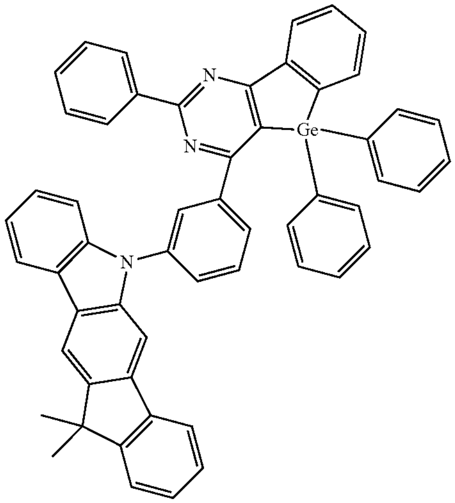
2162
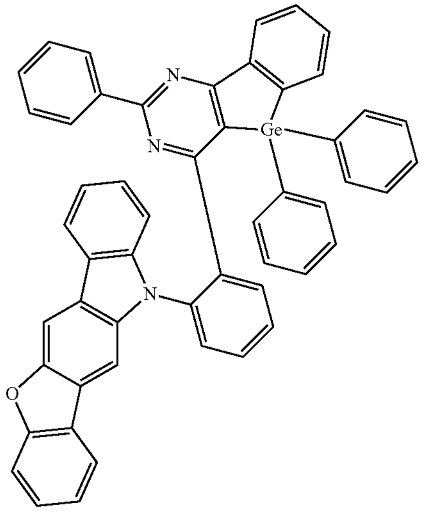
-continued
2163
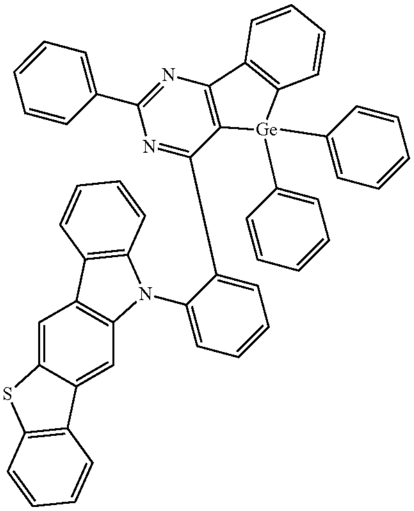
2164
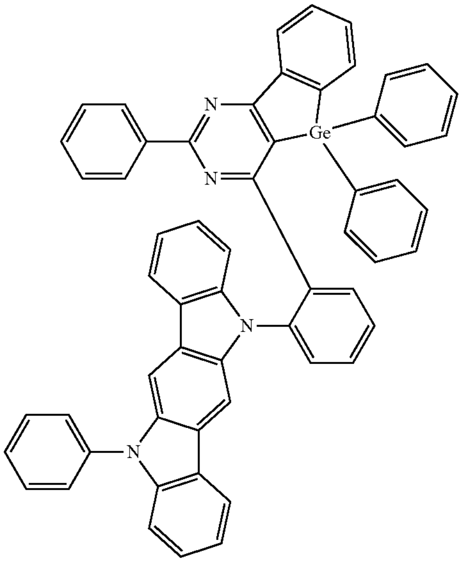
2165
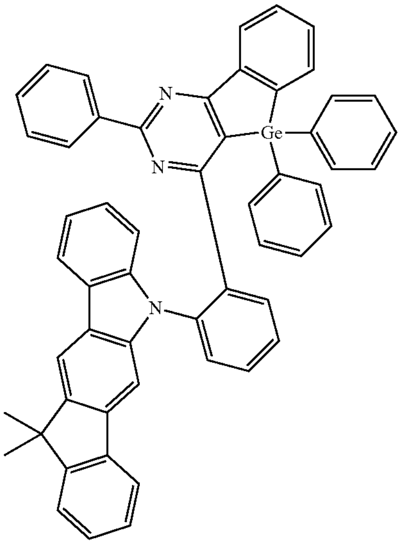

-continued
2166
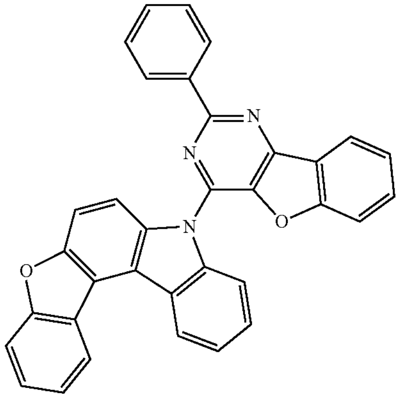
2167
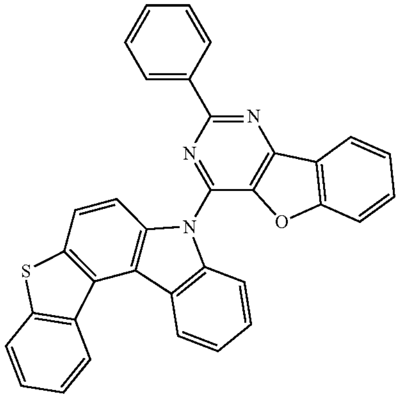
2168
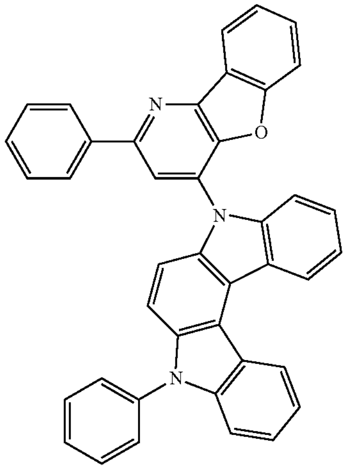
-continued
2169
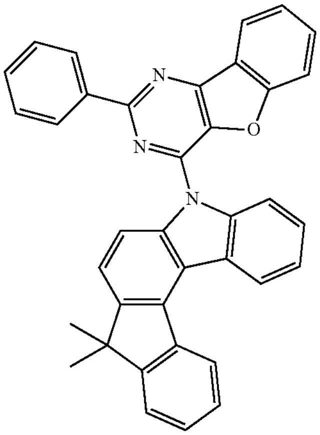
2170
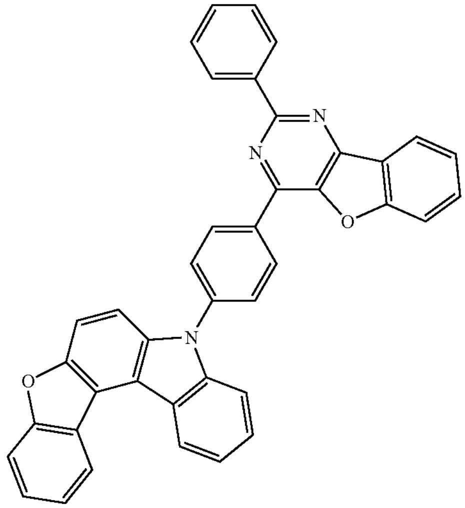
2171
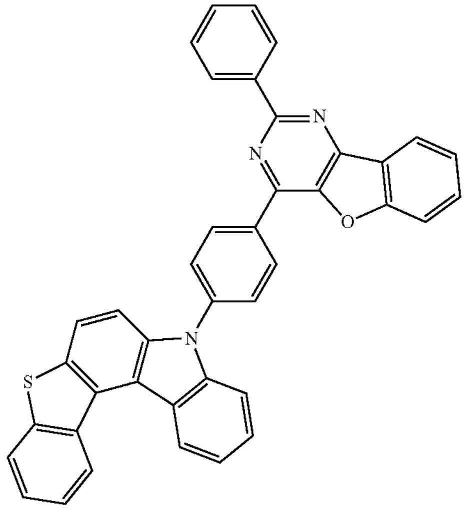

-continued
2172
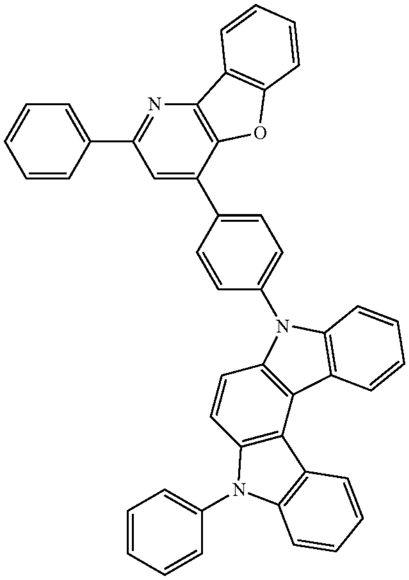
2173
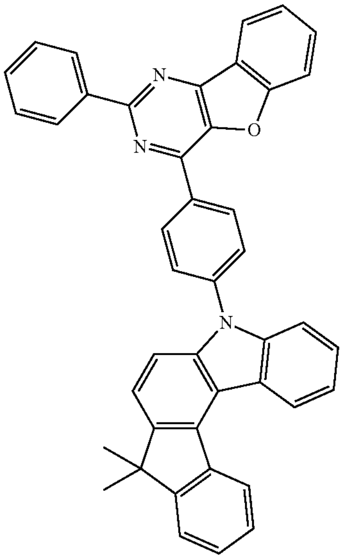
2174
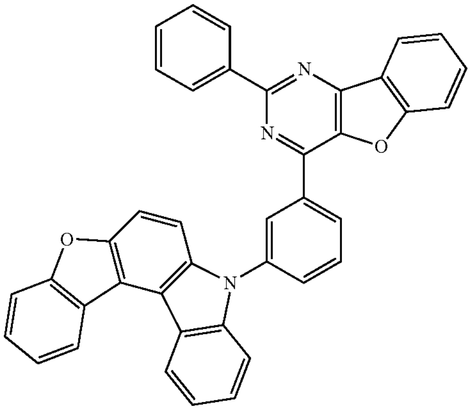
-continued
2175
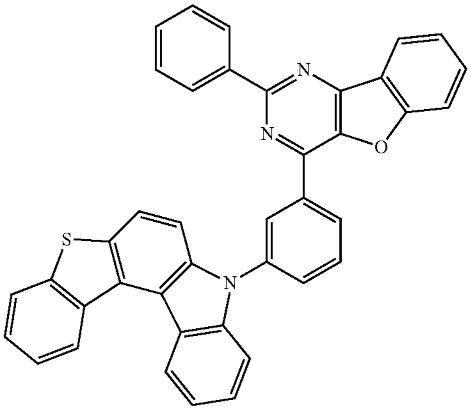
2176
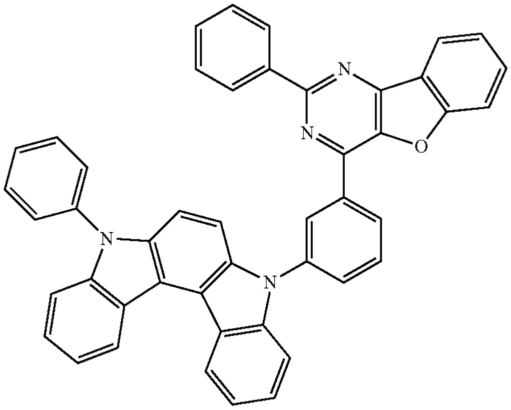
2177
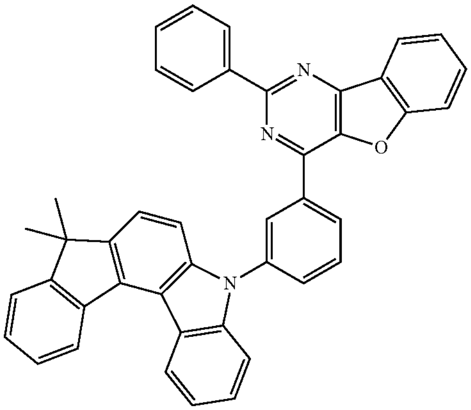
2178
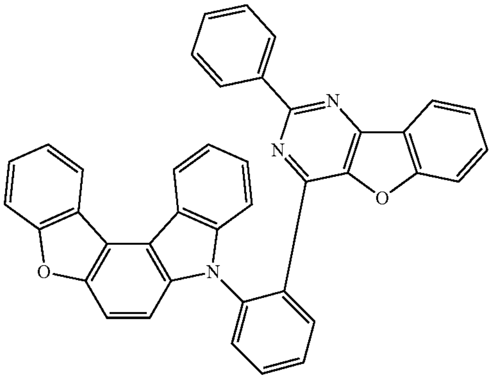

2179
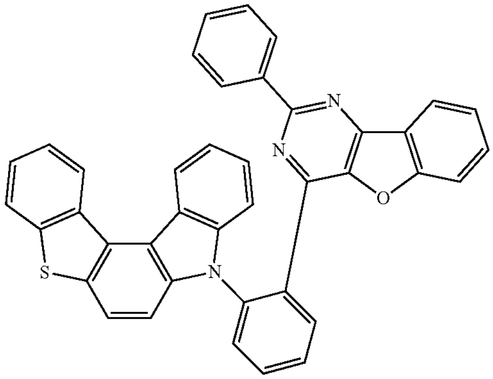
2180
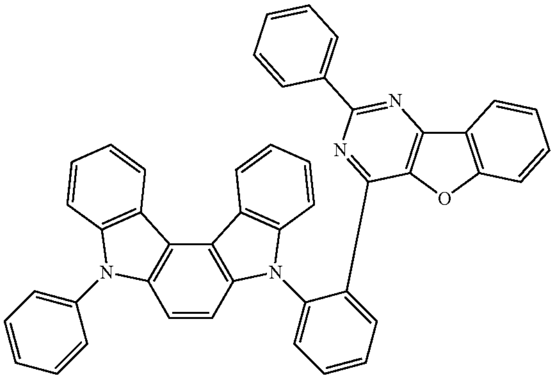
2181
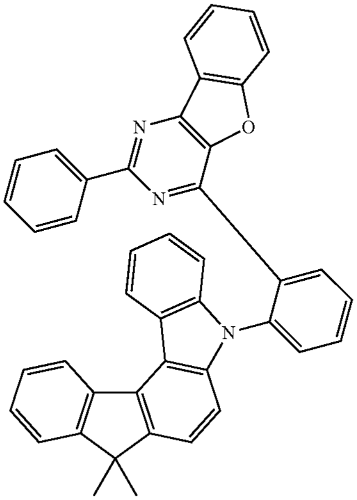
2182
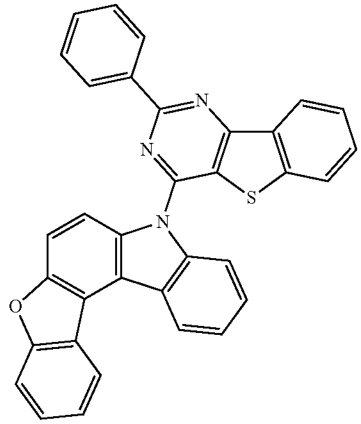
2183
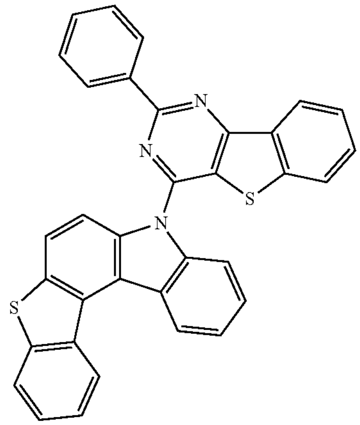
2184
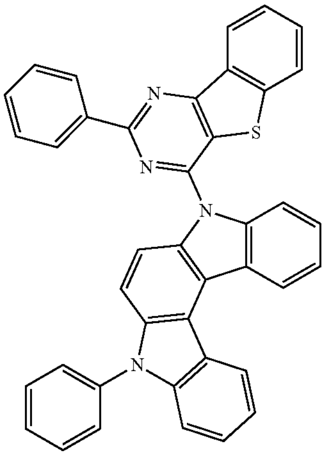

733
-continued
2185
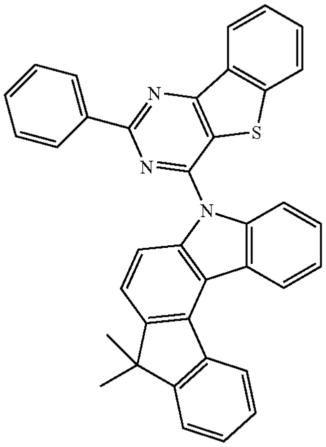
2186
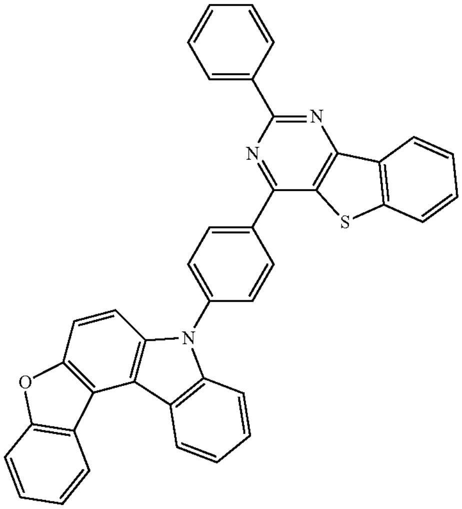
2187
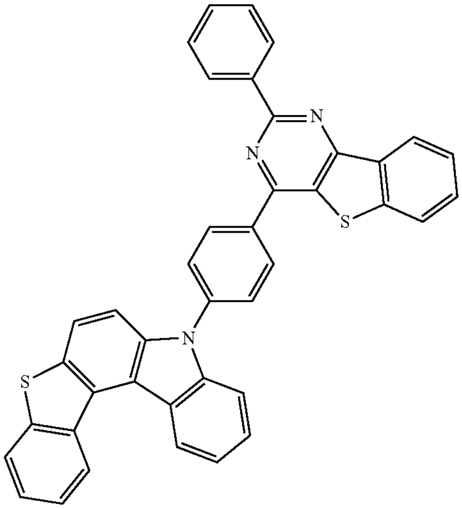
734
-continued
2188
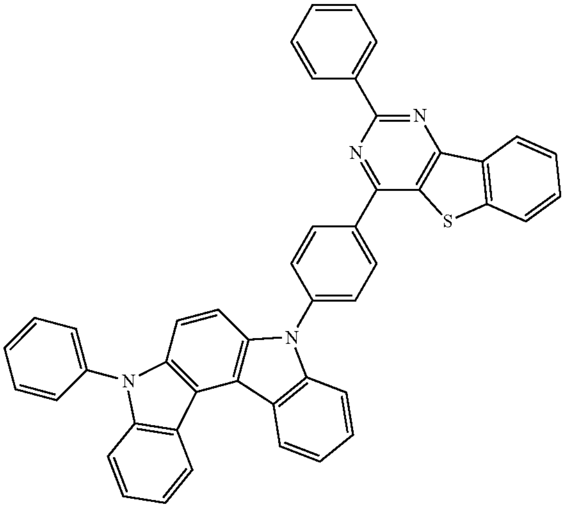
2189
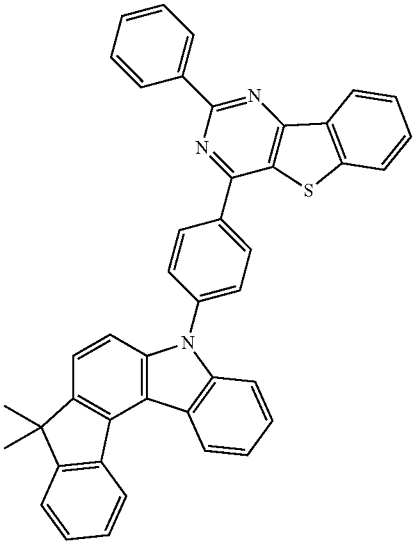
2190
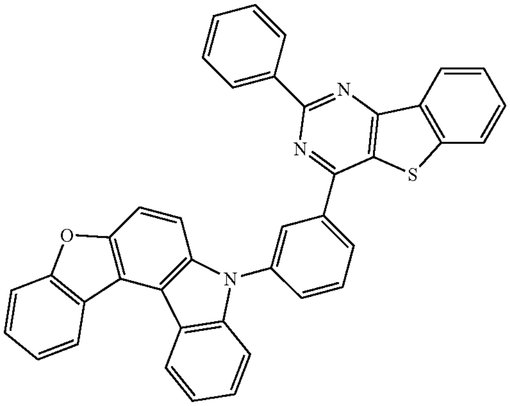

-continued
2191
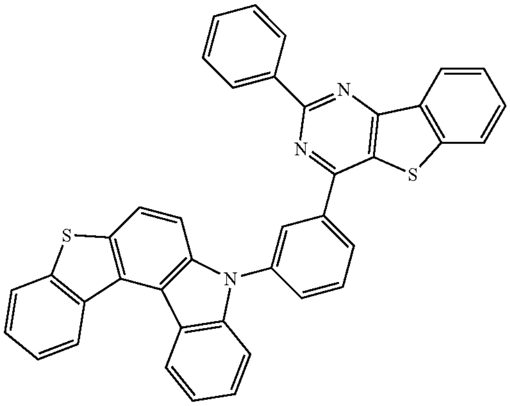
2192
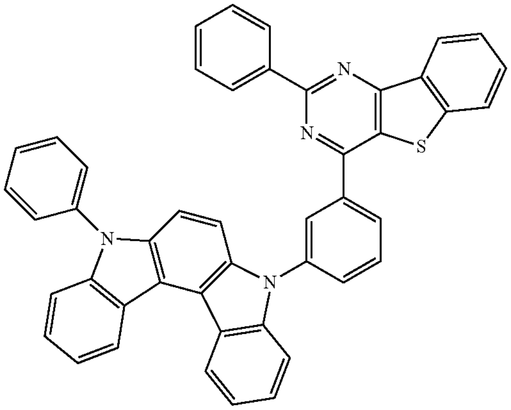
2193
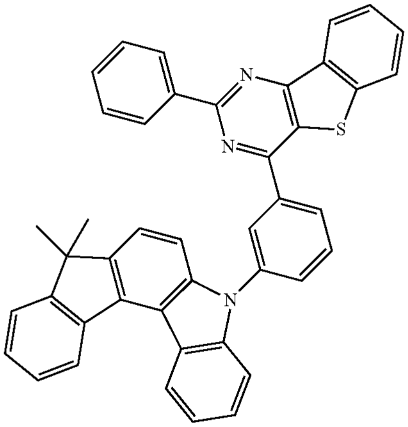
-continued
2194
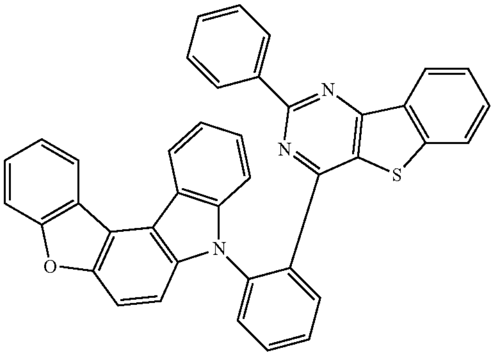
2195
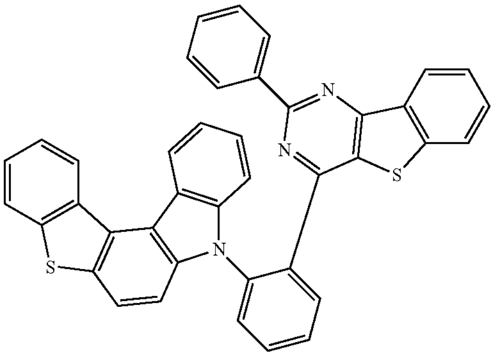
2196
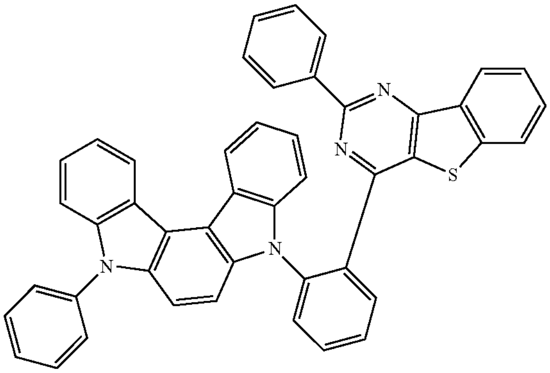
2197
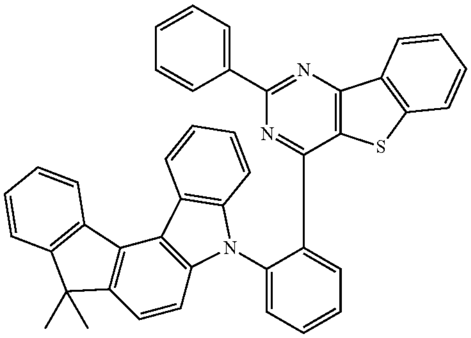

-continued
2198
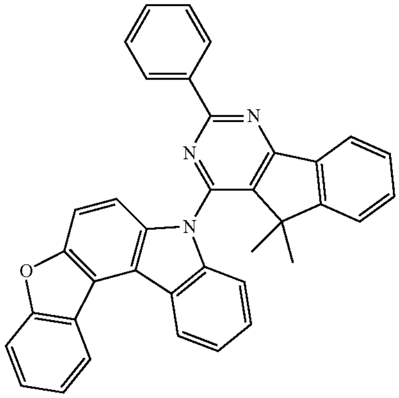
2199
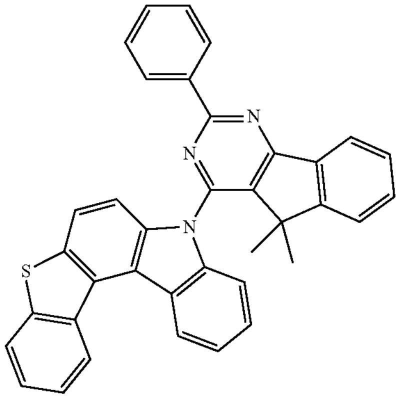
2200
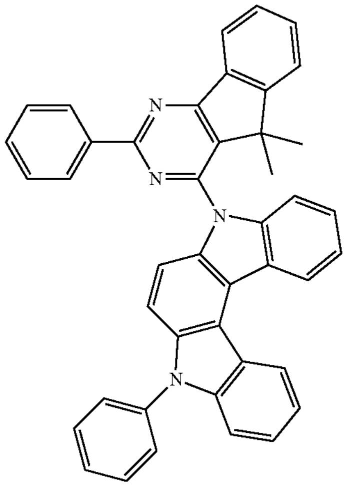
-continued
2201
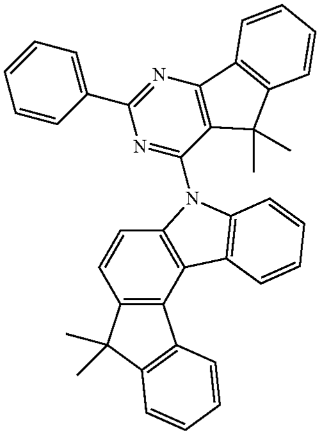
2202
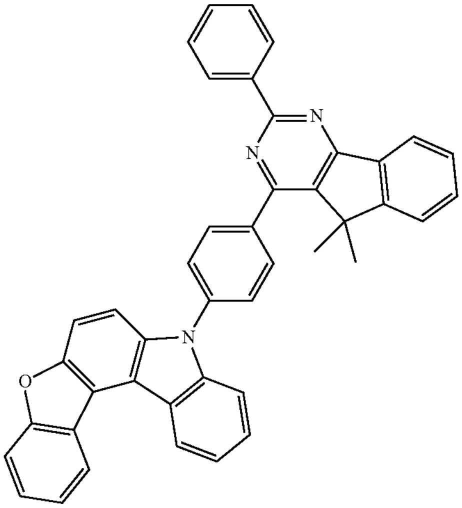
2203
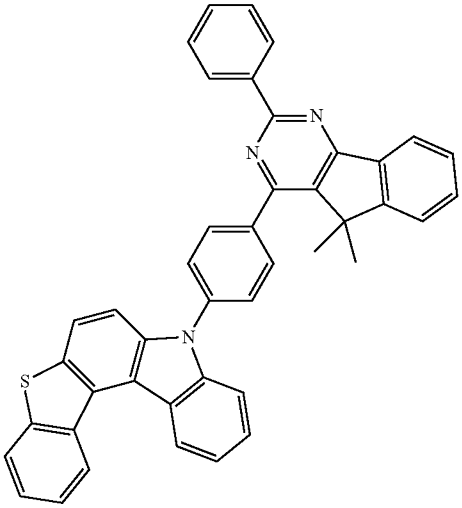

-continued
2204
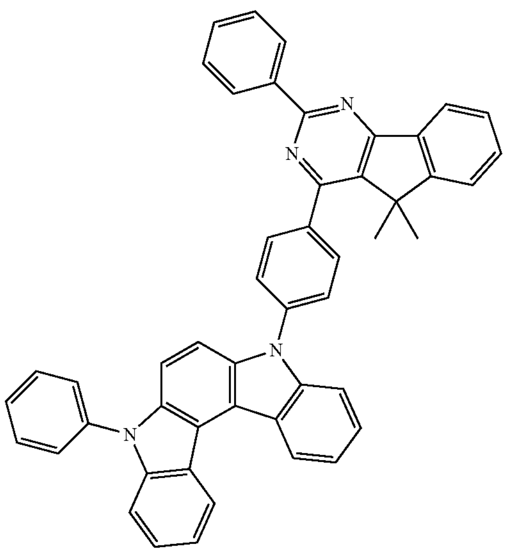
2205
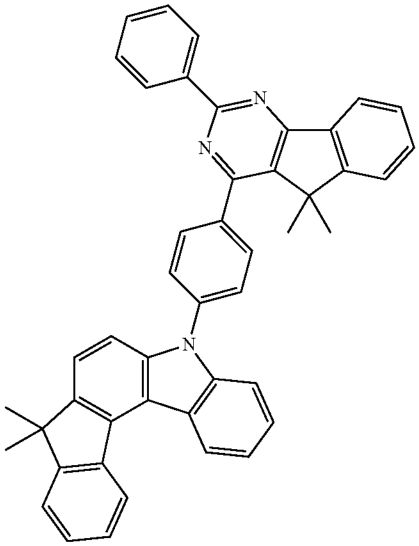
2206
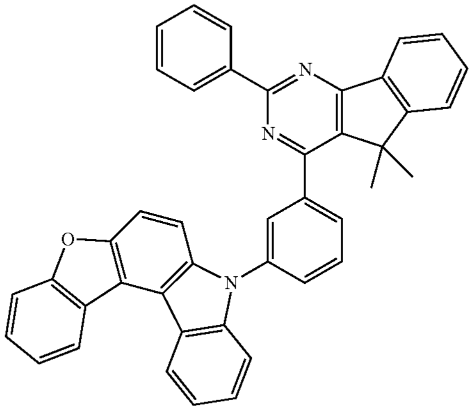
-continued
2207
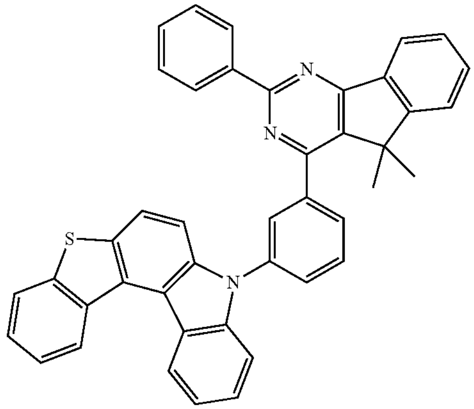
2208
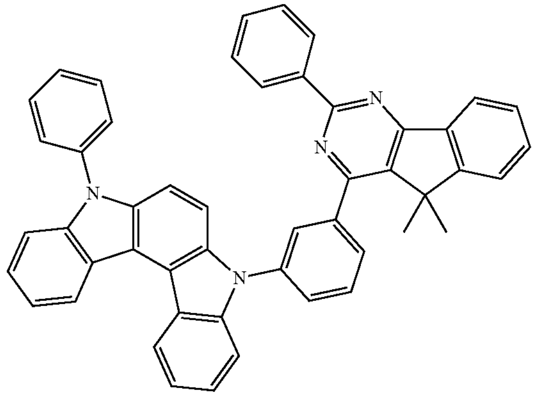
2209
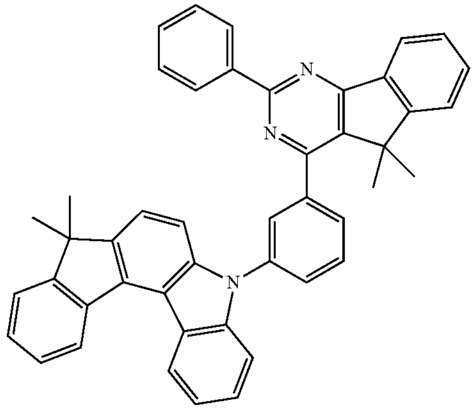

-continued
2210
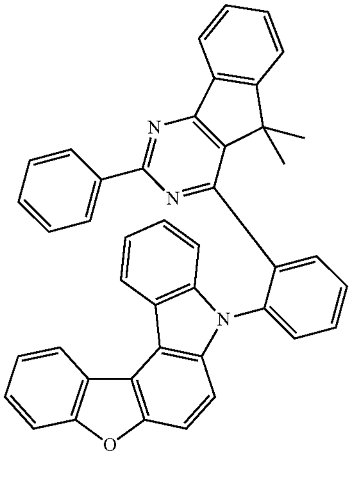
2211
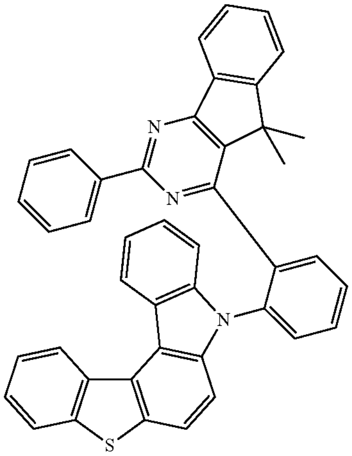
2212
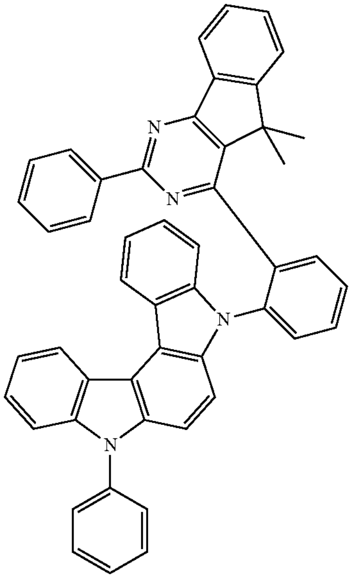
-continued
2213
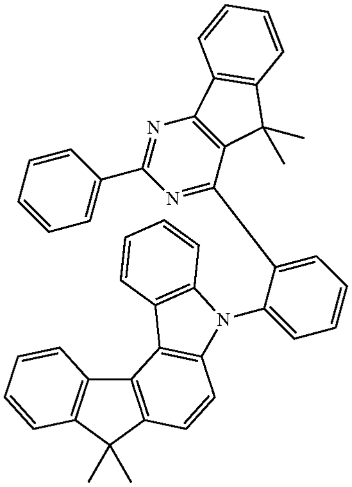
2214
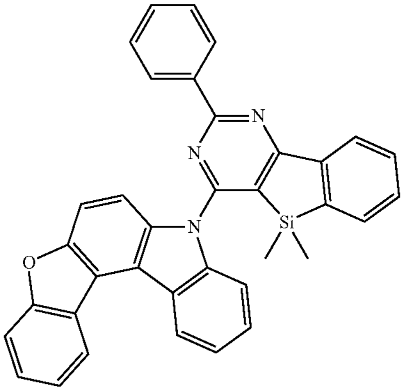
2215
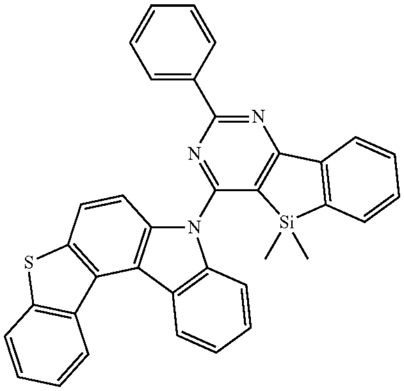

-continued
2216
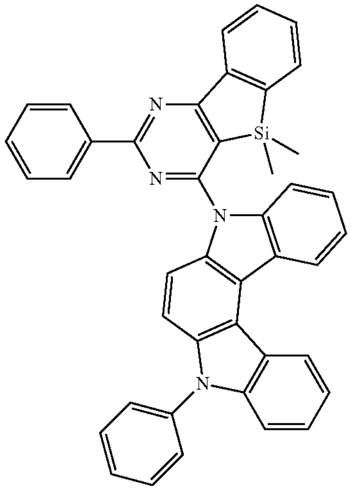
2217
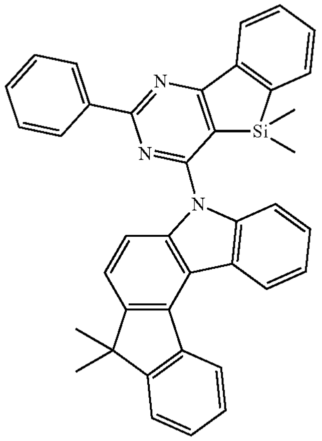
2218
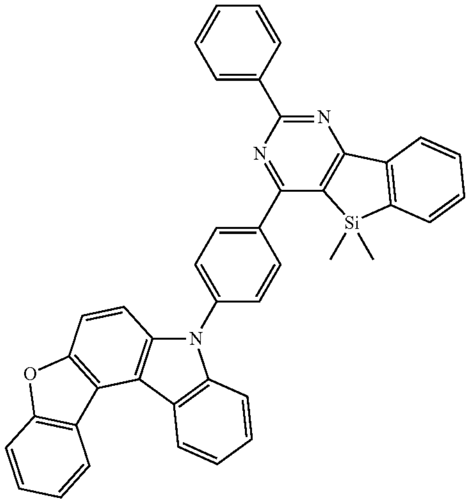
-continued
2219
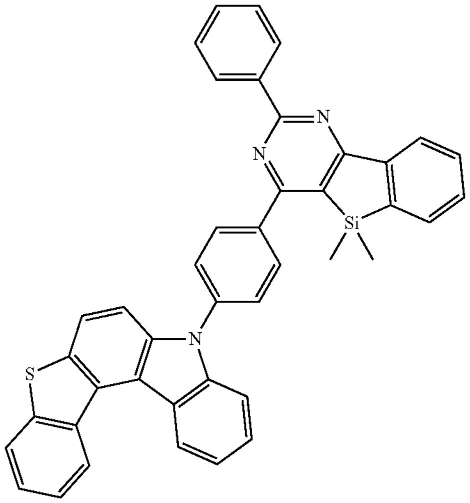
2220
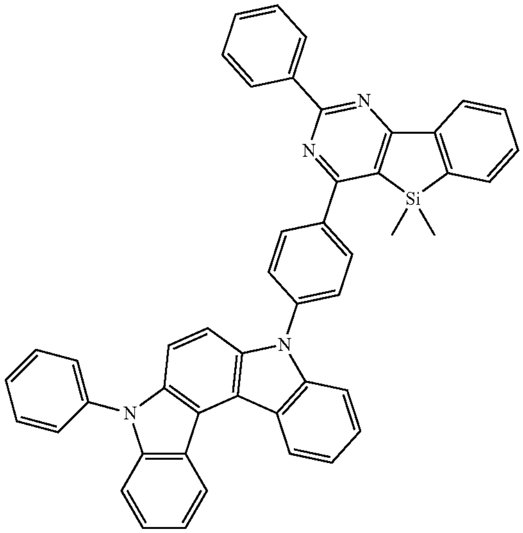
2221
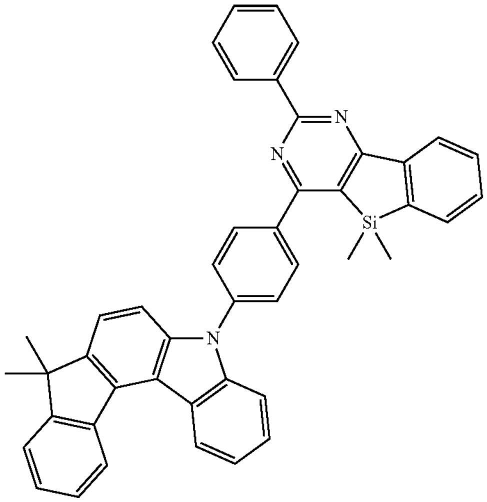

2222
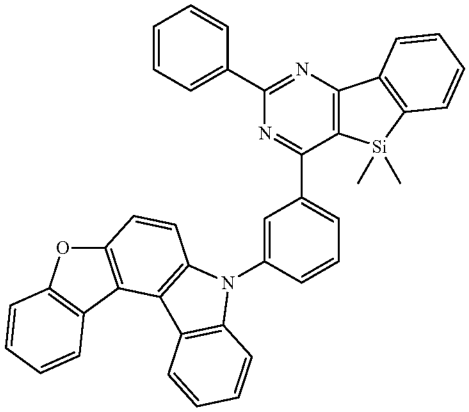
2223
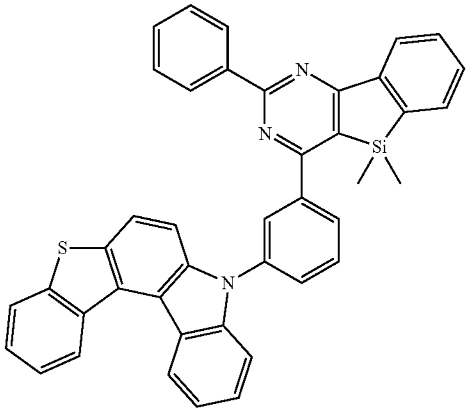
2224
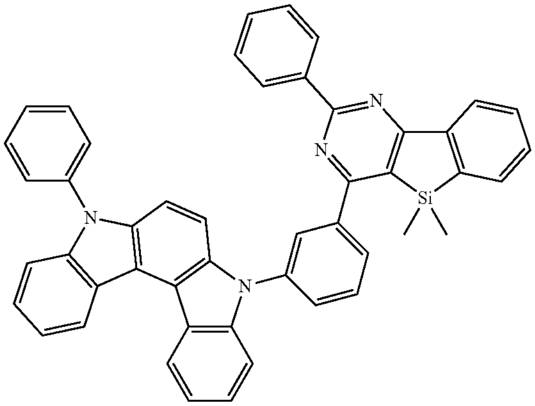
2225
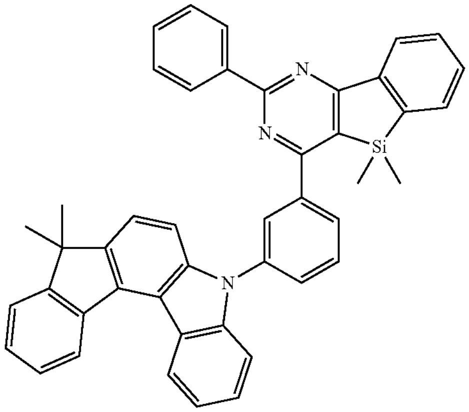
2226
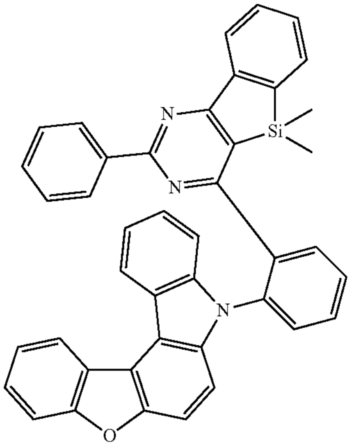
2227
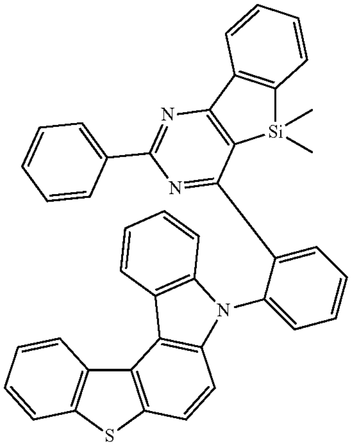

-continued
2228
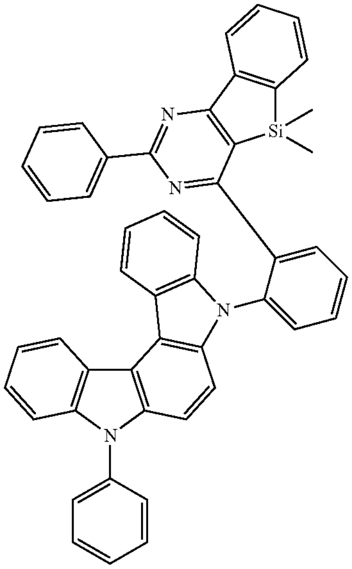
2229
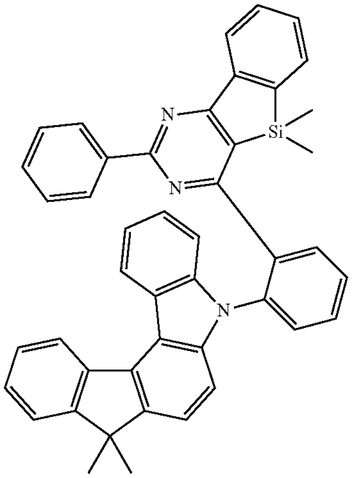
2230
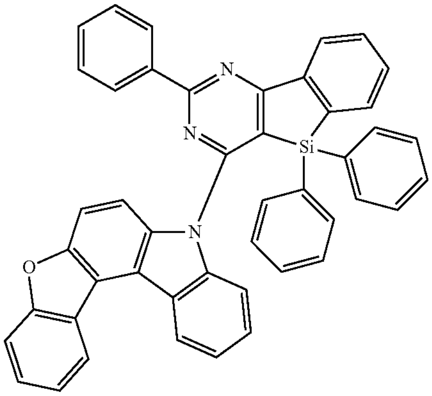
-continued
2231
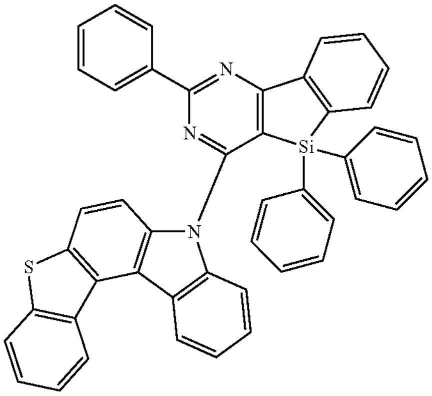
2232
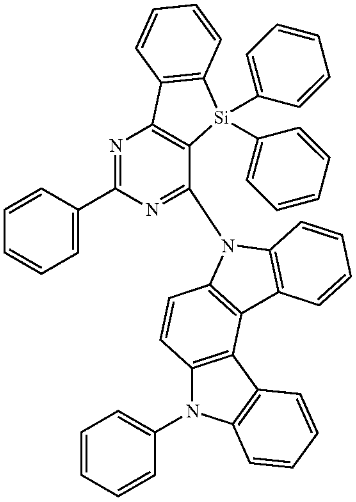
2233
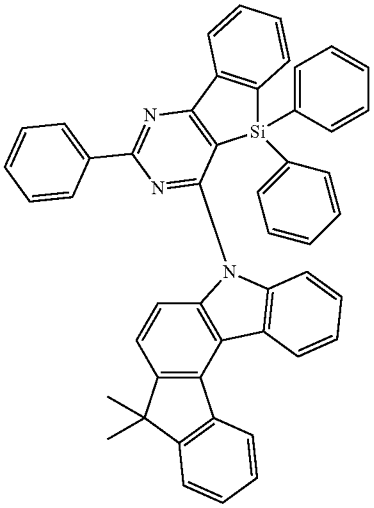

-continued
2234
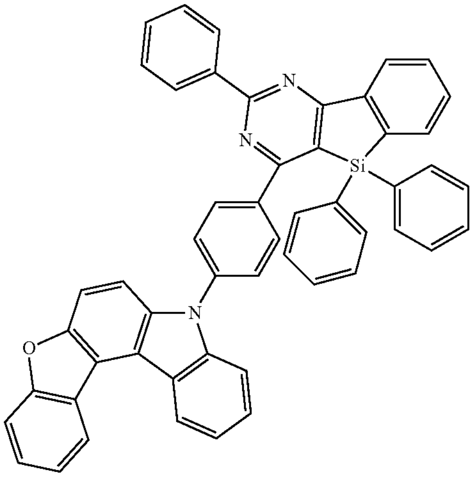
2235
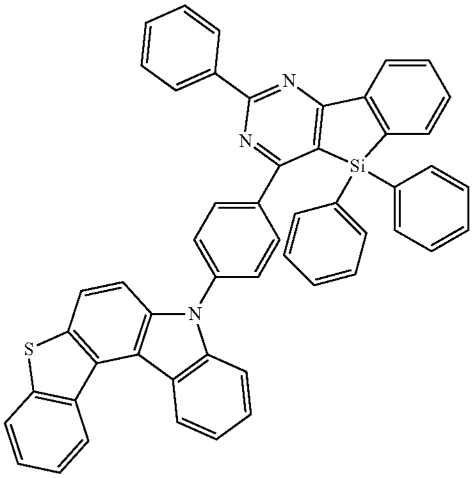
2236
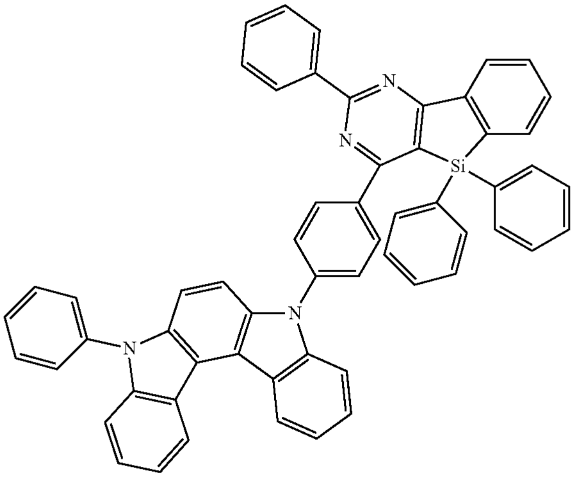
-continued
2237
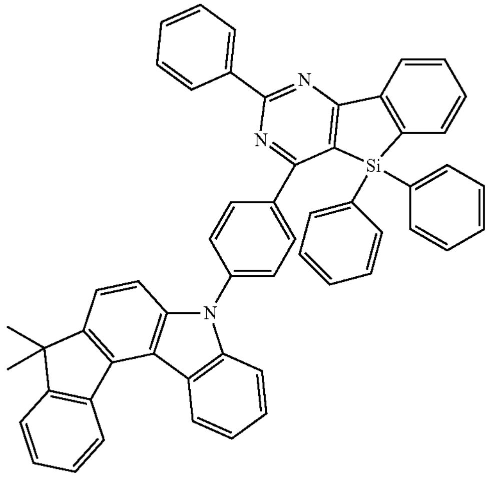
2238
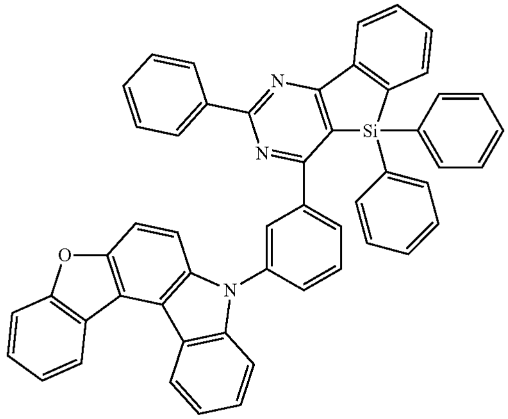
2239
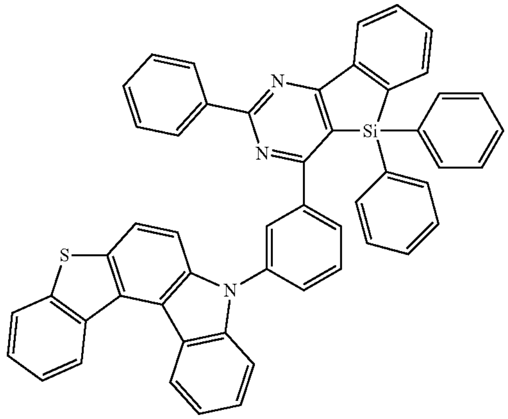

-continued
2240
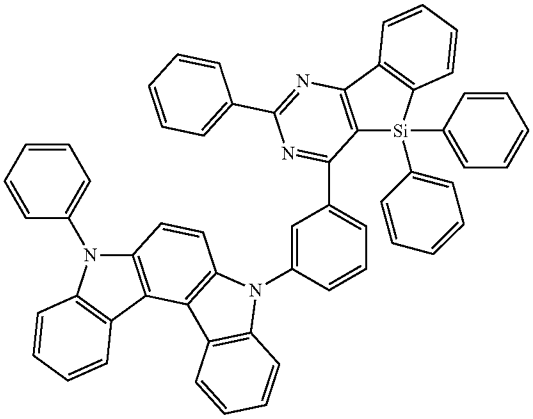
2241
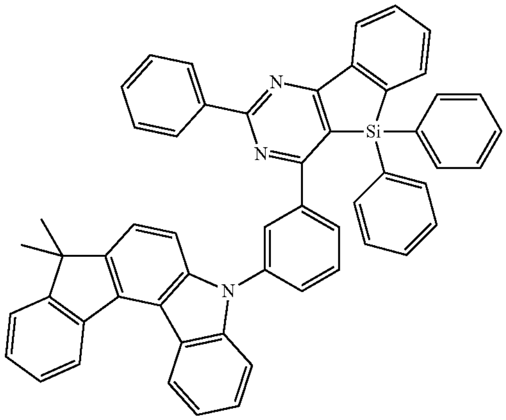
2242
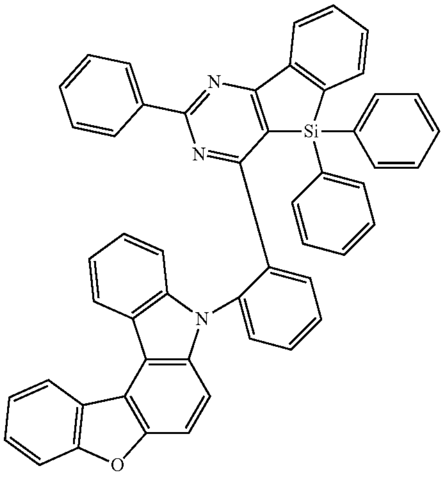
-continued
2243
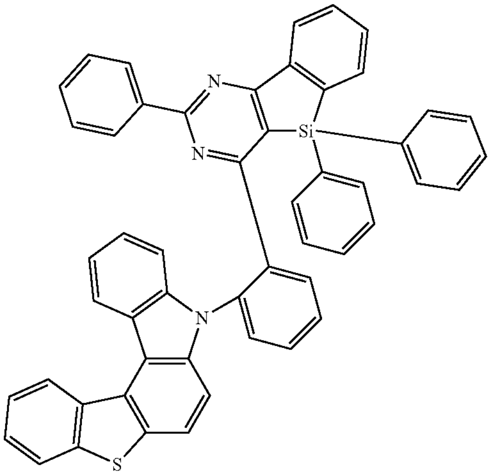
2244
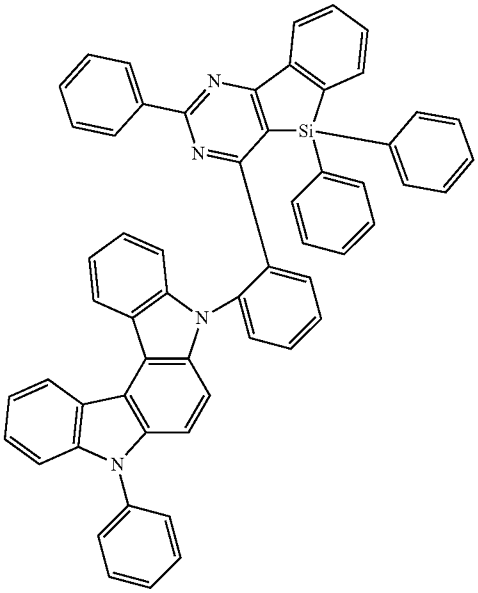
2245
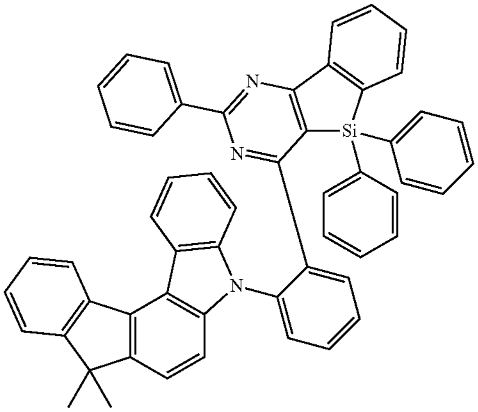

-continued
2246
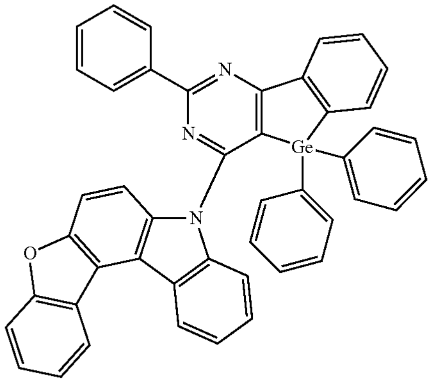
2247
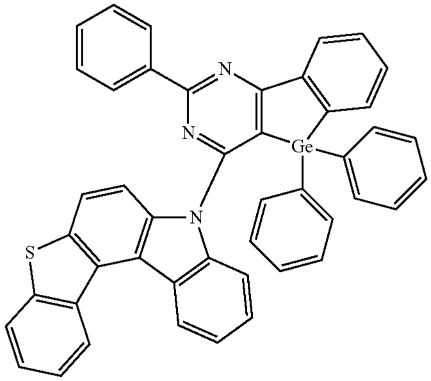
2248
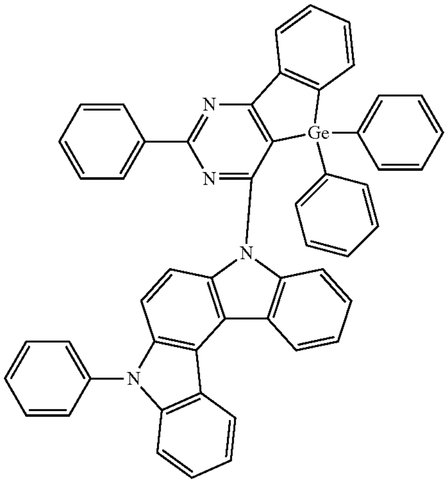
-continued
2249
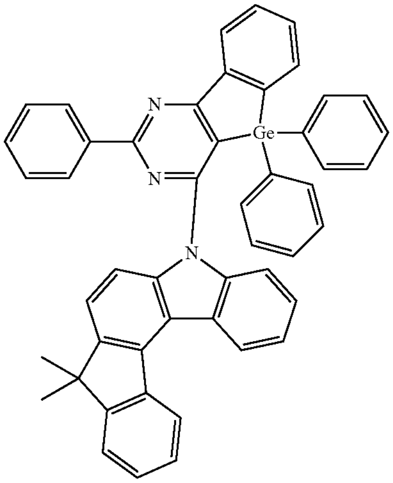
2250
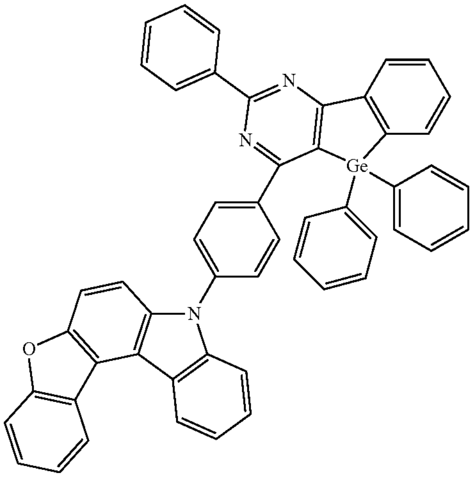
2251
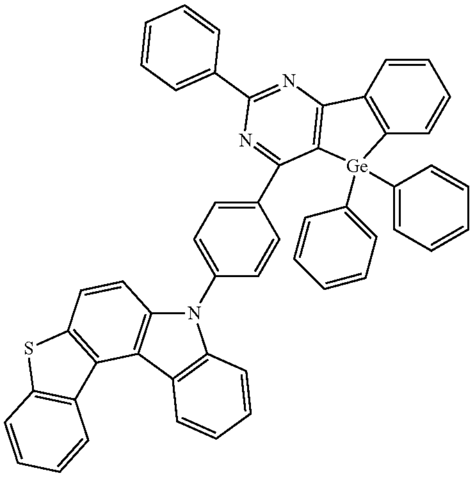

-continued
2252
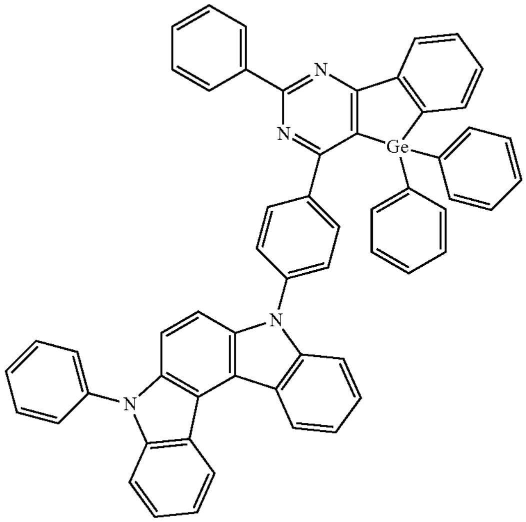
2253
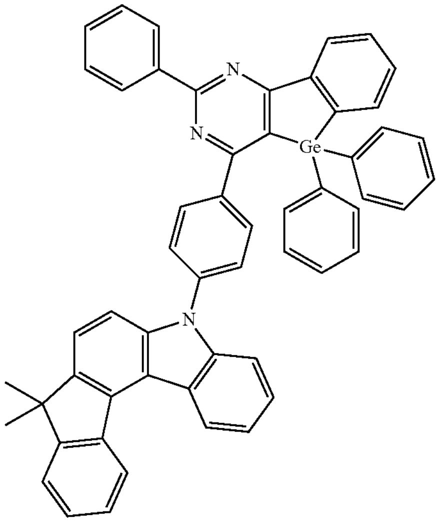
2254
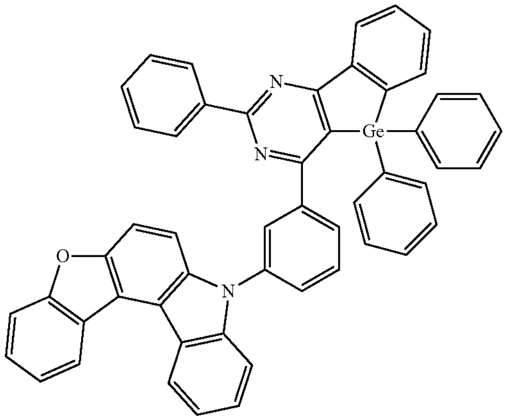
-continued
2255
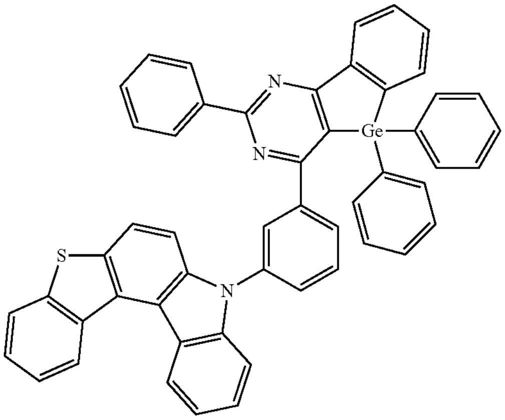
2256
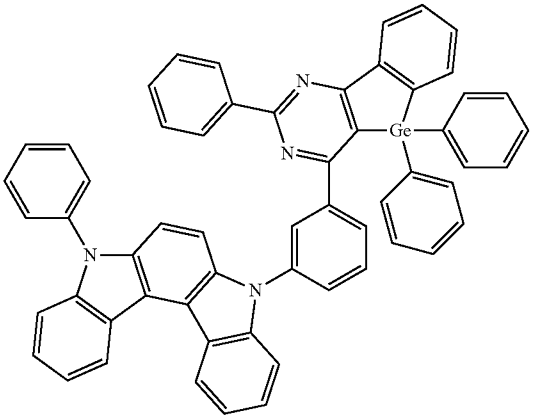
2257
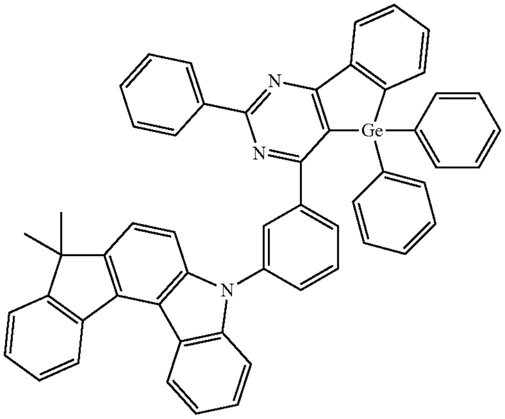

-continued
2258
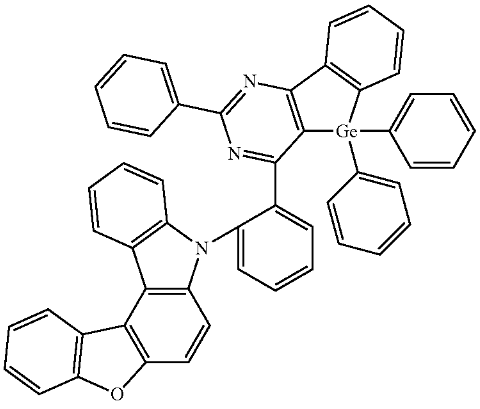
2259
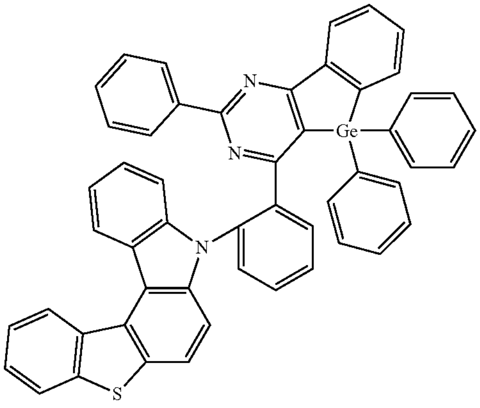
2260
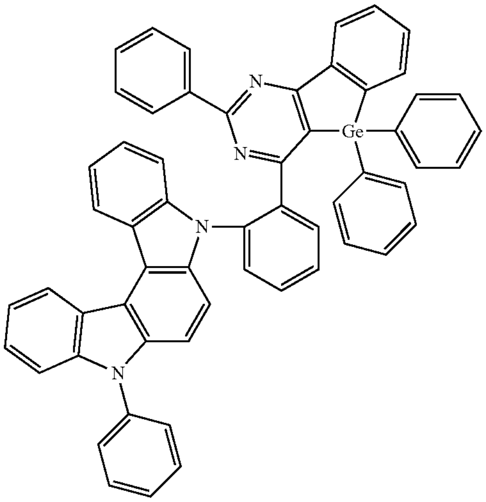
-continued
2261
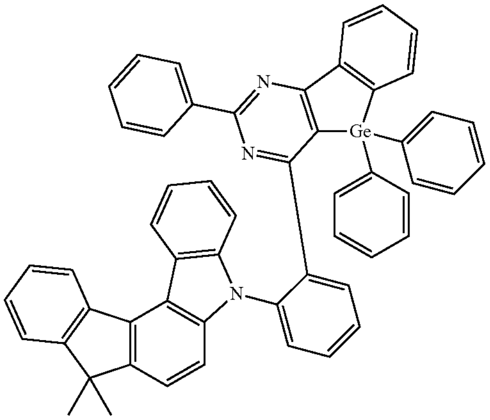
2262
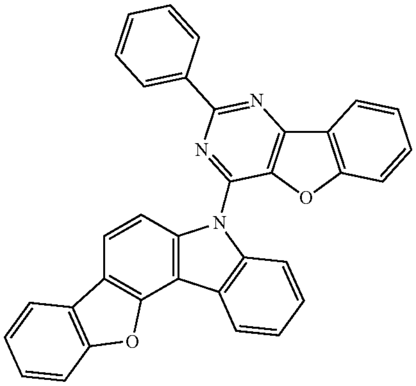
2263
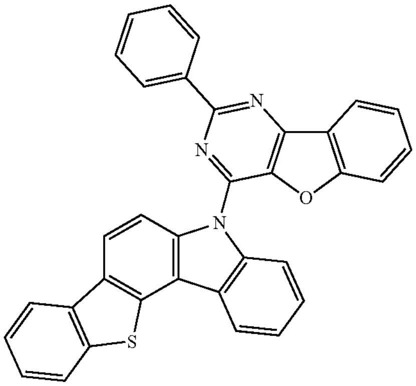

-continued
2264
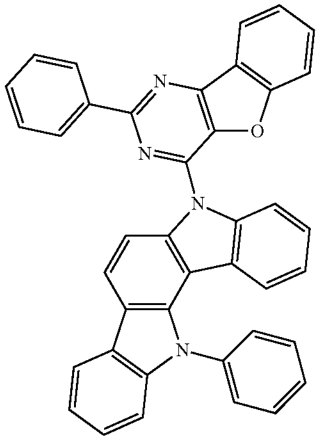
2265
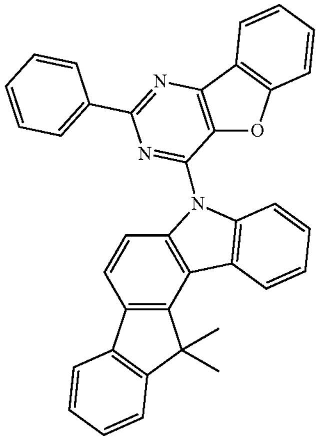
2266
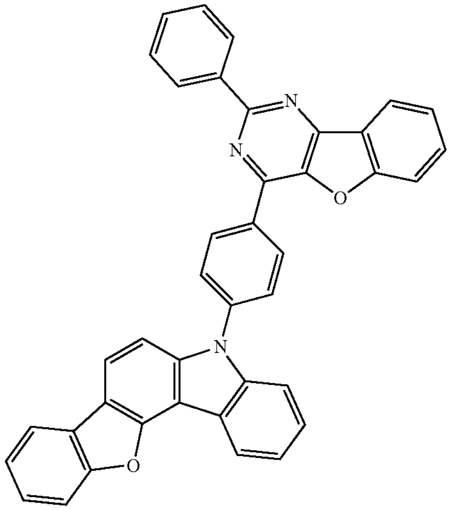
-continued
2267
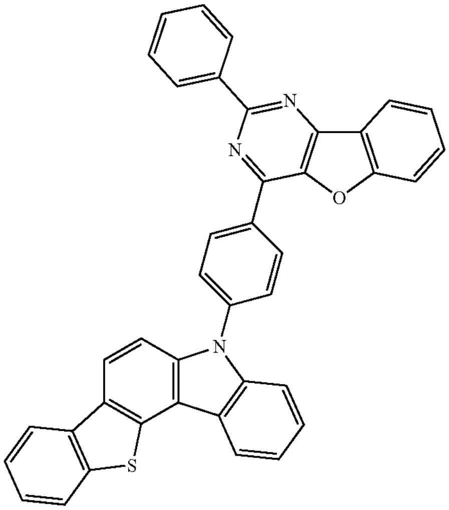
2268
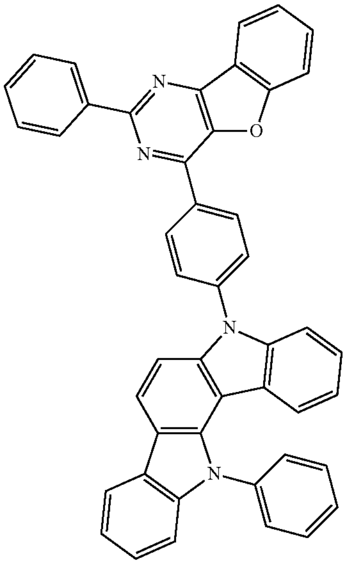
2269
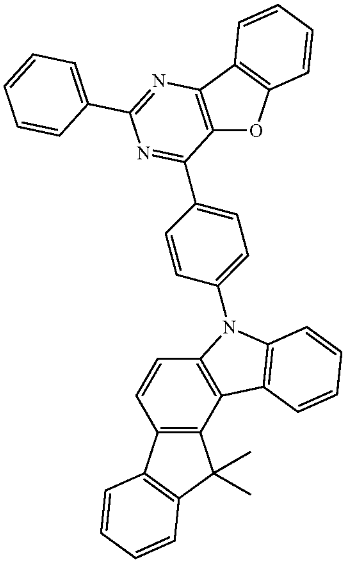

-continued
2270
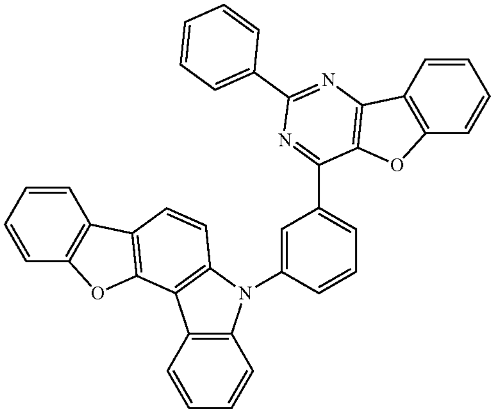
2271
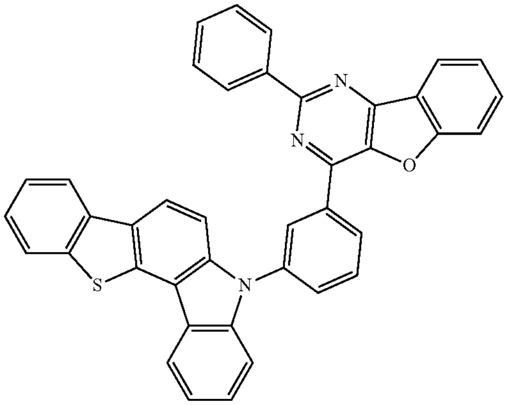
2272
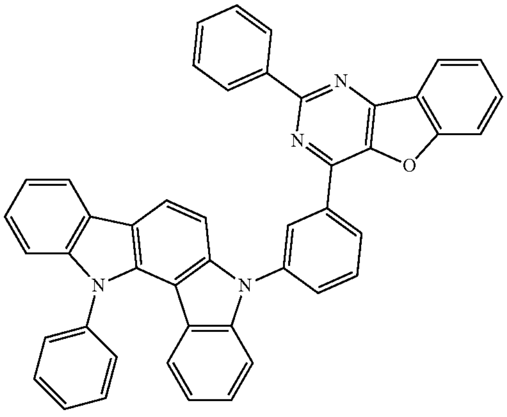
-continued
2273
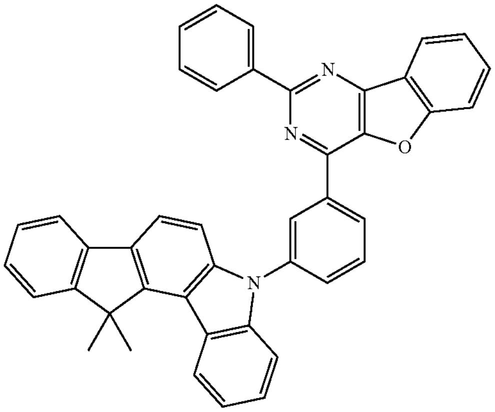
2274
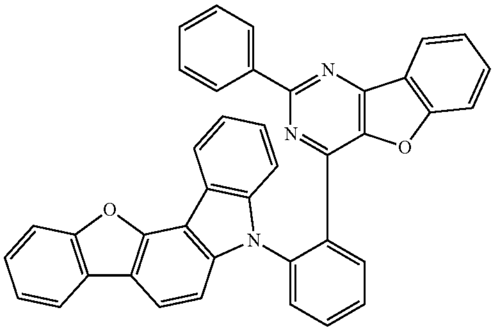
2275
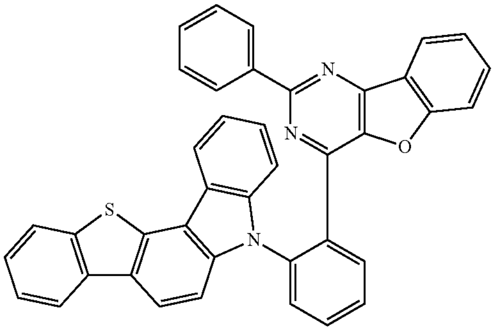
2276
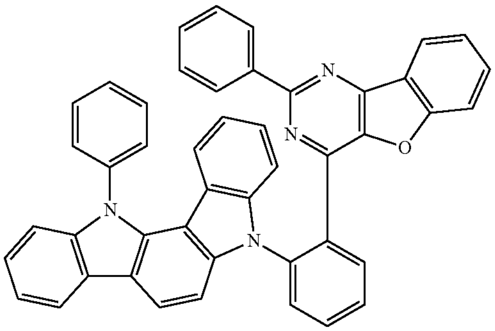

-continued
2277
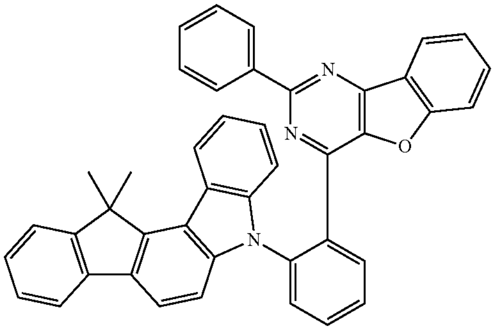
2278
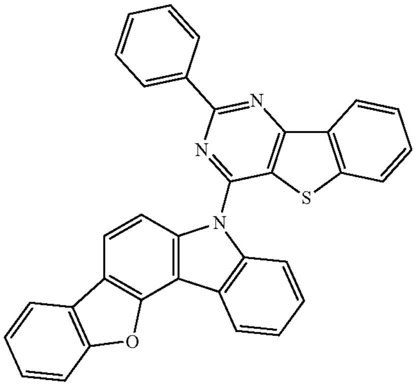
2279
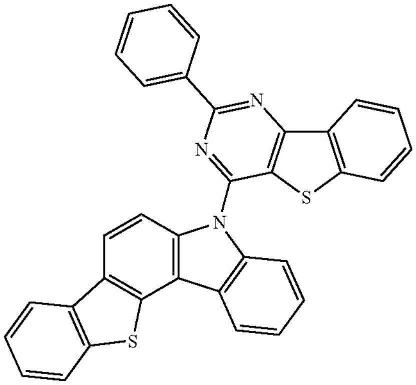
2280
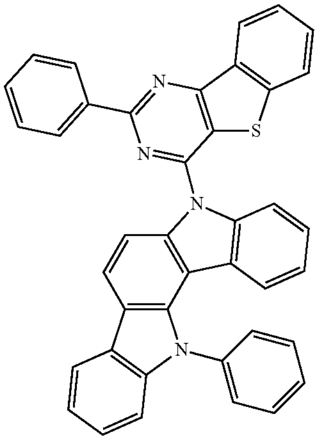
-continued
2281
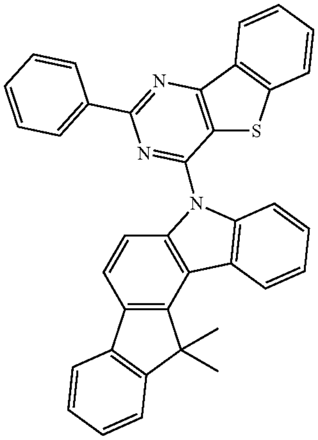
2282
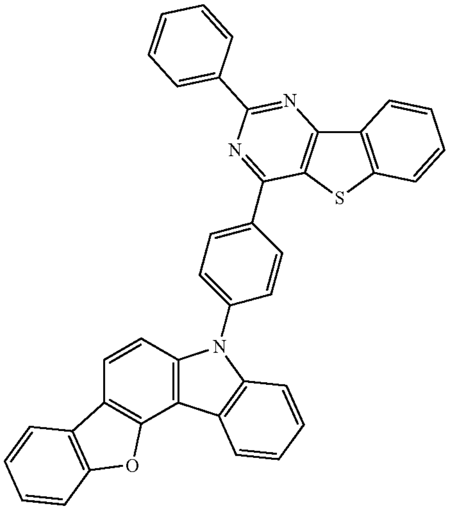
2283
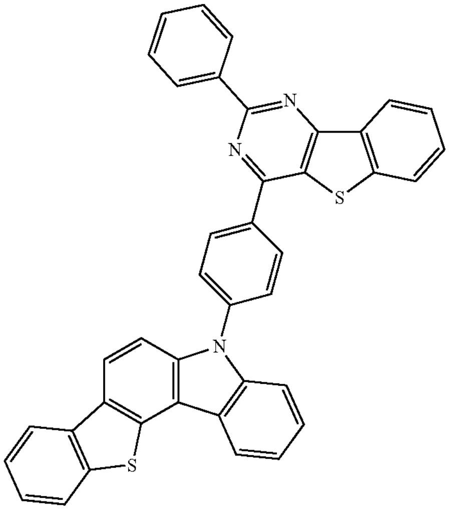

-continued
2284
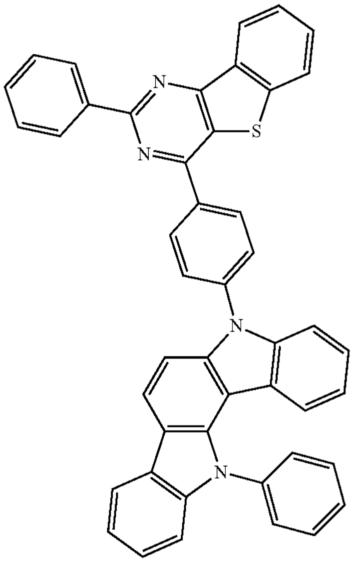
2285
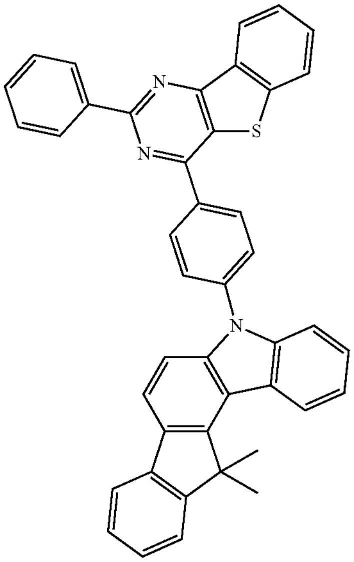
2286
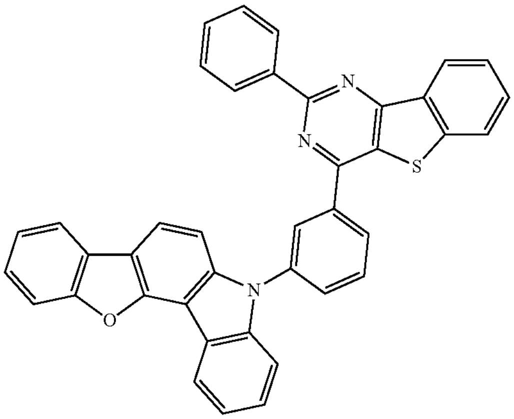
-continued
2287
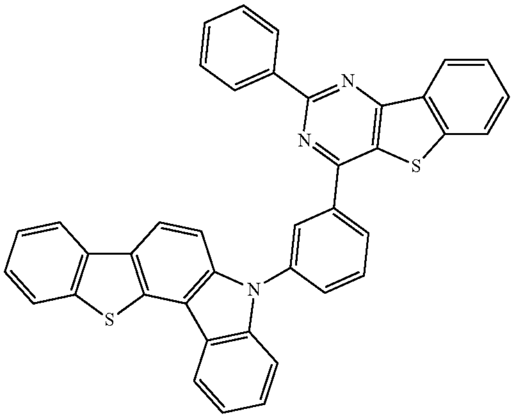
2288
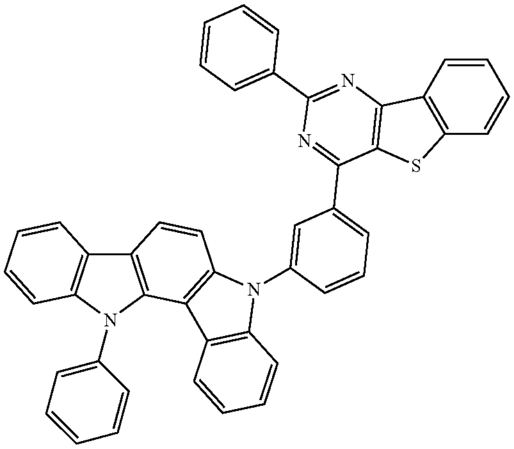
2289
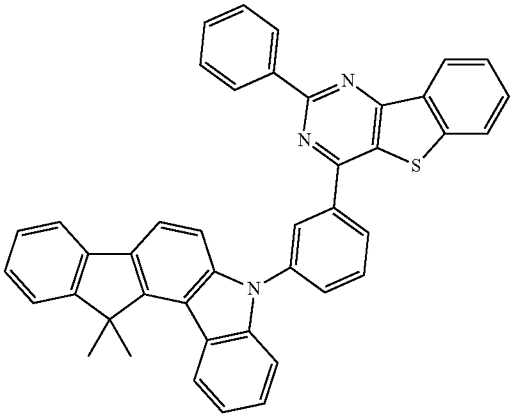

-continued
2290
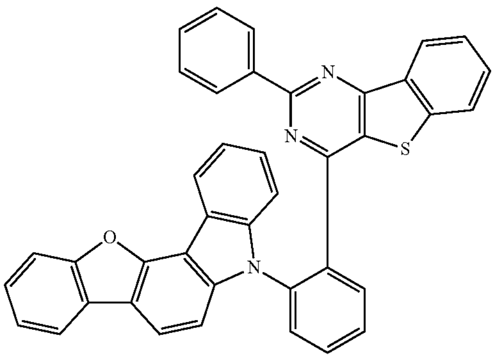
2291
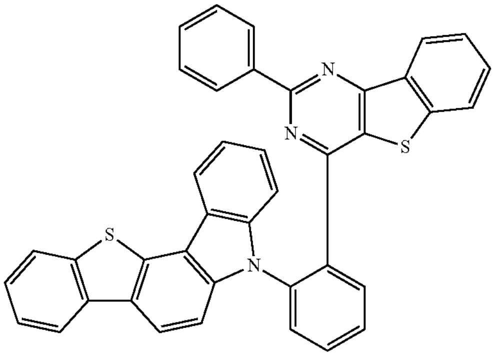
2292
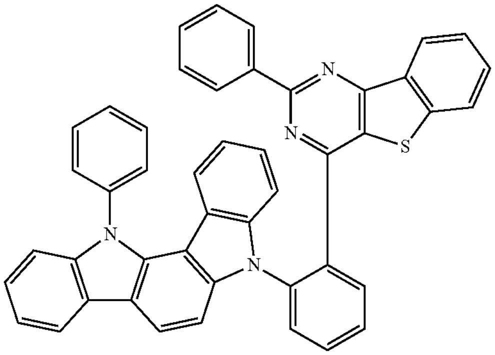
2293
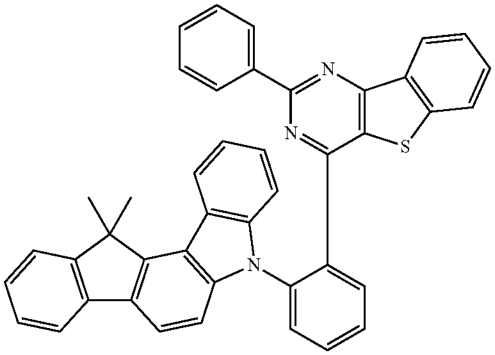
-continued
2294
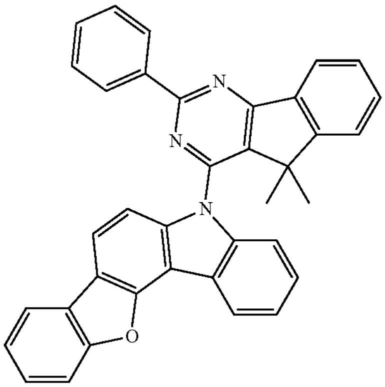
2295
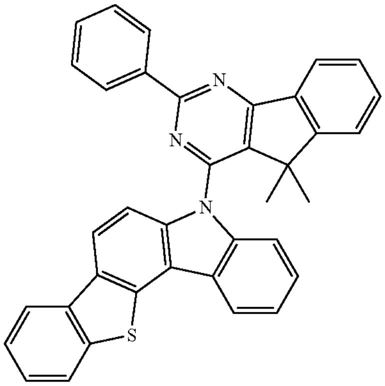
2296
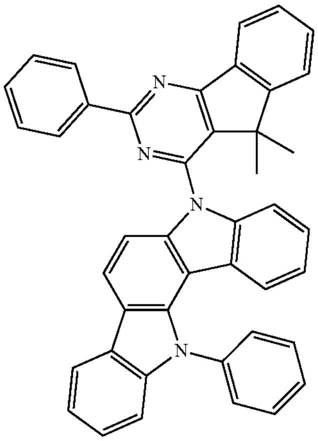

-continued
2297
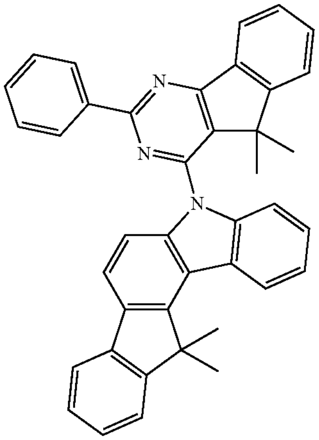
2298
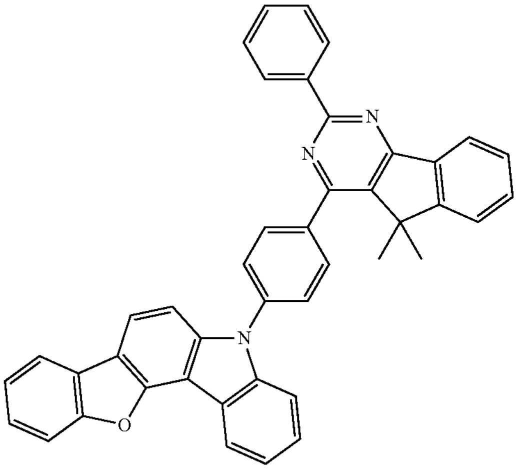
2299
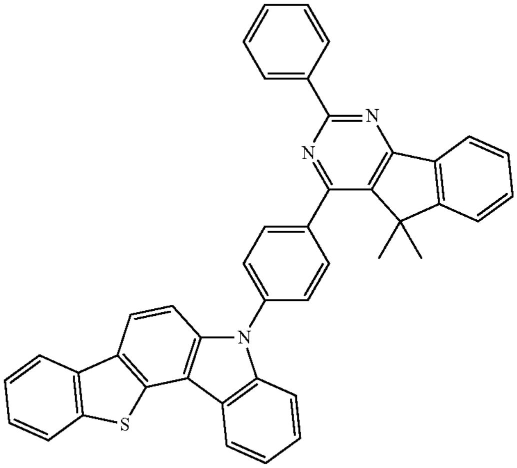
-continued
2300
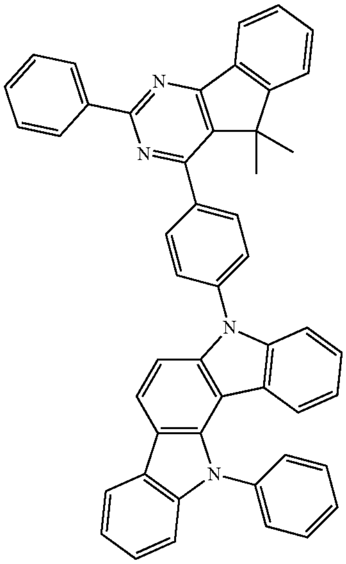
2301
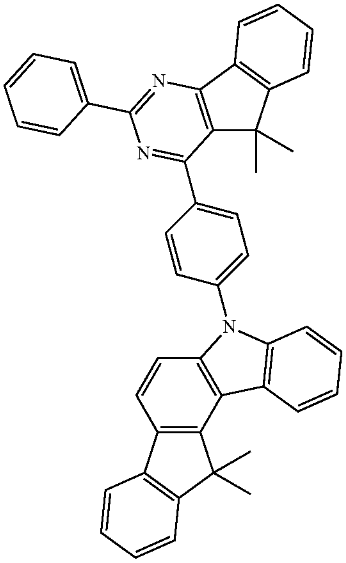
2302
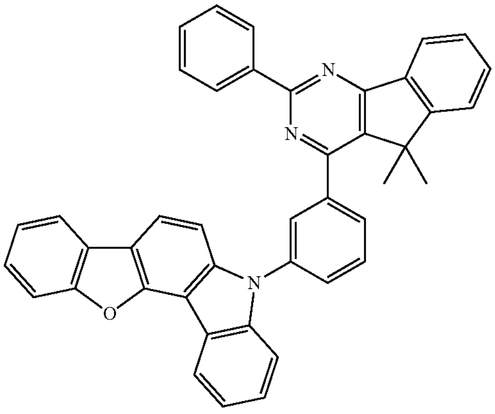

-continued
2303
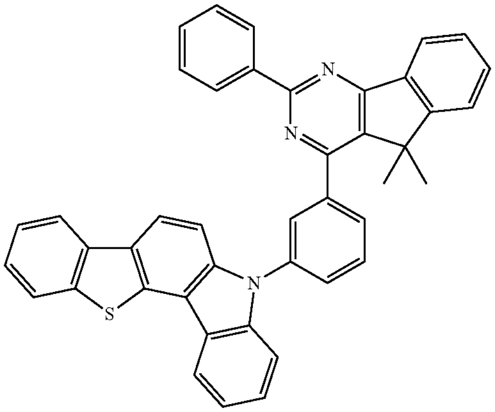
2304
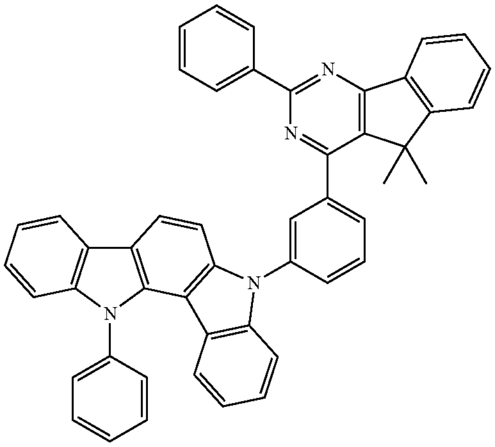
2305
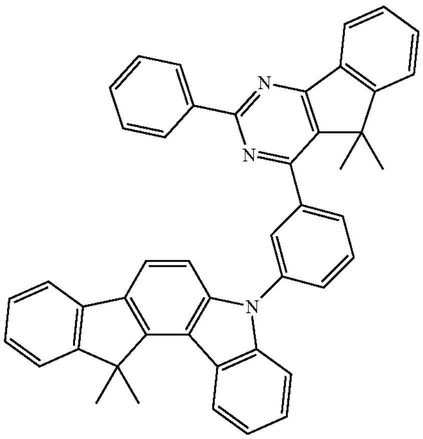
-continued
2306
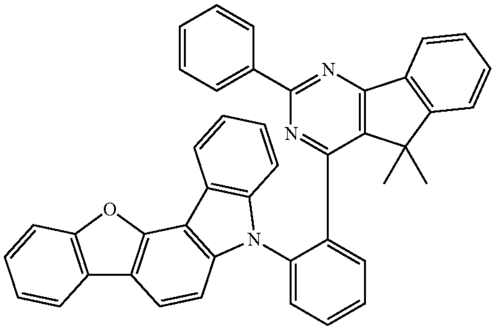
2307
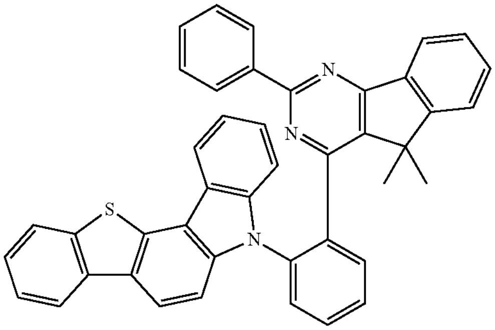
2308
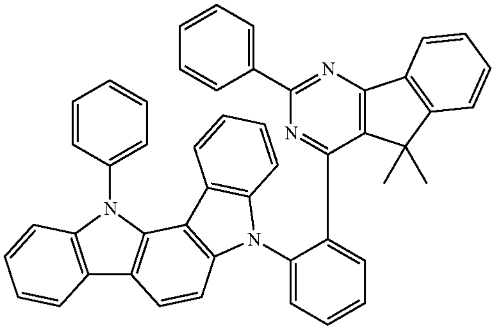
2309
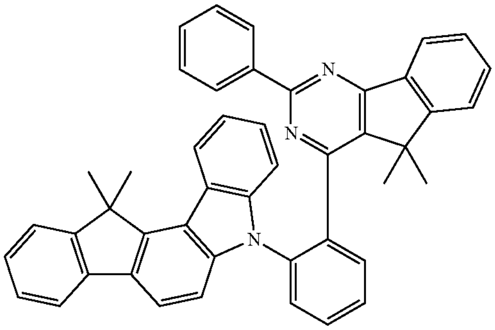

-continued
2310
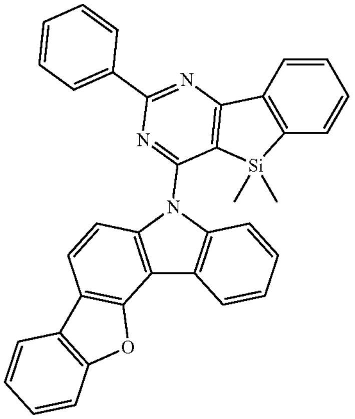
2311
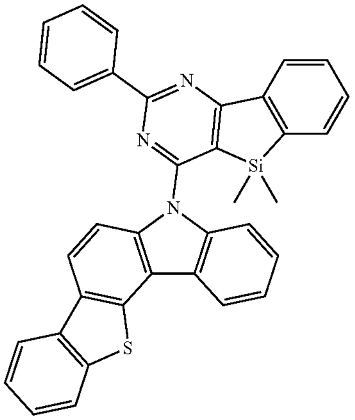
2312
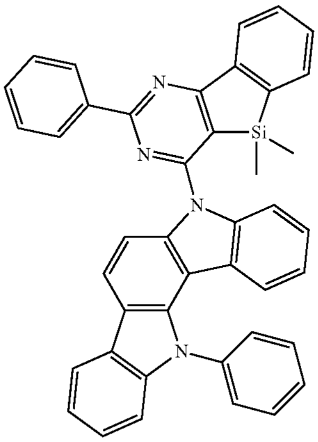
-continued
2313
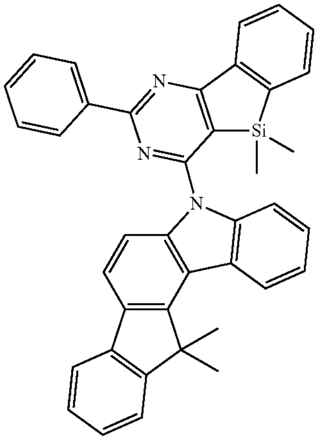
2314
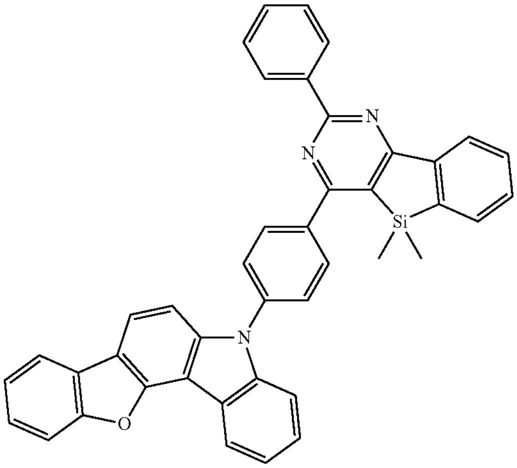
2315
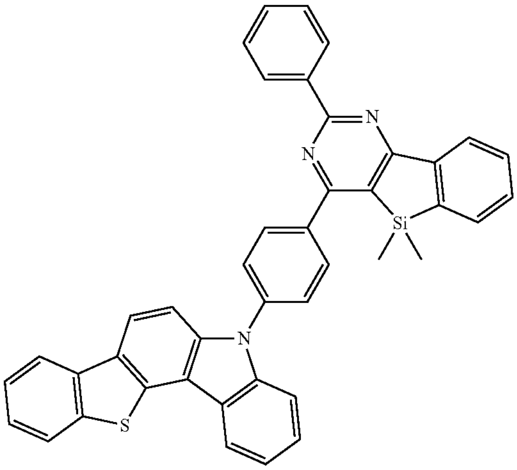

-continued
2316
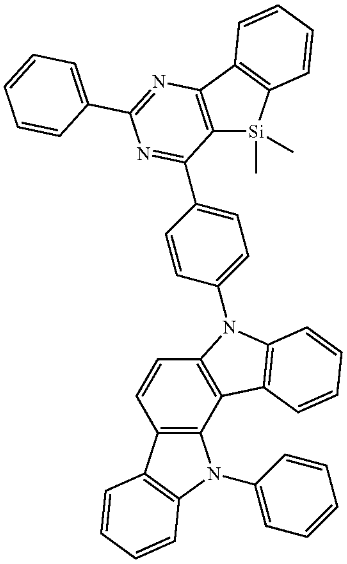
2317
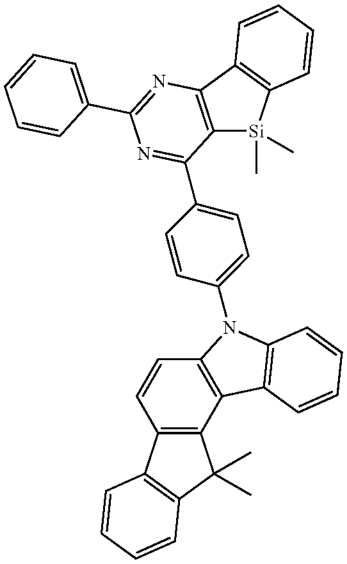
2318
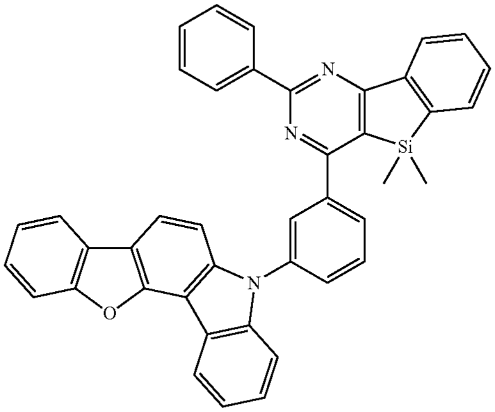
-continued
2319
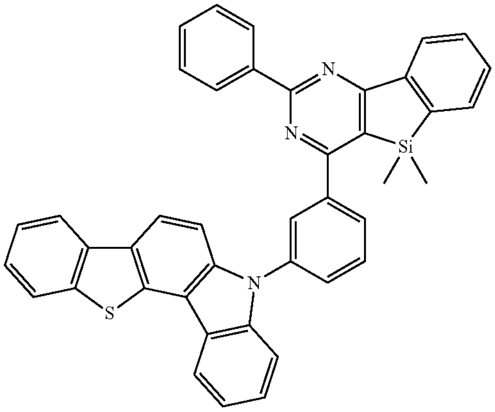
2320
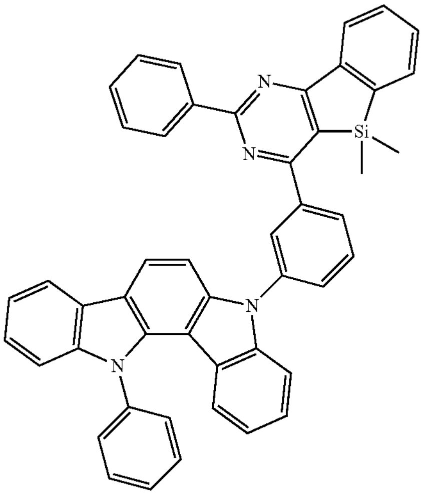
2321
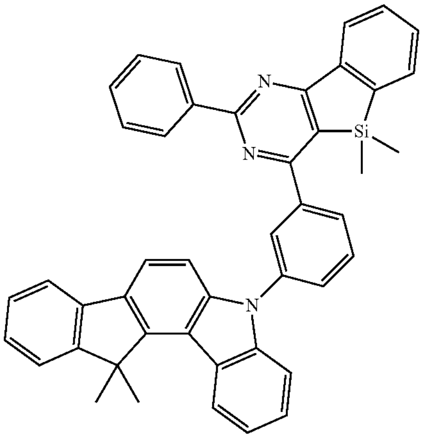

-continued
2322
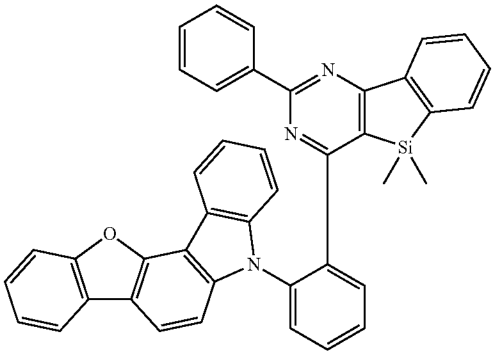
2323
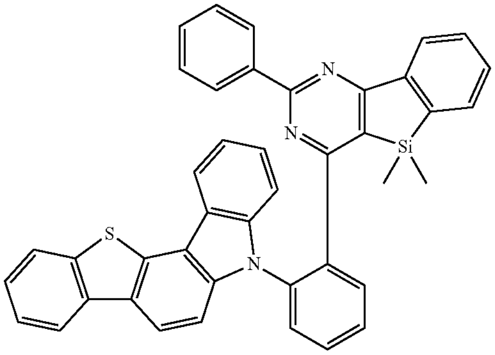
2324
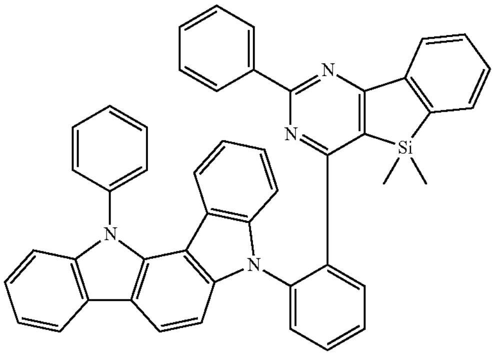
2325
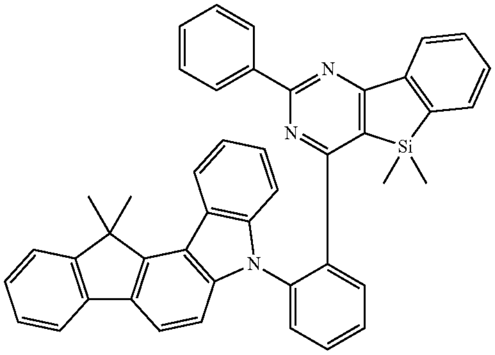
-continued
2326
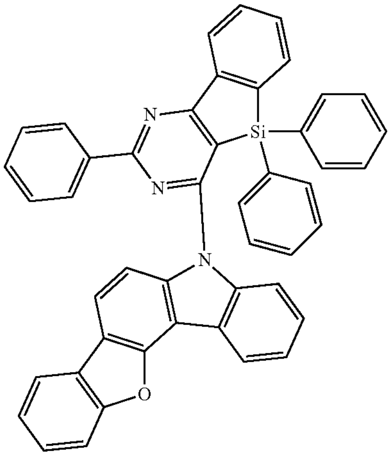
2327
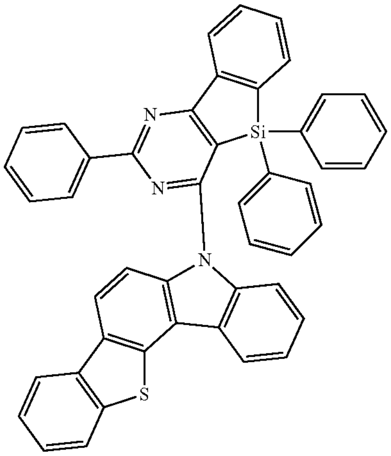
2328
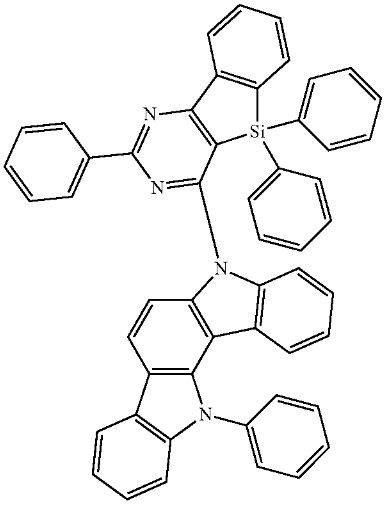

-continued
2329
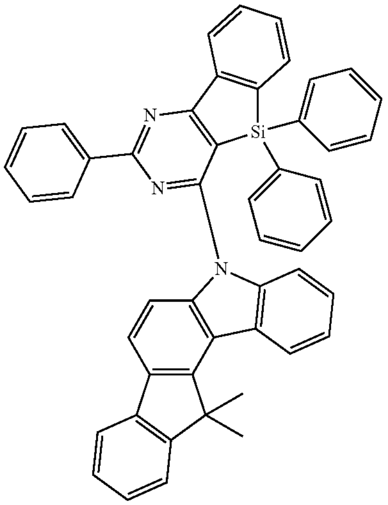
2330
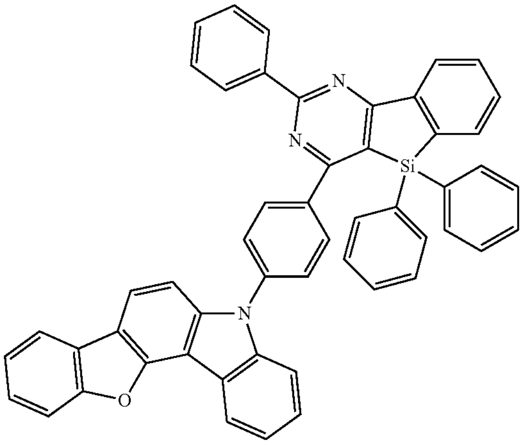
2331
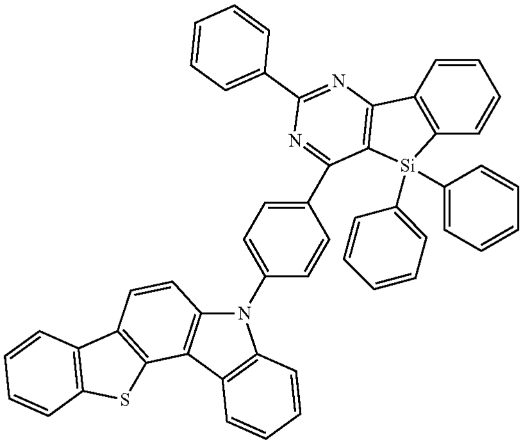
-continued
2332
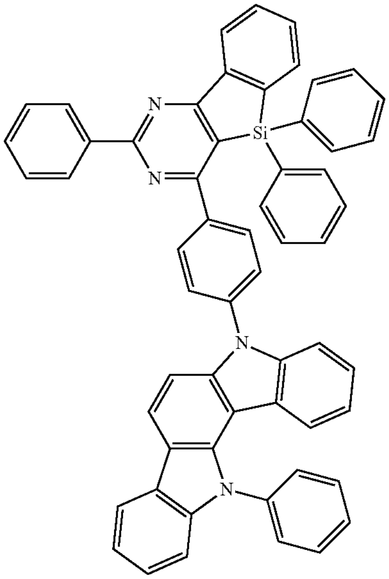
2333
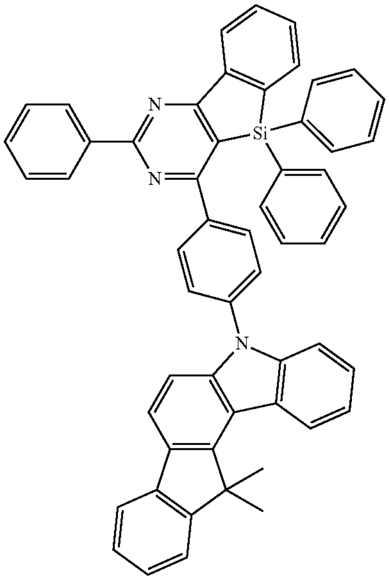
2334
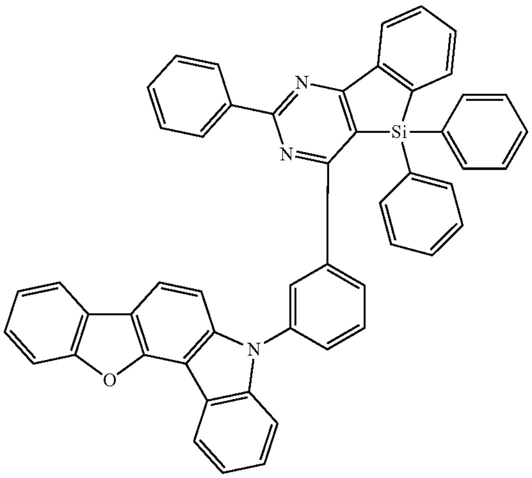

-continued
2335
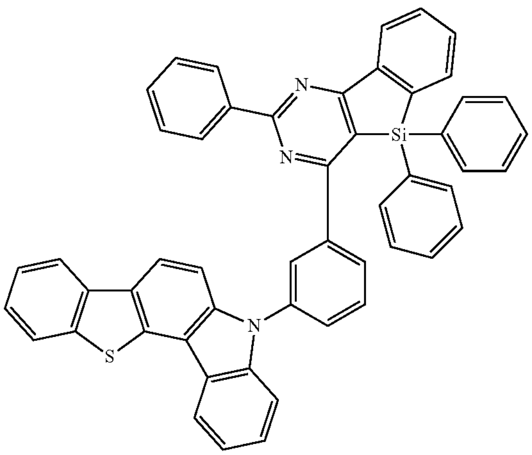
2336
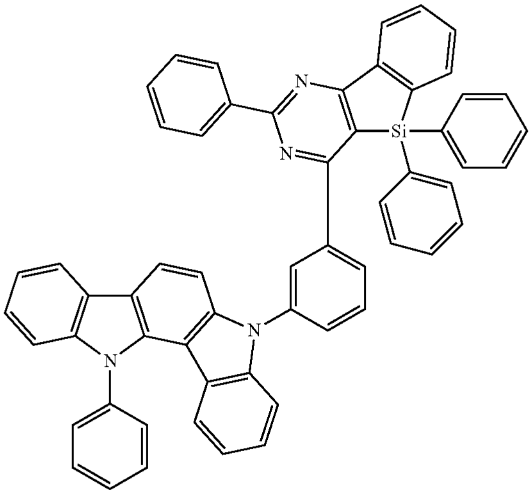
2337
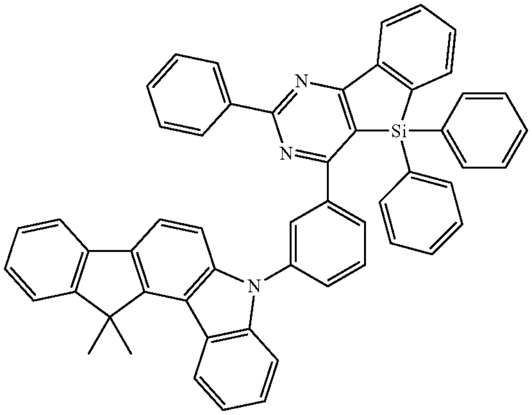
-continued
2338
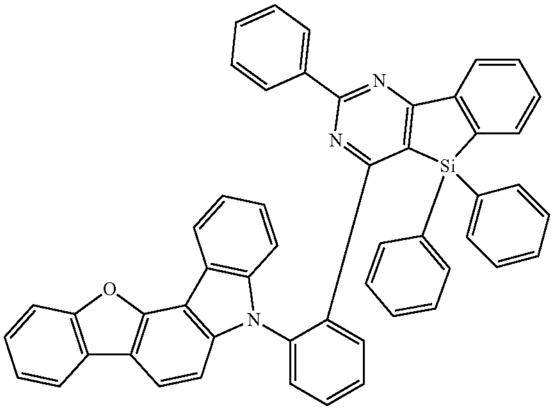
2339
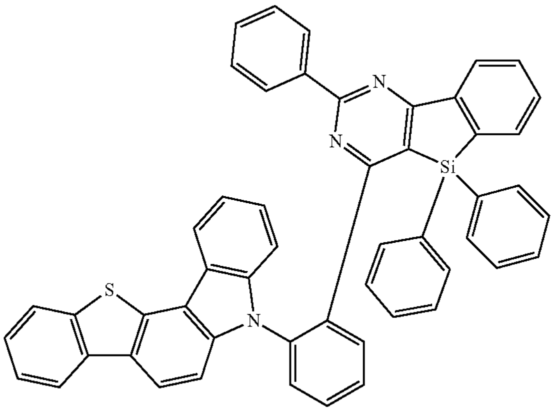
2340
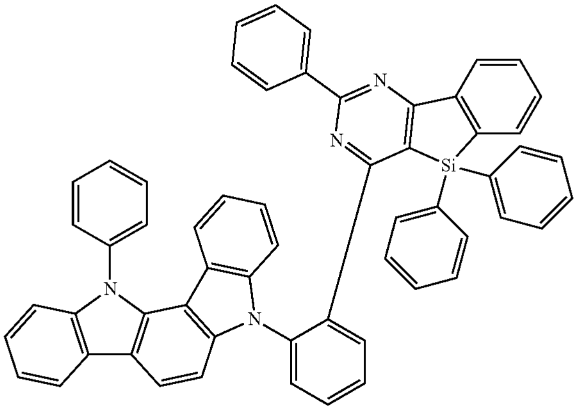

-continued
2341
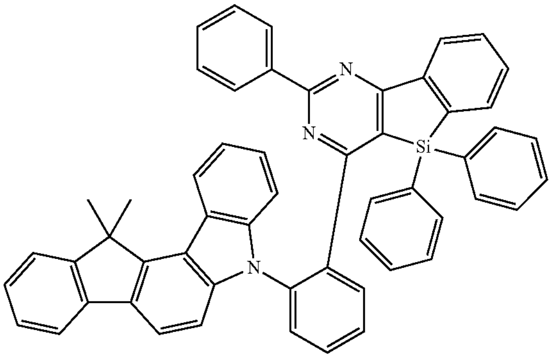
2342
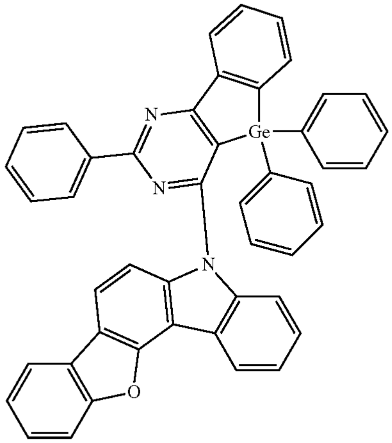
2343
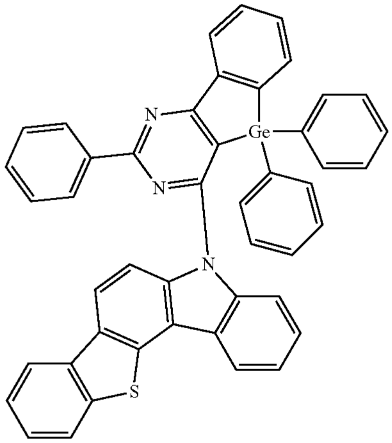
-continued
2344
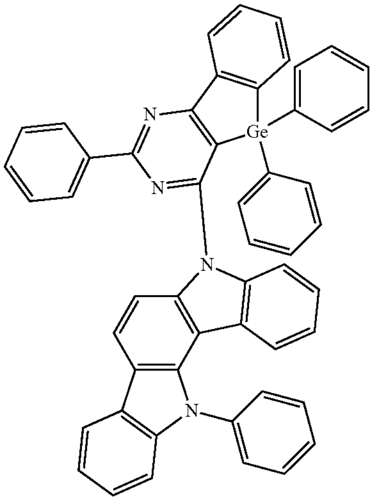
2345
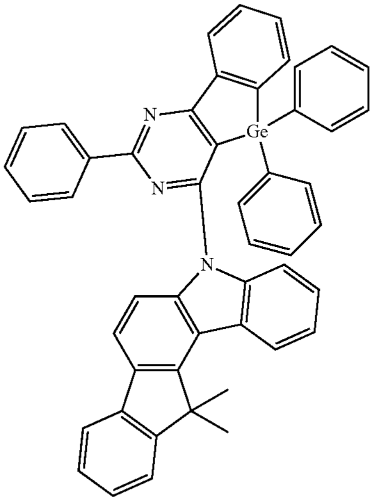
2346
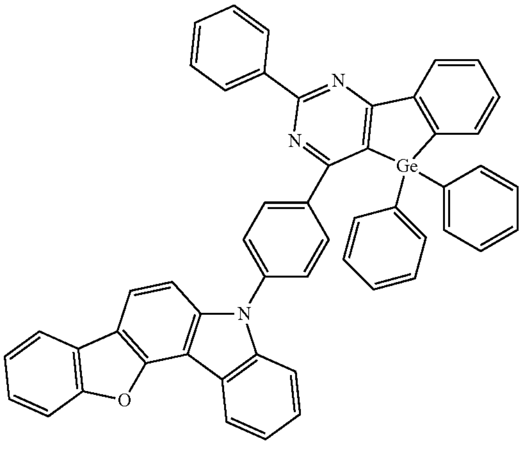

-continued
2347
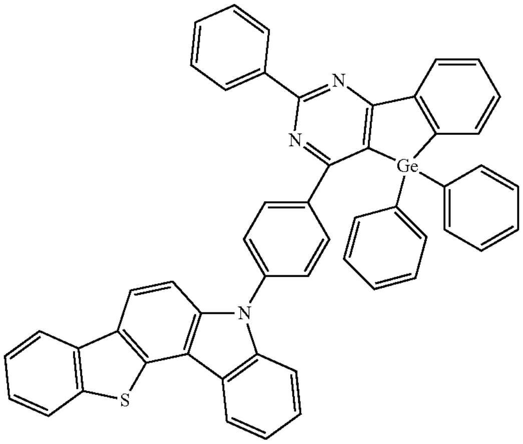
2348
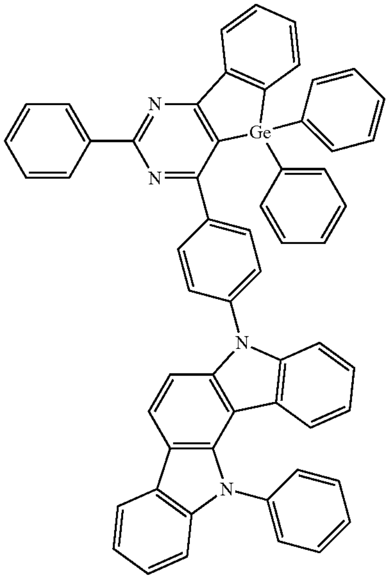
2349
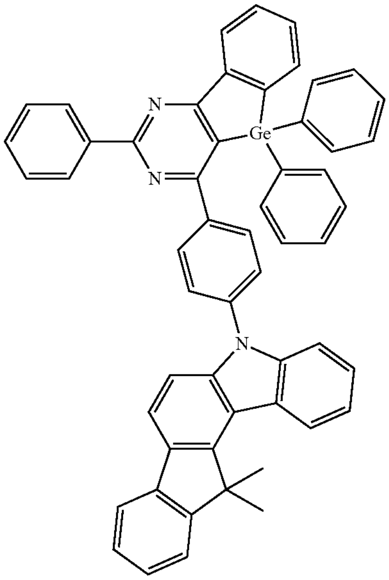
-continued
2350
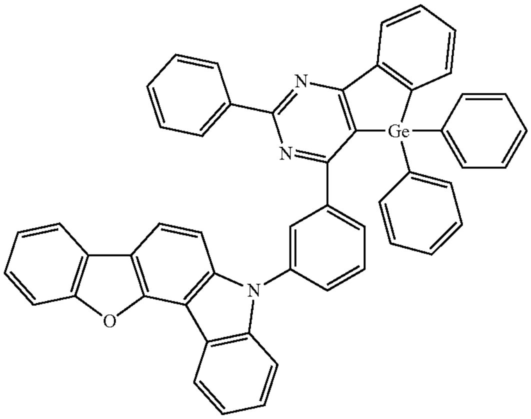
2351
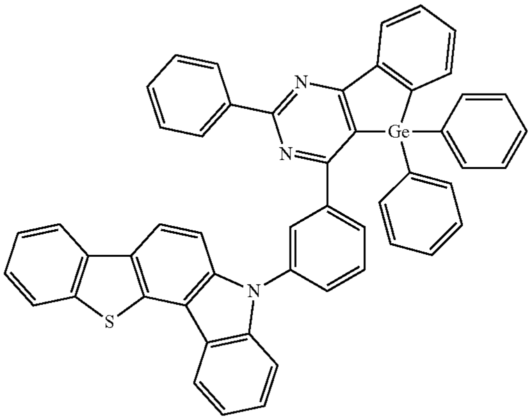
2352
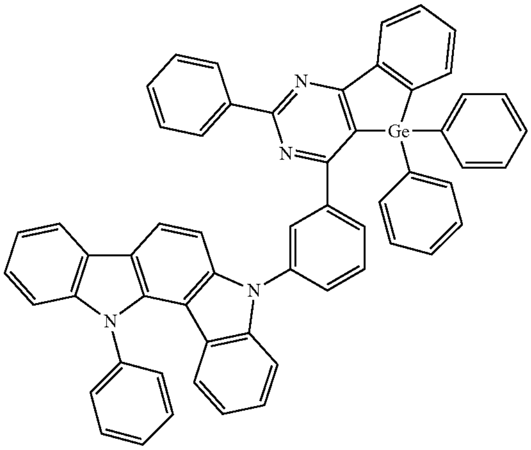

-continued
2353
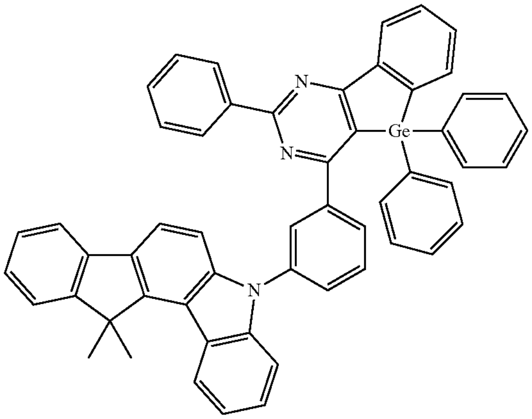
2354
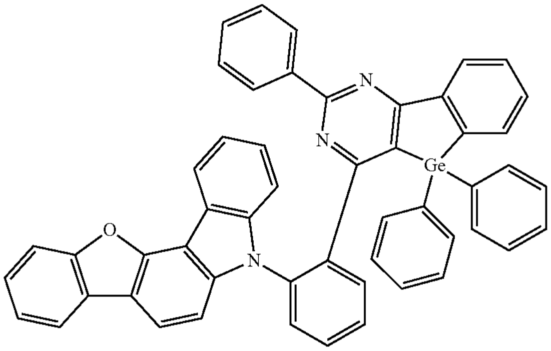
2355
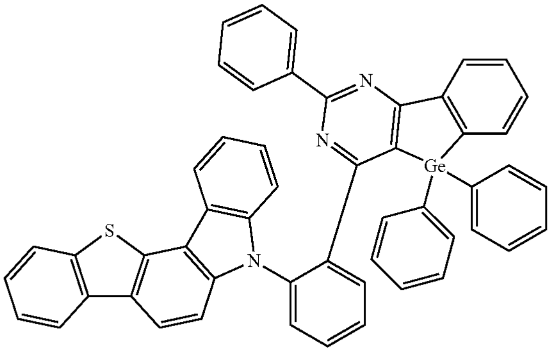
2356
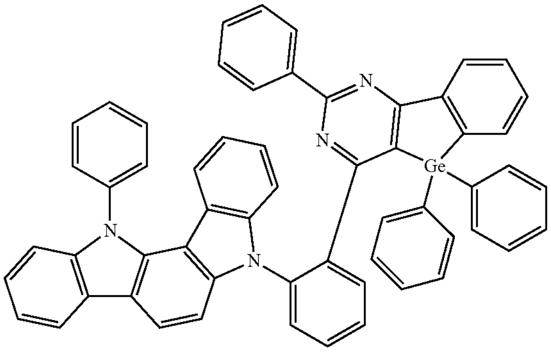
-continued
2357
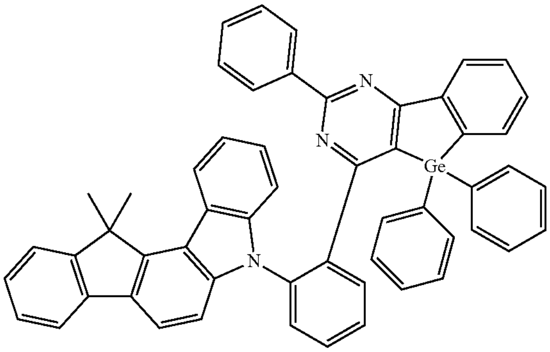
2358
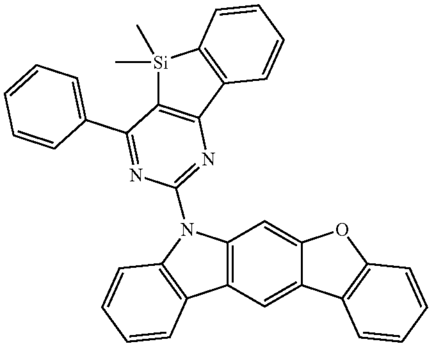
2359
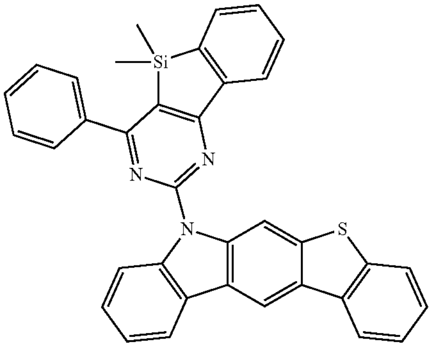
2360
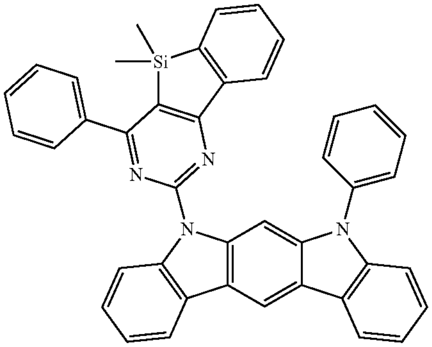

-continued
2361
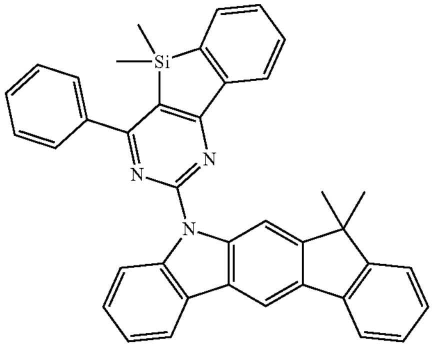
2362
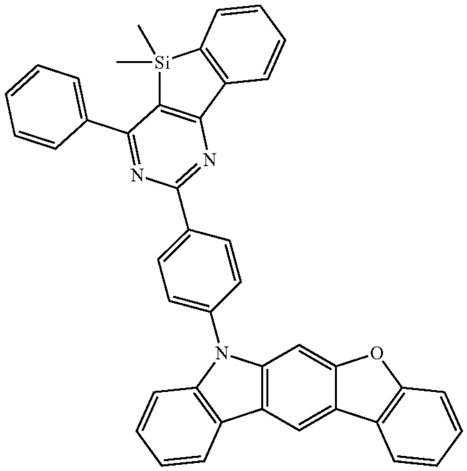
2363
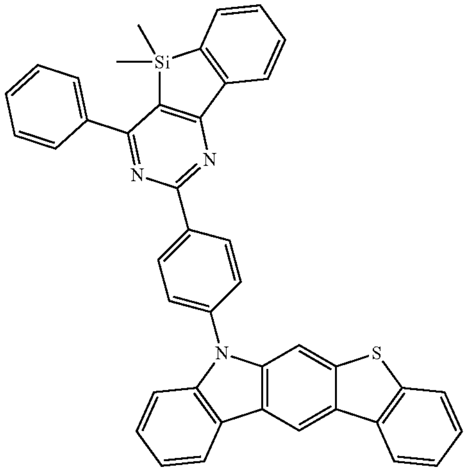
-continued
2364
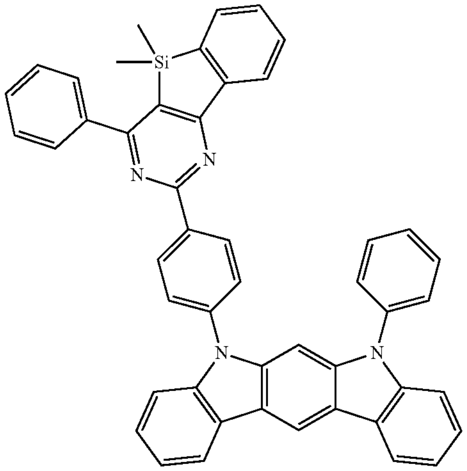
2365
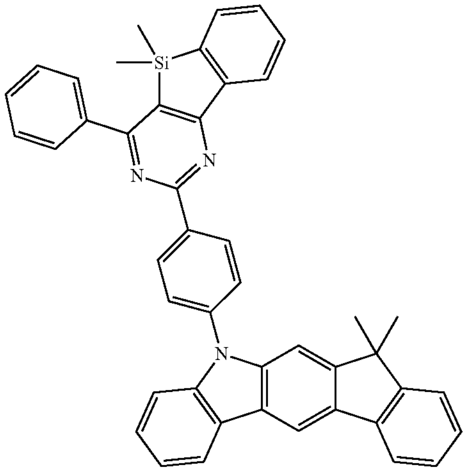
2366
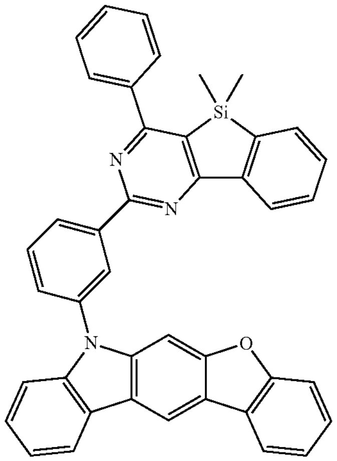

-continued
2367
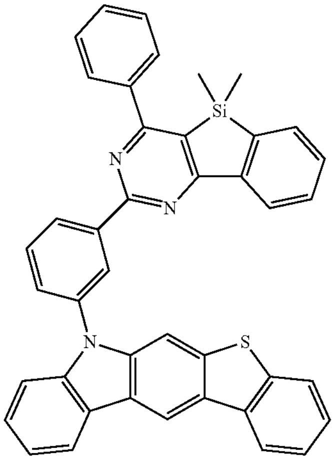
2368
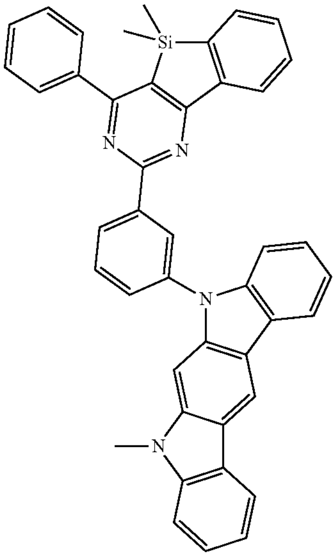
2369
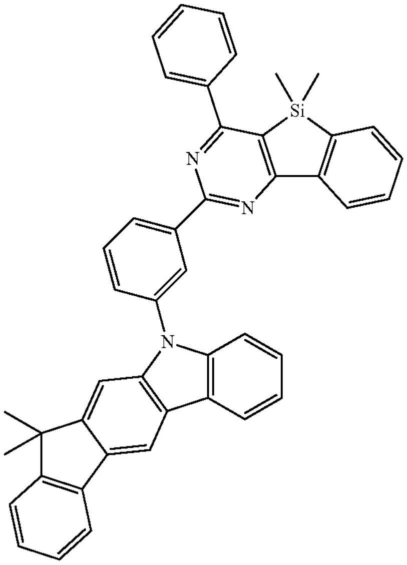
-continued
2370
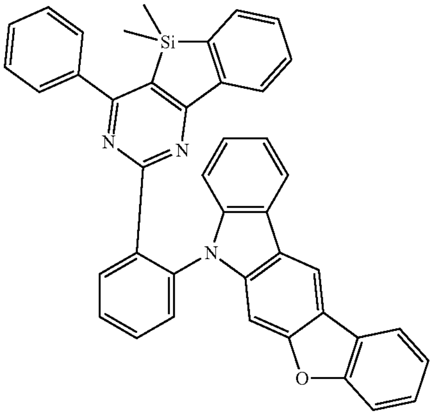
2371
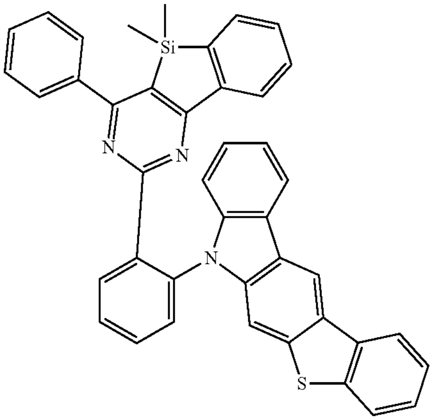
2372
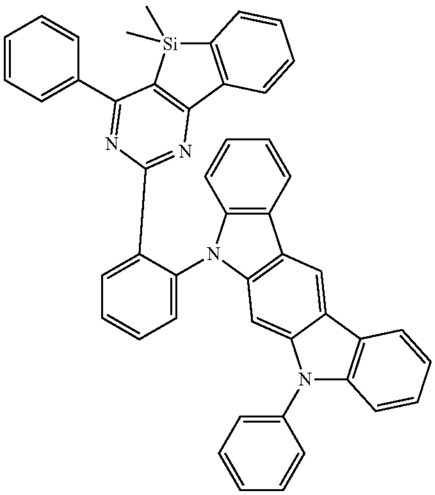

-continued
2373
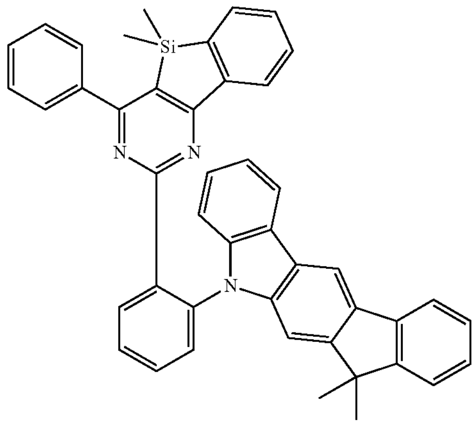
2374
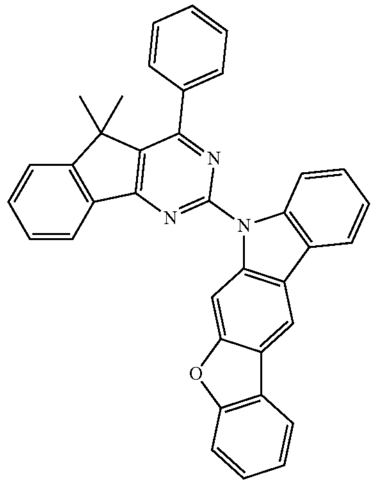
2375
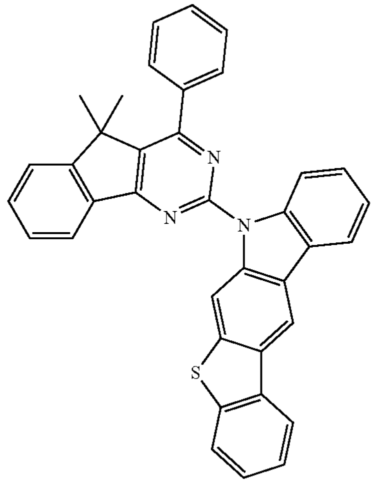
-continued
2376
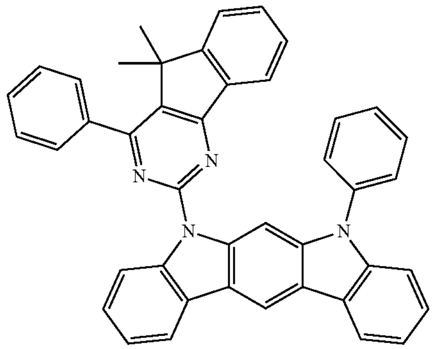
2377
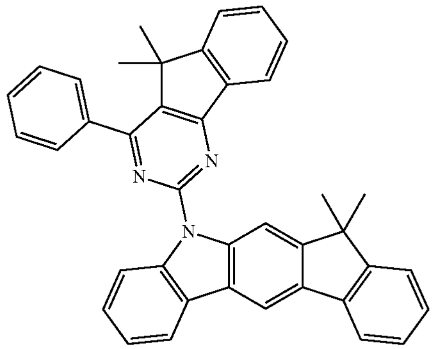
2378
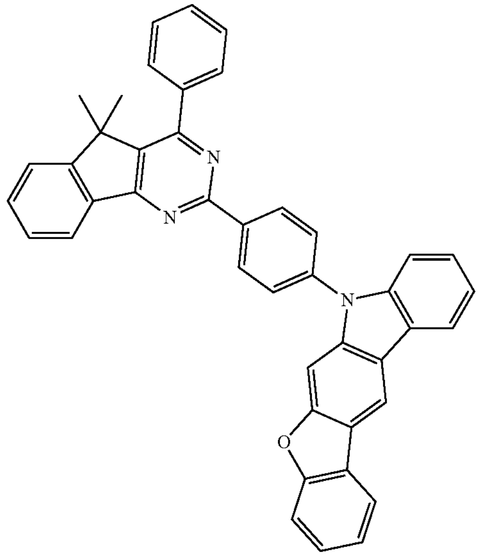

-continued
2379
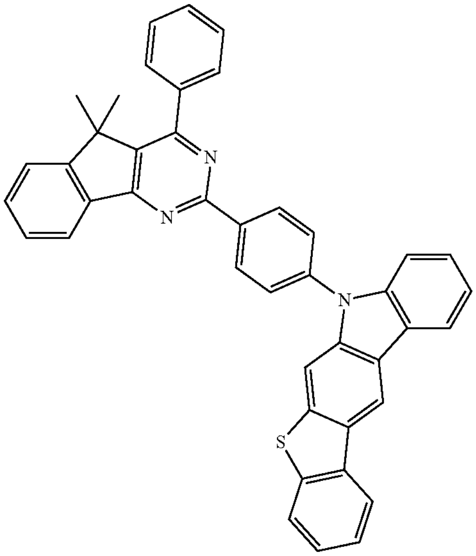
2380
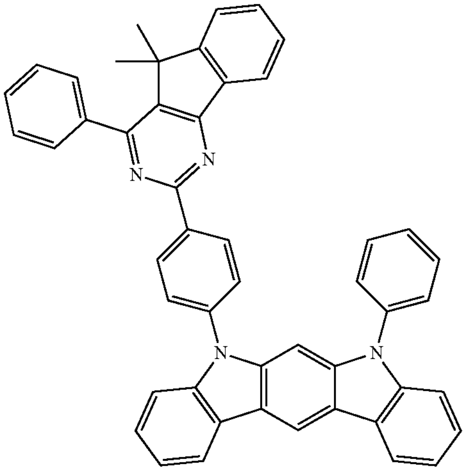
2381
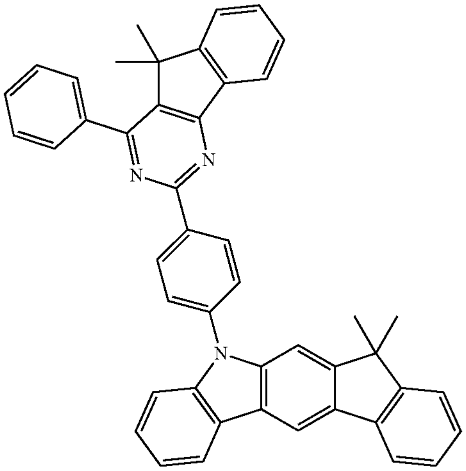
-continued
2382
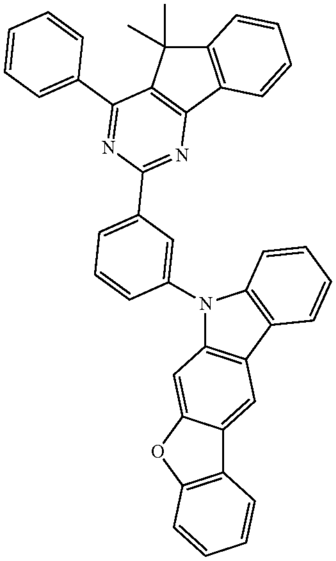
2383
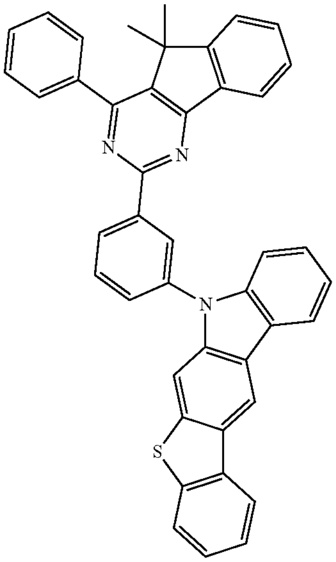

-continued
2384
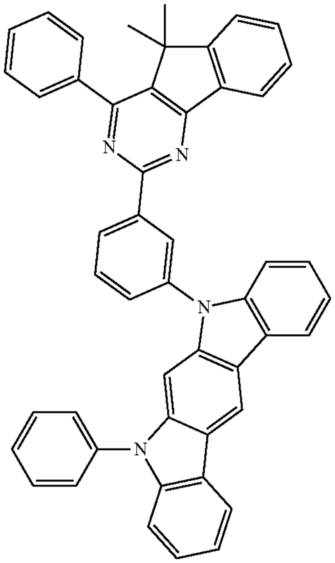
2385
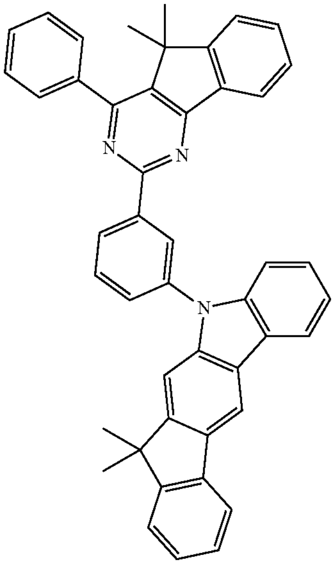
-continued
2386
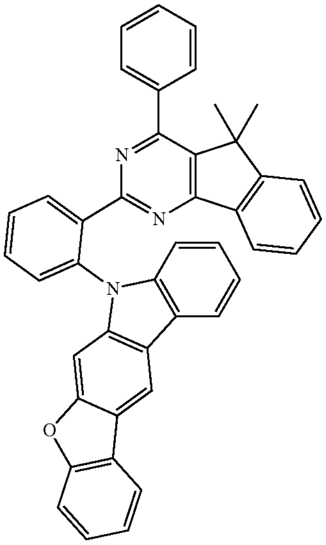
2387
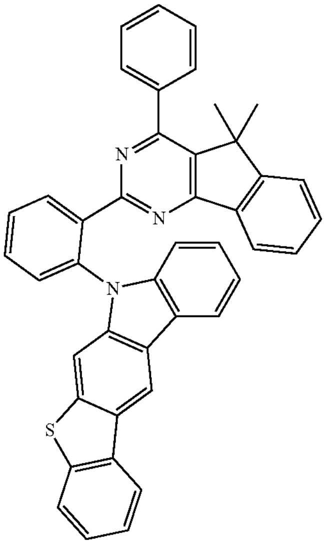
2388
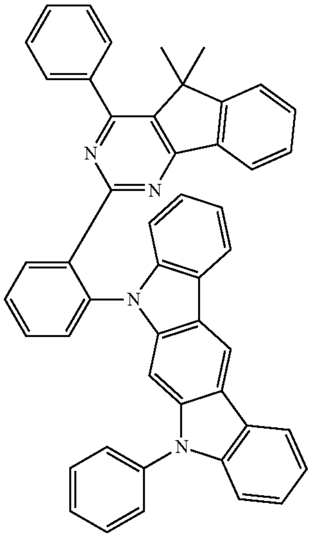

-continued

2389

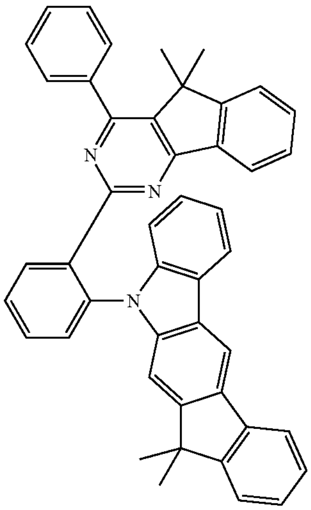

As an example shown in Formula 1', the condensed cyclic compound represented by Formula 1 has a donor moiety linked to an acceptor moiety. This particular arrangement allows efficient thermal activated delayed fluorescence emission to take place through charge migration between the acceptor moiety and the donor moiety.

Formula 1'

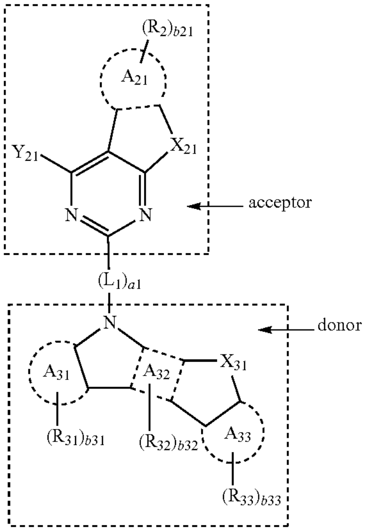

Also, the condensed cyclic compound represented by Formula 1 includes an acceptor moiety including a heteroatom (e.g., an oxygen atom or a sulfur atom) as shown in Formula 1', thereby improving thermally stability compared to an acceptor moiety that has a structure which does not include a heteroatom.

When a heteroatom (e.g., an oxygen atom or a sulfur atom) is included in the acceptor moiety (that is represented by $X_{21}$ in Formula 1') as shown in Formula 1', the condensed cyclic compound represented by Formula 1 may control the lowest unoccupied molecular orbital (LUMO) energy level and may emit deep blue light through combination with the donor moiety.

When the donor moiety and the acceptor moiety each has a separate molecular structure as shown in Formula 1', the condensed cyclic compound represented by Formula 1 may have a separate highest occupied molecular orbital (HOMO) energy and an LUMO energy, and such molecular structure may lower the $\Delta E_{ST}$ value, which allows efficient thermal activated delayed fluorescence emission.

Therefore, an organic light-emitting device including the condensed cyclic compound represented by Formula 1 may provide improved lifespan and high purity.

For example, the results of simulation evaluation of HOMO energy level, LUMO energy level, $T_1$ energy level, $S_1$ energy level, $\Delta E_{ST}$, and f (oscillator strength) performed on Compounds 790, 1884, 1900, 1882, 1889, 1883, 2284, 2268, 1142, 1126, A, and B by using the Gaussian program are as shown in Table 1:

TABLE 1

| Compound No. | HOMO (eV) | LUMO (eV) | $T_1$ (eV) | $S_1$ (eV) | $\Delta E_{ST}$ (eV) | f |
|---|---|---|---|---|---|---|
| 790 | −4.95 | −1.88 | 2.71 | 2.76 | 0.05 | 0.00 |
| 1184 | −5.05 | −2.01 | 2.56 | 2.66 | 0.10 | 0.03 |
| 1900 | −5.06 | −1.90 | 2.68 | 2.78 | 0.10 | 0.02 |
| 1882 | −5.38 | −2.11 | 2.64 | 2.84 | 0.20 | 0.11 |
| 1899 | −5.41 | −1.97 | 2.76 | 3.04 | 0.28 | 0.10 |
| 1883 | −5.39 | −2.07 | 2.65 | 2.93 | 0.28 | 0.12 |
| 2284 | −5.07 | −1.93 | 2.58 | 2.76 | 0.18 | 0.20 |
| 2268 | −5.05 | −2.02 | 2.46 | 2.66 | 0.20 | 0.22 |
| 1142 | −4.96 | −1.89 | 2.65 | 2.75 | 0.10 | 0.02 |
| 1126 | −4.94 | −1.99 | 2.58 | 2.65 | 0.07 | 0.01 |
| A | −5.05 | −1.78 | 2.76 | 2.88 | 0.11 | 0.03 |
| B | −5.40 | −2.04 | 2.72 | 2.90 | 0.18 | 0.12 |

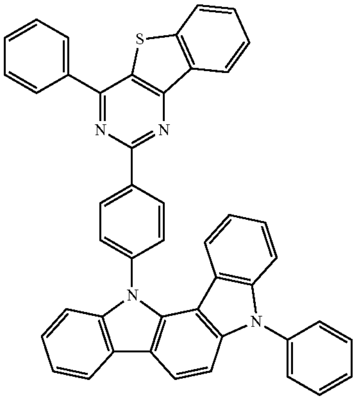

790

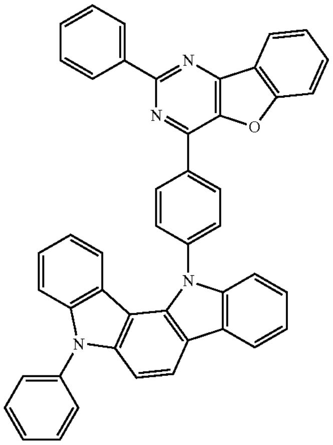

1884

TABLE 1-continued
| Compound No. | HOMO (eV) | LUMO (eV) | $T_1$ (eV) | $S_1$ (eV) | $\Delta E_{ST}$ (eV) | f |
|---|---|---|---|---|---|---|
| 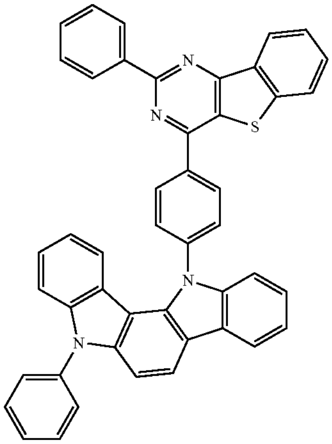 1900 | | | | | | |
| 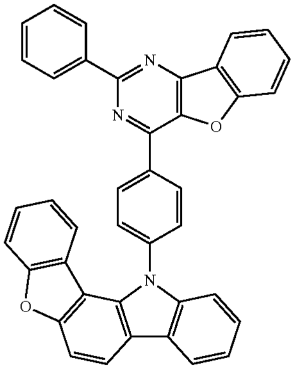 1882 | | | | | | |
| 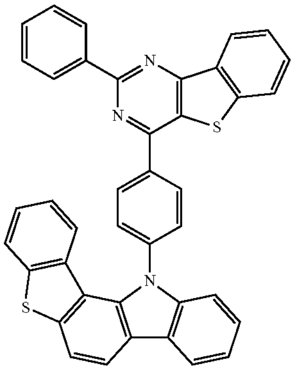 1899 | | | | | | |
TABLE 1-continued
| Compound No. | HOMO (eV) | LUMO (eV) | $T_1$ (eV) | $S_1$ (eV) | $\Delta E_{ST}$ (eV) | f |
|---|---|---|---|---|---|---|
| 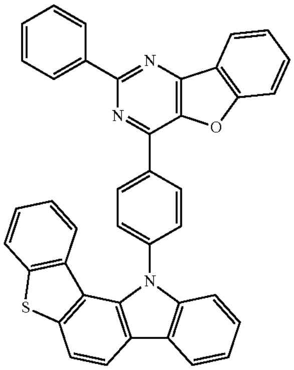 1883 | | | | | | |
| 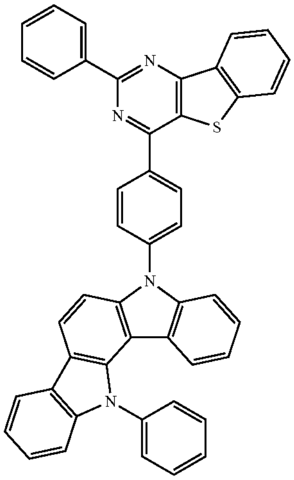 2284 | | | | | | |
| 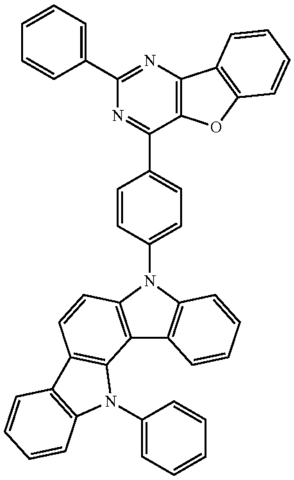 2268 | | | | | | |

TABLE 1-continued

| Compound No. | HOMO (eV) | LUMO (eV) | $T_1$ (eV) | $S_1$ (eV) | $\Delta E_{ST}$ (eV) | f |
|---|---|---|---|---|---|---|
| 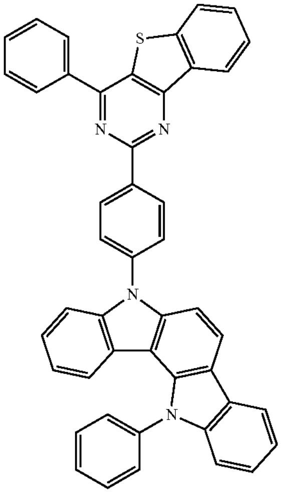 1142 | | | | | | |
| 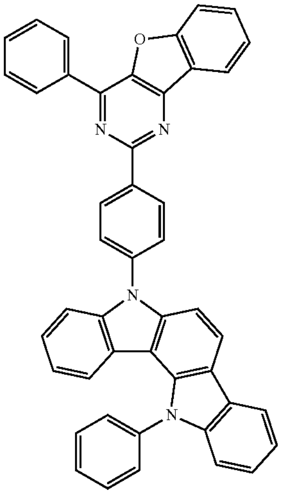 1126 | | | | | | |
| 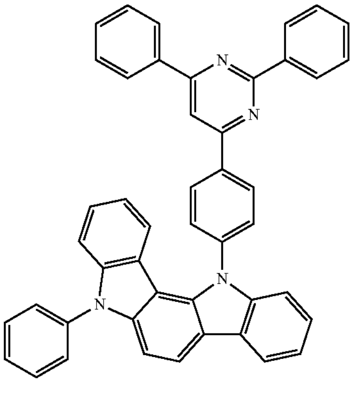 A | | | | | | |

TABLE 1-continued

| Compound No. | HOMO (eV) | LUMO (eV) | $T_1$ (eV) | $S_1$ (eV) | $\Delta E_{ST}$ (eV) | f |
|---|---|---|---|---|---|---|
| 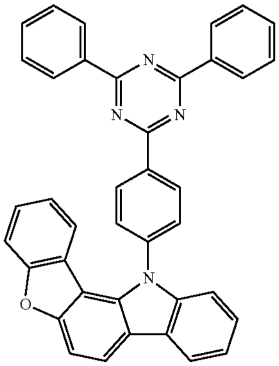 B | | | | | | |

Based on the results shown in Table 1, it may be determined that Compounds 790, 1884, 1900, 1882, 1889, 1883, 2284, 2268, 1142, and 1126 had a low $\Delta E_{ST}$ of 0.3 electron volts (eV) or lower, and thus may allow efficient thermal activated delayed fluorescence emission and deep blue light emission.

A synthesis method of the condensed cyclic compound represented by Formula 1 may be understood by those of ordinary skill in the art with reference to Synthesis Examples provided herein.

Since the condensed cyclic compound represented by Formula 1 is suitable for use as a dopant (e.g., a TADF dopant) of an organic layer, or, for example, an emission layer in the organic layer, of an organic light-emitting device, according to another aspect of the present disclosure, an organic light-emitting device includes:

a first electrode;

a second electrode; and an organic layer disposed between the first electrode and the second electrode, wherein the organic layer includes the condensed cyclic compound represented by Formula 1.

The organic light-emitting device may have high efficiency, long lifespan, and high color purity by including the organic layer having the condensed cyclic compound represented by Formula 1.

For example, the condensed cyclic compound represented by Formula 1 may be included in the emission layer.

In some embodiments, the condensed cyclic compound represented by Formula 1 may be included in the emission layer, and the condensed cyclic compound represented by Formula 1 may be a delayed fluorescent material.

In an embodiment, the emission layer includes a host and a dopant (wherein, the amount of the host is greater than the amount of the dopant), and the dopant may include the condensed cyclic compound represented by Formula 1. The condensed cyclic compound, which serves as a dopant, may emit delayed fluorescent light according to delayed fluorescence emission mechanism. The host may be selected from materials available as a host in the art.

The emission layer may emit red light, green light, or blue light.

In an embodiment, the emission layer may be a blue (e.g., deep-blue) emission layer that includes the condensed cyclic compound represented by Formula 1, but embodiments are not limited thereto.

As used herein, the expression "(an organic layer) includes at least one condensed cyclic compound" may include a case in which "(an organic layer) includes identical condensed cyclic compounds represented by Formula 1 and a case in which (an organic layer) includes two or more different condensed cyclic compounds represented by Formula 1.

For example, the organic layer may include only Compound 1 as the condensed cyclic compound. Then, Compound 1 may be included in the emission layer of the organic light-emitting device. In some embodiments, the organic layer may include Compound 1 and Compound 2 as the condensed cyclic compounds. Then, Compound 1 and Compound 2 may be included in the same layer (for example, both Compound 1 and Compound 2 may be included in the emission layer).

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region that is disposed between the first electrode and the emission layer, wherein the hole transport region may include at least one selected from a hole injection layer, a hole transport layer, and an electron blocking layer; and ii) an electron transport region that is disposed between the emission layer and the second electrode, wherein the electron transport region may include at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, the structure of an organic light-emitting device according to an embodiment and a method of manufacturing an organic light-emitting device, according to an embodiment, will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode The first electrode 11 may have a single-layer structure or a multi-layer structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer may be formed on the first electrode 11 by using one or more suitable methods selected from vacuum deposition, spin coating, casting, or a Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (A/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrene sulfonate) (PEDOT/PSS), polyaniline/camphor sulfonic acid (Pani/CSA), (polyaniline)/poly(4-styrene sulfonate) (Pani/PSS), a compound represented by Formula 201 below, and a compound represented by Formula 202 below:

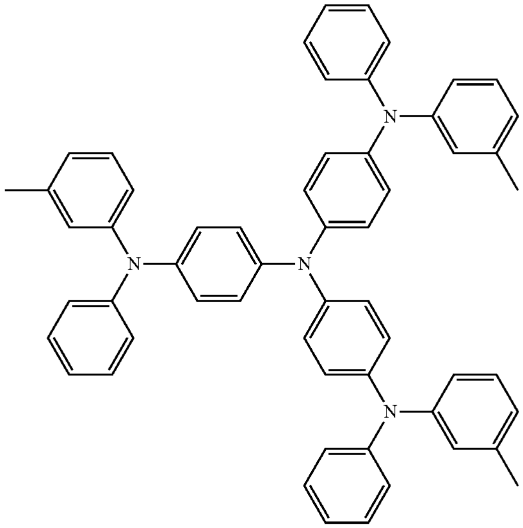
m-MTDATA
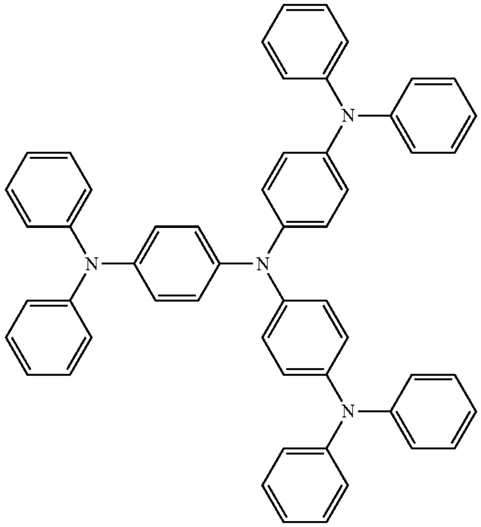
TDATA
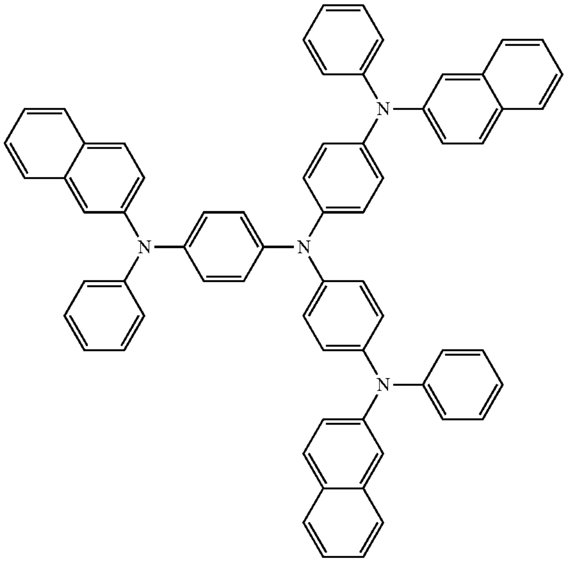
2-TNATA
-continued
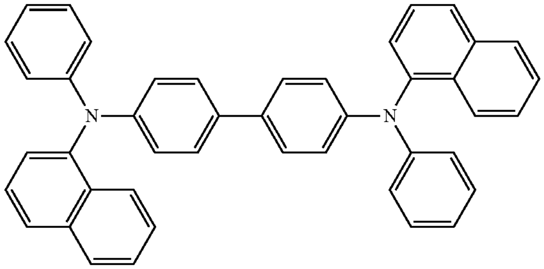
NPB
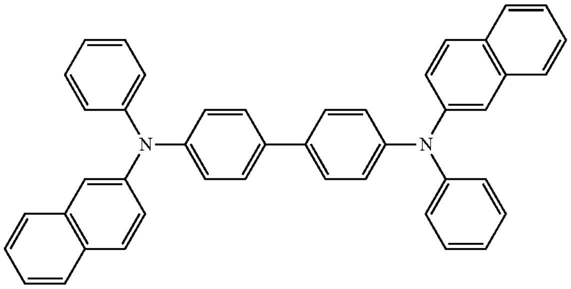
β-NPB
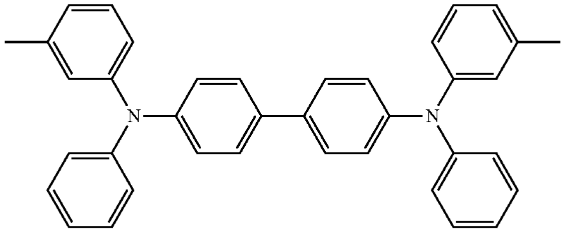
TPD
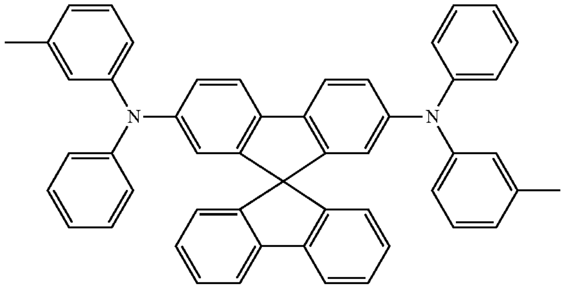
Spiro-TPD
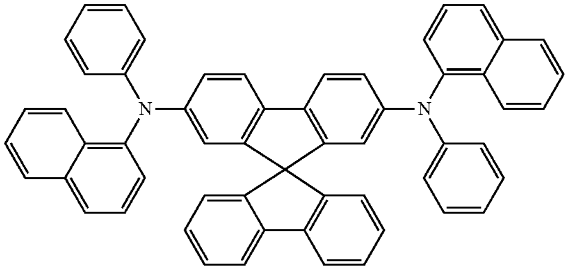
Spiro-NPB -continued

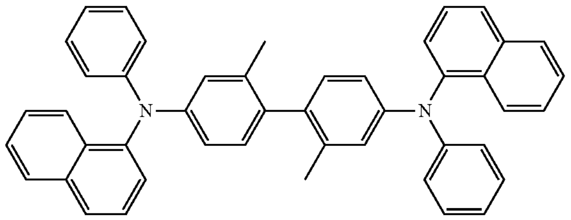

methylated NPB

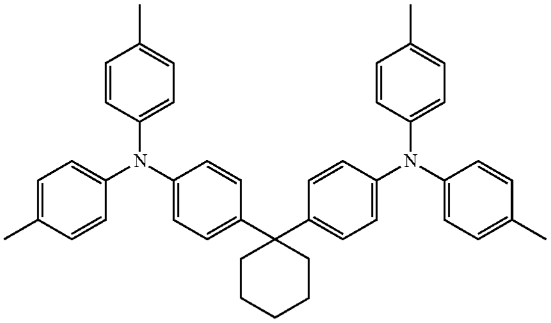

TAPC

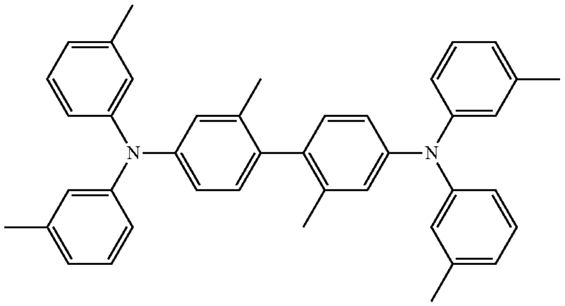

HMTPD

Formula 201

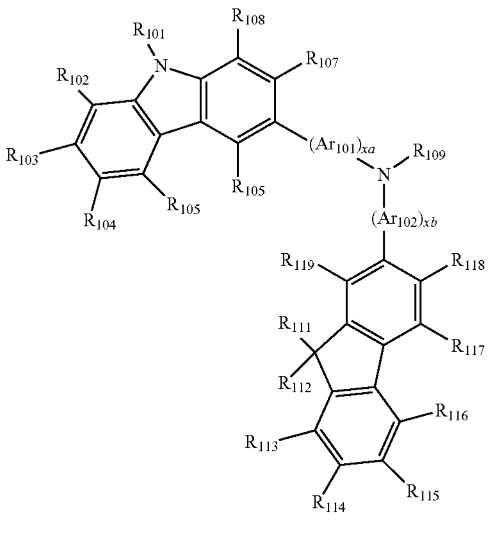

-continued

Formula 202

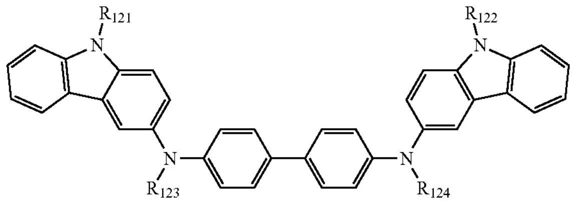

In Formula 201, $Ar_{101}$ and $Ar_{102}$ may each independently be selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or 0, 1, or 2. For example, xa may be 1 and xb may be 0, but they are not limited thereto.

$R_{101}$ to $R_{108}$, $R_{111}$ to $R_{119}$, and $R_{121}$ to $R_{124}$ in Formulae 201 and 202 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but is not limited thereto:

Formula 201A

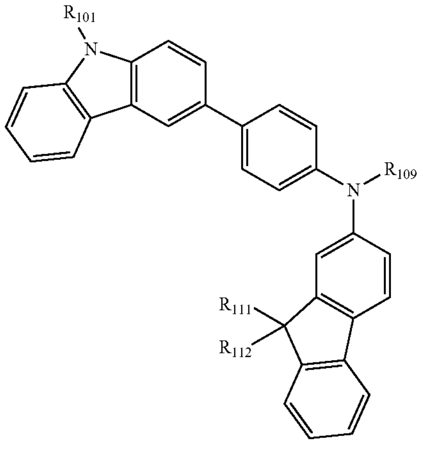

$R_{101}$, $R_{111}$, $R_{112}$, and $R_{109}$ in Formula 201A may be understood by referring to the description provided herein.

For example, the compound represented by Formula 201 and the compound represented by Formula 202 may include compounds HT1 to HT20 illustrated below, but are not limited thereto:

HT1

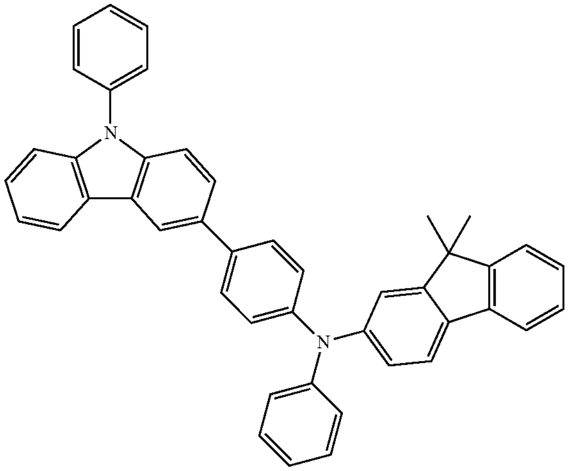

HT2

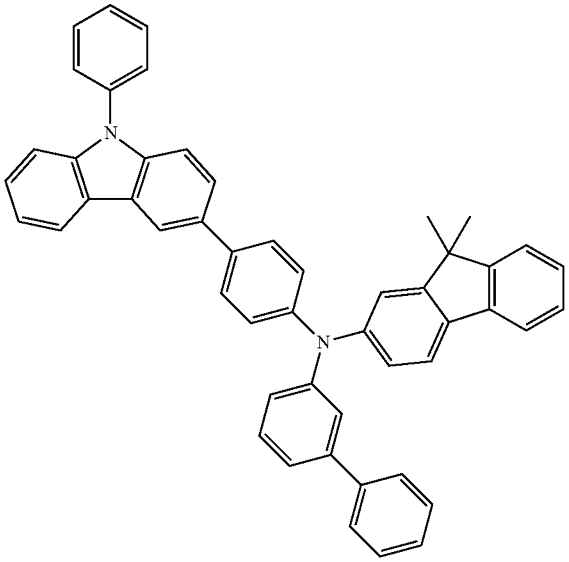

-continued
HT3
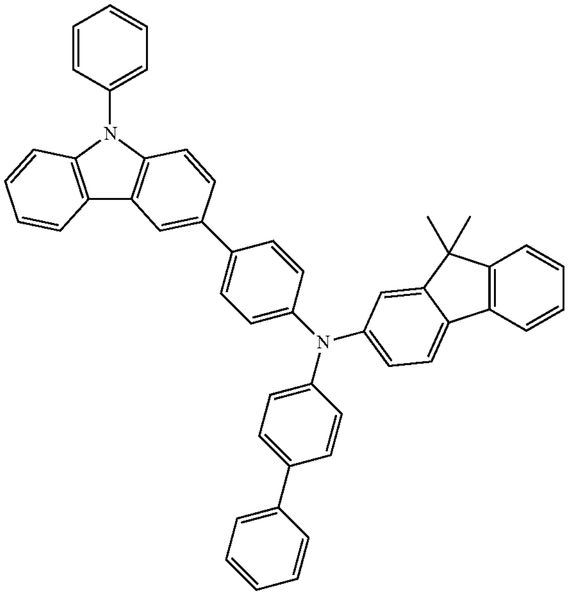
HT4
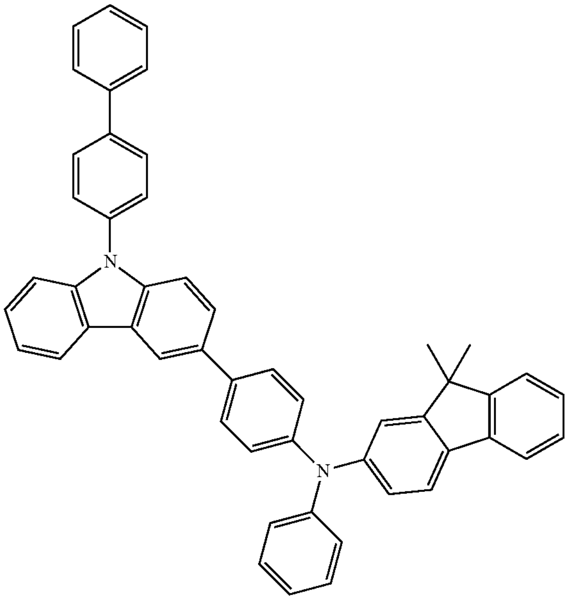
-continued
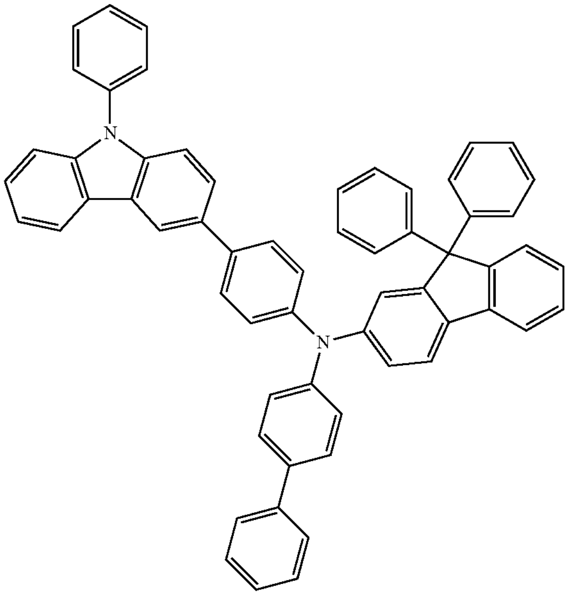
HT6
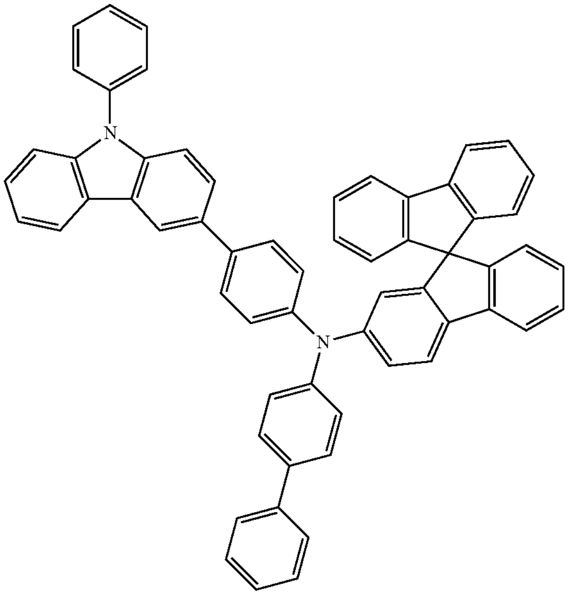

-continued
HT7
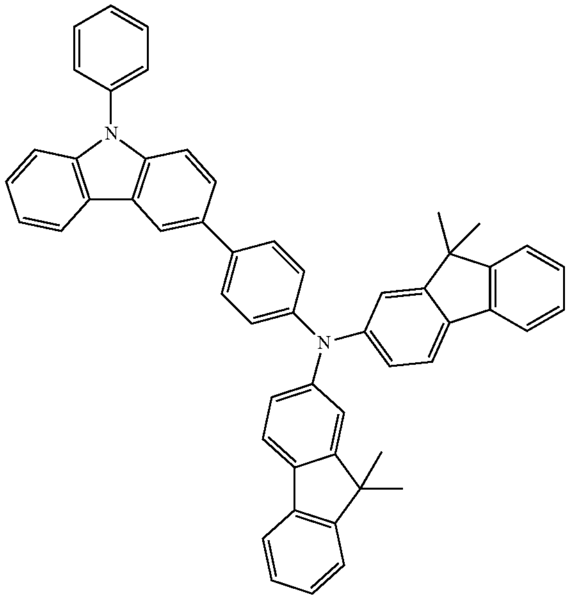
HT8
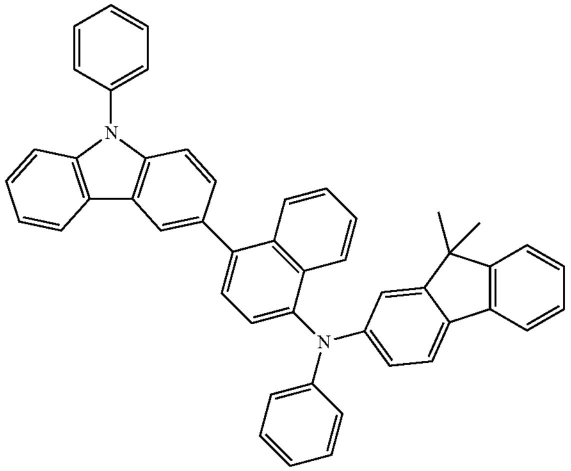
HT9
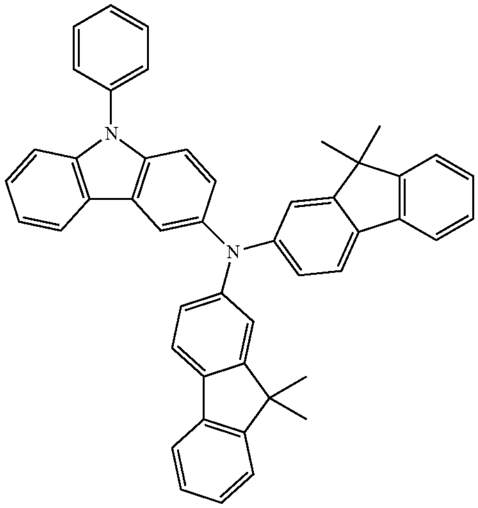
-continued
HT10
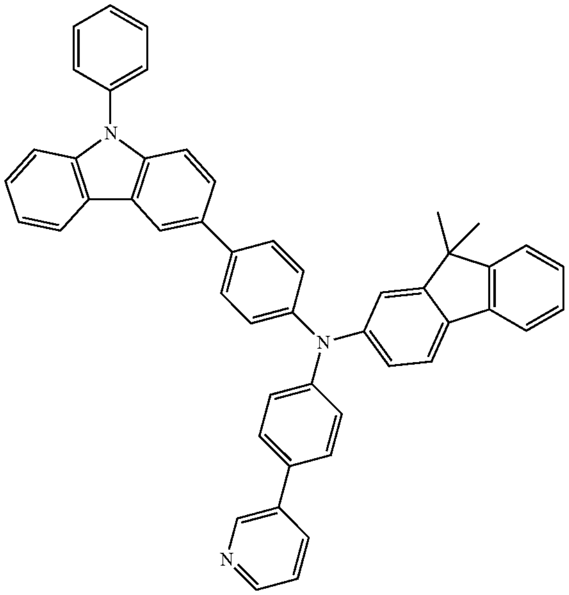
HT11
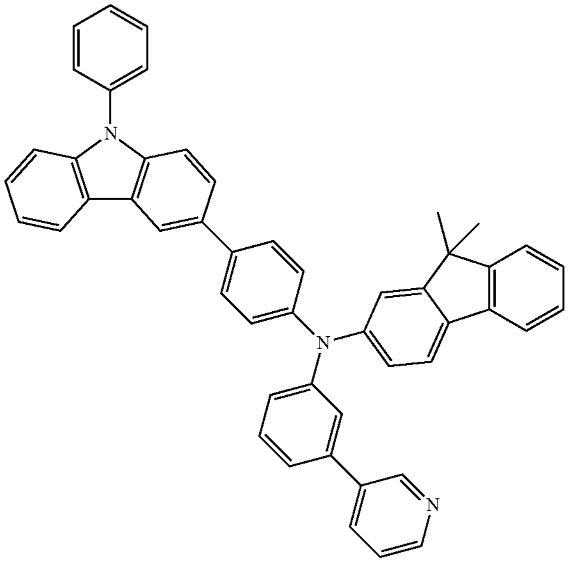

-continued
HT12
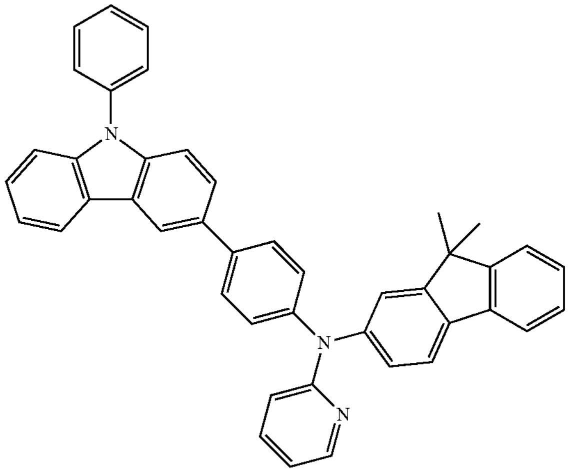
HT13
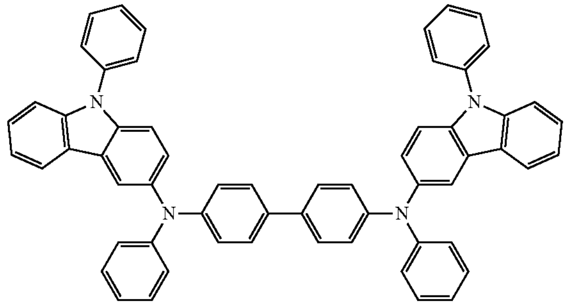
HT14
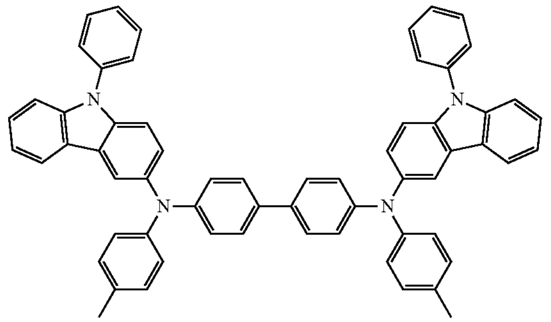
HT15
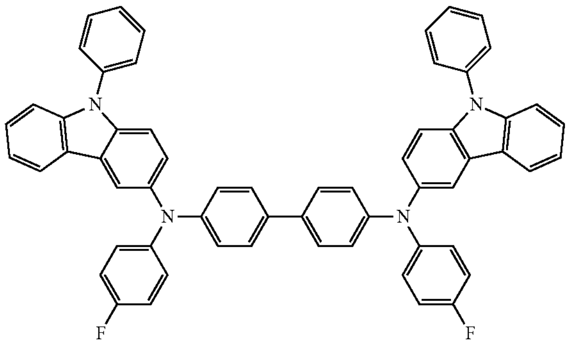
-continued
HT16
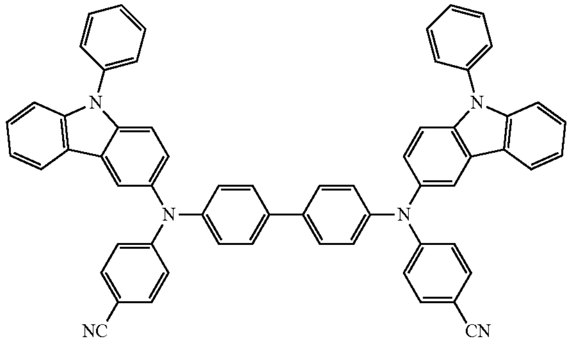
HT17
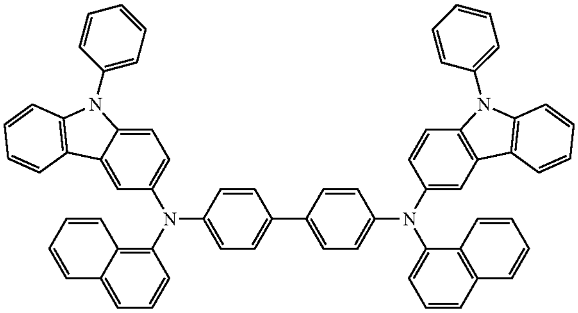
HT18
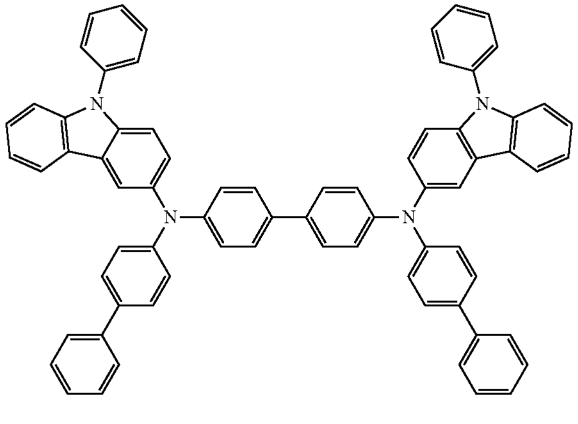
HT19
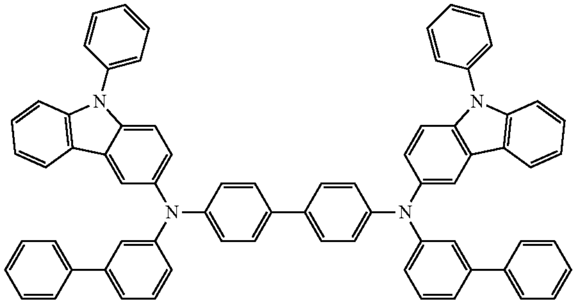

-continued

HT20

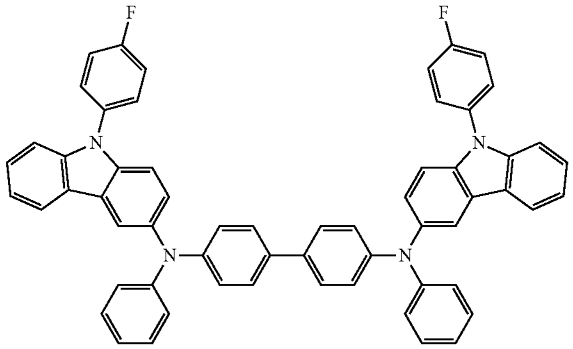

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thickness values of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto.

Compound HT-D1

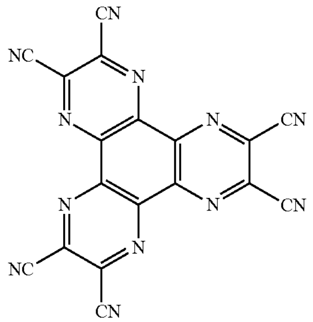

-continued

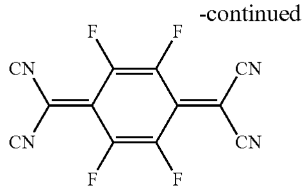

F4-TCNQ

Compound HT-D2

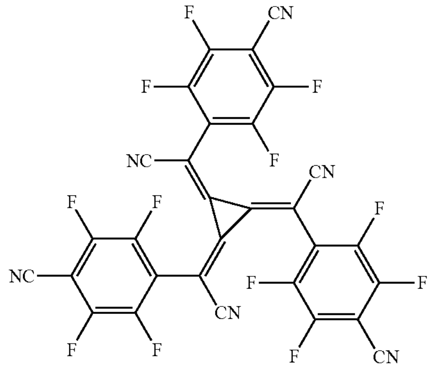

The hole transport region may further include a buffer layer.

Also, the buffer layer may compensate for an optical resonance distance according to a wavelength of light emitted from the emission layer, and thus, the efficiency of an organic light-emitting device thus formed may improve.

The electron transport region may further include an electron blocking layer. The electron blocking layer may include, for example, mCP, but a material therefor is not limited thereto.

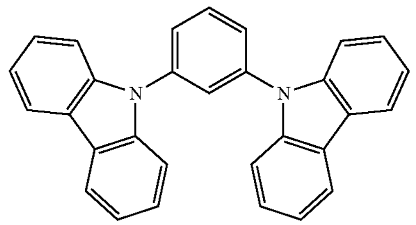

mCP

A thickness of the electron blocking layer may be in a range of about 50 Å to about 1,000 Å, for example, about 70 Å to about 500 Å. While not wishing to be bound by theory it is understood that when the thickness of the electron blocking layer is within this range, excellent electron blocking characteristics may be obtained without a substantial increase in driving voltage.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant.

The host may include at least one selected from CBP, CDBP, TCP, mCP, PPF, and DPEPO.

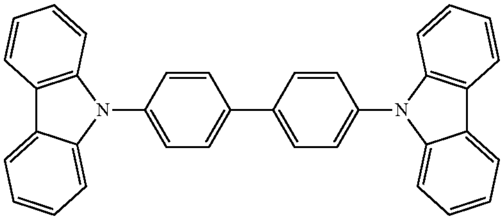

CBP

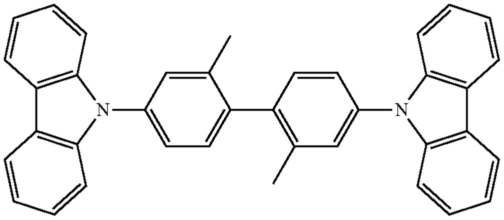

CDBP

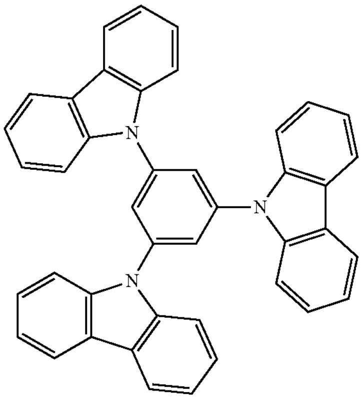

TCP

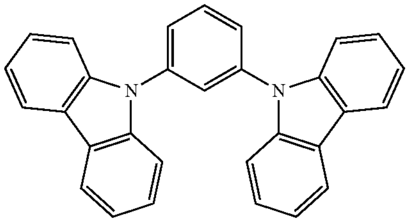

mCP

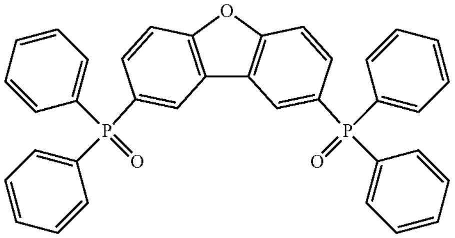

PPF

-continued

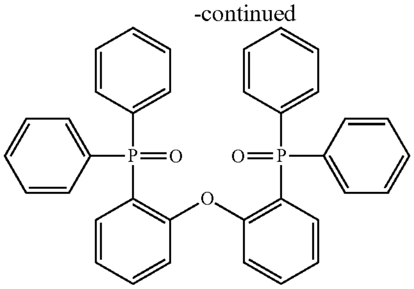

DPEPO

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include a host and a fluorescent dopant, and the host and the fluorescent dopant are substantially the same as described above.

A thickness of the emission layer may be in a range of about 100 Å to about 1,000 Å, for example, about 200 Å to about 600 Å. While not wishing to be bound by theory it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials:

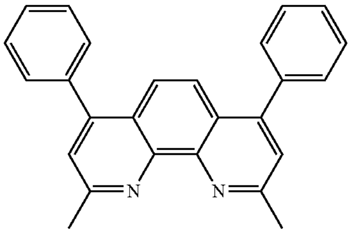

BCP

-continued

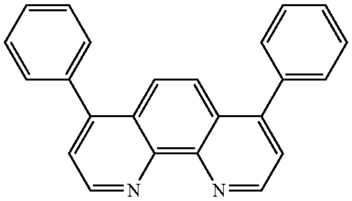

Bphen ,

A thickness of the hole blocking layer may be in a range of about 20 Å to about 1,000 Å, for example, about 30 Å to about 300 Å. While not wishing to be bound by theory it is understood that when the thickness of the hole blocking layer is within these ranges, the hole blocking layer may have improved hole blocking ability without a substantial increase in driving voltage.

The electron transport layer may further include at least one selected from BCP, Bphen, Alq3, Balq, TAZ, and NTAZ.

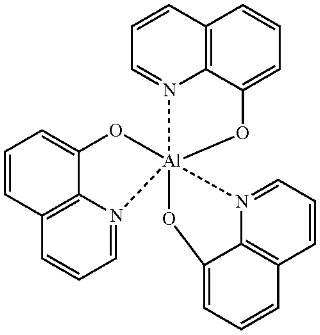

$Alq_3$

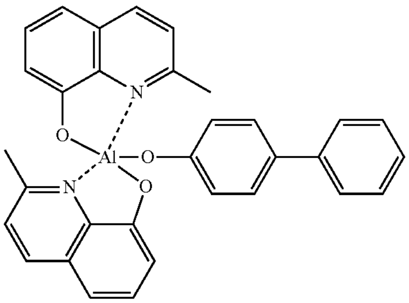

BAlq

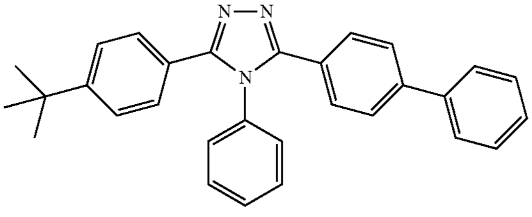

TAZ

-continued

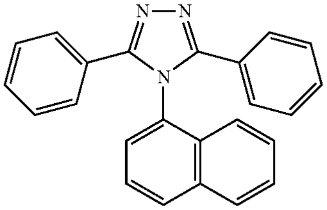

NTAZ

In some embodiments, the electron transport layer may include at least one selected from Compounds ET1 to ET19, but embodiments are not limited thereto:

ET1

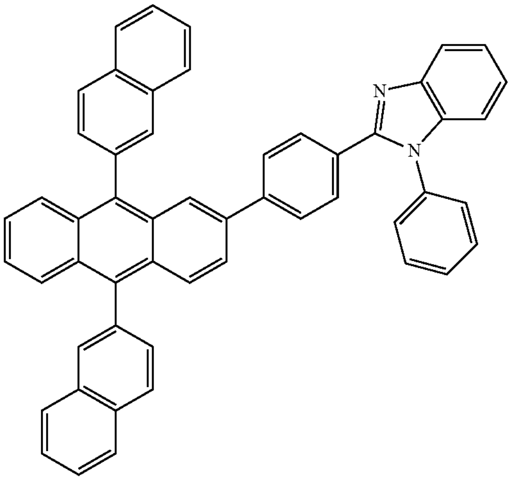

ET2

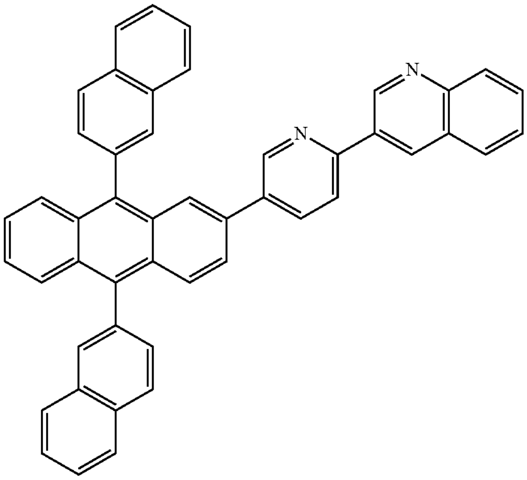

-continued
ET3
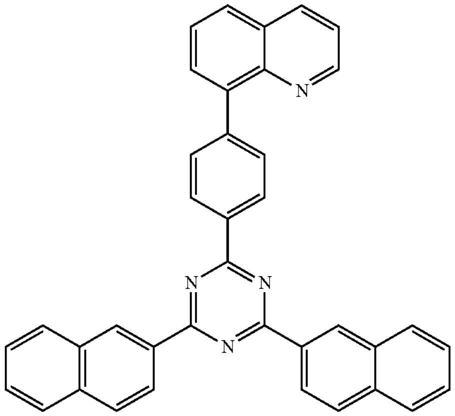
ET4
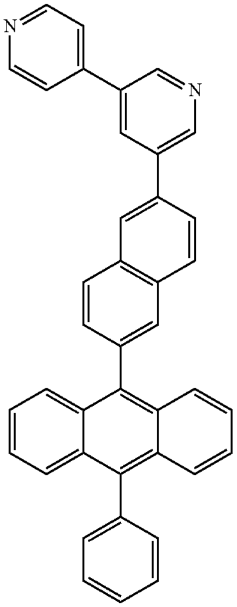
ET5
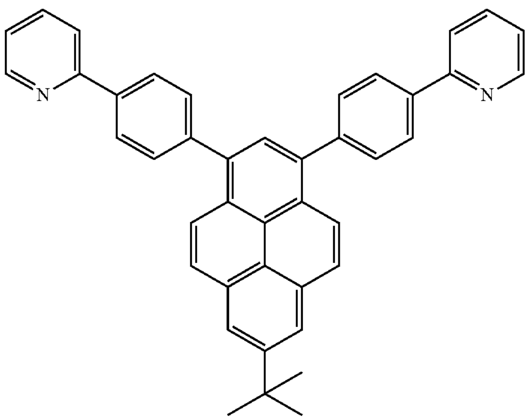
-continued
ET6
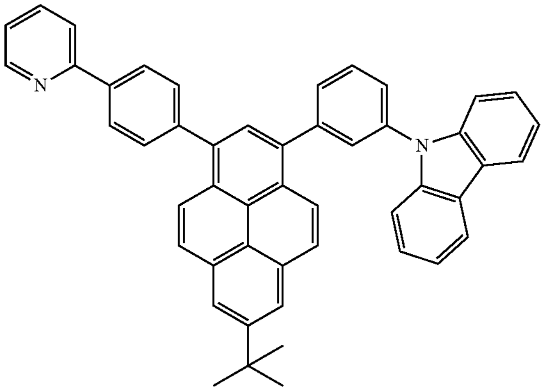
ET7
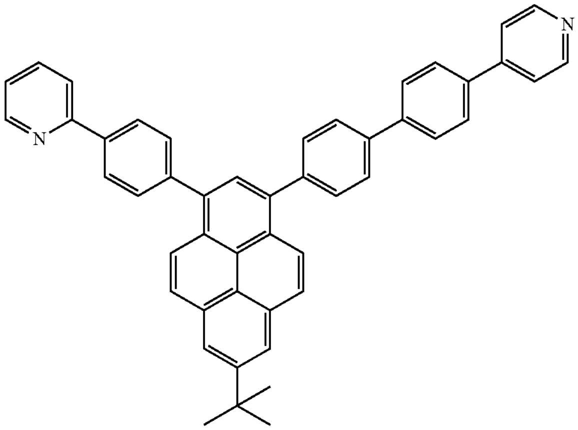
ET8
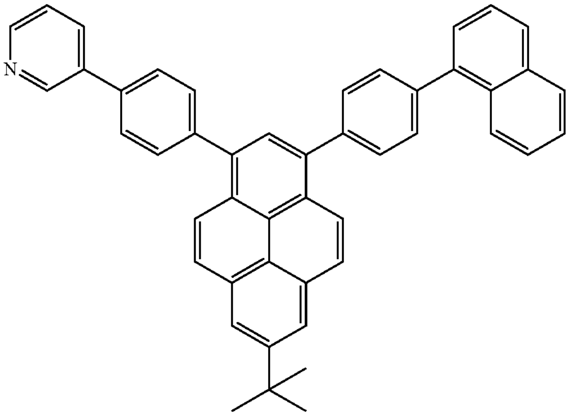

-continued
ET9
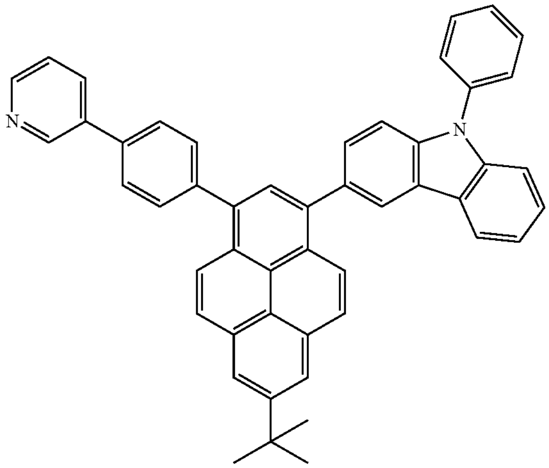
ET10
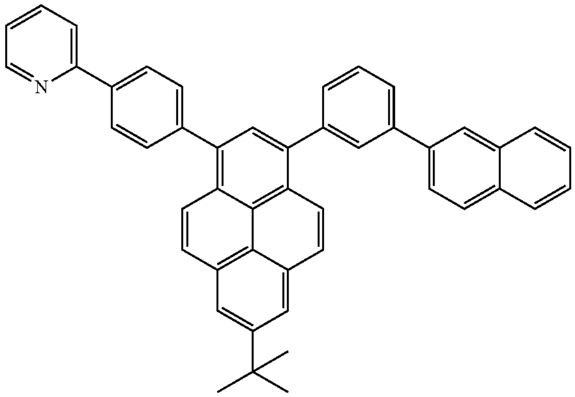
ET11
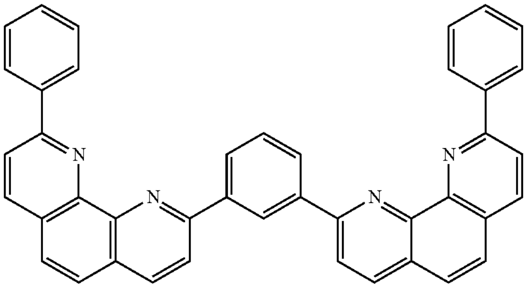
ET12
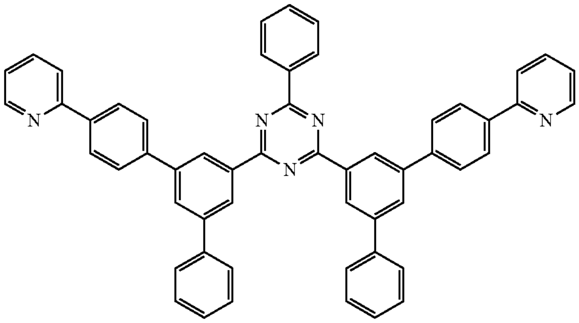
-continued
ET13
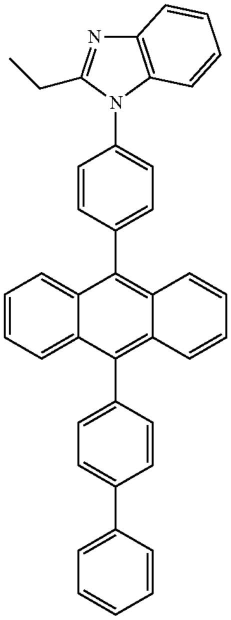
ET14
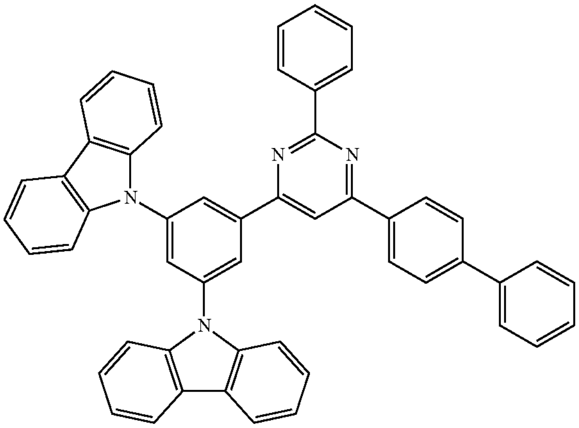
ET15
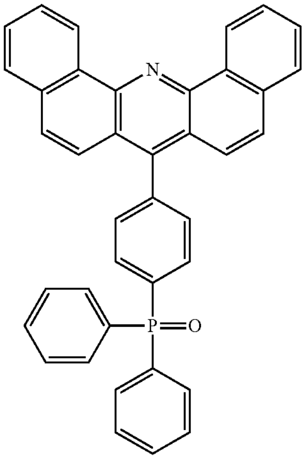

-continued

ET16

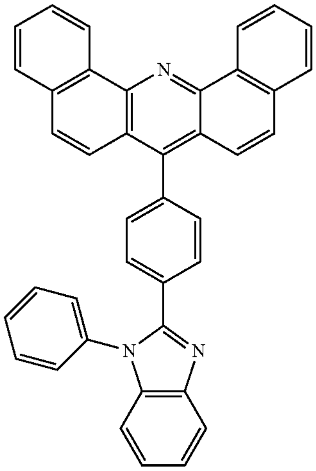

ET17

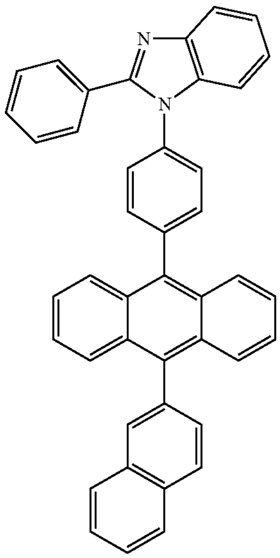

ET18

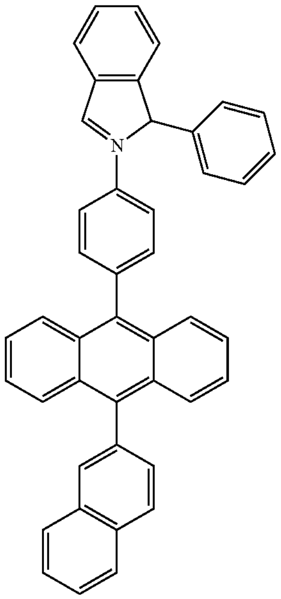

-continued

ET19

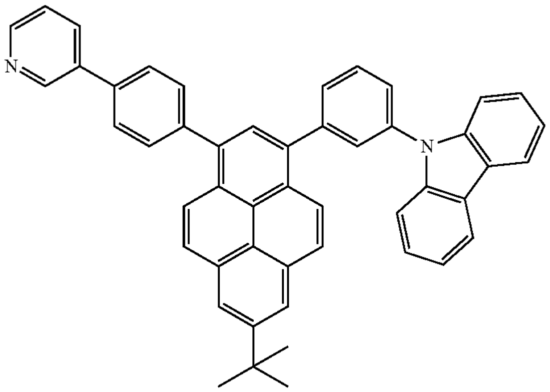

A thickness of the electron transport layer may be in a range of about 100 Å to about 1,000 Å, for example, about 150 Å to about 500 Å. While not wishing to be bound by theory it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-DI

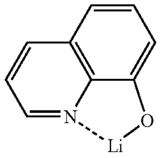

ET-D2

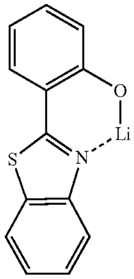

The electron transport region may include an electron injection layer that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. While not wishing to be bound by theory it is understood that when the thickness of the electron injection layer is within the range described above, the electron injection layer may have satisfactory electron injection characteristics without a substantial increase in driving voltage.

The second electrode 19 may be disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In some embodiments, to manufacture a top emission-type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{60}$ alkyl group," as used herein, refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group," as used herein, refers to a divalent group having the same structure as the $C_1$-$C_{60}$ alkyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy (iso-propoxy) group.

The term "$C_2$-$C_{60}$ alkenyl group," as used herein, refers to a hydrocarbon group formed by including at least one carbon-carbon double bond in the middle or at the terminal of the $C_2$-$C_{60}$ alkyl group, and examples thereof are an ethenyl group, a propenyl group, and a butenyl group. The term "$C_2$-$C_{60}$ alkenylene group," as used herein, refers to a divalent group having the same structure as the $C_2$-$C_{60}$ alkenyl group.

The term "$C_2$-$C_{60}$ alkynyl group," as used herein, refers to a hydrocarbon group formed by including at least one carbon-carbon triple bond in the middle or at the terminal of the $C_2$-$C_{60}$ alkyl group, and examples thereof are an ethynyl group, and a propynyl group. The term "$C_2$-$C_{60}$ alkynylene group," as used herein, refers to a divalent group having the same structure as the $C_2$-$C_{60}$ alkynyl group.

The term "$C_3$-$C_{10}$ cycloalkyl group," as used herein, refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having the same structure as the $C_3$-$C_{10}$ cycloalkyl group.

The term "$C_2$-$C_{10}$ heterocycloalkyl group," as used herein, refers to a monovalent monocyclic group having at least one heteroatom selected from N, O, P, Si and S as a ring-forming atom and 2 to 10 carbon atoms, and non-limiting examples thereof include a tetrahydrofuranyl group and a tetrahydrothiophenyl group. The term "$C_2$-$C_{10}$ heterocycloalkylene group," as used herein, refers to a divalent group having the same structure as the $C_2$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and which is not aromatic. Non-limiting examples thereof include a cyclopentenyl group, a cyclohexenyl group, and a cycloheptenyl group. The term "$C_3$-$C_{10}$ cycloalkenylene group," as used herein, refers to a divalent group having the same structure as the $C_3$-$C_{10}$ cycloalkenyl group.

The term "$C_2$-$C_{10}$ heterocycloalkenyl group," as used herein, refers to a monovalent monocyclic group that has at least one heteroatom selected from N, O, P, Si, and S as a ring-forming atom, 2 to 10 carbon atoms, and at least one double bond in its ring. Non-limiting examples of the $C_2$-$C_{10}$ heterocycloalkenyl group include a 2,3-dihydrofuranyl group and a 2,3-dihydrothiophenyl group. The term "$C_2$-$C_{10}$ heterocycloalkenylene group," as used herein, refers to a divalent group having the same structure as the $C_2$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group," as used herein, refers to a monovalent group having an aromatic system that has at least one heteroatom selected from N, O, P, Si, and S as a ring-forming atom, and 2 to 60 carbon atoms. The term "$C_2$-$C_{60}$ heteroarylene group," as used herein refers to a divalent group having a carbocyclic aromatic system that has at least one heteroatom selected from N, O, P, Si, and S as a ring-forming atom, and 2 to 60 carbon atoms. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "monovalent non-aromatic condensed polycyclic group," as used herein, refers to a monovalent group that has two or more rings condensed to each other, only carbon atoms (for example, the number of carbon atoms may be in a range of 8 to 60) as a ring forming atom, and which is non-aromatic in the entire molecular structure. Non-limiting examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group," as used herein, refers to a monovalent group that has two or more rings condensed to each other, has a heteroatom selected from N, O P, Si, and S, other than carbon atoms (for example, the number of carbon atoms may be in a range of 2 to 60), as a ring forming atom, and which is non-aromatic in the entire molecular structure. Non-limiting examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1: Synthesis of Compound 790

Compound 790 was synthesized according to the following reaction scheme.

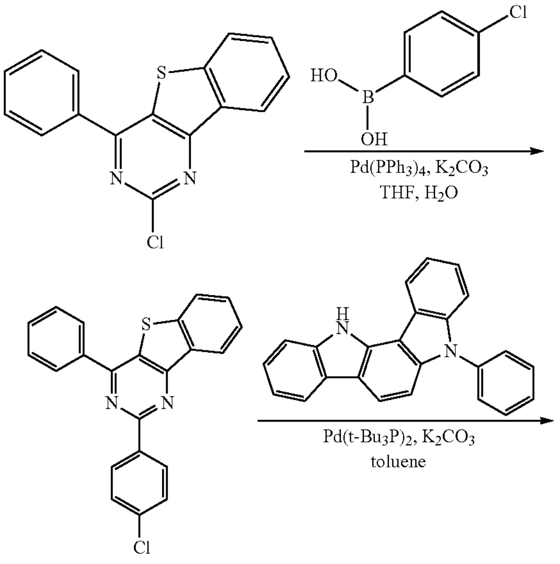

(A)

-continued

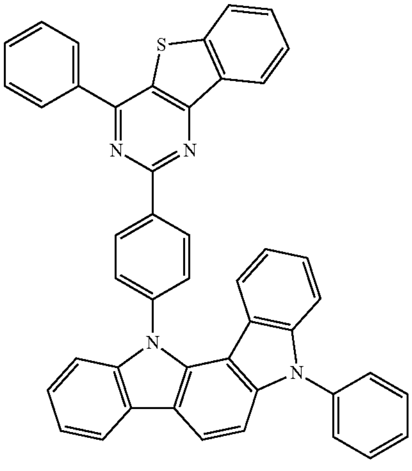

Compound 790

(1) Synthesis of Intermediate (A)

14.8 grams (g) (50 millimoles, mmol) of 2-chloro-4-phenylbenzo[4,5]thieno[3,2-d]pyrimidine, 7.8 g (50 mmol) of 4-chlorophenyl)boronic acid, 2.9 g (2.5 mmol) of tetrakistriphenylphosphine palladium(0) ($Pd(PPh_3)_4$), and 20.7 g (150 mmol) of potassium carbonate were added to a solution mixture including 75 milliliters (ml) of THF and 25 ml of water, and the mixture was stirred under reflux. Once the reaction was completed, the reaction product was cooled to room temperature, an aqueous solution layer was removed by extraction, the resultant was filtered at a reduced pressure through a silica gel, and the filtrate was concentrated at a reduced pressure. The product was separated by using silica gel column chromatography. The product was re-crystallized with dichloromethane (DCM)/methanol (MeOH) to obtain 14.5 g of Intermediate (A) (yield: 78%).

LC-Mass (calculated value: 372.87 g/mol, measured value: M+1=373 g/mol).

(2) Synthesis of Compound 790

7.5 g (20 mmol) of Intermediate (A), 7.3 g (22 mmol) of 5-phenyl-5,12-dihydroindolo[3,2-a]carbazole, 1.0 g (2 mmol) of bis(tri-tert-butylphosphine)palladium(0) ($Pd(t-Bu_3P)_2$), and 8.3 g (66 mmol) of potassium carbonate were added to 100 ml of toluene, and the mixture was stirred under reflux. Once the reaction was completed, the reaction product was cooled to room temperature, an aqueous solution layer was removed by extraction, the resultant was filtered at a reduced pressure through a silica gel, and the filtrate was concentrated at a reduced pressure. The product was separated by using silica gel column chromatography. The product was re-crystallized with dichloromethane (DCM)/methanol (MeOH) to obtain 11.4 g of Compound 790 (yield: 85%).

LC-Mass (calculated value: 668.81 g/mol, measured value: M+1=669 g/mol).

Synthesis Example 2: Synthesis of Compound 1884

Compound 1884 was synthesized according to the following reaction scheme.

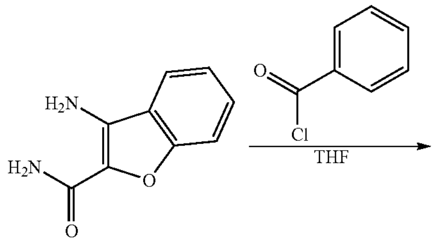

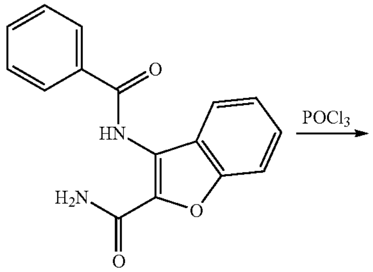

(B)

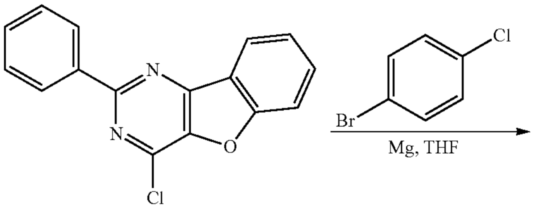

(D)

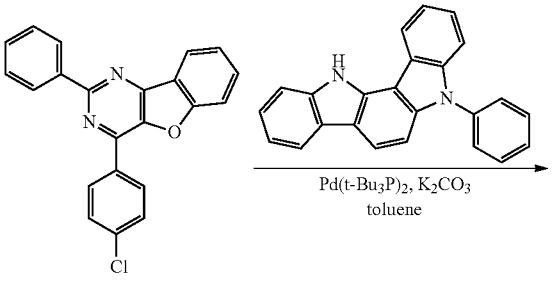

(E)

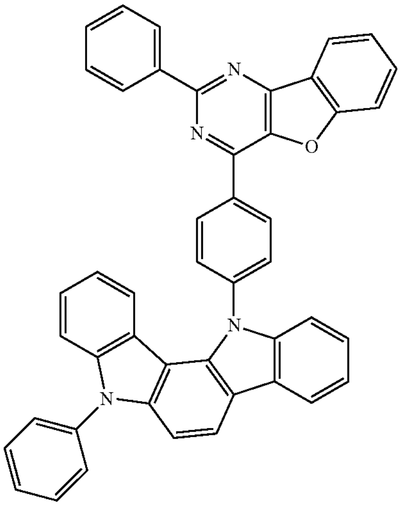

Compound 1884

(1) Synthesis of Intermediate (B)

31 g (180 mmol) of 3-aminobenzofuran-2-carboxamide and 49 ml of triethylamine were added to 900 ml of THF, the mixture was cooled to a temperature of 0° C., 22.4 ml of benzoyl chloride was added by drops thereto over 10 minutes, and the mixture was allowed to react at room temperature for 4 hours. Once the reaction was completed, a solvent was removed from the reaction product, 500 ml of methanol was added thereto, and the solid thus obtained was filtered at a reduced pressure and dried to obtain 46.7 g of Intermediate (B) (yield: 95%).

LC-Mass (calculated value: 280.28 g/mol, measured value: M+1=281 g/mol).

(2) Synthesis of Intermediate (D)

42 ml of phosphoryl chloride ($POCl_3$) was slowly added to a mixture including 43.1 g (154 mmol) of Intermediate (B) and 80 ml of triethylamine, and the resulting mixture was heated at a temperature of 60° C. Once the reaction was completed, the reaction product was cooled to room temperature, and ice water was added thereto. An aqueous solution was removed from the reaction product by extraction, the resultant was filtered at a reduced pressure through a silica gel, and the filtrate was concentrated at a reduced pressure. The product was separated by using silica gel column chromatography. The product was re-crystallized with hexane to obtain 33.6 g of Intermediate (D) (yield: 78%).

LC-Mass (calculated value: 280.71 g/mol, measured value: M+1=281 g/mol).

(3) Synthesis of Intermediate (E)

2.8 g of magnesium (Mg) was added to a mixture solution including 25.3 g (132 mmol) of 1-bromo-4-chlorobenzene and 120 ml THF, and the mixture was heated to a temperature of 50° C. and then stirred under reflux. Once the reaction was completed, the reaction product was cooled to room temperature, water and hydrochloric acid were added thereto, an aqueous solution layer was removed by extraction, the resultant was filtered at a reduced pressure through a silica gel, and the filtrate was concentrated at a reduced pressure. The product was washed by using each of dichloromethane ($CH_2Cl_2$), ethyl acetate (AcOEt), and ethanol (EtOH) and then dried to obtain 25.4 g of Intermediate (E) (yield: 65%).

LC-Mass (calculated value: 356.80 g/mol, measured value: M+1=357 g/mol).

(4) Synthesis of Compound 1884

9.14 g of Compound 1884 (yield: 70%) was obtained by using the same synthesis method used in the synthesis of Compound 790, except that 7.1 g (20 mmol) of Intermediate (E) was used instead of Intermediate (A) during the synthesis.

LC-Mass (calculated value: 652.74 g/mol, measured value: M+1=653 g/mol).

Synthesis Example 3: Synthesis of Compound 1900

Compound 1900 was synthesized according to the following reaction scheme.

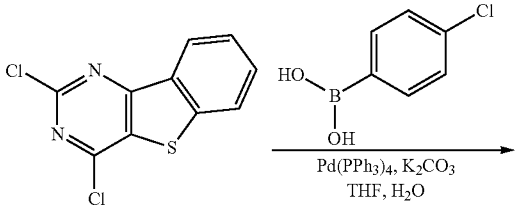

-continued

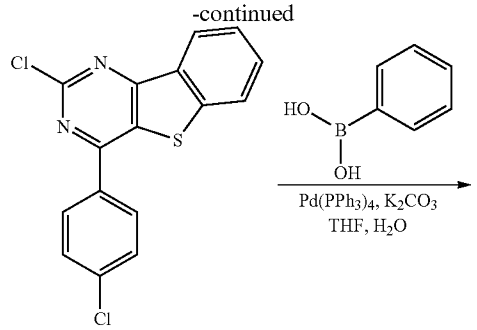

(F)

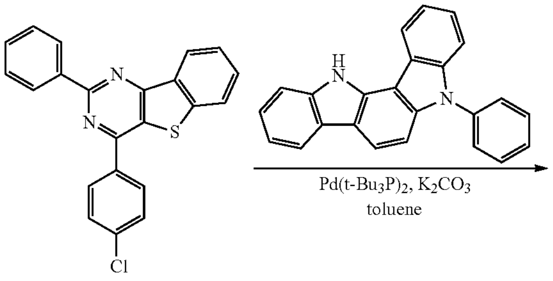

(G)

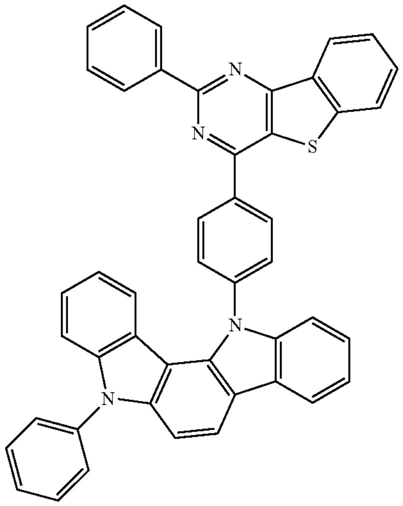

Compound 1900

(1) Synthesis of Intermediate (F)

15.6 g of Intermediate (F) (yield: 79%) was obtained by using the same synthesis method used in the synthesis of Intermediate (A), except that 15.3 g (60 mmol) of 2,4-dichlorobenzo[4,5]thieno[3,2-d]pyrimidine was used instead of 2-chloro-4-phenylbenzo[4,5]thieno[3,2-d]pyrimidine during the synthesis.

LC-Mass (calculated value: 331.22 g/mol, measured value: M+1=332 g/mol).

(2) Synthesis of Intermediate (G)

14.2 g of Intermediate (G) (yield: 85%) was obtained by using the same synthesis method used in the synthesis of Intermediate (A), except that 14.6 g (44 mmol) of Intermediate (F) and 5.4 g (44 mmol) of phenylboronic acid were used instead of 2-chloro-4-phenylbenzo[4,5]thieno[3,2-d]pyrimidine and (4-chlorophenyl)boronic acid during the synthesis.

LC-Mass (calculated value: 372.87 g/mol, measured value: M+1=373 g/mol).

(3) Synthesis of Compound 1900

10.0 g of Compound 1900 (yield: 83%) was obtained by using the same synthesis method used in the synthesis of Compound 790, except that 6.7 g (18 mmol) of Intermediate (G) was used instead of Intermediate (A) during the synthesis.

LC-Mass (calculated value: 668.81 g/mol, measured value: M+1=669 g/mol).

Synthesis Example 4: Synthesis of Compound 1882

Compound 1882 was synthesized according to the following reaction scheme.

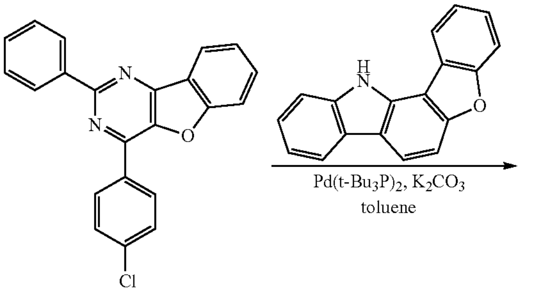

E

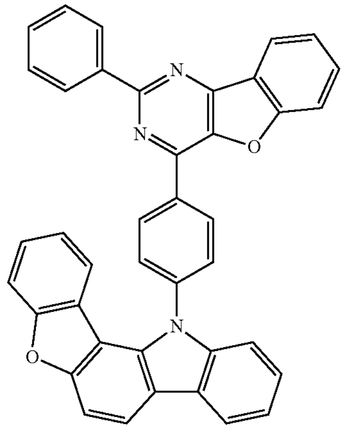

Compound 1882

8.0 g of Compound 1882 (yield: 72%) was obtained by using the same synthesis method used in the synthesis of Compound 790, except that 7.1 g (20 mmol) of Intermediate (E) and 5.7 g (22 mmol) of 12H-benzofuro[3,2-a]carbazole were used instead of Intermediate (A) and 5-phenyl-5,12-dihydroindolo[3,2-a]carbazole during the synthesis.

LC-Mass (calculated value: 577.63 g/mol, measured value: M+1=578 g/mol).

Synthesis Example 5: Synthesis of Compound 1899

Compound 1899 was synthesized according to the following reaction scheme.

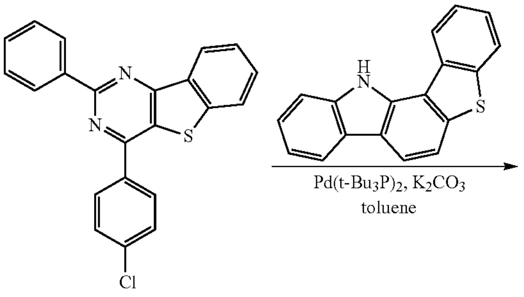

G

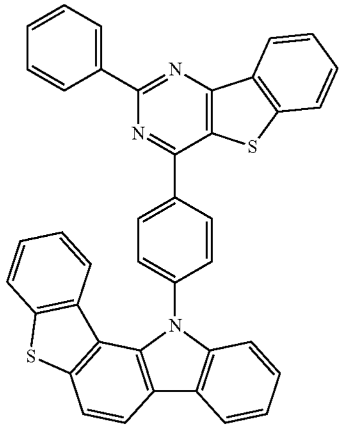

Compound 1899

8.3 g of Compound 1899 (yield: 76%) was obtained by using the same synthesis method used in the synthesis of Compound 790, except that 6.7 g (18 mmol) of Intermediate (G) and 5.5 g (20 mmol) of 12H-benzo[4,5]thieno[3,2-a]carbazole were used instead of Intermediate (A) and 5-phenyl-5,12-dihydroindolo[3,2-a]carbazole during the synthesis.

LC-Mass (calculated value: 609.76 g/mol, measured value: M+1=610 g/mol).

Synthesis Example 6: Synthesis of Compound 1883

Compound 1883 was synthesized according to the following reaction scheme.

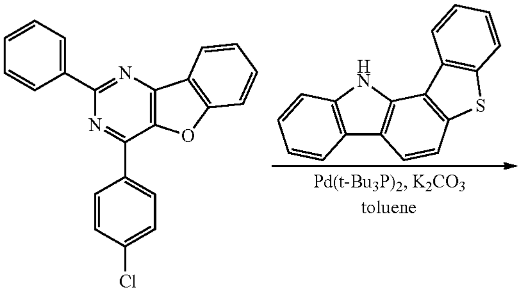

E

-continued

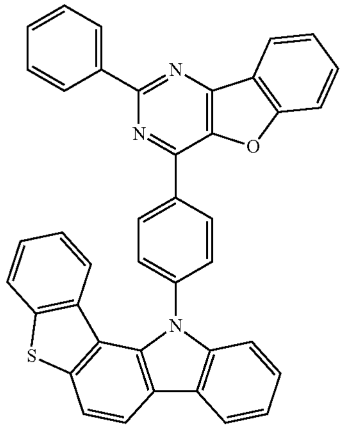

Compound 1883

6.7 g of Compound 1883 (yield: 75%) was obtained by using the same synthesis method used in the synthesis of Compound 790, except that 5.4 g (15 mmol) of Intermediate (E) and 4.7 g (17 mmol) of 12H-benzo[4,5]thieno[3,2-a]carbazole were used instead of Intermediate (A) and 5-phenyl-5,12-dihydroindolo[3,2-a]carbazole during the synthesis.

LC-Mass (calculated value: 593.70 g/mol, measured value: M+1=594 g/mol).

Synthesis Example 7: Synthesis of Compound 2284

Compound 2284 was synthesized according to the following reaction scheme.

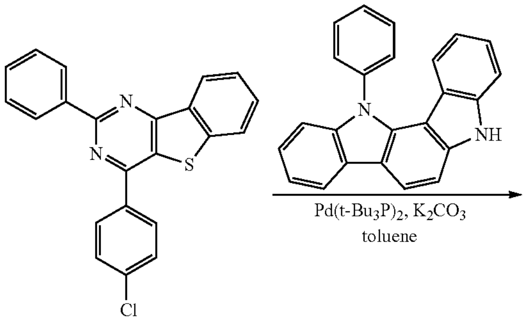

G

-continued

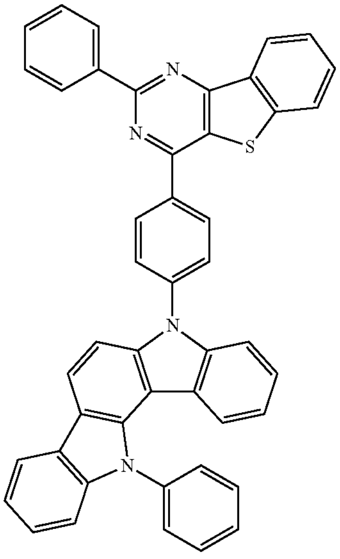

Compound 2284

9.4 g of Compound 2284 (yield: 78%) was obtained by using the same synthesis method used in the synthesis of Compound 790, except that 6.7 g (18 mmol) of Intermediate (G) and 6.7 g (20 mmol) of 12-phenyl-5,12-dihydroindolo[3,2-a]carbazole were used instead of Intermediate (A) and 5-phenyl-5,12-dihydroindolo[3,2-a]carbazole during the synthesis.

LC-Mass (calculated value: 668.81 g/mol, measured value: M+1=669 g/mol).

Synthesis Example 8: Synthesis of Compound 2268

Compound 2268 was synthesized according to the following reaction scheme.

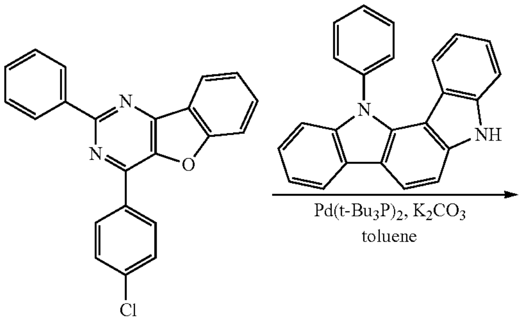

E

-continued

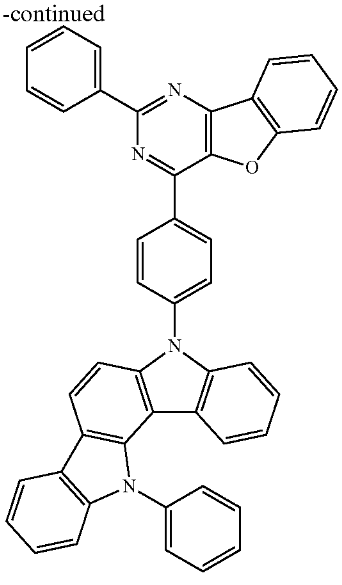

Compound 2268

7.3 g of Compound 2268 (yield: 75%) was obtained by using the same synthesis method used in the synthesis of Compound 790, except that 5.4 g (15 mmol) of Intermediate (E) and 5.7 g (17 mmol) of 12-phenyl-5,12-dihydroindolo [3,2-a]carbazole were used instead of Intermediate (A) and 5-phenyl-5,12-dihydroindolo[3,2-a]carbazole during the synthesis.

LC-Mass (calculated value: 652.74 g/mol, measured value: M+1=653 g/mol).

Synthesis Example 9: Synthesis of Compound 1142

Compound 1142 was synthesized according to the following reaction scheme.

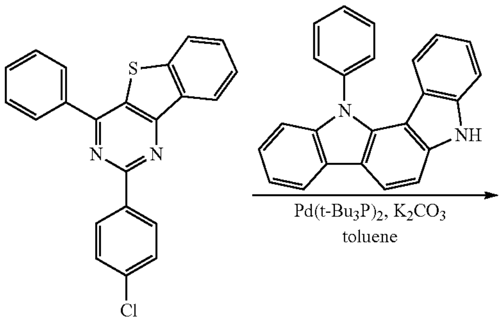

(A)

-continued

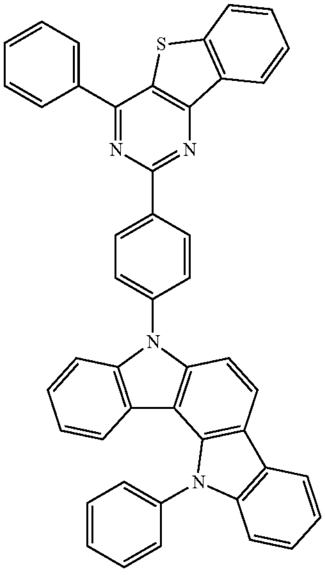

Compound 1142

10.7 g of Compound 1142 (yield: 89%) was obtained by using the same synthesis method used in the synthesis of Compound 790, except that 6.6 g (20 mmol) of 12-phenyl-5,12-dihydroindolo[3,2-a]carbazole was used instead of 5-phenyl-5,12-dihydroindolo[3,2-a]carbazole during the synthesis.

LC-Mass (calculated value: 668.81 g/mol, measured value: M+1=669 g/mol).

Synthesis Example 10: Synthesis of Compound 1126

Compound 1126 was synthesized according to the following reaction scheme.

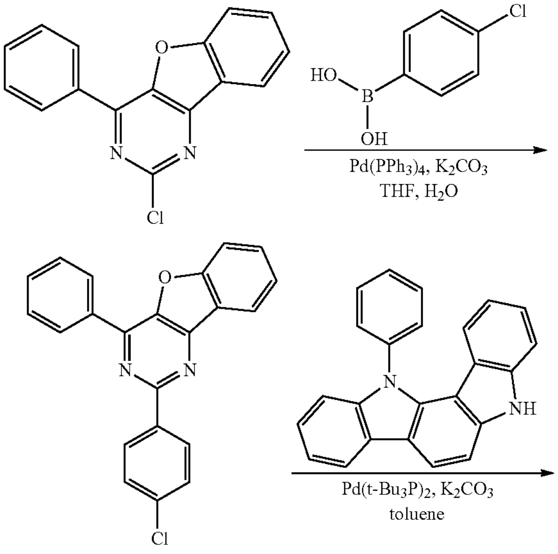

(H)

-continued

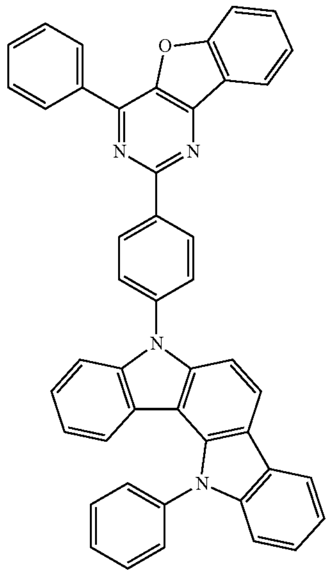

Compound 1126

(1) Synthesis of Intermediate (H)

11.8 g of Intermediate (H) (yield: 72%) was obtained by using the same synthesis method used in the synthesis of Intermediate (A), except that 14.0 g (50 mmol) of 2-chloro-4-phenylbenzofuro[3,2-d]pyrimidine was used instead of 2-chloro-4-phenylbenzo[4,5]thieno[3,2-d]pyrimidine during the synthesis.

LC-Mass (calculated value: 356.80 g/mol, measured value: M+1=357 g/mol).

(2) Synthesis of Compound 1126

7.3 g of Compound 1126 (yield: 75%) was obtained by using the same synthesis method used in the synthesis of Compound 790, except that 5.4 g (15 mmol) of Intermediate (H) and 6.0 g (18 mmol) of 12-phenyl-5,12-dihydroindolo[3,2-a]carbazole were used instead of Intermediate (A) and 5-phenyl-5,12-dihydroindolo[3,2-a]carbazole during the synthesis.

LC-Mass (calculated value: 652.74 g/mol, measured value: M+1=653 g/mol).

Evaluation Example 1: HOMO Energy Level, LUMO Energy Level, Singlet (S1) Energy Level, Triplet (T1) Energy Level, and $\Delta E_{ST}$ Evaluation HOMO, LUMO, singlet (S1), and triplet (T1) energy levels of Compounds 790, 1884, 1900, 1882, 1889, 1883, 2284, 2268, 1142, 1126, A, and B were evaluated according to Table 2, and the results are shown in Table 3.

TABLE 2

| | |
|---|---|
| HOMO energy level evaluation method | A potential (V)-current (A) graph of each compound was obtained by using cyclic voltammetry (CV) (electrolyte: 0.1 molar (M) $Bu_4NClO_4$/solvent: $CH_2Cl_2$/electrode: 3 electrode system (working electrode: GC, reference electrode: Ag/AgCl, auxiliary electrode: Pt)). From reduction onset of the graph, a HOMO energy level of the compound was then calculated. |
| LUMO energy level evaluation method | Each compound was diluted at a concentration of $1 \times 10^{-5}$M in $CHCl_3$, and an ultra-violet (UV) absorption spectrum thereof was measured at room temperature by using a Shimadzu UV-350 Spectrometer, and a LUMO energy level thereof was calculated by using an optical band gap ($E_g$) from an edge of the absorption spectrum. |
| S1 energy level evaluation method | Photoluminescence spectrum of a mixture including toluene and each of the compounds (diluted at a concentration of $1 \times 10^{-4}$M) was measured by using a photoluminescence measuring device at room temperature, and peaks obtained therefrom were analyzed to calculate an S1 energy level. |
| T1 energy level evaluation method | Photoluminescence spectrum of a mixture including toluene and each of the compounds (diluted at a concentration of $1 \times 10^{-4}$M) in a quartz cell in liquid nitrogen (at 77 Kelvin, K) was measured by using a photoluminescence measuring device, and peaks that were only obtained at a low temperature compared to the general room temperature photoluminescence spectrum were analyzed to calculate a T1 energy level. |
| $\Delta E_{ST}$ | A gap between an S1 energy level and a T1 energy level was calculated. |

TABLE 3

| Compound No. | HOMO (eV) | LUMO (eV) | S1 energy level (eV) | T1 energy level (eV) | $\Delta E_{ST}$ (eV) |
|---|---|---|---|---|---|
| 790 | −5.42 | −2.24 | 2.87 | 2.66 | 0.21 |
| 1184 | −5.40 | −2.41 | 2.63 | 2.63 | 0.00 |
| 1900 | −5.73 | −2.70 | 2.67 | 2.61 | 0.06 |
| 1882 | −5.45 | −2.50 | 2.88 | 2.62 | 0.26 |
| 1899 | −5.51 | −2.32 | 2.91 | 2.67 | 0.24 |
| 1883 | −5.47 | −2.41 | 2.90 | 2.61 | 0.29 |
| 2284 | −5.68 | −2.75 | 2.68 | 2.60 | 0.08 |
| 2268 | −5.41 | −2.51 | 2.62 | 2.63 | 0.01 |
| 1142 | −5.40 | −2.29 | 2.88 | 2.67 | 0.21 |
| 1126 | −5.45 | −2.31 | 2.84 | 2.69 | 0.15 |
| A | −5.42 | −2.29 | 2.75 | 2.78 | 0.03 |
| B | −5.39 | −2.04 | 2.87 | 2.62 | 0.26 |

Referring to Table 3, it may be confirmed that Compounds 790, 1884, 1900, 1882, 1889, 1883, 2284, 2268, 1142, and 1126 may emit deep-blue light and thermal activated delayed fluorescence light.

Evaluation Example 2: Thermal Characteristics Evaluation

Each of Compounds 790, 1884, 1900, 1882, 1889, 1883, 2284, 2268, 1142, 1126, A, and B was subjected to thermal analysis ($N_2$ atmosphere, temperature range: room temperature to 800° C. (10 degrees Centigrade per minute, ° C./min)-TGA, room temperature to 400° C.-DSC, Pan Type: Pt Pan in disposable Al Pan(TGA), disposable Al pan(DSC)) using thermogravimetric analysis (TGA) and differential scanning calorimetry (DSC), and the obtained results are shown in Table 4 below. From the results shown in Table 4, it was determined that Compounds 790, 1884, 1900, 1882, 1889, 1883, 2284, 2268, 1142, and 1126 had excellent thermal stability, compared to those of Compounds A and B.

TABLE 4

| Compound No. | $T_g$ (° C.) |
|---|---|
| 790 | 169 |
| 1184 | 164 |
| 1900 | 157 |
| 1882 | 146 |
| 1899 | 150 |
| 1883 | 152 |
| 2284 | 165 |
| 2268 | 167 |
| 1142 | 162 |
| 1126 | 168 |
| A | 145 |
| B | 130 |

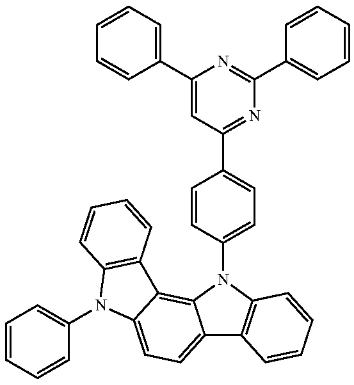

A

TABLE 4-continued

| Compound No. | $T_g$ (° C.) |
|---|---|
| 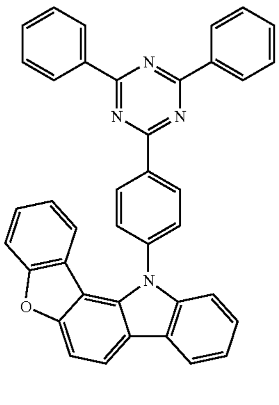 B | |

Evaluation Example 3: Photoluminescence Quantum Yield Evaluation

A sample was prepared by vacuum-depositing each of Compounds 1884, 1900, 1882, 1889, 1883, 2284, 2268, A, and B, as a dopant (15 percent by weight, wt %) on a quartz cell at a thickness of 100 Angstroms (Å) with mCP (a host). The sample was excited by excitation light having a wavelength of 340 nanometers (nm) in a nitrogen atmosphere by using C9920-02 and PMA-11 available from Hamamatsu Photonics, and thus a photoluminescence (PL) quantum yield of the sample was measured. The results are shown in Table 5. The PL quantum yields shown in Table 5 are relative values with respect to the PL quantum yield of Compound A. Based on the results shown in Table 5, it may be determined that Compounds 1884, 1900, 1882, 1889, 1883, 2284, and 2268 have higher PL quantum yields compared to those of Compounds A and B.

TABLE 5

| Compound No. | PL quantum yield (%) (relative value) |
|---|---|
| 1184 | 1.41 |
| 1900 | 1.52 |
| 1882 | 1.52 |
| 1899 | 1.48 |
| 1883 | 1.42 |
| 2284 | 1.29 |
| 2268 | 1.45 |
| A | 1.00 |
| B | 1.05 |

Example 1

A glass substrate with a 1500 Å-thick ITO (Indium tin oxide) electrode (first electrode, anode) formed thereon was washed with distilled water and ultrasonic waves. When the washing with distilled water was completed, sonicated washing was performed using a solvent, such as iso-propyl alcohol, acetone, or methanol. The resultant was dried and transferred to a plasma washer, and the resultant substrate was washed with oxygen plasma for 5 minutes and transferred to a vacuum depositor.

Compound HT3 was vacuum-deposited on the ITO electrode on the glass substrate to form a first hole injection layer having a thickness of 100 Å, Compound HT-D1 was vacuum-deposited on the first hole injection layer to form a second hole injection layer having a thickness of 100 Å, and mCP was deposited on the second hole injection layer to form an electron blocking layer having a thickness of 100 Å, thereby completing the manufacture of a hole transport region.

Compound 1900 (dopant, 15 wt %) and mCP (host) were co-deposited on the hole transport region to form an emission layer having a thickness of 400 Å.

Compound ET3 was vacuum-deposited on the emission layer to form an electron transport layer having a thickness of 300 Å, ET-D1(Liq) was deposited on the electron transport layer to form an electron injection layer having a thickness of 10 Å, and an Al second electrode (cathode) having a thickness of 1,200 Å was formed on the electron injection layer, thereby completing the manufacture of an organic light-emitting device.

Examples 2 to 5 Comparative Examples 1 and 2

Organic light-emitting devices were manufactured in the same manner as in Example 1, except that the compounds shown in Table 6 were used as a dopant of the emission layer, instead of Compound 1900.

TABLE 6

| | Dopant |
|---|---|
| Example 1 | Compound 1900 |
| Example 2 | Compound 1884 |
| Example 3 | Compound 1899 |
| Example 4 | Compound 2284 |
| Example 5 | Compound 2268 |
| Comparative Example 1 | Compound A |
| Comparative Example 2 | Compound B |

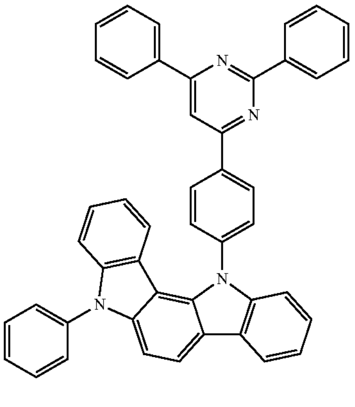

A

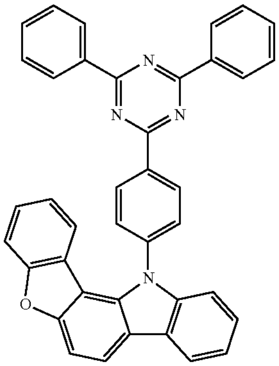

B

Evaluation Example 4: Evaluation on Characteristics of Organic Light-Emitting Devices The driving voltage, external quantum efficiency (EQE), lifespan ($T_{95}$), and color of emitted light of the organic light-emitting devices of Examples 1 to 5 and Comparatives Example 1 and 2 were measured by using a current-voltage meter (Keithley 2400) and a luminance meter (Minolta Cs-1000A), and the results thereof are shown in Table 7. $T_{95}$ (at 500 candelas per square meter, cd/$m^2$) in Table 7 indicates the amount of time that lapsed when 100% of the initial luminance was decreased to 95%. The driving voltage, EQE, and lifespan ($T_{95}$) are relative values that were converted with respect to Comparative Example 1.

TABLE 7

| | Dopant | Driving voltage (relative value) | External quantum efficiency (relative value) | Lifespan ($T_{95}$) (relative value) | Color of emitted light |
|---|---|---|---|---|---|
| Example 1 | Compound 1900 | 0.98 | 3.86 | 32.1 | blue |
| Example 2 | Compound 1884 | 0.88 | 4.83 | 19.95 | blue |
| Example 3 | Compound 1899 | 1.06 | 2.24 | 5.10 | blue |

TABLE 7-continued

| | Dopant | Driving voltage (relative value) | External quantum efficiency (relative value) | Lifespan ($T_{95}$) (relative value) | Color of emitted light |
|---|---|---|---|---|---|
| Example 4 | Compound 2284 | 0.97 | 3.38 | 27.7 | blue |
| Example 5 | Compound 2268 | 0.95 | 3.72 | 20.6 | blue |
| Comparative Example 1 | Compound A | 1.00 | 1.00 | 1.00 | blue |
| Comparative Example 2 | Compound B | 1.04 | 1.52 | 4.50 | blue |

Based on the results shown in Table 7, it may be determined that the organic light-emitting devices of Examples 1 to 5 had high efficiency and long lifespan compared to those characteristics of the organic light-emitting device of Comparative Examples 1 and 2.

As described above, according to the one or more of the above embodiments of the present disclosure, the condensed cyclic compound has excellent optical characteristics, electric characteristics, and thermal stability, and thus, when an organic light-emitting device includes the condensed cyclic compound, the organic light-emitting device may have high efficiency and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. A condensed cyclic compound represented by Formula 1:

Formula 1

$$Ar_1—(L_1)_{a1}—Ar_2$$

Formula 2-2

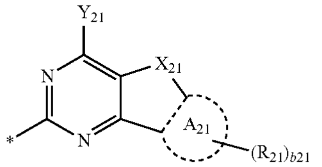

Formula 2-4

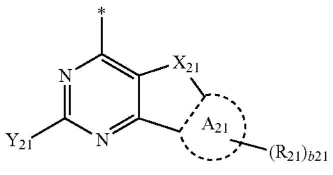

3-12

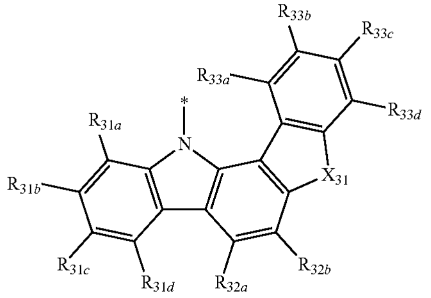

3-15

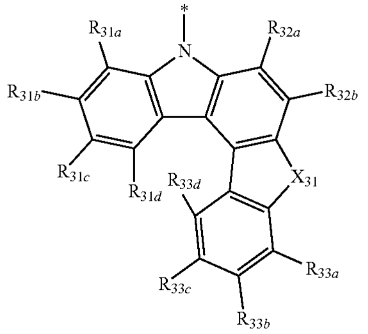

3-16

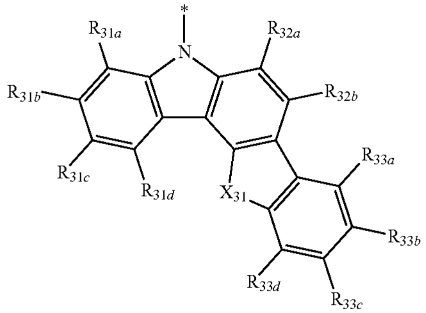

wherein, in Formulae 1, 2-2, 2-4, 3-12, 3-15, and 3-16, $Ar_1$ is selected from groups represented by Formulae 2-2 and 2-4;

$Ar_2$ is selected from groups represented by Formulae 3-12, 3-15, and 3-16;

$L_1$ is selected from a substituted or unsubstituted $C_6$-$C_{60}$ arylene group and a substituted or unsubstituted $C_1$-$C_{60}$ heteroarylene group;

a1 is selected from 1, 2, and 3;

$X_{21}$ is selected from O, S, $C(R_{22})(R_{23})$, $Si(R_{22})(R_{23})$, $Ge(R_{22})(R_{23})$, and $P(=O)(R_{22})$;

$X_{31}$ is selected from O, S, $N(R_{34})$, $C(R_{34})(R_{35})$, $Si(R_{34})(R_{35})$, and $Ge(R_{34})(R_{35})$;

provided that when $Ar_1$ is Formula 2-4 and $Ar_2$ is Formula 3-12, when $X_{21}$ is S, then $X_{31}$ is selected from O, S, $C(R_{34})(R_{35})$, $Si(R_{34})(R_{35})$, and $Ge(R_{34})(R_{35})$;

$A_{21}$ is selected from a $C_5$-$C_{20}$ carbocyclic group and a $C_4$-$C_{20}$ heterocyclic group;

$Y_{21}$ is selected from a substituted or unsubstituted $C_6$-$C_{60}$ aryl group and a substituted or unsubstituted $C_1$-$C_{60}$ heteroaryl group;

$R_{21}$ to $R_{23}$, $R_{31a}$ to $R_{31d}$, $R_{32a}$ to $R_{32d}$, $R_{33a}$ to $R_{33d}$, $R_{34}$, and $R_{35}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 is selected from 1, 2, 3, 4, 5, 6, 7, and 8; and

* denotes a binding site to a neighboring atom.

2. The condensed cyclic compound of claim 1, wherein $L_1$ is selected from a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group.

3. The condensed cyclic compound of claim 1, wherein $L_1$ is selected from a single bond and groups represented by Formulae 4-1 to 4-15:

4-1

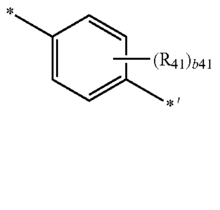

-continued 4-2

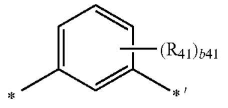

4-3

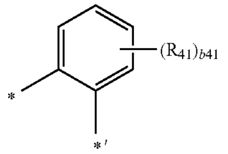

4-4

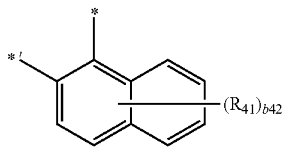

4-5

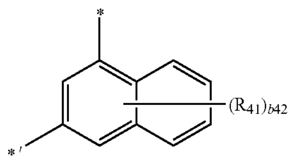

4-6

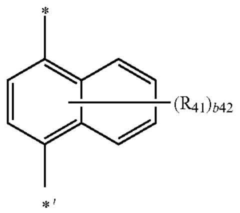

4-7

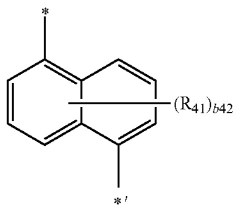

4-8

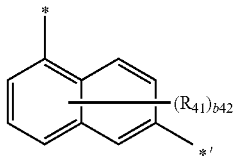

4-9

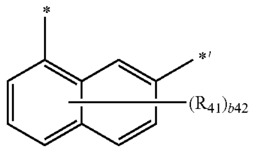

4-10

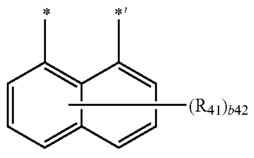

-continued 4-11

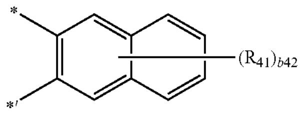

4-12

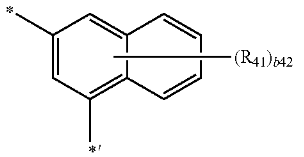

4-13

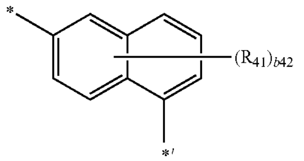

4-14

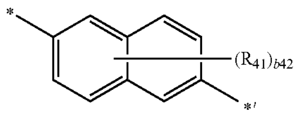

4-15

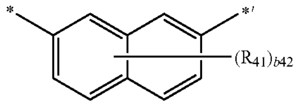

wherein, in Formulae 4-1 to 4-15, $R_{41}$ is selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group;

b41 is selected from 1, 2, 3, and 4;

b42 is selected from 1, 2, 3, 4, 5, and 6; and

* and *' each independently denote a binding site to a neighboring atom.

4. The condensed cyclic compound of claim 1, wherein a1 is 1.

5. The condensed cyclic compound of claim 1, wherein $(L_1)_{a1}$ is selected from groups represented by Formulae 5-1 to 5-3:

5-1

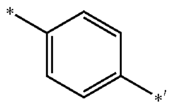

5-2

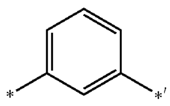

-continued 5-3

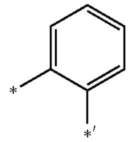

wherein, in Formulae 5-1 to 5-3,

* and *' each independently denote a binding site to a neighboring atom.

6. The condensed cyclic compound of claim 1, wherein $A_{21}$ is selected from a benzene group, a naphthalene group, an anthracene group, a phenanthrene group, a triphenylene group, a pyridine group, a pyrimidine group, a pyrazine group, a quinoline group, an isoquinoline group, 2,6-naphthyridine group, 1,8-naphthyridine group, 1,5-naphthyridine group, 1,6-naphthyridine group, 1,7-naphthyridine group, 2,7-naphthyridine group, a quinoxaline group, a phthalazine group, a quinazoline group, and a cinnoline group.

7. The condensed cyclic compound of claim 1, wherein $A_{21}$ is selected from a benzene group and a naphthalene group.

8. The condensed cyclic compound of claim 1, wherein $Y_{21}$ is selected from a phenyl group, a biphenyl group, a terphenyl group, a pentalenyl group, a naphthyl group, an azulenyl group, a heptalenyl group, an indacenyl group, an acenaphthyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a furanyl group, a benzofuranyl group, a thiophenyl group, a benzothiophenyl group, and a triazinyl group; and a phenyl group, a biphenyl group, a terphenyl group, a pentalenyl group, a naphthyl group, an azulenyl group, a heptalenyl group, an indacenyl group, an acenaphthyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a furanyl group, a benzofuranyl group, a thiophenyl group, a benzothiophenyl group, and a triazinyl group, each substituted with at least one selected from deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, and a naphthyl group.

9. The condensed cyclic compound of claim 1, wherein $Y_{21}$ is selected from a phenyl group, a biphenyl group, a terphenyl group, a naphthyl group, a phenanthrenyl group, an anthracenyl group, a triphenylenyl group, a pyrenyl group, and a chrysenylgroup; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, and a naphthyl group.

10. The condensed cyclic compound of claim 1, wherein $Y_{21}$ is selected from groups represented by Formulae 6-1 to 6-4:

6-1

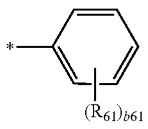

6-2

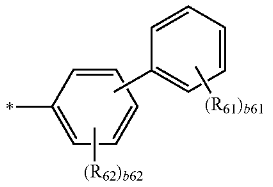

6-3

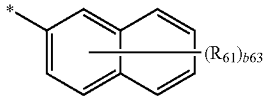

6-4

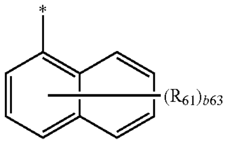

wherein, in Formulae 6-1 to 6-4, $R_{61}$ is selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b61 is selected from 1, 2, 3, 4, and 5;

b62 is selected from 1, 2, 3, and 4;

b63 is selected from 1, 2, 3, 4, 5, 6, and 7; and

* denotes a binding site to a neighboring atom.

11. The condensed cyclic compound of claim 1, wherein $R_{21}$ to $R_{23}$, $R_{31a}$ to $R_{31d}$, $R_{32a}$ to $R_{32d}$, $R_{33a}$ to $R_{33d}$, $R_{34}$, and $R_{35}$ are each independently selected from hydrogen, deuterium, —F, —Cl, —Br, —I, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

12. The condensed cyclic compound of claim 1, wherein $Ar_1$ is selected from groups represented by Formulae 2-11 to 2-14:

2-12

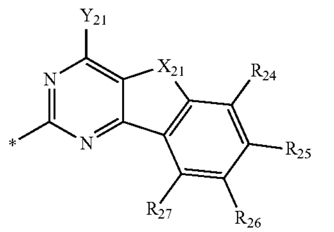

2-14

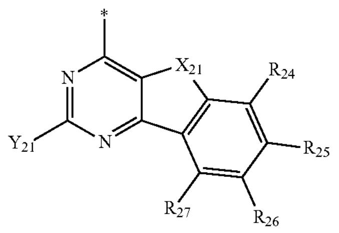

wherein, in Formulae 2-12 and 2-14, $Y_{21}$ and $X_{21}$ are the same as described in connection with Formulae 2-2 and 2-4;

$R_{24}$ to $R_{27}$ are the same as described in connection with $R_{21}$ in Formulae 2-2 and 2-4;

provided that when $Ar_1$ is Formula 2-14 and $Ar_2$ is Formula 3-12, when $X_{21}$ is S, then $X_{31}$ is selected from O, S, $C(R_{34})(R_{35})$, $Si(R_{34})(R_{35})$, and $Ge(R_{34})(R_{35})$; and

* denotes a binding site to a neighboring atom.

13. The condensed cyclic compound of claim 1, wherein the condensed cyclic compound represented by Formula 1 is selected from compounds represented by Formulae 1-8, 1-11, 1-12, 1-20, 1-23, and 1-24:

1-8

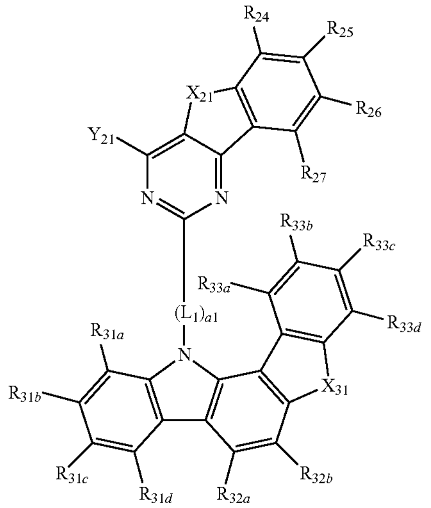

-continued 1-11

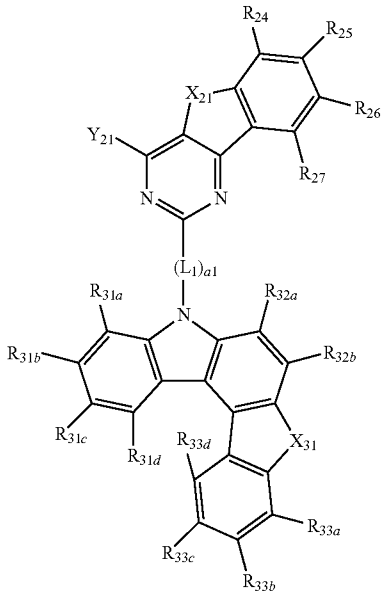

1-12

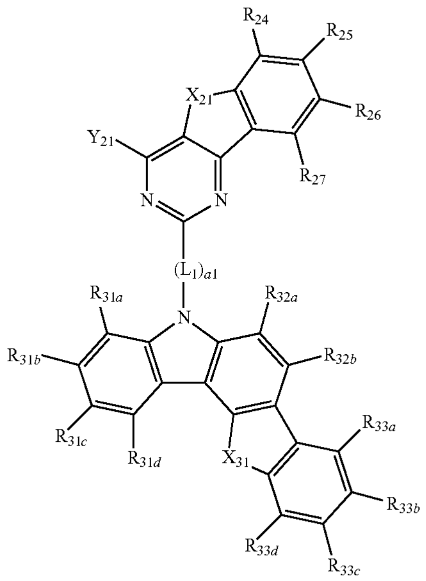

1-20

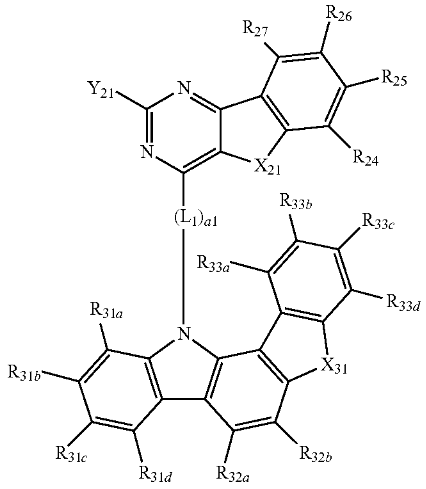

-continued 1-23

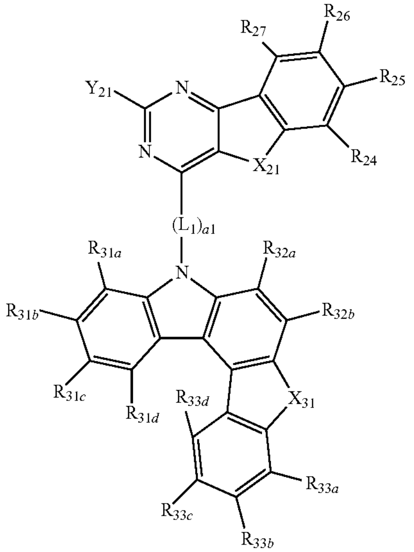

1-24

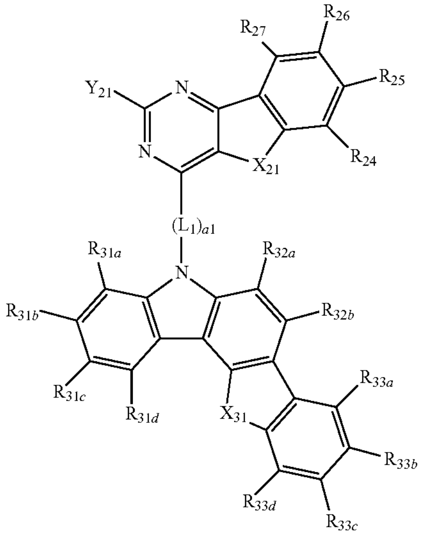

wherein, in Formulae 1-8, 1-11, 1-12, 1-20, 1-23, and 1-24, $L_1$ is selected from a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group;

a1 is 1;

$Y_{21}$ and $X_{21}$ are the same as described in connection with Formulae 2-2 and 2-4;

$R_{24}$ to $R_{27}$ are the same as described in connection with $R_{21}$ in Formulae 2-2 and 2-4;

$X_{31}$ is the same as described in connection with Formulae 3-12, 3-15, and 3-16;

provided that in Formula 1-20, when $X_{21}$ is S, then $X_{31}$ is selected from O, S, $C(R_{34})(R_{35})$, $Si(R_{34})(R_{35})$, and $Ge(R_{34})(R_{35})$;

$R_{31a}$, $R_{31b}$, $R_{31c}$, and $R_{31d}$ are each independently the same as described in connection with $R_{31}$ in Formulae 3-12, 3-15 and 3-16;

$R_{32a}$ and $R_{32b}$ are each independently the same as described in connection with $R_{32}$ in Formulae 3-12, 3-15, and 3-16; and $R_{33a}$, $R_{33b}$, $R_{33c}$, and $R_{33d}$ are each independently the same as described in connection with $R_{33}$ in Formulae 3-12, 3-15, and 3-16.

14. The condensed cyclic compound of claim 1, wherein $(L_1)_{a1}$ is selected from groups represented by Formulae 5-1 to 5-3:

5-1

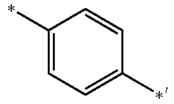

5-2

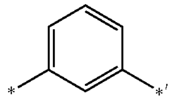

5-3

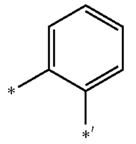

wherein, in Formulae 5-1 to 5-3,

* and *' each independently denote a binding site to a neighboring atom.

15. An organic light-emitting device comprising:

a first electrode;

a second electrode; and an organic layer disposed between the first electrode and the second electrode, wherein the organic layer comprises an emission layer and at least one condensed cyclic compound of claim 1.

16. The organic light-emitting device of claim 15, wherein the emission layer comprises the condensed cyclic compound.

17. An organic light-emitting device comprising:

a first electrode;

a second electrode; and an organic layer disposed between the first electrode and the second electrode, wherein the organic layer comprises an emission layer and at least one condensed cyclic compound represented by Formula 1, wherein the emission layer emits blue light:

Formula 1

$$Ar_1—(L_1)_{a1}—Ar_2$$

Formula 2-1

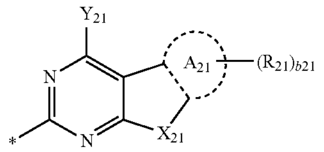

-continued

Formula 2-2

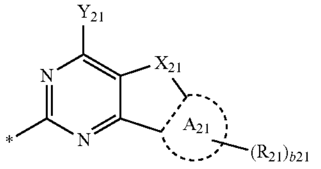

Formaul 2-3

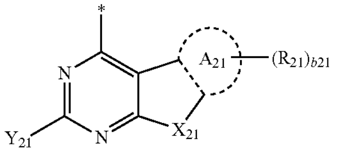

Formula 2-4

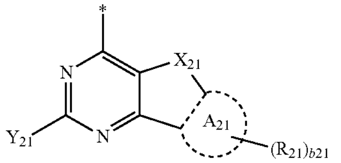

Formula 3-1

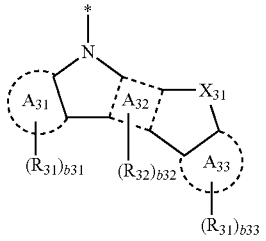

Formula 3-2

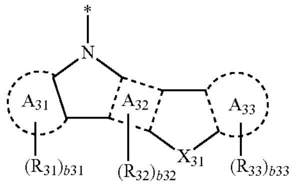

wherein, in Formulae 1, 2-1 to 2-4, 3-1, and 3-2, $Ar_1$ is selected from groups represented by Formulae 2-1 to 2-4;

$Ar_2$ is selected from groups represented by Formulae 3-1 and 3-2;

$L_1$ is selected from a substituted or unsubstituted $C_6$-$C_{60}$ arylene group and a substituted or unsubstituted $C_1$-$C_{60}$ heteroarylene group;

a1 is selected from 1, 2, and 3;

$X_{21}$ is selected from O, S, $C(R_{22})(R_{23})$, $Si(R_{22})(R_{23})$, $Ge(R_{22})(R_{23})$, and $P(=O)(R_{22})$;

$X_{31}$ is selected from O, S, $N(R_{34})$, $C(R_{34})(R_{35})$, $Si(R_{34})(R_{35})$, and $Ge(R_{34})(R_{35})$;

$A_{21}$, $A_{31}$, and $A_{33}$ are each independently selected from a $C_5$-$C_{20}$ carbocyclic group and a $C_4$-$C_{20}$ heterocyclic group;

$A_{32}$ is selected from a $C_5$-$C_{20}$ carbocyclic group;

$Y_{21}$ is selected from a substituted or unsubstituted $C_6$-$C_{60}$ aryl group and a substituted or unsubstituted $C_1$-$C_{60}$ heteroaryl group;

$R_{21}$ to $R_{23}$ and $R_{31}$ to $R_{35}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 is selected from 1, 2, 3, 4, 5, 6, 7, and 8;

b31 to b33 are each independently selected from 1, 2, 3, 4, 5, and 6; and

* denotes a binding site to a neighboring atom, wherein the emission layer comprises the condensed cyclic compound, wherein the emission layer further comprises a host, and wherein the condensed cyclic compound is a dopant.

18. The condensed cyclic compound of claim 17, wherein $A_{32}$ is selected from a benzene group, a naphthalene group, an anthracene group, a phenanthrene group, and a triphenylene group.

19. The condensed cyclic compound of claim 17, wherein $A_{32}$ is selected from a benzene group and a naphthalene group.

* * * * *